US008071562B2

(12) United States Patent
Bader et al.

(10) Patent No.: US 8,071,562 B2
(45) Date of Patent: Dec. 6, 2011

(54) MIR-124 REGULATED GENES AND PATHWAYS AS TARGETS FOR THERAPEUTIC INTERVENTION

(75) Inventors: Andreas G. Bader, Austin, TX (US); Jason F. Wiggins, Austin, TX (US); Lubna Patrawala, Cambridge, MA (US); Kevin Kelnar, Kyle, TX (US); Mike Byrom, Austin, TX (US); David Brown, Austin, TX (US)

(73) Assignee: Mirna Therapeutics, Inc., Austin, TX (US)

( * ) Notice: Subject to any disclaimer, the term of this patent is extended or adjusted under 35 U.S.C. 154(b) by 43 days.

(21) Appl. No.: 12/325,917

(22) Filed: Dec. 1, 2008

(65) Prior Publication Data
US 2009/0192111 A1 Jul. 30, 2009

Related U.S. Application Data

(60) Provisional application No. 60/991,709, filed on Dec. 1, 2007.

(51) Int. Cl.
A01N 43/04 (2006.01)
A61K 31/70 (2006.01)
(52) U.S. Cl. ................................... 514/44 A
(58) Field of Classification Search .............. 514/44
See application file for complete search history.

(56) References Cited

U.S. PATENT DOCUMENTS

| 4,683,195 A | 7/1987 | Mullis et al. ............... 435/6 |
| 4,683,202 A | 7/1987 | Mullis ........................ 435/91 |
| 4,876,187 A | 10/1989 | Duck et al. ................. 435/6 |
| 4,999,290 A | 3/1991 | Lee ............................. 435/6 |
| 5,011,769 A | 4/1991 | Duck et al. ................. 435/6 |
| 5,188,934 A | 2/1993 | Menchen et al. ........... 435/6 |
| 5,256,555 A | 10/1993 | Milburn et al. ........... 435/195 |
| 5,260,191 A | 11/1993 | Yang ........................... 435/6 |
| 5,262,311 A | 11/1993 | Pardee et al. ............ 435/91.2 |
| 5,366,860 A | 11/1994 | Bergot et al. ............... 435/6 |
| 5,432,272 A | 7/1995 | Benner ..................... 536/25.3 |
| 5,486,603 A | 1/1996 | Buhr ........................ 536/24.3 |
| 5,538,848 A | 7/1996 | Livak et al. ................. 435/5 |
| 5,543,296 A | 8/1996 | Sobol et al. ................ 435/6 |
| 5,545,522 A | 8/1996 | Van Gelder et al. ........ 435/6 |
| 5,660,988 A | 8/1997 | Duck et al. ................. 435/6 |
| 5,723,591 A | 3/1998 | Livak et al. .............. 536/22.1 |
| 5,739,169 A | 4/1998 | Ocain et al. .............. 514/658 |
| 5,766,888 A | 6/1998 | Sobol et al. ............. 435/91.2 |
| 5,800,996 A | 9/1998 | Lee et al. ................... 435/6 |
| 5,801,005 A | 9/1998 | Cheever et al. .......... 435/724 |
| 5,801,155 A | 9/1998 | Kutyavin et al. .......... 514/44 |
| 5,824,311 A | 10/1998 | Greene et al. ........... 424/438.1 |
| 5,830,880 A | 11/1998 | Sedlacek et al. .......... 514/44 |
| 5,847,162 A | 12/1998 | Lee et al. ................. 549/227 |
| 5,859,221 A | 1/1999 | Cook et al. .............. 536/23.1 |
| 5,861,245 A | 1/1999 | McClelland ................ 435/6 |
| 5,863,727 A | 1/1999 | Lee et al. ................... 435/6 |
| 5,871,697 A | 2/1999 | Rothberg et al. ........ 422/68.1 |
| 5,898,031 A | 4/1999 | Crooke .................... 435/172.3 |
| 5,925,517 A | 7/1999 | Tyagi et al. ................ 435/6 |
| 5,936,087 A | 8/1999 | Benson et al. ............. 546/33 |
| 5,942,398 A | 8/1999 | Tartaglia et al. ........... 435/6 |
| 5,945,526 A | 8/1999 | Lee et al. ................ 536/26.6 |
| 5,965,364 A | 10/1999 | Benner ..................... 435/6 |
| 5,976,567 A | 11/1999 | Wheeler et al. ........... 424/450 |
| 5,998,203 A * | 12/1999 | Matulic-Adamic et al. .. 435/325 |
| 6,001,983 A | 12/1999 | Benner ................... 536/23.1 |
| 6,004,755 A | 12/1999 | Wang ......................... 435/6 |
| 6,008,379 A | 12/1999 | Benson et al. ........... 549/224 |
| 6,020,481 A | 2/2000 | Benson et al. .......... 536/26.6 |
| 6,037,129 A | 3/2000 | Cole et al. ................... 435/6 |
| 6,040,138 A | 3/2000 | Lockhart et al. ............ 435/6 |
| 6,051,719 A | 4/2000 | Benson et al. ........... 548/416 |
| 6,057,105 A | 5/2000 | Hoon et al. ................. 435/6 |
| 6,084,102 A | 7/2000 | Kutyavin et al. .......... 548/100 |
| 6,096,314 A | 8/2000 | Cohen et al. ............ 424/185.1 |
| 6,103,476 A | 8/2000 | Tyagi et al. ................ 435/6 |
| 6,107,094 A | 8/2000 | Crooke ..................... 435/455 |
| 6,111,095 A | 8/2000 | Benseler et al. ......... 536/25.3 |
| 6,132,997 A | 10/2000 | Shannon ................. 435/91.21 |
| 6,140,054 A | 10/2000 | Wittwer et al. ............. 435/6 |
| 6,140,500 A | 10/2000 | Yan et al. ................... 544/99 |
| 6,150,097 A | 11/2000 | Tyagi et al. ................ 435/6 |
| 6,153,737 A | 11/2000 | Manoharan et al. ...... 536/22.1 |
| 6,174,670 B1 | 1/2001 | Wittwer et al. ............. 435/6 |
| 6,184,037 B1 | 2/2001 | Rolland et al. ........... 435/455 |

(Continued)

FOREIGN PATENT DOCUMENTS
EP 0416817 * 3/1991
(Continued)

OTHER PUBLICATIONS

"Human miRNA targets," for "mmu-miR-126-3p" Apr. 2005 version, accessed and retrieved from miRanda webserver at www.microrna.org and http://cbio.mskcc.org/cgi-bin/mirnaviewer, on Dec. 31, 2009. Page 1 of the 23 print-out pages included.

Aiello et al., "Suppression of retinal neovascularization in vivo by inhibition of vascular endothelial growth factor (VEGF) using soluble VEGF-receptor chimeric proteins," Proc. Natl. Acad. Sci. USA. 92(23):10457-10461, 1995.

Bedell et al., "Amplification of human papillomavirus genomes in vitro is dependent on epithelial differentiation," J Virol., 65(5):2254-60, 1991.

Bommer et al., "p53-mediated activation of miRNA34 candidate tumor-suppressor genes," Current Biology, 17:1298-1307, mailed 2007.

(Continued)

Primary Examiner — Brian Whiteman
(74) Attorney, Agent, or Firm — Fulbright & Jaworski L.L.P.

(57) ABSTRACT

The present invention concerns methods and compositions for identifying genes or genetic pathways modulated by miR-124, using miR-124 to modulate a gene or gene pathway, using this profile in assessing the condition of a patient and/or treating the patient with an appropriate miRNA.

11 Claims, 12 Drawing Sheets

U.S. PATENT DOCUMENTS

| | | |
|---|---|---|
| 6,191,278 B1 | 2/2001 | Lee et al. .................. 546/41 |
| 6,232,066 B1 | 5/2001 | Felder et al. ................... 435/6 |
| 6,238,869 B1 | 5/2001 | Kris et al. ..................... 435/6 |
| 6,287,792 B1 | 9/2001 | Pardridge et al. ............ 435/7.5 |
| 6,344,316 B1 | 2/2002 | Lockhart et al. ................ 435/6 |
| 6,355,421 B1 | 3/2002 | Coull et al. .................... 435/6 |
| 6,383,752 B1 | 5/2002 | Agrawal et al. ................ 435/6 |
| 6,418,382 B2 | 7/2002 | Rothberg et al. .............. 702/20 |
| 6,435,245 B1 | 8/2002 | Sette et al. ................... 156/745 |
| 6,458,382 B1 | 10/2002 | Herweijer et al. ............ 424/450 |
| 6,458,533 B1 | 10/2002 | Felder et al. .................... 435/6 |
| 6,476,205 B1 | 11/2002 | Buhr .......................... 536/23.1 |
| 6,485,901 B1 | 11/2002 | Gildea et al. ................... 435/5 |
| 6,506,559 B1 | 1/2003 | Driver et al. ................... 435/6 |
| 6,511,832 B1 | 1/2003 | Guarino et al. .............. 435/91.1 |
| 6,548,250 B1 | 4/2003 | Sorge |
| 6,573,048 B1 | 6/2003 | VanAtta et al. ................. 435/6 |
| 6,573,099 B2 | 6/2003 | Graham ....................... 435/455 |
| 6,586,218 B2 | 7/2003 | Milburn et al. ............... 435/195 |
| 6,586,219 B2 | 7/2003 | Milburn et al. ............... 435/195 |
| 6,589,743 B2 | 7/2003 | Sorge .............................. 435/6 |
| 6,590,091 B2 | 7/2003 | Albagli et al. .............. 536/24.3 |
| 6,593,091 B2 | 7/2003 | Keys et al. ..................... 435/6 |
| 6,596,490 B2 | 7/2003 | Dattagupta ..................... 435/6 |
| 6,706,480 B1 | 3/2004 | Armour .......................... 435/6 |
| 6,720,138 B2 * | 4/2004 | Sharma et al. ................. 435/6 |
| 6,723,509 B2 * | 4/2004 | Ach ............................... 435/6 |
| 6,730,477 B1 | 5/2004 | Sun et al. ....................... 435/6 |
| 6,787,335 B2 | 9/2004 | Salceda et al. .............. 435/69.1 |
| 6,797,471 B2 | 9/2004 | Katz et al. ...................... 435/6 |
| 6,815,432 B2 | 11/2004 | Wheeler et al. ................ 514/44 |
| 6,858,225 B2 | 2/2005 | Semple et al. ............... 424/450 |
| 6,964,847 B1 * | 11/2005 | Englert ............................ 435/6 |
| 6,967,016 B2 | 11/2005 | Van Gemen et al. ........... 424/9.2 |
| 6,998,268 B2 | 2/2006 | Terada et al. ................. 435/455 |
| 7,001,724 B1 * | 2/2006 | Greenfield ...................... 435/6 |
| 7,005,261 B1 * | 2/2006 | Lloyd et al. .................... 435/6 |
| 7,014,838 B2 | 3/2006 | Mueller et al. .............. 424/1.69 |
| 7,015,047 B2 | 3/2006 | Huang et al. ................. 436/526 |
| 7,056,704 B2 | 6/2006 | Tuschl et al. ................. 435/91.1 |
| 7,078,180 B2 | 7/2006 | Genetta ....................... 435/7.23 |
| 7,078,196 B2 | 7/2006 | Tuschl et al. ................. 435/91.1 |
| 7,109,167 B2 | 9/2006 | Von Wronski et al. .......... 514/12 |
| 7,141,372 B2 * | 11/2006 | Spivack et al. .................. 435/6 |
| 7,171,311 B2 * | 1/2007 | Dai et al. ....................... 702/219 |
| 7,192,586 B2 | 3/2007 | Bander ....................... 424/155.1 |
| 7,205,105 B2 * | 4/2007 | Afonina et al. ................. 435/6 |
| 7,232,806 B2 * | 6/2007 | Tuschl et al. .................... 514/44 |
| 7,282,564 B2 * | 10/2007 | Mello et al. ................... 530/350 |
| 7,297,480 B2 | 11/2007 | Vogt ............................... 435/6 |
| 7,306,906 B2 * | 12/2007 | Maruyama et al. .............. 435/6 |
| 7,307,067 B2 | 12/2007 | Sarnow et al. .................. 514/44 |
| 7,354,725 B2 * | 4/2008 | Muraca ......................... 435/7.1 |
| 7,365,058 B2 | 4/2008 | Stoffel et al. .................... 514/44 |
| 7,368,098 B2 * | 5/2008 | Mueller et al. .............. 424/1.49 |
| 7,390,792 B2 | 6/2008 | Srivastava et al. .............. 514/44 |
| 7,402,389 B2 * | 7/2008 | Mousses et al. ................. 435/6 |
| 7,452,987 B2 | 11/2008 | Giese et al. ................. 536/24.5 |
| 7,459,547 B2 | 12/2008 | Zamore et al. ............. 536/24.5 |
| 7,473,525 B2 | 1/2009 | Kreutzer et al. ................. 435/6 |
| 7,495,073 B2 * | 2/2009 | Hsu et al. ..................... 530/350 |
| 7,582,744 B2 | 9/2009 | Manoharan et al. ......... 536/24.5 |
| 7,592,441 B2 | 9/2009 | Bentwich et al. ............ 536/24.5 |
| 7,642,348 B2 | 1/2010 | Bentwich et al. ............ 536/24.5 |
| 7,655,785 B1 | 2/2010 | Bentwich .................... 536/24.1 |
| 7,683,036 B2 * | 3/2010 | Esau et al. ...................... 514/44 |
| 7,723,510 B1 * | 5/2010 | Tuschl et al. ................ 536/24.5 |
| 2002/0006630 A1 | 1/2002 | Sirbasku ......................... 514/1 |
| 2002/0037540 A1 | 3/2002 | Ali et al. ...................... 424/1.49 |
| 2002/0065396 A1 | 5/2002 | Yang et al. ................... 424/1.49 |
| 2002/0065406 A1 | 5/2002 | Meyers ........................... 435/6 |
| 2002/0068307 A1 | 6/2002 | Pluta et al. ................... 435/7.23 |
| 2002/0086356 A1 | 7/2002 | Tuschl et al. ................ 435/69.1 |
| 2002/0094546 A1 | 7/2002 | Shimkets et al. ............ 435/69.4 |
| 2002/0119156 A1 | 8/2002 | Chen et al. ................. 424/155.1 |
| 2002/0165189 A1 | 11/2002 | Crooke ........................... 514/44 |
| 2003/0009295 A1 | 1/2003 | Markowitz et al. ............ 702/20 |
| 2003/0027783 A1 | 2/2003 | Zernicka-Goetz et al. ..... 514/44 |
| 2003/0031678 A1 | 2/2003 | Ali et al. ..................... 424/185.1 |
| 2003/0033614 A1 | 2/2003 | French et al. ...................... 800/3 |
| 2003/0084471 A1 | 5/2003 | Beach et al. ................ 800/278 |
| 2003/0099976 A1 | 5/2003 | Chang .............................. 435/6 |
| 2003/0108923 A1 | 6/2003 | Tuschl et al. .................... 435/6 |
| 2003/0124114 A1 | 7/2003 | McIntire et al. ............ 424/94.63 |
| 2003/0157030 A1 | 8/2003 | Davis et al. .................... 424/46 |
| 2003/0170623 A1 | 9/2003 | Chen et al. ...................... 435/6 |
| 2003/0175768 A1 | 9/2003 | Carson et al. ................... 435/6 |
| 2003/0180298 A1 | 9/2003 | Old et al. .................... 424/144.1 |
| 2003/0204322 A1 | 10/2003 | Loehrlein et al. ............... 702/20 |
| 2003/0215842 A1 | 11/2003 | Sledziewski et al. ............ 435/6 |
| 2004/0001841 A1 | 1/2004 | Nagavarapu et al. ....... 424/178.1 |
| 2004/0010001 A1 | 1/2004 | Au et al. ........................ 514/283 |
| 2004/0029121 A1 | 2/2004 | Cottrell et al. ................... 435/6 |
| 2004/0029128 A1 | 2/2004 | Cottrell et al. ................... 435/6 |
| 2004/0053411 A1 | 3/2004 | Cullen et al. .................... 514/44 |
| 2004/0058373 A1 | 3/2004 | Winkler et al. .............. 435/91.2 |
| 2004/0063197 A1 | 4/2004 | Tilles et al. ................. 435/287.2 |
| 2004/0063654 A1 | 4/2004 | Davis et al. ..................... 514/44 |
| 2004/0072164 A1 | 4/2004 | Maruyama et al. .............. 435/6 |
| 2004/0086504 A1 | 5/2004 | Sampath et al. ............ 424/143.1 |
| 2004/0110191 A1 | 6/2004 | Winkler et al. .................. 435/6 |
| 2004/0114800 A1 | 6/2004 | Ponomarev et al. ........... 382/173 |
| 2004/0115630 A1 | 6/2004 | Olek et al. ....................... 435/6 |
| 2004/0115671 A1 | 6/2004 | Zlokovic et al. ................. 435/6 |
| 2004/0147027 A1 | 7/2004 | Troy et al. .................... 435/458 |
| 2004/0152112 A1 | 8/2004 | Croce et al. ..................... 435/6 |
| 2004/0166511 A1 | 8/2004 | Clasina Timmermans et al. ............................... 435/6 |
| 2004/0175732 A1 | 9/2004 | Rana ............................... 435/6 |
| 2004/0203145 A1 | 10/2004 | Zamore et al. ................ 435/375 |
| 2004/0214198 A1 | 10/2004 | Rana ............................... 435/6 |
| 2004/0215651 A1 | 10/2004 | Markowitz et al. ........... 707/102 |
| 2004/0224337 A1 | 11/2004 | Foehr et al. ..................... 435/6 |
| 2004/0229211 A1 | 11/2004 | Yeung ............................. 435/5 |
| 2004/0236516 A1 | 11/2004 | Brandon ........................ 702/20 |
| 2004/0243362 A1 | 12/2004 | Liebman .......................... 703/2 |
| 2004/0259247 A1 | 12/2004 | Tuschl et al. ................. 435/375 |
| 2005/0020521 A1 | 1/2005 | Rana ............................... 514/44 |
| 2005/0026278 A1 | 2/2005 | Tuschl et al. ................. 435/375 |
| 2005/0033030 A1 | 2/2005 | Lo et al. ..................... 530/388.15 |
| 2005/0037362 A1 | 2/2005 | Remacle et al. ................. 435/6 |
| 2005/0059024 A1 | 3/2005 | Conrad ........................... 435/6 |
| 2005/0065333 A1 | 3/2005 | Seth ........................... 536/23.5 |
| 2005/0074788 A1 | 4/2005 | Dahlberg et al. ................ 435/6 |
| 2005/0075492 A1 | 4/2005 | Chen et al. ................... 536/23.1 |
| 2005/0095646 A1 | 5/2005 | Sherman ....................... 435/7.1 |
| 2005/0112604 A1 | 5/2005 | Fujimoto et al. ................ 435/6 |
| 2005/0125161 A1 | 6/2005 | Cairney et al. ................. 702/20 |
| 2005/0130170 A1 | 6/2005 | Harvey et al. ................... 435/6 |
| 2005/0130172 A1 | 6/2005 | Beard et al. ..................... 435/6 |
| 2005/0142556 A1 | 6/2005 | Hoon et al. ...................... 435/6 |
| 2005/0153337 A1 | 7/2005 | Manoharan ..................... 435/6 |
| 2005/0176018 A1 | 8/2005 | Thompson et al. .............. 435/6 |
| 2005/0181382 A1 | 8/2005 | Zamore et al. ................... 435/6 |
| 2005/0182005 A1 | 8/2005 | Tuschl et al. .................... 514/44 |
| 2005/0186586 A1 | 8/2005 | Zamore et al. ................... 435/6 |
| 2005/0208493 A1 | 9/2005 | Alon ............................... 435/6 |
| 2005/0234006 A1 | 10/2005 | Tuschl et al. .................... 514/44 |
| 2005/0234007 A1 | 10/2005 | Tuschl et al. .................... 514/44 |
| 2005/0261218 A1 | 11/2005 | Esau et al. ....................... 514/44 |
| 2005/0266418 A1 | 12/2005 | Chen et al. ...................... 435/6 |
| 2005/0287539 A1 | 12/2005 | Pasloske et al. ................. 435/6 |
| 2006/0051768 A1 | 3/2006 | Hoon et al. ...................... 435/6 |
| 2006/0078894 A1 | 4/2006 | Winkler et al. .................. 435/6 |
| 2006/0088521 A1 | 4/2006 | Mahadevan ................. 424/133.1 |
| 2006/0095980 A1 | 5/2006 | Petitte et al. ................... 800/19 |
| 2006/0105350 A1 | 5/2006 | Qiao et al. ....................... 435/6 |
| 2006/0105360 A1 | 5/2006 | Croce et al. ..................... 435/6 |
| 2006/0134639 A1 | 6/2006 | Huffel et al. .................... 435/6 |
| 2006/0134661 A1 | 6/2006 | Essner ............................ 435/6 |
| 2006/0154275 A1 | 7/2006 | Sgarlato et al. .................. 435/6 |
| 2006/0165659 A1 | 7/2006 | Croce et al. .................. 424/93.2 |
| 2006/0183128 A1 | 8/2006 | Berlin et al. ..................... 435/6 |
| 2006/0185026 A1 | 8/2006 | Sacktor et al. ................ 800/12 |
| 2006/0185027 A1 | 8/2006 | Bartel et al. .................. 800/14 |
| 2006/0189557 A1 | 8/2006 | Slack et al. ..................... 514/44 |
| 2006/0195269 A1 | 8/2006 | Yeatman et al. ................ 702/20 |

| | | | | | | | |
|---|---|---|---|---|---|---|---|
| 2006/0210979 | A1 | 9/2006 | Yang et al. ............... 435/6 | WO | WO 02/00169 | | 1/2002 |
| 2006/0247193 | A1 | 11/2006 | Taira et al. ................ 514/44 | WO | WO 02/64835 | | 1/2002 |
| 2006/0252057 | A1 | 11/2006 | Raponi et al. ............. 435/6 | WO | WO 02/44321 | * | 6/2002 |
| 2006/0258566 | A1 | 11/2006 | Von Wronski et al. ..... 514/7 | WO | WO 03/020931 | | 3/2003 |
| 2006/0271309 | A1 | 11/2006 | Showe et al. .............. 702/20 | WO | WO 2003/020898 | | 3/2003 |
| 2006/0292616 | A1 | 12/2006 | Neely et al. ............... 435/6 | WO | WO 2003/022421 | | 3/2003 |
| 2007/0003960 | A1 | 1/2007 | Tuschl et al. .............. 435/6 | WO | WO 2003/023058 | | 3/2003 |
| 2007/0003961 | A1 | 1/2007 | Tuschl et al. .............. 435/6 | WO | WO 2003/029459 | | 4/2003 |
| 2007/0003962 | A1 | 1/2007 | Tuschl et al. .............. 435/6 | WO | WO 2003/029485 | | 4/2003 |
| 2007/0003963 | A1 | 1/2007 | Tuschl et al. .............. 435/6 | WO | WO 2003/040410 | | 5/2003 |
| 2007/0009484 | A1 | 1/2007 | Hunt et al. ................. 424/450 | WO | WO 2003/053586 | | 7/2003 |
| 2007/0025997 | A1 | 2/2007 | Nagavarapu et al. ...... 424/155.1 | WO | WO 2003/066906 | | 8/2003 |
| 2007/0031840 | A1 | 2/2007 | Klussmann et al. ....... 435/6 | WO | WO 2003/067217 | | 8/2003 |
| 2007/0031873 | A1 | 2/2007 | Wang et al. ................ 435/6 | WO | WO 2003/076928 | | 9/2003 |
| 2007/0041934 | A1 | 2/2007 | William et al. ............ 424/78.3 | WO | WO 2003/087297 | | 10/2003 |
| 2007/0048758 | A1 | 3/2007 | Lokhov et al. ............. 435/6 | WO | WO 2003/091426 | | 11/2003 |
| 2007/0050146 | A1 | 3/2007 | Bentwich et al. .......... 702/19 | WO | WO 2003/093810 | | 11/2003 |
| 2007/0054287 | A1 | 3/2007 | Bloch ........................ 435/6 | WO | WO 2003/100012 | | 12/2003 |
| 2007/0065844 | A1 | 3/2007 | Golub et al. ............... 435/6 | WO | WO 2003/100448 | | 12/2003 |
| 2007/0072204 | A1 | 3/2007 | Hannon et al. ............. 435/6 | WO | WO 2004/020085 | | 3/2004 |
| 2007/0093445 | A1 | 4/2007 | Tuschl et al. .............. 514/44 | WO | WO 2004/027093 | | 4/2004 |
| 2007/0099196 | A1 | 5/2007 | Kauppinen et al. ........ 435/6 | WO | WO 2004/029212 | * | 4/2004 |
| 2007/0161004 | A1 | 7/2007 | Brown et al. .............. 435/6 | WO | WO 2004/043387 | | 5/2004 |
| 2007/0213292 | A1 | 9/2007 | Stoffel et al. .............. 514/44 | WO | WO 2004/046324 | * | 6/2004 |
| 2007/0259827 | A1 | 11/2007 | Aronin et al. .............. 514/44 | WO | WO 2004/050125 | | 6/2004 |
| 2007/0287179 | A1 | 12/2007 | Tuschl et al. .............. 435/455 | WO | WO 2004/057017 | | 7/2004 |
| 2007/0299030 | A1 | 12/2007 | Dmitrovsky et al. ....... 514/44 | WO | WO 2004/066183 | | 8/2004 |
| 2008/0026951 | A1 | 1/2008 | Brown et al. .............. 435/6 | WO | WO 2004/074509 | * | 9/2004 |
| 2008/0050744 | A1 | 2/2008 | Brown et al. .............. 536/24.5 | WO | WO 2004/076622 | | 9/2004 |
| 2008/0076674 | A1 | 3/2008 | Litman et al. .............. 506/9 | WO | WO 2005/013901 | | 2/2005 |
| 2008/0131878 | A1 | 6/2008 | Latham et al. ............. 435/200 | WO | WO 2005/078139 | | 8/2005 |
| 2008/0132461 | A1 | 6/2008 | Tuschi et al. .............. 514/44 | WO | WO 2005/079397 | * | 9/2005 |
| 2008/0171667 | A1 | 7/2008 | Brown et al. .............. 536/24.5 | WO | WO 2005/116261 | | 12/2005 |
| 2008/0171715 | A1 | 7/2008 | Brown et al. .............. 514/44 | WO | WO 2005/118806 | | 12/2005 |
| 2008/0176766 | A1 | 7/2008 | Brown et al. .............. 435/6 | WO | WO 2006/028967 | | 3/2006 |
| 2008/0182237 | A1 | 7/2008 | Bentwich et al. .......... 435/6 | WO | WO 2006/033928 | | 3/2006 |
| 2008/0182245 | A1 | 7/2008 | Brown et al. .............. 435/6 | WO | WO 2006/101173 | | 9/2006 |
| 2008/0261908 | A1 | 10/2008 | Croce et al. ............... 514/44 | WO | WO 2006/113679 | | 10/2006 |
| 2008/0269147 | A1 | 10/2008 | Tuschl et al. .............. 514/44 | WO | WO 2006/119365 | | 11/2006 |
| 2008/0306006 | A1 | 12/2008 | Croce ........................ 514/12 | WO | WO 2006/128245 | | 12/2006 |
| 2008/0306017 | A1 | 12/2008 | Croce et al. ............... 514/44 | WO | WO 2006/135765 | | 12/2006 |
| 2008/0306018 | A1 | 12/2008 | Croce et al. ............... 514/44 | WO | WO 2006/137941 | | 12/2006 |
| 2009/0029932 | A1 | 1/2009 | Voinnet et al. ............. 514/44 | WO | WO 2007/016548 | | 2/2007 |
| 2009/0092974 | A1 | 4/2009 | Davison et al. ............ 435/91.1 | WO | WO 2007/033023 | | 3/2007 |
| 2009/0175827 | A1* | 7/2009 | Byrom et al. .............. 424/93.2 | WO | WO 2007/073737 | * | 7/2007 |
| 2009/0176723 | A1* | 7/2009 | Brown et al. .............. 514/44 | WO | WO 2007/081720 | | 7/2007 |
| 2009/0186353 | A1 | 7/2009 | Aharonov et al. .......... 435/6 | WO | WO 2007/081740 | | 7/2007 |
| 2009/0186843 | A1* | 7/2009 | Tuschl et al. .............. 514/44 | WO | WO 2007/087113 | | 8/2007 |
| 2009/0192114 | A1* | 7/2009 | Ovcharenko et al. ...... 514/44 | WO | WO 2008/014008 | * | 1/2008 |
| 2010/0087507 | A1 | 4/2010 | Ochiya et al. .............. 514/44 | WO | WO 2008/095096 | | 9/2008 |
| 2010/0144850 | A1 | 6/2010 | Croce ........................ 514/44 | WO | WO 2008/136971 | | 11/2008 |
| 2010/0203544 | A1 | 8/2010 | Croce et al. ............... 435/6 | WO | WO 2008/137867 | | 11/2008 |
| 2010/0234241 | A1 | 9/2010 | Croce et al. ............... 506/9 | | | | |
| 2010/0257618 | A1 | 10/2010 | Croce et al. ............... 800/10 | | | | |
| 2010/0286232 | A1 | 11/2010 | Schmittgen et al. ........ 514/44 | | | | |

FOREIGN PATENT DOCUMENTS

| | | | |
|---|---|---|---|
| EP | 0870842 | * | 10/1998 |
| EP | 0921195 | * | 6/1999 |
| EP | 1 627 925 | | 2/2006 |
| EP | 1352061 | | 5/2006 |
| FR | 2877350 | * | 5/2006 |
| JP | 2005-296014 | | 10/2005 |
| WO | WO 93/21329 | * | 10/1993 |
| WO | WO 97/27317 | * | 7/1997 |
| WO | WO 97/43450 | * | 11/1997 |
| WO | WO 97/45539 | * | 12/1997 |
| WO | WO 98/08973 | * | 3/1998 |
| WO | WO 99/21881 | * | 5/1999 |
| WO | WO 99/23256 | * | 5/1999 |
| WO | WO 99/36760 | * | 7/1999 |
| WO | WO 00/05409 | | 2/2000 |
| WO | WO 00/24939 | | 5/2000 |
| WO | WO 2000/44895 | | 8/2000 |
| WO | WO 00/56748 | | 9/2000 |
| WO | WO 00/66604 | | 11/2000 |
| WO | WO 00/75356 | | 12/2000 |
| WO | WO 01/68255 | | 9/2001 |
| WO | WO 01/75164 | * | 10/2001 |

OTHER PUBLICATIONS

Bonci et al., "The *miR-15a-miR-16-1* cluster controls prostate cancer by targeting multiple oncogenic activities," *Nature Medicine*, 14(11):1271-1277, 2008.

Bosch and de Sanjosé, "The epidemiology of human papillomavirus infection and cervical cancer," *Dis Markers.*, 23(4):213-27, 2007.

Brown and Regillo, "Anti-VEGF agents in the treatment of neovascular age-related macular degeneration: applying clinical trial results to the treatment of everyday patients," Am. *J Ophthalmol.*, 144(4):627-637, 2007.

Bullinger et al., "Gene expression profiling in acute myeloid leukemia," *Journal of Clinical Oncology*, 23(26):6296-6305, 2005.

Cai et al., "Human papillomavirus genotype 31 does not express detectable microRNA levels during latent or productive virus replication," *J. Virol.*, 80(21):10890-3, 2006.

Campochiaro and Hackett, "Ocular neovascularization: a valuable model system," *Oncogene*, 22(42):6537-6548, 2003.

Clifford et al., "Human papillomavirus types in invasive cervical cancer worldwide: a meta-analysis," *Br. J. Cancer*, 88(1):63-73, 2003.

Cogliano et al., "Carcinogenicity of human papillomaviruses," *Lancet Oncol.*, 6(4):204, 2005.

Costinean et al., "Pre-B cell proliferation and lymphoblastic leukemia/high-grade lymphoma in Eμ-miR155 transgenic mice," *Proc. Natl. Acad. Sci. USA*, 103(18):7024-7029, 2006.

Cox, "Epidemiology and natural history of HPV," *J. Fam. Pract.*, Suppl:3-9, 2006.

Crnogorac-Jurcevic et al., "Proteomic analysis of chronic pancreatitis and pancreatic adenocarcinoma," *Gastroenterology*, 129:1454-1463, 2005.

Cummins and Velculescu, "Implications of micro-RNA profiling for cancer diagnosis," *Oncogene*, 25(46):6220-6227, 2006.

Dews et al., "Augmentation of tumor angiogenesis by a Myc-activated microRNA cluster," *Nat. Genet.*, 38(9):1060-1065, 2006.

D'Souza et al., "Case-control study of human papillomavirus and oropharyngeal cancer," *New Engl. J. Med.*, 356:1944-1956, 2007.

European Search Report issued in European Application No. 09154092.2, mailed Aug. 12, 2009.

Fazi et al., "A minicircuitry comprised of microRNA-223 and transcription factors NFI-A and C/EBPα regulates human granulopoiesis," *Cell*, 123:819-831, 2005.

Folkman, "Successful treatment of an angiogenic disease," *N. Engl J Med* 320:1211-1212, 1989.

Griffiths-Jones et al., "miRBase: tools for microRNA genomics," *Nucl. Acids Res.*, 36 (Database Issue):D154-D158, 2008.

Han et al., "Cyclin D I expression in human prostate carcinoma cell lines and primary tumors," *The Prostate*, 35:95-101, 1998.

Harfe, "MicroRNAs in vertebrate development," *Curr. Opin. Genet. Dev.*, 15(4):410-5, 2005.

Hayashita et al., "A polycistronic microRNA cluster, *miR-17-92*, is overexpressed in human lung cancers and enhances cell proliferation," *Cancer Res.*, 65(21):9628-9632, 2005.

He et al., "A microRNA component of the p53 tumour suppressor network," *Nature*, 447(7148):1130-1134, 2007.

Hermeking, "p53 enters the microRNA world," *Cancer Cell*, 12(5):414-418, 2007.

Hornstein et al., "The microRNA *mir-196* acts upstream of Hoxb8 and Shh in limb development," *Nature*, 438:671-674, 2005.

Houbaviy et al., "Embryonic stem cell-specific micro-RNAs," *Developmental Cell*, 5:351-358, 2003.

Hummel et al., "Differentiation-induced and constitutive transcription of human papillomavirus type 31b in cell lines containing viral episomes," *J. Virol.*, 66(10):6070-80, 1992.

Ji et al., "Restoration of tumor suppressor miR-34 inhibits human p53-mutant gastric cancer tumorspheres," *BMC Cancer*, 8:266, 2008.

John et al., "Human microRNA targets," *PLOS Biology*, 2(11):1862-1879, 2004.

Jopling et al., "Modulation of hepatitis C virus RNA abundance by a liver-specific MicroRNA," *Science*, 309(5740):1577-81, 2005.

Kayed et al., "Hedgehog signaling in the normal and diseased pancreas," *Pancreas*, 32(2):119-129, 2006.

Kwak et al., "VEGF is major stimulator in model of choroidal neovascularization," *Invest. Ophthalmol. Vis. Sci.*, 41(10):3158-3164, 2000.

Lagos-Quintana et al., "Identification of tissue-specific microRNAs from mouse," *Current Biology*, 12:735-739, 2002.

Lecellier et al., "A cellular microRNA mediates antiviral defense in human cells," *Science*, 308(5721):557-60, 2005.

Lee et al., "The *C. elegans* heterochronic gene *lin-4* encodes small RNAs with antisense complementarity to *lin-14*," *Cell*, 75(5):843-854, 1993.

Lewis et al., "Conserved seed pairing, often flanked by adenosines, indicates that thousands of human genes are microRNA targets," *Cell*, 120:15-20, 2005.

Lilja et al., "Prostate-specific antigen and prostate cancer: prediction, detection and monitoring," *Nat. Rev. Cancer*, 8(4):268-278, 2008.

Lima e Silva et al., "The SDF-1/CXCR4 ligand/receptor pair is an important contributor to several types of ocular neovascularization," *FASEB J.*, 21(12):3219-3230, 2007.

Lui et al., "Patterns of known and novel small RNAs in human cervical cancer," *Cancer Res.*, 67(13):6031-6043, 2007.

Mahato et al., "Modulation of gene expression by antisense and antigene oligodeoxynucleotides and small interfering RNA," *Expert Opinion on Drug Delivery*, 2(1):3-28, 2005.

Mammalian Gene Collection (MGC) Program Team, "Generation and initial analysis of more than 15,000 full-length human and mouse cDNA sequences," *PNAS*, 99(26):16899-16903, 2002.

Martinez et al., "Human papillomavirus type 16 reduces the expression of microRNA-218 in cervical carcinoma cells," *Oncogene*, 27:2575-2582, 2008.

Mattie et al., "Optimized high-throughput microRNA expression profiling provides novel biomarker assessment of clinical prostate and breast cancer biopsies," *Mol. Cancer*, 5:24, 2006.

Michael and Oren, "The p53-Mdm2 module and the ubiquitin system," *Semin. Cancer Biol.* 13:49-58, 2003.

Miller et al., "Vascular endothelial growth factor/vascular permeability factor is temporally and spatially correlated with ocular angiogenesis in a primate mode," *Am. J. Pathol.*, 145(3):574-584, 1994.

Minakuchi et al., "Atelocollagen-mediated synthetic small interfering RNA delivery for effective gene silencing in vitro and in vivo," *Nucleic Acids Research*, 32(13):e109, 2004.

Office Action issued in Australian Application No. 2005250432, mailed Dec. 1, 2009.

Office Action issued in European Application No. 07871689.1, mailed Dec. 15, 2009.

Office Action issued in European Application No. 07871690.9, mailed Dec. 14, 2009.

Office Action issued in European Application No. 07871691.7, mailed Dec. 14, 2009.

Office Action issued in European Application No. 07871693.3, mailed Dec. 9, 2009.

Office Action issued in European Application No. 07871694.1, mailed Dec. 10, 2009.

Office Action issued in European Application No. 07871756.8, mailed Oct. 20, 2009.

Office Action issued in U.S. Appl. No. 11/141,707, mailed Jan. 6, 2010.

Office Action issued in U.S. Appl. No. 11/273,640, mailed Nov. 20, 2009.

Office Action issued in U.S. Appl. No. 11/567,082, mailed Sep. 30, 2009.

Office Action issued in U.S. Appl. No. 11/837,487, mailed Sep. 15, 2009.

Office Action issued in U.S. Appl. No. 11/837,488, mailed Feb. 19, 2010.

Office Action issued in U.S. Appl. No. 11/837,494, mailed Jan. 5, 2010.

Office Action issued in U.S. Appl. No. 11/837,495, mailed Jan. 5, 2010.

Office Action issued in U.S. Appl. No. 11/837,498, mailed Nov. 20, 2009.

Office Action issued in U.S. Appl. No. 11/857,948, mailed Nov. 3, 2009.

Office Action issued in U.S. Appl. No. 11/953,606, mailed Jan. 8, 2010.

Office Action issued in U.S. Appl. No. 11/967,663, mailed Feb. 12, 2010.

Office Action issued in U.S. Appl. No. 11/967,663, mailed Oct. 1, 2009.

Office Action issued in U.S. Appl. No. 12/112,291, mailed Nov. 16, 2009.

Office Action issued in U.S. Appl. No. 12/120,388, mailed Feb. 19, 2010.

Office Action issued in U.S. Appl. No. 12/124,394, mailed Feb. 5, 2010.

Office Action issued in U.S. Appl. No. 12/124,394, mailed Nov. 6, 2009.

Office Action issued in U.S. Appl. No. 12/125,412, mailed Feb. 16, 2010.

Office Action issued in U.S. Appl. No. 12/125,412, mailed Nov. 12, 2009.

Office Action issued in U.S. Appl. No. 12/125,675, mailed Sep. 10, 2009.

Office Action issued in U.S. Appl. No. 12/134,932, mailed Nov. 12, 2009.

Office Action issued in U.S. Appl. No. 12/167,492, mailed Feb. 12, 2010.

Ozaki et al., "Blockade of vascular endothelial cell growth factor receptor signaling is sufficient to completely prevent retinal neovascularization," *Am. J. Pathol.*, 156(2):697-707, 2000.
PCT International Preliminary Report on Patentability issued in International Application No. PCT/US2007/078952, mailed Feb. 11, 2010.
PCT International Preliminary Report on Patentability issued in International Application No. PCT/US2008/066025, mailed Dec. 23, 2009.
PCT International Search Report and Written Opinion issued in International Application No. PCT/US2009/036195, mailed Sep. 4, 2009.
PCT International Search Report and Written Opinion issued in International Application No. PCT/US2009/039935, mailed Sep. 17, 2009.
PCT International Search Report and Written Opinion issued in International Application No. PCT/US2008/066025, mailed Sep. 16, 2009.
PCT International Search Report and Written Opinion issued in International Application No. PCT/US2007/078952, mailed Jan. 26, 2010.
PCT International Search Report and Written Opinion issued in International Application No. PCT/US2009/043361, mailed Nov. 4, 2009.
PCT Invitation to Pay Additional Fees issued in International Application No. PCT/US2007/078952, mailed Sep. 22, 2009.
PCT Invitation to Pay Additional Fees issued in International Application No. PCT/US2008/087762, mailed Nov. 9, 2009.
Poliseno et al., "MicroRNAs modulate the angiogenic properties of HUVECs," *Blood* 108(9):3068-3071, 2006.
Porkka et al., "MicroRNA expression profiling in prostate cancer," *Cancer Res.*, 67(13):6130-6135, 2007.
Rader et al., "In vitro differentiation of epithelial cells from cervical neoplasias resembles in vivo lesions," *Oncogene*, 5(4):571-6, 1990.
Rosenfeld et al., "Ranibizumab: Phase III clinical trial results," *Ophthalmol. Clin. North Am.* 19(3):361-372, 2006.
Saiz et al., "MicroRNA expression profiling in acute myelogenous leukemia," *Blood, ASH Annual Meeting Abstracts*, 104:320a, Abstract No. 1131, Poster board No. session 285-I, 2004.
Scaria et al., "Host-virus genome interactions: macro roles for microRNAs," *Cell Microbiol.*, (12):2784-94 2007.
Scaria et al., "Host-virus interaction: a new role for microRNAs," *Retrovirology*, 3:68, 2006.
Scherer and Rossi, "Approaches for the sequence-specific knockdown of mRNA," *Nat. Biotechnol.*, 21(12):1457-1465, 2003.
Scott et al., "BCL2 antisense reduces prostate cancer cell survival following irradiation," *Cancer Biotherapy & Radiopharmaceuticals*, 17(6):647-656, 2002.
Segal et al., "A module map showing conditional activity of expression modules in cancer," *Nature Genetics*, 36(10):1090-1098, 2004.
Sellner et al., "Reverse transcriptase inhibits Taq polymerase activity," *Nucleic Acids Research*, 20(7):1487-1490, 1992.
Sevignani et al., "Mammalian microRNAs: a small world for fine-tuning gene expression," *Mamm. Genome*, 17(3):189-202, 2006.
Shen et al., "Oxidative damage in age-related macular degeneration," *Histol. Histopathol.* 22(12):1301-1308, 2007.
Si et al., "miR-21-mediated tumor growth," *Oncogene*, 26(19):2799-2803, 2007.
Smith et al., "Human papillomavirus type distribution in invasive cervical cancer and high-grade cervical lesions: a meta-analysis update," *Int. J. Cancer*, 121(3):621-32, 2007.
Smith et al., "Oxygen-induced retinopathy in the mouse," *Invest. Ophthalmol. Vis. Sci.* 35(1):101-111, 1994.
Sun et al., "Development of a micro-array to detect human and mouse microRNAs and characterization of expression in human organs," *Nucleic Acids Research*, 32(22):e188, 2004.
Sun et al., "Downregulation of CCND1 and CDK6 by miR-34a induces cell cycle arrest," *FEBS Letters*, 582:1564-1568, 2008.
Szafranska et al., "MicroRNA expression alterations are linked to tumorigenesis and non-neoplastic processes in pancreatic ductal adenocarcinoma," *Oncogene*, 26:4442-4452, 2007.

Takei et al., "A small interfering RNA targeting vascular endothelial growth factor as cancer therapeutics," *Cancer Research*, 64:3365-3370, 2004.
Tricoli et al., "MicroRNA: potential for cancer detection, diagnosis, and prognosis," *Cancer Res.*, 67(10):4553-4555, 2007.
Voorhoeve et al., "A genetic screen implicates miRNA-372 and miRNA-373 as oncogenes in testicular germ cell tumors," *Cell*, 124(6):1169-1181, 2006.
Walboomers et al., "Human papillomavirus is a necessary cause of invasive cervical cancer worldwide," *J. Pathol.*, 189(1):12-9, 1999.
White et al., "Treatment of pulmonary hemangiomatosis with recombinant interferon alfa-2a," *N Engl J Med* 320:1197-1200, 1989.
Wiemer, "The role of microRNAs in cancer: no small matter," *Eur. J. Cancer*, 43(10):1529-44, 2007.
Wilson and Laimins, "Differentiation of HPV-containing cells using organotypic "raft" culture or methylcellulose," *Methods Mol. Med.*, 119:157-69, 2005.
Yamato et al., "New highly potent and specific E6 and E7 siRNAs for treatment of HPV16 positive cervical cancer," *Cancer Gene Therapy*, 15:140-153, 2008.
Yang et al., "Dicer is required for embryonic angiogenesis during mouse development," *J. Biol. Chem.* 280(10):9330-9335, 2005.
Zhang et al., "microRNAs as oncogenes and tumor suppressors," *Dev. Biol.*, 302(1):1-12, 2007.
Aaboe et al., "Vitronectin in human breast carcinomas," *Biochem. Biophys. Acta.*, 1638 (1): 72-82, 2003.
Aagaard et al., "An inflammatory role for the mammalian carboxypeptidase inhibitor latexin: relationship to cystatins and the tumor suppressor TIG1," *Structure (Camb)*, 13: 309-317, 2005.
Abuharbeid et al., "The fibroblast growth factor-binding protein FGF-BP," *Int. J. Biochem. Cell Biol.*, 38(9):1463-1468, 2006.
Adams et al., "Infrequent mutation of TRAIL receptor 2 (TRAIL-R2/DR5) in transitional cell carcinoma of the bladder with 8p21 loss of heterozygosity," *Cancer Lett.* 220 (2): 137-144, 2005.
Akao et al., "let-7 microRNA functions as a potential growth suppressor in human colon cancer cells," *Biol. Pharm. Bull*, 29(5):903-906, 2006.
Akao et al., "MicroRNAs 143 and 145 are possible common onco-microRNAs in human cancers," *Oncology Reports*, 16:845-850, 2006.
Akiba et al., "Expression and function of interleukin-8 in human hepatocellular carcinoma," *Int. J. Oncol.*, 18 (2): 257-264, 2001.
Alevizos et al., "Oral cancer in vivo gene expression profiling assisted by laser capture microdissection and microarray analysis," *Oncogene*, 20(43):6196-6204, 2001.
Allawi et al., "Quantitation of MicroRNAs using a modified Invader assay," *RNA*, 10:1153-1161, 2004.
Altucci and Gronemeyer, "The promise of retinoids to fight against cancer," *Nat. Rev. Cancer*, 1:181-193, 2001.
Altucci and Gronemeyer, "Retinoids and TRAIL: two cooperating actors to fight against cancer," *Vitam. Horm.*, 67:319-345, 2004.
Ambion, Inc., "mMessage mMachine®," High Yield Capped RNA Transcription Kit, Catalog #1340, 1344, 1348; pp. 1-8.
Ambion, Inc., "mMessage mMachine®," Instruction Manual, Catalog #1340, 1344, 1348; pp. 1-31.
Ambros et al., "A uniform system for microRNA annotation," *RNA*, 9(3):277-279, 2003.
Ambros, "microRNAs: tiny regulators with great potential," *Cell*, 107(7):823-826, 2001.
Anatharaman and Aravind, "Evolutionary history, structural features and biochemical diversity of the N1pC/P60 superfamily of enzymes," *Genome Biol.*, 4: R11, 2003.
Ando et al., "Polo-like kinase 1 (Plk1) inhibits p53 function by physical interaction and phosphorylation," *J. Biol. Chem.*, 279 (24): 25549-25561, 2004.
Armour et al., "Measurement of locus copy number By hybridisation with amplifiable probes," *Nucleic Acids Research*, 28(2):605-609, 2000.
Association of Directors of Anatomic and Surgical Pathology, "Recommendations for the reporting of resected large intestinal carcinomas. Association of directors of anatomic and surgical pathology," *Am. J. Clin. Pathol.*, 106 (1): 12-15, 1996.

Astler and Coller, "The prognostic significance of direct extension of carcinoma of the colon and rectum," *Ann. Surg.*, 139: 846-852, 1954.

Asuragen, Inc. website, "Asuragen's DiscovArray miRNA Expression Profiling Service," located at http://www.asuragen.com/Services/solutions/discovarray.aspx, printed Mar. 6, 2009.

Baba et al., "Involvement of deregulated epiregulin expression in tumorigenesis in vivo through activated Ki-Ras signaling pathway in human colon cancer cells," *Cancer Res*, 60(24):6886-6889, 2000.

Bae et al., "MCL-1S, a splicing variant of the antiapoptotic BCL-2 family member MCL-1, encodes a proapoptotic protein possessing only the BH3 domain," *J. Biol. Chem.*, 275(33):25255-61, 2000.

Bagga et al., "Regulation by let-7 and lin-4 miRNAs results in target mRNA degradation," *Cell*, 122(4):553-563, 2005.

Bandres et al., "Identification by Real-time PCR of 13 mature microRNAs differentially expressed in colorectal cancer and non-tumoral tissues," *Mol. Cancer*, 5:29, 2006.

Bangoura et al., "Expression of HIF-2alpha/EPAS1 in hepatocellular carcinoma," *World J. Gastroenterol.*, 10(4):525-530, 2004.

Bartlett and Davis, "Effect of siRNA nuclease stability on the in vitro and in vivo kinetics of siRNA-mediated gene silencing," *Biotechnol. Bioeng.*, 97(4): 909-921, 2007.

Bartlett et al., "Impact of tumor-specific targeting on the biodistribution and efficacy of siRNA nanoparticles measured by multimodality in vivo imaging," 104(39):15549-15554, 2007.

Bartlett et al., "Insights into the kinetics of siRNA-mediated gene silencing from live-cell and live-animal bioluminescent imaging," *Nucleic Acids Research*, 34(1):322-333, 2006.

Barton et al., "Angiogenic protein expression in advanced epithelial ovarian cancer," *Clin. Cancer Res.*, 3 (9): 1579-1586, 1997.

Bellovin et al., "Reciprocal regulation of RhoA and RhoC characterizes the EMT and identifies RhoC as a prognostic marker of colon carcinoma," *Oncogene*, 25 (52): 6959-6967, 2006.

Bendtsen et al., "Feature-based prediction of non-classical and leaderless protein secretion," *Protein Eng. Des. Sel.*, 17: 349-356, 2004.

Bentwich et al., "Identification of hundreds of conserved and nonconserved human microRNAs," *Nat Genet.*, 37(7):766-770, 2005.

Berezikov et al, *Cell*, "Phylogenetic shadowing and computational identification of human microRNA genes," 120(1):21-24, 2005.

Billottet et al., "A selective inhibitor of the p110delta isoform of PI 3-kinase inhibits AML cell proliferation and survival and increases the cytotoxic effects of VP16," *Oncogene*, 25 (50): 6648-6659, 2006.

Birchmeier et al., "Met, metastasis, motility and more," *Nat Rev Mol Cell Biol*, 4(12):915-925, 2003.

Biswas et al., "Transforming growth factor beta receptor type II inactivation promotes the establishment and progression of colon cancer," *Cancer Res.*, 64 (14): 4687-4692, 2004.

Bitomsky etaL, "Transformation suppressor protein Pdcd4 interferes with JNK-mediated phosphorylation of c-Jun and recruitment of the coactivator p300 by c-Jun," *Oncogene*, 23(45):7484-93, 2004.

Black et al., "Expression of cyclin D1, cyclin E, EGFR, UBE1L and K167 in paired benign and malignant lung tissues," *Lung Cancer*, 49:S289, Abstract P-650, 2005.

Blanc et al., "Wnt-5a gene expression in malignant human neuroblasts," *Cancer Lett.*, 228 (1-2): 117-123, 2005.

Boccaccio and Comoglio, "Invasive growth: a MET-driven genetic programme for cancer and stem cells," *Nat Rev Cancer*, 6(8):637-645, 2006.

Bodner-Adler et al., "Serum levels of angiogenin (ANG) in invasive cervical cancer and in cervical intraepithelial neoplasia (CIN)," *Anticancer Res.*, 21 (1B): 809-812, 2001.

Bostwick et al., "Amphiregulin expression in prostatic intraepithelial neoplasia and adenocarcinoma: a study of 93 cases," *Prostate*, 58(2):164-168, 2004.

Bottoni et al., "miR-15a and miR-16-1 Down-Regulation in Pituitary Adenomas," *J. Cell. Physiol.*, 204:280-285, 2005.

Boultwood et al., "Low expression of the putative tumour suppressor gene gravin in chronic myeloid leukaemia, myelodysplastic syndromes and acute myeloid leukaemia," *Br J Haematol*, 126(4):508-511, 2004.

Brazma and Vilo, "Gene expression data analysis," *FEBS Letters*, 480:17-24, 2000.

Brennecke et al., "Bantam encodes a developmentally regulated microRNA that controls cell proliferation and regulates the proapoptotic gene hid in *Drosophila*," *Cell*, 113:25-36, 2003.

Bustin et al., "Real-time reverse transcription PCR (qRT-PCR) and its potential use in clinical diagnosis," *Clinical Science*, 109:365-379, 2005.

Byrd et al., "Pretreatment cytogenetic abnormalities are predictive of induction success, cumulative incidence of relapse, and overall survival in adult patients with de novo acute myeloid leukemia: results from Cancer and Leukemia Group B (CALGB 8461)" *Blood*, 100:4325-4336, 2002.

Calin and Croce, "Genomics of chronic lymphocytic leukemia microRNAs as new players with clinical significance," *Seminars in Oncology*, 33(2):167-173, 2006.

Calin and Croce, "MicroRNA signatures in human cancers," *Nat Rev Cancer*, 6(11):857-866, 2006.

Calin and Croce, "MicroRNA-cancer connection: the beginning of a new tale," *Cancer Res.*, 66 (15):7390-7394, 2006.

Calin and Croce, "MicroRNAs and chromosomal abnormalities in cancer cells," *Oncogene*, 25 (46):6202-6210, 2006.

Calin et al., "A MicroRNA signature associated with prognosis and progression in chronic lymphocytic leukemia," *New England Journal of Medicine*, 353(17):1793-1801, 2005.

Calin et al., "Frequent deletions and down-regulation of micro-RNA genes miR15 and miR16 at 13q14 in chronic lymphocytic leukemia," *Proc. Natl. Acad. Sci. USA*, 99:15524-15529, 2002.

Carrano et al., "SKP2 is required for ubiquitin-mediated degradation of the CDK inhibitor p27," *Nat. Cell. Biol.*, 1 (4): 193-199, 1999.

Carreiras et al., "Expression and localization of alpha v integrins and their ligand vitronectin in normal ovarian epithelium and in ovarian carcinoma," *Gynecol. Oncol.*, 62 (2): 260-267, 1996.

Carreiras et al., "Human ovarian adenocarcinoma cells synthesize vitronectin and use It to organize their adhesion," *Gynecol. Oncol.*, 72 (3): 312-322, 1999.

Carrington and Ambros, "Role of MicroRNAs in Plant and Animal Development," *Science*; 301:336-338; 2003.

Casanova et al., "The class II tumor-suppressor gene RARRES3 is expressed in B cell lymphocytic leukemias and down-regulated with disease progression," *Leukemia*, 15 (10): 1521-1526, 2001.

Castillo et al., "Amphiregulin contributes to the transformed phenotype of human hepatocellular carcinoma cells," *Cancer Res.*, 66(12):6129-6138, 2006.

Caudy et al., "Fragile X-related protein and VIG associate with the RNA interference machinery," *Genes & Development*, 16:2491-2496; 2002.

Chan et al., "Downregulation of ID4 by promoter hypermethylation in gastric adenocarcinoma," *Oncogene*, 22 (44): 6946-6953, 2003.

Chan et al., "MicroRNA-21 is an antiapoptotic factor in human glioblastoma cells," *Cancer Res.*, 65(14):6029-6033, 2005.

Chandler et al., "Prevalent expression of fibroblast growth factor (FGF) receptors and FGF2 in human tumor cell lines," *Int. J. Cancer*, 81(3):451-458, 1999.

Chang etaL, "Elevated circulating level of osteopontin is associated with advanced disease state of non-small cell lung cancer," *Lung Cancer*, 57(3):373-380, 2007.

Chang et al., "MicroRNAs act sequentially and asymmetrically to control chemosensory laterality in the nematode," *Nature*, 430(7001):785-789, 2004.

Chang et al., "Transactivation of miR-34a by p53 broadly influences gene expression and promotes apoptosis," *Mol. Cell.*, 26(5):745-752, 2007.

Chen et al., "Identification of trophinin as an enhancer for cell invasion and a prognostic factor for early stage lung cancer," *European Journal of Cancer*, 43(4):782-790, 2007.

Chen et al., "Loss of PDCD4 expression in human lung cancer correlates with tumour progression and prognosis," *J. Pathol.*, 200(5):640-646, 2003.

Chen et al., "MicroRNAs modulate hematopoietic lineage differentiation," *Science*, 303(5654):83-86, 2004.

Chen et al., "Real-time quanitfication of microRNAs by stem-loop RT-PCR," *Nucleic Acids Research*, 33(20): e179 (13 printed pages), 2005.

Cheng et al., "Antisense inhibition of human miRNAs and indications for an involvement of miRNA in cell growth and apoptosis," *Nucleic Acids Res.*, 33(4):1290-1297, 2005.

Choi et al., "AKAP12/Gravin is inactivated by epigenetic mechanism in human gastric carcinoma and shows growth suppressor activity," *Oncogene*, 23(42):7095-7103, 2004.

Ciafre et al., "Extensive modulation of a set of microRNAs in primary glioblastoma," *Biochem. Biophys. Res. Commun.*, 334(4):1351-1358, 2005.

Cimmino et al., "miR-15 and miR-16 induce apoptosis by targeting BCL2," *Proceedings of the National Academy of Sciences of the USA*, 102(39):13944-13949, 2005.

Ciocca et al., "Heat shock portein hsp70 in patients with axillary lymph node-negative breast cancer: Prognostic implications," *Journal of the National Cancer Institute*, 85(7):570-574, 1993.

Claudio et al., "Expression of cell-cycle-regulated proteins pRb2/p130, p107, p27(kip1), p53, mdm-2, and Ki-67 (MIB-1) in prostatic gland adenocarcinoma," *Clin Cancer Res*, 8(6):1808-1815, 2002.

Cohen et al., "Expression of a down-regulated target, SSeCKS, reverses v-Jun-induced transformation of 10T1/2 murine fibroblasts," *Oncogene*, 20(2):141-146, 2001.

Coleman et al., "Superior 5' homogeneity of RNA from ATP-initiated transcription under T7 Φ2.5 promoter," *Nucleic Acids Research*, 32(1):e14, 2004.

Cooper et al., "Molecular cloning of a new transforming gene from a chemically transformed human cell line," *Nature*, 311(5981):29-33, 1984.

Croci et al., "Inhibition of connective tissue growth factor (CTGF/CCN2) expression decreases the survival and myogenic differentiation of human rhabdomyosarcoma cells," *Cancer Res.*, 64(5):1730-1736, 2004.

Cross et al., "25-Hydroxyvitamin D (3)-lalpha-hydroxylase and vitamin D receptor gene expression in human colonic mucosa is elevated during early cancerogenesis," *Steroids*, 66: 287-292, 2001.

Cully et al., "Transforming acidic coiled coil 1 promotes transformation and mammary tumorigenesis," *Cancer Res.*, 65(22):10363-10370, 2005.

Danilkovitch-Miagkova and Zbar, "Dysregulation of Met receptor tyrosine kinase activity in invasive tumors," *J Clin Invest*, 109(7):863-867, 2002.

D'Antonio et al., "Transforming growth factor alpha, amphiregulin and cripto-1 are frequently expressed in advanced human ovarian carcinomas," *Int. J. Oncol.*, 21(5):941-948, 2002.

Database EMBL, "Human DNA related to regulating mammalian cells using miRNAs Seq 471," EBI Database Accession No. ADR83569, Dec. 2, 2004.

Davalos et al., "High EPHB2 mutation rate in gastric but not endometrial tumors with microsatellite instability," *Oncogene*, 26 (2): 308-311, 2006.

Davis et al., "Modeling of repeated-batch transcription for production of RNA," *Journal of Biotechnology*, 71:25-37, 1999.

De Candia et al., "Id4 messenger RNA and estrogen receptor expression: inverse correlation in human normal breast epithelium and carcinoma," *Hum. Pathol.*, 37 (8): 1032-1041, 2006.

De Nigris et al., "Induction of ETS-1 and ETS-2 transcription factors is required for thyroid cell transformation," *Cancer Res.*, 61 (5): 2267-2275, 2001.

Dean et al., "The human met oncogene is related to the tyrosine kinase oncogenes," *Nature*, 318(6044):385-388, 1985.

Denli and Hannon, "RNAi: an ever-growing puzzle," *Trends Biochem. Sci.*, 28:196, 2003.

Devine et al., "Serum markers CASA, CEA, CYFRA, TPS, and NSE in lung cancer," *Lung Cancer*, Abstract, 11:37, 1994.

Diederichs and Haber, "Sequence variations of microRNAs in human cancer: Alterations in predicted secondary structure do not affect processing," *Cancer Res.*, 66(12):6097-6104, 2006.

DiSepio et al., "Identification and characterization of a retinoid-induced class II tumor suppressor/growth regulatory gene," *Proc. Natl. Acad. Sci. USA*, 95: 14811-14815, 1998.

Doench and Sharp, "Specificity of microRNA target selection in translational repression," *Genes Dev*, 18(5):504-11, 2004.

Doench et al., "siRNAs can function as miRNAs," *Genes & Dev*, 17:438-442, 2003.

Dong et al., "Telomerase: regulation, function and transformation," *Crit Rev Oncol Hematol.* 54(2):85-93, 2005.

Donnellan and Chetty, "Cyclin D1 and human neoplasia," *Mol Pathol*, 51(1):1-7, 1998.

Dostie et al., "Numerous microRNPs in neuronal cells containing novel microRNAs," *RNA*, 9:180-186; 2003.

Duvic et al., "Expression of a retinoid-inducible tumor suppressor, tazarotene-inducible gene-3 is decreased in psoriasis and skin cancer," *Clin. Cancer Res.*, 6 (8): 3249-3259, 2000.

Duvic et al., "Tazarotene-induced gene 3 is suppressed in basal cell carcinomas and reversed in vivo by tazarotene application," *J. Invest. Dermatol.*, 121: 902-909, 2003.

Ebert et al., "Induction and expression of amphiregulin in human pancreatic cancer," *Cancer Res.*, 54(15):3959-3962, 1994.

Eferl et al., "Liver tumor development. c-Jun antagonizes the proapoptotic activity of p53," *Cell*, 112 (2): 181-192, 2003.

Einama at al., "High-level Skp2 expression in pancreatic ductal adenocarcinoma: correlation with the extent of lymph node metastasis, higher histological grade, and poorer patient outcome," *Pancreas*, 32(4):376-381, 2006.

Esau et al., "MicroRNA-143 regulates adipocyte differentiation," *Journal of Biological Chemistry*, 279(50):52361-52365, 2004.

Esquela-Kerscher and Slack, "Oncomirs—microRNAs with a role in cancer," *Nat Rev Cancer*, 6(4):259-269, 2006.

Ezzat et al., "Dual inhibition of RET and FGFR4 restrains medullary thyroid cancer cell growth," *Clin. Cancer Res.*, 11 (3): 1336-1341, 2005.

Faried et al., "RhoA and RhoC proteins promote both cell proliferation and cell invasion of human oesophageal squamous cell carcinoma cell lines in vitro and in vivo," *Eur. J. Cancer*, 42 (10): 1455-1465, 2006.

Fay et al., "Analysis of CUL-5 expression in breast epithelial cells, breast cancer cell lines, normal tissues and tumor tissues," *Mol. Cancer*, 2:40, 2003.

Feldman and Feldman, "The development of androgen-independent prostate cancer," *Nat. Rev. Cancer*, 1(1):34-45, 2001.

Fernandez et al., "The matrix metalloproteinase-9/neutrophil gelatinase-associated lipocalin complex plays a role in breast tumor growth and is present in the urine of breast cancer patients," *Clin. Cancer Res.*, 11(15):5390-5395, 2005.

Fesik, "Promoting apoptosis as a strategy for cancer drug discovery," *Nat Rev Cancer*, 5(11):876-885, 2005.

Firth and Baxter, "Cellular actions of the insulin-like growth factor binding proteins," *Endocrin. Rev.*, 23 (6): 824-854, 2002.

Fontana et al al., "MicroRNA's 17-5p-20a-106a control monocytopeiesis through AML1 targeting and M-CSF receptor upregulation," *Nature Cell Biology*, 9(7):775-787, 2007.

Freelove and Walling, "Pancreatic cancer: diagnosis and management," *Am. Fam. Physician*, 73(3):485-492, 2006.

Fujiwara et al., "Isolation of a candidate tumor suppressor gene on chromosome 8p21.3-p22 that is homologous to an extracellular domain of the PDGF receptor beta gene," *Oncogene*, 10(5):891-895, 1995.

Galardi et al., "miR-221 and miR-222 expression affects the proliferation potential of human prostate carcinoma cell lines by targeting p27Kip1," *J. Biol. Chem.*, 282(32):23716-23724, 2007.

Gao et al., "Frequent loss of PDCD4 expression in human glioma: possible role in the tumorigenesis of glioma," *Oncol. Rep.*, 17(1):123-128, 2007.

Garzon et al., "MicroRNA fingerprints during human megakaryocytopoiesis," *Proc. Natl. Acad. Sci. USA*, 103(13):5078-5083, 2006.

Garzon et al., "MicroRNA signatures associated with cytogenetics and outcome in acute myeloid leukemia. Session Type: Oral Session," *Blood*, 108(11): 49A, Abstract #151, 2006.

Giannakakis et al., "miRNA genetic alterations in human cacners," *Expert opinion on biological therapy*, 7(9):1375-1386, 2007.

Goke et al., "Programmed cell death protein 4 suppresses CDK1/cdc2 via induction of p21(Waf1/Cip1)," *Am. J. Physiol. Cell Physiol.*, 287(6):C1541-6, 2004.

Grandori et al., "The Myc/Max/Mad network and the transcriptional control of cell behavior," *Annu. Rev. Cell. Dev. Biol.*, 16: 653-699, 2000.

Grenier et al., "Cyfra 21-1, a new marker for lung cancer," *Nucl. Med. Biol.*, 21(3):471-476, 1994.

Griffiths-Jones et al., "miRBase: microRNA sequences, targets and gene nomenclature," *Nucleic Acids Res.*, 34 (Database Issue):D140-D144, 2006.

Grimwade, "The clinical significance of cytogenetic abnormalities in acute myeloid leukaemia," *Best. Pract. Res. Clin.Haematol.*, 14:497-529, 2001.

Grishok et al., "Genes and mechanisms related to RNA interference regulate expression of the small temporal RNAs that control *C. elegans* developmental timing," *Cell*, 106:23-34, 2001.

Grosshans et al., "The temporal patterning microRNA let-7 regulates several transcription factors at the larval to adult transition in *C. elegans*," *Dev. Cell*, 8(3):321-330, 2005.

Gstaiger et al., "Skp2 is oncogenic and overexpressed in human cancers," *Proc. Natl. Acad. Sci. USA*, 98(9):5043-5048, 2001.

Guda and Subramaniam, "TARGET: a new method for predicting protein subcellular localization in eukaryotes," *Bioinformatics*, 21: 3963-3969, 2005.

Guo et al., "Reduced expression of EphB2 that parallels invasion and metastasis in colorectal tumours," *Carcinogenesis*, 27(3):454-464, 2006.

Gurevich, "Preparative in vitro mRNA synthesis using SP6 and T7 RNA polymerases," *Anal Biochem.*, 195(2):207-213, 1991.

Ha et al., "A bulged lin-4/lin-14 RNA duplex is sufficient for *Caenorhabditis elegans* lin-14 temporal gradient formation," *Genes Dev.*, 10, 3041-3050, 1996.

Hajnal et al., "Subtaction cloning of H-rev107, a gene specifically expressed in H-ras resistant fibroblasts," *Oncogene*, 9: 479-490, 1994.

Hamamura et al., "Ganglioside GD3 promotes cell growth and invasion through p130Cas and paxillin in malignant melanoma cells," *Proc Natl Acad Sci U S A*, 102(31):11041-11046, 2005.

Hanahan and Weinberg, "The hallmarks of cancer," *Cell*, 100(1):57-70, 2000.

Hannigan et al., "Integrin-linked kinase: a cancer therapeutic target unique among its ILK," *Nat Rev Cancer*, 5(1):51-63, 2005.

Hardenbol et al.," Multiplexed genotyping with sequence-tagged molecular inversion probes," *Nat Biotechnol*, 21(6):673-678, 2003.

Hartmann et al., "Oxia-induced up-regulation of angiogenin in human malignant melanoma," *Cancer Res.*, 59 (7): 1578-1583, 1999.

He et al., "A microRNA polycistron as a potential human oncogene," *Nature*, 435(7043):828-833, 2005.

He et al., "The role of microRNA genes in papillary thyroid carcinoma," *Proc. Natl. Acad. Sci. USA*, 102(52):19075-19080, 2005.

Hishikawa et al., "Connective tissue growth factor induces apoptosis in human breast cancer cell line MCF-7," *J. Biol. Chem.*, 274(52):37461-37466, 1999.

Holmquist-Mengelbier et al., "Recruitment of HIF1alpha and HIF-2alpha to common target genes is differentially regulated in neuroblastoma: HIF-2alpha promotes an aggressive phenotype," *Cancer Cell*, 10(5):413-423, 2006.

Huang et al., "Cloning and characterization of a novel retinoid-inducible gene 1 (RIG1) deriving from human gastric cancer cells," *Mol. Cell. Endocrinol.*, 159: 15-24, 2000.

Huang et al., "Skp2 inhibits FOXO1 in tumor suppression through ubiquitin-mediated degradation," *Proc. Natl. Acad. Sci. USA*, 102(5):1649-1654, 2005.

Huang et al., "Skp2 overexpression is highly representative of intrinsic biological aggressiveness and independently associated with poor prognosis in primary localized myxofibrosarcomas," *Clin. Cancer Res.*, 12 (2): 487-498, 2006.

Huang et al., "The retinoid-inducible gene I: effect on apoptosis and mitogen-activated kinase signal pathways," *Anticancer Res.*, 22: 799-804, 2002.

Huang et al., "Wnt5a expression is associated with the tumor proliferation and the stromal vascular endothelial growth factor—an expression in non-small-cell lung cancer," *J. Clin. Oncol.*, 23 (34): 8765-8773, 2005.

Hutvagner and Zamore, "A microRNA in a multiple-turnover RNAi enzyme complex," *Science*, 297(5589):2056-2060, 2002.

Hutvagner et al., "Sequence-specific inhibition of small RNA function," *PLoS Biol.* 2(4):E98, 2004.

Huusko et al, "Nonsense-mediated decay microarray analysis identifies mutations of EPHB2 in human prostate cancer," *Nat. Genet.*, 36 (9): 979-983, 2004.

Hynes and Lane, "ERBB receptors and cancer: the complexity of targeted inhibitors," *Nat Rev Cancer*, 5(5):341-354, 2005.

Illmer et al., "MiRNA expression signatures in actue myeloid leukemia are predictors for patient outcome. Session Type: Oral Session," *Blood*, 108(11): 49A, Abstract #152, 2006.

Ishikawa et al., "Increases of amphiregulin and transforming growth factor-alpha in serum as predictors of poor response to gefitinib among patients with advanced non-small cell lung cancers," *Cancer Res.*, 65(20):9176-9184, 2005.

Ito et al., "Decreased expression of cyclin G2 is significantly linked to the malignant transformation of papillary carcinoma of the thyroid," *Anticancer Res.*, 23(3B):2335-2338, 2003.

Ito et al., "Decreased expression of p107 is correlated with anaplastic transformation in papillary carcinoma of the thyroid," *Anticancer Res.*, 23(5A):3819-3824, 2003.

Ito et al., "Expression of ets-1 and ets-2 in colonic neoplasms," *Anticancer Res.*, 22 (3): 1581-1584, 2002.

Ito et al., "Expression of p8 protein in medullary thyroid carcinoma," *Anticancer Res.*, 25 (5): 3419-3423, 2005.

Jaakkola et al., "Amplification of fgfr4 gene in human breast and gynecological cancers," *Int. J. Cancer*, 54 (3): 378-382, 1993.

Jaattela, "Over-expression of hsp70 confers tumorigenicity to mouse fibrosarcoma cells," *Int. J. Cancer*, 60(5):689-693, 1995.

Jansen et al., "Characterization of programmed cell death 4 in multiple human cancers reveals a novel enhancer of drug sensitivity," *Mol. Cancer Ther.*, 3(2):103-110, 2004.

Jansen et al., "Epidermal expression of the translation inhibitor programmed cell death 4 suppresses tumorigenesis," *Cancer Res.*, 65(14):6034-41, 2005.

Jemal et al., "Cancer statistics, 2007," *CA Cancer J. Clin.*, 57:43-66, 2007.

Jemielity et al., "Novel 'anti-reverse' cap analogs with superior translational properties," *RNA*, 9(9):1108-1122, 2003.

Jiang et al., "Decreased expression of type II tumor suppressor gene RARRES3 in tissues of hepatocellular carcinoma and cholangiocarcinoma," *World J. Gastroenterol.*, 11: 948-953, 2005.

Jiang et al., "RNA silencing of S-phase kinase-interacting protein 2 inhibits proliferation and centrosome amplification in lung cancer cells," *Oncogene*, 24(21):3409-3418, 2005.

Jin et al., "Tumorigenic transformation by CPI-17 through inhibition of a merlin phosphatase," *Nature*, 442 (7102): 576-579, 2006.

Jing et al., "Tazarotene-induced gene 1 (TIG1) expression in prostate carcinomas and its relationship to tumorigenicity," *J. Natl. Cancer Inst.*, 94: 482-490, 2002.

Johnson et al., "RAS is regulated by the let-7 microRNA family," *Cell*, 120:635-647, 2005.

Jönsson et al., "Loss of Wnt-5a protein is associated with early relapse in invasive ductal breast carcinomas," *Cancer Res.*, 62 (2): 409-416, 2002.

Jubb et al., "EphB2 is a prognostic factor in colorectal cancer," *Clin. Cancer Res.*, 11 (14): 5181-5187, 2005.

Kabbarah et al., "Expression Profiling of Mouse Endometrial Cancers Microdissected from Ethanol-Fixed, Paraffin-Embedded Tissues," *Am. J. Pathology*, 162:755-762, 2003.

Kallay et al., "Vitamin D receptor activity and prevention of colonic hyperproliferation and oxidative stress," *Food Chem. Toxicol.*, 40: 1191-1196, 2002.

Kamata et al., "High expression of skp2 correlates with poor prognosis in endometrial endometrioid adenocarcinoma," *J. Cancer Res. Clin. Oncol.*, 131(9):591-596, 2005.

Kato, "Adaptor-tagged competitive PCR: a novel method for measuring relative gene expression," *Nucleic Acids Research*, Oxford University Press, Surrey, GB, 25(22):4694-4696, 1997.

Kaufmann et al., "Elevated expression of the apoptotic regulator Mcl.-1 at the time of leukemic relapse," *Blood*, 91(3):991-1000, 1998.

Keen and Taylor, "Aurora-kinase inhibitors as anticancer agents," *Nat. Rev. Cancer*, 4(12):927-936, 2004.

Kern et al., "Application of a fed-batch system to produce RNA by in vitro transcription," *Biotechnol. Prog.*, 15:174-184, 1999.

Kern et al., "Application of solution equilibrium analysis to in vitro RNA transcription," *Biotechnol. Prog.*, 13:747-756, 1997.

Kim et al., "Genomics of microRNA," *Trends in Genetics*, 22:165-173, 2006.

Kim et al., "Identification of many microRNAs that copurify with polyribosomes in mammalian neurons," *Proc. Natl. Acad. Sci., USA*, 101:360-365, 2004.

Kiriakidou et al., "A combined computational-experimental approach predicts human microRNA targets," *Genes Dev.* 18(10):1165-78, 2004.

Kirikoshi et al., "Up-regulation of Frizzled-7 (FZD7) in human gastric cancer," *Int. J. Oncol.*, 19 (1): 111-115, 2001.

Kita et al., "Modulation of polygulutamine-induced cell death by genes identified by expression profiling," Human Molecular Genetics, 11(19):2279-2287, 2002.

Kitadai et al., "Expression of amphiregulin, a novel gene of the epidermal growth factor family, in human gastric carcinomas," *Jpn. J. Cancer Res.*, 84(8):879-884, 1993.

Kleer et al., "RhoC GTPase expression as a potential marker of lymph node metastasis in squamous cell carcinomas of the head and neck," *Clin. Cancer Res.*, 12 (15): 4485-4490, 2006.

Kohno and Pouyssegur, "Pharmacological inhibitors of the ERK signaling pathway: application as anticancer drugs," *Progress in Cell Cycle Research*,. (Meijer, L., Jezequel, A., and Roberge, M., Eds), Chapter 22, vol. 5:219-224, 2003.

Koivunen et al., "Protein kinase C (PKC) family in cancer progression," *Cancer Lett*, 235(1):1-10, 2006.

Koivunen et al., "Protein kinase C alpha/beta inhibitor Go6976 promotes formation of cell junctions and inhibits invasion of urinary bladder carcinoma cells," *Cancer Res*, 64(16):5693-5701, 2004.

Kokko et al., "EPHB2 germline variants in patients with colorectal cancer or hyperplastic polyposis," *BMC Cancer*, 6: 145, 2006.

Komatsu et al., "Increased expression of S100A6 (Calcyclin), a calcium-binding protein of the S100 family, in human colorectal adenocarcinomas," *Clin. Cancer Res.*, 6: 172-177, 2000.

Komiya et al., "PRLTS gene alterations in human prostate cancer," *Jpn. J. Cancer Res.*, 88(4):389-393, 1997.

Krek et al., "Combinatorial microRNA target predictions," *Nature Genet.*, 37:495-500, 2005.

Krichevsky et al., "A microRNA array reveals extensive regulation of microRNAs during brain development," *RNA*, 9(10):1274-1281, 2003.

Kubista et al., "Light-up probe based real-time Q-PCR," *SPIE*, 4264:53-58, 2001.

Kwong et al., "Silencing of the retinoid response gene TIG1 by promoter hypermethylation in nasopharyngeal carcinoma," *Int. J. Cancer*, 113 (3): 386-392, 2005.

L'hote and Knowles, "Cell responses to FGFR3 signalling: growth, differentiation and apoptosis," *Exp. Cell. Res.*, 304 (2): 417-431, 2005.

Labourier et al., "Improving in vitro transcription for large scale sytnthesis of human quality capped RNA," *Ambion Diagnostics, RNA Healthcare Solutions*, Eukaryotic mRNA Processing meeting, Cold Spring Harbor Laboratory, Cold Spring Harbor, NY, Aug. 2003.

Lagos-Quintana et al., "Identification of novel genes coding for small expressed RNAs," *Science*, 294(5543):853-858, 2001.

Lao et al., "Multiplexing RT-PCR for the detection of multiple miRNA species in small samples," *Biochemical and Biophysical Research Communications*, 343:85-89, 2006.

Lau et al., "An abundant class of tiny RNAs with probable regulatory roles in *Caenorhabditis elegans*," *Science*, 294(5543):858-862, 2001.

Lee and Ambros, "An extensive class of small RNAs in *Caenorhabditis elegans*," *Science*, 294(5543):862-864, 2001.

Lee et al., "A protein reacted with anti-vitronectin antibody accumulates in tumors derived from B16F10 melanoma cells," *Cell Struct. Funct.*, 23 (4): 193-199, 1998.

Lee et al., "Ectopic expression of neutrophil gelatinase-associated lipocalin suppresses the invasion and liver metastasis of colon cancer cells," *Int. J. Cancer*, 118(10):2490-2497, 2006.

Lee et al., "Expression profiling identifies stroma- and tumor-related microRNAs in pancreatic cancer," 97th Annual AACR, Washington D.C., Abstract No. 5725, 2006.

Lee et al., "MicroRNA maturation: stepwise processing and subcellular localization," *EMBO J.*, 21(17):4663-4670, 2002.

Lee et al., "The nuclear RNase III Drosha initiates microRNA processing," *Nature*, 425(6956):415-419, 2003.

Leprince et al., "A putative second cell-derived oncogene of the avian leukaemia retrovirus E26," *Nature*, 306 (5941): 395-397, 1983.

Leris et al., "WNT5A expression in human breast cancer," *Anticancer Res.*, 25 (2a): 731-734, 2005.

Lewis et al., "Prediction of mammalian microRNA targets," *Cell*, 115(7):787-798, 2003.

Li et al., "Overexpression of ETS2 in human esophageal squamous cell carcinoma," *World J. Gastroenterol.*, 9 (2): 205-208, 2003.

Lim et al., "Microarray analysis shows that some microRNAs downregulate large numbers of target mRNAs," *Nature*, 433(7027):769-773, 2005.

Lim et al., "The microRNAs of *Caenorhabditis elegans*," *Genes and Development*, 17:991-1008, 2003.

Lin and Gelman, "Reexpression of the major protein kinase C substrate, SSeCKS, suppresses v-src-induced morphological transformation and tumorigenesis," *Cancer Res*, 57(11):2304-2312, 1997.

Lin et al., "Connective tissue growth factor inhibits metastasis and acts as an independent prognostic marker in colorectal cancer," *Gastroenterology*, 128(1):9-23, 2005.

Lin et al., "The *C. elegans* hunchback homolog, *hbl-1*, controls temporal patterning and is a probable microRNA target," *Dev. Cell*, 4(5):639-650, 2003.

Linsley et al., "Transcripts targeted by the microRNA-16 family cooperatively regulate cell cycle progression," *Molecular and Cellular Biology*, 27(6):2240-2252, 2007.

Liu and Matsuura, "Inhibition of Smad antiproliferative function by CDK phosphorylation," *Cell Cycle*, 4(1):63-66, 2005.

Liu et al., "CpG island methylation and expression of the secreted frizzled-related protein gene family in chronic lymphocytic leukemia," *Cancer Res.*, 66 (2): 653-658, 2006.

Liu et al., "An oligonucleotide microchip for genome-wide micronRNA profiling in human and mouse tissue," *Proc. Nat. Acad. Sci. USA*, 101:9740-9744, 2004.

Liu et al., "FoxM1B is overexpressed in human glioblastomas and critically regulates the tumorigenicity of glioma cells," *Cancer Res.*, 66 (7): 3593-3602, 2006.

Lo et al., "High resolution allelotype of microdissected primary nasopharyngeal carcinoma," *Cancer Res.*, 60: 3348-3353, 2000.

Lo Vasco et al., "Inositide-specific phospholipase c beta1 gene deletion in the progression of myelodysplastic syndrome to acute myeloid leukemia," *Leukemia*, 18 (6): 1122-1126, 2004.

Lu et al., "MicroRNA expression profiles classify human cancers," *Nature*, 435(7043):834-838, 2005.

Lucke et al., "Inhibiting mutations in the transforming growth factor beta type 2 receptor in recurrent human breast cancer," *Cancer Res*, 61(2):482-485, 2001.

Maki et al., "Avian sarcoma virus 17 carries the jun oncogene," *Proc. Natl. Acad. Sci. USA*, 84 (9): 2848-2852, 1987.

Manion and Hockenbery, "Targeting Bcl-2-related proteins in cancer therapy," *Cancer Biol Ther*, 2(4 Suppl 1):S105-114, 2003.

Marcucci et al., "Prognostic factors and outcome of core binding factor acute myeloid leukemia patients with t(8;21) differ from those of patients with inv(16): a Cancer and Leukemia Group B study," *J.Clin.Oncol.*, 23:5705-5717, 2005.

Markowitz et al., "Inactivation of the type II TGF-beta receptor in colon cancer cells with microsatellite instability," *Science*, 268(5215):1336-1338, 1995.

Markowitz, "TGF-beta receptors and DNA repair genes, coupled targets in a pathway of human colon carcinogenesis," *Biochim. Biophys. Acta.*, 1470 (1): M13-20, 2000.

Marks, "Thioredoxin in cancer—role of histone deacetylase inhibitors," *Semin. Cancer Biol.*, 16(6):436-443, 2006.

Martello et al., "MicroRNA control of nodal signaling," *Nature*, 449(7159):183-188, 2007.

Martin and Keller, "Tailing and 3'-end labeling of RNA with yeast poly(A) polymerase and various nucleotides," *RNA*, 4(2):226-230, 1998.

Martin et al., "Molecular profiling of cervical neoplasia," *Expert Review of Molecular Diagnostics*, 6(2):217-229, 2006.

Martinez, "Identification of differentially expressed genes in HPV associated cancers using gene expression, tissue, and microRNA microarrays," Dissertation Abstract, University of Pittsburg, 2007.

Massague et al., "TGFbeta signaling in growth control, cancer, and heritable disorders," *Cell*, 103 (2): 295-309, 2000.

Matoba et al., "Gene expression in mouse cerebellum during its development," *Gene*, 241:125-131, 2000.

Matoba et al., "Gene expression profiling of mouse postnatal cerebellar development," *Physiol.Genomics*, 4:155-164, 2000.

McManus, "MicroRNAs and cancer," *Seminars in Cancer Biology*, 13:253-258, 2003.

Meister et al., "Sequence-specific inhibition of microRNA- and siRNA-induced RNA silencing," *RNA*, 10(3):544-50, 2004.

Meng et al., "Involvement of human micro-rna in growth and response to chemotherapy in human cholangiocarcinoma cell lines," *Gastroenterology*, 130(7):2113-2129, 2006.

Merle et al., "Functional consequences of frizzled-7 receptor overexpression in human hepatocellular carcinoma," *Gastroenterology*, 127 (4): 110-1122, 2004.

Metzler et al., "High Expression of Precursor MicroRNA-155/B/C RNA in Children with Burkitt Lymphoma," *Genes, Chromosomes, & Cancer* 39:167-169; 2004.

Michael et al., "Reduced accumulation of specific microRNAs in colorectal neoplasia," *Mol. Cancer Res.*, 1:882-891, 2003.

Miyake et al., "Increased angiogenin expression in the tumor tissue and serum of urothelial carcinoma patients is related to disease progression and recurrence," *Cancer*, 86 (2): 316-324, 1999.

Mizunuma et al., "The LIM-only protein, LMO4, and the LIM domain-binding protein, LDB1, expression in squamous cell carcinomas of the oral cavity," *Br J Cancer*, 88(10):1543-1548, 2003.

Mohanty and Kushner, "Polynucleotide phosphorylase functions both as a 3'-5' exonuclease and a poly(A) polymerase in *Escherichia coli*," *PNAS*, 97:11966-11971; 2000.

Moller et al., "Expression of APO-1 (CD95), a member of the NGF/TNF receptor superfamily, in normal and neoplastic colon epithelium," *Int J Cancer*, 57(3):371-377, 1994.

Montero et al., "Angiogenin expression and prognosis in primary breast carcinoma," *Clin. Cancer Res.*, 4 (9): 2161-2168, 1998.

Mori et al., "A genome-wide search identifies epigenetic silencing of somatostatin, tachykinin-1, and 5 other genes in colon cancer," *Gastroenterology*, 131(3):797-808, 2006.

Mrozek et al., "Clinical relevance of mutations and gene-expression changes in adult acute myeloid leukemia with normal cytogenetics: are we ready for a prognostically prioritized molecular classification?," *Blood*, 06-001149v1, 2006.

Mundt et al., "On the regulation and function of human polo-like kinase 1 (PLK1): effects of overexpression on cell cycle progression," *Biochem Biophys Res Commun*, 239(2):377-385, 1997.

Muralidhar et al., "Global microRNA profiles in cervical squamous cell carcinoma depend on Drosha expression levels," *J. Pathol.*, 212:368-377, 2007.

Nagpal et al., "Tazaratone-induced gen 1 (TIG1), a novel retinoic acid receptor-responsive gene in skin," *J. Invest. Dermatol.*, 106 (2): 269-274, 1996.

Nakada et al., "The phosphorylation of EphB2 receptor regulates migration and invasion of human glioma cells," *Cancer Res.*, 64 (9): 3179-3185, 2004.

Nelson et al., "Microarray-based, high-throughput gene expression profiling of microRNAs," *Nature Methods*, 1(2):1-7, 2004.

Nesbit et al., "MYC oncogenes and human neoplastic disease," *Oncogene*, 18 (19): 3004-3016, 1999.

O'Donnel et al., "c-Myc-regulated microRNA's modulcate E2F1 expression," *Nature*, 435(7043):839-4843, 2005.

Office Action issued in European Application No. 02720894.1, mailed Jul. 11, 2007.

Office Action issued in European Application No. 05804851.3, mailed Jul. 30, 2008.

Office Action issued in European Application No. 05804851.3, mailed Dec. 21, 2007.

Office Action issued in European Application No. 05815286.9, mailed Apr. 3, 2008.

Office Action issued in European Application No. 05858321.2, mailed Apr. 11, 2008.

Office Action issued in U.S. Appl. No. 10/632,534, mailed Jul. 11, 2006.

Office Action issued in U.S. Appl. No. 10/632,534, mailed Mar. 29, 2007.

Office Action issued in U.S. Appl. No. 10/632,534, mailed Mar. 24, 2006.

Office Action issued in U.S. Appl. No. 10/632,539, mailed Apr. 17, 2007.

Office Action issued in U.S. Appl. No. 10/632,539, mailed Jul. 27, 2006.

Office Action issued in U.S. Appl. No. 10/632,539, mailed Mar. 27, 2006.

Office Action issued in U.S. Appl. No. 10/880,350, mailed Feb. 21, 2006.

Office Action issued in U.S. Appl. No. 10/880,350, mailed Oct. 4, 2006.

Office Action issued in U.S. Appl. No. 10/880,350, mailed Sep. 10, 2007.

Office Action issued in U.S. Appl. No. 10/963,415, mailed Aug. 2, 2007.

Office Action issued in U.S. Appl. No. 10/963,415, mailed Apr. 13, 2007.

Office Action issued in U.S. Appl. No. 10/963,415, mailed Mar. 17, 2008.

Office Action issued in U.S. Appl. No. 11/141,707, mailed Feb. 9, 2009.

Office Action issued in U.S. Appl. No. 11/141,707, mailed Jul. 17, 2008.

Office Action issued in U.S. Appl. No. 11/141,707, mailed May 15, 2007.

Office Action issued in U.S. Appl. No. 11/141,707, mailed Oct. 17, 2007.

Office Action issued in U.S. Appl. No. 11/567,082, mailed Jan. 27, 2009.

Office Action issued in U.S. Appl. No. 11/567,082, mailed Jul. 21, 2008.

Office Action issued in U.S. Appl. No. 11/567,082, mailed Jul. 3, 2007.

Office Action issued in U.S. Appl. No. 11/567,082, mailed Nov. 13, 2007.

Office Action issued in U.S. Appl. No. 11/837,490, mailed Aug. 6, 2008.

Office Action issued in U.S. Appl. No. 11/837,490, mailed Jan. 13, 2009.

Office Action issued in U.S. Appl. No. 11/837,494, mailed Jan. 15, 2009.

Office Action issued in U.S. Appl. No. 11/837,494, mailed Mar. 5, 2009.

Office Acticin issued in U.S. Appl. No. 11/837,494, mailed Oct. 30, 2008.

Office Action issued in U.S. Appl. No. 11/837,495, mailed Mar. 5, 2009.

Office Action issued in U.S. Appl. No. 11/837,495, mailed Oct. 30, 2008.

Office Action issued in U.S. Appl. No. 11/837,498, mailed Jan. 15, 2009.

Office Action issued in U.S. Appl. No. 11/837,498, mailed Oct. 29, 2008.

Olsen and Ambros, "The lin-4 regulatory RNA controls developmental timing in *Caenorhabditis elegans* by blocking LIN-14 protein synthesis after the initiation of translation," *Dev. Biol.*, 216:671, 1999.

Ovcharenko et al., "High-throughput RNAi screening in vitro: from cell lines to primary cells," *RNA*, 11(6):985-93, 2005.

Palleres et al., "Structure of human carboxypeptidase A4: with its endogenous protein inhibitor, latexin," *Proc. Natl. Acad. Sci. USA*, 102: 3978-3983, 2005.

Parkin et al., "Global cancer statistics, 2002," *CA Cancer J. Clin.*, 55(2):74-108, 2005.

Pasquinelli and Ruvkun, "Control of developmental timing by micrornas and their targets," *Ann. Rev. Cell Dev. Biol.*, 18:495-513, 2002.

Pasquinelli et al., "Reverse 5' caps in RNAs made in vitro by phage RNA polymerases," *RNA*, 1:957-967, 1995.
PCT International Preliminary Report on Patentability and Written Opinion, issued in International Application No. PCT/US2005/018826, mailed Dec. 7, 2006.
PCT International Preliminary Report on Patentability and Written Opinion, issued in International Application No. PCT/US2005/022710, mailed Jan. 18, 2007.
PCT International Preliminary Report on Patentability and Written Opinion, issued in International Application No. PCT/US2005/036799, mailed Apr. 26, 2007.
PCT International Preliminary Report on Patentability and Written Opinion, issued in International Application No. PCT/US2005/041162, mailed Dec. 6, 2007.
PCT International Search Report and Written Opinion, issued in International Application No. PCT/US2005/036799, mailed Jun. 22, 2006.
PCT International Search Report and Written Opinion, issued in International Application No. PCT/US2005/022710, mailed Oct. 7, 2005.
PCT International Search Report and Written Opinion, issued in International Application No. PCT/US2005/041162, mailed Nov. 16, 2007.
PCT International Search Report and Written Opinion, issued in International Application No. PCT/US2007/078859, mailed Mar. 25, 2008.
PCT International Search Report and Written Opinion, issued in International Application No. PCT/US2007/078894, mailed Apr. 14, 2008.
PCT International Search Report and Written Opinion, issued in International Application No. PCT/US2007/078936, mailed Apr. 14, 2008.
PCT International Search Report and Written Opinion, issued in International Application No. PCT/US2007/086396, mailed May 30, 2008.
PCT International Search Report and Written Opinion, issued in International Application No. PCT/US2007/087021, mailed Sep. 3, 2008.
PCT International Search Report and Written Opinion, issued in International Application No. PCT/US2007/087037, mailed Jan. 12, 2009.
PCT International Search Report and Written Opinion, issued in International Application No. PCT/US2007/087038, mailed Oct. 17, 2008.
PCT International Search Report and Written Opinion, issued in International Application No. PCT/US2007/089206, mailed Aug. 26, 2008.
PCT International Search Report and Written Opinion, issued in International Application No. PCT/US2007/087029, mailed Jan. 13, 2009.
PCT International Search Report and Written Opinion, issued in International Application No. PCT/US2007/087031, mailed Jan. 13, 2009.
PCT International Search Report and Written Opinion, issued in International Application No. PCT/US2007/087033, mailed Jan. 13, 2009.
PCT International Search Report and Written Opinion, issued in International Application No. PCT/US2008/080318, mailed Feb. 9, 2009.
PCT International Search Report, issued in International Application No. PCT/US2002/003169, mailed Feb. 17, 2003.
PCT Invitation to Pay Additional Fees and Partial International Search, issued in International Application No. PCT/US2005/018826, mailed Mar. 20, 2006.
PCT Invitation to Pay Additional Fees and Partial International Search, issued in International Application No. PCT/US2005/041162, mailed Aug. 31, 2007.
PCT Invitation to Pay Additional Fees and Partial International Search, issued in International Application No. PCT/US2007/087031, mailed Sep. 10, 2008.
PCT Invitation to Pay Additional Fees and Partial International Search, issued in International Application No. PCTTUS2007/087033, mailed Sep. 5, 2008.
PCT Invitation to Pay Additional Fees and Partial International Search, issued in International Application No. PCT/US2007/087029, mailed Sep. 10, 2008.
PCT Invitation to Pay Additional Fees and Partial International Search, issued in International Application No. PCT/US2007/078859, mailed Jan. 28, 2008.
PCT Invitation to Pay Additional Fees and Partial International Search, issued in International Application No. PCT/US2007/078894, mailed Feb. 11, 2008.
PCT Invitation to Pay Additional Fees and Partial International Search, issued in International Application No. PCT/US2007/078936, mailed Feb. 5, 2008.
PCT Invitation to Pay Additional Fees and Partial International Search, issued in International Application No. PCT/US2007/087021, mailed Jul. 10, 2008.
PCT Invitation to Pay Additional Fees and Partial International Search, issued in International Application No. PCT/US2007/087037, mailed Aug. 25, 2008.
PCT Invitation to Pay Additional Fees and Partial International Search, issued in International Application No. PCT/US2007/087038, mailed Jul. 16, 2008.
PCT Invitation to Pay Additional Fees and Partial International Search, issued in International Application No. PCT/US2007/089206, mailed Jul. 7, 2008.
PCT Invitation to Pay Additional Fees and Partial International Search, issued in International Application No. PCT/US2008/076246, mailed Dec. 30, 2008.
Petit et al., "LHFP, a novel translocation partner gene of HMGIC in a lipoma, is a member of a new family of LHFP-like genes," *Genomics*, 57 (3): 438-441, 1999.
Phillips et al., "Antisense RNA amplification: A linear amplification method for analyzing the mRNA populaion," *Methods, a Companion to Methods in Enzymology*, 10(3):283-288, 1996.
Ree et al., "Expression of a novel factor in human breast cancer cells with metastatic potential," *Cancer Res.*, 59 (18): 4675-4680, 1999.
Reimer et al., "Altered regulation of cyclin G in human breast cancer and its specific localization at replication foci in response to DNA damage in p53+/+ cells," *J. Biol. Chem.*, 274 (16): 11022-11029, 1999.
Reinhart et al. "The 21-nucleotide let-7 RNA regulates developmental timing in *Caenorhabditis elegans*," *Nature*, 403:901-906, 2000.
Rickert et al., "Multiplexed Real-Time PCR Using Universal Reporters," *Clin. Chem.*, 50(9):1680-1683, 2004.
Rosenkilde and Schwartz, "The chemokine system— a major regulator of angiogenesis in health and disease," *Apmis*, 112(7-8):481-495, 2004.
Rossi et al., "Identification of inactivating mutations in the JAK1, SYNJ2, and CLPTM1 genes in prostate cancer cells using inhibition of nonsense-mediated decay and microarray analysis," *Cancer Genet. Cytogenet.*, 161 (2): 97-103, 2005.
Rubin and Gutmann, "Neurofibromatosis type 1—a model for nervous system tumour formation?," *Nat Rev Cancer*, 5(7):557-564, 2005.
Ruth et al., "RhoC promotes human melanoma invasion in a PI3K/Akt-dependent pathway," *J. Invest. Dermatol.*, 126 (4): 862-868, 2006.
Sacchi et al., "Hu-ets-1 and Hu-ets-2 genes are transposed in acute leukemias with (4;11) and (8;21) translocations," *Science*, 231 (4736): 379-382, 1986.
Saigusa et al., "Overexpressed Skp2 within 5p amplification detected by array-based comparative genomic hybridization is associated with poor prognosis of glioblastomas," *Cancer Sci*, 96(10):676-683, 2005.
Saitoh et al., "Frequent up-regulation of WNT5A mRNA in primary gastric cancer," *Int. J. Mol. Med.*, 9 (5): 515-519, 2002.
Sakai et al., "Microarray hybridization with fractionated cDNA: enhanced identification of differentially expressed genes," *Analytical Biochemistry*, 287(1):32-37, 2000.
Sampson and Uhlenbeck, "Bichemical and physical characterization of an unmodified yeast phenylalanine transfer RNA transcribed in vitro," *Proc. Natl. Acad. Sci., USA*, 85(4):1033-1037, 1988.
Sanger Institute, miRBase::Sequences —Stem-loop sequence MI0000268, Sep. 2008, located at http://microRNA.sanger.ac.ukm, printed on Dec. 23, 2008.

Sanger Institute, "miRBase" *miRBase Sequence Database*, located at http://microrna.sanger.ac.uk/, printed Jan. 21, 2009.
Schenborn and Stecha, "Ribo m$^7$G cap analog: A reagent for preparing in vitro capped transcripts", *Promega Notes*, 74:18-20, 2000.
Scherr et al., "Lentrivirus-mediated antagomir expression for specific inhibition of miRNA function," *Nucleic Acids Research*, 35(22):e149, 2007.
Schouten et al., "Relative quantification of 40 nucleic acid sequences by multiplex ligation-dependent probe amplification," *Nucleic Acids Research*, 30(12):e57, 2002.
Schulze-Bergkamen et al., "Suppression of Mcl-1 via RNA interference sensitizes human hepatocellular carcinoma cells towards apoptosis induction," *BMC Cancer*, 6:232, 2006.
Seggerson et al., "Two genetic circuits repress the *Caenorhabditis elegans* heterochronic gene lin-28 after translation initiation," *Dev. Biol.*, 243:215, 2002.
Sementchenko et al, "ETS2 function is required to maintain the transformed state of human prostate cancer cells," *Oncogene*, 17 (22): 2883-2888, 1998.
Shah et al., "FGFR4 overexpression in pancreatic cancer is mediated by an intronic enhancer activated by HNF1alpha," *Oncogene*, 21 (54): 8251-8261, 2002.
Shelly et al., "Epiregulin is a potent pan-ErbB ligand that preferentially activates heterodimeric receptor complexes," *J. Biol. Chem.*, 273 (17): 10496-10505, 1998.
Shelton et al., "MicroRNAs and Human Cancer," Abstract submitted for a Cold Spring Symposium in early Jun. 2006 — 71$^{st}$ Symposium: Regulatory RNAs.
Shi et al., "Facile means for quantifying microRNA expression by real-time PCR," *BioTechniques*, 39(4):519-524, 2005.
Shibahara et al., "Down-regulation of Skp2 is correlated with p27-associated cell cycle arrest induced by phenylacetate in human prostate cancer cells," *Anticancer Res.*, 25 (3b): 1881-1888, 2005.
Shigemasa et al., "Increased MCL-1 expression is associated with poor prognosis in ovarian carcinomas," *Jpn. J. Cancer Res.*, 93(5):542-550, 2002.
Shimo et al., "Connective tissue growth factor as a major angiogenic agent that is induced by hypoxia in a human breast cancer cell line," *Cancer Lett.*, 174(1):57-64, 2001.
Shimoyama et al., "Increased serum angiogenin concentration in colorectal cancer is correlated with cancer progression," *Clin. Cancer Res.*, 5 (5): 1125-1130, 1999.
Shingara et al., "An optimized isolation and labeling platform for accurate microRNA expression profiling," *RNA*, 11:1461-1470, 2005.
Shuldiner et al., "RNA template-specific polymerase chain reaction RS-PCR a novel strategy to reduce dramatically false positives," *Gene*, 91(1):139-142, 1990.
Shyu et al., "RARRES3 expression positively correlated to tumour differentiation in tissues of colorectal adenocarcinoma," *Br. J. Cancer*, 89 (1): 146-151, 2003.
Si et al., "miR-21-mediated tumor growth," *Oncogene*, 1-5, 2006.
Simpson et al., "Altered expression of Erg and Ets-2 transcription factors is associated with genetic changes at 21q22.2-22.3 in immortal and cervical carcinoma cell lines," *Oncogene*, 14 (18): 2149-2157, 1997.
Sirera et al., "The analysis of serum DNA concentration by means of hTERT quantification: A useful prognostic factor in advanced non-small cell lung cancer (NSCLC)," *Lung Cancer*, 49:S74, Abstract PD-026, 2005.
Skotzko et al., "Retroviral vector-mediated gene transfer of antisense cyclin G1 (CYCG1) inhibits proliferation of human osteogenic sarcoma cells," *Cancer Res.*, 55 (23): 5493-5498, 1995.
Slack et al., "The lin-41 RBCC gene acts in the *C. elegans* heterochronic pathway between the let-7 regulatory RNA and the LIN-29 transcription factor," *Molec. Cell*, 5(4):659-669, 2000.
Slack, "Control of developmental timing by microRNAs," believed at the time of the filing of this form to have been presented by Frank Slack at Santa Cruz in Aug. 2004.
Slack, "Control of Development by microRNAs," believed at the time of the filing of this form to have been presented by Frank Slack at IIT Bombay on Jan. 28, 2004.
Slack, "Control of Development by microRNAs," believed at the time of the filing of this form to have been presented by Frank Slack at Keystone miRNAs on Apr. 15, 2005.
Slack, "Control of Development by microRNAs," believed at the time of the filing of this form to have been presented by Frank Slack at UCT on Feb. 17, 2004.
Slack, "Control of Development by microRNAs," believed at the time of the filing of this form to have been presented by Frank Slack at UNMC on Mar. 29, 2004.
Slack, "MicroRNA control of oncogene expression," believed at the time of the filing of this form to have been presented by Frank Slack at Slack GTBIO on Nov. 8, 2004.
Slack, "MicroRNAs and cancer," believed at the time of the filing of this form to have been presented by Frank Slack at University of Puerto Rico Bayamon on Sep. 22, 2004.
Slack, "Multiple, dynamic microRNA ribonucleoprotein complexes with select microRNA cargos in *C. elegans*," believed at the time of the filing of this form to have been presented by Frank Slack at Gordon on Jun. 8, 2004.
Slack, "Small RNA genes as potential causes and treatments of cancer," believed at the time of the filing of this form to have been presented by Frank Slack at Jaslok on Feb. 1, 2004.
Slack, "Temporal patterning and biological timing," believed at the time of the filing of this form to have been presented by Frank Slack at Dartmouth on Mar. 19, 2004.
Smith et al., "Exclusive amplification of cDNA template (Exact) RT-PCR to avoid amplifying contaminating genomic pseudogenes," *BioTechniques*, 31(4): 776-778, 780, 782, 2001.
Smith et al., "Malignant transformation of mammalian cells initiated by constitutive expression of the polo-like kinase," *Biochem Biophys Res Commun*, 234(2):397-405, 1997.
Sparmann and Bar-Sagi, "Ras-induced interleukin-8 expression plays a critical role in tumor growth and angiogenesis," *Cancer Cell*, 6(5):447-458, 2004.
Stepinski et al., "Synthesis and properties of mRNAs containing the novel 'anti-reverse' cap analogs 7-methyl(3'O-methyl)GpppG and 7-methyl(e'-deoxy)GpppG," *RNA*, 7:1486-1495, 2001.
Stone et al., "Isolation of a human prostate carcinoma cell line (DU 145)," *Int. J. Cancer*, 21 (3): 274-281, 1978.
Strebhardt and Ullrich, "Targeting polo-like kinase 1 for cancer therapy," *Nat. Rev. Cancer*, 6 (4): 321-330, 2006.
Sturniolo et al., "A novel tumor suppressor protein promotes keratinocyte terminal differentiation via activation of type I transglutaminase," *J. Biol. Chem.*, 278 (48): 48066-48073, 2003.
Su et al,. "Overexpression of p8 is inversely correlated with apoptosis in pancreatic cancer," *Clin. Cancer Res.*, 7 (5): 1320-1324, 2001.
Sueoka et al., "Detection of plasma hnRNP B1 mRNA, a new cancer biomarker, in lung cancer patients by quantitative real-time polymerase chain reaction," *Lung Cancer*, 48(1):77-83, 2005.
Sui et al., "Clinical significance of Skp2 expression, alone and combined with Jab1 and p27 in epithelial ovarian tumors," *Oncol. Rep.*, 15 (4): 765-771, 2006.
Sum et al., "Overexpression of LMO4 induces mammary hyperplasia, promotes cell invasion, and is a predictor of poor outcome in breast cancer," *Proc Natl Acad Sci U S A*, 102(21):7659-7664, 2005.
Sum et al., "The LIM domain protein LMO4 interacts with the cofactor CtIP and the tumor suppressor BRCA1 and inhibits BRCA1 activity," *J Biol Chem*, 277(10):7849-7856, 2002.
Sunpaweravong et al., "Epidermal growth factor receptor and cyclin D1 are independently amplified and overexpressed in esophageal squamous cell carcinoma," *J Cancer Res Clin Oncol*, 131(2):111-119, 2005.
Szafranska et al., "A unique microRNA molecular signature for pancreatic carcinoma," AACR-Pancreatic Cancer: Early Detection and Novel Therapeutics, Chapel Hill, NC, Jun. 26-27, 2006.
Takamizawa et al., "Reduced expression of the let-7 microRNAs in human lung cancers in association with shortened postoperative survival," *Cancer Research*, 64:3753-3756, 2004.
Takanami, "The prognostic value of overexpression of Skp2 mRNA in non-small cell lung cancer.," *Oncol. Rep.*, 13 (4): 727-731, 2005.

Takimoto et al., "Genetic alterations in the retinoblastoma protein-related p107 gene in human hematologic malignancies," *Biochem Biophys Res Commun*, 251(1):264-268, 1998.

Tanaka et al., "A novel frizzled gene identified in human esophageal carcinoma mediates APC/beta-catenin signals," *Proc. Natl. Acad. Sci. USA*, 95 (17): 10164-10169, 1998.

Taniwaki et al., "Gene expression profiles of small-cell lung cancers: molecular signatures of lung cancer," *Int J Oncol*, 29(3):567-575, 2006.

Tassi et al., "Enhancement of fibroblast growth factor (FGF) activity by an FGF-binding protein," *J. Biol. Chem.*, 276(43):40247-40253, 2001.

Tazawa et al., "Tumor-suppressive *miR-34a* induces senescence-like growth arrest through modulation of the E2F pathway in human colon cancer cells," *PNAS*, 104(39):15472-15477, 2007.

Thøgersen et al., "A subclass of HER1 ligands are prognostic markers for survival in bladder cancer patients," *Cancer Res.*, 61 (16): 6227-6233, 2001.

Tomasini-Johansson et al., "Vitronectin in colorectal adenocarcinoma—synthesis by stromal cells in culture," *Exp. Cell. Res.*, 214 (1): 303-312, 1994.

Toning et al., "Increased expression of heparin binding EGF (HB-EGF), amphiregulin, TGF alpha and epiregulin in androgen-independent prostate cancer cell lines," *Anticancer Res.*, 20 (1a): 91-95, 2000.

Toyoda et al., "Distribution of mRNA for human epiregulin, a differentially expressed member of the epidermal growth factor family," *Biochem J*, 326 (Pt 1):69-75, 1997.

Traub et al., "Prognostic impact of Skp2 and p27 in human breast cancer.," *Breast Cancer Res. Treat.*, 99 (2): 185-191, 2006.

Tsai et al., "RIG1 inhibits the Ras/mitogen-activated protein kinase pathway by suppressing the activation of Ras.," *Cell Signal*, 18 (3): 349-358, 2006.

U.S. Appl. No. 11/273,640, entitled "Methods and compositions involving miRNA and miRNA inhibitors molecules," by David Brown et al., filed Nov. 14, 2005.

U.S. Appl. No. 11/855,792, entitled "Methods of normalization in microRNA detection assays," by Gary Latham et al., filed Sep. 14, 2007.

U.S. Appl. No. 11/857,948, entitled "MicroRNAs differentially expressed in pancreatic diseases and uses thereof," by Emmanuel Labourier et al., filed Sep. 19, 2007.

U.S. Appl. No. 11/967,639, entitled "Functions and targets of LET-7 micro RNAs," by Charles Johnson et al., filed Dec. 31, 2007.

U.S. Appl. No. 11/967,663, entitled "miR-16 regulated genes and pathways as targets for therapeutic intervention," by Mike Byrom et al., filed Dec. 31, 2007.

U.S. Appl. No. 12/112,291, entitled "miR-20 Regulated Genes and Pathways as Targets for Therapeutic Intervention ," by Andreas Bader et al., filed Apr. 30, 2008.

U.S. Appl. No. 12/120,388, entitled "miR-21 regulated genes and pathways as targets for therapeutic intervention," by Andreas Bader et al., filed May 14, 2008.

U.S. Appl. No. 12/124,394, entitled "miR-200 Regulated Genes and Pathways as Targets for Therapeutic Intervention," by Andreas Bader et al., filed May 21, 2008.

U.S. Appl. No. 12/125,412, entitled "miR-143 regulated genes and pathways as targets for therapeutic intervention," by Andreas Bader et al., filed May 22, 2008.

U.S. Appl. No. 12/125,675, entitled "miR-126 regulated genes and pathways as targets for therapeutic intervention," by Andreas Bader et al., filed May 22, 2008.

U.S. Appl. No. 12/134,932, entitled "miR-134 Regulated Genes and Pathways as Targets for Therapeutic Intervention," by Andreas Bader et al., filed Jun. 6, 2008.

U.S. Appl. No. 12/167,492, entitled "miR-15, miR-26, miR-31, miR-145, miR-147, miR-188, miR-215, miR-216, miR-331, mmu-miR-292-3P regulated genes and pathways as targets for therapeutic intervention," by Andreas Bader et al., filed Jul. 3, 2008.

U.S. Appl. No. 12/209,822, entitled "MicroRNAs idfferentially expressed in cervical cancer and uses thereof," by Sylvie Beaudenon et al., filed Sep. 12, 2008.

U.S. Appl. No. 12/253,718, entitled "MicroRNAs differentially expressed in lung diseases and uses thereof," by Gary J. Lathan et al., filed Oct. 17, 2008.

U.S. Appl. No. 12/340,329, entitled "miR-10 Regulated Genes and Pathways as Targets for Therapeutic Intervention," by Ovcharenko et al., filed Dec. 19, 2008.

U.S. Appl. No. 12/368,053, entitled "miRNAs Differentially Expressed in Lymph Nodes from Cancer Patients," by Sylvie Beaudenon et al., filed Feb. 9, 2009.

U.S. Appl. No. 12/398,852, entitled "MicroRNA markers for recurrence of colorectal cancer," by Elizabeth Mambo et al., filed Mar. 5, 2009.

U.S. Appl. No. 12/412,087, entitled "Compositions and methods related to miR-16 and therapy of prostate cancer," by Fumitaka Takeshita et al., filed Mar. 26, 2009.

U.S. Appl. No. 12/420,634, entitled "Methods and compositions for diagnosing and modulating human papillomavirus (HPV)," by Sylvie Beaudenon-Huibregtse, filed Apr. 8, 2009.

U.S. Appl. No. 12/437,899, entitled "Compositions and methods related to miRNA modulation of neovascularization or angiogenesis," by Jikui Shen et al., filed May 8, 2009.

U.S. Appl. No. 60/575,743, entitled "Methods and compositions involving MicroRNA," by David Brown et al., filed May 28, 2004.

U.S. Appl. No. 60/649,584, entitled "Methods and compositions involving MicroRNA," by David Brown et al., filed Feb. 3, 2005.

U.S. Appl. No. 60/650,807, entitled "Compositions and methods involving MDA-7 and COX-2 inhibitors for the treatment of cancer," by Sunil Chada et al., filed Feb. 8, 2005.

U.S. Appl. No. 60/906,028, entitled "Prostate cancer specific miRNAs," by David Brown, filed Mar. 9, 2007.

U.S. Appl. No. 61/113,385, entitled "Methods and compositions involving miRNAs in cancer stem cells," by Lubna Patrawala et al., filed Nov. 11, 2008.

Uhm et al., "Vitronectin, a glioma-derived extracellular matrix protein, protects tumor cells from apoptotic death," *Clin. Cancer Res.*, 5 (6): 1587-1594, 1999.

Ulisse et al., "Expression of Aurora kinases in human thyroid carcinoma cell lines and tissues," *Int. J. Cancer*, 119 (2): 275-282, 2006.

Vargas-Roig et al., "Heat shock protein expression and drug resistance in breast cancer patients treated with induction chemotherapy," *Cancer Detection and Prevention* 21(5):441-451, 1997.

Vella et al., "Architecture of a validated microRNA::target interaction," *Chem. Biol.*, 11(12):1619-1623, 2004.

Vella et al., "The *C. elegans* microRNA *let-7* binds to imperfect *let-7* complementary sites from the *lin-41* 3'UTR," *Genes Dev.*, 18(2):132-7, 2004.

Visvader et al., "The LIM domain gene LMO4 inhibits differentiation of mammary epithelial cells in vitro and is overexpressed in breast cancer," *Proc Natl Acad Sci U S A*, 98(25):14452-14457, 2001.

Volinia at al., "A microRNA expression signature of human solid tumors defines cancer gene targets," *Proc. Natl. Acad. Sci. USA*, 103(7):2257-2261, 2006.

Volloch and Sherman, "Oncogenic potential of Hsp72," *Oncogene*, 18(24):3648-3651, 1999.

Vos et al., "RASSF2 is a novel K-Ras-specific effector and potential tumor suppressor," *J Biol Chem*, 278(30):28045-28051, 2003.

Wade, "Transcriptional control at regulatory checkpoints by histone deacetylases: molecular connections between cancer and chromatin," *Hum. Mol. Genet.*, 10(7):693-698, 2001.

Wang et al., "Identification of rat lung-specific microRNAs by micoRNA microarray: valuable discoveries for the facilitation of lung research," *BMC Genomics*, 8:29-42, 2007.

Weeraratna at al., "Wnt5a signaling directly affects cell motility and invasion of metastatic melanoma," *Cancer Cell*, 1 (3): 279-288, 2002.

Weinstein, "Disorders in cell circuitry during multistage carcinogenesis, the role of homeostasis," *Carcinogenesis*, 21 (5): 857-864, 2000.

Weiss and Bohmann, "Deregulated repression of c-Jun provides a potential link to its role in tumorigenesis," *Cell Cycle*, 3 (2): 111-113, 2004.

Welsh et al., "Fingerprinting genomes using PCR with arbitrary primers," *Nucleic Acids Research*, Oxford University Press, Surrey, GB, 18(24):7213-7218, 1990.

Welsh et al., "Nucleic acid fingerprinting by PCR-based methods: applications to problems in aging and mutagenesis," *Mutation Research*, 338(1-6):215-229, 1995.

Wheeler and Ridley, "Why three Rho proteins? RhoA, RhoB, RhoC, and cell motility," *Exp. Cell. Res.*, 301 (1): 43-49, 2004.

Whitcombe et al., "A homogeneous fluorescence assay for PCR amplicons: its application to real-time, single-tube genotyping," *Clin. Chem.*, 44(5):918-923, 1998.

Whitcombe et al., "Advances in approaches to DNA-based diagnostics," *Curr. Opin. Biotechnol.*, 9(6):602-608, 1998.

Wikman et al., "Identification of differentially expressed genes in pulmonary adenocarcinoma by using cDNA array," *Oncogene*, 21(37):5804-5813, 2002.

Wood et al., "DNA microarray analysis of vitamin D-induced gene expression in a human colon carcinoma cell line," *Physiol. Genomics*, 17 (2): 122-129, 2004.

Wooster and Weber, "Breast and ovarian cancer," *N. Engl. J. Med.*, 348(23):2339-2347, 2003.

Wu et al., "Expression of Ephb2 and Ephb4 in breast carcinoma," *Pathol. Oncol. Res.*, 10 (1): 26-33, 2004.

Wu et al., "MicroRNA and cancer: current status and prospective," *International Journal of Cancer*, 120:953-960, 2006.

Wu et al., "p107 Expression in colorectal tumours rises during carcinogenesis and falls during invasion," *Eur J Cancer*, 38(14):1838-1848, 2002.

Wu et al., "RARRES1 expression is significantly related to tumour differentiation and staging in colorectal adenocarcinoma," *Eur. J. Cancer*, 42(4):557-565, 2006.

Wu et al., "RhoC induces differential expression of genes involved in invasion and metastasis in MCF10A breast cells," *Breast Cancer Res., Treat.*, 84 (1); 3-12, 2004.

Wu et al., "The prognostic impact of EphB2/B4 expression on patients with advanced ovarian carcinoma," *Gynecol. Oncol.*, 102 (1): 15-21, 2006.

Wyatt et al., "Synthesis and purification of large amounts of RNA oligonucleotides," *Biotechniques*, 11(6):764-769, 1991.

Wyttenbach et al., "Polyglutamine expansions cause decreased CRE-mediated transcription and early gene expression changes prior to cell death in an inducible cell model of Huntington's disease," *Human Molecular Genetics*, 10(17):1829-1845, 2001.

Xia et al., "Positive expression of HIF-2alpha/EPAS1 in invasive bladder cancer," *Urology*, 59(5):774-778, 2002.

Xia et al., "Regulation of vascular endothelial growth factor transcription by endothelial PAS domain protein 1 (EPAS1) and possible involvement of EPAS1 in the angiogenesis of renal cell carcinoma," *Cancer*, 91(8):1429-1436, 2001.

Xia et al., "The Src-suppressed C kinase substrate, SSeCKS, is a potential metastasis inhibitor in prostate cancer," *Cancer Res*, 61(14):5644-5651, 2001.

Xie et al., "Negative feedback regulation of Dicer-Like1 in *Arabidopsis* by microRNA-guided mRNA degradation," *Current Biology*, 13:784-789, 2003.

Xie, et al., "Systematic discovery of regulatory motifs in human promoters and 3' UTRs by comparison of several mammals," *Nature*, 434(7031):338-345, 2005.

Xu et al., "The *Drosophila* microRNA Mir-14 suppresses cell death and is required for normal fat metabolism," *Curr. Biol.*, 13:790-795, 2003.

Yanaihara et al., "Unique microRNA molecular profiles in lung cancer diagnosis and prognosis," *Cancer Cell*, 9:189-198, 2006.

Yang et al., "Differential expression of CCAAT/enhancer-binding protein-delta (c/EBPdelta) in rat androgen-dependent tissues and human prostate cancer," *J. Androl.*, 22 (3): 471-480, 2001.

Yang et al., "Smad3 reduces susceptibility to hepatocarcinoma by sensitizing hepatocytes to apoptosis through downregulation of Bcl-2," *Cancer Cell*, 9(6):445-457, 2006.

Yang et al., "Stromal expression of connective tissue growth factor promotes angiogenesis and prostate cancer tumorigenesis," *Cancer Res.*, 65(19):8887-8895, 2005.

Yang et al., "The transformation suppressor Pdcd4 is a novel eukaryotic translation initiation factor 4A binding protein that inhibits translation," *Mol. Cell Biol.*, 23(1):26-37, 2003.

Yang et al., "Tumorigenesis suppressor Pdcd4 down-regulates mitogen-activated protein kinase kinase kinase kinase 1 expression to suppress colon carcinoma cell invasion," *Mol Cell Biol*, 26(4):1297-1306, 2006.

Yao et al., "RhoC GTPase is required for PC-3 prostate cancer cell invasion but not motility," *Oncogene*, 25 (16): 2285-2296, 2006.

Yoon and De Micheli, "Prediction of regulatory modules comprising microRNAs and target genes," *Bioinformatics*, 21(Suppl.2):ii93-ii100, 2005.

Yoshida et al., "The clinical significance of Cyclin B1 and Wee1 expression in non-small-cell lung cancer," *Ann Oncol*, 15(2):252-256, 2004.

Yoshimura et al., "Prognostic impact of hypoxia-inducible factors 1alpha and 2alpha in colorectal cancer patients: correlation with tumor angiogenesis and cyclooxygenase-2 expression," *Clin. Cancer Res.*, 10(24):8554-8560, 2004.

Yoshioka et al,. "A role for LIM kinase in cancer invasion," *Proc. Natl. Acad. Sci. USA*, 100 (12): 7247-7252, 2003.

Youssef et al., "Hypermethylation and silencing of the putative tumor suppressor, Tazarotene-induced gene 1 in human cancers," *Cancer Res.*, 64 (7): 2411-2417, 2004.

Yu et al,. "Global assessment of promoter methylation in a mouse model of cancer identifies ID4 as a putative tumor-suppressor gene in human leukemia," *Nat. Genet.*, 37 (3): 265-274, 2005.

Zangemeister-Wittke and Huwiler, "Antisense targeting of Mc1-1 has therapeutic potential in gastric cancer," *Cancer Biol. Ther.*, 5(10):1355-1356, 2006.

Zeng et al., "Both natural and designed micro RNAs can inhibit the expression of cognate mRNAs when expressed in human cells," *Mol Cell.* 9, 1327-33, 2002.

Zeng et al., "MicroRNAs and small interfering RNAs can inhibit mRNA expression by similar mechanisms," *Proc. Natl. Acad. Sci.* 100: 9779-9784, 2003.

Zhang et al., "Involvement of programmed cell death 4 in transforming growth factor-beta1-induced apoptosis in human hepatocellular carcinoma," *Oncogene*, 25(45):6101-6112, 2006.

Zhang et al., "Methylation of the retinoid response gene TIG1 in prostate cancer correlates with methylation of the retinoic acid receptor beta gene," *Oncogene*, 23 (12): 2241-2249, 2004.

Zhao et al., "Cyclin G1 has growth inhibitory activity linked to the ARF-Mdm2-p53 and pRb tumor suppressor pathways," *Mol Cancer Res*, 1(3):195-206, 2003.

Zhu et al., "MicroRNA targets the tumor suppressor gene tropomyosin 1 (TIPM1)" *The Journal of Biological Chemistry*, 282(19):14328-14336, 2007.

Zhu et al., "Epiregulin is Up-regulated in pancreatic cancer and stimulates pancreatic cancer cell growth," *Biochem. Biophys. Res. Commun.*, 273 (3): 1019-1024, 2000.

Zimmerman et al., "Technical aspects of quantitative competitive PCR," *Biotechniques*, 21(2):268-270, 1996.

Calin et al., "Human microRNA genes are frequently located at fragile sites and genomic regions involved in cancers," *PNAS*, 101(9):2999-3004, 2004.

Cao et al., "A functional study of miR-124 in the developing neural tube," *Genes & Development*, 21(5):531-536, 2007.

Conaco et al., "Reciprocal actions of REST and a microRNA promote neuronal identity," *PNAS*, 103(7):2422-2427, 2006.

Decision on Appeal, Appeal 2008-002253, issued in U.S. Appl. No. 10/880,350, decided May 29, 2009.

Karginov et al., "A biochemical approach to identifying microRNA targets," *PNAS*, 104(49):19291-19296, 2007.

Lujambio et al., "Genetic unmasking of an epigenetically silenced microRNA in human cancer cells," *Cancer Research*, 67(4):1424-1429, 2007.

Makeyev et al., "The microRNA miR-124 promotes neuronal differentiation by triggering brain-specific alternative pre-mRNA splicing," *Molecular Cell*, 27(3):435-448, 2007.

Nakamura et al., "MARCH-II is a syntaxin-6-binding protein involved in endosomal trafficking," *Molecular Biology of the Cell*, 16(4):1696-1710, 2005.

Office Action issued in U.S. Appl. No. 09154092.2, mailed May 7, 2009.

Office Action issued in U.S. Appl. No. 10/963,415, mailed Mar. 9, 2009.
Office Action issued in U.S. Appl. No. 11/141,707, mailed Jun. 19, 2009.
Office Action issued in U.S. Appl. No. 11/273,640, mailed Jun. 26, 2009.
Office Action issued in U.S. Appl. No. 11/837,487, mailed Mar. 25, 2009.
Office Action issued in U.S. Appl. No. 11/837,498, mailed Apr. 30, 2009.
Office Action issued in U.S. Appl. No. 11/857,948, mailed Jun. 4, 2009.
Office Action issued in U.S. Appl. No. 11/967,639, mailed May 14, 2009.
Office Action issued in U.S. Appl. No. 11/967,639, mailed Mar. 13, 2009.
PCT International Preliminary Report on Patentability, issued in International Application No. PCT/US2007/078894, mailed Apr. 2, 2009.
PCT International Preliminary Report on Patentability, issued in International Application No. PCT/US2007/078936, mailed Apr. 2, 2009.
PCT International Preliminary Report on Patentability, issued in International Application No. PCT/US2007/078859, mailed Apr. 2, 2009.
PCT International Search Report and Written Opinion, issued in International Application No. PCT/US2008/076246, mailed Feb. 27, 2009.
PCT Invitation to Pay Additional Fees and Partial International Search, issued in International Application No. PCT/US2008/085178, mailed May 8, 2009.
Tang et al., "PS 7-2 microrna expression profile in cervical cancer and its derived cell lines," 23rd International Papillomavirus Conference and Clinical Workshop, Prague, Czech Republic, Sep. 1-7, 2006.
Visvanathan et al., "The microRNA miR-124 antagonizes the anti-neural REST/SCP1 pathway during embryonic CNS development," Genes & Development, 21(7):744-749, 2007.
Wang and Wang, "Systematic identification of microRNA functions by combining target prediction and expression profiling," Nucleic Acids Research, 34(5):1646-1652, 2006.
"Poster Abstracts," Annals of Surgical Oncology, 15(Suppl 1):33-64, 2008.*
Agrawal and Syngal, "Colon cancer screening strategies," Curr Opin Gastroenterol, 21(1):59-63, 2005.*
Aoki et al., "Proteasomal degradation of the FoxO1 transcriptional regulator in cells transformed by the P3k and Akt oncoproteins," Proc Natl Acad Sci U S A, 101(37):13613-13617, 2004.*
Austin and Cook, "Increased expression of Mcl-1 is required for protection against serum starvation in phosphatase and tensin homologue on chromosome 10 null mouse embryonic fibroblasts, but repression of Bim is favored in human glioblastomas," J Biol Chem, 280(39):33280-33288, 2005.*
Bader and Vogt, "An essential role for protein synthesis in oncogenic cellular transformation," Oncogene, 23(18):3145-3150, 2004.*
Bader et al.," Oncogenic PI3K deregulates transcription and translation," Nat Rev Cancer, 5(12):921-929, 2005.*
Baffa et al., "MicroRNA expression profiling of human metastatic cancers identifies cancer gene targets," J. Pathol., Epub Ahead of Print, 2009.
Bai et al., "Downregulation of selective microRNAs in trigeminal ganglion neurons following inflammatory muscle pain," Mol Pain, 3:15, 2007.
Bartel et al., "Alternative and aberrant splicing of MDM2 mRNA in human cancer," Cancer Cell, 2(1):9-15, 2002.
Beeram et al., "Raf: a strategic target for therapeutic development against cancer," J Clin Oncol, 23(27):6771-6790, 2005.
Bell and Dutta, "DNA replication in eukaryotic cells," Annu Rev Biochem, 71:333-374, 2002.
Bello et al., "Androgen responsive adult human prostatic epithelial cell lines immortalized by human papillomavirus 18," Carcinogenesis, 18(6):1215-1223, 1997.
Bertagnolli et al., "Sentinel node staging of resectable colon cancer: results of a multicenter study," Ann. Surg., 240(4):624-630, 2004.

Blobe et al., "Functional roles for the cytoplasmic domain of the type III transforming growth factor beta receptor in regulating transforming growth factor beta signaling," J Biol Chem, 276(27):24627-24637, 2001.
Brothman et al., "Metastatic properties of the human prostatic cell line, PPC-1, in athymic nude mice," J Urol., 145(5):1088-1091, 1991.
Calin et al., "MicroRNA profiling reveals distinct signatures in B cell chronic lymphocytic leukemias," Proc Natl Acad Sci USA, 101(32):11755-11760, 2004.
Carter and Brunet, "FOXO transcription factors," Curr Biol, 17(4):R113-114, 2007.
Caselitz et al., "Malignant melanomas contain only the vimentin type of intermediate filaments," Virchows Arch A Pathol Anat Histopathol, 400(1):43-51, 1983.
Chendrimada et al., "MicroRNA silencing through RISC recruitment of eIF6," Nature, 447(7146):823-828, 2007.
Chieffi et al., "Aurora B expression directly correlates with prostate cancer malignancy and influence prostate cell proliferation," Prostate, 66(3):326-333, 2006.
Chmielarz et al., "Prognostic factors for the time of occurrence and dynamics of distant metastases and local recurrences after radical treatment in patients with rectal cancer," Med Sci Monit., 7(6):1263-1269, 2001.
Churg, "Immunohistochemical staining for vimentin and keratin in malignant mesothelioma," Am J Surg Pathol, 9(5):360-365, 1985.
Cipriano and Chen, "Insensitivity to growth inhibition by TGF-beta1 correlates with a lack of inhibition of the CDK2 activity in prostate carcinoma cells," Oncogene, 17(12):1549-1556, 1998.
Coello et al., "Prognostic significance of micrometastasis in non-small-cell lung cancer," Clin. Lung Cancer, 5:214-225, 2004.
Cohen et al., "Prognosis of node-positive colon cancer," Cancer, 67(7):1859-1861, 1991.
Coll et al., "Molecular cloning of the avian acute transforming retrovirus MH2 reveals a novel cell-derived sequence (v-mil) in addition to the myc oncogene," Embo J, 2(12):2189-2194, 1983.
Costello et al., "Cyclin-dependent kinase 6 (CDK6) amplification in human gliomas identified using two-dimensional separation of genomic DNA," Cancer Res, 57(7):1250-1254, 1997.
Cox et al., "Significance of sentinel lymph node micrometastases in human breast cancer," J. Am. Coll. Surg., 206(2):261-268, 2008.
Dahl et al., "Identification of sentinel nodes in patients with colon cancer," Eur. J. Surg. Oncol., 31(4):381-385, 2005.
Davison et al., "Analyzing micro-RNA expression using microarrays," Meth. Enzymol., 411:14-34, 2006.
D'Cunha et al., "Poor correspondence between clinical and pathologic staging in stage 1 non-small cell lung cancer: results from CALGB 9761, a prospective trial," Lung Cancer, 48:241-246, 2005.
De Boer et al., "Micrometastases and isolated tumor cells: relevant and robust or rubbish? (MIRROR): preliminary results of the MIRROR study from the Dutch breast cancer trialists' group (BOOG)," San Antonio Breast Cancer Symposium, Abstract 23, 2008.
Dillon et al., "An APRIL to remember: novel TNG ligands as therapeutic targets," Nat Rev Drug Discov, 5(3):235-246, 2006.
Dittmer, "The biology of the Ets1 proto-oncogene," Mol Cancer, 2:29, 2003.
Dyer and Bremner, "The search for the retinoblastoma cell of origin," Nat Rev Cancer, 5(2):91-101, 2005.
Egle et al., "Bim is a suppressor of Myc-induced mouse B cell leukemia," Proc Natl Acad Sci U S A, 101(16):6164-6169, 2004.
Egloff et al., "Cyclin B1 and other cyclins as tumor antigens in immunosurveillance and immunotherapy of cancer," Cancer Res, 66(1):6-9, 2006.
Esser et al., "The role of sentinel lymph node mapping in staging of colon and rectal cancer," Dis Colon Rectum, 44(6):850-856, 2001.
European Search Report and Search Opinion issued in European Application No. 09154092.2, mailed Aug. 12, 2009.
Fakharzadeh et al., "Tumorigenic potential associated with enhanced expression of a gene that is amplified in a mouse tumor cell line," Embo J, 10(6):1565-1569, 1991.
Ferris at al., "Molecular staging of cervical lymph nodes in squamous cell carcinoma of the head and neck," Cancer Res., 65:2147-2156, 2005.

Gerald and Haber, "The EWS-WT1 gene fusion in desmoplastic small round cell tumor," *Semin Cancer Biol*, 15(3):197-205, 2005.

Gillanders et al., "Molecular detection of micrometastatic breast cancer in histopathology-negative axillary lymph nodes correlates with traditional predictors of prognosis: an interim analysis of a prospective multi-institutional cohort study," *Ann. Surg.*, 239:828-840, 2004.

Gilles et al., "Vimentin expression in cervical carcinomas: association with invasive and migratory potential," *J Pathol*, 180(2):175-180, 1996.

Gipponi et al., "Sentinel lymph node as a new marker for therapeutic planning in breast cancer patients," *J. Surg. Oncol.*, 85(3):102-111, 2004.

Gomez-Bougie et al., "The imbalance between Bim and Mcl-1 expression controls the survival of human myeloma cells," *Eur J Immunol*, 34(11):3156-3164, 2004.

Gonzalez et al., "Oncogenic activity of Cdc6 through repression of the INK4/ARF locus," *Nature*, 440(7084):702-706, 2006.

Goyns et al., "The c-ets-1 proto-oncogene is rearranged in some cases of acute lymphoblastic leukaemia," *Br J Cancer*, 56(5):611-613, 1987.

Hayette et al., "In B-cell chronic lymphocytic leukemias, 7q21 translocations lead to overexpression of the CDK6 gene," *Blood*, 102(4):1549-1550, 2003.

Ho et al., "Quantification of colorectal cancer micrometastases in lymph nodes by nested and real-time reverse transcriptase-PCR analysis for carcinoembryonic antigen," *Clin. Cancer Res.*, 10(17):5777-5784, 2004.

Hodge et al., "The role of IL-6 and STAT3 in inflammation and cancer," *Eur J Cancer*, 41(16):2502-2512, 2005.

Hoeflich et al., "Insulin-like growth factor-binding protein 2 in tumorigenesis: protector or promoter?" *Cancer Res*, 61(24):8601-8610, 2001.

Hofer et al., "The role of metastasis-associated protein 1 in prostate cancer progression," *Cancer Res*, 64(3):825-829, 2004.

Horoszewicz et al., "The LNCaP cell line—a new model for studies on human prostatic carcinoma," *Prog Clin Biol Res.*, 37:115-32, 1980.

Houston and O'Connell, "The Fas signalling pathway and its role in the pathogenesis of cancer," *Curr Opin Pharmacol*, 4(4):321-326, 2004.

Houvenaeghel et al., "Micrometastases in sentinel lymph node in a multicentric study: predictive factors of nonsentinel lymph node involvement—Groupe des Chirurgiens de la Federation des Centres de Lutte Contre le Cancer," *J. Clin. Oncol.*, 24:1814-1822, 2006.

Hsu et al., "BOD (Bcl-2-related ovarian death gene) is an ovarian BH3 domain-containing proapoptotic Bcl-2 protein capable of dimerization with diverse antiapoptotic Bcl-2 members," *Mol Endocrinol*, 12(9):1432-1440, 1998.

Huber et al., "Variance stabilization applied to microarray data calibration and to the quantification of differential expression," *Bioinformatics*, 18:Suppl 1:S96-104, 2002.

Hughes et al., "A rapid, fully automated, molecular-based assay accurately analyzes sentinel lymph nodes for the presence of metastatic breast cancer," *Ann. Surg.*, 243:389-398, 2006.

Iorio et al., "MicroRNA gene expression deregulation in human breast cancer," *Cancer Res*, 65(16):7065-7070, 2005.

Islam et al., "Vimentin expression in human squamous carcinoma cells: relationship with phenotypic changes and cadherin-based cell adhesion," *J Cell Biochem*, 78(1):141-150, 2000.

Jackson and Foster, "The enigmatic protein kinase Cdelta: complex roles in cell proliferation and survival," *Faseb J*, 18(6):627-636, 2004.

Jang et al., "MTA1 overexpression correlates significantly with tumor grade and angiogenesis in human breast cancers," *Cancer Sci*, 97(5):374-379, 2006.

Janknecht, "EWS-ETS oncoproteins: the linchpins of Ewing tumors," *Gene*, 363:1-14, 2005.

Jansen et al., "Two unrelated cell-derived sequences in the genome of avian leukemia and carcinoma inducing retrovirus MH2," *Embo J*, 2(11):1969-1975, 1983.

Kalin et al., "Increased levels of the FoxM1 transcription factor accelerate development and progression of prostate carcinomas in both TRAMP and LADY transgenic mice," *Cancer Res*, 66(3):1712-1720, 2006.

Kalinichenko et al., "Foxm1b transcription factor is essential for development of hepatocellular carcinomas and is negatively regulated by the p19ARF tumor suppressor," *Genes Dev*, 18(7):830-850, 2004.

Kammula et al., "Serial follow-up and the prognostic significance of reverse transcriptase-polymerase chain reaction—staged sentinel lymph nodes from melanoma patients," *J. Clin. Oncol.*, 22:3989-3996, 2004.

Kapsimali et al., "MicroRNAs show a wide diversity of expression profiles in the developing and mature central nervous system," *Genome Biol*, 8(8):R173, 2007.

Karakaidos et al., "Overexpression of the replication licensing regulators hCdt1 and hCdc6 characterizes a subset of non-small-cell lung carcinomas: synergistic effect with mutant p53 on tumor growth and chromosomal instability—evidence of E2F-1 transcriptional control over hCdt1," *Am J Pathol*, 165(4):1351-1365, 2004.

Karin et al., "NFf-kappaB in cancer: from innocent bystander to major culprit," *Nat Rev Cancer*, 2(4):301-310, 2002.

Kastan and Lim, "The many substrates and functions of ATM," *Nat Rev Mol Cell Biol*, 1(3):179-186, 2000.

Kim et al., "The Forkhead Box m1 transcription factor stimulates the proliferation of tumor cells during development of lung cancer," *Cancer Res*, 66(4):2153-2161, 2006.

Kiriakidou et al., "An mRNA m7G cap binding-like motif within human Ago2 represses translation," *Cell*, 129(6):1141-1151, 2007.

Kops et al., "On the road to cancer: aneuploidy and the mitotic checkpoint," *Nat Rev Cancer*, 5(10):773-785. 2005.

Kristjánsdóttir and Rudolph, "Cdc25 phosphatases and cancer," *Chem Biol*, 11(8):1043-1051, 2004.

Kuehbacher et al., "Targeting microRNA expression to regulate angiogenesis," *Trends Pharmacol Sci.*, 29(1):12-15, 2008.

Kuhajda, "Fatty acid synthase and cancer: new application of an old pathway," *Cancer Res*, 66(12):5977-5980, 2006.

Lagos-Quintana et al., "New microRNAs from mouse and human," *RNA*, 9(2):175-179, 2003.

Lam et al., "Expression of p19INK4d, CDK4, CDK6 in glioblastoma multiforme," *Br J Neurosurg*, 14(1):28-32, 2000.

Lee et al., "Altered microRNA expression in cervical carcinomas," *Clin Cancer Res*, 14(9):2535-2542, 2008.

Li et al., "Apoptosis of non-small-cell lung cancer cell lines after paclitaxel treatment involves the BH3-only proapoptotic protein Bim," *Cell Death Differ*, 12(3):292-303, 2005.

Li et al., "PDGF-D is a potent transforming and angiogenic growth factor," *Oncogene*, 22(10):1501-1510, 2003.

Liang et al., "Chacterization of microRNA expression profiles in normal human tissues," *BMC Genomics*, 8:166, 2007.

Liu and Erikson, "Polo-like kinase (Plk)1 depletion induces apoptosis in cancer cells," *Proc Natl Acad Sci U S A*, 100(10):5789-5794, 2003.

Lukiw, "Micro-RNA speciation in fetal, adult and Alzheimer's disease hippocampus," *Neuroreport*, 18(3):297-300, 2007.

Ma et al., "Tumour invasion and metastasis initiated by microRNA-10b in breast cancer," *Nature*, 449(7163):682-688, 2007.

Malumbres and Barbacid, "To cycle or not to cycle: a critical decision in cancer," *Nat Rev Cancer*, 1(3):222-231, 2001.

Marone et al., "Analysis of cyclin E and CDK2 in ovarian cancer: gene amplification and RNA overexpression," *Int J Cancer*, 75(1):34-39, 1998.

McInroy and Määttä, "Down-regulation of vimentin expression inhibits carcinoma cell migration and adhesion," *Biochem Biophys Res Commun*, 360(1):109-114, 2007.

Mendrzyk et al., "Genomic and protein expression profiling identifies CDK6 as novel independent prognostic marker in medulloblastoma," *J Clin Oncol*, 23(34):8853-8862, 2005.

Mishima et al., "RT-PCR-based analysis of microRNA (miR-1 and -124) expression in mouse CNS," *Brain Res*, 1131(1):37-43, Epub Dec 19, 2006. 2007.

Momand et al., "The MDM2 gene amplification database," *Nucleic Acids Res*, 26(15):3453-3459, 1998.

Morton et al., "Sentinel-node biopsy or nodal observation in melanoma," *N. Engl. J. Med.*, 355(13):1307-1317, 2006.
Morton et al., "Technical details of intraoperative lymphatic mapping for early stage melanoma," *Arch Surg*, 127(4):392-399, 1992.
Murphy et al., "p16INK4A, CDC6, and MCM5: predictive biomarkers in cervical preinvasive neoplasia and cervical cancer," *J Clin Pathol*, 58(5):525-534, 2005.
Nauert et al., "Gravin, an autoantigen recognized by serum from myasthenia gravis patients, is a kinase scaffold protein, " *Curr Biol*, 7(1):52-62, 1997.
Nerlov, "C/EBPalpha mutations in acute myeloid leukaemias," *Nat Rev Cancer*, 4(5):394-400, 2004.
Ngan et al., "Quantitative evaluation of vimentin expression in tumour stroma of colorectal cancer," *Br J Cancer*, 96(6):986-992, 2007.
Nordgård et al., "Quantitative RT-PCR detection of tumor cells in sentinel lymph nodes isolated from colon cancer patients with an ex vivo approach," *Annals of Surgery*, 249(4):602-607, 2009.
Öberg et al., "Detection of occult tumour cells in lymph nodes of colorectal cancer patients using real-time quantitative RT-PCR for CEA and CK20 mRNAS," *Int. J. Cancer*, 111(1):101-110, 2004.
O'Connor et al., "Bim: a novel member of the Bcl-2 family that promotes apoptosis," *Embo J*, 17(2):384-395, 1998.
Office Action issued in U.S. Appl. No. 11/837,490, mailed Aug. 18, 2009.
Office Action issued in U.S. Appl. No. 11/953,606, mailed Aug. 10, 2009.
Ohlsson et al., "Biomarker selection for detection of occult tumour cells in lymph nodes of colorectal cancer patients using real-time quantitative RT-PCR," *Br. J. Cancer*, 95(2):218-225, 2006.
Ohsaki et al., "Antitumor activity of magainin analogues against human lung cancer cell lines," *Cancer Res*, 52(13):3534-3538, 1992.
Ollila et al., "Metastatic melanoma cells in the sentinel node cannot be ignored," *J. Am. Coll. Surg.*, 208(5):924-929, 2009.
Paik et al., "FoxOs are lineage-restricted redundant tumor suppressors and regulate endothelial cell homeostasis," *Cell*, 128(2):309-323, 2007.
Paramo et al., "Validation of sentinel node mapping in patients with colon cancer," *Ann Surg Oncol*, 9(6):550-554, 2002.
Payton and Coats, "Cyclin E2, the cycle continues," *Int J Biochem Cell Biol*, 34(4):315-320, 2002.
Payton et al., "Deregulation of cyclin E2 expression and associated kinase activity in primary breast tumors," *Oncogene*, 21(55):8529-8534, 2002.
PCT International Preliminary Report on Patentability and Written Opinion, issued in International Application No. PCT/US2007/087033, mailed Jun. 18, 2009.
PCT International Preliminary Report on Patentability and Written Opinion, issued in International Application No. PCT/US2007/087031, mailed Jun. 18, 2009.
PCT International Preliminary Report on Patentability and Written Opinion, issued in International Application No. PCT/US2007/087029, mailed Jun. 18, 2009.
PCT International Preliminary Report on Patentability and Written Opinion, issued in International Application No. PCT/US2007/087037, mailed Jun. 18, 2009.
PCT International Preliminary Report on Patentability and Written Opinion, issued in International Application No. PCT/US2007/086396, mailed Jun. 18, 2009.
PCT International Preliminary Report on Patentability and Written Opinion, issued in International Application No. PCT/US2007/087021, mailed Jun. 18, 2009.
PCT International Preliminary Report on Patentability and Written Opinion, issued in International Application No. PCT/US2007/089206, mailed Jun. 18, 2009.
PCT International Preliminary Report on Patentability and Written Opinion, issued in International Application No. PCT/US2007/087038, mailed Jun. 18, 2009.
PCT International Search Report and Written Opinion, issued in International Application No. PCT/US2008/085178, mailed Aug. 21, 2009.
PCT International Search Report and Written Opinion, issued in International Application No. PCT/US2009/033556, mailed Aug. 4, 2009.
PCT Invitation to Pay Additional Fees and Partial International Search, issued in International Application No. PCT/US2009/043361, mailed Jul. 22, 2009.
PCT Invitation to Pay Additional Fees and Partial International Search, issued in International Application No. PCT/US2009/036195, mailed Jul. 2, 2009.
PCT Invitation to Pay Additional Fees and Partial International Search, issued in International Application No. PCT/US2009/033556, mailed Jun. 5, 2009.
Pendas et al., "Worldwide experience with lymphatic mapping for invasive breast cancer," *Semin. Oncol.*, 31(3):318-323, 2004.
Phan et al., "Sentinel lymph node biopsy for melanoma: indications and rationale," *Cancer Control*, 16(3):234-239, 2009.
Pietras et al., "PDGF receptors as cancer drug targets," *Cancer Cell*, 3(5):439-443, 2003.
Pretlow et al., "K-ras mutations in putative preneoplastic lesions in human colon," *J. Natl Cancer Inst.*, 85(24):2004-2007, 1993.
Qian et al., "Expression profiling of CD34+ hematopoietic stem/progenitor cells reveals distinct subtypes of therapy-related acute myeloid leukemia," *Proc Natl Acad Sci U S A*, 99(23):14925-14930, 2002.
Quan et al., "The evolution of lymph node assessment in breast cancer," *Journal of Surgical Oncology*, 2008.
Rapp et al., "Structure and biological activity of v-raf, a unique oncogene transduced by a retrovirus," *Proc Natl Acad Sci U S A*, 80(14):4218-4222, 1983.
Redston et al., "Analysis of micrometastatic disease in sentinel lymph nodes from resectable colon cancer: results of Cancer and Leukemia Group B Trial 80001," *J. Clin. Oncol.*, 24(6):878-883, 2006.
Reintgen et al., "Sentinel Node Biopsy in Breast Cancer: An Overview," *Breast J.*, 6(5):299-305, 2000.
Reshmi and Pillai, "Beyond HPV: oncomirs as new players in cervical cancer," *FEBS Letters*, 582:4113-4116, 2008.
Roberts et al., "Interpretive disparity among pathologists in breast sentinel lymph node evaluation," *Am. J. Surg.*, 186:324-329, 2003.
Rous, "A sarcoma of the fowl transmissible by an agent separable from the tumor cells," *J Exp Med*, 13:397-411, 1911.
Ryan et al., "MicroRNAs of the mammalian eye display distinct and overlapping tissue specificity," *Molecular Vision*, 12:1175-1184, 2006.
Saha et al., "Historical review of lymphatic mapping in gastrointestinal malignancies," *Ann Surg Oncol*, 11(3 Suppl):245S-249S, 2004.
Saha et al., "Ultrastaging of colorectal cancer by sentinel lymph node mapping technique—a multicenter trial," *Ann. Surg. Oncol.*, 8(9 Suppl):94S-98S, 2001.
Sasaki et al., "Expression of the MTA1 mRNA in advanced lung cancer," *Lung Cancer*, 35(2):149-154, 2002.
Schepeler et al., "Diagnostic and prognostic microRNAs in stage II colon cancer," *Cancer Research*, 68(15):6416-6424, 2008.
Schetter et al., "MicroRNA expression profiles associated with prognosis and therapeutic outcome in colon adenocarcinoma," *JAMA*, 299(4):425-436, 2008.
Schurr et al., "Lymphatic spread and microinvolvement in adenocarcinoma of the esophago-gastric junction," *J. Surg. Oncol.*, 94:307-315, 2006.
Schuster and Porse, "C/EBPalpha: a tumour suppressor in multiple tissues?" *Biochim Biophys Acta*, 1766(1):88-103, 2006.
Scoggins et al., "Prospective multi-institutional study of reverse transcriptase polymerase chain reaction for molecular staging of melanoma," *J. Clin. Oncol.*, 24:2849-2857, 2006.
Semple and Duncker, "ORC-associated replication factors as biomarkers for cancer," *Biotechnol Adv*, 22(8):621-631, 2004.
Shen et al., "MicroRNAs regulate ocular neovascularization," *Molecular Therapy*, 16(7):1208-1216, 2008.
Shen et al., "Suppression of ocular neovascularization with siRNA targeting VEGF receptor 1," *Gene Therapy*, 13:225-234, 2006.
Sherr and McCormick, "The RB and p53 pathways in cancer," *Cancer Cell*, 2(2):103-112, 2002.

Sherr and Roberts, "CDK inhibitors: positive and negative regulators of G1-phase progression," *Genes Dev*, 13(12):1501-1512, 1999.

Singh et al., "Overexpression of vimentin: role in the invasive phenotype in an androgen-independent model of prostate cancer," *Cancer Res*, 63(9):2306-2311, 2003.

Slaby et al., "Altered expression of miR-21, miR-31, miR-143 and miR-145 is related to clinicopathologic features of colorectal cancer," *Oncology*, 72(5-6):397-402, 2007.

Smirnova et al., "Regulation of miRNA expression during neural cell specification," *Eur J Neurosci*, 21(6):1469-1477, 2005.

Smith et al., "Overexpression of aurora B kinase (AURKB) in primary non-small cell lung carcinoma is frequent, generally driven from one allele, and correlates with the level of genetic instability," *Br J Cancer*, 93(6):719-729, 2005.

Sommers et al., "Loss of epithelial markers and acquisition of vimentin expression in adriamycin- and vinblastine-resistant human breast cancer cell lines," *Cancer Res*, 52(19):5190-5197, 1992.

Stehelin et al., "DNA related to the transforming gene(s) of avian sarcoma viruses is present in normal avian DNA," *Nature*, 260(5547):170-173, 1976.

Swanson et al., "The prognosis of T3N0 colon cancer is dependent on the number of lymph nodes examined," *Ann. Surg. Oncol.*, 10(1):65-71, 2003.

Tagawa et al., "Genome-wide array-based CGH for mantle cell lymphoma: identification of homozygous deletions of the proapoptotic gene BIM," *Oncogene*, 24(8):1348-1358, 2005.

Takeuchi et al., "Prognostic significance of molecular upstaging of paraffin-embedded sentinel lymph nodes in melanoma patients," *J. Clin. Oncol.*, 22:2671-2680, 2004.

Toh et al., "A novel candidate metastasis-associated gene, mta1, differentially expressed in highly metastatic mammary adenocarcinoma cell lines. cDNA cloning, expression, and protein analyses," *J Biol Chem*, 269(37):22958-22963, 1994.

Toh et aL, "Overexpression of metastasis-associated MTA1 mRNA in invasive oesophageal carcinomas," *Br J Cancer*, 79(11-12):1723-1726, 1999.

Toh et al., "Overexpression of the MTA1 gene in gastrointestinal carcinomas: correlation with invasion and metastasis," *Int J Cancer*, 74(4):459-463, 1997.

Tsai et al., "Correlation of intrinsic chemoresistance of non-small-cell lung cancer cell lines with HER-2/neu gene expression but not with ras gene mutations," *J Natl Cancer Inst*, 85(11):897-901,1993.

Turner et al., "Hallmarks of 'BRCAness' in sporadic cancers," *Nat Rev Cancer*, 4(10):814-819, 2004.

Tuveson et al., "BRAF as a potential therapeutic target in melanoma and other malignancies," *Cancer Cell*, 4(2):95-98, 2003.

Upton et al., "Expression of vimentin in surgically resected adenocarcinomas and large cell carcinomas of lung," *Am J Surg Pathol*, 10(8):560-567, 1986.

Vanhaesebroeck et al., "Phosphoinositide 3-kinases: a conserved family of signal transducers," *Trends Biochem Sci*, 22(7):267-272, 1997.

Vogt et al., "Triple layer control: phosphorylation, acetylation and ubiquitination of FOXO proteins," *Cell Cycle*, 4(7):908-913, 2005.

Wagner and Sondak, "The sentinel lymph node: more than just another blue lymph node," *Cancer*, 97(8):1821-1823, 2003.

Wang et al., "Aberrant expression of oncogenic and tumor-suppressive microRNAs in cervical cancer is required for cancer cell growth," *PLoS One*, 3(7):e2557, 2008.

Wang et al., "Increased levels of forkhead box M1B transcription factor in transgenic mouse hepatocytes prevent age-related proliferation defects in regenerating liver," *Proc Natl Acad Sci U S A*, 98(20):11468-11473, 2001.

Wang et al., "Oncogenic HPV infection interrupts the expression of tumor-suppressive miR-34a through viral oncoprotein E6," *RNA*, 15(4):637-647, 2009.

Weil et al., "Targeting the kinesin Eg5 to monitor siRNA transfection in mammalian cells," *Biotechniques*, 33(6):1244-1248, 2002.

Wiemer, "The role of microRNAs in cancer: no small matter," *Eur J Cancer*, 43(10):1529-1544, 2007.

Wong et al., "Number of nodes examined and staging accuracy in colorectal carcinoma," *J. Clin. Oncol.*, 17(9):2896-2900, 1999.

Wood et al., "One hundred consecutive cases of sentinel lymph node mapping in early colorectal carcinoma: detection of missed micrometastases," *J. Gastrointest Surg.*, 6(3):322-330, 2002.

Xi et al., "A combination of molecular markers accurately detects lymph node metastasis in non-small cell lung cancer patients," *Clin. Cancer Res.*, 12:2484-2491, 2006.

Xi et al., "Identification of mRNA markers for molecular staging of lymph nodes in colorectal cancer," *Clin. Chem.*, 52(3):520-523, 2006.

Xi et al., "Molecular staging of lymph nodes from patients with esophageal adenocarcinoma," *Clin. Cancer Res.*, 11:1099-1109, 2005.

Yamamoto et al., "Cdk2/cdc2 expression in colon carcinogenesis and effects of cdk2/cdc2 inhibitor in colon cancer cells," *Int J Oncol*, 13(2):233-239, 1998.

Yeatman, "A renaissance for SRC," *Nat Rev Cancer*, 4(6):470-480, 2004.

Yi et al., "The association of the expression of MTA1, nm23H1 with the invasion, metastasis of ovarian carcinoma," *Chin Med Sci J*, 18(2):87-92, 2003.

Yu et al., "Crosstalk between cancer and immune cells: role of STAT3 in the tumour microenvironment," *Nat Rev Immunol*, 7(1):41-51, 2007.

Zhang et al., "Enhancement of hematopoietic stem cell repopulating capacity and self-renewal in the absence of the transcription factor C/EBP alpha," Immunity, 21(6):853-863, 2004.

Agrawal and Kandimalla, "Antisense therapeutics: is it as simple as complementary base recognition," *Molecular Medicine Today*, 6:72-81, 2000.

Benlloch et al., "Role of CEA, PLUNC and CK19 mRNA expression in lymph nodes from resected stage I non-small cell lung cancer (NSCLC) patients as markers of occult micrometastasis: A pilot study," *Lung Cancer*, Abstract No. P-649, 49(1):S289, 2005.

Chirila et al., "The use of synthetic polymers for delivery of therapeutic antisense oligodeoxynucleotides," *Biomaterials*, 23:321-342, 2002.

Crooke, "Progress in antisense technology," *Annu. Rev. Med.*, 55:61-95, 2004.

Jang et al., "Gene delivery from polymer scaffolds for tissue engineering," *Expert Rev. Medical Devices*, 1(1):127-138, 2004.

Logsdon et al., "Molecular profiling of pancreatic adenocarcinoma and chronic pancreatitis identifies multiple genes differentially regulated in pancreatic cancer," *Cancer Research*, 63:2649-2657, 2003.

Office Action issued in Australian Application No. 2005250432, mailed Aug. 25, 2010.

Office Action issued in European Application No. 07871756.8, mailed Jun. 30, 2010.

Office Action issued in European Application No. 08770269.2, mailed Jul. 30, 2010.

Office Action issued in U.S. Appl. No. 11/141,707, mailed Sep. 2, 2010.

Office Action issued in U.S. Appl. No. 11/837,495, mailed Sep. 2, 2010.

Office Action issued in U.S. Appl. No. 11/857,948, mailed Aug. 24, 2010.

Office Action issued in U.S. Appl. No. 11/953,606, mailed Jul. 1, 2010.

Office Action issued in U.S. Appl. No. 12/120,388, mailed Jul. 21, 2010.

Office Action issued in U.S. Appl. No. 12/167,492, mailed Aug. 12, 2010.

Office Action issued in U.S. Appl. No. 12/253,718, mailed Jun. 11, 2010.

Office Action issued in U.S. Appl. No. 12/368,053, mailed Aug. 19, 2010.

Office Action issued in U.S. Appl. No. 12/420,634, mailed Aug. 30, 2010.

Office Action issued in U.S. Appl. No. 12/616,616, mailed Aug. 13, 2010.

Opalinska and Gewirtz, "Nucleic-acid therapeutics: basic principles and recent applications," *Nature Reviews*, 1:503-514, 2002.

PCT International Preliminary Report on Patentability and Written Opinion issued in International Application No. PCT/US2008/080318, mailed Apr. 29, 2010.
PCT International Preliminary Report on Patentability and Written Opinion issued in International Application No. PCT/US2008/085178, mailed Jun. 10, 2010.
PCT International Preliminary Report on Patentability and Written Opinion issued in International Application No. PCT/US2008/087762, mailed Jul. 1, 2010.
PCT International Search Report and Written Opinion issued in International Application No. PCT/US2009/064015, mailed Jul. 26, 2010.
Peracchi, "Prospects for antiviral ribozymes and deoxyribozymes," Rev. Med. Virol., 14:47-64, 2004.
Al-Hajj et al., "Prospective identification of tumorigenic breast cancer cells," Proc. Natl. Acad. Sci. U S A, 100(7):3983-8, 2003.*
Bao et al., "Glioma stem cells promote radioresistance by preferential activation of the DNA damage response," Nature, 444(7120):756-60, 2006.*
Bartel, "MicroRNAs: genomics, biogenesis, mechanism, and function," Cell, 116:281-297, 2004.*
Basturk et al., "MicroRNA expression in androgen independent and metastatic prostate cancer," Modern Pathology, Abstract No. 669, 21(Suppl. 1):148A, 2008.
Beier et al., "CD133(+) and CD133(−) glioblastoma-derived cancer stem cells show differential growth characteristics and molecular profiles," Cancer Res., 67(9):4010-5, 2007.
Ben-Porath et al., "An embryonic stem cell-like gene expression signature in poorly differentiated aggressive human tumors," Nat. Genet., 40(5):499-507, 2008.
Berman et al., "Medulloblastoma growth inhibition by hedgehog pathway blockade," Science, 297(5586):1559-61, 2002.
Birnie et al., "Gene expression profiling of human prostate cancer stem cells reveals a pro-inflammatory phenotype and the importance of extracellular matrix interactions," Genome Biol., 9(5):R83. [Epub ahead of print], 2008.
Blower et al., "MicroRNAs modualte the chemosensitivity of tumor cells," Mol Cancer Ther, 7(1):1-9, 2008.
Bonci et al., "The miR-15A/miR-16-1 cluster controls prostate cancer progression by targeting multiple oncogenic activities," European Urology Supplements, Abstract No. 802, 7(3):271, 2008.
Bourguignon et al., "Hyaluronan-CD44 interaction activates stem cell marker Nanog, Stat-3-mediated MDR1 gene expression, and ankyrin-regulated multidrug efflux in breast and ovarian tumor cells," J. Biol. Chem., 283(25): 17635-51, 2008.
Büssing et al.,"let-7 microRNAs in development, stem cells and cancer," Trends in Molecular Medicine, 14(9):400-409, 2008.
Clement et al., "HEDGEHOG-GLI1 signaling regulates human glioma growth, cancer stem cell self-renewal, and tumorigenicity," Curr. Biol., 17(2): 165-72, 2007.
Collins et al., "Prospective identification of tumorigenic prostate cancer stem cells," Cancer Res., 65(23):10946-51, 2005.
Cummins et al., "The colorectal microRNAome," Proc. Natl. Acad. Sci. USA, 103(10):3687-3692, 2006.
Dai et al., "Prostate cancer induces bone metastasis through Wnt-induced bone morphogenetic protein-dependent and independent mechanisms," Cancer Res., 68(14): 5785-94, 2008.
Declaration of Dr. David P. Bartel under 37 C.F.R. 1.132, submitted in U.S. Appl. No. 10/913,288, 2009.
Dontu et al., "In vitro propagation and transcriptional profiling of human mammary stem/progenitor cells," Genes Dev., 17:1253-70, 2003.
Doyle and Ross, "Multidrug resistance mediated by the breast cancer resistance protein BCRP (ABCG2)," Oncogene, 22(47):7340-58, 2003.
Dröge and Davey, "Do cells let-7 determine stemness?" Cell Stem Cell, 2(1):8-9, 2008.
Dylla et al., "Colorectal cancer stem cells are enriched in xenogeneic tumors following chemotherapy," PLoS One, 3(6):e2428, 13 pages, 2008.
Engelmann et al., "MCF7 side population cells with characteristics of cancer stem/progenitor cells express the tumor antigen MUC1," Cancer Res., 68(7):2419-26, 2008.
Esquela-Kerscher et al., "The let-7 microRNA reduces tumor growth in mouse models of lung cancer," Cell Cycle, 7(6):759-764, 2008.
Fan et al., "Hedgehog signaling promotes prostate xenograft tumor growth," Endocrinology, 145: 3961-3970, 2004.
Fan et al., "Notch pathway inhibition depletes stem-like cells and blocks engraftment in embryonal brain tumors," Cancer Res., 66(15): 7445-52, 2006.
Francipane et al., "Crucial role of interleukin-4 in the survival of colon cancer stem cells," Cancer Res., 68 (11):4022-4025, 2008.
Ginestier et al., "ALDH1 is a marker of normal and malignant human mammary stem cells and a predictor of poor clinical outcome," Cell Stem Cell, 1(5):555-567, 2007.
Goodell et al., "Isolation and functional properties of murine hematopoietic stem cells that are replicating in vivo," J. Exp. Med., 183(4):1797-806, 1996.
Gu et al., "Prostate cancer cells with stem cell characteristics reconstitute the original human tumor in vivo," Cancer Res., 67(10):4807-15, 2007.
Hambardzumyan et al., "PI3K pathway regulates survival of cancer stem cells residing in the perivascular niche following radiation in medulloblastoma in vivo," Genes Dev., 22(4):436-48, 2008.
Hermann et al., "Distinct populations of cancer stem cells determine tumor growth and metastatic activity in human pancreatic cancer," Cell Stem Cell, 1(3):313-23, 2007.
Hirschmann-Jax et al., "A distinct "side population" of cells with high drug efflux capacity in human tumor cells," Proc. Natl. Acad. Sci. USA, 101:14228-33, 2004.
Ho et al., "MDR1 and BCRP1 expression in leukemic progenitors correlates with chemotherapy response in acute myeloid leukemia," Exp. Hematol., 36(4): 433-42, 2008.
Hurt et al., "CD44+ CD24(−) prostate cells are early cancer progenitor/stem cells that provide a model for patients with poor prognosis," Br. J. Cancer, 98(4):756-65, 2008.
Ibarra et al., "A role for microRNAs in maintenance of mouse mammary epithelial progenitor cells", Genes Dev., 21(24):3238-3243, 2007.
Isbarn et al., "Association of numerous micro-RNAs (µRNAs) with prostate cancer initiation and progression," European Urology Supplements, Abstract No. 429, 6(2):130, 2007.
Jamieson et al., "Granulocyte-macrophage progenitors as candidate leukemic stem cells in blast-crisis CML," N. Engl. J. Med., 351(7):657-67, 2004.
Jiang et al., "Real-time expression profiling of microRNA precursors in human cancer cell lines," Nucleic Acids Research, 33(17):5394-5403, 2005.
Johnson et al., "The let-7 microRNA represses cell proliferation pathways in human cells," Cancer Res, 67(16):7713-7722, 2007.
Karhadkar et al., "Hedgehog signalling in prostate regeneration, neoplasia and metastasis," Nature, 431(7009):707-12, 2004.
Keshet et al., "MDR1 expression identifies human melanoma stem cells," Biochem. Biophys. Res. Commun., 368(4):930-6, 2008.
Konopleva et al., "Mechanisms of apoptosis sensitivity and resistance to the BH3 mimetic ABT-737 in acute myeloid leukemia," Cancer Cell, 10(5):375-88, 2006.
Kumar et al., "Suppression of non-small cell lung tumor development by the let-7 microRNA family," PNAS, 105(10):3903-3908, 2008.
Lanza et al., "mRNA/microRNA gene expression profile in microsatellite unstable colorectal cancer," Molec Cancer, 6:54, 2007.
Lechner et al., "Nestin-positive progenitor cells derived from adult human pancreatic islets of Langerhans contain side population (SP) cells defined by expression of the ABCG2 (BCRP1) ATP-binding cassette transporter," Biochem. Biophys. Res. Commun., 293(2):670-674, 2002.
Leong and Gao, "The Notch pathway in prostate development and cancer," Differentiation, 76(6): 699-716, 2008.
Lessard and Sauvageau, "Bmi-1 determines the proliferative capacity of normal and leukaemic stem cells," Nature, 423(6937):255-60, 2003.
Li et al., "Evidence that transgenes encoding components of the Wnt signaling pathway preferentially induce mammary cancers from progenitor cells," Proc Natl Acad Sci USA, 100(26):15853-8, 2003.
Li et al., "Intrinsic resistance of tumorigenic breast cancer cells to chemotherapy," J. Natl. Cancer Inst., 100(9):672-9, 2008.

Li at al., "Mutant TNFalpha negatively regulates human breast cancer stem cells from MCF7 in vitro," *Cancer Biol. Ther.*, 6(9):1480-9, 2007.

Liu et al., "Functional studies of BCL11A: characterization of the conserved BCL11A-XL splice variant and its interaction with BCL6 in nuclear paraspeckles of germinal center B cells," *Mol. Cancer*, 5:18, 2006.

Liu et al., "Hedgehog signaling and Bmi-1 regulate self-renewal of normal and malignant human mammary stem cells," *Cancer Res.*, 66(12):6063-71, 2006.

Liu et al., "Sex-determining region Y box 4 is a transforming oncogene in human prostate cancer cells," *Cancer Res.*, 66(8):4011-9, 2006.

Liu et al., "The prognostic role of a gene signature from tumorigenic breast-cancer cells," *N. Engl. J. Med.*, 356(3):217-26, 2007.

Lu et al., "Defined culture conditions of human embryonic stem cells," *Proc. Natl. Acad. Sci. USA*, 103(15): 5688-93, 2006.

Maitland & Collins, "Prostate cancer stem cells: a new target for therapy", *J Clin Oncol.*, 26(17):2862-70, 2008. (Abstract).

Malanchi et al., "Cutaneous cancer stem cell maintenance is dependent on beta-catenin signalling," *Nature*, 452(7187):650-3, 2008.

Miki & Rhim, "Prostate cell cultures as in vitro models for the study of normal stem cells and cancer stem cells", *Prost. Can. Prost. Dis.*, 11:32-39, 2008.

Miki et al., "Identification of putative stem cell markers, CD133 and CXCR4, in hTERT-immortalized primary nonmalignant and malignant tumor-derived human prostate epithelial cell lines and in prostate cancer specimens," *Cancer Res.*, 67(7):3153-61, 2007.

Nykänen et al., "ATP requirements and small interfering RNA structure in the RNA interference pathway," *Cell*, 107:309-321, 2001.

Office Action issued in European Application No. 05858321.2., mailed Apr. 16, 2010.

Office Action issued in European Application No. 09154092.2, mailed Apr. 1, 2010.

Office Action issued in U.S. Appl. No. 11/141,707, mailed Mar. 11, 2010.

Office Action issued in U.S. Appl. No. 11/273,640, mailed May 5, 2010.

Office Action issued in U.S. Appl. No. 11/837,487, mailed May 28, 2010.

Office Action issued in U.S. Appl. No. 11/837,490, mailed Apr. 9, 2010.

Office Action issued in U.S. Appl. No. 11/837,498, mailed May 7, 2010.

Office Action issued in U.S. Appl. No. 11/857,948, mailed May 25, 2010.

Office Action issued in U.S. Appl. No. 11/967,639, mailed May 14, 2010.

Office Action issued in U.S. Appl. No. 11/967,639, mailed Mar. 24, 2010.

Office Action issued in U.S. Appl. No. 12/112,291, mailed Mar. 1, 2010.

Office Action issued in U.S. Appl. No. 12/125,675, mailed Apr. 22, 2010.

Office Action issued in U.S. Appl. No. 12/134,932, mailed Mar. 24, 2010.

Office Action issued in U.S. Appl. No. 12/420,634, mailed May 26, 2010.

Patrawala et al., "Hierarchical organization of prostate cancer cells in xenograft tumors: the CD44+alpha2beta1+ cell population is enriched in tumor-initiating cells," *Cancer Res.*, 67(14):6796-805, 2007.

Patrawala et al., "Highly purified CD44+ prostate cancer cells from xenograft human tumors are enriched in tumorigenic and metastatic progenitor cells," *Oncogene*, 25(12):1696-708, 2006.

Patrawala et al., "MicroRNAs in prostate cancer stem cells", AACR Cancer Stem Cell Special Conference—Los Angeles, Feb 12-15 2008.

Patrawala et al., "Side population is enriched in tumorigenic, stem-like cancer cells, whereas ABCG2+ and ABCG2− cancer cells are similarly tumorigenic," *Cancer Res.*, 65(14):6207-19, 2005.

PCT International Preliminary Report on Patentability issued in International Application No. PCT/US2008/076246, mailed Mar. 16, 2010.

PCT International Search Report and Written Opinion issued in International Application No. PCT/US2008/087762, mailed Mar. 16, 2010.

PCT International Search Report and Written Opinion issued in International Application No. PCT/US2009/038399, mailed Mar. 3, 2010.

PCT International Search Report and Written Opinion issued in International Application No. PCT/US2009/064015, mailed May 11, 2010.

Peacock et al., "Hedgehog signaling maintains a tumor stem cell compartment in multiple myeloma," *Proc. Natl. Acad. Sci. USA*, 104(10):4048-53, 2007.

Peng et al., "Overexpression of microRNA let-7c in prostate cancer," *Modern Pathology*, Abstract No. 788, 20 (Suppl. 2):169A, 2007.

Reiter and Sawyers, "Xenograft models and the molecular biology of human prostate cancer," In :*Prostate Cancer: Biology, Genetics, and the New Therapeutics*, Totowa, NJ, 163-173, 2001.

Richardson et al., "CD133, a novel marker for human prostatic epithelial stem cells," *J. Cell Sci.*, 117(Pt 16):3539-45, 2004.

Schwarz et al., "Asymmetry in the assembly of the RNAi enzyme complex," *Cell*, 115:199-208, 2003.

Shepherd et al., "Expression profiling of CD133+ and CD133− epithelial cells from human prostate," *Prostate*, 68(9):1007-1024, 2008.

Shipitsin et al., "Molecular definition of breast tumor heterogeneity," *Cancer Cell*, 11(3):259-73, 2007.

Singh et al., "Identification of a cancer stem cell in human brain tumors," *Cancer Res.*, 63(18):5821-8, 2003.

Sinner et al., "Sox1 7 and Sox4 differentially regulate beta-catenin/T-cell factor activity and proliferation of colon carcinoma cells," *Mol. Cell Biol.*, 27(22):7802-15, 2007.

Takeshita et al., "Systemic delivery of synthetic microRNA-16 inhibits the growth of metastatic prostate tumors via downregulation of multiple cell-cycle genes," *Molecular Therapy*, 18(1):181-187, 2010.

Tang et al., "Prostate cancer stem/progenitor cells: identification, characterization, and implications," *Mol. Carcinog.*, 46(1):1-14, 2007.

Tang et al., "Transforming growth factor-beta can suppress tumorigenesis through effects on the putative cancer stem or early progenitor cell and committed progeny in a breast cancer xenograft model," Cancer Res., 67(18):8643-52, 2007.

Thiyagarajan et al., "Role of GLI2 transcription factor in growth and tumorigenicity of prostate cells," *Cancer Res.*, 67(22):10642-6, 2007.

Tijsterman and Plasterk, "Dicers at RISC: the mechanism of RNAi," *Cell*, 117:1-4, 2004.

Tockman et al., "Considerations in bringing a cancer biomarker to clinical application," *Cancer Research*, 52:2711s-2718s, 1992.

Trang et al., "Regression of murine lung tumors by the *let-7* microRNA," *Oncogene*, 29(11):1580-1587, Epub 2009.

U.S. Appl. No. 10/778,908, entitled "Anti-microRNA oligonucleotide molecules," by Thomas Tuschl et al., filed Feb. 13, 2004.

U.S. Appl. No. 60/869,295 entitled "MicroRNAs Differentially Expressed in Leukemia and Uses Thereof" by Tim Davison, et al., submitted Dec. 8, 2006.

Vermeulen et al., "Single-cell cloning of colon cancer stem cells reveals a multi-lineage differentiation capacity," *PNAS*, 105(360):13427-13432, 2008.

Vezina & Bushman, "Hedgehog signaling in prostate growth and benign prostate hyperplasia," *Curr. Urol. Rep.*, 8(4): 275-80, 2007.

Wang & Dick, "Cancer stem cells:lessons from leukemia", *Trends Cell Biol.*, 15(9):494-501, 2005.

Wang et al., "Pten deletion leads to the expansion of a prostatic stem/progenitor cell subpopulation and tumor initiation," *Proc. Natl. Acad. Sci. USA*, 103(5):1480-1485, 2006.

Watabe et al., "Growth, regeneration, and tumorigenesis of the prostate activates the PSCA promoter," *Proc Natl Acad Sci USA*, 99(1):401-6, 2002.

Weidhaas et al., "MicroRNAs as potential agents to alter resistance to cytotoxic anticancer therapy," *Cancer Res*, 67(23):11111-11116, 2007.

Willert et al., "Wnt proteins are lipid-modified and can act as stem cell growth factors," *Nature*, 423(6938):448-52, 2003.

Xi et al., "Differentially regulated micro-RNAs and actively translated messenger RNA transcripts by tumor suppressor p53 in colon cancer," *Clin Cancer Res.*, 12:2014-2024, 2006b.

Xi et al., "Prognostic Values of microRNAs in Colorectal Cancer," *Biomark Insights*, 2:113-121, 2006a.

Yang et al., "Significance of CD90+ cancer stem cells in human liver cancer," *Cancer Cell*, 13(2):153-66, 2008.

Yu et al., "*let-7* regulates self renewal and tumorigenicity of breast cancer cells," *Cell*, 131:1109-1123, 2007.

Zhang et al., "Identification and characterization of ovarian cancer-initiating cells from primary human tumors," *Cancer Res.*, 68(11):4311-20, 2008.

Zhang et al., "NANOGP8 is a retrogene expressed in cancers," *FEBS J.*, 273(8):1723-30, 2006.

Zhou et al., "Activation of the PTEN/mTOR/STAT3 pathway in breast cancer stem-like cells is required for viability and maintenance," *Proc. Natl. Acad. Sci. USA*, 104(41):16158-63, 2007.

Zhou et al., "The ABC transporter Bcrp1/ABCG2 is expressed in a wide variety of stem cells and is a molecular determinant of the side-population phenotype," *Nat. Med.*, 7(9):1028-1034, 2001.

Extended European Search Report issued in European Application No. 10183451.3, mailed Jan. 12, 2011.

Extended European Search Report issued in European Application No. 10183456.2, mailed Jan. 12, 2011.

Extended European Search Report issued in European Application No. 10183481.0, mailed Jan. 7, 2011.

Extended European Search Report issued in European Application No. 10183538.7, mailed Jan. 12, 2011.

Extended European Search Report issued in European Application No. 10183560.1, mailed Jan. 7, 2011.

Extended European Search Report issued in European Application No. 10183567.6, mailed Jan. 7, 2011.

Extended European Search Report issued in European Application No. 10183589.0, mailed Jan. 7, 2011.

Extended European Search Report issued in European Application No. 10183611.2, mailed Jan. 7, 2011.

Office Action issued in Japanese Application No. 2007-515415, mailed Jan. 26, 2011 (and English language translation thereof).

Office Action issued in U.S. Appl. No. 11/837,488, mailed Feb. 15, 2011.

Office Action issued in U.S. Appl. No. 11/837,494, mailed Dec. 9, 2010.

Office Action issued in U.S. Appl. No. 11/857,948, mailed Jan. 26, 2011.

Office Action issued in U.S. Appl. No. 12/125,675, mailed Jan. 28, 2011.

Office Action issued in U.S. Appl. No. 12/134,932, mailed Feb. 24, 2011.

Office Action issued in U.S. Appl. No. 12/167,492, mailed Feb. 25, 2011.

Office Action issued in U.S. Appl. No. 12/368,053, mailed Dec. 21, 2010.

Suh et al., "Human embryonic stem cells express a unique set of microRNAs," *Developmental Biology*, 270:488-498, 2004.

Extended European Search Report issued in European Application No. 10183577.5, mailed Feb. 14, 2011.

Extended European Search Report issued in European Application No. 10183543.7, mailed Feb. 4, 2011.

Extended European Search Report issued in European Application No. 10183534.5, mailed Feb. 15, 2011.

Extended European Search Report issued in European Application No. 10183525.4, mailed Feb. 7, 2011.

Extended European Search Report issued in European Application No. 10183596.5, mailed Feb. 14, 2011.

Extended European Search Report issued in European Application No. 10183490.1, mailed Feb. 4, 2011.

Extended European Search Report issued in European Application No. 10183515.5, mailed Feb. 7, 2011.

Extended European Search Report issued in European Application No. 10183462.0, mailed Feb. 4, 2011.

Extended European Search Report issued in European Application No. 10183470.3, mailed Feb. 3, 2011.

Extended European Search Report issued in European Application No. 10183639.3, mailed Mar. 2, 2011.

Mourelatos et al., "miRNPs: a novel class of ribonucleoproteins containing numerous microRNAs," *Genes & Development*, 16:720-728, 2002.

Notice of Allowance issued in U.S. Appl. No. 11/141,707, mailed Oct. 4, 2010.

Notice of Allowance issued in U.S. Appl. No. 11/837,490, mailed Apr. 1, 2011.

Notice of Allowance issued in U.S. Appl. No. 11/837,495, mailed Dec. 2, 2010.

Office Action issued in Australian Application No. 2005250432, mailed Mar. 29, 2011.

Office Action issued in Australian Application No. 2005333165, mailed Feb. 7, 2011.

Office Action issued in Chinese Application No. 200780050263.1, mailed Mar. 28, 2011, and English language translation thereof. (Mrna:008CN).

Office Action issued in European Application No. 05 858 321.2, mailed Apr. 16, 2010.

Office Action issued in European Application No. 07 871 691.7, mailed Oct. 28, 2010.

Office Action issued in European Application No. 07 871 693.3, mailed Oct. 18, 2010.

Office Action issued in European Application No. 08 831 073.5, mailed Aug. 16, 2010.

Office Action issued in European Application No. 08831073.5, mailed Feb. 25, 2011.

Office Action issued in European Application No. 09 154 092.2, mailed Nov. 10, 2010.

Office Action issued in European Application No. 09717913.9, mailed Mar. 7, 2011.

Office Action issued in U.S. Appl. No. 11/837,487, mailed Nov. 22, 2010.

Office Action issued in U.S. Appl. No. 11/953,606, mailed Oct. 1, 2010.

Office Action issued in U.S. Appl. No. 12/125,675, mailed Oct. 14, 2010.

Office Action issued in U.S. Appl. No. 12/134,932, mailed Nov. 4, 2010.

Office Action issued in U.S. Appl. No. 12/209,822, mailed Mar. 15, 2011.

Office Action issued in U.S. Appl. No. 12/253,718, mailed Nov. 1, 2010.

Office Action issued in U.S. Appl. No. 12/340,329, mailed Sep. 28, 2010.

Office Action issued in U.S. Appl. No. 12/398,852, mailed Mar. 7, 2011.

Office Action issued in U.S. Appl. No. 12/437,899, mailed Mar. 7, 2011.

PCT International Preliminary Report on Patentability issued in International Application No. PCT/US2009/033556, mailed Aug. 19, 2010.

PCT International Preliminary Report on Patentability issued in International Application No. PCT/US2009/036195, mailed Sep. 16, 2010.

PCT International Preliminary Report on Patentability issued in International Application No. PCT/US2009/038399, mailed Oct. 7, 2010.

PCT International Preliminary Report on Patentability issued in International Application No. PCT/US2009/039935, mailed Oct. 21, 2010.

PCT International Preliminary Report on Patentability issued in International Application No. PCT/US2009/043361, mailed Nov. 18, 2010.

Takeshita et al., "Efficient delivery of small interfering RNA to bone-metastatic tumors by using atelocollagen in vivo," *PNAS*, 102(34):12177-12182, 2005.

Mansfield et al., "MicroRNA-responsive 'sensor' transgenes uncover Hox-like and other developmentally regulated patterns of vertebrate microRNA expression," *Nature Genetics*, 36(10):1079-1083, 2004.

Office Action issued in Australian Application No. 2005250432, mailed Jun. 10, 2001.

Office Action issued in Chinese Application No. 200780050263.1, issued Mar. 28, 2011.

Office Action issued in European Application No. 07 814 937.4, mailed Apr. 8, 201.

Office Action issued in European Application No. 09 154 092.2, mailed Mar. 30, 2011.

Office Action issued in Japanese Application No. 2007-541398, dated Mar. 28, 2011.

Office Action issued in U.S. Appl. No. 12/167,492, mailed Jun. 7, 2011.

Office Action issued in U.S. Appl. No. 12/253,718, mailed Apr. 22, 2011.

Office Action issued in U.S. Appl. No. 12/368,053, mailed Jun. 22, 2011.

Office Action issued in U.S. Appl. No. 12/412,087, mailed Apr. 22, 2011.

Office Action issued in U.S. Appl. No. 12/420, 634, mailed Apr. 29, 2011.

Afanasyeva et al., "New miRNAs cloned from neuroblastoma," *BMC Genomics*, 9(1):52, 2008.

Barnetson et al., "Genetic analysis of multiple sporadic colon carcinomas from a single patient," *Int J Colorectal Dis*, 15:83-86, 2000.

Braasch et aL, "RNA interference in mammalian cells by chemically-modified RNA," *Biochemistry*, 42:7967-7975,2003.

Brioschi et al., "Down-regulation of microRNAs 222/221 in acute myelogenous leukemia with deranged core-binding factor subunits," *Neoplasia*, 12(11):866-876, 2010.

Burdy et al., "Identifying patients with T3-T4 node-negative colon cancer at high risk of recurrence," *Dis Colon Rectum*, 44:1682-1688, 2001.

Chiaretti et al., "Gene expression profiling identifies a subset of adult T-cell acute lymphoblastic leukemia with myeloid-like gene features and over-expression of miR-223," *Haematologica*, 95(7):1114-1121, 2010.

Extended European Search Report issued in European Application No. 10181821.9, mailed Jul. 29, 2011.

Extended European Search Report issued in European Application No. 10181728.6, mailed Jul. 8, 2011.

Extended European Search Report issued in European Application No. 10181713.8, mailed Jun. 24, 2011.

Honma et al., "The role of atelocollagen-based cell transfection array in high-throughput screening of gene functions and in drug discovery," *Current Drug Discovery Technologies*, 1(4):287-294, 2004.

Kasashima et al., "Altered expression profiles of microRNAs during TPA-induced differentiation of HL-60 cells," *Biochemical and Biophysical Research Communications*, 322(2):403-410, 2004.

Mi et al., "MicroRNA expression signatures accurately discriminate acute lymphoblastic leukemia from acute myeloid leukemia," *PNAS*, 104(50):19971-19976, 2007.

Nikiforova et al., "MicroRNA expression profiling of thyroid tumors: biological significance and diagnostic utility," 93(5):1600-1608, 2008.

Office Action issued in U.S. Appl. No. 11/273,640, mailed Jul. 26, 2011.

Office Action issued in U.S. Appl. No. 12/398,852, mailed Aug. 11, 2011.

Office Action issued in U.S. Appl. No. 12/412,087, mailed Aug. 18, 2011.

Office Action issued in U.S. Appl. No. 12/437,899, mailed Jun. 29, 2011.

Scherr et al., "Modulation of gene expression by lentiviral-mediated delivery of small interfering RNA," *Cell Cycle*, 2(3):251-257, 2003.

\* cited by examiner

SEQUENCE LISTING

```
<160> NUMBER OF SEQ ID NOS: 52

<210> SEQ ID NO 1
<211> LENGTH: 20
<212> TYPE: RNA
<213> ORGANISM: Homo sapiens

<400> SEQUENCE: 1
uaaggcacgc ggugaaugcc                                              20

<210> SEQ ID NO 2
<211> LENGTH: 22
<212> TYPE: RNA
<213> ORGANISM: Fugu rubripes

<400> SEQUENCE: 2
uaaggcacgc ggugaaugcc aa                                           22

<210> SEQ ID NO 3
<211> LENGTH: 23
<212> TYPE: RNA
<213> ORGANISM: Apis mellifera

<400> SEQUENCE: 3
uaaggcacgc ggugaaugcc aag                                          23

<210> SEQ ID NO 4
<211> LENGTH: 22
<212> TYPE: RNA
<213> ORGANISM: Mondelphis domestica

<400> SEQUENCE: 4
uuaaggcacg cggugaaugc ca                                           22

<210> SEQ ID NO 5
<211> LENGTH: 23
<212> TYPE: RNA
<213> ORGANISM: Bos taurus

<400> SEQUENCE: 5
uuaaggcacg cggugaaugc caa                                          23

<210> SEQ ID NO 6
<211> LENGTH: 21
<212> TYPE: RNA
<213> ORGANISM: Caenorhabditis briggsae
```

-continued

<400> SEQUENCE: 6
uaaggcacgc ggugaaugcc a                                        21

<210> SEQ ID NO 7
<211> LENGTH: 22
<212> TYPE: RNA
<213> ORGANISM: Gallus gallus

<400> SEQUENCE: 7
uuaaggcacg cagugaaugc ca                                       22

<210> SEQ ID NO 8
<211> LENGTH: 20
<212> TYPE: RNA
<213> ORGANISM: Homo sapiens

<400> SEQUENCE: 8
uaaggcacgc ggugaaugcc                                          20

<210> SEQ ID NO 9
<211> LENGTH: 85
<212> TYPE: RNA
<213> ORGANISM: Homo sapiens

<400> SEQUENCE: 9
aggccucucu cuccguguuc acagcggacc uugauuuaaa uguccauaca auuaaggcac    60
gcggugaaug ccaagaaugg ggcug                                        85

<210> SEQ ID NO 10
<211> LENGTH: 109
<212> TYPE: RNA
<213> ORGANISM: Homo sapiens

<400> SEQUENCE: 10
aucaagauua gaggcucugc ucuccguguu cacagcggac cuugauuuaa ugucauacaa    60
uuaaggcacg cggugaaugc caagagcgga gccuacggcu gcacuugaa              109

<210> SEQ ID NO 11
<211> LENGTH: 87
<212> TYPE: RNA
<213> ORGANISM: Homo sapiens

<400> SEQUENCE: 11
ugagggcccc ucugcguguu cacagcggac cuugauuuaa ugucuauaca auuaaggcac    60
gcggugaaug ccaagagagg cgccucc                                      87

<210> SEQ ID NO 12
<211> LENGTH: 83
<212> TYPE: RNA
<213> ORGANISM: Anopheles gambiae

<400> SEQUENCE: 12
cguuuuucuc cugguguuca cuguaggccu guauguucua uugcggauuu cauaaggcac    60
gcggugaaug ccaagagcga acg                                         83

<210> SEQ ID NO 13
<211> LENGTH: 107
<212> TYPE: RNA
<213> ORGANISM: Ateles geoffroyi

<400> SEQUENCE: 13

```
aucaagauca gaggcucugc ccuccguguu cacagcggac cuugauuuaa ugucauacaa    60
uuaaggcacg cggugaaugc caagagcgga gccuacggcu gcacuug                 107

<210> SEQ ID NO 14
<211> LENGTH: 77
<212> TYPE: RNA
<213> ORGANISM: Apis mellifera

<400> SEQUENCE: 14
ugcuccuugc guucacugcg ggcuuccaug ugccaacuuu ucaaaauuca uaaggcacgc    60
ggugaaugcc aagagcg                                                  77

<210> SEQ ID NO 15
<211> LENGTH: 85
<212> TYPE: RNA
<213> ORGANISM: Bombyx mori

<400> SEQUENCE: 15
caguccaccu ccucgcguuc acugccggag ccguuaugua uauuuaaaau ucauaaggca    60
cgcggugaau gccaagagcg gacuc                                         85

<210> SEQ ID NO 16
<211> LENGTH: 85
<212> TYPE: RNA
<213> ORGANISM: Bos taurus

<400> SEQUENCE: 16
aggccucucu cuccguguuc acagcggacc uugauuuaaa uguccauaca auuaaggcac    60
gcggugaaug ccaagaaugg ggcug                                         85

<210> SEQ ID NO 17
<211> LENGTH: 98
<212> TYPE: RNA
<213> ORGANISM: Caenorhabditis briggsae

<400> SEQUENCE: 17
uuuccagucg ucauauggcg uccaccugag ugacuuuagu ggacauguau aguuccaac    60 uaaggcacgc ggugaaugcc acguggcaau ucgggau                            98

<210> SEQ ID NO 18
<211> LENGTH: 96
<212> TYPE: RNA
<213> ORGANISM: Caenorhabditis elegans

<400> SEQUENCE: 18
gucccacuug ucaucuggca ugcacccuag ugacuuuagu ggacaucuaa gucuuccaac    60
uaaggcacgc ggugaaugcc acguggccau gauggg                             96

<210> SEQ ID NO 19
<211> LENGTH: 100
<212> TYPE: RNA
<213> ORGANISM: Drosophila melanogaster

<400> SEQUENCE: 19
ucauuuggua cguuuuucuc cugguaucca cguuaggccu auauguauuu ccaccauaag    60
gcacgcggug aaugccaaga gcgaacgcag uucuacaaau                         100

<210> SEQ ID NO 20
<211> LENGTH: 98
```

```
<212> TYPE: RNA
<213> ORGANISM: Drosophila pseudoobscura

<400> SEQUENCE: 20
ucguuuggua cguuuucuc cugguaucca cuguaggccu auauguauuu cgaccauaag      60
gcacgcggug aaugccaaga gcggacgaaa cucuacua                            98

<210> SEQ ID NO 21
<211> LENGTH: 82
<212> TYPE: RNA
<213> ORGANISM: Danio rerio

<400> SEQUENCE: 21
ggcucucgcu guacguguuc acaguggacc uugauuuauu guauuucaau uaaggcacgc     60
ggugaaugcc aacagcacag cc                                             82

<210> SEQ ID NO 22
<211> LENGTH: 83
<212> TYPE: RNA
<213> ORGANISM: Danio rerio

<400> SEQUENCE: 22
ccugcuuuuc uucguguuca cagcggaccu ugauuuaaau guccauacaa uuaaggcacg     60
cggugaaugc caagagagau ggc                                            83

<210> SEQ ID NO 23
<211> LENGTH: 117
<212> TYPE: RNA
<213> ORGANISM: Danio rerio

<400> SEQUENCE: 23
ggcucugugg gauuucagac ucuggcuuuc cguguucaca gcggaccuug auuuaauguc     60
uuacaauuaa ggcacgcggu gaaugccaag agcggagccu uuuaacauca gcaggcc      117

<210> SEQ ID NO 24
<211> LENGTH: 83
<212> TYPE: RNA
<213> ORGANISM: Danio rerio

<400> SEQUENCE: 24
gguuuuugcu cuuuguguuc acaguggacc uugauuuaau uucaauacaa uuaaggcacg     60
cggugaaugc caagagagaa gcc                                            83

<210> SEQ ID NO 25
<211> LENGTH: 129
<212> TYPE: RNA
<213> ORGANISM: Danio rerio

<400> SEQUENCE: 25
ggguuuugcu cgugcguucu uuugagauuc ucgcucugcg guucacagc ggaccuugau      60 uuaaugucca uacaauuaag gcacgcggug aaugccaaga gaagaaucuc uccagcaacg    120
aguuugcgc                                                           129

<210> SEQ ID NO 26
<211> LENGTH: 113
<212> TYPE: RNA
<213> ORGANISM: Danio rerio

<400> SEQUENCE: 26
ggguggugac acaggcccgc cacucugcgu guucacggcg gaccuugauu uaauauccau     60
```

-continued

```
acaauuaagg cacgcgguga augccaagag aggggucuua aaacgacaaa ccc          113
```

<210> SEQ ID NO 27
<211> LENGTH: 77
<212> TYPE: RNA
<213> ORGANISM: Fugu rubripes

<400> SEQUENCE: 27

```
gguugugucu cuccguguuc acagcggacc uugauuuaau gucuuacaau uaaggcacgc   60
ggugaaugcc aagagau                                                  77
```

<210> SEQ ID NO 28
<211> LENGTH: 78
<212> TYPE: RNA
<213> ORGANISM: Fugu rubripes

<400> SEQUENCE: 28

```
cuggucucuc cucguguuca cagcggaccu ugauuuaaau guccauacaa uuaaggcacg   60
cggugaaugc caagagag                                                 78
```

<210> SEQ ID NO 29
<211> LENGTH: 83
<212> TYPE: RNA
<213> ORGANISM: Fugu rubripes

<400> SEQUENCE: 29

```
gguuugagcu cuuuguguuc acaguggacc uugauuuaau uucaauacaa uuaaggcacg   60
cggugaaugc caagagagaa gcc                                           83
```

<210> SEQ ID NO 30
<211> LENGTH: 96
<212> TYPE: RNA
<213> ORGANISM: Gallus gallus

<400> SEQUENCE: 30

```
aggcucugcc ucuccuguuu cacagcggac cuugauuuaa ugucauacaa uuaaggcacg   60
cggugaaugc caagagcgga uccuccaggc ggcauu                             96
```

<210> SEQ ID NO 31
<211> LENGTH: 93
<212> TYPE: RNA
<213> ORGANISM: Gallus gallus

<400> SEQUENCE: 31

```
agccccagcg uuuguguuc acugcagacc uugauuuaau gucacacgau uaaggcacgc    60
agugaaugcc aaaguuuggg gcagccuggg cug                                93
```

<210> SEQ ID NO 32
<211> LENGTH: 93
<212> TYPE: RNA
<213> ORGANISM: Gallus gallus

<400> SEQUENCE: 32

```
agccccagcg uuuguguuc acugcagacc uugauuuaau gucacacgau uaaggcacgc    60
agugaaugcc aaaguuuggg gcagccuggg cug                                93
```

<210> SEQ ID NO 33
<211> LENGTH: 109
<212> TYPE: RNA
<213> ORGANISM: Gorilla gorilla

```
<400> SEQUENCE: 33
aucaagauua gaggcucugc ucuccguguu cacagcggac cuugauuuaa ugucauacaa    60
uuaaggcacg cggugaaugc caagagcgga gccuacggcu gcacuugaa               109

<210> SEQ ID NO 34
<211> LENGTH: 107
<212> TYPE: RNA
<213> ORGANISM: Lagothrix lagotricha

<400> SEQUENCE: 34
aucaagauca gaggcucugc ccuccguguu cacagcggac cuugauuuaa ugucauacaa    60
uuaaggcacg cggugaaugc caagagcgga gccuacgacu gcacuug                 107

<210> SEQ ID NO 35
<211> LENGTH: 85
<212> TYPE: RNA
<213> ORGANISM: Monodelphis domestica

<400> SEQUENCE: 35
aggccucucu cuccguguuc acagcggacc uugauuuaaa uguccauaca auuaaggcac    60
gcggugaaug ccaagaaugg ggcug                                          85

<210> SEQ ID NO 36
<211> LENGTH: 93
<212> TYPE: RNA
<213> ORGANISM: Monodelphis domestica

<400> SEQUENCE: 36
aucagagacu cugucucucc guguucacag cggaccuuga uuuaauguca uacaauuaag    60
gcacgcggug aaugccaaga gcggagccug aaa                                 93

<210> SEQ ID NO 37
<211> LENGTH: 68
<212> TYPE: RNA
<213> ORGANISM: Monodelphis domestica

<400> SEQUENCE: 37
cucugcgugu ucacagcgga ccuugauuua augucuauac aauuaaggca cgcggugaau    60
gccaagag                                                             68

<210> SEQ ID NO 38
<211> LENGTH: 109
<212> TYPE: RNA
<213> ORGANISM: Macaca mulatta

<400> SEQUENCE: 38
aucaagauca gaggcucugc ccuccguguu cacagcggac cuugauuuaa ugucauacaa    60
uuaaggcacg cggugaaugc caagagcgga gccuacggcu gcacuugaa               109

<210> SEQ ID NO 39
<211> LENGTH: 85
<212> TYPE: RNA
<213> ORGANISM: Mus musculus

<400> SEQUENCE: 39
aggccucucu cuccguguuc acagcggacc uugauuuaaa uguccauaca auuaaggcac    60
gcggugaaug ccaagaaugg ggcug                                          85
```

```
<210> SEQ ID NO 40
<211> LENGTH: 109
<212> TYPE: RNA
<213> ORGANISM: Mus musculus

<400> SEQUENCE: 40
aucaagauca gagacucugc ucuccguguu cacagcggac cuugauuuaa ugucauacaa    60
uuaaggcacg cggugaaugc caagagcgga gccuacggcu gcacuugaa               109

<210> SEQ ID NO 41
<211> LENGTH: 68
<212> TYPE: RNA
<213> ORGANISM: Mus musculus

<400> SEQUENCE: 41
cucugcgugu ucacagcgga ccuugauuua augucuauac aauuaaggca cgcggugaau    60
gccaagag                                                             68

<210> SEQ ID NO 42
<211> LENGTH: 109
<212> TYPE: RNA
<213> ORGANISM: Pan paniscus

<400> SEQUENCE: 42
aucaagauua gaggcucugc ucuccguguu cacagcggac cuugauuuaa ugucauacaa    60
uuaaggcacg cggugaaugc caagagcgga gccuacggcu gcacuugaa               109

<210> SEQ ID NO 43
<211> LENGTH: 109
<212> TYPE: RNA
<213> ORGANISM: Pongo pygmaeus

<400> SEQUENCE: 43
aucaagauua gaggcucugc ccuccguguu cacagcggac cuugauuuaa ugucauacaa    60
uuaaggcacg cggugaaugc caagagcgga gccuacggcu gcacuugaa               109

<210> SEQ ID NO 44
<211> LENGTH: 109
<212> TYPE: RNA
<213> ORGANISM: Pan troglodytes

<400> SEQUENCE: 44
aucaagauua gaggcucugc ucuccguguu cacagcggac cuugauuuaa ugucauacaa    60
uuaaggcacg cggugaaugc caagagcgga gccuacggcu gcacuugaa               109

<210> SEQ ID NO 45
<211> LENGTH: 85
<212> TYPE: RNA
<213> ORGANISM: Rattus norvegicus

<400> SEQUENCE: 45
aggccucucu cuccguguuc acagcggacc uugauuuaaa uguccauaca auuaaggcac    60
gcggugaaug ccaagaaugg ggcug                                          85

<210> SEQ ID NO 46
<211> LENGTH: 109
<212> TYPE: RNA
<213> ORGANISM: Rattus norvegicus

<400> SEQUENCE: 46
aucaagauca gagacucugc ucuccguguu cacagcggac cuugauuuaa ugucauacaa    60
```

```
uuaaggcacg cggugaaugc caagagcgga gccuacggcu gcacuugaa           109

<210> SEQ ID NO 47
<211> LENGTH: 87
<212> TYPE: RNA
<213> ORGANISM: Rattus norvegicus

<400> SEQUENCE: 47
ugagggcccc ucugcguguu cacagcggac cuugauuuaa ugucuauaca auuaaggcac    60
gcggugaaug ccaagagagg cgccucc                                       87

<210> SEQ ID NO 48
<211> LENGTH: 85
<212> TYPE: RNA
<213> ORGANISM: Sus scrofa

<400> SEQUENCE: 48
aggccucucu cuccguguuc acagcggacc uugaguuaaa uguccauaca auuaaggcac    60
gcggugaaug ccaagaaugg ggcug                                         85

<210> SEQ ID NO 49
<211> LENGTH: 67
<212> TYPE: RNA
<213> ORGANISM: Tetraodon nigroviridis

<400> SEQUENCE: 49
cucuccgugu ucacagcgga ccuugauuua augucuuaca auuaaggcac gcggugaaug    60
ccaagag                                                             67

<210> SEQ ID NO 50
<211> LENGTH: 75
<212> TYPE: RNA
<213> ORGANISM: Tetraodon nigroviridis

<400> SEQUENCE: 50
gccucuccuc guguucacag cggaccuuga uuuaaauguc cauacaauua aggcacgcgg    60
ugaaugccaa gagag                                                    75

<210> SEQ ID NO 51
<211> LENGTH: 80
<212> TYPE: RNA
<213> ORGANISM: Tetraodon nigroviridis

<400> SEQUENCE: 51
gguuugagcu cuuuguguuc acaguggacc uugauuuaau uucaauacaa uuaaggcacg    60
cggugaaugc caagagagaa                                               80

<210> SEQ ID NO 52
<211> LENGTH: 88
<212> TYPE: RNA
<213> ORGANISM: Xenopus tropicalis

<400> SEQUENCE: 52
uaagucucug acucuccgug uucacagcgg accuugauuu aaugucauac aauuaaggca    60
cgcggugaau gccaagagug gagccuac                                      88
```

MIR-124 REGULATED GENES AND PATHWAYS AS TARGETS FOR THERAPEUTIC INTERVENTION

This application claims priority to U.S. Provisional Application Ser. No. 60/991,709 filed Dec. 1, 2007, which is incorporated herein by reference in its entirety.

BACKGROUND OF THE INVENTION

I. Field of the Invention

The present invention relates to the fields of molecular biology and medicine. More specifically, the invention relates to methods and compositions for the treatment of diseases or conditions that are affected by microRNA (miRNA) miR-124 expression or lack thereof, and genes and cellular pathways directly and indirectly modulated by such.

II. Background

In 2001, several groups used a cloning method to isolate and identify a large group of "microRNAs" (miRNAs) from *C. elegans*, *Drosophila*, and humans (Lau et al., 2001; Lee and Ambros, 2001; Lagos-Quintana et al., 2003). Several hundreds of miRNAs have been identified in plants and animals—including humans—which do not appear to have endogenous siRNAs. Thus, while similar to siRNAs, miRNAs are distinct.

miRNAs thus far observed have been approximately 21-22 nucleotides in length, and they arise from longer precursors, which are transcribed from non-protein-encoding genes (Carrington and Ambros, 2003). The precursors form structures that fold back on themselves in self-complementary regions; they are then processed by the nuclease Dicer (in animals) or DCL1 (in plants) to generate the short double-stranded miRNA. One of the miRNA strands is incorporated into a complex of proteins and miRNA called the RNA-induced silencing complex (RISC). The miRNA guides the RISC complex to a target mRNA, which is then cleaved or translationally silenced, depending on the degree of sequence complementarity of the miRNA to its target mRNA. Currently, it is believed that perfect or nearly perfect complementarity leads to mRNA degradation, as is most commonly observed in plants. In contrast, imperfect base pairing, as is primarily found in animals, leads to translational silencing. However, recent data suggest additional complexity (Bagga et al., 2005; Lim et al., 2005), and mechanisms of gene silencing by miRNAs remain under intense study (Chendrimada et al., 2007; Kiriakidou et al., 2007).

Recent studies have shown that changes in the expression levels of numerous miRNAs are associated with various cancers (reviewed in (Calin and Croce, 2006; Esquela-Kerscher and Slack, 2006; Wiemer, 2007). miRNAs have also been implicated in regulating cell growth and cell and tissue differentiation—cellular processes that are associated with the development of cancer.

The inventors previously demonstrated that hsa-miR-124 is involved with the regulation of numerous cell activities that represent intervention points for cancer therapy and for therapy of other diseases and disorders (U.S. patent application Ser. No. 11/141,707 filed May 31, 2005 and Ser. No. 11/273,640 filed Nov. 14, 2005, each of which is incorporated herein by reference in its entirety). For example, cell proliferation, cell division, and cell survival are frequently altered in human cancers. Transfection of human lung carcinoma cells (A549) and human cervical cancer cells (HeLa) with synthetic hsa-miR-124 reduced viable cell numbers. In addition, the inventors showed that miR-124 significantly increased the capacity of two therapeutic compounds (TRAIL, an apoptosis pathway activator in cancer cells, and etoposide, a topoisomerase II inhibitor that activates the apoptosis pathway in cancer cells and normal cells) to induce cell death in A549 or HeLa cells. Overexpression of synthetic miR-124 in various cell lines decreased cell proliferation. In those studies, the inventors observed reduced proliferation of human breast cancer cells, (BT549), normal human breast epithelial cells (MCF12A), human cervical cancer cells (HeLa), human prostate carcinoma cells (22RV1), human basal cell carcinoma cells (TE 354.T), normal human skin cells (TE 353.Sk), and human lung carcinoma cells (A549, CRL-5826, HTB-57). Overexpression of miR-124 in HeLa cells significantly reduced the number of cells in the G2/M phase of the cell cycle when compared to cells transfected with a negative control miRNA. Also, others have recently observed that epigenetic silencing of miR-124a in cancers cells modulates activity the oncogene, CDK6 and the tumor suppressor gene, Rb (Lujambio et al., 2007).

Bioinformatics analyses suggest that any given miRNA may bind to and alter the expression of up to several hundred different genes. In addition, a single gene may be regulated by several miRNAs. Thus, each miRNA may regulate a complex interaction among genes, gene pathways, and gene networks. Mis-regulation or alteration of these regulatory pathways and networks involving miRNAs are likely to contribute to the development of disorders and diseases such as cancer. Although bioinformatics tools are helpful in predicting miRNA binding targets, all have limitations. Because of the imperfect complementarity with their target binding sites, it is difficult to accurately predict the mRNA targets of miRNAs with bioinformatics tools alone. Furthermore, the complicated interactive regulatory networks among miRNAs and target genes make it difficult to accurately predict which genes will actually be mis-regulated in response to a given miRNA.

Correcting gene expression errors by manipulating miRNA expression or by repairing miRNA mis-regulation represent promising methods to repair genetic disorders and cure diseases like cancer. A current, disabling limitation of this approach is that, as mentioned above, the details of the regulatory pathways and gene networks that are affected by any given miRNA, have been largely unknown. This represents a significant limitation for treatment of cancers in which a specific miRNA may play a role. A need exists to identify the genes, genetic pathways, and genetic networks that are regulated by or that may regulate expression of miRNAs.

SUMMARY OF THE INVENTION

The present invention provides additional compositions and methods by identifying genes that are direct targets for miR-124 regulation or that are indirect or downstream targets of regulation following the miR-124-mediated modification of another gene(s) expression. Furthermore, the invention describes gene, disease, and/or physiologic pathways and networks that are influenced by miR-124 and its family members. In certain aspects, compositions of the invention are administered to a subject having, suspected of having, or at risk of developing a metabolic, an immunologic, an infectious, a cardiovascular, a digestive, an endocrine, an ocular, a genitourinary, a blood, a musculoskeletal, a nervous system, a congenital, a respiratory, a skin, or a cancerous disease or condition.

In particular aspects, a subject or patient may be selected for treatment based on expression and/or aberrant expression of one or more miRNA or mRNA. In a further aspect, a subject or patient may be selected for treatment based on aberrations in one or more biologic or physiologic pathway(s), including aberrant expression of one or more gene associated with a pathway, or the aberrant expression of one or more protein encoded by one or more gene associated with a pathway. In still a further aspect, a subject or patient may be selected based on aberrations in miRNA expression, or biologic and/or physiologic pathway(s). A subject may be assessed for sensitivity, resistance, and/or efficacy of a therapy or treatment regime based on the evaluation and/or analysis of miRNA or mRNA expression or lack thereof. A subject may be evaluated for amenability to certain therapy prior to, during, or after administration of one or therapy to a subject or patient. Typically, evaluation or assessment may be done by analysis of miRNA and/or mRNA, as well as combination of other assessment methods that include but are not limited to histology, immunohistochemistry, blood work, etc.

In some embodiments, an infectious disease or condition includes a bacterial, viral, parasite, or fungal infection. Many of these genes and pathways are associated with various cancers and other diseases. Cancerous conditions include, but are not limited to astrocytoma, anaplastic large cell lymphoma, acute lymphoblastic leukemia, acute myeloid leukemia, angiosarcoma, breast carcinoma, B-cell lymphoma, Burkitt's lymphoma, bladder carcinoma, cholangiocarcinoma, cervical carcinoma, carcinoma of the head and neck, chronic lymphoblastic leukemia, chronic myeloid leukemia, colorectal carcinoma, endometrial carcinoma, Ewing's sarcoma, glioma, glioblastoma, glioblastoma multiforme, gastric carcinoma, hepatoblastoma, hepatocellular carcinoma, Hodgkin lymphoma, Kaposi's sarcoma, leukemia, lung carcinoma, lipoma, leiomyosarcoma, liposarcoma, laryngeal squamous cell carcinoma, melanoma, mucosa-associated lymphoid tissue B-cell lymphoma, medulloblastoma, mantle cell lymphoma, myxofibrosarcoma, meningioma, multiple myeloma, neuroblastoma, non-Hodgkin lymphoma, nasopharyngeal carcinoma, non-small cell lung carcinoma, ovarian carcinoma, oesophageal carcinoma, oropharyngeal carcinoma, osteosarcoma, pancreatic carcinoma, papillary carcinoma, prostate carcinoma, retinoblastoma, renal cell carcinoma, rhabdomyosarcoma, squamous cell carcinoma of the head and neck, schwannoma, small cell lung cancer, salivary gland tumor, thyroid carcinoma, testicular tumor, urothelial carcinoma, Wilm's tumor, wherein the modulation of one or more gene is sufficient for a therapeutic response. Typically a cancerous condition is an aberrant hyperproliferative condition associated with the uncontrolled growth or inability to undergo cell death, including apoptosis.

In still a further aspect, a nervous system condition can include a disease or injury to a neuronal cell or a nerve that includes, but is not limited to brain tumors; neuronal degeneration; mental retardation; Cerebral degeneration (Leukodystrophy (Krabbe disease, Pelizaeus-Merzbacher disease), Cerebral lipidoses (Tay-Sachs disease), Alzheimer's disease, Pick's disease, obstructive Hydrocephalus, Reye's syndrome, Parkinson's disease); extrapyramidal disease and abnormal movement disorders (Olivopontocerebellar atrophy, Shy-Drager syndrome, Essential tremor/familial tremor, Myoclonus (Lafora's disease or Unverricht disease), Huntington's chorea, torsion dystonia, Blepharospasm, Restless legs, Serotonin syndrome); Spinocerebellar disease (Friedreich's ataxia (Spinocerebellar ataxia), Hereditary spastic paraplegia, Primary cerebellar degeneration, cerebellar ataxia, ataxia-telangiectasia [Louis-Bar syndrome], Corticostriatal-spinal degeneration); Anterior horn cell disease (Motor neuron disease (Amyotrophic lateral sclerosis, Progressive muscular atrophy, Progressive bulbar palsy, Pseudobulbar palsy, Primary lateral sclerosis); Syringomyelia and syringobulbia; Disorders of the autonomic nervous system (Reflex sympathetic dystrophy); or multiple sclerosis. Nerve injuries include three main types of nerve fiber injury axonotmesis, neurapraxia and neurotmesis.

Axonotmesis involves loss of the relative continuity of the axon and its covering of myelin, but preservation of the connective tissue framework of the nerve (the encapsulating tissue, the epineurium and perineurium, are preserved). Because axonal continuity is lost, wallerian degeneration occurs. Typically, recovery occurs only through regeneration of the axons, a process requiring time. Axonotmesis is usually the result of a more severe crush or contusion than neurapraxia.

Neurapraxia is an interruption in conduction of the impulse down the nerve fiber, and recovery takes place without wallerian degeneration. This is the mildest form of nerve injury. This is probably a biochemical lesion caused by a concussion or other shock-like injuries to the fiber. In the case of the role nerve, neurapraxia is brought about by compression or relatively mind, blunt blows, including some low-velocity missile injuries close to the nerve.

Neurotmesis is the most severe lesion. It occurs on severe contusion, stretch, laceration, or Local Anesthetic Toxicity. Not only the axon, but the encapsulating connective tissue lose their continuity. The last (extreme) degree of neurotmesis is transsection, but most neurotmetic injuries do not produce gross loss of continuity of the nerve but rather than internal disruption of the architecture of the nerve sufficient to involve perineurium and endoneuruim as well as axons and their covering. There is typically a complete loss of motor, sensory and autonomic function. For neurotmesis, the Sunderland System is typically used for classification.

The present invention provides methods and compositions for identifying genes that are direct targets for miR-124 regulation or that are downstream targets of regulation following the miR-124-mediated modification of upstream gene expression. Furthermore, the invention describes gene pathways and networks that are influenced by miR-124 expression in biological samples. Many of these genes and pathways are associated with various cancers and other diseases. The altered expression or function of miR-124 in cells would lead to changes in the expression of these genes and contribute to the development of disease or other conditions. Introducing miR-124 (for diseases where the miRNA is down-regulated) or a miR-124 inhibitor (for diseases where the miRNA is up-regulated) into disease cells or tissues or subjects would result in a therapeutic response. The identities of key genes that are regulated directly or indirectly by miR-124 and the disease with which they are associated are provided herein.

In certain aspects a cell may be an epithelial, an endothelial, a mesothelial, a glial, a stromal, or a mucosal cell. The cell can be, but is not limited to a brain, a neuronal, a blood, an endometrial, a meninges, an esophageal, a lung, a cardiovascular, a liver, a lymphoid, a breast, a bone, a connective tissue, a fat, a retinal, a thyroid, a glandular, an adrenal, a pancreatic, a stomach, an intestinal, a kidney, a bladder, a colon, a prostate, a uterine, an ovarian, a cervical, a testicular, a splenic, a skin, a smooth muscle, a cardiac muscle, or a striated muscle cell. A cell, tissue, or subject may be a cancer cell, a cancerous tissue, harbor cancerous tissue, or be a subject or patient diagnosed or at risk of developing a disease or condition. In still a further aspect cancer includes, but is not limited to astrocytoma, anaplastic large cell lymphoma, acute lymphoblastic leukemia, acute myeloid leukemia, angiosarcoma, breast carcinoma, B-cell lymphoma, Burkitt's lymphoma, bladder carcinoma, cholangiocarcinoma, cervical carcinoma, carcinoma of the head and neck, chronic lymphoblastic leukemia, chronic myeloid leukemia, colorectal carcinoma, endometrial carcinoma, Ewing's sarcoma, glioma, glioblastoma, glioblastoma multiforme, gastric carcinoma, hepatoblastoma, hepatocellular carcinoma, Hodgkin lymphoma, Kaposi's sarcoma, leukemia, lung carcinoma, lipoma, leiomyosarcoma, liposarcoma, laryngeal squamous cell carcinoma, melanoma, mucosa-associated lymphoid tissue B-cell lymphoma, medulloblastoma, mantle cell lymphoma, myxofibrosarcoma, meningioma, multiple myeloma, neuroblastoma, non-Hodgkin lymphoma, nasopharyngeal carcinoma, non-small cell lung carcinoma, ovarian carcinoma, oesophageal carcinoma, oropharyngeal carcinoma, osteosarcoma, pancreatic carcinoma, papillary carcinoma, prostate carcinoma, retinoblastoma, renal cell carcinoma, rhabdomyosarcoma, squamous cell carcinoma of the head and neck, schwannoma, small cell lung cancer, salivary gland tumor, thyroid carcinoma, testicular tumor, urothelial carcinoma, or Wilm's tumor.

In certain aspects, the cell, tissue, or target may not be defective in miRNA expression yet may still respond therapeutically to expression or over expression of a miRNA. miR-124 could be used as a therapeutic target for any of these diseases. In certain embodiments miR-124 or its compliment can be used to modulate the activity of miR-124 in a subject, organ, tissue, or cell.

A cell, tissue, or subject may be a cancer cell, a cancerous tissue, harbor cancerous tissue, or be a subject or patient diagnosed or at risk of developing a disease or condition. In certain aspects a cancer cell is a neuronal, glial, lung, liver, brain, breast, bladder, blood, leukemic, colon, endometrial, stomach, skin, ovarian, fat, bone, cervical, esophageal, pancreatic, prostate, kidney, epithelial, intestinal, muscle, adrenal, salivary gland, or thyroid cell. In still a further aspect cancer includes, but is not limited to astrocytoma, anaplastic large cell lymphoma, acute lymphoblastic leukemia, acute myeloid leukemia, angiosarcoma, breast carcinoma, B-cell lymphoma, bladder carcinoma, cervical carcinoma, carcinoma of the head and neck, chronic lymphocytic leukemia, chronic myeloid leukemia, colorectal carcinoma, endometrial carcinoma, glioma, glioblastoma, gastric carcinoma, gastrinoma, hepatoblastoma, hepatocellular carcinoma, Hodgkin lymphoma, Kaposi's sarcoma, leukemia, lung carcinoma, leiomyosarcoma, laryngeal squamous cell carcinoma, melanoma, mucosa-associated lymphoid tissue B-cell lymphoma, medulloblastoma, mantle cell lymphoma, meningioma, myeloid leukemia, multiple myeloma, high-risk myelodysplastic syndrome, mesothelioma, neurofibroma, non-Hodgkin lymphoma, non-small cell lung carcinoma, ovarian carcinoma, esophageal carcinoma, oropharyngeal carcinoma, osteosarcoma, pancreatic carcinoma, papillary carcinoma, prostate carcinoma, pheochromocytoma, rhabdomyosarcoma, squamous cell carcinoma of the head and neck, schwannoma, small cell lung cancer, salivary gland tumor, sporadic papillary renal carcinoma, thyroid carcinoma, testicular tumor, or urothelial carcinoma.

Embodiments of the invention include methods of modulating gene expression, or biologic or physiologic pathways in a cell, a tissue, or a subject comprising administering to the cell, tissue, or subject an amount of an isolated nucleic acid or mimetic thereof comprising a miR-124 nucleic acid, mimetic, or inhibitor sequence in an amount sufficient to modulate the expression of a gene positively or negatively modulated by a miR-124 miRNA. A "miR-124 nucleic acid sequence" or "miR-124 inhibitor" includes the full length precursor of miR-124, or complement thereof or processed (i.e., mature) sequence of miR-124 and related sequences set forth herein, as well as 5, 6, 7, 8, 9, 10, 11, 12, 13, 14, 15, 16, 17, 18, 19, 20, 21, 22, 23, 24, 25, 26, 27, 28, 29 or more nucleotides of a precursor miRNA or its processed sequence, or complement thereof, including all ranges and integers there between. In certain embodiments, the miR-124 nucleic acid sequence or miR-124 inhibitor contains the full-length processed miRNA sequence or complement thereof and is referred to as the "miR-124 full-length processed nucleic acid sequence" or "miR-124 full-length processed inhibitor sequence." In still further aspects, the miR-124 nucleic acid comprises at least 5, 6, 7, 8, 9, 10, 11, 12, 13, 14, 15, 16, 17, 18, 19, 20, 21, 22, 23, 24, 25, 50 nucleotide segment (including all ranges and integers there between) or complementary segment of a miR-124 that is at least 75, 80, 85, 90, 95, 98, 99 or 100% identical to SEQ ID NO:1 to SEQ ID NO:52. The general term miR-124 includes all members of the miR-124 family that share at least part of a mature miR-124 sequence. Mature miR-124 sequences include hsa-miR-124 (MIMAT0000422), rno-miR-124 (MIMAT0000828), mmu-miR-124 (MIMAT0000134), UAAGGCACGCGGUGAAUGCC (SEQ ID NO:1); fru-miR-124 (MIMAT0002896), tni-miR-124 (MIMAT0002897), dre-miR-124 (MIMAT0001819), UAAGGCACGCGGUGAAUGCCAA (SEQ ID NO:2); ame-miR-124 (MIMAT0001473), aga-miR-124 (MIMAT0001499), bmo-miR-124 (MIMAT0004198), dps-miR-124 (MIMAT0001229), dme-miR-124 (MIMAT0000351), UAAGGCACGCGGUGAAUGCCAAG (SEQ ID NO:3); mdo-miR-124a (MIMAT0004102), ggo-miR-124a (MIMAT0002465), lla-miR-124a (MIMAT0002471), ptr-miR-124a (MIMAT0002469), ppa-miR-124a (MIMAT0002467), gga-miR-124a (MIMAT0001128), xtr-miR-124 (MIMAT0003683), ppy-miR-124a (MIMAT0002468), mml-miR-124a (MIMAT0002470), age-miR-124a (MIMAT0002466), ssc-miR-124a (MIMAT0002156), UUAAGGCACGCGGUGAAUGCCA (SEQ ID NO:4); bta-miR-124a (MIMAT0003811), UUAAGGCACGCGGUGAAUGCCAA (SEQ ID NO:5); cbr-miR-124 (MIMAT0000494), cel-miR-124 (MIMAT0000282), UAAGGCACGCGGUGAAUGCCA (SEQ ID NO:6); gga-miR-124b (MIMAT0001174), UUAAGGCACGCAGUGAAUGCCA (SEQ ID NO:7), or a complement thereof. In certain aspects, a subset of these miRNAs will be used that include some but not all of the listed miR-124 family members. In one aspect, miR-124 sequences have a core consensus sequence of [U/-]UAAGGCACGCGGUGAAUGCC[-/A][-/A][-/G] (SEQ ID NO:8, wherein the bracketed nucleotides are optional). In one embodiment only sequences comprising the consensus sequence of UAAGGCACGCGGUGAAUGCC (SEQ ID NO:1)) will be included with all other miRNAs excluded. The term miR-124 includes all members of the miR-124 family unless specifically identified. In certain aspects, a subset of these miRNAs will be used that include some but not all of the listed miR-124 family members. For instance, in one embodiment only sequences comprising the consensus sequence of SEQ ID NO:1 will be included with all other miRNAs excluded.

In a further aspect, a "miR-124 nucleic acid sequence" includes all or a segment of the full length precursor of miR-124 family members. Stem-loop sequences of miR-124 family members include hsa-mir-124-1 (MI0000443, AGGCCUCUCUCUCCGUGUUCACAGCGGACCUUGAUUUAAA UGUCCAUACAAUUAA GGCACGCGGUGAAUGCCAAGAAUGGGGCUG (SEQ ID NO:9)), hsa-mir-124-2 (MI0000444, AUCAAGAUUAGAGGCUCUGCUCUCCGUGUUCACAGCGGACCUUGAUUUAAUGUC AUACAAUUAAGGCACGCGGUGAAUGCCAA GAGCGGAGCCUACGGCUGCACUUGA A (SEQ ID NO:10)), hsa-mir-124-3 (MI0000445, UGAGGGCCCCUCUGCGUGUUCACAGCGGACCUUGA UUUAAUGUCUAUACAAUUA AGGCACGCGGUGAAUGCCAAGAGAGGCGCCUCC (SEQ ID NO:11)), aga-mir-124 (MI0001604, CGUUUUU-CUCCUGGUGUUCACUGUAGGCCUGUAUG-UUCUAUUGCGGAUUUCAUA AGGCACGCG-GUGAAUGCCAAGAGCGAACG (SEQ ID NO:12)), age-mir-124a (MI0002762, AUCAAGAUCAGAGGCUCUGCCCUCCGUG-UUCACAGCGGACCUUGAUUUAAUGUCA UACAA-UUAAGGCACGCGGUGAAUGCCAAGAGCG-GAGCCUACGGCUGCACUUG (SEQ ID NO:13)), ame-mir-124 (MI0001577, UGCUCCUUGCGUUCACUGCGGGCUUC-CAUGUGCCAACUUUUCAAAAUUCAUAAGG CACGCGGUGAAUGCCAAGAGCG (SEQ ID NO:14)), bmo-mir-124 (MI0004976, CAGUCCACCUCCUCGCG-UUCACUGCCGGAGCCGUUAUGUAUAU-UUAAAAUUCAUA AGGCACGCGGUGAAUGCCAA-GAGCGGACUC (SEQ ID NO:15)), bta-mir-124a (MI0005027, AGGCCUCUCUCUCCGUGUUCACAGCG-GACCUUGAUUUAAUGUCCAUACAAUUAA GGCACGCGGUGAAUGCCAAGAAUGGGGCUG (SEQ ID NO:16)), cbr-mir-124 (MI0000525, UUUCCAGUCGU-CAUAUGGCGUCCACCUGAGUGACU-UUAAGUGGACAUGUAUAGUU UCCAACUAAG-GCACGCGGUGAAUGCCACGUGGCAAUUCUGGGAU (SEQ ID NO:17)), cel-mir-124 (MI0000302, GUCCCACU-UGUCAUCUGGCAUGCACCCUAGUGACU-UUAGUGGACAUCUAAGUCUU CCAACUAAG-GCACGCGGUGAAUGCCACGUGGCCAUGAUGGG (SEQ ID NO:18)), dme-mir-124 (MI0000373, UCAUUUG-GUACGUUUUCUCCUGGUAUCCACU-GUAGGCCUAUAUGUAUUCCACC AUAAG-GCACGCGGUGAAUGCCAAGAGCGAACGCAGUUCU ACAAAU (SEQ ID NO:19)), dps-mir-124 (MI0001323, UCGUUUGGUACGUUUUCUCCUGGUAUC-CACUGUAGGCCUAUAUGUAUUCGAC CAUAAG-GCACGCGGUGAAUGCCAAGAGCGGAC-GAAACUCUACUA (SEQ ID NO:20)), dre-mir-124-1 (MI0001966, GGCUCUCGCUGUACGUGUUCA-CAGUGGACCUUGAUUUAUUGUAUUUCAAUUAAG GCACGCGGUGAAUGCCAACAGCACAGCC (SEQ ID NO:21)), dre-mir-124-2 (MI0001967, CCUGCUUUUCU-UCGUGUUCACAGCGGACCUUGA-UUUAAAUGUCCAUACAAUUAA GGCACGCG-GUGAAUGCCAAGAGAGAUGGC (SEQ ID NO:22)), dre-mir-124-3 (MI0001968, GGCUCUGUGGGAUUUCAGACUCUGGCU-UUCCGUGUUCACAGCGGACCUUGAUUU AAUGU-CUUACAAUUAAGGCACGCGGUGAAUGC-CAAGAGCGGAGCCUUUUAACAU CAGCAGGCC (SEQ ID NO:23)), dre-mir-124-4 (MI0001969, GGU-UUUUGCUCUUUGUGUUCACAGUGGACCU-UGAUUUAAUUUCAAUACAAUUAA GGCACGCG-GUGAAUGCCAAGAGAGAAGCC (SEQ ID NO:24)), dre-mir-124-5 (MI0001970, GGGUUUUGCUCGUGCGUUCUUUUUGAG-UUCUCGCUCUGCGUGUUCACAGCGGACC UUGA-UUUAAUGUCCAUACAAUUAAGGCACGCG-GUGAAUGCCAAGAGAAGAAUCU CUCCAGCAACGAGUUUGCGC (SEQ ID NO:25)), dre-mir-124-6 (MI0001971, GGGUGGUGACACAGGCCCGC-CACUCUGCGUGUUCACGGCGGACCUUGA-UUUAAUA UCCAUACAAUUAAGGCACGCG-GUGAAUGCCAAGAGAGGGGUCUUAAAACGACAA ACCC (SEQ ID NO:26)), fru-mir-124-1 (MI0003287, GGUUGUGUCUCUCCGUGUUCACAGCG-GACCUUGAUUUAAUGUCUUACAAUUAAG GCACGCGGUGAAUGCCAAGAGAU (SEQ ID NO:27)), fru-mir-124-2 (MI0003354, CUGGUCUCUCCUCGUG-UUCACAGCGGACCUUGAUUUAAAUGUC-CAUACAAUUAAG GCACGCGGUGAAUGCCAA-GAGAG (SEQ ID NO:28)), fru-mir-124-3 (MI0003211, GGUUUGAGCUCUUUGUGUUCACAGUG-GACCUUGAUUUAAUUUCAAUACAAUUAA GGCACGCGGUGAAUGCCAAGAGAGAAGCC (SEQ ID NO:29)), gga-mir-124a (MI0001197, AGGCUCUGCCU-CUCCGUGUUCACAGCGGACCUUGA-UUUAAUGUCAUACAAUUAAG GCACGCG-GUGAAUGCCAAGAGCGGAUCCUCCAGGCGGCAUU (SEQ ID NO:30)), gga-mir-124b-1 (MI0001252, AGC-CCAGCGUUUUGUGUUCACUGCAGACCU-UGAUUUAAUGUCACACGAUUAAG GCACG-CAGUGAAUGCCAAAGUUUGGGGCAGCCUGGGCUG (SEQ ID NO:31)), gga-mir-124b-2 (MI0001253, AGC-CCAGCGUUUUGUGUUCACUGCAGACCU-UGAUUUAAUGUCACACGAUUAAG GCACG-CAGUGAAUGCCAAAGUUUGGGGCAGCCUGGGCUG (SEQ ID NO:32)), ggo-mir-124a (MI0002761, AUCAAGA-UUAGAGGCUCUGCUCUCCGUGUUCA-CAGCGGACCUUGAUUUAAUGUC AUACAAUUAAG-GCACGCGGUGAAUGCCAAGAGCGGAGCCUACGGC UGCACUUGA A (SEQ ID NO:33)), lla-mir-124a (MI0002767, AUCAAGAUCAGAGGCUCUGCCCUC-CGUGUUCACAGCGGACCUUGAUUUAAUGUCA UACAAUUAAGGCACGCGGUGAAUGCCAA-GAGCGGAGCCUACGACUGCACUUG (SEQ ID NO:34)), mdo-mir-124a-1 (MI0005288, AGGCCUCUCU-CUCCGUGUUCACAGCGGACCUUGA-UUUAAAUGUCCAUACAAUUAA GGCACGCG-GUGAAUGCCAAGAAUGGGGCUG (SEQ ID NO:35)), mdo-mir-124a-2 (MI0005289, AUCAGAGACUCUGUCU-CUCCGUGUUCACAGCGGACCUUGA-UUUAAUGUCAUACAA UUAAGGCACGCG-GUGAAUGCCAAGAGCGGAGCCUGAAA (SEQ ID NO:36)), mdo-mir-124a-3 (MI0005290, CUCUGCGUG-UUCACAGCGGACCUUGAUUUAAUGUC-UAUACAAUUAAGGCACGCG GUGAAUGCCAAGAG (SEQ ID NO:37)), mml-mir-124a (MI0002766, AUCAA-GAUCAGAGGCCCUCCGUGUUCA-CAGCGGACCUUGAUUUAAUGUCA UACAAUUAAG-GCACGCGGUGAAUGCCAAGAGCGGAGCCUACGGC UGCACUUGAA (SEQ ID NO:38)), mmu-mir-124-1 (MI0000716, AGGCCUCUCUCUCCGUGUUCACAGCG-GACCUUGAUUUAAAUGUCCAUACAAUUAA GGCACGCGGUGAAUGCCAAGAAUGGGGCUG (SEQ ID NO:39)), mmu-mir-124-2 (MI0000717, AUCAA-GAUCAGAGACUCUGCUCUCCGUGUUCA-CAGCGGACCUUGAUUUAAUGUCA UACAAUUAAG-GCACGCGGUGAAUGCCAAGAGCGGAGCCUACGGC UGCACUUGAA (SEQ ID NO:40)), mmu-mir-124-3 (MI0000150, CUCUGCGUGUUCACAGCGGACCUUGA-UUUAAUGUCUAUACAAUUAAGGCACGCG GUGAAUGCCAAGAG (SEQ ID NO:41)), ppa-mir-124a (MI0002763, AUCAAGAUUAGAGGCUCUGCUCUC-CGUGUUCACAGCGGACCUUGAUUUAAUGUC AUA-CAAUUAAGGCACGCGGUGAAUGCCAA-GAGCGGAGCCUACGGCUGCACUUGA A (SEQ ID NO:42)), ppy-mir-124a (MI0002764, AUCAAGAUUA-GAGGCUCUGCCCUCCGUGUUCACAGCG-GACCUUGAUUUAAUGUCA UACAAUUAAG-GCACGCGGUGAAUGCCAAGAGCGGAGCCUACGGC UGCACUUGAA (SEQ ID NO:43)), ptr-mir-124a (MI0002765, AUCAAGAUUAGAGGCUCUGCUCUC- CGUGUUCACAGCGGACCUUGAUUUAAUGUC AUA-CAAUUAAGGCACGCGGUGAAUGCCAA-GAGCGGAGCCUACGGCUGCACUUGA A (SEQ ID NO:44)), rno-mir-124-1 (MI0000893, AGGCCUCUCU-CUCCGUGUUCACAGCGGACCUUGA-UUUAAAUGUCCAUACAAUUAA GGCACGCG-GUGAAUGCCAAGAAUGGGGCUG (SEQ ID NO:45)), mo-mir-124-2 (MI0000894, AUCAAGAUCAGAGACU-CUGCUCUCCGUGUUCACAGCGGACCU-UGAUUUAAUGUCA UACAAUUAAGGCACGCG-GUGAAUGCCAAGAGCGGAGCCUACGGCUGCACUU GAA (SEQ ID NO:46)), rno-mir-124-3 (MI0000892, UGAGGGCCCCUCUGCGUGUUCACAGCG-GACCUUGAUUUAAUGUCUAUACAAUUA AGGCACGCGGUGAAUGCCAAGAGAGGCGCCUCC (SEQ ID NO:47)), ssc-mir-124a (MI0002450, AGGCCU-CUCUCUCCGUGUUCACAGCGGACCU-UGAGUUAAAUGUCCAUACAAUUAA GGCACGCG-GUGAAUGCCAAGAAUGGGGCUG (SEQ ID NO:48)), tni-mir-124-1 (MI0003288, CUCUCCGUGUUCACAGCG-GACCUUGAUUUAAUGUCUUACAAUUAAG-GCACGCGGU GAAUGCCAAGAG (SEQ ID NO:49)), tni-mir-124-2 (MI0003355, GCCUCUCCUCGUGUUCACAGCGGACCU-UGAUUUAAAUGUCCAUACAAUUAAGGCA CGCG-GUGAAUGCCAAGAGAG (SEQ ID NO:50)), tni-mir-124-3 (MI0003212, GGUUUGAGCUCUUUGUGUUCACAGUG-GACCUUGAUUUAAUUUCAAUACAAUUAA GGCACGCGGUGAAUGCCAAGAGAGAA (SEQ ID NO:51)), xtr-mir-124 (MI0004930, UAAGUCUCUGACU-CUCCGUGUUCACAGCGGACCUUGA-UUUAAUGUCAUACAAUU AAGGCACGCG-GUGAAUGCCAAGAGUGGAGCCUAC (SEQ ID NO:52)), or a complement thereof.

In certain aspects, a miR-124 nucleic acid, or a segment or a mimetic thereof, will comprise 5, 6, 7, 8, 9, 10, 11, 12, 13, 14, 15, 16, 17, 18, 19, 20, 21, 22, 23, 24, 25, 26, 27, 28, 29 or more nucleotides of the precursor miRNA or its processed sequence, including all ranges and integers there between. In certain embodiments, the miR-124 nucleic acid sequence contains the full-length processed miRNA sequence and is referred to as the "miR-124 full-length processed nucleic acid sequence." In still further aspects, a miR-124 comprises at least one 5, 6, 7, 8, 9, 10, 11, 12, 13, 14, 15, 16, 17, 18, 19, 20, 21, 22, 23, 24, 25, 50 nucleotide (including all ranges and integers there between) segment of miR-124 that is at least 75, 80, 85, 90, 95, 98, 99 or 100% identical to SEQ ID NOs provided herein.

In specific embodiments, a miR-124 or miR-124 inhibitor containing nucleic acid is hsa-miR-124 or hsa-miR-124 inhibitor, or a variation thereof. In a further aspect, a miR-124 nucleic acid or miR-124 inhibitor can be administered with 1, 2, 3, 4, 5, 6, 7, 8, 9, 10 or more miRNAs or miRNA inhibitors. miRNAs or their complements can be administered concurrently, in sequence, or in an ordered progression. In certain aspects, a miR-124 or miR-124 inhibitor can be administered in combination with one or more of let-7, miR-15, miR-16, miR-20, miR-21, miR-26a, miR-126, miR-143, miR-147, miR-188, miR-200, miR-215, miR-216, miR-292-3p, and/or miR-331. All or combinations of miRNAs or inhibitors thereof may be administered in a single formulation. Administration may be before, during or after a second therapy.

miR-124 nucleic acids or complements thereof may also include various heterologous nucleic acid sequences, i.e., those sequences not typically found operatively coupled with miR-124 in nature, such as promoters, enhancers, and the like. The miR-124 nucleic acid is a recombinant nucleic acid, and can be a ribonucleic acid and/or a deoxyribonucleic acid. The recombinant nucleic acid may comprise a miR-124 or miR-124 inhibitor expression cassette, i.e., a nucleic acid segment that expresses a nucleic acid when introduce into an environment containing components for nucleic acid synthesis. In a further aspect, the expression cassette is comprised in a viral vector, or plasmid DNA vector or other therapeutic nucleic acid vector or delivery vehicle, including liposomes and the like. In a particular aspect, the miR-124 nucleic acid is a synthetic nucleic acid. Moreover, nucleic acids of the invention may be fully or partially synthetic. In certain aspects, viral vectors can be administered at $1 \times 10^2$, $1 \times 10^3$, $1 \times 10^4$ $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$ pfu or viral particle (vp).

In a particular aspect, the miR-124 nucleic acid or miR-124 inhibitor is a synthetic nucleic acid. Moreover, nucleic acids of the invention may be fully or partially synthetic. In still further aspects, a DNA encoding such a nucleic acid of the invention can be administered at 0.001, 0.01, 0.1, 1, 10, 20, 30, 40, 50, 100, 200, 400, 600, 800, 1000, 2000, to 4000 µg or mg, including all values and ranges there between. In yet a further aspect, nucleic acids of the invention, including synthetic nucleic acid, can be administered at 0.001, 0.01, 0.1, 1, 10, 20, 30, 40, 50, 100, to 200 µg or mg per kilogram (kg) of body weight. Each of the amounts described herein may be administered over a period of time, including 0.5, 1, 2, 3, 4, 5, 6, 7, 8, 9, 10, minutes, hours, days, weeks, months or years, including all values and ranges there between.

In certain embodiments, administration of the composition(s) can be enteral or parenteral. In certain aspects, enteral administration is oral. In further aspects, parenteral administration is intralesional, intravascular, intracranial, intrapleural, intratumoral, intraperitoneal, intramuscular, intralymphatic, intraglandular, subcutaneous, topical, intrabronchial, intratracheal, intranasal, inhaled, or instilled. Compositions of the invention may be administered regionally or locally and not necessarily directly into a lesion.

In certain aspects, the gene or genes modulated comprises 1, 2, 3, 4, 5, 6, 7, 8, 9, 10, 11, 12, 13, 14, 15, 20, 25, 30, 35, 40, 45, 50, 100, 150, 200 or more genes or combinations of genes identified in Tables 1, 3, 4, and/or 5. In still further aspects, the gene or genes modulated may exclude 1, 2, 3, 4, 5, 6, 7, 8, 9, 10, 11, 12, 13, 14, 15, 20, 25, 30, 35, 40, 45, 50, 100, 150, 175 or more genes or combinations of genes identified in Tables 1, 3, 4, and/or 5. Modulation includes modulating transcription, mRNA levels, mRNA translation, and/or protein levels in a cell, tissue, or organ. In certain aspects the expression of a gene or level of a gene product, such as mRNA or encoded protein, is down-regulated or up-regulated. In a particular aspect the gene modulated comprises or is selected from (and may even exclude) 1, 2, 3, 4, 5, 6, 7, 8, 9, 10, 11, 12, 13, 14, 15, 16, 17, 18, 19, 20, 21, 22, 23, 24, 25, 26. 27, 28, or all of the genes identified in Tables 1, 3, 4, and/or 5, or any combinations thereof. In certain embodiments a gene modulated or selected to be modulated is from Table 1. In further embodiments a gene modulated or selected to be modulated is from Table 3. In still further embodiments a gene modulated or selected to be modulated is from Table 4. In yet further embodiments a gene modulated or selected to be modulated is from Table 5.

Embodiments of the invention may also include obtaining or assessing a gene expression profile or miRNA profile of a target cell prior to selecting the mode of treatment, e.g., administration of a miR-124 nucleic acid, inhibitor of miR-124, or mimetics thereof. The database content related to all nucleic acids and genes designated by an accession number or a database submission are incorporated herein by reference as of the filing date of this application. In certain aspects of the invention one or more miRNA or miRNA inhibitor may modulate a single gene. In a further aspect, one or more genes in one or more genetic, cellular, or physiologic pathways can be modulated by one or more miRNAs or complements thereof, including miR-124 nucleic acids and miR-124 inhibitors in combination with other miRNAs.

miR-124 nucleic acids may also include various heterologous nucleic acid sequences, i.e., those sequences not typically found operatively coupled with miR-124 in nature, such as promoters, enhancers, and the like. The miR-124 nucleic acid is a recombinant nucleic acid, and can be a ribonucleic acid or a deoxyribonucleic acid. The recombinant nucleic acid may comprise a miR-124 expression cassette. In a further aspect, the expression cassette is comprised in a viral, or plasmid DNA vector or other therapeutic nucleic acid vector or delivery vehicle, including liposomes and the like. In a particular aspect, the miR-124 nucleic acid is a synthetic nucleic acid. Moreover, nucleic acids of the invention may be fully or partially synthetic.

A further embodiment of the invention is directed to methods of modulating a cellular pathway comprising administering to the cell an amount of an isolated nucleic acid comprising a miR-124 nucleic acid sequence in an amount sufficient to modulate the expression, function, status, or state of a cellular pathway, in particular those pathways described in Table 2 or the pathways known to include one or more genes from Table 1, 3, 4, and/or 5. Modulation of a cellular pathway includes, but is not limited to modulating the expression of one or more gene. Modulation of a gene can include inhibiting the function of an endogenous miRNA or providing a functional miRNA to a cell, tissue, or subject. Modulation refers to the expression levels or activities of a gene or its related gene product or protein, e.g., the mRNA levels may be modulated or the translation of an mRNA may be modulated, etc. Modulation may increase or up regulate a gene or gene product or it may decrease or down regulate a gene or gene product.

Still a further embodiment includes methods of treating a patient with a pathological condition comprising one or more of step of (a) administering to the patient an amount of an isolated nucleic acid comprising a miR-124 nucleic acid sequence in an amount sufficient to modulate the expression of a cellular pathway; and (b) administering a second therapy, wherein the modulation of the cellular pathway sensitizes the patient to the second therapy. A cellular pathway may include, but is not limited to one or more pathway described in Table 2 below or a pathway that is know to include one or more genes of Tables 1, 3, 4, and/or 5. A second therapy can include administration of a second miRNA or therapeutic nucleic acid, or may include various standard therapies, such as chemotherapy, radiation therapy, drug therapy, immunotherapy, and the like. Embodiments of the invention may also include the determination or assessment of a gene expression profile for the selection of an appropriate therapy.

Embodiments of the invention include methods of treating a subject with a pathological condition comprising one or more of the steps of (a) determining an expression profile of one or more genes selected from Table 1, 3, 4, and/or 5; (b) assessing the sensitivity of the subject to therapy based on the expression profile; (c) selecting a therapy based on the assessed sensitivity; and (d) treating the subject using selected therapy. Typically, the pathological condition will have as a component, indicator, or result the mis-regulation of one or more gene of Table 1, 3, 4, and/or 5.

Further embodiments include the identification and assessment of an expression profile indicative of miR-124 status in a cell or tissue comprising expression assessment of one or more gene from Table 1, 3, 4, and/or 5, or any combination thereof.

The term "miRNA" is used according to its ordinary and plain meaning and refers to a microRNA molecule found in eukaryotes that is involved in RNA-based gene regulation. See, e.g., Carrington et al., 2003, which is hereby incorporated by reference. The term can be used to refer to the single-stranded RNA molecule processed from a precursor or in certain instances the precursor itself.

In some embodiments, it may be useful to know whether a cell expresses a particular miRNA endogenously or whether such expression is affected under particular conditions or when it is in a particular disease state. Thus, in some embodiments of the invention, methods include assaying a cell or a sample containing a cell for the presence of one or more marker gene or mRNA or other analyte indicative of the expression level of a gene of interest. Consequently, in some embodiments, methods include a step of generating an RNA profile for a sample. The term "RNA profile" or "gene expression profile" refers to a set of data regarding the expression pattern for one or more gene or genetic marker in the sample (e.g., a plurality of nucleic acid probes that identify one or more markers from Tables 1, 3, 4, and/or 5); it is contemplated that the nucleic acid profile can be obtained using a set of RNAs, using for example nucleic acid amplification or hybridization techniques well know to one of ordinary skill in the art. The difference in the expression profile in the sample from the patient and a reference expression profile, such as an expression profile from a normal or non-pathologic sample, is indicative of a pathologic, disease, or cancerous condition. A nucleic acid or probe set comprising or identifying a segment of a corresponding mRNA can include all or part of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 100, 200, 500, or more nucleotides, including any integer or range derivable there between, of a gene, genetic marker, a nucleic acid, mRNA or a probe representative thereof that is listed in Tables 1, 3, 4, and/or 5 or identified by the methods described herein.

Certain embodiments of the invention are directed to compositions and methods for assessing, prognosing, or treating a pathological condition in a patient comprising measuring or determining an expression profile of one or more marker(s) in a sample from the patient, wherein a difference in the expression profile in the sample from the patient and an expression profile of a normal sample or reference expression profile is indicative of pathological condition and particularly cancer (e.g., In certain aspects of the invention, the cellular pathway, gene, or genetic marker is or is representative of one or more pathway or marker described in Table 1, 2, 3, 4, and/or 5, including any combination thereof.

Aspects of the invention include diagnosing, assessing, or treating a pathologic condition or preventing a pathologic condition from manifesting. For example, the methods can be used to screen for a pathological condition; assess prognosis of a pathological condition; stage a pathological condition; assess response of a pathological condition to therapy; or to modulate the expression of a gene, genes, or related pathway as a first therapy or to render a subject sensitive or more responsive to a second therapy. In particular aspects, assessing the pathological condition of the patient can be assessing prognosis of the patient. Prognosis may include, but is not limited to an estimation of the time or expected time of survival, assessment of response to a therapy, and the like. In certain aspects, the altered expression of one or more gene or marker is prognostic for a patient having a pathologic condition, wherein the marker is one or more of Table 1, 3, 4, and/or 5, including any combination thereof.

A further embodiment of the invention is directed to methods of modulating a cellular pathway comprising administering to the cell an amount of an isolated nucleic acid comprising a miR-124 nucleic acid sequence or a miR-124 inhibitor. A cell, tissue, or subject may be a cancer cell, a cancerous tissue or harbor cancerous tissue, or a cancer patient. The database content related to all nucleic acids and genes designated by an accession number or a database submission are incorporated herein by reference as of the filing date of this application.

A further embodiment of the invention is directed to methods of modulating a cellular pathway comprising administering to the cell an amount of an isolated nucleic acid comprising a miR-124 nucleic acid sequence in an amount sufficient to modulate the expression, function, status, or state of a cellular pathway, in particular those pathways described in Table 2 or the pathways known to include one or more genes from Table 1, 3, 4, and/or 5. Modulation of a cellular pathway includes, but is not limited to modulating the expression of one or more gene(s). Modulation of a gene can include inhibiting the function of an endogenous miRNA or providing a functional miRNA to a cell, tissue, or subject. Modulation refers to the expression levels or activities of a gene or its related gene product (e.g., mRNA) or protein, e.g., the mRNA levels may be modulated or the translation of an mRNA may be modulated. Modulation may increase or up regulate a gene or gene product or it may decrease or down regulate a gene or gene product (e.g., protein levels or activity).

Still a further embodiment includes methods of administering an miRNA or mimic thereof, and/or treating a subject or patient having, suspected of having, or at risk of developing a pathological condition comprising one or more of step (a) administering to a patient or subject an amount of an isolated nucleic acid comprising a miR-124 nucleic acid sequence or a miR-124 inhibitor in an amount sufficient to modulate expression of a cellular pathway; and (b) administering a second therapy, wherein the modulation of the cellular pathway sensitizes the patient or subject, or increases the efficacy of a second therapy. An increase in efficacy can include a reduction in toxicity, a reduced dosage or duration of the second therapy, or an additive or synergistic effect. A cellular pathway may include, but is not limited to one or more pathway described in Table 2 below or a pathway that is know to include one or more genes of Tables 1, 3, 4, and/or 5. The second therapy may be administered before, during, and/or after the isolated nucleic acid or miRNA or inhibitor is administered A second therapy can include administration of a second miRNA or therapeutic nucleic acid such as a siRNA or antisense oligonucleotide, or may include various standard therapies, such as pharmaceuticals, chemotherapy, radiation therapy, drug therapy, immunotherapy, and the like. Embodiments of the invention may also include the determination or assessment of gene expression or gene expression profile for the selection of an appropriate therapy. In a particular aspect, a second therapy is a chemotherapy. A chemotherapy can include, but is not limited to paclitaxel, cisplatin, carboplatin, doxorubicin, oxaliplatin, larotaxel, taxol, lapatinib, docetaxel, methotrexate, capecitabine, vinorelbine, cyclophosphamide, gemcitabine, amrubicin, cytarabine, etoposide, camptothecin, dexamethasone, dasatinib, tipifarnib, bevacizumab, sirolimus, temsirolimus, everolimus, lonafamib, cetuximab, erlotinib, gefitinib, imatinib mesylate, rituximab, trastuzumab, nocodazole, sorafenib, sunitinib, bortezomib, alemtuzumab, gemtuzumab, tositumomab or ibritumomab.

Embodiments of the invention include methods of treating a subject with a disease or condition comprising one or more of the steps of (a) determining an expression profile of one or more genes selected from Table 1, 3, 4, and/or 5; (b) assessing the sensitivity of the subject to therapy based on the expression profile; (c) selecting a therapy based on the assessed sensitivity; and (d) treating the subject using a selected therapy. Typically, the disease or condition will have as a component, indicator, or resulting mis-regulation of one or more gene of Table 1, 3, 4, and/or 5.

In certain aspects, 2, 3, 4, 5, 6, 7, 8, 9, 10, or more miRNA may be used in sequence or in combination; for instance, any combination of miR-124 or a miR-124 inhibitor with another miRNA. Further embodiments include the identification and assessment of an expression profile indicative of miR-124 status in a cell or tissue comprising expression assessment of one or more gene from Table 1, 3, 4, and/or 5, or any combination thereof.

The term "miRNA" is used according to its ordinary and plain meaning and refers to a microRNA molecule found in eukaryotes that is involved in RNA-based gene regulation. See, e.g., Carrington et al., 2003, which is hereby incorporated by reference. The term can be used to refer to the single-stranded RNA molecule processed from a precursor or in certain instances the precursor itself.

In some embodiments, it may be useful to know whether a cell expresses a particular miRNA endogenously or whether such expression is affected under particular conditions or when it is in a particular disease state. Thus, in some embodiments of the invention, methods include assaying a cell or a sample containing a cell for the presence of one or more marker gene or mRNA or other analyte indicative of the expression level of a gene of interest. Consequently, in some embodiments, methods include a step of generating an RNA profile for a sample. The term "RNA profile" or "gene expression profile" refers to a set of data regarding the expression pattern for one or more gene or genetic marker or miRNA in the sample (e.g., a plurality of nucleic acid probes that identify one or more markers from Tables 1, 3, 4, and/or 5); it is contemplated that the nucleic acid profile can be obtained using a set of RNAs, using for example nucleic acid amplification or hybridization techniques well know to one of ordinary skill in the art. The difference in the expression profile in the sample from the patient and a reference expression profile, such as an expression profile of one or more genes or miRNAs, are indicative of which miRNAs to be administered.

In certain aspects, miR-124 and let-7 can be administered to patients with acute lymphoblastic leukemia, acute myeloid leukemia, angiosarcoma, breast carcinoma, bladder carcinoma, cervical carcinoma, carcinoma of the head and neck, chronic lymphoblastic leukemia, chronic myeloid leukemia, colorectal carcinoma, endometrial carcinoma, glioma, glioblastoma, gastric carcinoma, hepatocellular carcinoma, Hodgkin lymphoma, Kaposi's sarcoma, leukemia, lung carcinoma, leiomyosarcoma, melanoma, medulloblastoma, myxofibrosarcoma, multiple myeloma, neuroblastoma, non-Hodgkin lymphoma, non-small cell lung carcinoma, ovarian carcinoma, oesophageal carcinoma, pancreatic carcinoma, prostate carcinoma, squamous cell carcinoma of the head and neck, salivary gland tumor, thyroid carcinoma, or urothelial carcinoma.

Further aspects include administering miR-124 and miR-15 to patients with astrocytoma, acute myeloid leukemia, breast carcinoma, B-cell lymphoma, bladder carcinoma, cervical carcinoma, carcinoma of the head and neck, chronic myeloid leukemia, colorectal carcinoma, endometrial carcinoma, glioma, glioblastoma, gastric carcinoma, hepatoblastoma, hepatocellular carcinoma, Hodgkin lymphoma, lung carcinoma, laryngeal squamous cell carcinoma, melanoma, medulloblastoma, mantle cell lymphoma, myxofibrosarcoma, multiple myeloma, neuroblastoma, non-Hodgkin lymphoma, non-small cell lung carcinoma, ovarian carcinoma, oesophageal carcinoma, pancreatic carcinoma, prostate carcinoma, renal cell carcinoma, rhabdomyosarcoma, squamous cell carcinoma of the head and neck, or thyroid carcinoma.

In still further aspects, miR-124 and miR-16 are administered to patients with astrocytoma, breast carcinoma, B-cell lymphoma, bladder carcinoma, colorectal carcinoma, endometrial carcinoma, glioblastoma, gastric carcinoma, hepatoblastoma, hepatocellular carcinoma, Hodgkin lymphoma, laryngeal squamous cell carcinoma, melanoma, medulloblastoma, mantle cell lymphoma, myxofibrosarcoma, multiple myeloma, non-small cell lung carcinoma, ovarian carcinoma, oesophageal carcinoma, pancreatic carcinoma, prostate carcinoma, renal cell carcinoma, rhabdomyosarcoma, squamous cell carcinoma of the head and neck, or thyroid carcinoma.

In certain aspects, miR-124 and miR-20 are administered to patients with astrocytoma, acute myeloid leukemia, breast carcinoma, bladder carcinoma, cervical carcinoma, colorectal carcinoma, endometrial carcinoma, glioma, glioblastoma, gastric carcinoma, hepatocellular carcinoma, Hodgkin lymphoma, leukemia, lipoma, melanoma, mantle cell lymphoma, myxofibrosarcoma, multiple myeloma, neuroblastoma, non-Hodgkin lymphoma, non-small cell lung carcinoma, ovarian carcinoma, oesophageal carcinoma, osteosarcoma, pancreatic carcinoma, prostate carcinoma, squamous cell carcinoma of the head and neck, thyroid carcinoma, or urothelial carcinoma.

Aspects of the invention include methods where miR-124 and miR-21 are administered to patients with astrocytoma, acute lymphoblastic leukemia, acute myeloid leukemia, breast carcinoma, Burkitt's lymphoma, bladder carcinoma, colorectal carcinoma, endometrial carcinoma, glioma, glioblastoma, gastric carcinoma, hepatocellular carcinoma, melanoma, mantle cell lymphoma, neuroblastoma, non-small cell lung carcinoma, ovarian carcinoma, oesophageal carcinoma, pancreatic carcinoma, prostate carcinoma, renal cell carcinoma, rhabdomyosarcoma, or squamous cell carcinoma of the head and neck.

In still further aspects, miR-124 and miR-26a are administered to patients with anaplastic large cell lymphoma, acute lymphoblastic leukemia, acute myeloid leukemia, angiosarcoma, breast carcinoma, B-cell lymphoma, Burkitt's lymphoma, bladder carcinoma, cervical carcinoma, carcinoma of the head and neck, chronic lymphoblastic leukemia, chronic myeloid leukemia, colorectal carcinoma, glioma, glioblastoma, gastric carcinoma, hepatocellular carcinoma, Kaposi's sarcoma, leukemia, lung carcinoma, leiomyosarcoma, melanoma, multiple myeloma, neuroblastoma, non-Hodgkin lymphoma, non-small cell lung carcinoma, ovarian carcinoma, oesophageal carcinoma, osteosarcoma, pancreatic carcinoma, prostate carcinoma, renal cell carcinoma, rhabdomyosarcoma, small cell lung cancer, or testicular tumor.

In yet further aspects, miR-124 and miR-126 are administered to patients with astrocytoma, acute myeloid leukemia, breast carcinoma, Burkitt's lymphoma, bladder carcinoma, cervical carcinoma, colorectal carcinoma, endometrial carcinoma, Ewing's sarcoma, glioma, glioblastoma, gastric carcinoma, hepatoblastoma, hepatocellular carcinoma, Hodgkin lymphoma, leukemia, lung carcinoma, melanoma, mantle cell lymphoma, meningioma, non-Hodgkin lymphoma, non-small cell lung carcinoma, ovarian carcinoma, oesophageal carcinoma, oropharyngeal carcinoma, osteosarcoma, pancreatic carcinoma, papillary carcinoma, prostate carcinoma, renal cell carcinoma, rhabdomyosarcoma, squamous cell carcinoma of the head and neck, schwannoma, small cell lung cancer, or thyroid carcinoma In a further aspect, miR-124 and miR-143 are administered to patients with astrocytoma, anaplastic large cell lymphoma, acute lymphoblastic leukemia, acute myeloid leukemia, breast carcinoma, B-cell lymphoma, bladder carcinoma, cervical carcinoma, chronic lymphoblastic leukemia, chronic myeloid leukemia, colorectal carcinoma, endometrial carcinoma, glioma, glioblastoma, gastric carcinoma, hepatocellular carcinoma, Hodgkin lymphoma, leukemia, lung carcinoma, melanoma, medulloblastoma, mantle cell lymphoma, multiple myeloma, non-Hodgkin lymphoma, non-small cell lung carcinoma, ovarian carcinoma, oesophageal carcinoma, osteosarcoma, pancreatic carcinoma, prostate carcinoma, renal cell carcinoma, squamous cell carcinoma of the head and neck, small cell lung cancer, thyroid carcinoma, or testicular tumor.

In still a further aspect, miR-124 and miR-147 are administered to patients with astrocytoma, breast carcinoma, bladder carcinoma, cervical carcinoma, colorectal carcinoma, endometrial carcinoma, glioma, glioblastoma, gastric carcinoma, hepatocellular carcinoma, Hodgkin lymphoma, leukemia, lipoma, melanoma, mantle cell lymphoma, myxofibrosarcoma, multiple myeloma, non-Hodgkin lymphoma, non-small cell lung carcinoma, ovarian carcinoma, oesophageal carcinoma, osteosarcoma, pancreatic carcinoma, prostate carcinoma, renal cell carcinoma, squamous cell carcinoma of the head and neck, or thyroid carcinoma.

In yet another aspect, miR-124 and miR-188 are administered to patients with astrocytoma, anaplastic large cell lymphoma, acute myeloid leukemia, breast carcinoma, B-cell lymphoma, Burkitt's lymphoma, bladder carcinoma, cervical carcinoma, chronic lymphoblastic leukemia, colorectal carcinoma, endometrial carcinoma, glioma, glioblastoma, gastric carcinoma, hepatocellular carcinoma, leukemia, lung carcinoma, melanoma, multiple myeloma, non-Hodgkin lymphoma, non-small cell lung carcinoma, ovarian carcinoma, oesophageal carcinoma, pancreatic carcinoma, prostate carcinoma, renal cell carcinoma, squamous cell carcinoma of the head and neck, thyroid carcinoma, or testicular tumor.

In yet a further aspect, miR-124 and miR-200b/c are administered to patients with anaplastic large cell lymphoma, breast carcinoma, B-cell lymphoma, cervical carcinoma, chronic lymphoblastic leukemia, colorectal carcinoma, glioma, glioblastoma, gastric carcinoma, hepatocellular carcinoma, leukemia, lung carcinoma, lipoma, multiple myeloma, non-small cell lung carcinoma, ovarian carcinoma, oesophageal carcinoma, osteosarcoma, pancreatic carcinoma, prostate carcinoma, rhabdomyosarcoma, squamous cell carcinoma of the head and neck, thyroid carcinoma, or testicular tumor.

In other aspects, miR-124 and miR-215 are administered to patients with astrocytoma, anaplastic large cell lymphoma, acute lymphoblastic leukemia, acute myeloid leukemia, angiosarcoma, breast carcinoma, B-cell lymphoma, bladder carcinoma, cervical carcinoma, chronic lymphoblastic leukemia, chronic myeloid leukemia, colorectal carcinoma, endometrial carcinoma, Ewing's sarcoma, glioma, glioblastoma, gastric carcinoma, hepatoblastoma, hepatocellular carcinoma, Hodgkin lymphoma, Kaposi's sarcoma, leukemia, lung carcinoma, lipoma, leiomyosarcoma, liposarcoma, melanoma, mucosa-associated lymphoid tissue B-cell lymphoma, mantle cell lymphoma, myxofibrosarcoma, multiple myeloma, neuroblastoma, non-Hodgkin lymphoma, nasopharyngeal carcinoma, non-small cell lung carcinoma, ovarian carcinoma, oesophageal carcinoma, osteosarcoma, pancreatic carcinoma, prostate carcinoma, retinoblastoma, renal cell carcinoma, rhabdomyosarcoma, squamous cell carcinoma of the head and neck, schwannoma, small cell lung cancer, salivary gland tumor, thyroid carcinoma, testicular tumor, urothelial carcinoma, or Wilm's tumor.

In certain aspects, miR-124 and miR-216 are administered to patients with astrocytoma, breast carcinoma, cervical carcinoma, carcinoma of the head and neck, colorectal carcinoma, endometrial carcinoma, glioma, glioblastoma, gastric carcinoma, hepatocellular carcinoma, Hodgkin lymphoma, leukemia, lung carcinoma, mucosa-associated lymphoid tissue B-cell lymphoma, non-Hodgkin lymphoma, non-small cell lung carcinoma, ovarian carcinoma, oesophageal carcinoma, osteosarcoma, prostate carcinoma, squamous cell carcinoma of the head and neck, or testicular tumor.

In a further aspect, miR-124 and miR-292-3p are administered to patients with astrocytoma, anaplastic large cell lymphoma, acute lymphoblastic leukemia, acute myeloid leukemia, angiosarcoma, breast carcinoma, B-cell lymphoma, bladder carcinoma, cervical carcinoma, chronic myeloid leukemia, colorectal carcinoma, endometrial carcinoma, Ewing's sarcoma, glioma, glioblastoma, gastric carcinoma, hepatoblastoma, hepatocellular carcinoma, Kaposi's sarcoma, leukemia, lung carcinoma, lipoma, leiomyosarcoma, liposarcoma, laryngeal squamous cell carcinoma, melanoma, myxofibrosarcoma, multiple myeloma, neuroblastoma, non-Hodgkin lymphoma, nasopharyngeal carcinoma, non-small cell lung carcinoma, ovarian carcinoma, oesophageal carcinoma, osteosarcoma, pancreatic carcinoma, prostate carcinoma, renal cell carcinoma, rhabdomyosarcoma, squamous cell carcinoma of the head and neck, schwannoma, small cell lung cancer, thyroid carcinoma, testicular tumor, urothelial carcinoma, or Wilm's tumor.

In still a further aspect, miR-124 and miR-331 are administered to patients with astrocytoma, anaplastic large cell lymphoma, acute lymphoblastic leukemia, acute myeloid leukemia, angiosarcoma, breast carcinoma, B-cell lymphoma, bladder carcinoma, cervical carcinoma, carcinoma of the head and neck, chronic lymphoblastic leukemia, colorectal carcinoma, endometrial carcinoma, glioma, glioblastoma, gastric carcinoma, hepatocellular carcinoma, Kaposi's sarcoma, leukemia, lung carcinoma, leiomyosarcoma, laryngeal squamous cell carcinoma, melanoma, myxofibrosarcoma, multiple myeloma, neuroblastoma, non-Hodgkin lymphoma, ovarian carcinoma, oesophageal carcinoma, osteosarcoma, pancreatic carcinoma, prostate carcinoma, renal cell carcinoma, rhabdomyosarcoma, squamous cell carcinoma of the head and neck, small cell lung cancer, thyroid carcinoma, or testicular tumor.

It is contemplated that when miR-124 or a miR-124 inhibitor is given in combination with one or more other miRNA molecules, the two different miRNAs or inhibitors may be given at the same time or sequentially. In some embodiments, therapy proceeds with one miRNA or inhibitor and that therapy is followed up with therapy with the other miRNA or inhibitor 1, 2, 3, 4, 5, 6, 7, 8, 9, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, or 1, 2, 3, 4, 5, 6, 7, 8, 9, 10, 11, or 12 months or any such combination later.

Further embodiments include the identification and assessment of an expression profile indicative of miR-124 status in a cell or tissue comprising expression assessment of one or more gene from Table 1, 3, 4, and/or 5, or any combination thereof.

The term "miRNA" is used according to its ordinary and plain meaning and refers to a microRNA molecule found in eukaryotes that is involved in RNA-based gene regulation. See, e.g., Carrington et al., 2003, which is hereby incorporated by reference. The term can be used to refer to the single-stranded RNA molecule processed from a precursor or in certain instances the precursor itself or a mimetic thereof.

In some embodiments, it may be useful to know whether a cell expresses a particular miRNA endogenously or whether such expression is affected under particular conditions or when it is in a particular disease state. Thus, in some embodiments of the invention, methods include assaying a cell or a sample containing a cell for the presence of one or more miRNA marker gene or mRNA or other analyte indicative of the expression level of a gene of interest. Consequently, in some embodiments, methods include a step of generating an RNA profile for a sample. The term "RNA profile" or "gene expression profile" refers to a set of data regarding the expression pattern for one or more gene or genetic marker in the sample (e.g., a plurality of nucleic acid probes that identify one or more markers or genes from Tables 1, 3, 4, and/or 5); it is contemplated that the nucleic acid profile can be obtained using a set of RNAs, using for example nucleic acid amplification or hybridization techniques well know to one of ordinary skill in the art. The difference in the expression profile in the sample from a patient and a reference expression profile, such as an expression profile from a normal or non-pathologic sample, or a digitized reference, is indicative of a pathologic, disease, or cancerous condition. In certain aspects the expression profile is an indicator of a propensity to or probability of (i.e., risk factor for a disease or condition) developing such a condition(s). Such a risk or propensity may indicate a treatment, increased monitoring, prophylactic measures, and the like. A nucleic acid or probe set may comprise or identify a segment of a corresponding mRNA and may include all or part of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 100, 200, 500, or more segments, including any integer or range derivable there between, of a gene or genetic marker, or a nucleic acid, mRNA or a probe representative thereof that is listed in Tables 1, 3, 4, and/or 5 or identified by the methods described herein.

Certain embodiments of the invention are directed to compositions and methods for assessing, prognosing, or treating a pathological condition in a patient comprising measuring or determining an expression profile of one or more miRNA or marker(s) in a sample from the patient, wherein a difference in the expression profile in the sample from the patient and an expression profile of a normal sample or reference expression profile is indicative of pathological condition and particularly cancer (e.g., In certain aspects of the invention, the miRNAs, cellular pathway, gene, or genetic marker is or is representative of one or more pathway or marker described in Table 1, 2, 3, 4, and/or 5, including any combination thereof.

Aspects of the invention include diagnosing, assessing, or treating a pathologic condition or preventing a pathologic condition from manifesting. For example, the methods can be used to screen for a pathological condition; assess prognosis of a pathological condition; stage a pathological condition; assess response of a pathological condition to therapy; or to modulate the expression of a gene, genes, or related pathway as a first therapy or to render a subject sensitive or more responsive to a second therapy. In particular aspects, assessing the pathological condition of the patient can be assessing prognosis of the patient. Prognosis may include, but is not limited to an estimation of the time or expected time of survival, assessment of response to a therapy, and the like. In certain aspects, the altered expression of one or more gene or marker is prognostic for a patient having a pathologic condition, wherein the marker is one or more of Table 1, 3, 4, and/or 5, including any combination thereof.

Predicted gene targets are shown in Table 3. Target genes whose mRNA expression levels are affected by hsa-miR-124 represent particularly useful candidates for cancer therapy and therapy of other diseases or conditions through manipulation of their expression levels.

Certain embodiments of the invention include determining expression of one or more marker, gene, or nucleic acid segment representative of one or more genes, by using an amplification assay, a hybridization assay, or protein assay, a variety of which are well known to one of ordinary skill in the art. In certain aspects, an amplification assay can be a quantitative amplification assay, such as quantitative RT-PCR or the like. In still further aspects, a hybridization assay can include array hybridization assays or solution hybridization assays. The nucleic acids from a sample may be labeled from the sample and/or hybridizing the labeled nucleic acid to one or more nucleic acid probes. Nucleic acids, mRNA, and/or nucleic acid probes may be coupled to a support. Such supports are well known to those of ordinary skill in the art and include, but are not limited to glass, plastic, metal, or latex. In particular aspects of the invention, the support can be planar or in the form of a bead or other geometric shapes or configurations known in the art. Proteins are typically assayed by immunoblotting, chromatography, or mass spectrometry or other methods known to those of ordinary skill in the art.

The present invention also concerns kits containing compositions of the invention or compositions to implement methods of the invention. In some embodiments, kits can be used to evaluate one or more marker molecules, and/or express one or more miRNA or miRNA inhibitor. In certain embodiments, a kit contains, contains at least or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 100, 150, 200 or more probes, recombinant nucleic acid, or synthetic nucleic acid molecules related to the markers to be assessed or an miRNA or miRNA inhibitor to be expressed or modulated, and may include any range or combination derivable therein. Kits may comprise components, which may be individually packaged or placed in a container, such as a tube, bottle, vial, syringe, or other suitable container means. Individual components may also be provided in a kit in concentrated amounts; in some embodiments, a component is provided individually in the same concentration as it would be in a solution with other components. Concentrations of components may be provided as 1×, 2×, 5×, 10×, or 20× or more. Kits for using probes, synthetic nucleic acids, recombinant nucleic acids, or non-synthetic nucleic acids of the invention for therapeutic, prognostic, or diagnostic applications are included as part of the invention. Specifically contemplated are any such molecules corresponding to any miRNA reported to influence biological activity or expression of one or more marker gene or gene pathway described herein. In certain aspects, negative and/or positive controls are included in some kit embodiments. The control molecules can be used to verify transfection efficiency and/or control for transfection-induced changes in cells.

Certain embodiments are directed to a kit for assessment of a pathological condition or the risk of developing a pathological condition in a patient by nucleic acid profiling of a sample comprising, in suitable container means, two or more nucleic acid hybridization or amplification reagents. The kit can comprise reagents for labeling nucleic acids in a sample and/or nucleic acid hybridization reagents. The hybridization reagents typically comprise hybridization probes. Amplification reagents include, but are not limited to amplification primers, reagents, and enzymes.

In some embodiments of the invention, an expression profile is generated by steps that include: (a) labeling nucleic acid in the sample; (b) hybridizing the nucleic acid to a number of probes, or amplifying a number of nucleic acids, and (c) determining and/or quantitating nucleic acid hybridization to the probes or detecting and quantitating amplification products, wherein an expression profile is generated. See U.S. Provisional Patent Application 60/575,743 and the U.S. Provisional Patent Application 60/649,584, and U.S. patent application Ser. Nos. 11/141,707 and 11/273,640, all of which are hereby incorporated by reference.

Methods of the invention involve diagnosing and/or assessing the prognosis of a patient based on a miRNA and/or a marker nucleic acid expression profile. In certain embodiments, the elevation or reduction in the level of expression of a particular gene or genetic pathway or set of nucleic acids in a cell is correlated with a disease state or pathological condition compared to the expression level of the same in a normal or non-pathologic cell or tissue sample. This correlation allows for diagnostic and/or prognostic methods to be carried out when the expression level of one or more nucleic acid is measured in a biological sample being assessed and then compared to the expression level of a normal or non-pathologic cell or tissue sample. It is specifically contemplated that expression profiles for patients, particularly those suspected of having or having a propensity for a particular disease or condition such as cancer, can be generated by evaluating any of or sets of the miRNAs and/or nucleic acids discussed in this application. The expression profile that is generated from the patient will be one that provides information regarding the particular disease or condition. In many embodiments, the profile is generated using nucleic acid hybridization or amplification, (e.g., array hybridization or RT-PCR). In certain aspects, an expression profile can be used in conjunction with other diagnostic and/or prognostic tests, such as histology, protein profiles in the serum and/or cytogenetic assessment.

The methods can further comprise one or more of the steps including: (a) obtaining a sample from the patient, (b) isolating nucleic acids from the sample, (c) labeling the nucleic acids isolated from the sample, and (d) hybridizing the labeled nucleic acids to one or more probes. Nucleic acids of the invention include one or more nucleic acid comprising at least one segment having a sequence or complementary sequence of to a nucleic acid representative of one or more of genes or markers in Table 1, 3, 4, and/or 5.

It is contemplated that any method or composition described herein can be implemented with respect to any other method or composition described herein and that different embodiments may be combined. It is specifically contemplated that any methods and compositions discussed herein with respect to miRNA molecules, miRNA, genes, and Certain embodiments of the invention include determining expression of one or more marker, gene, or nucleic acid representative thereof, by using an amplification assay, a hybridization assay, or protein assay, a variety of which are well known to one of ordinary skill in the art. In certain aspects, an amplification assay can be a quantitative amplification assay, such as quantitative RT-PCR or the like. In still further aspects, a hybridization assay can include array hybridization assays or solution hybridization assays. The nucleic acids from a sample may be labeled from the sample and/or hybridizing the labeled nucleic acid to one or more nucleic acid probes. Nucleic acids, mRNA, and/or nucleic acid probes may be coupled to a support. Such supports are well known to those of ordinary skill in the art and include, but are not limited to glass, plastic, metal, or latex. In particular aspects of the invention, the support can be planar or in the form of a bead or other geometric shapes or configurations known in the art. Protein are typically assayed by immunoblotting, chromatography, or mass spectrometry or other methods known to those of ordinary skill in the art.

The present invention also concerns kits containing compositions of the invention or compositions to implement methods of the invention. In some embodiments, kits can be used to evaluate one or more marker molecules, and/or express one or more miRNA. In certain embodiments, a kit contains, contains at least or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 100, 150, 200 or more probes, recombinant nucleic acid, or synthetic nucleic acid molecules related to the markers to be assessed or an miRNA to be expressed or modulated, and may include any range or combination derivable therein. Kits may comprise components, which may be individually packaged or placed in a container, such as a tube, bottle, vial, syringe, or other suitable container means. Individual components may also be provided in a kit in concentrated amounts; in some embodiments, a component is provided individually in the same concentration as it would be in a solution with other components. Concentrations of components may be provided as 1×, 2×, 5×, 10×, or 20× or more. Kits for using probes, synthetic nucleic acids, recombinant nucleic acids, or non-synthetic nucleic acids of the invention for therapeutic, prognostic, or diagnostic applications are included as part of the invention. Specifically contemplated are any such molecules corresponding to any miRNA reported to influence biological activity or expression of one or more marker gene or gene pathway described herein. In certain aspects, negative and/or positive controls are included in some kit embodiments. The control molecules can be used to verify transfection efficiency and/or control for transfection-induced changes in cells.

Certain embodiments are directed to a kit for assessment of a pathological condition or the risk of developing a pathological condition in a patient by nucleic acid profiling of a sample comprising in suitable container means, two or more nucleic acid hybridization or amplification reagents. The kit can comprise reagents for labeling nucleic acids in a sample and/or nucleic acid hybridization reagents. The hybridization reagents typically comprise hybridization probes. Amplification reagents include, but are not limited to amplification primers, reagents, and enzymes.

In some embodiments of the invention, an expression profile is generated by steps that include: (a) labeling nucleic acid in the sample; (b) hybridizing the nucleic acid to a number of probes, or amplifying a number of nucleic acids, and (c) determining and/or quantitating nucleic acid hybridization to the probes or detecting and quantitating amplification products, wherein an expression profile is generated. See U.S. Provisional Patent Application 60/575,743 and the U.S. Provisional Patent Application 60/649,584, and U.S. patent application Ser. Nos. 11/141,707 and 11/273,640, all of which are hereby incorporated by reference.

Methods of the invention involve diagnosing and/or assessing the prognosis of a patient based on a miRNA and/or a marker nucleic acid expression profile. In certain embodiments, the elevation or reduction in the level of expression of a particular gene or genetic pathway or set of nucleic acids in a cell is correlated with a disease state or pathological condition compared to the expression level of the same in a normal or non-pathologic cell or tissue sample. This correlation allows for diagnostic and/or prognostic methods to be carried out when the expression level of one or more nucleic acid is measured in a biological sample being assessed and then compared to the expression level of a normal or non-pathologic cell or tissue sample. It is specifically contemplated that expression profiles for patients, particularly those suspected of having or having a propensity for a particular disease or condition such as cancer, can be generated by evaluating any of or sets of the miRNAs and/or nucleic acids discussed in this application. The expression profile that is generated from the patient will be one that provides information regarding the particular disease or condition. In many embodiments, the profile is generated using nucleic acid hybridization or amplification, (e.g., array hybridization or RT-PCR). In certain aspects, an expression profile can be used in conjunction with other diagnostic and/or prognostic tests, such as histology, protein profiles in the serum and/or cytogenetic assessment.

The methods can further comprise one or more of the steps including: (a) obtaining a sample from the patient, (b) isolating nucleic acids from the sample, (c) labeling the nucleic acids isolated from the sample, and (d) hybridizing the labeled nucleic acids to one or more probes. Nucleic acids of the invention include one or more nucleic acid comprising at least one segment having a sequence or complementary sequence of to a nucleic acid representative of one or more of genes or markers in Table 1, 3, 4, and/or 5.

It is contemplated that any method or composition described herein can be implemented with respect to any other method or composition described herein and that different embodiments may be combined. It is specifically contemplated that any methods and compositions discussed herein with respect to miRNA molecules, miRNA, genes and nucleic acids representative of genes may be implemented with respect to synthetic nucleic acids. In some embodiments the synthetic nucleic acid is exposed to the proper conditions to allow it to become a processed or mature nucleic acid, such as a miRNA under physiological circumstances. The claims originally filed are contemplated to cover claims that are multiply dependent on any filed claim or combination of filed claims.

Also, any embodiment of the invention involving specific genes (including representative fragments there of), mRNA, or miRNAs by name is contemplated also to cover embodiments involving miRNAs whose sequences are at least 80, 81, 82, 83, 84, 85, 86, 87, 88, 89, 90, 91, 92, 93, 94, 95, 96, 97, 98, 99% identical to the mature sequence of the specified miRNA.

It will be further understood that shorthand notations are employed such that a generic description of a gene or marker thereof, or of a miRNA refers to any of its gene family members (distinguished by a number) or representative fragments thereof, unless otherwise indicated. It is understood by those of skill in the art that a "gene family" refers to a group of genes having the same coding sequence or miRNA coding sequence. Typically, miRNA members of a gene family are identified by a number following the initial designation. For example, miR-16-1 and miR-16-2 are members of the miR-16 gene family and "mir-7" refers to miR-7-1, miR-7-2 and miR-7-3. Moreover, unless otherwise indicated, a shorthand notation refers to related miRNAs (distinguished by a letter). Exceptions to these shorthand notations will be otherwise identified.

Other embodiments of the invention are discussed throughout this application. Any embodiment discussed with respect to one aspect of the invention applies to other aspects of the invention as well and vice versa. The embodiments in the Example and Detailed Description section are understood to be embodiments of the invention that are applicable to all aspects of the invention.

The terms "inhibiting," "reducing," or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

or with a negative control miRNA (NC, white squares) on days 38 and 40 (arrows). Standard deviations are shown in the graph. The p value for data points obtained on day 41 is shown (p=0.0266). Abbreviation: miR-124a, hsa-miR-124a; NC, negative control miRNA.

Figure 12:
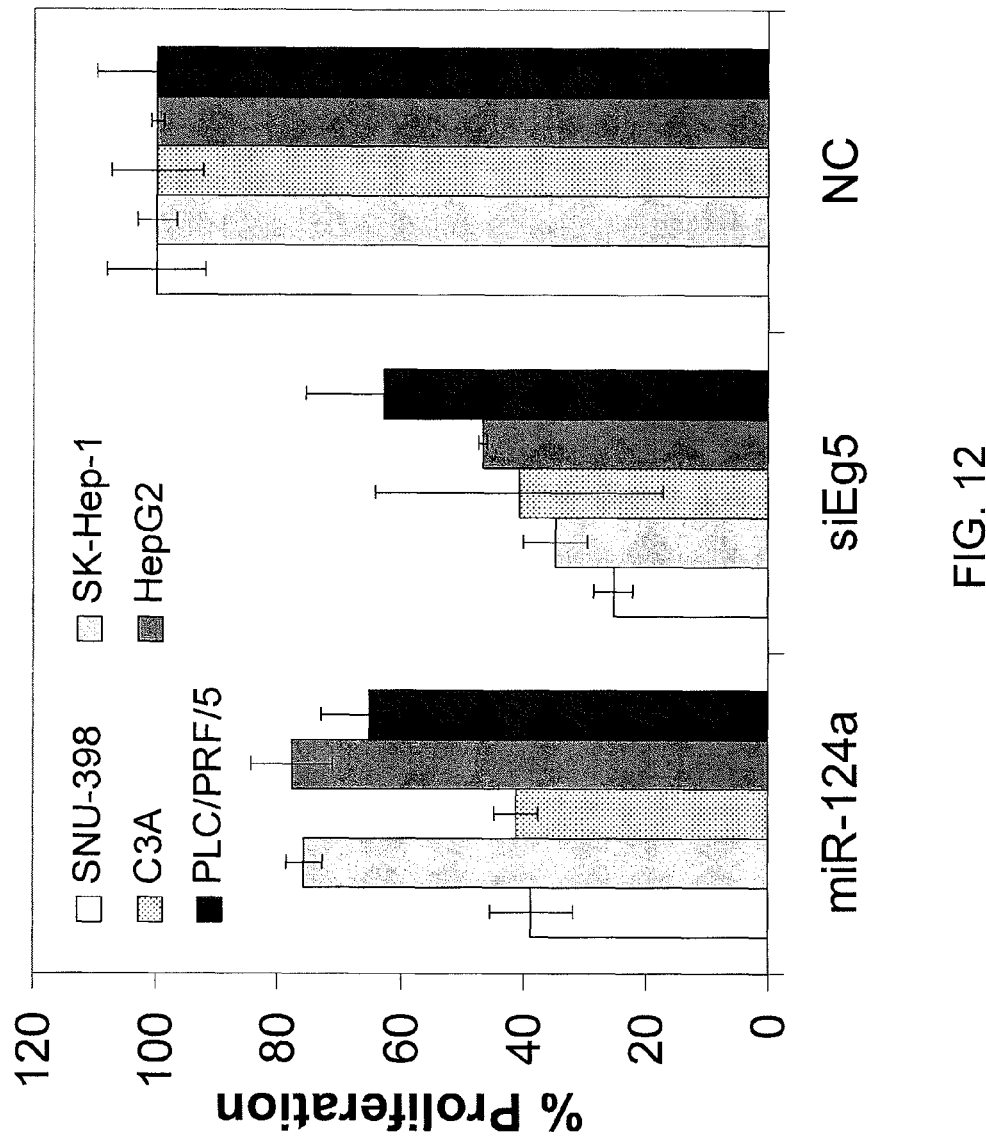

FIG. 12. Percent (%) proliferation of hsa-miR-124a treated human liver cancer cells relative to cells treated with negative control miRNA (100%). Abbreviations: miR-124a, hsa-miR-124a; siEg5, siRNA against the motor protein kinesin 11 (Eg5); NC, negative control miRNA. Standard deviations are indicated in the graph.

DETAILED DESCRIPTION OF THE INVENTION

The present invention is directed to compositions and methods relating to the identification and characterization of genes and biological pathways related to these genes as represented by the expression of the identified genes, as well as use of miRNAs related to such, for therapeutic, prognostic, and diagnostic applications, particularly those methods and compositions related to assessing and/or identifying pathological conditions directly or indirectly related to miR-124 expression or the aberrant expression thereof.

In certain aspects, the invention is directed to methods for the assessment, analysis, and/or therapy of a cell or subject where certain genes have a reduced or increased expression (relative to normal) as a result of an increased or decreased expression of any one or a combination of miR-124 family members (including, but not limited to SEQ ID NO:1 to SEQ ID NO:52) and/or genes with an increased expression (relative to normal) as a result of an increased or decreased expression of one or a combination of miR-124 family members. The expression profile and/or response to miR-124 expression or inhibition may be indicative of a disease or an individual with a condition, e.g., cancer.

Prognostic assays featuring any one or combination of the miRNAs listed or the markers listed (including nucleic acids representative thereof) could be used in assessment of a patient to determine what if any treatment regimen is justified. As with the diagnostic assays mentioned above, the absolute values that define low expression will depend on the platform used to measure the miRNA(s). The same methods described for the diagnostic assays could be used for prognostic assays.

I. Therapeutic methods

Embodiments of the invention concern nucleic acids that perform the activities of or inhibit endogenous miRNAs when introduced into cells. In certain aspects, nucleic acids are synthetic or non-synthetic miRNA. Sequence-specific miRNA inhibitors can be used to inhibit sequentially or in combination the activities of one or more endogenous miRNAs in cells, as well those genes and associated pathways modulated by the endogenous miRNA.

The present invention concerns, in some embodiments, short nucleic acid molecules that function as miRNAs or as inhibitors of miRNA in a cell. The term "short" refers to a length of a single polynucleotide that is 15, 16, 17, 18, 19, 20, 21, 22, 23, 24, 25, 50, 100, or 150 nucleotides or fewer, including all integers or ranges derivable there between. The nucleic acid molecules are typically synthetic. The term "synthetic" refers to nucleic acid molecule that is isolated and not produced naturally in a cell. In certain aspects the sequence (the entire sequence) and/or chemical structure deviates from a naturally-occurring nucleic acid molecule, such as an endogenous precursor miRNA or miRNA molecule or complement thereof. While in some embodiments, nucleic acids of the invention do not have an entire sequence that is identical or complementary to a sequence of a naturally-occurring nucleic acid, such molecules may encompass all or part of a naturally-occurring sequence or a complement thereof. It is contemplated, however, that a synthetic nucleic acid administered to a cell may subsequently be modified or altered in the cell such that its structure or sequence is the same as non-synthetic or naturally occurring nucleic acid, such as a mature miRNA sequence. For example, a synthetic nucleic acid may have a sequence that differs from the sequence of a precursor miRNA, but that sequence may be altered once in a cell to be the same as an endogenous, processed miRNA or an inhibitor thereof. The term "isolated" means that the nucleic acid molecules of the invention are initially separated from different (in terms of sequence or structure) and unwanted nucleic acid molecules such that a population of isolated nucleic acids is at least about 90% homogenous, and may be at least about 95, 96, 97, 98, 99, or 100% homogenous with respect to other polynucleotide molecules. In many embodiments of the invention, a nucleic acid is isolated by virtue of it having been synthesized in vitro separate from endogenous nucleic acids in a cell. It will be understood, however, that isolated nucleic acids may be subsequently mixed or pooled together. In certain aspects, synthetic miRNA of the invention are RNA or RNA analogs. miRNA inhibitors may be DNA or RNA, or analogs thereof. miRNA and miRNA inhibitors of the invention are collectively referred to as "synthetic nucleic acids."

In some embodiments, there is a miRNA or a synthetic miRNA having a length of between 17 and 130 residues. The present invention concerns miRNA or synthetic miRNA molecules that are, are at least, or are at most 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 140, 145, 150, 160, 170, 180, 190, 200 or more residues in length, including any integer or any range there between.

In certain embodiments, synthetic miRNA have (a) a "miRNA region" whose sequence or binding region from 5' to 3' is identical or complementary to all or a segment of a mature miRNA sequence, and (b) a "complementary region" whose sequence from 5' to 3' is between 60% and 100% complementary to the miRNA sequence in (a). In certain embodiments, these synthetic miRNA are also isolated, as defined above. The term "miRNA region" refers to a region on the synthetic miRNA that is at least 75, 80, 85, 90, 95, or 100% identical, including all integers there between, to the entire sequence of a mature, naturally occurring miRNA sequence or a complement thereof. In certain embodiments, the miRNA region is or is at least 90, 91, 92, 93, 94, 95, 96, 97, 98, 99, 99.1, 99.2, 99.3, 99.4, 99.5, 99.6, 99.7, 99.8, 99.9 or 100% identical to the sequence of a naturally-occurring miRNA or complement thereof.

The term "complementary region" or "complement" refers to a region of a nucleic acid or mimetic that is or is at least 60% complementary to the mature, naturally occurring miRNA sequence. The complementary region is or is at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein. With single polynucleotide sequences, there may be a hairpin loop structure as a result of chemical bonding between the miRNA region and the complementary region. In other embodiments, the complementary region is on a different nucleic acid molecule than the miRNA region, in which case the complementary region is on the complementary strand and the miRNA region is on the active strand.

In other embodiments of the invention, there are synthetic nucleic acids that are miRNA inhibitors. A miRNA inhibitor is between about 17 to 25 nucleotides in length and comprises a 5' to 3' sequence that is at least 90% complementary to the 5' to 3' sequence of a mature miRNA. In certain embodiments, a miRNA inhibitor molecule is 17, 18, 19, 20, 21, 22, 23, 24, or 25 nucleotides in length, or any range derivable therein. Moreover, an miRNA inhibitor may have a sequence (from 5' to 3') that is or is at least 70, 75, 80, 85, 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein, to the 5' to 3' sequence of a mature miRNA, particularly a mature, naturally occurring miRNA. One of skill in the art could use a portion of the miRNA sequence that is complementary to the sequence of a mature miRNA as the sequence for a miRNA inhibitor. Moreover, that portion of the nucleic acid sequence can be altered so that it is still comprises the appropriate percentage of complementarity to the sequence of a mature miRNA.

In some embodiments, of the invention, a synthetic miRNA or inhibitor contains one or more design element(s). These design elements include, but are not limited to: (i) a replacement group for the phosphate or hydroxyl of the nucleotide at the 5' terminus of the complementary region; (ii) one or more sugar modifications in the first or last 1 to 6 residues of the complementary region; or, (iii) noncomplementarity between one or more nucleotides in the last 1 to 5 residues at the 3' end of the complementary region and the corresponding nucleotides of the miRNA region. A variety of design modifications are known in the art, see below.

In certain embodiments, a synthetic miRNA has a nucleotide at its 5' end of the complementary region in which the phosphate and/or hydroxyl group has been replaced with another chemical group (referred to as the "replacement design"). In some cases, the phosphate group is replaced, while in others, the hydroxyl group has been replaced. In particular embodiments, the replacement group is biotin, an amine group, a lower alkylamine group, an aminohexyl phosphate group, an acetyl group, 2'O-Me (2'oxygen-methyl), DMTO (4,4'-dimethoxytrityl with oxygen), fluorescein, a thiol, or acridine, though other replacement groups are well known to those of skill in the art and can be used as well. This design element can also be used with a miRNA inhibitor.

Additional embodiments concern a synthetic miRNA having one or more sugar modifications in the first or last 1 to 6 residues of the complementary region (referred to as the "sugar replacement design"). In certain cases, there is one or more sugar modifications in the first 1, 2, 3, 4, 5, 6 or more residues of the complementary region, or any range derivable therein. In additional cases, there are one or more sugar modifications in the last 1, 2, 3, 4, 5, 6 or more residues of the complementary region, or any range derivable therein, have a sugar modification. It will be understood that the terms "first" and "last" are with respect to the order of residues from the 5' end to the 3' end of the region. In particular embodiments, the sugar modification is a 2'O-Me modification, a 2'F modification, a 2'H modification, a 2'amino modification, a 4'thioribose modification or a phosphorothioate modification on the carboxy group linked to the carbon at position 6'. In further embodiments, there are one or more sugar modifications in the first or last 2 to 4 residues of the complementary region or the first or last 4 to 6 residues of the complementary region. This design element can also be used with a miRNA inhibitor. Thus, a miRNA inhibitor can have this design element and/or a replacement group on the nucleotide at the 5' terminus, as discussed above.

In other embodiments of the invention, there is a synthetic miRNA or inhibitor in which one or more nucleotides in the last 1 to 5 residues at the 3' end of the complementary region are not complementary to the corresponding nucleotides of the miRNA region ("noncomplementarity") (referred to as the "noncomplementarity design"). The noncomplementarity may be in the last 1, 2, 3, 4, and/or 5 residues of the complementary miRNA. In certain embodiments, there is non-complementarity with at least 2 nucleotides in the complementary region.

It is contemplated that synthetic miRNA of the invention have one or more of the replacement, sugar modification, or noncomplementarity designs. In certain cases, synthetic RNA molecules have two of them, while in others these molecules have all three designs in place.

The miRNA region and the complementary region may be on the same or separate polynucleotides. In cases in which they are contained on or in the same polynucleotide, the miRNA molecule will be considered a single polynucleotide. In embodiments in which the different regions are on separate polynucleotides, the synthetic miRNA will be considered to be comprised of two polynucleotides.

When the RNA molecule is a single polynucleotide, there can be a linker region between the miRNA region and the complementary region. In some embodiments, the single polynucleotide is capable of forming a hairpin loop structure as a result of bonding between the miRNA region and the complementary region. The linker constitutes the hairpin loop. It is contemplated that in some embodiments, the linker region is, is at least, or is at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 residues in length, or any range derivable therein. In certain embodiments, the linker is between 3 and 30 residues (inclusive) in length.

In addition to having a miRNA or inhibitor region and a complementary region, there may be flanking sequences as well at either the 5' or 3' end of the region. In some embodiments, there is or is at least 1, 2, 3, 4, 5, 6, 7, 8, 9, 10 nucleotides or more, or any range derivable therein, flanking one or both sides of these regions.

Methods of the invention include reducing or eliminating activity of one or more miRNAs in a cell comprising introducing into a cell a miRNA inhibitor (which may be described generally herein as an miRNA, so that a description of miRNA, where appropriate, also will refer to a miRNA inhibitor); or supplying or enhancing the activity of one or more miRNAs in a cell. The present invention also concerns inducing certain cellular characteristics by providing to a cell a particular nucleic acid, such as a specific synthetic miRNA molecule or a synthetic miRNA inhibitor molecule. However, in methods of the invention, the miRNA molecule or miRNA inhibitor need not be synthetic. They may have a sequence that is identical to a naturally occurring miRNA or they may not have any design modifications. In certain embodiments, the miRNA molecule and/or the miRNA inhibitor are synthetic, as discussed above.

The particular nucleic acid molecule provided to the cell is understood to correspond to a particular miRNA in the cell, and thus, the miRNA in the cell is referred to as the "corresponding miRNA." In situations in which a named miRNA molecule is introduced into a cell, the corresponding miRNA will be understood to be the induced or inhibited miRNA function. It is contemplated, however, that the miRNA molecule introduced into a cell is not a mature miRNA but is capable of becoming or functioning as a mature miRNA under the appropriate physiological conditions. In cases in which a particular corresponding miRNA is being inhibited by a miRNA inhibitor, the particular miRNA will be referred to as the "targeted miRNA." It is contemplated that multiple corresponding miRNAs may be involved. In particular embodiments, more than one miRNA molecule is introduced into a cell. Moreover, in other embodiments, more than one miRNA inhibitor is introduced into a cell. Furthermore, a combination of miRNA molecule(s) and miRNA inhibitor(s) may be introduced into a cell. The inventors contemplate that a combination of miRNA may act at one or more points in cellular pathways of cells with aberrant phenotypes and that such combination may have increased efficacy on the target cell while not adversely effecting normal cells. Thus, a combination of miRNA may have a minimal adverse effect on a subject or patient while supplying a sufficient therapeutic effect, such as amelioration of a condition, growth inhibition of a cell, death of a targeted cell, alteration of cell phenotype or physiology, slowing of cellular growth, sensitization to a second therapy, sensitization to a particular therapy, and the like.

Methods include identifying a cell or patient in need of inducing those cellular characteristics. Also, it will be understood that an amount of a synthetic nucleic acid that is provided to a cell or organism is an "effective amount," which refers to an amount needed (or a sufficient amount) to achieve a desired goal, such as inducing a particular cellular characteristic(s).

In certain embodiments of the methods include providing or introducing to a cell a nucleic acid molecule corresponding to a mature miRNA in the cell in an amount effective to achieve a desired physiological result.

Moreover, methods can involve providing synthetic or nonsynthetic miRNA molecules. It is contemplated that in these embodiments, that methods may or may not be limited to providing only one or more synthetic miRNA molecules or only one or more nonsynthetic miRNA molecules. Thus, in certain embodiments, methods may involve providing both synthetic and nonsynthetic miRNA molecules. In this situation, a cell or cells are most likely provided a synthetic miRNA molecule corresponding to a particular miRNA and a nonsynthetic miRNA molecule corresponding to a different miRNA. Furthermore, any method articulated using a list of miRNAs using Markush group language may be articulated without the Markush group language and a disjunctive article (i.e., or) instead, and vice versa.

In some embodiments, there is a method for reducing or inhibiting cell proliferation in a cell comprising introducing into or providing to the cell an effective amount of (i) an miRNA inhibitor molecule or (ii) a synthetic or nonsynthetic miRNA molecule that corresponds to a miRNA sequence. In certain embodiments the methods involves introducing into the cell an effective amount of (i) a miRNA inhibitor molecule having a 5' to 3' sequence that is at least 90% complementary to the 5' to 3' sequence of one or more mature miRNA.

Certain embodiments of the invention include methods of treating a pathologic condition, in particular cancer, e.g., lung or liver cancer. In one aspect, the method comprises contacting a target cell with one or more nucleic acid, synthetic miRNA, or miRNA comprising at least one nucleic acid segment having all or a portion of a miRNA sequence. The segment may be 5, 6, 7, 8, 9, 10, 11, 12, 13, 14, 15, 16, 17, 18, 19, 20, 21, 22, 23, 24, 25, 30 or more nucleotides or nucleotide analog, including all integers there between. An aspect of the invention includes the modulation of gene expression, miRNA expression or function or mRNA expression or function within a target cell, such as a cancer cell.

Typically, an endogenous gene, miRNA or mRNA is modulated in the cell. In particular embodiments, the nucleic acid sequence comprises at least one segment that is at least 70, 75, 80, 85, 90, 95, or 100% identical in nucleic acid sequence to one or more miRNA or gene sequence. Modulation of the expression or processing of an endogenous gene, miRNA, or mRNA can be through modulation of the processing of a mRNA, such processing including transcription, transportation and/or translation with in a cell. Modulation may also be effected by the inhibition or enhancement of miRNA activity with a cell, tissue, or organ. Such processing may affect the expression of an encoded product or the stability of the mRNA. In still other embodiments, a nucleic acid sequence can comprise a modified nucleic acid sequence. In certain aspects, one or more miRNA sequence may include or comprise a modified nucleobase or nucleic acid sequence.

It will be understood in methods of the invention that a cell or other biological matter such as an organism (including patients) can be provided a miRNA or miRNA molecule corresponding to a particular miRNA by administering to the cell or organism a nucleic acid molecule that functions as the corresponding miRNA once inside the cell. The form of the molecule provided to the cell may not be the form that acts a miRNA once inside the cell. Thus, it is contemplated that in some embodiments, a synthetic miRNA or a nonsynthetic miRNA is provided such that it becomes processed into a mature and active miRNA once it has access to the cell's miRNA processing machinery. In certain embodiments, it is specifically contemplated that the miRNA molecule provided is not a mature miRNA molecule but a nucleic acid molecule that can be processed into the mature miRNA once it is accessible to miRNA processing machinery. The term "non-synthetic" in the context of miRNA means that the miRNA is not "synthetic," as defined herein. Furthermore, it is contemplated that in embodiments of the invention that concern the use of synthetic miRNAs, the use of corresponding nonsynthetic miRNAs is also considered an aspect of the invention, and vice versa. It will be understand that the term "providing" an agent is used to include "administering" the agent to a patient.

In certain embodiments, methods also include targeting a miRNA to modulate in a cell or organism. The term "targeting a miRNA to modulate" means a nucleic acid of the invention will be employed so as to modulate the selected miRNA. In some embodiments the modulation is achieved with a synthetic or non-synthetic miRNA that corresponds to the targeted miRNA, which effectively provides the targeted miRNA to the cell or organism (positive modulation). In other embodiments, the modulation is achieved with a miRNA inhibitor, which effectively inhibits the targeted miRNA in the cell or organism (negative modulation).

In some embodiments, the miRNA targeted to be modulated is a miRNA that affects a disease, condition, or pathway. In certain embodiments, the miRNA is targeted because a treatment can be provided by negative modulation of the targeted miRNA. In other embodiments, the miRNA is targeted because a treatment can be provided by positive modulation of the targeted miRNA or its targets.

In certain methods of the invention, there is a further step of administering the selected miRNA modulator to a cell, tissue, organ, or organism (collectively "biological matter") in need of treatment related to modulation of the targeted miRNA or in need of the physiological or biological results discussed herein (such as with respect to a particular cellular pathway or result like decrease in cell viability). Consequently, in some methods of the invention there is a step of identifying a patient in need of treatment that can be provided by the miRNA modulator(s). It is contemplated that an effective amount of a miRNA modulator can be administered in some embodiments. In particular embodiments, there is a therapeutic benefit conferred on the biological matter, where a "therapeutic benefit" refers to an improvement in the one or more conditions or symptoms associated with a disease or condition or an improvement in the prognosis, duration, or status with respect to the disease. It is contemplated that a therapeutic benefit includes, but is not limited to, a decrease in pain, a decrease in morbidity, a decrease in a symptom. For example, with respect to cancer, it is contemplated that a therapeutic benefit can be inhibition of tumor growth, prevention of metastasis, reduction in number of metastases, inhibition of cancer cell proliferation, induction of cell death in cancer cells, inhibition of angiogenesis near cancer cells, induction of apoptosis of cancer cells, reduction in pain, reduction in risk of recurrence, induction of chemo- or radiosensitivity in cancer cells, prolongation of life, and/or delay of death directly or indirectly related to cancer.

Furthermore, it is contemplated that the miRNA compositions may be provided as part of a therapy to a patient, in conjunction with traditional therapies or preventative agents. Moreover, it is contemplated that any method discussed in the context of therapy may be applied as preventatively, particularly in a patient identified to be potentially in need of the therapy or at risk of the condition or disease for which a therapy is needed.

In addition, methods of the invention concern employing one or more nucleic acids corresponding to a miRNA and a therapeutic drug. The nucleic acid can enhance the effect or efficacy of the drug, reduce any side effects or toxicity, modify its bioavailability, and/or decrease the dosage or frequency needed. In certain embodiments, the therapeutic drug is a cancer therapeutic. Consequently, in some embodiments, there is a method of treating cancer in a patient comprising administering to the patient the cancer therapeutic and an effective amount of at least one miRNA molecule that improves the efficacy of the cancer therapeutic or protects non-cancer cells. Cancer therapies also include a variety of combination therapies with both chemical and radiation based treatments. Combination chemotherapies include but are not limited to, for example, 5-fluorouracil, alemtuzumab, amrubicin, bevacizumab, bleomycin, bortezomib, busulfan, camptothecin, capecitabine, cisplatin (CDDP), carboplatin, cetuximab, chlorambucil, cisplatin (CDDP), cyclophosphamide, camptothecin, COX-2 inhibitors (e.g., celecoxib), cyclophosphamide, cytarabine, dactinomycin, dasatinib, daunorubicin, dexamethasone, docetaxel, doxorubicin (adriamycin), EGFR inhibitors (gefitinib and cetuximab), erlotinib, estrogen receptor binding agents, etoposide (VP16), everolimus, farnesyl-protein transferase inhibitors, gefitinib, gemcitabine, gemtuzumab, ibritumomab, ifosfamide, imatinib mesylate, larotaxel, lapatinib, lonafarnib, mechlorethamine, melphalan, methotrexate, mitomycin, navelbine, nitrosurea, nocodazole, oxaliplatin, paclitaxel, plicomycin, procarbazine, raloxifene, rituximab, sirolimus, sorafenib, sunitinib, tamoxifen, taxol, taxotere, temsirolimus, tipifarnib, tositumomab, transplatinum, trastuzumab, vinblastin, vincristin, or vinorelbine or any analog or derivative variant of the foregoing.

Generally, inhibitors of miRNAs can be given to decrease the activity of an endogenous miRNA. Similarly, nucleic acid molecules corresponding to the mature miRNA can be given to achieve the opposite effect as compared to when inhibitors of the miRNA are given. For example, inhibitors of miRNA molecules that increase cell proliferation can be provided to cells to increase proliferation or decrease cell proliferation. The present invention contemplates these embodiments in the context of the different physiological effects observed with the different miRNA molecules and miRNA inhibitors disclosed herein. These include, but are not limited to, the following physiological effects: increase and decreasing cell proliferation, increasing or decreasing apoptosis, increasing transformation, increasing or decreasing cell viability, activating or inhibiting a kinase (e.g., Erk), activating/inducing or inhibiting hTert, inhibit stimulation of growth promoting pathway (e.g., Stat 3 signaling), reduce or increase viable cell number, and increase or decrease number of cells at a particular phase of the cell cycle. Methods of the invention are generally contemplated to include providing or introducing one or more different nucleic acid molecules corresponding to one or more different miRNA molecules. It is contemplated that the following, at least the following, or at most the following number of different nucleic acid or miRNA molecules may be provided or introduced: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or any range derivable therein. This also applies to the number of different miRNA molecules that can be provided or introduced into a cell.

II. Pharmaceutical Formulations and Delivery

Methods of the present invention include the delivery of an effective amount of a miRNA or an expression construct encoding the same. An "effective amount" of the pharmaceutical composition, generally, is defined as that amount sufficient to detectably and repeatedly to achieve the stated desired result, for example, to ameliorate, reduce, minimize or limit the extent of the disease or its symptoms. Other more rigorous definitions may apply, including elimination, eradication or cure of disease.

A. Administration

In certain embodiments, it is desired to kill cells, inhibit cell growth, inhibit metastasis, decrease tumor or tissue size, and/or reverse or reduce the malignant or disease phenotype of cells. The routes of administration will vary, naturally, with the location and nature of the lesion or site to be targeted, and include, e.g., intradermal, subcutaneous, regional, parenteral, intravenous, intramuscular, intranasal, systemic, and oral administration and formulation. Direct injection, intratumoral injection, or injection into tumor vasculature is specifically contemplated for discrete, solid, accessible tumors, or other accessible target areas. Local, regional, or systemic administration also may be appropriate. For tumors of >4 cm, the volume to be administered will be about 4-10 ml (preferably 10 ml), while for tumors of <4 cm, a volume of about 1-3 ml will be used (preferably 3 ml).

Multiple injections delivered as a single dose comprise about 0.1 to about 0.5 ml volumes. Compositions of the invention may be administered in multiple injections to a tumor or a targeted site. In certain aspects, injections may be spaced at approximately 1 cm intervals.

In the case of surgical intervention, the present invention may be used preoperatively, to render an inoperable tumor subject to resection. Alternatively, the present invention may be used at the time of surgery, and/or thereafter, to treat residual or metastatic disease. For example, a resected tumor bed may be injected or perfused with a formulation comprising a miRNA or combinations thereof. Administration may be continued post-resection, for example, by leaving a catheter implanted at the site of the surgery. Periodic post-surgical treatment also is envisioned. Continuous perfusion of an expression construct or a viral construct also is contemplated.

Continuous administration also may be applied where appropriate, for example, where a tumor or other undesired affected area is excised and the tumor bed or targeted site is treated to eliminate residual, microscopic disease. Delivery via syringe or catherization is contemplated. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs.

Treatment regimens may vary as well and often depend on tumor type, tumor location, immune condition, target site, disease progression, and health and age of the patient. Certain tumor types will require more aggressive treatment. The clinician will be best suited to make such decisions based on the known efficacy and toxicity (if any) of the therapeutic formulations.

In certain embodiments, the tumor or affected area being treated may not, at least initially, be resectable. Treatments with compositions of the invention may increase the resectability of the tumor due to shrinkage at the margins or by elimination of certain particularly invasive portions. Following treatments, resection may be possible. Additional treatments subsequent to resection may serve to eliminate microscopic residual disease at the tumor or targeted site.

Treatments may include various "unit doses." A unit dose is defined as containing a predetermined quantity of a therapeutic composition(s). The quantity to be administered, and the particular route and formulation, are within the skill of those in the clinical arts. A unit dose need not be administered as a single injection but may comprise continuous infusion over a set period of time. With respect to a viral component of the present invention, a unit dose may conveniently be described in terms of μg or mg of miRNA or miRNA mimetic. Alternatively, the amount specified may be the amount administered as the average daily, average weekly, or average monthly dose.

miRNA can be administered to the patient in a dose or doses of about or of at least about 0.5, 1, 5, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 μg or mg, or more, or any range derivable therein. Alternatively, the amount specified may be the amount administered as the average daily, average weekly, or average monthly dose, or it may be expressed in terms of mg/kg, where kg refers to the weight of the patient and the mg is specified above. In other embodiments, the amount specified is any number discussed above but expressed as mg/m$^2$ (with respect to tumor size or patient surface area).

B. Injectable Compositions and Formulations

In some embodiments, the method for the delivery of a miRNA or an expression construct encoding such or combinations thereof is via systemic administration. However, the pharmaceutical compositions disclosed herein may also be administered parenterally, subcutaneously, directly, intratracheally, intravenously, intradermally, intramuscularly, or even intraperitoneally as described in U.S. Pat. Nos. 5,543, 158; 5,641,515 and 5,399,363 (each specifically incorporated herein by reference in its entirety).

Injection of nucleic acids may be delivered by syringe or any other method used for injection of a solution, as long as the nucleic acid and any associated components can pass through the particular gauge of needle required for injection. A syringe system has also been described for use in gene therapy that permits multiple injections of predetermined quantities of a solution precisely at any depth (U.S. Pat. No. 5,846,225).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, mixtures thereof, and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In certain formulations, a water-based formulation is employed while in others, it may be lipid-based. In particular embodiments of the invention, a composition comprising a tumor suppressor protein or a nucleic acid encoding the same is in a water-based formulation. In other embodiments, the formulation is lipid based.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral, intralesional, and intraperitoneal administration. In this connection, sterile aqueous media which can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Moreover, for human administration, preparations should meet sterility, pyrogenicity, general safety and purity standards as required by FDA Office of Biologics standards.

As used herein, a "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a human.

The nucleic acid(s) are administered in a manner compatible with the dosage formulation, and in such amount as will be therapeutically effective. The quantity to be administered depends on the subject to be treated, including, e.g., the aggressiveness of the disease or cancer, the size of any tumor(s) or lesions, the previous or other courses of treatment. Precise amounts of active ingredient required to be administered depend on the judgment of the practitioner. Suitable regimes for initial administration and subsequent administration are also variable, but are typified by an initial administration followed by other administrations. Such administration may be systemic, as a single dose, continuous over a period of time spanning 10, 20, 30, 40, 50, 60 minutes, and/or 1, 2, 3, 4, 5, 6, 7, 8, 9, 10, 11, 12, 13, 14, 15, 16, 17, 18, 19, 20, 21, 22, 23, 24 or more hours, and/or 1, 2, 3, 4, 5, 6, 7, days or more. Moreover, administration may be through a time release or sustained release mechanism, implemented by formulation and/or mode of administration.

C. Combination Treatments

In certain embodiments, the compositions and methods of the present invention involve a miRNA, or expression construct encoding such. These miRNA composition can be used in combination with a second therapy to enhance the effect of the miRNA therapy, or increase the therapeutic effect of another therapy being employed. These compositions would be provided in a combined amount effective to achieve the desired effect, such as the killing of a cancer cell and/or the inhibition of cellular hyperproliferation. This process may involve contacting the cells with the miRNA or second therapy at the same or different time. This may be achieved by contacting the cell with one or more compositions or pharmacological formulation that includes or more of the agents, or by contacting the cell with two or more distinct compositions or formulations, wherein one composition provides (1) miRNA; and/or (2) a second therapy. A second composition or method may be administered that includes a chemotherapy, radiotherapy, surgical therapy, immunotherapy or gene therapy.

It is contemplated that one may provide a patient with the miRNA therapy and the second therapy within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

In certain embodiments, a course of treatment will last 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 days or more. It is contemplated that one agent may be given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, any combination thereof, and another agent is given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, or any combination thereof. Within a single day (24-hour period), the patient may be given one or multiple administrations of the agent(s). Moreover, after a course of treatment, it is contemplated that there is a period of time at which no treatment is administered. This time period may last 1, 2, 3, 4, 5, 6, 7 days, and/or 1, 2, 3, 4, 5 weeks, and/or 1, 2, 3, 4, 5, 6, 7, 8, 9, 10, 11, 12 months or more, depending on the condition of the patient, such as their prognosis, strength, health, etc.

Various combinations may be employed, for example miRNA therapy is "A" and a second therapy is "B":

```
A/B/A  B/A/B  B/B/A  A/A/B  A/B/B  B/A/A  A/B/B/B

B/A/B/B  B/B/B/A  B/B/A/B  A/A/B/B  A/B/A/B  A/B/B/A

B/B/A/A  B/A/B/A  B/A/A/B  A/A/A/B  B/A/A/A  A/B/A/A

A/A/B/A
```

Administration of any compound or therapy of the present invention to a patient will follow general protocols for the administration of such compounds, taking into account the toxicity, if any, of the vector or any protein or other agent. Therefore, in some embodiments there is a step of monitoring toxicity that is attributable to combination therapy. It is expected that the treatment cycles would be repeated as necessary. It also is contemplated that various standard therapies, as well as surgical intervention, may be applied in combination with the described therapy.

In specific aspects, it is contemplated that a second therapy, such as chemotherapy, radiotherapy, immunotherapy, surgical therapy or other gene therapy, is employed in combination with the miRNA therapy, as described herein.

1. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

a. Alkylating Agents

Alkylating agents are drugs that directly interact with genomic DNA to prevent the cancer cell from proliferating. This category of chemotherapeutic drugs represents agents that affect all phases of the cell cycle, that is, they are not phase-specific. Alkylating agents can be implemented to treat chronic leukemia, non-Hodgkin's lymphoma, Hodgkin's disease, multiple myeloma, and particular cancers of the breast, lung, and ovary. They include: busulfan, chlorambucil, cisplatin, cyclophosphamide (cytoxan), dacarbazine, ifosfamide, mechlorethamine (mustargen), and melphalan. Troglitazaone can be used to treat cancer in combination with any one or more of these alkylating agents.

b. Antimetabolites

Antimetabolites disrupt DNA and RNA synthesis. Unlike alkylating agents, they specifically influence the cell cycle during S phase. They have been used to combat chronic leukemias in addition to tumors of breast, ovary and the gastrointestinal tract. Antimetabolites include 5-fluorouracil (5-FU), cytarabine (Ara-C), fludarabine, gemcitabine, and methotrexate.

5-Fluorouracil (5-FU) has the chemical name of 5-fluoro-2,4(1H,3H)-pyrimidinedione. Its mechanism of action is thought to be by blocking the methylation reaction of deoxyuridylic acid to thymidylic acid. Thus, 5-FU interferes with the synthesis of deoxyribonucleic acid (DNA) and to a lesser extent inhibits the formation of ribonucleic acid (RNA). Since DNA and RNA are essential for cell division and proliferation, it is thought that the effect of 5-FU is to create a thymidine deficiency leading to cell death. Thus, the effect of 5-FU is found in cells that rapidly divide, a characteristic of metastatic cancers.

c. Antitumor Antibiotics

Antitumor antibiotics have both antimicrobial and cytotoxic activity. These drugs also interfere with DNA by chemically inhibiting enzymes and mitosis or altering cellular membranes. These agents are not phase specific so they work in all phases of the cell cycle. Thus, they are widely used for a variety of cancers. Examples of antitumor antibiotics include bleomycin, dactinomycin, daunorubicin, doxorubicin (Adriamycin), and idarubicin, some of which are discussed in more detail below. Widely used in clinical setting for the treatment of neoplasms, these compounds are administered through bolus injections intravenously at doses ranging from 25-75 mg/m$^2$ at 21 day intervals for adriamycin, to 35-100 mg/m$^2$ for etoposide intravenously or orally.

d. Mitotic Inhibitors

Mitotic inhibitors include plant alkaloids and other natural agents that can inhibit either protein synthesis required for cell division or mitosis. They operate during a specific phase during the cell cycle. Mitotic inhibitors comprise docetaxel, etoposide (VP16), paclitaxel, taxol, taxotere, vinblastine, vincristine, and vinorelbine.

e. Nitrosureas

Nitrosureas, like alkylating agents, inhibit DNA repair proteins. They are used to treat non-Hodgkin's lymphomas, multiple myeloma, malignant melanoma, in addition to brain tumors. Examples include carmustine and lomustine.

2. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly. Radiotherapy may be used to treat localized solid tumors, such as cancers of the skin, tongue, larynx, brain, breast, or cervix. It can also be used to treat leukemia and lymphoma (cancers of the blood-forming cells and lymphatic system, respectively).

Radiation therapy used according to the present invention may include, but is not limited to, the use of γ-rays, X-rays, and/or the directed delivery of radioisotopes to tumor cells. Other forms of DNA damaging factors are also contemplated such as microwaves, proton beam irradiation (U.S. Pat. Nos. 5,760,395 and 4,870,287) and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells. Radiotherapy may comprise the use of radiolabeled antibodies to deliver doses of radiation directly to the cancer site (radioimmunotherapy). Once injected into the body, the antibodies actively seek out the cancer cells, which are destroyed by the cell-killing (cytotoxic) action of the radiation. This approach can minimize the risk of radiation damage to healthy cells.

Stereotactic radio-surgery (gamma knife) for brain and other tumors does not use a knife, but very precisely targeted beams of gamma radiotherapy from hundreds of different angles. Only one session of radiotherapy, taking about four to five hours, is needed. For this treatment a specially made metal frame is attached to the head. Then, several scans and x-rays are carried out to find the precise area where the treatment is needed. During the radiotherapy for brain tumors, the patient lies with their head in a large helmet, which has hundreds of holes in it to allow the radiotherapy beams through. Related approaches permit positioning for the treatment of tumors in other areas of the body.

3. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor or disease cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, gamma-IFN, chemokines such as MIP-1, MCP-1, IL-8 and growth factors such as FLT3 ligand. Combining immune stimulating molecules, either as proteins or using gene delivery in combination with a tumor suppressor such as MDA-7 has been shown to enhance antitumor effects (Ju et al., 2000). Moreover, antibodies against any of these compounds can be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739, 169; Hui and Hashimoto, 1998; Christodoulides et al., 1998), cytokine therapy e.g., interferons α, β and γ; IL-1, GM-CSF and TNF (Bukowski et al., 1998; Davidson et al., 1998; Hellstrand et al., 1998) gene therapy e.g., TNF, IL-1, IL-2, p53 (Qin et al., 1998; Austin-Ward and Villaseca, 1998; U.S. Pat. Nos. 5,830,880 and 5,846,945) and monoclonal antibodies e.g., anti-ganglioside GM2, anti-HER-2, anti-p185; Pietras et al., 1998; Hanibuchi et al., 1998; U.S. Pat. No. 5,824,311). Herceptin (trastuzumab) is a chimeric (mouse-human) monoclonal antibody that blocks the HER2-neu receptor. It possesses anti-tumor activity and has been approved for use in the treatment of malignant tumors (Dillman, 1999). A non-limiting list of several known anti-cancer immunotherapeutic agents and their targets includes (Generic Name/Target) Cetuximab/EGFR, Panitumuma/EGFR, Trastuzumab/erbB2 receptor, Bevacizumab/VEGF, Alemtuzumab/CD52, Gemtuzumab ozogamicin/CD33, Rituximab/CD20, Tositumomab/CD20, Matuzumab/EGFR, Ibritumomab tiuxetan/CD20, Tositumomab/CD20, HuPAM4/MUC1, MORAb-009/Mesothelin, G250/carbonic anhydrase IX, mAb 8H9/8H9 antigen, M195/CD33, Ipilimumab/CTLA4, HuLuc63/CS1, Alemtuzumab/CD53, Epratuzumab/CD22, BC8/CD45, HuJ591/Prostate specific membrane antigen, hA20/CD20, Lexatumumab/TRAIL receptor-2, Pertuzumab/HER-2 receptor, Mik-beta-1/IL-2R, RAV12/RAAG12, SGN-30/CD30, AME-133v/CD20, HeFi-1/CD30, BMS-663513/CD137, Volociximab/anti-α5β1 integrin, GC1008/TGFβ, HCD122/CD40, Siplizumab/CD2, MORAb-003/Folate receptor alpha, CNTO 328/IL-6, MDX-060/CD30, Ofatumumab/CD20, and SGN-33/CD33. It is contemplated that one or more of these therapies may be employed with the miRNA therapies described herein.

A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

4. Gene Therapy

In yet another embodiment, a combination treatment involves gene therapy in which a therapeutic polynucleotide is administered before, after, or at the same time as one or more therapeutic miRNA. Delivery of a therapeutic polypeptide or encoding nucleic acid in conjunction with a miRNA may have a combined therapeutic effect on target tissues. A variety of proteins are encompassed within the invention, some of which are described below. Various genes that may be targeted for gene therapy of some form in combination with the present invention include, but are not limited to inducers of cellular proliferation, inhibitors of cellular proliferation, regulators of programmed cell death, cytokines and other therapeutic nucleic acids or nucleic acid that encode therapeutic proteins.

The tumor suppressor oncogenes function to inhibit excessive cellular proliferation. The inactivation of these genes destroys their inhibitory activity, resulting in unregulated proliferation. The tumor suppressors (e.g., therapeutic polypeptides) p53, FHIT, p16 and C-CAM can be employed.

In addition to p53, another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the G1. The activity of this enzyme may be to phosphorylate Rb at late G1. The activity of CDK4 is controlled by an activating subunit, D-type cyclin, and by an inhibitory subunit, the p16INK4 has been biochemically characterized as a protein that specifically binds to and inhibits CDK4, and thus may regulate Rb phosphorylation (Serrano et al., 1993; Serrano et al., 1995). Since the p16INK4 protein is a CDK4 inhibitor (Serrano, 1993), deletion of this gene may increase the activity of CDK4, resulting in hyperphosphorylation of the Rb protein. p16 also is known to regulate the function of CDK6.

p16INK4 belongs to a newly described class of CDK-inhibitory proteins that also includes p16B, p19, p21WAF1, and p27KIP1. The p16INK4 gene maps to 9p21, a chromosome region frequently deleted in many tumor types. Homozygous deletions and mutations of the p16INK4 gene are frequent in human tumor cell lines. This evidence suggests that the p16INK4 gene is a tumor suppressor gene. This interpretation has been challenged, however, by the observation that the frequency of the p16INK4 gene alterations is much lower in primary uncultured tumors than in cultured cell lines (Caldas et al., 1994; Cheng et al., 1994; Hussussian et al., 1994; Kamb et al., 1994; Mori et al., 1994; Okamoto et al., 1994; Nobori et al., 1995; Orlow et al., 1994; Arap et al., 1995). Restoration of wild-type p16INK4 function by transfection with a plasmid expression vector reduced colony formation by some human cancer cell lines (Okamoto, 1994; Arap, 1995).

Other genes that may be employed according to the present invention include Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, antithrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

5. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

6. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Apo2 ligand (Apo2L, also called TRAIL) is a member of the tumor necrosis factor (TNF) cytokine family. TRAIL activates rapid apoptosis in many types of cancer cells, yet is not toxic to normal cells. TRAIL mRNA occurs in a wide variety of tissues. Most normal cells appear to be resistant to TRAIL's cytotoxic action, suggesting the existence of mechanisms that can protect against apoptosis induction by TRAIL. The first receptor described for TRAIL, called death receptor 4 (DR4), contains a cytoplasmic "death domain"; DR4 transmits the apoptosis signal carried by TRAIL. Additional receptors have been identified that bind to TRAIL. One receptor, called DR5, contains a cytoplasmic death domain and signals apoptosis much like DR4. The DR4 and DR5 mRNAs are expressed in many normal tissues and tumor cell lines. Recently, decoy receptors such as DcR1 and DcR2 have been identified that prevent TRAIL from inducing apoptosis through DR4 and DR5. These decoy receptors thus represent a novel mechanism for regulating sensitivity to a pro-apoptotic cytokine directly at the cell's surface. The preferential expression of these inhibitory receptors in normal tissues suggests that TRAIL may be useful as an anticancer agent that induces apoptosis in cancer cells while sparing normal cells. (Marsters et al., 1999).

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

This application incorporates U.S. application Ser. No. 11/349,727 filed on Feb. 8, 2006 claiming priority to U.S. Provisional Application Ser. No. 60/650,807 filed Feb. 8, 2005 herein by references in its entirety.

III. miRNA Molecules

MicroRNA molecules ("miRNAs") are generally 21 to 22 nucleotides in length, though lengths of 19 and up to 23 nucleotides have been reported. The miRNAs are each processed from a longer precursor RNA molecule ("precursor miRNA"). Precursor miRNAs are transcribed from non-protein-encoding genes. The precursor miRNAs have two regions of complementarity that enables them to form a stem-loop- or fold-back-like structure, which is cleaved in animals by a ribonuclease III-like nuclease enzyme called Dicer. The processed miRNA is typically a portion of the stem.

The processed miRNA (also referred to as "mature miRNA") becomes part of a large complex to down-regulate a particular target gene or its gene product. Examples of animal miRNAs include those that imperfectly basepair with the target, which halts translation (Olsen et al., 1999; Seggerson et al., 2002). siRNA molecules also are processed by Dicer, but from a long, double-stranded RNA molecule. siRNAs are not naturally found in animal cells, but they can direct the sequence-specific cleavage of an mRNA target through a RNA-induced silencing complex (RISC) (Denli et al., 2003).

A. Array Preparation

Certain embodiments of the present invention concerns the preparation and use of mRNA or nucleic acid arrays, miRNA or nucleic acid arrays, and/or miRNA or nucleic acid probe arrays, which are macroarrays or microarrays of nucleic acid molecules (probes) that are fully or nearly complementary (over the length of the prove) or identical (over the length of the prove) to a plurality of nucleic acid, mRNA or miRNA molecules, precursor miRNA molecules, or nucleic acids derived from the various genes and gene pathways modulated by miR-124 miRNAs and that are positioned on a support or support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of marker RNA and/or miRNA-complementing nucleic acid samples, the position of each sample can be tracked and linked to the original sample.

A variety of different array devices in which a plurality of distinct nucleic acid probes are stably associated with the surface of a solid support are known to those of skill in the art. Useful substrates for arrays include nylon, glass, metal, plastic, latex, and silicon. Such arrays may vary in a number of different ways, including average probe length, sequence or types of probes, nature of bond between the probe and the array surface, e.g. covalent or non-covalent, and the like. The labeling and screening methods of the present invention and the arrays are not limited in its utility with respect to any parameter except that the probes detect miRNA, or genes or nucleic acid representative of genes; consequently, methods and compositions may be used with a variety of different types of nucleic acid arrays.

Representative methods and apparatus for preparing a microarray have been described, for example, in U.S. Pat. Nos. 5,143,854; 5,202,231; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 5,492,806; 5,525,464; 5,503,980; 5,510,270; 5,525,464; 5,527,681; 5,529,756; 5,532,128; 5,545,531; 5,547,839; 5,554,501; 5,556,752; 5,561,071; 5,571,639; 5,580,726; 5,580,732; 5,593,839; 5,599,695; 5,599,672; 5,610,287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; 6,004,755; 6,087,102; 6,368,799; 6,383,749; 6,617,112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO0138580; WO 0168255; WO 03020898; WO 03040410; WO 03053586; WO 03087297; WO 03091426; WO03100012; WO 04020085; WO 04027093; EP 373 203; EP 785 280; EP 799 897 and UK 8 803 000; the disclosures of which are all herein incorporated by reference.

It is contemplated that the arrays can be high density arrays, such that they contain 2, 20, 25, 50, 80, 100 or more different probes. It is contemplated that they may contain 1000, 16,000, 65,000, 250,000 or 1,000,000 or more different probes. The probes can be directed to mRNA and/or miRNA targets in one or more different organisms or cell types. The oligonucleotide probes range from 5 to 50, 5 to 45, 10 to 40, 9 to 34, or 15 to 40 nucleotides in length in some embodiments. In certain embodiments, the oligonucleotide probes are 5, 10, 15, to 20, 25, 30, 35, 40 nucleotides in length including all integers and ranges there between.

The location and sequence of each different probe sequence in the array are generally known. Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per $cm^2$. The surface area of the array can be about or less than about 1, 1.6, 2, 3, 4, 5, 6, 7, 8, 9, or 10 $cm^2$.

Moreover, a person of ordinary skill in the art could readily analyze data generated using an array. Such protocols are disclosed above, and include information found in WO 9743450; WO 03023058; WO 03022421; WO 03029485; WO 03067217; WO 03066906; WO 03076928; WO 03093810; WO 03100448A1, all of which are specifically incorporated by reference.

B. Sample Preparation

It is contemplated that the RNA and/or miRNA of a wide variety of samples can be analyzed using the arrays, index of probes, or array technology of the invention. While endogenous miRNA is contemplated for use with compositions and methods of the invention, recombinant miRNA—including nucleic acids that are complementary or identical to endogenous miRNA or precursor miRNA—can also be handled and analyzed as described herein. Samples may be biological samples, in which case, they can be from biopsy, fine needle aspirates, exfoliates, blood, tissue, organs, semen, saliva, tears, other bodily fluid, hair follicles, skin, or any sample containing or constituting biological cells, particularly cancer or hyperproliferative cells. In certain embodiments, samples may be, but are not limited to, biopsy, or cells purified or enriched to some extent from a biopsy or other bodily fluids or tissues. Alternatively, the sample may not be a biological sample, but be a chemical mixture, such as a cell-free reaction mixture (which may contain one or more biological enzymes).

C. Hybridization

After an array or a set of probes is prepared and/or the nucleic acid in the sample or probe is labeled, the population of target nucleic acids is contacted with the array or probes under hybridization conditions, where such conditions can be adjusted, as desired, to provide for an optimum level of specificity in view of the particular assay being performed. Suitable hybridization conditions are well known to those of skill in the art and reviewed in Sambrook et al. (2001) and WO 95/21944. Of particular interest in many embodiments is the use of stringent conditions during hybridization. Stringent conditions are known to those of skill in the art.

It is specifically contemplated that a single array or set of probes may be contacted with multiple samples. The samples may be labeled with different labels to distinguish the samples. For example, a single array can be contacted with a tumor tissue sample labeled with Cy3, and normal tissue sample labeled with Cy5. Differences between the samples for particular miRNAs corresponding to probes on the array can be readily ascertained and quantified.

The small surface area of the array permits uniform hybridization conditions, such as temperature regulation and salt content. Moreover, because of the small area occupied by the high density arrays, hybridization may be carried out in extremely small fluid volumes (e.g., about 250 µl or less, including volumes of about or less than about 5, 10, 25, 50, 60, 70, 80, 90, 100 µl, or any range derivable therein). In small volumes, hybridization may proceed very rapidly.

D. Differential Expression Analyses

Arrays of the invention can be used to detect differences between two samples. Specifically contemplated applications include identifying and/or quantifying differences between miRNA or gene expression from a sample that is normal and from a sample that is not normal, between a disease or condition and a cell not exhibiting such a disease or condition, or between two differently treated samples. Also, miRNA or gene expression may be compared between a sample believed to be susceptible to a particular disease or condition and one believed to be not susceptible or resistant to that disease or condition. A sample that is not normal is one exhibiting phenotypic or genotypic trait(s) of a disease or condition, or one believed to be not normal with respect to that disease or condition. It may be compared to a cell that is normal with respect to that disease or condition. Phenotypic traits include symptoms of, or susceptibility to, a disease or condition of which a component is or may or may not be genetic, or caused by a hyperproliferative or neoplastic cell or cells.

An array comprises a solid support with nucleic acid probes attached to the support. Arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., (1991), each of which is incorporated by reference in its entirety for all purposes. Techniques for the synthesis of these arrays using mechanical synthesis methods are described in, e.g., U.S. Pat. No. 5,384,261, incorporated herein by reference in its entirety for all purposes. Although a planar array surface is used in certain aspects, the array may be fabricated on a surface of virtually any shape or even a multiplicity of surfaces. Arrays may be nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800,992, which are hereby incorporated in their entirety for all purposes. Arrays may be packaged in such a manner as to allow for diagnostics or other manipulation of an all inclusive device, see for example, U.S. Pat. Nos. 5,856,174 and 5,922,591 incorporated in their entirety by reference for all purposes. See also U.S. patent application Ser. No. 09/545,207, filed Apr. 7, 2000 for additional information concerning arrays, their manufacture, and their characteristics, which is incorporated by reference in its entirety for all purposes.

Particularly, arrays can be used to evaluate samples with respect to pathological condition such as cancer and related conditions. It is specifically contemplated that the invention can be used to evaluate differences between stages or sub-classifications of disease, such as between benign, cancerous, and metastatic tissues or tumors.

Phenotypic traits to be assessed include characteristics such as longevity, morbidity, expected survival, susceptibility or receptivity to particular drugs or therapeutic treatments (drug efficacy), and risk of drug toxicity. Samples that differ in these phenotypic traits may also be evaluated using the compositions and methods described.

In certain embodiments, miRNA and/or expression profiles may be generated to evaluate and correlate those profiles with pharmacokinetics or therapies. For example, these profiles may be created and evaluated for patient tumor and blood samples prior to the patient's being treated or during treatment to determine if there are miRNA or genes whose expression correlates with the outcome of the patient's treatment. Identification of differential miRNAs or genes can lead to a diagnostic assay for evaluation of tumor and/or blood samples to determine what drug regimen the patient should be provided. In addition, it can be used to identify or select patients suitable for a particular clinical trial. If an expression profile is determined to be correlated with drug efficacy or drug toxicity, that profile is relevant to whether that patient is an appropriate patient for receiving a drug, for receiving a combination of drugs, or for a particular dosage of the drug.

In addition to the above prognostic assay, samples from patients with a variety of diseases can be evaluated to determine if different diseases can be identified based on miRNA and/or related gene expression levels. A diagnostic assay can be created based on the profiles that doctors can use to identify individuals with a disease or who are at risk to develop a disease. Alternatively, treatments can be designed based on miRNA profiling. Examples of such methods and compositions are described in the U.S. Provisional Patent Application entitled "Methods and Compositions Involving miRNA and miRNA Inhibitor Molecules" filed on May 23, 2005 in the names of David Brown, Lance Ford, Angie Cheng and Rich Jarvis, which is hereby incorporated by reference in its entirety.

E. Other Assays

In addition to the use of arrays and microarrays, it is contemplated that a number of different assays could be employed to analyze miRNAs or related genes, their activities, and their effects. Such assays include, but are not limited to, nucleic acid amplification, polymerase chain reaction, quantitative PCR, RT-PCR, in situ hybridization, Northern hybridization, hybridization protection assay (HPA) (Gen-Probe), branched DNA (bDNA) assay (Chiron), rolling circle amplification (RCA), single molecule hybridization detection (US Genomics), Invader assay (ThirdWave Technologies), and/or Bridge Litigation Assay (Genaco).

IV. Nucleic Acids

The present invention concerns nucleic acids, modified or mimetic nucleic acids, miRNAs, mRNAs, genes, and representative fragments thereof that can be labeled, used in array analysis, or employed in diagnostic, therapeutic, or prognostic applications, particularly those related to pathological conditions such as cancer. The molecules may have been endogenously produced by a cell, or been synthesized or produced chemically or recombinantly. They may be isolated and/or purified. Each of the miRNAs described herein and includes the corresponding SEQ ID NO and accession numbers for these miRNA sequences. The name of a miRNA is often abbreviated and referred to without a "hsa-" prefix and will be understood as such, depending on the context. Unless otherwise indicated, miRNAs referred to in the application are human sequences identified as miR-X or let-X, where X is a number and/or letter.

In certain aspects, a miRNA probe designated by a suffix "5P" or "3P" can be used. "5P" indicates that the mature miRNA derives from the 5' end of the precursor and a corresponding "3P" indicates that it derives from the 3' end of the precursor, as described on the world wide web at sanger.ac.uk. Moreover, in some embodiments, a miRNA probe is used that does not correspond to a known human miRNA. It is contemplated that these non-human miRNA probes may be used in embodiments of the invention or that there may exist a human miRNA that is homologous to the non-human miRNA. In other embodiments, any mammalian cell, biological sample, or preparation thereof may be employed.

In some embodiments of the invention, methods and compositions involving miRNA may concern miRNA, markers (mRNAs), and/or other nucleic acids. Nucleic acids may be, be at least, or be at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides, or any range derivable therein, in length. Such lengths cover the lengths of processed miRNA, miRNA probes, precursor miRNA, miRNA containing vectors, mRNA, mRNA probes, control nucleic acids, and other probes and primers.

In many embodiments, miRNA are 19-24 nucleotides in length, while miRNA probes are 19-35 nucleotides in length, depending on the length of the processed miRNA and any flanking regions added. miRNA precursors are generally between 62 and 110 nucleotides in humans.

Nucleic acids of the invention may have regions of identity or complementarity to another nucleic acid. It is contemplated that the region of complementarity or identity can be at least 5 contiguous residues, though it is specifically contemplated that the region is, is at least, or is at most 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 contiguous nucleotides. It is further understood that the length of complementarity within a precursor miRNA or other nucleic acid or between a miRNA probe and a miRNA or a miRNA gene are such lengths. Moreover, the complementarity may be expressed as a percentage, meaning that the complementarity between a probe and its target is 90% or greater over the length of the probe. In some embodiments, complementarity is or is at least 90%, 95% or 100%. In particular, such lengths may be applied to any nucleic acid comprising a nucleic acid sequence identified in any of SEQ ID NOs described herein, accession number, or any other sequence disclosed herein. Typically, the commonly used name of the miRNA is given (with its identifying source in the prefix, for example, "hsa" for human sequences) and the processed miRNA sequence. Unless otherwise indicated, a miRNA without a prefix will be understood to refer to a human miRNA. Moreover, a lowercase letter in a miRNA name may or may not be lowercase; for example, hsa-mir-130b can also be referred to as miR-130B. The term "miRNA probe" refers to a nucleic acid probe that can identify a particular miRNA or structurally related miRNAs.

It is understood that some nucleic acids are derived from genomic sequences or a gene. In this respect, the term "gene" is used for simplicity to refer to the genomic sequence encoding the precursor nucleic acid or miRNA for a given miRNA or gene. However, embodiments of the invention may involve genomic sequences of a miRNA that are involved in its expression, such as a promoter or other regulatory sequences.

The term "recombinant" may be used and this generally refers to a molecule that has been manipulated in vitro or that is a replicated or expressed product of such a molecule.

The term "nucleic acid" is well known in the art. A "nucleic acid" as used herein will generally refer to a molecule (one or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid."

The term "miRNA" generally refers to a single-stranded molecule, but in specific embodiments, molecules implemented in the invention will also encompass a region or an additional strand that is partially (between 10 and 50% complementary across length of strand), substantially (greater than 50% but less than 100% complementary across length of strand) or fully complementary to another region of the same single-stranded molecule or to another nucleic acid. Thus, nucleic acids of the invention may encompass a molecule that comprises one or more complementary or self-complementary strand(s) or "complement(s)" of a particular sequence. For example, precursor miRNA may have a self-complementary region, which is up to 100% complementary. miRNA probes or nucleic acids of the invention can include, can be or can be at least 60, 65, 70, 75, 80, 85, 90, 95, 96, 97, 98, 99 or 100% complementary to their target.

It is understood that a "synthetic nucleic acid" of the invention means that the nucleic acid does not have all or part of a chemical structure or sequence of a naturally occurring nucleic acid. Consequently, it will be understood that the term "synthetic miRNA" refers to a "synthetic nucleic acid" that functions in a cell or under physiological conditions as a naturally occurring miRNA.

While embodiments of the invention may involve synthetic miRNAs or synthetic nucleic acids, in some embodiments of the invention, the nucleic acid molecule(s) need not be "synthetic." In certain embodiments, a non-synthetic nucleic acid or miRNA employed in methods and compositions of the invention may have the entire sequence and structure of a naturally occurring mRNA or miRNA precursor or the mature mRNA or miRNA. For example, non-synthetic miRNAs used in methods and compositions of the invention may not have one or more modified nucleotides or nucleotide analogs. In these embodiments, the non-synthetic miRNA may or may not be recombinantly produced. In particular embodiments, the nucleic acid in methods and/or compositions of the invention is specifically a synthetic miRNA and not a non-synthetic miRNA (that is, not a miRNA that qualifies as "synthetic"); though in other embodiments, the invention specifically involves a non-synthetic miRNA and not a synthetic miRNA. Any embodiments discussed with respect to the use of synthetic miRNAs can be applied with respect to non-synthetic miRNAs, and vice versa.

It will be understood that the term "naturally occurring" refers to something found in an organism without any intervention by a person; it could refer to a naturally-occurring wildtype or mutant molecule. In some embodiments a synthetic miRNA molecule does not have the sequence of a naturally occurring miRNA molecule. In other embodiments, a synthetic miRNA molecule may have the sequence of a naturally occurring miRNA molecule, but the chemical structure of the molecule, particularly in the part unrelated specifically to the precise sequence (non-sequence chemical structure) differs from chemical structure of the naturally occurring miRNA molecule with that sequence. In some cases, the synthetic miRNA has both a sequence and non-sequence chemical structure that are not found in a naturally-occurring miRNA. Moreover, the sequence of the synthetic molecules will identify which miRNA is effectively being provided or inhibited; the endogenous miRNA will be referred to as the "corresponding miRNA." Corresponding miRNA sequences that can be used in the context of the invention include, but are not limited to, all or a portion of those sequences in the SEQ IDs provided herein, as well as any other miRNA sequence, miRNA precursor sequence, or any sequence complementary thereof. In some embodiments, the sequence is or is derived from or contains all or part of a sequence identified herein to target a particular miRNA (or set of miRNAs) that can be used with that sequence. Any 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130 140, 150, 160, 170, 180, 190, 200, 210, 220, 230, 240, 250, 260 or any number or range of sequences there between may be selected to the exclusion of all non-selected sequences.

As used herein, "hybridization", "hybridizes" or "capable of hybridizing" is understood to mean the forming of a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but preclude hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.5 M NaCl at temperatures of about 42° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions," and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

A. Nucleobase, Nucleoside, Nucleotide, and Modified Nucleotides

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in a manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, carboxyalkyl, amino, hydroxyl, halogen (i.e., fluoro, chloro, bromo, or iodo), thiol or alkylthiol moiety. Preferred alkyl (e.g., alkyl, carboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-dimethyladenine, an azaadenines, a 8-bromoadenine, a 8-hydroxyadenine, a 6-hydroxyaminopurine, a 6-thiopurine, a 4-(6-aminohexyl/cytosine), and the like. Other examples are well known to those of skill in the art.

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring. Different types of covalent attachment(s) of a nucleobase to a nucleobase linker moiety are known in the art (Kornberg and Baker, 1992).

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

A nucleic acid may comprise, or be composed entirely of, a derivative or analog of a nucleobase, a nucleobase linker moiety and/or backbone moiety that may be present in a naturally occurring nucleic acid. RNA with nucleic acid analogs may also be labeled according to methods of the invention. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides or nucleic acids include those in: U.S. Pat. Nos. 5,681,947, 5,652,099 and 5,763,167, 5,614,617, 5,670,663, 5,872,232, 5,859,221, 5,446,137, 5,886,165, 5,714,606, 5,672,697, 5,466,786, 5,792,847, 5,223,618, 5,470,967, 5,378,825, 5,777,092, 5,623,070, 5,610,289, 5,602,240, 5,858,988, 5,214,136, 5,700,922, 5,708,154, 5,728,525, 5,637,683, 6,251,666, 5,480,980, and 5,728,525, each of which is incorporated herein by reference in its entirety.

Labeling methods and kits of the invention specifically contemplate the use of nucleotides that are both modified for attachment of a label and can be incorporated into a miRNA molecule. Such nucleotides include those that can be labeled with a dye, including a fluorescent dye, or with a molecule such as biotin. Labeled nucleotides are readily available; they can be acquired commercially or they can be synthesized by reactions known to those of skill in the art.

Modified nucleotides for use in the invention are not naturally occurring nucleotides, but instead, refer to prepared nucleotides that have a reactive moiety on them. Specific reactive functionalities of interest include: amino, sulfhydryl, sulfoxyl, aminosulfhydryl, azido, epoxide, isothiocyanate, isocyanate, anhydride, monochlorotriazine, dichlorotriazine, mono- or dihalogen substituted pyridine, mono- or disubstituted diazine, maleimide, epoxide, aziridine, sulfonyl halide, acid halide, alkyl halide, aryl halide, alkylsulfonate, N-hydroxysuccinimide ester, imido ester, hydrazine, azidonitrophenyl, azide, 3-(2-pyridyl dithio)-propionamide, glyoxal, aldehyde, iodoacetyl, cyanomethyl ester, p-nitrophenyl ester, o-nitrophenyl ester, hydroxypyridine ester, carbonyl imidazole, and the other such chemical groups. In some embodiments, the reactive functionality may be bonded directly to a nucleotide, or it may be bonded to the nucleotide through a linking group. The functional moiety and any linker cannot substantially impair the ability of the nucleotide to be added to the miRNA or to be labeled. Representative linking groups include carbon containing linking groups, typically ranging from about 2 to 18, usually from about 2 to 8 carbon atoms, where the carbon containing linking groups may or may not include one or more heteroatoms, e.g. S, O, N etc., and may or may not include one or more sites of unsaturation. Of particular interest in many embodiments is alkyl linking groups, typically lower alkyl linking groups of 1 to 16, usually 1 to 4 carbon atoms, where the linking groups may include one or more sites of unsaturation. The functionalized nucleotides (or primers) used in the above methods of functionalized target generation may be fabricated using known protocols or purchased from commercial vendors, e.g., Sigma, Roche, Ambion, Biosearch Technologies and NEN. Functional groups may be prepared according to ways known to those of skill in the art, including the representative information found in U.S. Pat. Nos. 4,404,289; 4,405,711; 4,337,063 and 5,268,486, and U.K. Patent 1,529,202, which are all incorporated by reference.

Amine-modified nucleotides are used in several embodiments of the invention. The amine-modified nucleotide is a nucleotide that has a reactive amine group for attachment of the label. It is contemplated that any ribonucleotide (G, A, U, or C) or deoxyribonucleotide (G, A, T, or C) can be modified for labeling. Examples include, but are not limited to, the following modified ribo- and deoxyribo-nucleotides: 5-(3-aminoallyl)-UTP; 8-[(4-amino)butyl]-amino-ATP and 8-[(6-amino)butyl]-amino-ATP; N6-(4-amino)butyl-ATP, N6-(6-amino)butyl-ATP, N4-[2,2-oxy-bis-(ethylamine)]-CTP; N6-(6-Amino)hexyl-ATP; 8-[(6-Amino)hexyl]-amino-ATP; 5-propargylamino-CTP, 5-propargylamino-UTP; 5-(3-aminoallyl)-dUTP; 8-[(4-amino)butyl]-amino-dATP and 8-[(6-amino)butyl]-amino-dATP; N6-(4-amino)butyl-dATP, N6-(6-amino)butyl-dATP, N4-[2,2-oxy-bis-(ethylamine)]-dCTP; N6-(6-Amino)hexyl-dATP; 8-[(6-Amino)hexyl]-amino-dATP; 5-propargylamino-dCTP, and 5-propargylamino-dUTP. Such nucleotides can be prepared according to methods known to those of skill in the art. Moreover, a person of ordinary skill in the art could prepare other nucleotide entities with the same amine-modification, such as a 5-(3-aminoallyl)-CTP, GTP, ATP, dCTP, dGTP, dTTP, or dUTP in place of a 5-(3-aminoallyl)-UTP.

B. Preparation of Nucleic Acids

A nucleic acid may be made by any technique known to one of ordinary skill in the art, such as for example, chemical synthesis, enzymatic production, or biological production. It is specifically contemplated that miRNA probes of the invention are chemically synthesized.

In some embodiments of the invention, miRNAs are recovered or isolated from a biological sample. The miRNA may be recombinant or it may be natural or endogenous to the cell (produced from the cell's genome). It is contemplated that a biological sample may be treated in a way so as to enhance the recovery of small RNA molecules such as miRNA. U.S. patent application Ser. No. 10/667,126 describes such methods and it is specifically incorporated by reference herein. Generally, methods involve lysing cells with a solution having guanidinium and a detergent.

Alternatively, nucleic acid synthesis is performed according to standard methods. See, for example, Itakura and Riggs (1980) and U.S. Pat. Nos. 4,704,362, 5,221,619, and 5,583,013, each of which is incorporated herein by reference. Non-limiting examples of a synthetic nucleic acid (e.g., a synthetic oligonucleotide), include a nucleic acid made by in vitro chemically synthesis using phosphotriester, phosphite, or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. Nos. 4,683,202 and 4,682,195, each incorporated herein by reference), or the synthesis of an oligonucleotide described in U.S. Pat. No. 5,645,897, incorporated herein by reference. See also Sambrook et al., 2001, incorporated herein by reference).

Oligonucleotide synthesis is well known to those of skill in the art. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

Recombinant methods for producing nucleic acids in a cell are well known to those of skill in the art. These include the use of vectors (viral and non-viral), plasmids, cosmids, and other vehicles for delivering a nucleic acid to a cell, which may be the target cell (e.g., a cancer cell) or simply a host cell (to produce large quantities of the desired RNA molecule). Alternatively, such vehicles can be used in the context of a cell free system so long as the reagents for generating the RNA molecule are present. Such methods include those described in Sambrook, 2003, Sambrook, 2001 and Sambrook, 1989, which are hereby incorporated by reference.

C. Isolation of Nucleic Acids

Nucleic acids may be isolated using techniques well known to those of skill in the art, though in particular embodiments, methods for isolating small nucleic acid molecules, and/or isolating RNA molecules can be employed. Chromatography is a process often used to separate or isolate nucleic acids from protein or from other nucleic acids. Such methods can involve electrophoresis with a gel matrix, filter columns, alcohol precipitation, and/or other chromatography. If miRNA from cells is to be used or evaluated, methods generally involve lysing the cells with a chaotropic (e.g., guanidinium isothiocyanate) and/or detergent (e.g., N-lauroyl sarcosine) prior to implementing processes for isolating particular populations of RNA.

In particular methods for separating miRNA from other nucleic acids, a gel matrix is prepared using polyacrylamide, though agarose can also be used. The gels may be graded by concentration or they may be uniform. Plates or tubing can be used to hold the gel matrix for electrophoresis. Usually one-dimensional electrophoresis is employed for the separation of nucleic acids. Plates are used to prepare a slab gel, while the tubing (glass or rubber, typically) can be used to prepare a tube gel. The phrase "tube electrophoresis" refers to the use of a tube or tubing, instead of plates, to form the gel. Materials for implementing tube electrophoresis can be readily prepared by a person of skill in the art or purchased, such as from C.B.S. Scientific Co., Inc. or Scie-Plas.

Methods may involve the use of organic solvents and/or alcohol to isolate nucleic acids, particularly miRNA used in methods and compositions of the invention. Some embodiments are described in U.S. patent application Ser. No. 10/667,126, which is hereby incorporated by reference. Generally, this disclosure provides methods for efficiently isolating small RNA molecules from cells comprising: adding an alcohol solution to a cell lysate and applying the alcohol/lysate mixture to a solid support before eluting the RNA molecules from the solid support. In some embodiments, the amount of alcohol added to a cell lysate achieves an alcohol concentration of about 55% to 60%. While different alcohols can be employed, ethanol works well. A solid support may be any structure, and it includes beads, filters, and columns, which may include a mineral or polymer support with electronegative groups. A glass fiber filter or column has worked particularly well for such isolation procedures.

In specific embodiments, miRNA isolation processes include: a) lysing cells in the sample with a lysing solution comprising guanidinium, wherein a lysate with a concentration of at least about 1 M guanidinium is produced; b) extracting miRNA molecules from the lysate with an extraction solution comprising phenol; c) adding to the lysate an alcohol solution for forming a lysate/alcohol mixture, wherein the concentration of alcohol in the mixture is between about 35% to about 70%; d) applying the lysate/alcohol mixture to a solid support; e) eluting the miRNA molecules from the solid support with an ionic solution; and, f) capturing the miRNA molecules. Typically the sample is dried and resuspended in a liquid and volume appropriate for subsequent manipulation.

V. Labels and Labeling Techniques

In some embodiments, the present invention concerns miRNA that are labeled. It is contemplated that miRNA may first be isolated and/or purified prior to labeling. This may achieve a reaction that more efficiently labels the miRNA, as opposed to other RNA in a sample in which the miRNA is not isolated or purified prior to labeling. In many embodiments of the invention, the label is non-radioactive. Generally, nucleic acids may be labeled by adding labeled nucleotides (one-step process) or adding nucleotides and labeling the added nucleotides (two-step process).

A. Labeling Techniques

In some embodiments, nucleic acids are labeled by catalytically adding to the nucleic acid an already labeled nucleotide or nucleotides. One or more labeled nucleotides can be added to miRNA molecules. See U.S. Pat. No. 6,723,509, which is hereby incorporated by reference.

In other embodiments, an unlabeled nucleotide or nucleotides is catalytically added to a miRNA, and the unlabeled nucleotide is modified with a chemical moiety that enables it to be subsequently labeled. In embodiments of the invention, the chemical moiety is a reactive amine such that the nucleotide is an amine-modified nucleotide. Examples of amine-modified nucleotides are well known to those of skill in the art, many being commercially available such as from Ambion, Sigma, Jena Bioscience, and TriLink.

In contrast to labeling of cDNA during its synthesis, the issue for labeling miRNA is how to label the already existing molecule. The present invention concerns the use of an enzyme capable of using a di- or tri-phosphate ribonucleotide or deoxyribonucleotide as a substrate for its addition to a miRNA. Moreover, in specific embodiments, it involves using a modified di- or tri-phosphate ribonucleotide, which is added to the 3' end of a miRNA. Enzymes capable of adding such nucleotides include, but are not limited to, poly (A) polymerase, terminal transferase, and polynucleotide phosphorylase. In specific embodiments of the invention, a ligase is contemplated as not being the enzyme used to add the label, and instead, a non-ligase enzyme is employed. Terminal transferase catalyzes the addition of nucleotides to the 3' terminus of a nucleic acid. Polynucleotide phosphorylase can polymerize nucleotide diphosphates without the need for a primer.

B. Labels

Labels on miRNA or miRNA probes may be colorimetric (includes visible and UV spectrum, including fluorescent), luminescent, enzymatic, or positron emitting (including radioactive). The label may be detected directly or indirectly. Radioactive labels include $^{125}$I, $^{32}$P, $^{33}$P, and $^{35}$S. Examples of enzymatic labels include alkaline phosphatase, luciferase, horseradish peroxidase, and β-galactosidase. Labels can also be proteins with luminescent properties, e.g., green fluorescent protein and phycoerythrin.

The colorimetric and fluorescent labels contemplated for use as conjugates include, but are not limited to, Alexa Fluor dyes, BODIPY dyes, such as BODIPY FL; Cascade Blue; Cascade Yellow; coumarin and its derivatives, such as 7-amino-4-methylcoumarin, aminocoumarin and hydroxycoumarin; cyanine dyes, such as Cy3 and Cy5; eosins and erythrosins; fluorescein and its derivatives, such as fluorescein isothiocyanate; macrocyclic chelates of lanthanide ions, such as Quantum Dye™; Marina Blue; Oregon Green; rhodamine dyes, such as rhodamine red, tetramethylrhodamine and rhodamine 6G; Texas Red; fluorescent energy transfer dyes, such as thiazole orange-ethidium heterodimer; and, TOTAB.

Specific examples of dyes include, but are not limited to, those identified above and the following: Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODIPY 530/550, BODIPY 558/568, BODIPY 564/570, BODIPY 576/589, BODIPY 581/591, BODIPY 630/650, BODIPY 650/655, BODIPY FL, BODIPY R6G, BODIPY TMR, and, BODIPY-TR; Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, and TET.

Specific examples of fluorescently labeled ribonucleotides are available from Molecular Probes, and these include, Alexa Fluor 488-5-UTP, Fluorescein-12-UTP, BODIPY FL-14-UTP, BODIPY TMR-14-UTP, Tetramethylrhodamine-6-UTP, Alexa Fluor 546-14-UTP, Texas Red-5-UTP, and BODIPY TR-14-UTP. Other fluorescent ribonucleotides are available from Amersham Biosciences, such as Cy3-UTP and Cy5-UTP.

Examples of fluorescently labeled deoxyribonucleotides include Dinitrophenyl (DNP)-11-dUTP, Cascade Blue-7-dUTP, Alexa Fluor 488-5-dUTP, Fluorescein-12-dUTP, Oregon Green 488-5-dUTP, BODIPY FL-14-dUTP, Rhodamine Green-5-dUTP, Alexa Fluor 532-5-dUTP, BODIPY TMR-14-dUTP, Tetramethylrhodamine-6-dUTP, Alexa Fluor 546-14-dUTP, Alexa Fluor 568-5-dUTP, Texas Red-12-dUTP, Texas Red-5-dUTP, BODIPY TR-14-dUTP, Alexa Fluor 594-5-dUTP, BODIPY 630/650-14-dUTP, BODIPY 650/665-14-dUTP; Alexa Fluor 488-7-OBEA-dCTP, Alexa Fluor 546-16-OBEA-dCTP, Alexa Fluor 594-7-OBEA-dCTP, Alexa Fluor 647-12-OBEA-dCTP.

It is contemplated that nucleic acids may be labeled with two different labels. Furthermore, fluorescence resonance energy transfer (FRET) may be employed in methods of the invention (e.g., Klostermeier et al., 2002; Emptage, 2001; Didenko, 2001, each incorporated by reference).

Alternatively, the label may not be detectable per se, but indirectly detectable or allowing for the isolation or separation of the targeted nucleic acid. For example, the label could be biotin, digoxigenin, polyvalent cations, chelator groups and the other ligands, include ligands for an antibody.

C. Visualization Techniques

A number of techniques for visualizing or detecting labeled nucleic acids are readily available. Such techniques include, microscopy, arrays, Fluorometry, Light cyclers or other real time PCR machines, FACS analysis, scintillation counters, Phosphoimagers, Geiger counters, MRI, CAT, antibody-based detection methods (Westerns, immunofluorescence, immunohistochemistry), histochemical techniques, HPLC (Griffey et al., 1997), spectroscopy, capillary gel electrophoresis (Cummins et al., 1996), spectroscopy; mass spectroscopy; radiological techniques; and mass balance techniques.

When two or more differentially colored labels are employed, fluorescent resonance energy transfer (FRET) techniques may be employed to characterize association of one or more nucleic acid. Furthermore, a person of ordinary skill in the art is well aware of ways of visualizing, identifying, and characterizing labeled nucleic acids, and accordingly, such protocols may be used as part of the invention. Examples of tools that may be used also include fluorescent microscopy, a BioAnalyzer, a plate reader, Storm (Molecular Dynamics), Array Scanner, FACS (fluorescent activated cell sorter), or any instrument that has the ability to excite and detect a fluorescent molecule.

VI. Kits

Any of the compositions described herein may be comprised in a kit. In a non-limiting example, reagents for isolating miRNA, labeling miRNA, and/or evaluating a miRNA population using an array, nucleic acid amplification, and/or hybridization can be included in a kit, as well reagents for preparation of samples from blood samples. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. In certain aspects, the kit can include amplification reagents. In other aspects, the kit may include various supports, such as glass, nylon, polymeric beads, and the like, and/or reagents for coupling any probes and/or target nucleic acids. It may also include one or more buffers, such as reaction buffer, labeling buffer, washing buffer, or a hybridization buffer, compounds for preparing the miRNA probes, and components for isolating miRNA. Other kits of the invention may include components for making a nucleic acid array comprising miRNA, and thus, may include, for example, a solid support.

Kits for implementing methods of the invention described herein are specifically contemplated. In some embodiments, there are kits for preparing miRNA for multi-labeling and kits for preparing miRNA probes and/or miRNA arrays. In these embodiments, kit comprise, in suitable container means, 1, 2, 3, 4, 5, 6, 7, 8, 9, 10, 11, 12 or more of the following: (1) poly(A) polymerase; (2) unmodified nucleotides (G, A, T, C, and/or U); (3) a modified nucleotide (labeled or unlabeled); (4) poly(A) polymerase buffer; and, (5) at least one microfilter; (6) label that can be attached to a nucleotide; (7) at least one miRNA probe; (8) reaction buffer; (9) a miRNA array or components for making such an array; (10) acetic acid; (11) alcohol; (12) solutions for preparing, isolating, enriching, and purifying miRNAs or miRNA probes or arrays. Other reagents include those generally used for manipulating RNA, such as formamide, loading dye, ribonuclease inhibitors, and DNase.

In specific embodiments, kits of the invention include an array containing miRNA probes, as described in the application. An array may have probes corresponding to all known miRNAs of an organism or a particular tissue or organ in particular conditions, or to a subset of such probes. The subset of probes on arrays of the invention may be or include those identified as relevant to a particular diagnostic, therapeutic, or prognostic application. For example, the array may contain one or more probes that is indicative or suggestive of (1) a disease or condition (acute myeloid leukemia), (2) susceptibility or resistance to a particular drug or treatment; (3) susceptibility to toxicity from a drug or substance; (4) the stage of development or severity of a disease or condition (prognosis); and (5) genetic predisposition to a disease or condition.

For any kit embodiment, including an array, there can be nucleic acid molecules that contain or can be used to amplify a sequence that is a variant of, identical to or complementary to all or part of any of SEQ IDs described herein. In certain embodiments, a kit or array of the invention can contain one or more probes for the miRNAs identified by the SEQ IDs described herein. Any nucleic acid discussed above may be implemented as part of a kit.

The components of the kits may be packaged either in aqueous media or in lyophilized form. The container means of the kits will generally include at least one vial, test tube, flask, bottle, syringe or other container means, into which a component may be placed, and preferably, suitably aliquotted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means. In some embodiments, labeling dyes are provided as a dried power. It is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 µg or at least or at most those amounts of dried dye are provided in kits of the invention. The dye may then be resuspended in any suitable solvent, such as DMSO.

Such kits may also include components that facilitate isolation of the labeled miRNA. It may also include components that preserve or maintain the miRNA or that protect against its degradation. Such components may be RNAse-free or protect against RNAses. Such kits generally will comprise, in suitable means, distinct containers for each individual reagent or solution.

A kit will also include instructions for employing the kit components as well the use of any other reagent not included in the kit. Instructions may include variations that can be implemented.

Kits of the invention may also include one or more of the following: Control RNA; nuclease-free water; RNase-free containers, such as 1.5 ml tubes; RNase-free elution tubes; PEG or dextran; ethanol; acetic acid; sodium acetate; ammonium acetate; guanidinium; detergent; nucleic acid size marker; RNase-free tube tips; and RNase or DNase inhibitors. It is contemplated that such reagents are embodiments of kits of the invention. Such kits, however, are not limited to the particular items identified above and may include any reagent used for the manipulation or characterization of miRNA.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Gene Expression Analysis Following Transfection with Hsa-miR-124a miRNAs are believed to regulate gene expression by binding to target mRNA transcripts and (1) initiating transcript degradation or (2) altering protein translation from the transcript. Translational regulation leading to an up or down change in protein expression may lead to changes in activity and expression of downstream gene products and genes that are in turn regulated by those proteins. These numerous regulatory effects may be revealed as changes in the global mRNA expression profile. Microarray gene expression analyses were performed to identify genes that are mis-regulated by hsa-miR-124a expression.

Synthetic Pre-miR™-hsa-miR-124a (Ambion; Austin, Tex., USA) or two negative control (NC) miRNAs (Pre-miR™ microRNA Precursor Molecule-Negative Control #1, Ambion, cat. no. AM17110 and Pre-miR™ microRNA Precursor Molecule-Negative Control #2, Ambion, cat. no. AM17111) were reverse transfected into quadruplicate samples of A549 cells for each of three time points. Cells were transfected using siPORT™ NeoFX™ (Ambion, cat. no. AM4511) according to the manufacturer's recommendations using the following parameters: 200,000 cells per well in a 6 well plate, 5.0 µl of NeoFX, 30 nM final concentration of miRNA in 2.5 ml. Cells were harvested at 4 h, 24 h, and 72 h post transfection. Total RNA was extracted using RNAqueous®-4PCR (Ambion) according to the manufacturer's recommended protocol.

mRNA array analyses were performed by Asuragen Services (Asuragen, Inc.; Austin, Tex., USA), according to the company's standard operating procedures. Using the MessageAmp™ II-96 aRNA Amplification Kit (Ambion, cat. no. 1819) 2 µg of total RNA were used for target preparation and labeling with biotin. cRNA yields were quantified using an Agilent Bioanalyzer 2100 (Agilent Technologies, Inc.; Santa Clara, Calif., USA) capillary electrophoresis protocol. Labeled target was hybridized to Affymetrix mRNA arrays (Human HG-U133A 2.0 arrays; Affymetrix, Inc.; Santa Clara, Calif., USA) using the manufacturer's recommendations and the following parameters. Hybridizations were carried out at 45° C. for 16 hr in an Affymetrix Model 640 hybridization oven. Arrays were washed and stained on an Affymetrix FS450 Fluidics station, running the wash script Midi_euk2v3_450. The arrays were scanned on a Affymetrix GeneChip Scanner 3000. Summaries of the image signal data, group mean values, p-values with significance flags, log ratios and gene annotations for every gene on the array were generated using the Affymetrix Statistical Algorithm MAS 5.0 (GCOS v1.3). Data were reported in a file (cabinet) containing the Affymetrix data and result files and in files (.cel) containing the primary image and processed cell intensities of the arrays. Data were normalized for the effect observed by the average of two negative control microRNA sequences and then were averaged together for presentation. A list of genes whose expression levels varied by at least 0.7 $\log_2$ from the average negative control was assembled. Results of the microarray gene expression analysis are shown in Table 1.

TABLE 1

Genes with increased (positive values) or decreased (negative values) expression following transfection of human cancer cells with pre-miR hsa-miR-124a.

| UniGene ID | Gene Title | Gene Symbol | Log2 (mir124 − NC #2) |
|---|---|---|---|
| Hs.445113 | membrane-associated ring finger (C3HC4) 2 | MARCH2 | 1.44651 |
| Hs.567284 | membrane-associated ring finger (C3HC4) 5 | MARCH5 | −1.1922 |
| Hs.432862 | membrane-associated ring finger (C3HC4) 6 | MARCH6 | −1.44433 |
| Hs.65377 | membrane-associated ring finger (C3HC4) 9 | MARCH9 | 1.42294 |
| Hs.469615 | septin 10 | SEPT10 | −2.05922 |
| Hs.469615 | septin 10 | SEPT10 | −2.02304 |
| Hs.128199 | septin 11 | SEPT11 | −1.73143 |
| Hs.128199 | septin 11 | SEPT11 | −1.49535 |
| Hs.510949 | cDNA clone IMAGE: 5296106 | — | −2.8575 |
| — | — | — | −2.85197 |
| Hs.128753 | full-length cDNA clone CS0DD009YB17 of Neuroblastoma Cot 50-normalized of *Homo sapiens* (human) | — | −2.72106 |
| Hs.560444 | Transcribed locus | — | −2.57552 |
| Hs.55028 | cDNA clone IMAGE: 6043059 | — | −2.42829 |
| Hs.440492 | cDNA FLJ43100 fis, clone CTONG2003100 | — | −2.32519 |
| Hs.454036 | cDNA clone IMAGE: 4814292 | — | −2.18762 |
| Hs.88045 | cDNA FLJ45482 fis, clone BRTHA2001953 | — | −2.14874 |
| — | — | — | −2.14729 |
| — | — | — | −2.10765 |
| Hs.383050 | Similar to esterase/N-deacetylase (EC 3.5.1.—), 50K hepatic-rabbit | — | −2.02776 |
| Hs.355655 /// Hs.547541 | cDNA FLJ36584 fis, clone TRACH2013450 /// MRNA; cDNA DKFZp564A222 | — | −2.02022 |
| Hs.562593 | Transcribed locus | — | −1.96501 |
| — | — | — | −1.82654 |
| Hs.549889 | cDNA FLJ12874 fis, clone NT2RP2003769 | — | −1.79133 |
| Hs.561352 | Transcribed locus | — | −1.78964 |
| Hs.100261 | cDNA FLJ26539 fis, clone KDN09310 | — | −1.72363 |
| Hs.44380 | Transcribed locus, weakly similar to NP_060312.1 hypothetical protein FLJ20489 | — | −1.66449 |
| Hs.135904 | cDNA FLJ26959 fis, clone SLV00568 | — | −1.65519 |
| Hs.191482 | cDNA clone IMAGE: 4769453 | — | −1.61616 |
| Hs.372378 | cDNA clone IMAGE: 4797099 | — | −1.61128 |
| Hs.406574 | Transcribed locus | — | −1.59362 |
| Hs.173030 | cDNA FLJ34013 fis, clone FCBBF2002111 | — | −1.59231 |
| Hs.9585 | cDNA FLJ30010 fis, clone 3NB692000154 | — | −1.59113 |
| Hs.27463 | Transcribed locus, weakly similar to NP_055301.1 neuronal thread protein AD7c-NT | — | −1.58144 |
| Hs.547551 | Transcribed locus | — | −1.56679 |
| Hs.463677 | cDNA FLJ11381 fis, clone HEMBA1000501 | — | −1.56053 |
| Hs.491872 | Transcribed locus, weakly similar to NP_694983.1 hypothetical protein FLJ25952 | — | −1.55238 |
| Hs.507978 | cDNA FLJ34896 fis, clone NT2NE2018180 | — | −1.53383 |
| Hs.560381 | cDNA FLJ37777 fis, clone BRHIP2026274 | — | −1.53149 |
| Hs.238996 | Transcribed locus, weakly similar to XP_510104.1 | — | −1.51518 |
| Hs.499682 | Transcribed locus | — | −1.51318 |
| — | — | — | −1.49041 |
| Hs.29464 | mRNA; cDNA DKFZp566C034 (from clone DKFZp566C034) | — | −1.48947 |
| Hs.550906 | cDNA FLJ33653 fis, clone BRAMY2024715 | — | −1.47234 |
| Hs.356530 | Transcribed locus, strongly similar to XP_421205. | — | −1.45472 |
| — | — | — | −1.40051 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.212709 | full-length cDNA clone CS0DJ013YE21 of T cells (Jurkat cell line) Cot 10-normali | — | −1.39206 |
| Hs.167371 | LOC440702 | — | −1.38094 |
| Hs.102941 | cDNA: FLJ21531 fis, clone COL06036 | — | −1.36543 |
| Hs.78050 | Transcribed locus, weakly similar to XP_510104.1 | — | −1.36494 |
| Hs.530328 | Arsenic transactivated protein 1 | — | −1.35564 |
| Hs.530762 | Transcribed locus | — | −1.3506 |
| Hs.483955 | Transcribed locus | — | −1.32209 |
| Hs.254006 | Transcribed locus | — | −1.30338 |
| Hs.406574 | Transcribed locus | — | −1.28178 |
| Hs.547396 | mRNA; cDNA DKFZp451K063 (from clone DKFZp451K063) | — | −1.26815 |
| — | — | — | −1.24766 |
| Hs.69504 | Hypothetical LOC133993 | — | −1.20301 |
| Hs.561587 | cDNA: FLJ22100 fis, clone HEP17127 | — | −1.19883 |
| Hs.467411 | Transcribed locus, moderately similar to XP_512541.1 | — | −1.19135 |
| Hs.24359 | cDNA FLJ11174 fis, clone PLACE1007367 | — | −1.1838 |
| — | — | — | −1.17196 |
| Hs.433345 | Full-length cDNA clone CL0BB014ZH04 of Neuroblastoma of Homo sapiens (human) | — | −1.16946 |
| — | — | — | −1.16405 |
| — | — | — | −1.15814 |
| — | — | — | −1.15514 |
| Hs.63187 | cDNA FLJ41910 fis, clone PEBLM2007834 | — | −1.14991 |
| Hs.561587 | cDNA: FLJ22100 fis, clone HEP17127 | — | −1.14801 |
| Hs.141003 | cDNA: FLJ21691 fis, clone COL09555 | — | −1.14667 |
| Hs.5724 | cDNA clone IMAGE: 5286019 | — | −1.09054 |
| Hs.96918 | LOH11CR1J gene, loss of heterozygosity, 11, chromosomal region 1 gene J product | — | −1.08984 |
| Hs.516159 | Hypothetical LOC388969 | — | −1.04658 |
| — | — | — | 1.00113 |
| Hs.432924 | Full length insert cDNA YI37C01 | — | 1.01289 |
| Hs.44698 | cDNA FLJ42484 fis, clone BRACE2032182 | — | 1.02778 |
| — | — | — | 1.04706 |
| Hs.176376 | Transcribed locus | — | 1.048 |
| Hs.30977 | cDNA FLJ31513 fis, clone NT2RI1000127 | — | 1.05056 |
| Hs.143746 | cDNA FLJ43450 fis, clone OCBBF2032968 | — | 1.06817 |
| Hs.561280 | Transcribed locus | — | 1.08508 |
| Hs.518129 | Transcribed locus, weakly similar to XP_510104.1 | — | 1.10663 |
| Hs.406990 | Phosphodiesterase 4D interacting protein (myomegalin) | — | 1.10734 |
| Hs.561676 | Transcribed locus | — | 1.13407 |
| Hs.360028 | Transcribed locus | — | 1.14717 |
| Hs.530168 | Transcribed locus, weakly similar to NP_689672.2 hypothetical protein MGC45438 [ | — | 1.15046 |
| Hs.34068 | Homo sapiens, clone IMAGE: 3930408, mRNA | — | 1.15922 |
| Hs.103159 | Full length insert cDNA clone ZD51F08 | — | 1.16506 |
| Hs.128076 | Transcribed locus | — | 1.17721 |
| Hs.526422 /// Hs.567354 | Similar to ankyrin repeat domain 20A /// Hypothetical gene supported by NM_03225 | — | 1.18723 |
| Hs.360028 | Transcribed locus | — | 1.19194 |
| Hs.416155 | Glioma amplified sequence 64 | — | 1.19709 |
| — | — | — | 1.20401 |
| Hs.452398 | cDNA FLJ30740 fis, clone FEBRA2000319 | — | 1.20445 |
| Hs.562715 | Transcribed locus | — | 1.21733 |
| Hs.440643 | mRNA; cDNA DKFZp779L1068 (from clone DKFZp779L1068) | — | 1.21741 |
| Hs.370049 | Hypothetical protein LOC157278 | — | 1.22335 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.113631 | Transcribed locus, weakly similar to NP_062553.1 hypothetical protein FLJ11267 [ | — | 1.22639 |
| Hs.44898 | cDNA FLJ40901 fis, clone UTERU2003704 | — | 1.23966 |
| Hs.145804 | cDNA clone IMAGE: 5312086 | — | 1.2741 |
| Hs.87734 | Homo sapiens, Similar to deafness, autosomal dominant 5 homolog (human), clone I | — | 1.27749 |
| Hs.200141 | Transcribed locus | — | 1.27791 |
| Hs.387014 | Hypothetical LOC219638 | — | 1.28599 |
| Hs.446559 | Full-length cDNA clone CS0DK010YA20 of HeLa cells Cot 25-normalized of Homo sapiens (human) | — | 1.29046 |
| Hs.14691 | Transcribed locus | — | 1.29222 |
| Hs.408455 | cDNA FLJ33993 fis, clone DFNES2007757 | — | 1.31387 |
| Hs.44698 | cDNA FLJ42484 fis, clone BRACE2032182 | — | 1.31419 |
| Hs.22545 | cDNA FLJ12935 fis, clone NT2RP2004982 | — | 1.31854 |
| Hs.322761 | Hypothetical LOC497257 | — | 1.32524 |
| — | — | — | 1.32571 |
| Hs.120170 | Transcribed locus, moderately similar to XP_512541.1 | — | 1.33979 |
| Hs.374451 | Homo sapiens, clone IMAGE: 4454331, mRNA | — | 1.34083 |
| Hs.23606 | Transcribed locus | — | 1.34158 |
| Hs.446446 | Hypothetical LOC375010 | — | 1.34249 |
| Hs.536567 | cDNA FLJ37859 fis, clone BRSSN2015369 | — | 1.35057 |
| Hs.302631 | cDNA clone IMAGE: 5286843 | — | 1.36052 |
| Hs.174273 | Transcribed locus | — | 1.38715 |
| Hs.371609 | cDNA FLJ31683 fis, clone NT2RI2005353 | — | 1.39164 |
| Hs.527872 | Transcribed locus | — | 1.39529 |
| Hs.371609 | cDNA FLJ31683 fis, clone NT2RI2005353 | — | 1.40524 |
| Hs.5096 | Homo sapiens, clone IMAGE: 3858719, mRNA | — | 1.40929 |
| Hs.282800 | Transcribed locus | — | 1.41445 |
| Hs.8379 | Full-length cDNA clone CS0DJ001YJ05 of T cells (Jurkat cell line) Cot 10-normali | — | 1.41851 |
| Hs.552018 | Transcribed locus | — | 1.42347 |
| Hs.88156 | Transcribed locus | — | 1.42705 |
| Hs.151334 | Transcribed locus | — | 1.42983 |
| Hs.405427 | Homo sapiens, clone IMAGE: 5175565, mRNA | — | 1.43347 |
| Hs.13500 | cDNA FLJ31593 fis, clone NT2RI2002481 | — | 1.44009 |
| Hs.535360 | cDNA clone IMAGE: 6500775 | — | 1.45009 |
| Hs.21423 | cDNA FLJ30424 fis, clone BRACE2008881, weakly similar to ZINC FINGER PROTEIN 195 | — | 1.45296 |
| Hs.21423 | cDNA FLJ30424 fis, clone BRACE2008881, weakly similar to ZINC FINGER PROTEIN 195 | — | 1.46056 |
| Hs.27688 | Full-length cDNA clone CS0DF012YD09 of Fetal brain of Homo sapiens (human) | — | 1.46675 |
| Hs.536439 | Transcribed locus | — | 1.47116 |
| — | — | — | 1.49415 |
| Hs.22380 | Full length insert cDNA clone ZD79H10 | — | 1.49977 |
| Hs.314414 | Homo sapiens, clone IMAGE: 5743779, mRNA | — | 1.56512 |
| Hs.234478 | cDNA: FLJ22648 fis, clone HSI07329 | — | 1.57549 |
| — | — | — | 1.58385 |
| Hs.178144 | Homo sapiens, clone IMAGE: 5743799, mRNA | — | 1.67264 |
| — | — | — | 1.68495 |
| Hs.548682 | Full-length cDNA clone CS0DM011YC22 of Fetal liver of Homo sapiens (human) | — | 1.68836 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 − NC #2) |
|---|---|---|---|
| Hs.126893 | Transcribed locus | — | 1.69863 |
| Hs.328236 | cDNA clone IMAGE: 4806358 | — | 1.70004 |
| Hs.88156 | Transcribed locus | — | 1.70768 |
| — | — | — | 1.70885 |
| — | — | — | 1.71742 |
| Hs.440643 | mRNA; cDNA DKFZp779L1068 (from clone DKFZp779L1068) | — | 1.78147 |
| Hs.53126 | Transcribed locus, moderately similar to XP_517655.1 PREDICTED: similar to KIAA0 | — | 1.81242 |
| — | — | — | 1.81859 |
| Hs.444083 | Transcribed locus | — | 1.83349 |
| — | — | — | 1.83583 |
| Hs.516367 | mRNA; cDNA DKFZp686P18215 (from clone DKFZp686P18215) | — | 1.84302 |
| Hs.370049 | Hypothetical protein LOC157278 | — | 1.91193 |
| Hs.351126 | Transcribed locus, moderately similar to XP_517655.1 PREDICTED: similar to KIAA0 | — | 1.99147 |
| — | — | — | 2.01427 |
| Hs.446671 | Transcribed locus, strongly similar to NP_003156.1 syntaxin binding protein 1; s | — | 2.04867 |
| Hs.47208 | cDNA FLJ45259 fis, clone BRHIP2020695 | — | 2.14126 |
| — | — | — | 2.18694 |
| Hs.160711 | Transcribed locus | — | 2.28638 |
| Hs.436057 | Transcribed locus | — | 2.28848 |
| Hs.418040 | cDNA clone IMAGE: 30367357 | — | 2.41037 |
| Hs.443798 | Transcribed locus | — | 2.48069 |
| Hs.146317 | Transcribed locus, weakly similar to XP_517655.1 PREDICTED: similar to KIAA0825 | — | 2.48636 |
| Hs.308060 | LOC440570 | — | 2.548 |
| Hs.99785 | cDNA: FLJ21245 fis, clone COL01184 | — | 2.69373 |
| Hs.523897 | cDNA FLJ38112 fis, clone D3OST2002272 | — | 3.38473 |
| — | — | — | 3.49831 |
| Hs.462598 | 82-kD FMRP Interacting Protein | I82-FIP | −1.77251 |
| Hs.462598 | 82-kD FMRP Interacting Protein | I82-FIP | −1.34345 |
| Hs.552584 | AP2 associated kinase 1 | AAK1 | 1.23153 |
| Hs.336768 | 4-aminobutyrate aminotransferase | ABAT | 1.20681 |
| Hs.336768 | 4-aminobutyrate aminotransferase | ABAT | 1.23674 |
| Hs.429294 | ATP-binding cassette, sub-family A (ABC1), member 1 | ABCA1 | 1.8146 |
| Hs.429294 | ATP-binding cassette, sub-family A (ABC1), member 1 | ABCA1 | 1.99636 |
| Hs.134585 | ATP-binding cassette, sub-family A (ABC1), member 12 | ABCA12 | 4.51284 |
| Hs.124649 | ATP-binding cassette, sub-family G (WHITE), member 1 | ABCG1 | 2.67865 |
| Hs.508148 | abl-interactor 1 | ABI1 | −1.1678 |
| Hs.200136 | acetyl-Coenzyme A acyltransferase 2 (mitochondrial 3-oxoacyl-Coenzyme A thiolase | ACAA2 | −3.11952 |
| Hs.445040 | acyl-Coenzyme A dehydrogenase, C-4 to C-12 straight chain | ACADM | −1.48728 |
| Hs.81934 | acyl-Coenzyme A dehydrogenase, short/branched chain | ACADSB | 1.29385 |
| Hs.363137 | acetyl-Coenzyme A acetyltransferase 2 (acetoacetyl Coenzyme A thiolase) | ACAT2 | −1.77551 |
| Hs.446685 | acyl-CoA thioesterase 2 | ACOT2 | 1.07252 |
| Hs.464137 | acyl-Coenzyme A oxidase 1, palmitoyl | ACOX1 | −1.37507 |
| Hs.444959 | acyl-Coenzyme A oxidase 2, branched chain | ACOX2 | −1.78602 |
| Hs.255491 | acid phosphatase-like 2 | ACPL2 | 2.42324 |
| Hs.160976 | acyl-CoA synthetase medium-chain family member 3 | ACSM3 | 2.0203 |
| Hs.160976 | acyl-CoA synthetase medium-chain family member 3 | ACSM3 | 2.47004 |
| Hs.500483 | actin, alpha 2, smooth muscle, aorta | ACTA2 | 1.81371 |
| Hs.438918 | activin A receptor, type IB | ACVR1B | 1.13551 |
| Hs.470174 | activin A receptor, type IIA | ACVR2A | 1.16595 |
| Hs.356247 | aminoacylase 1-like 2 | ACY1L2 | −1.22613 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 − NC #2) |
|---|---|---|---|
| Hs.516173 | acylphosphatase 2, muscle type | ACYP2 | 1.26039 |
| Hs.522433 | AD-003 protein | AD-003 | −1.1865 |
| Hs.483944 | ADAM metallopeptidase domain 19 (meltrin beta) | ADAM19 | 1.21804 |
| Hs.370287 | ADAM metallopeptidase domain 23 | ADAM23 | 1.03009 |
| Hs.370287 | ADAM metallopeptidase domain 23 | ADAM23 | 1.14332 |
| Hs.370287 | ADAM metallopeptidase domain 23 | ADAM23 | 1.64919 |
| Hs.534221 | ADAM metallopeptidase with thrombospondin type 1 motif, 15 | ADAMTS15 | 1.30093 |
| Hs.192215 | adenylate cyclase 1 (brain) | ADCY1 | 1.50926 |
| Hs.518892 | alcohol dehydrogenase 6 (class V) | ADH6 | 1.39262 |
| Hs.518892 | alcohol dehydrogenase 6 (class V) | ADH6 | 1.8487 |
| Hs.375179 | adenylosuccinate synthase like 1 | ADSSL1 | 1.96783 |
| Hs.248785 | 1-acylglycerol-3-phosphate O-acyltransferase 3 | AGPAT3 | 1.18995 |
| Hs.516543 | alkylglycerone phosphate synthase | AGPS | −2.01298 |
| Hs.516543 | alkylglycerone phosphate synthase | AGPS | −1.53364 |
| Hs.530009 | anterior gradient 2 homolog (*Xenopus laevis*) | AGR2 | −1.93668 |
| Hs.530009 | anterior gradient 2 homolog (*Xenopus laevis*) | AGR2 | −1.11235 |
| Hs.19383 | angiotensinogen (serpin peptidase inhibitor, clade A, member 8) | AGT | 1.48949 |
| Hs.502756 | AHNAK nucleoprotein (desmoyokin) | AHNAK | −1.17042 |
| Hs.502756 | AHNAK nucleoprotein (desmoyokin) | AHNAK | −1.02415 |
| — | adenylate kinase 2 | AK2 | −2.11505 |
| Hs.470907 | adenylate kinase 2 | AK2 | −1.70834 |
| Hs.493362 | adenylate kinase 3 | AK3 | −2.67095 |
| Hs.493362 | adenylate kinase 3 | AK3 | −2.32644 |
| Hs.10862 | adenylate kinase 3-like 1 | AK3L1 | 1.23455 |
| Hs.10862 | adenylate kinase 3-like 1 | AK3L1 | 1.43994 |
| Hs.510373 | adenylate kinase 7 | AK7 | 1.40726 |
| Hs.371240 | A kinase (PRKA) anchor protein (gravin) 12 | AKAP12 | 1.04634 |
| Hs.371240 | A kinase (PRKA) anchor protein (gravin) 12 | AKAP12 | 1.12727 |
| Hs.371240 | A kinase (PRKA) anchor protein (gravin) 12 | AKAP12 | 1.17874 |
| Hs.527348 | A kinase (PRKA) anchor protein (yotiao) 9 | AKAP9 | 1.22674 |
| Hs.512807 | aldo-keto reductase family 7, member A2 (aflatoxin aldehyde reductase) | AKR7A2 | −1.58112 |
| Hs.512807 | aldo-keto reductase family 7, member A2 (aflatoxin aldehyde reductase) | AKR7A2 | −1.47339 |
| Hs.515542 | AKT1 substrate 1 (proline-rich) | AKT1S1 | −1.17537 |
| Hs.150693 | Activated leukocyte cell adhesion molecule | ALCAM | 1.01184 |
| Hs.459538 | aldehyde dehydrogenase 1 family, member A3 | ALDH1A3 | 1.34102 |
| Hs.40919 | asparagine-linked glycosylation 2 homolog (yeast, alpha-1,3-mannosyltransferase) | ALG2 | −1.37104 |
| Hs.507769 | asparagine-linked glycosylation 5 homolog (yeast, dolichyl-phosphate beta-glucose | ALG5 | −1.42868 |
| Hs.184720 | Alstrom syndrome 1 | ALMS1 | 1.43349 |
| Hs.184720 | Alstrom syndrome 1 | ALMS1 | 1.61137 |
| Hs.471096 | amyotrophic lateral sclerosis 2 (juvenile) | ALS2 | 1.11459 |
| Hs.471130 | amyotrophic lateral sclerosis 2 (juvenile) chromosome region, candidate 13 | ALS2CR13 | 2.32442 |
| Hs.554880 | amyotrophic lateral sclerosis 2 (juvenile) chromosome region, candidate 15 | ALS2CR15 | 2.14659 |
| Hs.295137 | autocrine motility factor receptor | AMFR | −1.01434 |
| Hs.211021 | Alport syndrome, mental retardation, midface hypoplasia and elliptocytosis | AMMECR1 | −2.68372 |
| Hs.211021 | Alport syndrome, mental retardation, midface hypoplasia and elliptocytosis | AMMECR1 | −2.24775 |
| Hs.211021 | Alport syndrome, mental retardation, midface hypoplasia and elliptocytosis | AMMECR1 | −1.72189 |
| Hs.16229 | associated molecule with the SH3 domain of STAM (AMSH) like protein | AMSH-LP | −1.2422 |
| Hs.499725 | ankyrin 3, node of Ranvier (ankyrin G) | ANK3 | 2.14295 |
| Hs.513875 | ankyrin repeat and FYVE domain containing 1 | ANKFY1 | −1.32868 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 − NC #2) |
|---|---|---|---|
| Hs.513875 | ankyrin repeat and FYVE domain containing 1 | ANKFY1 | −1.2223 |
| Hs.156727 | ankylosis, progressive homolog (mouse) | ANKH | 1.09799 |
| Hs.156727 | ankylosis, progressive homolog (mouse) | ANKH | 2.03558 |
| Hs.239154 | ankyrin repeat, family A (RFXANK-like), 2 | ANKRA2 | 1.68394 |
| Hs.482853 | ankyrin repeat domain 32 | ANKRD32 | −1.49302 |
| Hs.463426 | ankyrin repeat domain 40 | ANKRD40 | −1.31517 |
| Hs.530199 | ankyrin repeat domain 46 | ANKRD46 | 2.45585 |
| Hs.112909 | ankyrin repeat domain 6 | ANKRD6 | 1.07684 |
| Hs.62180 | anillin, actin binding protein (scraps homolog, Drosophila) | ANLN | −3.04043 |
| Hs.62180 | anillin, actin binding protein (scraps homolog, Drosophila) | ANLN | −2.92708 |
| Hs.385913 | acidic (leucine-rich) nuclear phosphoprotein 32 family, member E | ANP32E | −2.77779 |
| Hs.385913 | Acidic (leucine-rich) nuclear phosphoprotein 32 family, member E | ANP32E | −2.07845 |
| Hs.385913 | acidic (leucine-rich) nuclear phosphoprotein 32 family, member E | ANP32E | −1.72716 |
| Hs.165859 | anthrax toxin receptor 1 | ANTXR1 | −2.06308 |
| Hs.480653 | annexin A5 | ANXA5 | −3.00322 |
| Hs.386434 | annexin A7 | ANXA7 | −2.1409 |
| Hs.386434 | annexin A7 | ANXA7 | −1.90276 |
| Hs.430324 | annexin A9 | ANXA9 | 1.82787 |
| Hs.430324 | annexin A9 /// annexin A9 | ANXA9 | 2.24924 |
| Hs.406238 | aldehyde oxidase 1 | AOX1 | −1.25234 |
| Hs.101480 | AP1 gamma subunit binding protein 1 | AP1GBP1 | 2.66149 |
| Hs.18894 | adaptor-related protein complex 1, mu 2 subunit | AP1M2 | −1.94622 |
| Hs.18894 | adaptor-related protein complex 1, mu 2 subunit | AP1M2 | −1.93072 |
| Hs.121592 | adaptor-related protein complex 1, sigma 2 subunit | AP1S2 | −1.41432 |
| Hs.121592 | adaptor-related protein complex 1, sigma 2 subunit | AP1S2 | −1.24493 |
| Hs.387648 | adaptor-related protein complex 1, sigma 3 subunit | AP1S3 | −1.04504 |
| Hs.500104 | adaptor-related protein complex 3, mu 1 subunit | AP3M1 | −1.67829 |
| Hs.555936 | APEX nuclease (apurinic/apyrimidinic endonuclease) 2 | APEX2 | −1.17148 |
| Hs.74565 | amyloid beta (A4) precursor-like protein 1 | APLP1 | 1.97456 |
| Hs.226307 | apolipoprotein B mRNA editing enzyme, catalytic polypeptide-like 3B | APOBEC3B | −1.93604 |
| Hs.515465 | apolipoprotein E | APOE | 1.37948 |
| Hs.434980 | amyloid beta (A4) precursor protein (peptidase nexin-II, Alzheimer disease) | APP | 1.20229 |
| Hs.434980 | amyloid beta (A4) precursor protein (peptidase nexin-II, Alzheimer disease) | APP | 1.36582 |
| Hs.84084 | amyloid beta precursor protein (cytoplasmic tail) binding protein 2 | APPBP2 | 1.32834 |
| Hs.446641 | v-raf murine sarcoma 3611 viral oncogene homolog | ARAF | −1.45485 |
| Hs.416089 | ADP-ribosylation factor interacting protein 1 (arfaptin 1) | ARFIP1 | −2.66871 |
| Hs.416089 | ADP-ribosylation factor interacting protein 1 (arfaptin 1) | ARFIP1 | −1.78433 |
| Hs.138860 | Rho GTPase activating protein 1 | ARHGAP1 | −1.51577 |
| Hs.400818 | Rho GTPase activating protein 11A | ARHGAP11A | −2.16059 |
| Hs.159161 | Rho GDP dissociation inhibitor (GDI) alpha | ARHGDIA | −3.18235 |
| Hs.159161 | Rho GDP dissociation inhibitor (GDI) alpha | ARHGDIA | −2.07826 |
| Hs.159161 | Rho GDP dissociation inhibitor (GDI) alpha | ARHGDIA | −1.61522 |
| Hs.159161 | Rho GDP dissociation inhibitor (GDI) alpha /// Rho GDP dissociation inhibitor (G | ARHGDIA | −1.59814 |
| Hs.443460 | Rho guanine nucleotide exchange factor (GEF) 10-like | ARHGEF10L | 1.52476 |
| Hs.250009 | ADP-ribosylation factor-like 10C | ARL10C | −1.58997 |
| Hs.182215 | ADP-ribosylation factor-like 3 | ARL3 | 1.42368 |
| Hs.470233 | ADP-ribosylation factor-like 5 | ARL5 | 1.65731 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.190440 | ADP-ribosylation factor-like 6 interacting protein 2 | ARL6IP2 | −1.13113 |
| Hs.516468 | ADP-ribosylation-like factor 6 interacting protein 6 | ARL6IP6 | −2.72541 |
| Hs.516468 | ADP-ribosylation-like factor 6 interacting protein 6 | ARL6IP6 | −1.20713 |
| Hs.269542 | armadillo repeat containing 1 | ARMC1 | −1.64954 |
| Hs.269542 | armadillo repeat containing 1 | ARMC1 | −1.45211 |
| Hs.471610 | armadillo repeat containing 9 | ARMC9 | 1.5088 |
| Hs.459070 | aryl-hydrocarbon receptor nuclear translocator 2 | ARNT2 | 1.41846 |
| Hs.512908 | cyclic AMP phosphoprotein, 19 kD | ARPP-19 | −2.21964 |
| Hs.149103 | arylsulfatase B | ARSB | −1.27475 |
| Hs.528631 | arylsulfatase D | ARSD | −1.14781 |
| Hs.504187 | Adipocyte-specific adhesion molecule | ASAM | −1.75017 |
| Hs.16349 | ATM/ATR-Substrate Chk2-Interacting Zn2+-finger protein | ASCIZ | −1.28851 |
| Hs.26516 | ASF1 anti-silencing function 1 homolog B (S. cerevisiae) | ASF1B | −1.90378 |
| Hs.208414 | activator of S phase kinase | ASK | −2.051 |
| Hs.121028 | asp (abnormal spindle)-like, microcephaly associated (Drosophila) | ASPM | −2.10725 |
| Hs.558301 | argininosuccinate synthetase | ASS | 1.30242 |
| Hs.209217 | astrotactin 2 | ASTN2 | 2.09888 |
| Hs.209217 | astrotactin 2 | ASTN2 | 2.13406 |
| Hs.370834 | ATPase family, AAA domain containing 2 | ATAD2 | −3.16311 |
| Hs.370834 | ATPase family, AAA domain containing 2 | ATAD2 | −3.10193 |
| Hs.370834 | ATPase family, AAA domain containing 2 | ATAD2 | −2.67001 |
| Hs.370834 | ATPase family, AAA domain containing 2 | ATAD2 | −1.42371 |
| Hs.461285 | AT-binding transcription factor 1 | ATBF1 | 1.21411 |
| Hs.461285 | AT-binding transcription factor 1 | ATBF1 | 1.3555 |
| Hs.496487 | activating transcription factor 4 (tax-responsive enhancer element B67) | ATF4 | −1.49983 |
| Hs.492740 | Activating transcription factor 6 | ATF6 | 1.12993 |
| Hs.477126 | ATG3 autophagy related 3 homolog (S. cerevisiae) | ATG3 | −1.69524 |
| Hs.88252 | ATPase, Class VI, type 11C | ATP11C | 1.81479 |
| Hs.506759 | ATPase, Ca++ transporting, cardiac muscle, slow twitch 2 | ATP2A2 | 2.05217 |
| Hs.438489 | ATP synthase, H+ transporting, mitochondrial F0 complex, subunit s (factor B) | ATP5S | 1.2575 |
| Hs.484188 | ATPase, H+ transporting, lysosomal 9 kDa, V0 subunit e | ATP6V0E | −3.94802 |
| Hs.484188 | ATPase, H+ transporting, lysosomal 9 kDa, V0 subunit e /// ATPase, H+ transportin | ATP6V0E | −3.66723 |
| Hs.484188 | ATPase, H+ transporting, lysosomal 9 kDa, V0 subunit e | ATP6V0E | −3.50595 |
| Hs.484188 | ATPase, H+ transporting, lysosomal 9 kDa, V0 subunit e | ATP6V0E | −3.35879 |
| Hs.484188 | ATPase, H+ transporting, lysosomal 9 kDa, V0 subunit e | ATP6V0E | −3.06293 |
| Hs.484188 | ATPase, H+ transporting, lysosomal 9 kDa, V0 subunit e | ATP6V0E | −2.27251 |
| Hs.388654 | ATPase, H+ transporting, lysosomal 13 kDa, V1 subunit G isoform 1 | ATP6V1G1 | −1.21519 |
| Hs.491737 | ATPase, H+ transporting, lysosomal 50/57 kDa, V1 subunit H | ATP6V1H | 1.14584 |
| Hs.368002 | ATPase, Class II, type 9A | ATP9A | 1.75501 |
| Hs.465475 | ATPase, Class II, type 9B | ATP9B | −1.27448 |
| Hs.533526 | alpha thalassemia/mental retardation syndrome X-linked (RAD54 homolog, S. cerevisiae) | ATRX | 1.21083 |
| Hs.434961 | ataxin 1 | ATXN1 | 1.78989 |
| Hs.526425 | ataxin 3 | ATXN3 | 1.7092 |
| Hs.442658 | aurora kinase B | AURKB | −3.28843 |
| Hs.272011 | UDP-Gal:betaGlcNAc beta 1,4-galactosyltransferase, polypeptide 1 | B4GALT1 | −2.18016 |
| Hs.272011 | UDP-Gal:betaGlcNAc beta 1,4-galactosyltransferase, polypeptide 1 | B4GALT1 | −1.68723 |
| Hs.272011 | UDP-Gal:betaGlcNAc beta 1,4-galactosyltransferase, polypeptide 1 | B4GALT1 | −1.55955 |
| Hs.272011 | UDP-Gal:betaGlcNAc beta 1,4-galactosyltransferase, polypeptide 1 | B4GALT1 | −1.30327 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.464848 | UDP-Gal:betaGlcNAc beta 1,4-galactosyltransferase, polypeptide 6 | B4GALT6 | −1.74964 |
| Hs.464848 | UDP-Gal:betaGlcNAc beta 1,4-galactosyltransferase, polypeptide 6 | B4GALT6 | −1.58614 |
| Hs.464848 | UDP-Gal:betaGlcNAc beta 1,4-galactosyltransferase, polypeptide 6 | B4GALT6 | −1.27649 |
| Hs.524138 | brain-specific angiogenesis inhibitor 2 | BAI2 | 2.82064 |
| Hs.54089 | BRCA1 associated RING domain 1 | BARD1 | −1.18684 |
| Hs.509140 | bromodomain adjacent to zinc finger domain, 1A | BAZ1A | −1.45554 |
| Hs.509140 | bromodomain adjacent to zinc finger domain, 1A | BAZ1A | −1.30967 |
| Hs.502915 | Bardet-Biedl syndrome 1 | BBS1 | 1.92669 |
| Hs.208681 | Bardet-Biedl syndrome 4 | BBS4 | 1.15935 |
| Hs.438993 | branched chain aminotransferase 1, cytosolic | BCAT1 | −2.45797 |
| Hs.438993 | branched chain aminotransferase 1, cytosolic | BCAT1 | −2.14227 |
| Hs.438993 | branched chain aminotransferase 1, cytosolic | BCAT1 | −2.04249 |
| Hs.193516 | B-cell CLL/lymphoma 10 | BCL10 | 1.80226 |
| Hs.469658 | BCL2-like 11 (apoptosis facilitator) | BCL2L11 | 1.24619 |
| Hs.469658 | BCL2-like 11 (apoptosis facilitator) | BCL2L11 | 1.76976 |
| Hs.478588 | B-cell CLL/lymphoma 6 (zinc finger protein 51) | BCL6 | 1.24494 |
| Hs.486542 | BCL2-associated transcription factor 1 | BCLAF1 | −1.2496 |
| Hs.212172 | beta-carotene 15,15'-monooxygenase 1 | BCMO1 | 1.12146 |
| Hs.525572 | bradykinin receptor B2 | BDKRB2 | 1.20304 |
| Hs.502182 | Brain-derived neurotrophic factor opposite strand | BDNF | 1.15806 |
| Hs.502182 | brain-derived neurotrophic factor | BDNF | 1.16325 |
| Hs.502182 | brain-derived neurotrophic factor | BDNF | 2.66234 |
| Hs.184736 | brain expressed X-linked-like 1 | BEXL1 | 1.05078 |
| Hs.514527 | baculoviral IAP repeat-containing 5 (survivin) | BIRC5 | −2.92443 |
| Hs.514527 | baculoviral IAP repeat-containing 5 (survivin) | BIRC5 | −2.84713 |
| Hs.514527 | baculoviral IAP repeat-containing 5 (survivin) | BIRC5 | −2.48729 |
| Hs.514527 | Effector cell peptidase receptor 1 | BIRC5 | −1.55356 |
| Hs.288809 | basic, immunoglobulin-like variable motif containing | BIVM | 1.60758 |
| Hs.169348 | Bloom syndrome | BLM | −1.56775 |
| Hs.283532 | uncharacterized bone marrow protein BM039 | BM039 | −2.5703 |
| Hs.283532 | uncharacterized bone marrow protein BM039 | BM039 | −1.57091 |
| Hs.1274 | bone morphogenetic protein 1 | BMP1 | 1.07616 |
| Hs.1274 | bone morphogenetic protein 1 | BMP1 | 1.22004 |
| Hs.283454 | BCL2/adenovirus E1B 19 kDa interacting protein 2 | BNIP2 | 1.35501 |
| — | v-raf murine sarcoma viral oncogene homolog B1 | BRAF | 1.03351 |
| Hs.194143 | breast cancer 1, early onset | BRCA1 | −2.32949 |
| Hs.194143 | breast cancer 1, early onset | BRCA1 | −1.40615 |
| Hs.34012 | breast cancer 2, early onset | BRCA2 | −2.63976 |
| Hs.532799 | BRCA1 interacting protein C-terminal helicase 1 | BRIP1 | −1.37567 |
| Hs.532799 | BRCA1 interacting protein C-terminal helicase 1 | BRIP1 | −1.20299 |
| Hs.525299 | breast cancer metastasis-suppressor 1-like | BRMS1L | 1.34896 |
| Hs.525299 | breast cancer metastasis-suppressor 1-like | BRMS1L | 1.60725 |
| Hs.308045 | barren homolog (*Drosophila*) | BRRN1 | −1.94109 |
| Hs.244590 | BTB (POZ) domain containing 3 | BTBD3 | 1.56315 |
| Hs.517830 | biotinidase | BTD | −1.34728 |
| Hs.519162 | BTG family, member 2 | BTG2 | 1.40327 |
| Hs.469649 | BUB1 budding uninhibited by benzimidazoles 1 homolog (yeast) | BUB1 | −2.72123 |
| Hs.469649 | BUB1 budding uninhibited by benzimidazoles 1 homolog (yeast) | BUB1 | −2.66112 |
| Hs.36708 | BUB1 budding uninhibited by benzimidazoles 1 homolog beta (yeast) | BUB1B | −2.4014 |

TABLE 1-continued

Genes with increased (positive values) or decreased (negative values) expression
following transfection of human cancer cells with pre-miR hsa-miR-124a.

| UniGene ID | Gene Title | Gene Symbol | Log2 (mir124 − NC #2) |
|---|---|---|---|
| Hs.418533 | BUB3 budding uninhibited by benzimidazoles 3 homolog (yeast) | BUB3 | −1.2881 |
| Hs.124246 | chromosome 10 open reading frame 119 | C10orf119 | −1.09868 |
| Hs.14559 | chromosome 10 open reading frame 3 | C10orf3 | −2.96399 |
| Hs.34492 | chromosome 10 open reading frame 32 | C10orf32 | 1.21753 |
| Hs.446315 | chromosome 10 open reading frame 45 | C10orf45 | −1.09303 |
| Hs.446315 | chromosome 10 open reading frame 45 | C10orf45 | −1.03421 |
| Hs.446315 | Chromosome 10 open reading frame 45 | C10orf45 | 1.64975 |
| Hs.420024 | chromosome 10 open reading frame 46 | C10orf46 | −1.07798 |
| Hs.499833 | chromosome 10 open reading frame 74 | C10orf74 | −1.99852 |
| Hs.499833 | chromosome 10 open reading frame 74 | C10orf74 | −1.82678 |
| Hs.93667 | chromosome 10 open reading frame 78 | C10orf78 | −1.3269 |
| Hs.93667 | chromosome 10 open reading frame 78 | C10orf78 | −1.21737 |
| Hs.14745 | chromosome 10 open reading frame 9 | C10orf9 | 1.04082 |
| — | chromosome 11 open reading frame 32 | C11orf32 | 1.80699 |
| Hs.473109 | chromosome 11 open reading frame 9 | C11orf9 | −1.0544 |
| Hs.88523 | chromosome 13 open reading frame 3 | C13orf3 | −1.60434 |
| Hs.493062 | chromosome 13 open reading frame 7 | C13orf7 | −1.19491 |
| Hs.446850 | chromosome 14 open reading frame 100 | C14orf100 | −1.37992 |
| Hs.146040 | chromosome 14 open reading frame 105 | C14orf105 | 3.08437 |
| Hs.437941 | chromosome 14 open reading frame 106 | C14orf106 | −1.58434 |
| Hs.437941 | chromosome 14 open reading frame 106 | C14orf106 | −1.25714 |
| Hs.343173 | chromosome 14 open reading frame 111 | C14orf111 | −1.73122 |
| Hs.437831 | chromosome 14 open reading frame 111 /// chromosome 14 open reading frame 32 | C14orf111/// C14orf32 | −2.07398 |
| Hs.137108 | chromosome 14 open reading frame 112 | C14orf112 | −1.26989 |
| Hs.9043 | chromosome 14 open reading frame 120 | C14orf120 | −1.56964 |
| Hs.370299 | chromosome 14 open reading frame 125 | C14orf125 | −1.57587 |
| Hs.20142 | chromosome 14 open reading frame 142 | C14orf142 | −1.92889 |
| Hs.123232 | chromosome 14 open reading frame 143 | C14orf143 | −1.16551 |
| Hs.162889 | chromosome 14 open reading frame 145 | C14orf145 | −2.40228 |
| Hs.162889 | chromosome 14 open reading frame 145 | C14orf145 | −1.4913 |
| Hs.29706 | chromosome 14 open reading frame 149 | C14orf149 | −1.58168 |
| Hs.510407 | chromosome 14 open reading frame 154 | C14orf154 | 1.44686 |
| Hs.309849 | chromosome 14 open reading frame 159 | C14orf159 | 1.23828 |
| Hs.446357 | chromosome 14 open reading frame 24 | C14orf24 | −2.88651 |
| Hs.82098 | chromosome 14 open reading frame 28 | C14orf28 | 1.05861 |
| Hs.82098 | chromosome 14 open reading frame 28 | C14orf28 | 1.19184 |
| Hs.179260 | chromosome 14 open reading frame 4 | C14orf4 | 1.52554 |
| Hs.550547 | Chromosome 14 open reading frame 44 | C14orf44 | 1.12787 |
| Hs.260555 | chromosome 14 open reading frame 45 | C14orf45 | 1.82442 |
| Hs.513392 | chromosome 14 open reading frame 46 | C14orf46 | −1.12219 |
| Hs.441783 | chromosome 14 open reading frame 78 | C14orf78 | 1.29638 |
| Hs.532683 | chromosome 14 open reading frame 87 | C14orf87 | −1.69987 |
| Hs.112160 | chromosome 15 open reading frame 20 | C15orf20 | −1.06547 |
| Hs.525796 | chromosome 15 open reading frame 23 | C15orf23 | −2.21496 |
| Hs.160565 | chromosome 15 open reading frame 24 | C15orf24 | −1.14621 |
| Hs.14347 | chromosome 15 open reading frame 25 | C15orf25 | −1.39177 |
| Hs.510938 | Chromosome 15 open reading frame 29 | C15orf29 | 1.33202 |
| Hs.513261 | chromosome 16 open reading frame 34 | C16orf34 | −2.53906 |
| Hs.513261 | chromosome 16 open reading frame 34 | C16orf34 | −1.74123 |
| Hs.203594 | chromosome 16 open reading frame 46 | C16orf46 | 1.25378 |
| Hs.498890 | chromosome 16 open reading frame 52 | C16orf52 | 1.44987 |
| Hs.558473 | Chromosome 18 open reading frame 10 | C18orf10 | −1.16121 |
| Hs.134726 | chromosome 18 open reading frame 24 | C18orf24 | −2.79183 |
| Hs.208701 | chromosome 18 open reading frame 54 | C18orf54 | −1.84765 |
| Hs.532835 | chromosome 18 open reading frame 55 | C18orf55 | −1.02679 |
| — | chromosome 18 open reading frame 56 | C18orf56 | 1.17245 |
| Hs.76277 | chromosome 19 open reading frame 32 | C19orf32 | 1.16451 |
| Hs.239666 | core 1 synthase, glycoprotein-N-acetylgalactosamine 3-beta-galactosyltransferase | C1GALT1 | −1.34248 |
| Hs.202207 | chromosome 1 open reading frame 102 | C1orf102 | 1.34343 |
| Hs.293563 | chromosome 1 open reading frame 108 | C1orf108 | −1.35689 |
| Hs.443551 | chromosome 1 open reading frame 112 | C1orf112 | −3.33816 |
| Hs.130746 | chromosome 1 open reading frame 114 | C1orf114 | 1.2474 |
| Hs.498317 | chromosome 1 open reading frame 121 | C1orf121 | −1.3606 |
| Hs.498317 | chromosome 1 open reading frame 121 | C1orf121 | −1.17342 |
| Hs.554892 | chromosome 1 open reading frame 124 | C1orf124 | −1.16234 |
| Hs.556017 | chromosome 1 open reading frame 131 | C1orf131 | −1.45997 |
| Hs.252967 | chromosome 1 open reading frame 144 | C1orf144 | −1.38903 |
| Hs.252967 | chromosome 1 open reading frame 144 | C1orf144 | −1.3514 |
| Hs.434498 | chromosome 1 open reading frame 155 | C1orf155 | −2.07 |

TABLE 1-continued

Genes with increased (positive values) or decreased (negative values) expression
following transfection of human cancer cells with pre-miR hsa-miR-124a.

| UniGene ID | Gene Title | Gene Symbol | Log2 (mir124 - NC #2) |
|---|---|---|---|
| Hs.434498 | chromosome 1 open reading frame 155 | C1orf155 | −1.66964 |
| Hs.523811 | chromosome 1 open reading frame 22 | C1orf22 | −1.69074 |
| Hs.523811 | chromosome 1 open reading frame 22 | C1orf22 | −1.32688 |
| Hs.523811 | chromosome 1 open reading frame 22 | C1orf22 | −1.2394 |
| Hs.518662 | chromosome 1 open reading frame 24 | C1orf24 | −1.7059 |
| Hs.112949 | chromosome 1 open reading frame 34 | C1orf34 | 1.2974 |
| Hs.520192 | chromosome 1 open reading frame 55 | C1orf55 | −1.75702 |
| Hs.520192 | chromosome 1 open reading frame 55 | C1orf55 | −1.67518 |
| Hs.528699 | chromosome 1 open reading frame 79 | C1orf79 | −1.45216 |
| Hs.528699 | chromosome 1 open reading frame 79 | C1orf79 | −1.16355 |
| Hs.156625 | chromosome 1 open reading frame 80 | C1orf80 | −2.24918 |
| Hs.156625 | chromosome 1 open reading frame 80 | C1orf80 | −2.19773 |
| Hs.172510 | chromosome 1 open reading frame 88 | C1orf88 | 1.64402 |
| Hs.556016 | chromosome 1 open reading frame 96 | C1orf96 | −1.98042 |
| Hs.524224 | complement component 1, r subcomponent | C1R | 1.2527 |
| Hs.525264 | complement component 1, r subcomponent-like | C1RL | 1.29964 |
| Hs.458355 | complement component 1, s subcomponent | C1S | 1.1701 |
| Hs.143736 | chromosome 20 open reading frame 108 | C20orf108 | 1.30283 |
| Hs.143736 | chromosome 20 open reading frame 108 | C20orf108 | 1.79836 |
| Hs.516977 | chromosome 20 open reading frame 112 | C20orf112 | 1.32831 |
| Hs.516977 | chromosome 20 open reading frame 112 | C20orf112 | 1.87434 |
| Hs.283869 | chromosome 20 open reading frame 121 | C20orf121 | −1.38738 |
| Hs.283869 | chromosome 20 open reading frame 121 | C20orf121 | −1.07381 |
| Hs.472716 | chromosome 20 open reading frame 129 | C20orf129 | −1.36816 |
| Hs.266273 | chromosome 20 open reading frame 172 | C20orf172 | −2.0766 |
| Hs.274422 | chromosome 20 open reading frame 27 | C20orf27 | −1.9419 |
| Hs.274422 | chromosome 20 open reading frame 27 | C20orf27 | −1.72317 |
| Hs.320823 | chromosome 20 open reading frame 72 | C20orf72 | −1.37017 |
| Hs.190518 | chromosome 21 open reading frame 45 | C21orf45 | −1.88741 |
| Hs.190518 | chromosome 21 open reading frame 45 | C21orf45 | −1.41595 |
| Hs.208358 | chromosome 21 open reading frame 63 | C21orf63 | −1.52188 |
| Hs.208912 | chromosome 22 open reading frame 18 | C22orf18 | −1.57651 |
| Hs.516707 | chromosome 2 open reading frame 17 | C2orf17 | 1.51246 |
| Hs.516707 | chromosome 2 open reading frame 17 | C2orf17 | 1.52854 |
| Hs.553512 | putative protein similar to nessy (*Drosophila*) | C3F | −1.33476 |
| Hs.55131 | chromosome 3 open reading frame 23 | C3orf23 | 1.68914 |
| Hs.55131 | chromosome 3 open reading frame 23 | C3orf23 | 2.64324 |
| Hs.478682 | chromosome 3 open reading frame 6 | C3orf6 | −1.71881 |
| Hs.368454 | chromosome 4 open reading frame 15 | C4orf15 | −1.1094 |
| Hs.435991 | chromosome 4 open reading frame 16 | C4orf16 | −1.22157 |
| Hs.166551 | chromosome 5 open reading frame 3 | C5orf3 | −1.04141 |
| Hs.483473 | chromosome 5 open reading frame 5 | C5orf5 | 1.22807 |
| Hs.555954 | chromosome 6 open reading frame 107 | C6orf107 | −1.69873 |
| Hs.520287 | chromosome 6 open reading frame 111 | C6orf111 | 1.4713 |
| Hs.88663 | chromosome 6 open reading frame 139 | C6orf139 | −3.44482 |
| Hs.485528 | chromosome 6 open reading frame 141 | C6orf141 | 1.13191 |
| Hs.21945 | chromosome 6 open reading frame 152 | C6orf152 | 1.2155 |
| Hs.21945 | chromosome 6 open reading frame 152 | C6orf152 | 1.46547 |
| Hs.309231 | chromosome 6 open reading frame 153 | C6orf153 | −1.31388 |
| Hs.486401 | chromosome 6 open reading frame 173 | C6orf173 | −2.22501 |
| Hs.31917 | chromosome 6 open reading frame 176 | C6orf176 | −3.52107 |
| Hs.59554 | chromosome 6 open reading frame 182 | C6orf182 | −1.30989 |
| Hs.347144 | chromosome 6 open reading frame 192 | C6orf192 | −1.57852 |
| Hs.418520 | chromosome 6 open reading frame 51 | C6orf51 | −1.14052 |
| Hs.519930 | Chromosome 6 open reading frame 62 | C6orf62 | −1.29276 |
| Hs.214043 | chromosome 6 open reading frame 79 | C6orf79 | −1.41464 |
| Hs.283683 | chromosome 8 open reading frame 4 | C8orf4 | 1.39952 |
| Hs.171455 | chromosome 8 open reading frame 47 | C8orf47 | 1.40888 |
| Hs.368402 | chromosome 8 open reading frame 55 | C8orf55 | −1.25513 |
| — | chromosome 8 open reading frame 61 | C8orf61 | 1.17136 |
| Hs.414028 | chromosome 9 open reading frame 116 | C9orf116 | 1.54706 |
| Hs.201258 | chromosome 9 open reading frame 122 | C9orf122 | 2.47079 |
| Hs.388742 | Chromosome 9 open reading frame 125 | C9orf125 | 1.14297 |
| Hs.493808 | chromosome 9 open reading frame 127 | C9orf127 | 1.13038 |
| Hs.535972 | chromosome 9 open reading frame 132 | C9orf132 | 1.19294 |
| Hs.522412 | chromosome 9 open reading frame 16 | C9orf16 | 1.32418 |
| Hs.522412 | chromosome 9 open reading frame 16 | C9orf16 | 1.62565 |
| Hs.435381 | chromosome 9 open reading frame 39 | C9orf39 | 1.54663 |
| Hs.257556 | chromosome 9 open reading frame 41 | C9orf41 | −1.70667 |
| Hs.257556 | chromosome 9 open reading frame 41 | C9orf41 | −1.50723 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.308074 | Chromosome 9 open reading frame 5 | C9orf5 | −1.46697 |
| Hs.208914 | chromosome 9 open reading frame 64 | C9orf64 | −1.66481 |
| Hs.530283 | chromosome 9 open reading frame 80 | C9orf80 | −1.34228 |
| Hs.374421 | chromosome 9 open reading frame 81 | C9orf81 | −1.17057 |
| Hs.428446 | carbonic anhydrase XI | CA11 | 1.53318 |
| Hs.155097 | carbonic anhydrase II | CA2 | −2.25715 |
| Hs.63287 | carbonic anhydrase IX | CA9 | 1.81937 |
| Hs.443891 | cache domain containing 1 | CACHD1 | 1.4437 |
| Hs.476358 | Calcium channel, voltage-dependent, L type, alpha 1D subunit | CACNA1D | 1.34205 |
| Hs.476358 | calcium channel, voltage-dependent, L type, alpha 1D subunit | CACNA1D | 2.50302 |
| Hs.194746 | calcium channel, voltage-dependent, alpha 1G subunit | CACNA1G | 3.39333 |
| Hs.194746 | calcium channel, voltage-dependent, alpha 1G subunit | CACNA1G | 3.42834 |
| Hs.490203 | caldesmon 1 | CALD1 | 1.86428 |
| Hs.435457 | calmodulin-like 4 | CALML4 | −1.15167 |
| Hs.7753 | calumenin | CALU | −1.7749 |
| Hs.7753 | calumenin | CALU | −1.32093 |
| Hs.7753 | calumenin | CALU | −1.27131 |
| Hs.7753 | calumenin | CALU | −1.13115 |
| Hs.144114 | Calcium/calmodulin-dependent protein kinase (CaM kinase) II delta | CAMK2D | 1.05161 |
| Hs.144114 | Calcium/calmodulin-dependent protein kinase (CaM kinase) II delta | CAMK2D | 1.12993 |
| Hs.144114 | calcium/calmodulin-dependent protein kinase (CaM kinase) II delta | CAMK2D | 1.33867 |
| Hs.144114 | calcium/calmodulin-dependent protein kinase (CaM kinase) II delta | CAMK2D | 1.39652 |
| Hs.144114 | calcium/calmodulin-dependent protein kinase (CaM kinase) II delta | CAMK2D | 1.47631 |
| Hs.370581 | CAP, adenylate cyclase-associated protein 1 (yeast) | CAP1 | −1.13885 |
| Hs.370581 | CAP, adenylate cyclase-associated protein 1 (yeast) | CAP1 | −1.12518 |
| Hs.502842 | calpain 1, (mu/I) large subunit | CAPN1 | 1.0046 |
| Hs.350899 | calpain 2, (m/II) large subunit | CAPN2 | −2.05455 |
| Hs.248153 | calpain 5 | CAPN5 | 1.24763 |
| Hs.512867 | cancer susceptibility candidate 4 | CASC4 | −1.44102 |
| Hs.181855 | cancer susceptibility candidate 5 | CASC5 | −2.52077 |
| Hs.368982 | caspase 2, apoptosis-related cysteine peptidase (neural precursor cell expressed | CASP2 | −1.37039 |
| Hs.368982 | caspase 2, apoptosis-related cysteine peptidase (neural precursor cell expressed | CASP2 | −1.34704 |
| Hs.368982 | caspase 2, apoptosis-related cysteine peptidase (neural precursor cell expressed | CASP2 | −1.30026 |
| Hs.368982 | caspase 2, apoptosis-related cysteine peptidase (neural precursor cell expressed | CASP2 | −1.25427 |
| Hs.3280 | caspase 6, apoptosis-related cysteine peptidase | CASP6 | −1.39542 |
| Hs.9216 | caspase 7, apoptosis-related cysteine peptidase | CASP7 | −2.06042 |
| Hs.74034 | caveolin 1, caveolae protein, 22 kDa | CAV1 | −2.78632 |
| Hs.74034 | caveolin 1, caveolae protein, 22 kDa | CAV1 | −2.1214 |
| Hs.153934 | core-binding factor, runt domain, alpha subunit 2; translocated to, 2 | CBFA2T2 | 1.20888 |
| Hs.460988 | core-binding factor, beta subunit | CBFB | −2.70489 |
| Hs.460988 | core-binding factor, beta subunit | CBFB | −1.58035 |
| Hs.349283 | Chromobox homolog 5 (HP1 alpha homolog, Drosophila) | CBX5 | −1.99947 |
| Hs.55846 | coiled-coil domain containing 10 | CCDC10 | 1.33261 |
| Hs.412019 | coiled-coil domain containing 28A | CCDC28A | −1.23644 |
| Hs.327068 | coiled-coil domain containing 6 | CCDC6 | −2.15971 |
| Hs.327068 | coiled-coil domain containing 6 | CCDC6 | −2.01278 |
| Hs.303649 | chemokine (C-C motif) ligand 2 | CCL2 | −1.74877 |
| Hs.85137 | cyclin A2 | CCNA2 | −3.33175 |
| Hs.85137 | Cyclin A2 | CCNA2 | −2.60576 |
| Hs.23960 | cyclin B1 | CCNB1 | −2.80793 |
| Hs.23960 | cyclin B1 | CCNB1 | −2.64472 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.194698 | cyclin B2 | CCNB2 | −2.2702 |
| Hs.408658 | cyclin E2 | CCNE2 | −2.27126 |
| Hs.408658 | cyclin E2 | CCNE2 | −1.71865 |
| Hs.1600 | chaperonin containing TCP1, subunit 5 (epsilon) | CCT5 | −1.5989 |
| Hs.520313 | CD164 antigen, sialomucin | CD164 | −3.41558 |
| Hs.520313 | CD164 antigen, sialomucin | CD164 | −3.38079 |
| Hs.520313 | CD164 antigen, sialomucin | CD164 | −3.25399 |
| Hs.375108 | CD24 antigen (small cell lung carcinoma cluster 4 antigen) | CD24 | 1.13881 |
| Hs.479214 | CD38 antigen (p45) | CD38 | −1.72773 |
| Hs.374127 | CDC16 cell division cycle 16 homolog (S. cerevisiae) | CDC16 | −1.17129 |
| Hs.374127 | CDC16 cell division cycle 16 homolog (S. cerevisiae) | CDC16 | −1.02271 |
| Hs.334562 | cell division cycle 2, G1 to S and G2 to M | CDC2 | −2.74273 |
| Hs.334562 | cell division cycle 2, G1 to S and G2 to M | CDC2 | −2.63937 |
| Hs.334562 | Cell division cycle 2, G1 to S and G2 to M | CDC2 | −2.61709 |
| Hs.334562 | Cell division cycle 2, G1 to S and G2 to M | CDC2 | −2.36056 |
| Hs.524947 | CDC20 cell division cycle 20 homolog (S. cerevisiae) | CDC20 | −3.03263 |
| Hs.153546 | CDC23 (cell division cycle 23, yeast, homolog) | CDC23 | −1.77994 |
| Hs.1634 | cell division cycle 25A | CDC25A | −2.82429 |
| Hs.1634 | cell division cycle 25A | CDC25A | −2.79743 |
| Hs.656 | cell division cycle 25C | CDC25C | −1.73437 |
| Hs.656 | cell division cycle 25C | CDC25C | −1.31429 |
| Hs.463295 | Cell division cycle 27 | CDC27 | −1.97837 |
| Hs.463295 | cell division cycle 27 | CDC27 | −1.41185 |
| Hs.463295 | cell division cycle 27 | CDC27 | −1.36668 |
| Hs.463295 | cell division cycle 27 | CDC27 | −1.34818 |
| Hs.467637 | cell division cycle 42 (GTP binding protein, 25 kDa) | CDC42 | −1.17023 |
| Hs.467637 | cell division cycle 42 (GTP binding protein, 25 kDa) | CDC42 | 2.53366 |
| Hs.467637 | cell division cycle 42 (GTP binding protein, 25 kDa) | CDC42 | 3.27549 |
| Hs.369574 | CDC42 effector protein (Rho GTPase binding) 3 | CDC42EP3 | 1.38367 |
| Hs.369574 | CDC42 effector protein (Rho GTPase binding) 3 | CDC42EP3 | 1.91269 |
| Hs.369574 | CDC42 effector protein (Rho GTPase binding) 3 | CDC42EP3 | 2.01896 |
| Hs.508829 | CDC42 small effector 2 | CDC42SE2 | −2.14599 |
| Hs.508829 | CDC42 small effector 2 | CDC42SE2 | −1.56215 |
| Hs.508829 | CDC42 small effector 2 | CDC42SE2 | −1.56059 |
| Hs.474217 | CDC45 cell division cycle 45-like (S. cerevisiae) | CDC45L | −1.66652 |
| Hs.405958 | CDC6 cell division cycle 6 homolog (S. cerevisiae) | CDC6 | −3.94951 |
| Hs.405958 | CDC6 cell division cycle 6 homolog (S. cerevisiae) | CDC6 | −3.29246 |
| Hs.234545 | cell division cycle associated 1 | CDCA1 | −3.47053 |
| Hs.33366 | cell division cycle associated 2 | CDCA2 | −1.49882 |
| Hs.524216 | cell division cycle associated 3 /// cell division cycle associated 3 | CDCA3 | −2.18457 |
| Hs.524216 | cell division cycle associated 3 | CDCA3 | −2.12949 |
| Hs.34045 | cell division cycle associated 4 | CDCA4 | −1.40998 |
| Hs.434886 | cell division cycle associated 5 | CDCA5 | −2.09246 |
| Hs.520245 | cell division cycle associated 7-like | CDCA7L | −1.05903 |
| Hs.524571 | cell division cycle associated 8 | CDCA8 | −1.40849 |
| Hs.461086 | cadherin 1, type 1, E-cadherin (epithelial) | CDH1 | 1.70513 |
| Hs.89436 | cadherin 17, LI cadherin (liver-intestine) | CDH17 | 1.63977 |
| Hs.19192 | cyclin-dependent kinase 2 | CDK2 | −2.72265 |
| Hs.19192 | cyclin-dependent kinase 2 | CDK2 | −2.43817 |
| Hs.95577 | cyclin-dependent kinase 4 | CDK4 | −2.95739 |
| Hs.119882 | cyclin-dependent kinase 6 | CDK6 | −2.36362 |
| Hs.119882 | cyclin-dependent kinase 6 | CDK6 | −2.00742 |
| Hs.119882 | cyclin-dependent kinase 6 | CDK6 | −1.82506 |
| Hs.382306 | Cyclin-dependent kinase 8 | CDK8 | −1.69632 |
| Hs.382306 | Cyclin-dependent kinase 8 | CDK8 | −1.56738 |
| Hs.525324 | cyclin-dependent kinase inhibitor 2C (p18, inhibits CDK4) | CDKN2C | −1.37376 |
| Hs.84113 | cyclin-dependent kinase inhibitor 3 (CDK2-associated dual specificity phosphatase | CDKN3 | −2.65384 |

TABLE 1-continued

Genes with increased (positive values) or decreased (negative values) expression
following transfection of human cancer cells with pre-miR hsa-miR-124a.

| UniGene ID | Gene Title | Gene Symbol | Log2 (mir124 − NC #2) |
|---|---|---|---|
| Hs.84113 | cyclin-dependent kinase inhibitor 3 (CDK2-associated dual specificity phosphatase | CDKN3 | −2.56885 |
| Hs.444924 | CDP-diacylglycerol synthase (phosphatidate cytidylyltransferase) 1 | CDS1 | 1.66719 |
| Hs.444924 | CDP-diacylglycerol synthase (phosphatidate cytidylyltransferase) 1 | CDS1 | 1.84326 |
| Hs.122908 | DNA replication factor | CDT1 | −2.04126 |
| Hs.122908 | DNA replication factor | CDT1 | −1.77088 |
| Hs.512682 | carcinoembryonic antigen-related cell adhesion molecule 1 (biliary glycoprotein) | CEACAM1 | 2.24852 |
| Hs.495230 | cerebral endothelial cell adhesion molecule 1 | CEECAM1 | 1.25972 |
| Hs.57652 | cadherin, EGF LAG seven-pass G-type receptor 2 (flamingo homolog, *Drosophila*) | CELSR2 | 1.76312 |
| Hs.57652 | cadherin, EGF LAG seven-pass G-type receptor 2 (flamingo homolog, *Drosophila*) | CELSR2 | 1.86204 |
| Hs.1594 | centromere protein A, 17 kDa | CENPA | −3.18771 |
| Hs.1594 | centromere protein A, 17 kDa | CENPA | −1.7703 |
| Hs.75573 | centromere protein E, 312 kDa | CENPE | −2.09409 |
| Hs.497741 | centromere protein F, 350/400ka (mitosin) | CENPF | −2.37959 |
| Hs.497741 | centromere protein F, 350/400ka (mitosin) | CENPF | −2.10529 |
| Hs.200395 | centromere protein H | CENPH | −1.50918 |
| Hs.533828 | centromere protein J | CENPJ | −1.5592 |
| Hs.503165 | centaurin, delta 2 | CENTD2 | 1.12553 |
| Hs.504009 | KIAA1052 protein | Cep164 | −1.04867 |
| Hs.363396 | complement factor H | CFH | 1.30117 |
| Hs.363396 | complement factor H | CFH | 2.43226 |
| Hs.154224 | complement factor H /// complement factor H-related 1 | CFH /// CFHL1 | 2.13324 |
| Hs.558457 | complement factor H-related 4 /// complement factor H-related 3 | CFHL4 /// CFHL3 | 1.98765 |
| Hs.180141 | cofilin 2 (muscle) | CFL2 | −2.93902 |
| Hs.180141 | cofilin 2 (muscle) /// cofilin 2 (muscle) | CFL2 | −2.85342 |
| Hs.180141 | cofilin 2 (muscle) | CFL2 | −2.71961 |
| Hs.444818 | CGG triplet repeat binding protein 1 | CGGBP1 | −1.33141 |
| Hs.501513 | comparative gene identification transcript 37 | CGI-37 | −1.26782 |
| Hs.501513 | comparative gene identification transcript 37 | CGI-37 | −1.26573 |
| Hs.463465 | WD repeat domain 50 | CGI-48 | −1.64651 |
| Hs.79018 | chromatin assembly factor 1, subunit A (p150) | CHAF1A | −1.23151 |
| Hs.25601 | chromodomain helicase DNA binding protein 3 | CHD3 | 1.57624 |
| Hs.24529 | CHK1 checkpoint homolog (*S. pombe*) | CHEK1 | −2.28739 |
| Hs.24529 | CHK1 checkpoint homolog (*S. pombe*) | CHEK1 | −2.22291 |
| Hs.24529 | CHK1 checkpoint homolog (*S. pombe*) | CHEK1 | −2.18967 |
| Hs.434286 | checkpoint suppressor 1 | CHES1 | 1.49966 |
| Hs.434286 | checkpoint suppressor 1 | CHES1 | 1.57973 |
| Hs.516874 | chromogranin B (secretogranin 1) | CHGB | 1.72318 |
| Hs.496323 | Cysteine-rich hydrophobic domain 1 | CHIC1 | −1.69798 |
| Hs.476930 | chromatin modifying protein 2B | CHMP2B | −1.27962 |
| Hs.279704 | chromatin accessibility complex 1 | CHRAC1 | −1.23092 |
| Hs.534593 | Similar to RIKEN cDNA 1700009P17 | chromosome 1 open reading frame 192 | −1.28965 |
| Hs.110488 | carbohydrate (chondroitin) synthase 1 | CHSY1 | −1.31988 |
| Hs.198998 | conserved helix-loop-helix ubiquitous kinase | CHUK | −1.98322 |
| Hs.135471 | calcium and integrin binding 1 (calmyrin) | CIB1 | −1.05209 |
| Hs.129634 | Cyclin-dependent kinase 2-interacting protein | CINP | −1.32371 |
| Hs.119594 | citron (rho-interacting, serine/threonine kinase 21) | CIT | −1.25598 |
| Hs.444028 | cytoskeleton associated protein 2 | CKAP2 | −1.24034 |
| Hs.173724 | creatine kinase, brain | CKB | 1.83826 |
| Hs.298198 | chemokine-like factor superfamily 3 | CKLFSF3 | −1.6061 |

TABLE 1-continued

Genes with increased (positive values) or decreased (negative values) expression
following transfection of human cancer cells with pre-miR hsa-miR-124a.

| UniGene ID | Gene Title | Gene Symbol | Log2 (mir124 - NC #2) |
|---|---|---|---|
| Hs.298198 | chemokine-like factor superfamily 3 | CKLFSF3 | −1.29543 |
| Hs.380627 | chemokine-like factor superfamily 6 | CKLFSF6 | −2.84068 |
| Hs.380627 | chemokine-like factor superfamily 6 | CKLFSF6 | −2.8031 |
| Hs.440494 | chemokine-like factor superfamily 7 | CKLFSF7 | −1.20631 |
| Hs.374378 | CDC28 protein kinase regulatory subunit 1B | CKS1B | −2.84574 |
| Hs.83758 | CDC28 protein kinase regulatory subunit 2 | CKS2 | −1.81245 |
| Hs.554803 | chloride channel CLIC-like 1 | CLCC1 | −1.23379 |
| Hs.495674 | Chloride channel 4 | CLCN4 | 1.06607 |
| Hs.439060 | claudin 1 | CLDN1 | −2.15902 |
| Hs.439060 | claudin 1 | CLDN1 | −2.08021 |
| Hs.86368 | calmegin | CLGN | −1.01082 |
| Hs.301478 | calmin (calponin-like, transmembrane) | CLMN | 1.92181 |
| Hs.175613 | claspin homolog (*Xenopus laevis*) | CLSPN | −1.23104 |
| Hs.29665 | calsyntenin 1 | CLSTN1 | 1.45359 |
| Hs.11463 | cytidylate kinase | CMPK | −1.47314 |
| Hs.5719 | chromosome condensation-related SMC-associated protein 1 | CNAP1 | −1.45856 |
| Hs.148590 | cornifelin /// cornifelin | CNFN | 1.99736 |
| Hs.483454 | calponin 3, acidic | CNN3 | −2.24638 |
| Hs.483454 | Calponin 3, acidic | CNN3 | −1.66067 |
| Hs.274579 | cyclin M1 | CNNM1 | 1.01851 |
| Hs.460923 | CCR4-NOT transcription complex, subunit 1 | CNOT1 | −1.34874 |
| Hs.157606 | CCR4-NOT transcription complex, subunit 6 | CNOT6 | 1.39775 |
| Hs.523446 | collagen, type XI, alpha 1 | COL11A1 | 1.36205 |
| Hs.523446 | collagen, type XI, alpha 1 | COL11A1 | 1.66296 |
| Hs.101302 | collagen, type XII, alpha 1 | COL12A1 | −2.03051 |
| Hs.172928 | collagen, type I, alpha 1 | COL1A1 | 1.45332 |
| Hs.172928 | collagen, type I, alpha 1 | COL1A1 | 2.20304 |
| Hs.172928 | collagen, type I, alpha 1 | COL1A1 | 2.80419 |
| Hs.47629 | collagen, type XXI, alpha 1 /// collagen, type XXI, alpha 1 | COL21A1 | 1.21918 |
| Hs.17441 | collagen, type IV, alpha 1 | COL4A1 | −1.71965 |
| Hs.17441 | collagen, type IV, alpha 1 | COL4A1 | −1.58672 |
| Hs.471525 | collagen, type IV, alpha 3 (Goodpasture antigen) | COL4A3 | 1.55068 |
| Hs.369089 | collagen, type IV, alpha 5 (Alport syndrome) | COL4A5 | 1.39226 |
| Hs.145586 | collagen, type IV, alpha 6 | COL4A6 | 1.6256 |
| Hs.145586 | collagen, type IV, alpha 6 | COL4A6 | 1.87491 |
| Hs.210283 | collagen, type V, alpha 1 | COL5A1 | 1.36412 |
| Hs.210283 | collagen, type V, alpha 1 | COL5A1 | 1.48443 |
| Hs.476218 | collagen, type VII, alpha 1 | COL7A1 | 1.05271 |
| Hs.476218 | collagen, type VII, alpha 1 | COL7A1 | 1.09717 |
| Hs.2076 | COMM domain containing 5 /// COMM domain containing 5 | COMMD5 | −1.18784 |
| Hs.532231 | coatomer protein complex, subunit gamma 2 | COPG2 | 1.48591 |
| Hs.505652 | coatomer protein complex, subunit zeta 1 | COPZ1 | −1.9788 |
| Hs.289092 | coactosin-like 1 (*Dictyostelium*) | COTL1 | −1.48488 |
| Hs.289092 | coactosin-like 1 (*Dictyostelium*) | COTL1 | −1.32679 |
| Hs.75360 | carboxypeptidase E | CPE | 1.19391 |
| Hs.127126 | cytoplasmic polyadenylation element binding protein 4 | CPEB4 | 1.06491 |
| Hs.127126 | cytoplasmic polyadenylation element binding protein 4 | CPEB4 | 1.41208 |
| Hs.199877 | copine IV | CPNE4 | 1.69765 |
| Hs.476982 | coproporphyrinogen oxidase | CPOX | −1.26337 |
| Hs.149252 | carbamoyl-phosphate synthetase 1, mitochondrial | CPS1 | −1.69539 |
| Hs.149252 | carbamoyl-phosphate synthetase 1, mitochondrial | CPS1 | −1.44753 |
| Hs.503043 | carnitine palmitoyltransferase 1A (liver) | CPT1A | −1.34021 |
| Hs.150319 | Crumbs homolog 3 (*Drosophila*) | CRB3 | 1.14995 |
| Hs.924 | crystallin, mu | CRYM | 1.1329 |
| Hs.474833 | casein kinase 1, epsilon | CSNK1E | 1.17153 |
| Hs.443681 | chondroitin sulfate proteoglycan 2 (versican) | CSPG2 | 1.07451 |
| Hs.443681 | chondroitin sulfate proteoglycan 2 (versican) | CSPG2 | 1.08543 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.443681 | chondroitin sulfate proteoglycan 2 (versican) | CSPG2 | 1.1818 |
| Hs.24485 | chondroitin sulfate proteoglycan 6 (bamacan) | CSPG6 | −1.56026 |
| Hs.24485 | chondroitin sulfate proteoglycan 6 (bamacan) | CSPG6 | −1.17463 |
| Hs.530904 | cysteine and glycine-rich protein 2 | CSRP2 | −1.60358 |
| Hs.444468 | CTD (carboxy-terminal domain, RNA polymerase II, polypeptide A) small phosphatas | CTDSP1 | −1.09632 |
| Hs.445981 | catenin (cadherin-associated protein), alpha 1, 102 kDa | CTNNA1 | −1.94658 |
| Hs.58488 | catenin (cadherin-associated protein), alpha-like 1 | CTNNAL1 | −1.7894 |
| Hs.166011 | catenin (cadherin-associated protein), delta 1 | CTNND1 | −1.66793 |
| Hs.128065 | cathepsin C | CTSC | −1.30469 |
| Hs.128065 | cathepsin C | CTSC | −1.25866 |
| Hs.546248 | cathepsin D (lysosomal aspartyl peptidase) | CTSD | 1.11754 |
| Hs.181301 | cathepsin S | CTSS | 1.44435 |
| Hs.789 | chemokine (C—X—C motif) ligand 1 (melanoma growth stimulating activity, alpha) | CXCL1 | −2.7128 |
| Hs.75765 | chemokine (C—X—C motif) ligand 2 | CXCL2 | −2.68663 |
| Hs.89714 | chemokine (C—X—C motif) ligand 5 | CXCL5 | −2.89046 |
| Hs.89714 | chemokine (C—X—C motif) ligand 5 | CXCL5 | −1.6063 |
| Hs.89714 | chemokine (C—X—C motif) ligand 5 | CXCL5 | −1.55161 |
| Hs.443061 | Chromosome X open reading frame 45 | CXorf45 | 1.47797 |
| Hs.443061 | chromosome X open reading frame 45 | CXorf45 | 1.92828 |
| Hs.443061 | chromosome X open reading frame 45 | CXorf45 | 2.97671 |
| Hs.12248 | CXXC finger 4 | CXXC4 | 1.48583 |
| Hs.189119 | CXXC finger 5 /// CXXC finger 5 | CXXC5 | 1.47101 |
| Hs.465413 | cytochrome b-5 | CYB5 | −1.22343 |
| Hs.465413 | cytochrome b-5 | CYB5 | −1.20915 |
| Hs.465413 | cytochrome b-5 | CYB5 | −1.18979 |
| Hs.221941 | cytochrome b reductase 1 | CYBRD1 | −1.71885 |
| Hs.437060 | cytochrome c, somatic | CYCS | −1.39544 |
| Hs.26704 | Cytoplasmic FMR1 interacting protein 1 | CYFIP1 | −1.23593 |
| Hs.519702 | cytoplasmic FMR1 interacting protein 2 | CYFIP2 | 2.18417 |
| Hs.519702 | cytoplasmic FMR1 interacting protein 2 /// cytoplasmic FMR1 interacting protein | CYFIP2 | 2.55062 |
| Hs.95120 | cytoglobin | CYGB | 1.41563 |
| Hs.255664 | cytoplasmic linker 2 /// cytoplasmic linker 2 | CYLN2 | 1.21467 |
| Hs.522863 | Chromosome Y open reading frame 15A | CYorf15A | −1.0077 |
| Hs.154654 | cytochrome P450, family 1, subfamily B, polypeptide 1 | CYP1B1 | −2.16666 |
| Hs.154654 | cytochrome P450, family 1, subfamily B, polypeptide 1 | CYP1B1 | −1.87882 |
| Hs.154654 | cytochrome P450, family 1, subfamily B, polypeptide 1 | CYP1B1 | −1.62631 |
| Hs.91546 | cytochrome P450, family 26, subfamily B, polypeptide 1 | CYP26B1 | −1.22772 |
| Hs.150276 | cytochrome P450, family 3, subfamily A, polypeptide 5 | CYP3A5 | 1.20104 |
| Hs.150276 | cytochrome P450, family 3, subfamily A, polypeptide 5 | CYP3A5 | 1.35169 |
| Hs.150276 | cytochrome P450, family 3, subfamily A, polypeptide 5 | CYP3A5 | 1.54568 |
| Hs.417077 | cytochrome P450, family 51, subfamily A, polypeptide 1 | CYP51A1 | −1.4555 |
| Hs.417077 | cytochrome P450, family 51, subfamily A, polypeptide 1 | CYP51A1 | −1.32422 |
| Hs.371597 | dynein 2 light intermediate chain | D2LIC | 1.32776 |
| Hs.371597 | dynein 2 light intermediate chain | D2LIC | 1.51611 |
| Hs.75189 | death-associated protein | DAP | −1.49054 |
| Hs.270570 | dihydrolipoamide branched chain transacylase E2 | DBT | −1.2195 |
| Hs.458320 | DC12 protein | DC12 | −1.10743 |
| Hs.507755 | doublecortin and CaM kinase-like 1 | DCAMKL1 | −2.902 |
| Hs.567333 | discoidin, CUB and LCCL domain containing 1 | DCBLD1 | 1.05197 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 − NC #2) |
|---|---|---|---|
| Hs.567333 | discoidin, CUB and LCCL domain containing 1 | DCBLD1 | 1.48436 |
| Hs.315167 | defective in sister chromatid cohesion homolog 1 (S. cerevisiae) | DCC1 | −2.34375 |
| Hs.443875 | DCP2 decapping enzyme homolog (S. cerevisiae) | DCP2 | −1.81125 |
| Hs.328865 | dynactin 4 (p62) | DCTN4 | −2.02467 |
| Hs.328865 | dynactin4 (p62) | DCTN4 | −1.31851 |
| Hs.179852 | Dendritic cell-derived ubiquitin-like protein | DC-UbP | 1.32734 |
| Hs.446564 | damage-specific DNA binding protein 2, 48 kDa /// LIM homeobox 3 | DDB2 /// LHX3 | 1.14095 |
| Hs.520004 | discoidin domain receptor family, member 1 | DDR1 | 1.4327 |
| Hs.520004 | discoidin domain receptor family, member 1 | DDR1 | 1.68595 |
| Hs.520004 | discoidin domain receptor family, member 1 | DDR1 | 1.80256 |
| Hs.520004 | discoidin domain receptor family, member 1 | DDR1 | 1.89648 |
| Hs.503794 | DEAD (Asp-Glu-Ala-Asp) box polypeptide 10 | DDX10 | −1.42152 |
| Hs.363492 | DEAD (Asp-Glu-Ala-Asp) box polypeptide 18 | DDX18 | −1.05918 |
| Hs.223141 | DEAD (Asp-Glu-Ala-Asp) box polypeptide 21 /// zinc finger protein 596 | DDX21 /// ZNF596 | −1.30791 |
| Hs.510328 | DEAD (Asp-Glu-Ala-Asp) box polypeptide 24 | DDX24 | −1.19965 |
| Hs.311609 | DEAD (Asp-Glu-Ala-Asp) box polypeptide 39 | DDX39 | −1.08985 |
| Hs.99120 | DEAD (Asp-Glu-Ala-Asp) box polypeptide 3, Y-linked | DDX3Y | 1.50168 |
| Hs.8765 | DEAD (Asp-Glu-Ala-Asp) box polypeptide 42 | DDX42 | −1.1377 |
| Hs.190622 | DEAD (Asp-Glu-Ala-Asp) box polypeptide 58 | DDX58 | 1.18939 |
| Hs.190622 | DEAD (Asp-Glu-Ala-Asp) box polypeptide 58 | DDX58 | 1.20084 |
| Hs.299878 | degenerative spermatocyte homolog 1, lipid desaturase (Drosophila) | DEGS1 | −1.77701 |
| Hs.22393 | density-regulated protein | DENR | −1.37677 |
| Hs.22393 | density-regulated protein | DENR | −1.25724 |
| Hs.445098 | DEP domain containing 1 | DEPDC1 | −3.6264 |
| Hs.445098 | DEP domain containing 1 | DEPDC1 | −3.46414 |
| Hs.445098 | DEP domain containing 1 | DEPDC1 | −2.92426 |
| Hs.445098 | DEP domain containing 1 | DEPDC1 | −2.39652 |
| Hs.482233 | DEP domain containing 1B | DEPDC1B | −3.43354 |
| Hs.524488 | diacylglycerol kinase, alpha 80 kDa | DGKA | 1.2677 |
| Hs.469022 | deoxyguanosine kinase | DGUOK | 1.04628 |
| Hs.503134 | 7-dehydrocholesterol reductase | DHCR7 | −1.80162 |
| Hs.503134 | 7-dehydrocholesterol reductase | DHCR7 | −1.72273 |
| Hs.83765 | dihydrofolate reductase | DHFR | −2.16081 |
| Hs.83765 | dihydrofolate reductase | DHFR | −2.0783 |
| Hs.83765 | dihydrofolate reductase | DHFR | −1.72997 |
| Hs.83765 | dihydrofolate reductase | DHFR | −1.7002 |
| Hs.18788 | dehydrogenase/reductase (SDR family) member 10 | DHRS10 | 1.23476 |
| Hs.18788 | dehydrogenase/reductase (SDR family) member 10 | DHRS10 | 1.55439 |
| Hs.18788 | dehydrogenase/reductase (SDR family) member 10 | DHRS10 | 1.66056 |
| Hs.326950 | dehydrogenase/reductase (SDR family) member 4 | DHRS4 | −1.01155 |
| Hs.29403 | DEAH (Asp-Glu-Ala-His) box polypeptide 40 | DHX40 | 2.06771 |
| Hs.191518 | DEAH (Asp-Glu-Ala-His) box polypeptide 9 | DHX9 | −1.59238 |
| Hs.283127 | Diaphanous homolog 3 (Drosophila) | DIAPH3 | −2.38043 |
| Hs.508141 | diaphanous homolog 3 (Drosophila) | DIAPH3 | −2.25026 |
| Hs.87889 | Dicer1, Dcr-1 homolog (Drosophila) | DICER1 | −1.58904 |
| Hs.87889 | Dicer1, Dcr-1 homolog (Drosophila) | DICER1 | −1.5863 |
| Hs.506603 | DIP13 beta | DIP13B | 1.05222 |
| Hs.177275 | hypothetical protein dJ122O8.2 | DJ122O8.2 | −1.19499 |
| Hs.177275 | Hypothetical protein dJ122O8.2 | DJ122O8.2 | −1.04671 |
| Hs.4747 | dyskeratosis congenita 1, dyskerin | DKC1 | −2.11937 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.4747 | dyskeratosis congenita 1, dyskerin | DKC1 | −2.05753 |
| Hs.4747 | dyskeratosis congenita 1, dyskerin | DKC1 | −1.97153 |
| Hs.511979 | DKFZP434B0335 protein | DKFZP434B0335 | 1.06548 |
| Hs.294103 | LMBR1 domain containing 2 | DKFZp434H2226 | −1.03157 |
| Hs.444668 | hypothetical protein DKFZp434K2435 | DKFZp434K2435 | 1.7496 |
| Hs.485899 | CTTNBP2 N-terminal like | DKFZp547A023 | 1.34904 |
| Hs.491626 | Ring finger protein 170 | DKFZp564A022 | 1.75121 |
| Hs.410889 | putative ankyrin-repeat containing protein | DKFZP564D166 | 1.01131 |
| Hs.356719 | DKFZP564J0863 protein | DKFZP564J0863 | −3.57402 |
| Hs.323562 | implantation-associated protein | DKFZp564K142 | −4.39045 |
| Hs.323562 | implantation-associated protein | DKFZp564K142 | −3.5671 |
| Hs.386989 | DKFZP566O084 protein | DKFZp566O084 | −1.01449 |
| Hs.497518 | hypothetical protein DKFZp761N1114 | DKFZp761N1114 | 1.19395 |
| Hs.497518 | hypothetical protein DKFZp761N1114 | DKFZp761N1114 | 1.89937 |
| Hs.497518 | hypothetical protein DKFZp761N1114 | DKFZp761N1114 | 2.73396 |
| Hs.532968 | hypothetical protein DKFZp762E1312 | DKFZp762E1312 | −2.55383 |
| Hs.292156 | dickkopf homolog 3 (*Xenopus laevis*) | DKK3 | 1.1792 |
| Hs.292156 | Dickkopf homolog 3 (*Xenopus laevis*) | DKK3 | 1.19263 |
| Hs.292156 | dickkopf homolog 3 (*Xenopus laevis*) | DKK3 | 1.74194 |
| Hs.134296 | deleted in liver cancer 1 | DLC1 | −1.44525 |
| Hs.527922 | deleted in lymphocytic leukemia, 1 | DLEU1 | −1.40974 |
| Hs.548247 | deleted in lymphocytic leukemia, 2 /// BCMS upstream neighbor-like | DLEU2 /// BCMSUNL | −1.6719 |
| Hs.548247 | deleted in lymphocytic leukemia, 2 /// BCMS upstream neighbor-like | DLEU2 /// BCMSUNL | −1.31947 |
| Hs.77695 | discs, large homolog 7 (*Drosophila*) | DLG7 | −2.90398 |
| Hs.532446 | DNA2 DNA replication helicase 2-like (yeast) | DNA2L | −1.54051 |
| Hs.490745 | DnaJ (Hsp40) homolog, subfamily B, member 6 | DNAJB6 | −1.41306 |
| Hs.499000 | DnaJ (Hsp40) homolog, subfamily C, member 1 | DNAJC1 | −2.62796 |
| Hs.499000 | DnaJ (Hsp40) homolog, subfamily C, member 1 | DNAJC1 | −2.54013 |
| Hs.499000 | DnaJ (Hsp40) homolog, subfamily C, member 1 | DNAJC1 | −1.70042 |
| Hs.521764 | DnaJ (Hsp40) homolog, subfamily C, member 16 | DNAJC16 | 1.10086 |
| Hs.536063 | DnaJ (Hsp40) homolog, subfamily C, member 6 | DNAJC6 | 1.10817 |
| Hs.59125 | DnaJ (Hsp40) homolog, subfamily C, member 9 | DNAJC9 | −1.32488 |
| Hs.59125 | DnaJ (Hsp40) homolog, subfamily C, member 9 | DNAJC9 | −1.11517 |
| Hs.529495 | dynein, cytoplasmic, light intermediate polypeptide 1 | DNCLI1 | −1.1779 |
| Hs.159195 | dedicator of cytokinesis 1 | DOCK1 | 2.26656 |
| Hs.476284 | dedicator of cytokinesis 3 | DOCK3 | 1.66379 |
| Hs.406156 | dedicator of cytokinesis 7 | DOCK7 | −1.19771 |
| Hs.132599 | dedicator of cytokinesis 8 | DOCK8 | 1.50055 |
| Hs.132599 | dedicator of cytokinesis 8 | DOCK8 | 2.35211 |
| Hs.279832 | docking protein 4 | DOK4 | 1.3361 |
| Hs.279832 | docking protein 4 | DOK4 | 1.37223 |
| Hs.502914 | dipeptidylpeptidase 3 | DPP3 | 1.01747 |
| Hs.502914 | dipeptidylpeptidase 3 | DPP3 | 1.07768 |
| Hs.533644 | dpy-19-like 2 (*C. elegans*) | DPY19L2 | 1.1825 |
| Hs.335034 | dihydropyrimidine dehydrogenase | DPYD | −1.98042 |
| Hs.519659 | dihydropyrimidinase-like 3 | DPYSL3 | −1.73075 |
| Hs.519659 | dihydropyrimidinase-like 3 | DPYSL3 | −1.50947 |
| Hs.100058 | dihydropyrimidinase-like 4 | DPYSL4 | 1.09712 |
| Hs.100058 | dihydropyrimidinase-like 4 | DPYSL4 | 2.60688 |
| Hs.191705 | DEAQ box polypeptide 1 (RNA-dependent ATPase) | DQX1 | 1.27392 |
| Hs.148680 | dopamine receptor D1 interacting protein | DRD1IP | 1.07102 |
| Hs.279583 | DORA reverse strand protein 1 | DREV1 | 1.06286 |
| Hs.369998 | Dbf4-related factor 1 | DRF1 | −1.17251 |
| Hs.412597 | desmoglein 2 | DSG2 | −1.9102 |
| Hs.412597 | Desmoglein 2 | DSG2 | −1.34315 |
| Hs.126774 | denticleless homolog (*Drosophila*) | DTL | −4.10861 |
| Hs.126774 | denticleless homolog (*Drosophila*) | DTL | −3.43887 |
| Hs.471873 | deoxythymidylate kinase (thymidylate kinase) | DTYMK | −1.86636 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.471873 | deoxythymidylate kinase (thymidylate kinase) | DTYMK | −1.71737 |
| Hs.171695 | dual specificity phosphatase 1 | DUSP1 | −1.50727 |
| Hs.130988 | dual-specificity tyrosine-(Y)-phosphorylation regulated kinase 1B | DYRK1B | 1.35198 |
| Hs.126403 | dyslexia susceptibility 1 candidate 1 | DYX1C1 | 1.7048 |
| Hs.409210 | zinc finger DAZ interacting protein 3 | DZIP3 | 1.07621 |
| Hs.409210 | zinc finger DAZ interacting protein 3 | DZIP3 | 1.2468 |
| Hs.523526 | E2F transcription factor 8 | E2F8 | −3.18656 |
| Hs.474479 | ELL associated factor 1 | EAF1 | −2.10197 |
| Hs.522636 | emopamil binding protein (sterol isomerase) | EBP | −1.26922 |
| Hs.522636 | emopamil binding protein (sterol isomerase) | EBP | −1.25848 |
| Hs.196176 | enoyl Coenzyme A hydratase 1, peroxisomal | ECH1 | −1.42239 |
| Hs.518299 | epithelial cell transforming sequence 2 oncogene | ECT2 | −2.10847 |
| Hs.518299 | epithelial cell transforming sequence 2 oncogene | ECT2 | −1.73218 |
| Hs.492445 | E3 ubiquitin protein ligase, HECT domain containing, 1 | EDD | 2.022 |
| Hs.482730 | EGF-like repeats and discoidin I-like domains 3 | EDIL3 | 2.8031 |
| Hs.134857 | EF-hand calcium binding domain 2 | EFCAB2 | −1.71885 |
| Hs.134857 | EF-hand calcium binding domain 2 | EFCAB2 | −1.01445 |
| Hs.76224 | EGF-containing fibulin-like extracellular matrix protein 1 | EFEMP1 | −1.83654 |
| Hs.76224 | EGF-containing fibulin-like extracellular matrix protein 1 | EFEMP1 | −1.31285 |
| Hs.403594 | EF-hand domain family, member A2 | EFHA2 | 1.31663 |
| Hs.257224 | EF-hand domain family, member B | EFHB | 1.00964 |
| Hs.465374 | EF-hand domain family, member D2 | EFHD2 | −2.46123 |
| Hs.132483 | EGF-like-domain, multiple 4 | EGFL4 | 1.87874 |
| Hs.494977 | EGF-like-domain, multiple 5 | EGFL5 | 1.80931 |
| Hs.368808 | EH-domain containing 3 | EHD3 | 1.71415 |
| Hs.461178 | eukaryotic translation initiation factor 1A, Y-linked | EIF1AY | −1.10984 |
| Hs.449415 | Eukaryotic translation initiation factor 2C, 2 | EIF2C2 | −1.12295 |
| Hs.471492 | Eukaryotic translation initiation factor 2C, 4 | EIF2C4 | 1.80642 |
| Hs.151777 | eukaryotic translation initiation factor 2, subunit 1 alpha, 35 kDa | EIF2S1 | −2.73226 |
| Hs.151777 | eukaryotic translation initiation factor 2, subunit 1 alpha, 35 kDa | EIF2S1 | −2.09459 |
| Hs.404056 | eukaryotic translation initiation factor 3, subunit 1 alpha, 35 kDa | EIF3S1 | −2.28229 |
| Hs.404056 | eukaryotic translation initiation factor 3, subunit 1 alpha, 35 kDa | EIF3S1 | −1.79959 |
| Hs.404056 | eukaryotic translation initiation factor 3, subunit 1 alpha, 35 kDa | EIF3S1 | −1.4991 |
| Hs.129673 | Eukaryotic translation initiation factor 4A, isoform 1 | EIF4A1 | −1.15915 |
| Hs.476782 | eukaryotic translation initiation factor 4E member 3 | EIF4E3 | 1.41972 |
| Hs.476782 | eukaryotic translation initiation factor 4E member 3 | EIF4E3 | 1.5781 |
| Hs.411641 | eukaryotic translation initiation factor 4E binding protein 1 | EIF4EBP1 | −1.39677 |
| Hs.433750 | eukaryotic translation initiation factor 4 gamma, 1 | EIF4G1 | −1.03814 |
| Hs.467084 | eukaryotic translation initiation factor 4 gamma, 3 | EIF4G3 | 1.26523 |
| Hs.558325 | eukaryotic translation initiation factor 5 | EIF5 | −1.93228 |
| Hs.558325 | eukaryotic translation initiation factor 5 | EIF5 | −1.86911 |
| Hs.46523 | ELK3, ETS-domain protein (SRF accessory protein 2) | ELK3 | −2.45655 |
| Hs.46523 | ELK3, ETS-domain protein (SRF accessory protein 2) | ELK3 | −1.25066 |
| Hs.192221 | elongation factor, RNA polymerase II, 2 | ELL2 | −1.91899 |
| Hs.192221 | elongation factor, RNA polymerase II, 2 | ELL2 | −1.62813 |
| Hs.192221 | elongation factor, RNA polymerase II, 2 | ELL2 | −1.57786 |

TABLE 1-continued

Genes with increased (positive values) or decreased (negative values) expression
following transfection of human cancer cells with pre-miR hsa-miR-124a.

| UniGene ID | Gene Title | Gene Symbol | Log2 (mir124 - NC #2) |
|---|---|---|---|
| Hs.558550 | elongation factor RNA polymerase II-like 3 | ELL3 | 1.13084 |
| Hs.558550 | elongation factor RNA polymerase II-like 3 | ELL3 | 1.71885 |
| Hs.200100 | hypothetical protein Ells1 | Ells1 | 1.24292 |
| Hs.304578 | engulfment and cell motility 1 (ced-12 homolog, C. elegans) | ELMO1 | 1.22869 |
| Hs.25597 | elongation of very long chain fatty acids (FEN1/Elo2, SUR4/Elo3, yeast)-like 1 | ELOVL1 | −2.76914 |
| Hs.25597 | elongation of very long chain fatty acids (FEN1/Elo2, SUR4/Elo3, yeast)-like 1 | ELOVL1 | −2.59687 |
| Hs.101915 | elongation of very long chain fatty acids (FEN1/Elo2, SUR4/Elo3, yeast)-like 4 | ELOVL4 | 1.71465 |
| Hs.520189 | ELOVL family member 5, elongation of long chain fatty acids | ELOVL5 | −2.45897 |
| Hs.511915 | enolase 2 (gamma, neuronal) | ENO2 | 1.49254 |
| Hs.224171 | enolase 3 (beta, muscle) | ENO3 | 1.13782 |
| Hs.511916 | endosulfine alpha | ENSA | −1.27401 |
| Hs.511916 | endosulfine alpha | ENSA | −1.25068 |
| Hs.511916 | endosulfine alpha | ENSA | 1.18864 |
| Hs.444389 | ectonucleoside triphosphate diphosphohydrolase 4 | ENTPD4 | 1.05884 |
| Hs.437422 | erythrocyte membrane protein band 4.1-like 1 | EPB41L1 | 1.95706 |
| Hs.371218 | EPH receptor A4 | EPHA4 | 1.1881 |
| Hs.462445 | B9 protein | EPPB9 | 1.47687 |
| Hs.200412 | epiplakin 1 | EPPK1 | 1.15271 |
| Hs.200412 | epiplakin 1 | EPPK1 | 1.31746 |
| Hs.497788 | glutamyl-prolyl-tRNA synthetase | EPRS | −1.02469 |
| Hs.3426 | Era G-protein-like 1 (E. coli) | ERAL1 | −1.06767 |
| Hs.558519 | ERO1-like beta (S. cerevisiae) | ERO1LB | 1.04461 |
| Hs.99480 | establishment of cohesion 1 homolog 2 (S. cerevisiae) | ESCO2 | −2.44684 |
| Hs.99480 | establishment of cohesion 1 homolog 2 (S. cerevisiae) | ESCO2 | −1.78936 |
| Hs.153479 | extra spindle poles like 1 (S. cerevisiae) | ESPL1 | −1.91154 |
| Hs.153479 | extra spindle poles like 1 (S. cerevisiae) | ESPL1 | −1.82069 |
| Hs.369438 | v-ets erythroblastosis virus E26 oncogene homolog 1 (avian) | ETS1 | −1.6735 |
| Hs.22634 | ets variant gene 1 | ETV1 | −1.88347 |
| Hs.125867 | Enah/Vasp-like | EVL | 1.13764 |
| Hs.498248 | exonuclease 1 | EXO1 | −2.25023 |
| Hs.546354 | exosome component 2 | EXOSC2 | −1.3212 |
| Hs.493887 | exosome component 3 | EXOSC3 | −1.11772 |
| Hs.294041 | exosome component 8 | EXOSC8 | −1.5286 |
| Hs.357637 | exostoses (multiple)-like 2 | EXTL2 | −1.22071 |
| Hs.102408 | Eyes absent homolog 4 (Drosophila) | EYA4 | −1.19608 |
| Hs.194669 | enhancer of zeste homolog 1 (Drosophila) | EZH1 | 1.20347 |
| Hs.444082 | enhancer of zeste homolog 2 (Drosophila) | EZH2 | −1.78348 |
| Hs.517293 | F11 receptor | F11R | −1.8927 |
| Hs.517293 | F11 receptor | F11R | −1.85886 |
| Hs.435782 | coagulation factor XIII, B polypeptide | F13B | 1.78363 |
| Hs.482562 | coagulation factor II (thrombin) receptor | F2R | 2.34626 |
| Hs.42502 | coagulation factor II (thrombin) receptor-like 2 | F2RL2 | −2.82395 |
| Hs.30054 | coagulation factor V (proaccelerin, labile factor) | F5 | 1.78664 |
| Hs.413083 | coagulation factor VIII, procoagulant component (hemophilia A) | F8 | 1.97013 |
| Hs.503546 | fatty acid desaturase 1 | FADS1 | −1.6424 |
| Hs.444200 | fetal Alzheimer antigen | FALZ | 1.07428 |
| Hs.567322 | family with sequence similarity 13, member C1 | FAM13C1 | 1.79836 |
| Hs.436854 | family with sequence similarity 19 (chemokine (C-C motif)-like), member A5 | FAM19A5 | 1.40543 |
| Hs.548148 | family with sequence similarity 29, member A | FAM29A | −1.93931 |
| Hs.548148 | family with sequence similarity 29, member A | FAM29A | −1.82376 |
| Hs.533468 | family with sequence similarity 29, member A | FAM29A | −1.3457 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 − NC #2) |
|---|---|---|---|
| Hs.121536 | family with sequence similarity 54, member A | FAM54A | −2.61482 |
| Hs.121536 | family with sequence similarity 54, member A | FAM54A | −1.11101 |
| Hs.404323 | family with sequence similarity 64, member A | FAM64A | −1.37793 |
| Hs.495480 | family with sequence similarity 69, member B | FAM69B | 2.2303 |
| Hs.339665 | family with sequence similarity 72, member A | FAM72A | −2.16905 |
| — | family with sequence similarity 73, member A | FAM73A | −2.3104 |
| — | family with sequence similarity 73, member A | FAM73A | −2.1617 |
| Hs.124951 | family with sequence similarity 84, member B | FAM84B | 2.32367 |
| Hs.38516 | family with sequence similarity 89, member A | FAM89A | −2.11277 |
| Hs.284153 | Fanconi anemia, complementation group A | FANCA | −1.32474 |
| Hs.554740 | Fanconi anemia, complementation group B | FANCB | −1.13523 |
| Hs.208388 | Fanconi anemia, complementation group D2 | FANCD2 | −2.84826 |
| Hs.208388 | Fanconi anemia, complementation group D2 | FANCD2 | −1.60374 |
| Hs.434873 | Fanconi anemia, complementation group G | FANCG | −1.5852 |
| Hs.244139 | Fas (TNF receptor superfamily, member 6) | FAS | 1.17228 |
| Hs.244139 | Fas (TNF receptor superfamily, member 6) | FAS | 1.24654 |
| Hs.244139 | Fas (TNF receptor superfamily, member 6) | FAS | 1.31565 |
| Hs.244139 | Fas (TNF receptor superfamily, member 6) | FAS | 1.4722 |
| Hs.475872 | F-box and leucine-rich repeat protein 2 | FBXL2 | 1.17038 |
| Hs.558474 | F-box and leucine-rich repeat protein 21 | FBXL21 | 1.27072 |
| Hs.558474 | F-box and leucine-rich repeat protein 21 | FBXL21 | 2.34014 |
| Hs.558475 | F-box and leucine-rich repeat protein 4 | FBXL4 | −1.08835 |
| Hs.458959 | F-box protein 22 | FBXO22 | 1.33276 |
| Hs.64691 | F-box protein 28 | FBXO28 | −1.7029 |
| Hs.406787 | F-box protein 3 | FBXO3 | 1.62174 |
| Hs.421095 | F-box protein 30 | FBXO30 | −1.01912 |
| Hs.23158 | F-box protein 41 | FBXO41 | 1.55528 |
| Hs.339577 | F-box protein 43 | FBXO43 | −1.14098 |
| Hs.520506 | F-box protein 5 | FBXO5 | −1.48612 |
| Hs.520506 | F-box protein 5 | FBXO5 | −1.26949 |
| Hs.494985 | F-box and WD-40 domain protein 2 | FBXW2 | 1.58044 |
| Hs.519029 | F-box and WD-40 domain protein 7 (archipelago homolog, *Drosophila*) | FBXW7 | 1.64939 |
| Hs.445748 | FCH and double SH3 domains 2 | FCHSD2 | 1.02896 |
| Hs.335918 | farnesyl diphosphate synthase (farnesyl pyrophosphate synthetase, dimethylallyl | FDPS | −1.10151 |
| Hs.69745 | ferredoxin reductase | FDXR | 2.8746 |
| Hs.409065 | flap structure-specific endonuclease 1 | FEN1 | −2.23817 |
| Hs.409065 | flap structure-specific endonuclease 1 | FEN1 | −2.1121 |
| Hs.351593 | fibrinogen alpha chain | FGA | −2.37948 |
| Hs.351593 | fibrinogen alpha chain | FGA | −2.28712 |
| Hs.117835 | FYVE, RhoGEF and PH domain containing 4 | FGD4 | 1.13339 |
| Hs.284244 | fibroblast growth factor 2 (basic) | FGF2 | −1.70317 |
| Hs.1420 | fibroblast growth factor receptor 3 (achondroplasia, thanatophoric dwarfism) | FGFR3 | 2.07112 |
| Hs.436636 | formin homology 2 domain containing 3 | FHOD3 | 2.33086 |
| Hs.137516 | fidgetin-like 1 | FIGNL1 | −2.0818 |
| Hs.137516 | fidgetin-like 1 | FIGNL1 | −1.68787 |
| Hs.526972 | filamin A interacting protein 1 | FILIP1 | 1.55547 |
| Hs.529778 | leucine zipper protein FKSG14 | FKSG14 | −2.8554 |
| Hs.104650 | mago-nashi homolog | FLJ10292 | −1.21858 |
| Hs.513126 | hypothetical protein FLJ10719 | FLJ10719 | −2.38659 |
| Hs.513126 | hypothetical protein FLJ10719 | FLJ10719 | −2.04896 |
| Hs.513126 | hypothetical protein FLJ10719 | FLJ10719 | −1.25703 |
| Hs.8395 | hypothetical protein FLJ10781 | FLJ10781 | 1.22672 |
| Hs.212774 | hypothetical protein FLJ10808 | FLJ10808 | −1.39867 |
| Hs.212774 | hypothetical protein FLJ10808 | FLJ10808 | −1.34747 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.212774 | hypothetical protein FLJ10808 | FLJ10808 | −1.06753 |
| Hs.556432 | Hypothetical protein FLJ10979 | FLJ10979 | 1.12946 |
| Hs.152385 | hypothetical protein FLJ10980 | FLJ10980 | 1.58824 |
| Hs.567288 | hypothetical protein FLJ11000 | FLJ11000 | 1.06971 |
| Hs.274448 | Hypothetical protein FLJ11029 | FLJ11029 | −2.28046 |
| Hs.368853 | hypothetical protein FLJ12443 | FLJ12443 | 1.3187 |
| Hs.482301 | Hypothetical protein FLJ13611 | FLJ13611 | 1.09987 |
| Hs.387057 | hypothetical protein FLJ13710 | FLJ13710 | 1.27871 |
| Hs.47125 | hypothetical protein FLJ13912 | FLJ13912 | −1.42993 |
| Hs.47125 | hypothetical protein FLJ13912 | FLJ13912 | −1.27517 |
| Hs.55148 | hypothetical protein FLJ14466 | FLJ14466 | −2.34469 |
| Hs.190983 | hypothetical protein FLJ14624 | FLJ14624 | 1.19615 |
| Hs.190983 | hypothetical protein FLJ14624 | FLJ14624 | 1.24685 |
| Hs.190983 | hypothetical protein FLJ14624 | FLJ14624 | 1.8325 |
| Hs.437195 | hypothetical protein FLJ14627 | FLJ14627 | 1.50921 |
| Hs.321689 | hypothetical protein FLJ14981 | FLJ14981 | 1.46622 |
| Hs.518926 | hypothetical protein FLJ20054 | FLJ20054 | −1.24644 |
| Hs.47558 | FLJ20105 protein | FLJ20105 | −1.64963 |
| Hs.418581 | FLJ20160 protein | FLJ20160 | 2.47673 |
| Hs.418581 | FLJ20160 protein | FLJ20160 | 2.48305 |
| Hs.148677 | hypothetical protein FLJ20232 | FLJ20232 | −1.17884 |
| Hs.518727 | RNA-binding protein | FLJ20273 | −1.65332 |
| Hs.518727 | RNA-binding protein | FLJ20273 | −1.61792 |
| Hs.518727 | RNA-binding protein | FLJ20273 | −1.37823 |
| Hs.351798 | FLJ20298 protein | FLJ20298 | 1.66429 |
| Hs.368710 | hypothetical protein FLJ20364 | FLJ20364 | −2.39146 |
| Hs.426696 | timeless-interacting protein | FLJ20516 | −1.487 |
| Hs.330663 | hypothetical protein FLJ20641 | FLJ20641 | −2.81289 |
| Hs.330663 | hypothetical protein FLJ20641 | FLJ20641 | −2.77079 |
| Hs.96852 | hypothetical protein FLJ21128 | FLJ21128 | −1.36176 |
| Hs.549331 | ASAP | FLJ21159 | 1.52083 |
| Hs.369368 | Hypothetical protein FLJ21924 | FLJ21924 | −1.52374 |
| Hs.187505 | hypothetical protein FLJ22222 | FLJ22222 | −1.25193 |
| Hs.424711 | hypothetical protein FLJ22313 | FLJ22313 | 1.5447 |
| Hs.424711 | hypothetical protein FLJ22313 | FLJ22313 | 1.66334 |
| Hs.424711 | hypothetical protein FLJ22313 | FLJ22313 | 1.80024 |
| Hs.459795 | leucine zipper domain protein | FLJ22386 | 1.25305 |
| Hs.114111 | limkain beta 2 | FLJ22471 | 1.06387 |
| Hs.209715 | FLJ22624 protein | FLJ22624 | −1.46878 |
| Hs.351173 | hypothetical protein FLJ25006 | FLJ25006 | 1.62739 |
| Hs.529340 | hypothetical protein FLJ25067 | FLJ25067 | 1.25011 |
| Hs.165607 | hypothetical protein FLJ25416 | FLJ25416 | −2.27211 |
| Hs.404000 | hypothetical protein FLJ30655 | FLJ30655 | −1.23773 |
| Hs.404000 | Hypothetical protein FLJ30655 | FLJ30655 | −1.19698 |
| Hs.556067 | hypothetical protein FLJ31306 | FLJ31306 | 1.20769 |
| Hs.349306 | Hypothetical protein FLJ31951 | FLJ31951 | −1.0858 |
| Hs.448041 | FLJ32363 protein | FLJ32363 | −1.56733 |
| Hs.362702 | hypothetical protein FLJ32745 | FLJ32745 | −1.55915 |
| Hs.406460 | hypothetical protein FLJ33814 | FLJ33814 | −2.20913 |
| Hs.462829 | likely ortholog of mouse schlafen 8/9 | FLJ34922 | −1.52667 |
| Hs.556039 | FLJ35348 | FLJ35348 | 1.84642 |
| Hs.400698 | hypothetical protein FLJ35630 | FLJ35630 | 1.73821 |
| Hs.91930 | hypothetical protein FLJ35808 | FLJ35808 | 1.96306 |
| Hs.29692 | Hypothetical protein FLJ36031 | FLJ36031 | 1.72685 |
| Hs.148768 | Hypothetical protein FLJ36166 | FLJ36166 | 2.08619 |
| Hs.234681 | hypothetical protein FLJ36812 | FLJ36812 | −1.32073 |
| Hs.289044 | CDC20-like protein | FLJ37927 | −2.39272 |
| Hs.210586 | hypothetical protein FLJ38725 | FLJ38725 | 2.06097 |
| Hs.210586 | hypothetical protein FLJ38725 | FLJ38725 | 2.57804 |
| Hs.44817 | FLJ40142 protein | FLJ40142 | 1.4769 |
| Hs.434250 | hypothetical protein FLJ40629 | FLJ40629 | −2.3014 |
| Hs.467793 | hypothetical protein FLJ40869 | FLJ40869 | −1.42174 |
| Hs.530438 | FLJ46154 protein | FLJ46154 | 3.28063 |
| Hs.506309 | FLJ46688 protein | FLJ46688 | −2.05925 |
| Hs.448889 | FLJ90757 protein | FLJ90757 | 1.22948 |
| Hs.448889 | FLJ90757 protein | FLJ90757 | 1.66574 |
| Hs.476448 | filamin B, beta (actin binding protein 278) | FLNB | −1.30095 |
| Hs.41296 | fibronectin leucine rich transmembrane protein 3 | FLRT3 | 1.50282 |
| Hs.459715 | FLYWCH-type zinc finger 1 | FLYWCH1 | 1.03851 |
| Hs.24889 | formin 2 | FMN2 | 1.35305 |
| Hs.303476 | flavin containing monooxygenase 5 | FMO5 | 1.72565 |
| Hs.203717 | fibronectin 1 | FN1 | 1.09597 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 − NC #2) |
|---|---|---|---|
| Hs.438064 | FN5 protein | FN5 | −1.39882 |
| Hs.189409 | formin binding protein 1 | FNBP1 | 1.32566 |
| Hs.298735 | formin binding protein 3 | FNBP3 | −2.29703 |
| Hs.298735 | formin binding protein 3 | FNBP3 | −2.23899 |
| Hs.298735 | formin binding protein 3 | FNBP3 | −1.95234 |
| Hs.239 | forkhead box M1 | FOXM1 | −1.63511 |
| Hs.370666 | forkhead box O1A (rhabdomyosarcoma) | FOXO1A | 1.16937 |
| Hs.297452 | forkhead box Q1 | FOXQ1 | −1.20527 |
| Hs.369448 | Fraser syndrome 1 | FRAS1 | 1.36333 |
| Hs.369448 | Fraser syndrome 1 | FRAS1 | 2.70237 |
| Hs.127535 | FERM domain containing 3 | FRMD3 | −1.75635 |
| Hs.127535 | FERM domain containing 3 | FRMD3 | −1.04118 |
| Hs.369384 | FERM domain containing 4A | FRMD4A | 1.28615 |
| Hs.30561 | fibrinogen silencer binding protein /// RAD54 homolog B (S. cerevisiae) | FSBP /// RAD54B | 1.35416 |
| Hs.348920 | FSH primary response (LRPR1 homolog, rat) 1 | FSHPRH1 | −2.69849 |
| Hs.348920 | FSH primary response (LRPR1 homolog, rat) 1 | FSHPRH1 | −1.74732 |
| Hs.513522 | fusion (involved in t(12; 16) in malignant liposarcoma) | FUS | −1.08667 |
| Hs.29978 | frataxin | FXN | −1.70992 |
| Hs.413137 | FXYD domain containing ion transport regulator 2 | FXYD2 | 1.14961 |
| Hs.413137 | FXYD domain containing ion transport regulator 2 | FXYD2 | 1.31436 |
| Hs.173859 | frizzled homolog 7 (Drosophila) | FZD7 | 1.05336 |
| Hs.3353 | Ras-GTPase-activating protein SH3-domain-binding protein | G3BP | −3.2146 |
| Hs.3353 | Ras-GTPase-activating protein SH3-domain-binding protein | G3BP | −2.67307 |
| Hs.3353 | Ras-GTPase-activating protein SH3-domain-binding protein | G3BP | −1.7465 |
| Hs.3353 | Ras-GTPase-activating protein SH3-domain-binding protein | G3BP | −1.16863 |
| Hs.167017 | gamma-aminobutyric acid (GABA) B receptor, 1 | GABBR1 | 1.64427 |
| Hs.511316 | GA binding protein transcription factor, beta subunit 2 | GABPB2 | −1.67162 |
| Hs.24969 | gamma-aminobutyric acid (GABA) A receptor, alpha 5 | GABRA5 | −1.70953 |
| Hs.24969 | gamma-aminobutyric acid (GABA) A receptor, alpha 5 | GABRA5 | −1.38757 |
| Hs.302352 | gamma-aminobutyric acid (GABA) A receptor, beta 3 | GABRB3 | −1.59092 |
| Hs.80409 | growth arrest and DNA-damage-inducible, alpha | GADD45A | 1.88766 |
| Hs.294088 | GAJ protein | GAJ | −2.79177 |
| Hs.278959 | galanin | GAL | −1.213 |
| Hs.329978 | UDP-N-acetyl-alpha-D-galactosamine:polypeptide N-acetylgalactosaminyltransferase | GALNT11 | 1.28416 |
| Hs.534374 | UDP-N-acetyl-alpha-D-galactosamine:polypeptide N-acetylgalactosaminyltransferase | GALNT4 | −1.82726 |
| Hs.501911 | UDP-N-acetyl-alpha-D-galactosamine:polypeptide N-acetylgalactosaminyltransferase | GALNTL4 | 1.52977 |
| Hs.499659 | GTPase activating Rap/RanGAP domain-like 4 | GARNL4 | 1.92745 |
| Hs.322852 | growth arrest-specific 2 like 1 | GAS2L1 | −1.61419 |
| Hs.20575 | Growth arrest-specific 2 like 3 | GAS2L3 | −1.9064 |
| Hs.75335 | glycine amidinotransferase (L-arginine:glycine amidinotransferase) | GATM | 1.22063 |
| Hs.556063 | opposite strand transcription unit to STAG3 | GATS | 1.20979 |
| Hs.62661 | guanylate binding protein 1, interferon-inducible, 67 kDa /// guanylate binding p | GBP1 | 1.12929 |
| Hs.62661 | guanylate binding protein 1, interferon-inducible, 67 kDa | GBP1 | 1.54182 |
| Hs.62661 | guanylate binding protein 1, interferon-inducible, 67 kDa /// guanylate binding p | GBP1 | 1.67365 |
| Hs.386567 | guanylate binding protein 2, interferon-inducible | GBP2 | 1.66864 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.386567 | guanylate binding protein 2, interferon-inducible /// guanylate binding protein | GBP2 | 1.99681 |
| Hs.86724 | GTP cyclohydrolase 1 (dopa-responsive dystonia) | GCH1 | −1.99276 |
| Hs.293971 | germ cell-less homolog 1 (Drosophila) | GCL | −1.14224 |
| Hs.484313 | germ cell-less homolog 1 (Drosophila) | GCL /// GMCL1L | −1.17319 |
| Hs.315562 | glutamate-cysteine ligase, modifier subunit | GCLM | −2.78511 |
| Hs.315562 | Glutamate-cysteine ligase, modifier subunit | GCLM | −2.45471 |
| Hs.315562 | glutamate-cysteine ligase, modifier subunit | GCLM | −1.26658 |
| Hs.435741 | glycine cleavage system protein H (aminomethyl carrier) | GCSH | −2.04979 |
| Hs.435741 | glycine cleavage system protein H (aminomethyl carrier) | GCSH | −1.18143 |
| Hs.515258 | growth differentiation factor 15 | GDF15 | 2.31472 |
| Hs.499620 | gem (nuclear organelle) associated protein 4 | GEMIN4 | −1.21779 |
| Hs.483921 | gem (nuclear organelle) associated protein 5 | GEMIN5 | −1.77235 |
| Hs.277154 | G elongation factor, mitochondrial 2 | GFM2 | −1.19729 |
| Hs.460336 | golgi associated, gamma adaptin ear containing, ARF binding protein 2 | GGA2 | −1.2013 |
| Hs.78619 | gamma-glutamyl hydrolase (conjugase, folylpolygammaglutamyl hydrolase) | GGH | −1.93222 |
| Hs.55498 | geranylgeranyl diphosphate synthase 1 | GGPS1 | −1.2686 |
| Hs.532593 | gap junction protein, alpha 7, 45 kDa (connexin 45) | GJA7 | −1.94477 |
| Hs.202011 | GK001 protein | GK001 | −1.11277 |
| Hs.522255 | G kinase anchoring protein 1 | GKAP1 | 1.27201 |
| Hs.69089 | galactosidase, alpha | GLA | −1.15553 |
| Hs.443031 | Galactosidase, beta 1 | GLB1 | −1.59027 |
| Hs.131673 | glucocorticoid induced transcript 1 | GLCCI1 | 1.00364 |
| Hs.111867 | GLI-Kruppel family member GLI2 | GLI2 | 1.25283 |
| Hs.116448 | glutaminase | GLS | −1.24749 |
| Hs.212606 | glutaminase 2 (liver, mitochondrial) | GLS2 | 1.14395 |
| Hs.381256 | glycolipid transfer protein | GLTP | −1.99754 |
| Hs.381256 | glycolipid transfer protein | GLTP | −1.21499 |
| Hs.368538 | glutamate dehydrogenase 2 | GLUD2 | −1.0293 |
| Hs.149585 | glutamate-ammonia ligase (glutamine synthetase) domain containing 1 | GLULD1 | 1.08826 |
| Hs.415312 | CG9886-like | GLYCTK | 1.20524 |
| Hs.551552 | KIAA1196 protein | GM632 | 1.03667 |
| Hs.551552 | KIAA1196 protein | GM632 | 1.05692 |
| Hs.234896 | geminin, DNA replication inhibitor | GMNN | −1.47841 |
| Hs.515018 | guanine nucleotide binding protein (G protein), alpha 13 | GNA13 | −2.47089 |
| Hs.515018 | Guanine nucleotide binding protein (G protein), alpha 13 | GNA13 | −1.58408 |
| Hs.515018 | guanine nucleotide binding protein (G protein), alpha 13 | GNA13 | −1.51352 |
| Hs.134587 | guanine nucleotide binding protein (G protein), alpha inhibiting activity polype | GNAI1 | 1.21805 |
| Hs.269782 | Guanine nucleotide binding protein (G protein), q polypeptide | GNAQ | 1.11832 |
| Hs.125898 | GNAS complex locus | GNAS | 1.0648 |
| Hs.125898 | GNAS complex locus | GNAS | 2.00192 |
| Hs.430425 | guanine nucleotide binding protein (G protein), beta polypeptide 1 | GNB1 | 1.83826 |
| Hs.430425 | guanine nucleotide binding protein (G protein), beta polypeptide 1 | GNB1 | 2.00349 |
| Hs.155090 | guanine nucleotide binding protein (G protein), beta 5 | GNB5 | 1.1154 |
| Hs.431101 | guanine nucleotide binding protein (G protein), gamma 12 | GNG12 | −1.91611 |
| Hs.431101 | guanine nucleotide binding protein (G protein), gamma 12 | GNG12 | −1.1241 |
| Hs.431101 | guanine nucleotide binding protein (G protein), gamma 12 | GNG12 | −1.03355 |
| Hs.532401 | golgi transport 1 homolog A (S. cerevisiae) | GOLT1A | 2.60705 |
| Hs.62275 | golgi transport 1 homolog B (S. cerevisiae) | GOLT1B | −1.40902 |
| Hs.62275 | golgi transport 1 homolog B (S. cerevisiae) | GOLT1B | −1.23646 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 − NC #2) |
|---|---|---|---|
| Hs.191539 | golgi associated PDZ and coiled-coil motif containing | GOPC | 1.20331 |
| Hs.191539 | golgi associated PDZ and coiled-coil motif containing | GOPC | 1.41408 |
| Hs.194691 | G protein-coupled receptor, family C, group 5, member A | GPCR5A | −1.40268 |
| Hs.148266 | glycerol-3-phosphate dehydrogenase 2 (mitochondrial) | GPD2 | −2.27771 |
| Hs.148266 | glycerol-3-phosphate dehydrogenase 2 (mitochondrial) | GPD2 | −1.85335 |
| Hs.190495 | glycoprotein (transmembrane) nmb | GPNMB | 1.60921 |
| Hs.558674 | G protein-coupled receptor 113 | GPR113 | 1.8613 |
| Hs.150131 | G protein-coupled receptor 115 | GPR115 | 1.31636 |
| Hs.516604 | G protein-coupled receptor 155 | GPR155 | 1.60148 |
| Hs.231320 | G protein-coupled receptor 160 | GPR160 | 1.34179 |
| Hs.194691 | G protein-coupled receptor, family C, group 5, member A | GPRC5A | −1.34424 |
| Hs.489353 | G-protein signalling modulator 2 (AGS3-like, *C. elegans*) | GPSM2 | −1.66056 |
| Hs.489353 | G-protein signalling modulator 2 (AGS3-like, *C. elegans*) | GPSM2 | −1.49301 |
| Hs.76686 | glutathione peroxidase 1 | GPX1 | 1.45177 |
| Hs.467733 | GREB1 protein | GREB1 | 4.41713 |
| Hs.369825 | grainyhead-like 3 (*Drosophila*) | GRHL3 | 2.39619 |
| Hs.514220 | granulin | GRN | 1.30359 |
| Hs.514220 | granulin | GRN | 1.37371 |
| Hs.514220 | granulin | GRN | 1.46186 |
| Hs.309763 | G-rich RNA sequence binding factor 1 | GRSF1 | −2.59626 |
| Hs.309763 | G-rich RNA sequence binding factor 1 | GRSF1 | −2.11956 |
| Hs.309763 | G-rich RNA sequence binding factor 1 | GRSF1 | −1.69432 |
| Hs.170904 | Growth hormone regulated TBC protein 1 | GRTP1 | 1.45126 |
| Hs.445733 | Glycogen synthase kinase 3 beta | GSK3B | 1.38957 |
| Hs.203634 | glutathione S-transferase omega 2 | GSTO2 | 1.52027 |
| Hs.520459 | general transcription factor II, i | GTF2I | −1.8785 |
| Hs.276925 | GTP binding protein 1 | GTPBP1 | 1.03123 |
| Hs.386189 | G-2 and S-phase expressed 1 | GTSE1 | −2.42102 |
| Hs.386189 | G-2 and S-phase expressed 1 | GTSE1 | −1.73016 |
| Hs.386189 | G-2 and S-phase expressed 1 | GTSE1 | −1.59681 |
| Hs.386189 | G-2 and S-phase expressed 1 /// hypothetical gene supported by BC069212 | GTSE1 /// LOC440834 | −2.397 |
| Hs.477879 | H2A histone family, member X | H2AFX | −2.1569 |
| Hs.119192 | H2A histone family, member Z | H2AFZ | −1.62167 |
| Hs.119192 | H2A histone family, member Z | H2AFZ | −1.4254 |
| Hs.518265 | hypothetical protein H41 | H41 | −1.78639 |
| Hs.518265 | Hypothetical protein H41 | H41 | −1.29288 |
| Hs.470611 | histone acetyltransferase 1 | HAT1 | −1.32684 |
| Hs.291079 | HESB like domain containing 1 | HBLD1 | −1.59109 |
| Hs.378532 | HBS1-like (*S. cerevisiae*) | HBS1L | −1.2303 |
| Hs.438550 | KIAA0056 protein | hCAP-D3 | −1.35079 |
| Hs.567295 | chromosome condensation protein G | HCAP-G | −3.46013 |
| Hs.567295 | chromosome condensation protein G | HCAP-G | −3.2148 |
| Hs.20516 | histone deacetylase 4 | HDAC4 | −1.3466 |
| Hs.438782 | histone deacetylase 5 | HDAC5 | 1.39836 |
| Hs.209958 | HEAT repeat containing 1 | HEATR1 | −1.25984 |
| Hs.546260 | Helicase, lymphoid-specific | HELLS | −1.8674 |
| Hs.546260 | helicase, lymphoid-specific | HELLS | −1.5462 |
| Hs.546260 | helicase, lymphoid-specific | HELLS | −1.50163 |
| Hs.529317 | hect domain and RLD 6 | HERC6 | 1.39401 |
| Hs.513008 | hexosaminidase A (alpha polypeptide) | HEXA | 1.52815 |
| Hs.58650 | hedgehog acyltransferase | HHAT | 1.6184 |
| Hs.142245 | HERV-H LTR-associating 3 | HHLA3 | −1.32593 |
| Hs.124156 | hippocampus abundant transcript 1 | HIAT1 | −1.36064 |
| Hs.555996 | hippocampus abundant transcript-like 1 | HIATL1 | −1.1823 |
| Hs.521171 | hypoxia-inducible protein 2 | HIG2 | 1.70536 |
| Hs.521171 | hypoxia-inducible protein 2 | HIG2 | 1.7415 |
| Hs.72325 | histidine triad nucleotide binding protein 3 | HINT3 | −1.84562 |
| Hs.397465 | Homeodomain interacting protein kinase 2 | HIPK2 | −1.15842 |
| Hs.7644 | histone 1, H1c | HIST1H1C | 4.14109 |
| Hs.484950 | histone 1, H2ac | HIST1H2AC | 1.91071 |
| Hs.51011 | histone 1, H2ag | HIST1H2AG | 2.46271 |
| Hs.546314 | histone 1, H2bc | HIST1H2BC | 1.72508 |
| Hs.546314 | histone 1, H2bc | HIST1H2BC | 2.80658 |
| Hs.130853 | histone 1, H2bd | HIST1H2BD | 1.39519 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 − NC #2) |
|---|---|---|---|
| Hs.130853 | histone 1, H2bd | HIST1H2BD | 1.72945 |
| Hs.130853 | Histone 1, H2bd | HIST1H2BD | 2.74242 |
| Hs.130853 | Histone 1, H2bd | HIST1H2BD | 3.31633 |
| Hs.70937 | histone 1, H3h | HIST1H3H | 2.30897 |
| Hs.46423 | histone 1, H4c | HIST1H4C | −1.98509 |
| Hs.421737 | histone 1, H4h | HIST1H4H | 3.01933 |
| Hs.421737 | histone 1, H4h | HIST1H4H | 3.29807 |
| Hs.530461 | Histone 2, H2aa | HIST2H2AA | 2.12275 |
| Hs.530461 | histone 2, H2aa | HIST2H2AA | 2.84316 |
| Hs.530461 | histone 2, H2aa | HIST2H2AA | 3.20575 |
| Hs.2178 | histone 2, H2be | HIST2H2BE | 3.2941 |
| Hs.55468 | Histone 2, H4 | HIST2H4 | 1.5663 |
| Hs.371350 | Holocarboxylase synthetase (biotin-(proprionyl-Coenzyme A-carboxylase (ATP-hydrolysing)) ligase) | HLCS | 2.21798 |
| Hs.196952 | hepatic leukemia factor | HLF | 1.04531 |
| Hs.197086 | high-mobility group protein 2-like 1 | HMG2L1 | −1.35713 |
| Hs.434953 | high-mobility group box 2 | HMGB2 | −2.03362 |
| Hs.72550 | hyaluronan-mediated motility receptor (RHAMM) | HMMR | −3.1347 |
| Hs.72550 | hyaluronan-mediated motility receptor (RHAMM) | HMMR | −2.73338 |
| Hs.42151 | histamine N-methyltransferase | HNMT | 1.19206 |
| Hs.42151 | histamine N-methyltransferase | HNMT | 1.93024 |
| Hs.202166 | heterogeneous nuclear ribonucleoprotein H1 (H) | HNRPH1 | −1.6109 |
| Hs.202166 | heterogeneous nuclear ribonucleoprotein H1 (H) | HNRPH1 | −1.08502 |
| Hs.129051 | homer homolog 1 (Drosophila) | HOMER1 | 1.80166 |
| Hs.378836 | Hook homolog 1 (Drosophila) | HOOK1 | 1.71795 |
| Hs.77348 | hydroxyprostaglandin dehydrogenase 15-(NAD) | HPGD | 1.061 |
| Hs.534169 | heat shock 70 kDa protein 14 | HSPA14 | −1.39294 |
| Hs.90093 | heat shock 70 kDa protein 4 | HSPA4 | −1.29062 |
| Hs.11614 | HSPC065 protein | HSPC065 | 2.57539 |
| Hs.529475 | hypothetical protein HSPC111 | HSPC111 | −1.27724 |
| Hs.372208 | HSPC159 protein | HSPC159 | 1.81017 |
| Hs.90753 | HIV-1 Tat interactive protein 2, 30 kDa | HTATIP2 | 2.35107 |
| Hs.421649 | 5-hydroxytryptamine (serotonin) receptor 2B | HTR2B | 1.42638 |
| Hs.546478 | IBR domain containing 3 | IBRDC3 | 1.01982 |
| Hs.353214 | intercellular adhesion molecule 3 | ICAM3 | −2.31627 |
| Hs.417022 | intestinal cell (MAK-like) kinase | ICK | 1.46572 |
| Hs.504609 | inhibitor of DNA binding 1, dominant negative helix-loop-helix protein | ID1 | −1.64509 |
| Hs.567240 | iduronate 2-sulfatase (Hunter syndrome) | IDS | 1.19532 |
| Hs.567240 | iduronate 2-sulfatase (Hunter syndrome) | IDS | 1.20866 |
| Hs.567240 | iduronate 2-sulfatase (Hunter syndrome) | IDS | 1.33917 |
| Hs.567240 | iduronate 2-sulfatase (Hunter syndrome) | IDS | 1.36826 |
| Hs.315177 | interferon-related developmental regulator 2 | IFRD2 | −1.2166 |
| Hs.401316 | insulin-like growth factor binding protein 1 | IGFBP1 | −1.64161 |
| Hs.450230 | insulin-like growth factor binding protein 3 | IGFBP3 | −2.6144 |
| Hs.450230 | insulin-like growth factor binding protein 3 | IGFBP3 | −2.4886 |
| Hs.252543 | IKK interacting protein | IKIP | −2.22335 |
| Hs.252543 | IKK interacting protein | IKIP | −2.14205 |
| Hs.467304 | interleukin 11 | IL11 | −3.67212 |
| Hs.130652 | Interleukin 17D | IL17D | 1.63864 |
| Hs.532082 | Interleukin 6 signal transducer (gp130, oncostatin M receptor) | IL6ST | 1.73339 |
| Hs.532082 | Interleukin 6 signal transducer (gp130, oncostatin M receptor) | IL6ST | 1.94406 |
| Hs.624 | interleukin 8 | IL8 | −2.07134 |
| Hs.465885 | interleukin enhancer binding factor 3, 90 kDa | ILF3 | −1.36934 |
| Hs.144936 | IGF-II mRNA-binding protein 1 | IMP-1 | −1.58159 |
| Hs.367992 | inositol(myo)-1(or 4)-monophosphatase 2 | IMPA2 | −1.00389 |
| Hs.438689 | inositol monophosphatase domain containing 1 | IMPAD1 | −1.2956 |
| Hs.438689 | inositol monophosphatase domain containing 1 | IMPAD1 | −1.22495 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.369755 | inositol polyphosphate-5-phosphatase F | INPP5F | 1.23448 |
| Hs.465744 | Insulin receptor | INSR | 1.06549 |
| Hs.465744 | insulin receptor | INSR | 1.1958 |
| Hs.465744 | Insulin receptor | INSR | 1.46677 |
| Hs.482269 | importin 11 | IPO11 | −1.07067 |
| Hs.411865 | importin 4 | IPO4 | −1.92311 |
| Hs.430551 | IQ motif containing GTPase activating protein 1 | IQGAP1 | −2.71932 |
| Hs.430551 | IQ motif containing GTPase activating protein 1 | IQGAP1 | −2.36104 |
| Hs.133294 | IQ motif containing GTPase activating protein 3 | IQGAP3 | −2.14329 |
| Hs.133294 | IQ motif containing GTPase activating protein 3 | IQGAP3 | −1.93274 |
| Hs.301904 | interferon stimulated exonuclease gene 20 kDa-like 2 | ISG20L2 | −1.20778 |
| Hs.301904 | interferon stimulated exonuclease gene 20 kDa-like 2 | ISG20L2 | −1.05117 |
| Hs.429052 | integrin, beta 1 | ITGB1 | −3.02802 |
| Hs.429052 | integrin, beta 1 | ITGB1 | −2.91707 |
| Hs.429052 | integrin, beta 1 | ITGB1 | −2.17534 |
| Hs.166539 | integrin beta 3 binding protein (beta3-endonexin) | ITGB3BP | −2.02551 |
| Hs.443650 | Jumonji, AT rich interactive domain 1B (RBP2-like) | JARID1B | 1.15969 |
| Hs.443650 | Jumonji, AT rich interactive domain 1B (RBP2-like) | JARID1B | 1.23534 |
| Hs.443650 | Jumonji, AT rich interactive domain 1B (RBP2-like) | JARID1B | 1.37239 |
| Hs.368944 | juxtaposed with another zinc finger gene 1 | JAZF1 | −2.16226 |
| Hs.531819 | jumonji domain containing 1A | JMJD1A | 1.01766 |
| Hs.371013 | jumonji domain containing 2B | JMJD2B | 1.6286 |
| Hs.371013 | jumonji domain containing 2B | JMJD2B | 1.95999 |
| Hs.334017 | tubulin, alpha, ubiquitous | K-ALPHA-1 | −1.35471 |
| Hs.334017 | tubulin, alpha, ubiquitous /// tubulin, alpha, ubiquitous | K-ALPHA-1 | −1.29311 |
| Hs.334017 | tubulin, alpha, ubiquitous | K-ALPHA-1 | −1.29099 |
| Hs.524390 | tubulin, alpha, ubiquitous /// tubulin, alpha, ubiquitous | K-ALPHA-1 | −1.25129 |
| Hs.524390 | tubulin, alpha, ubiquitous | K-ALPHA-1 | −1.13449 |
| Hs.131838 | katanin p60 (ATPase-containing) subunit A 1 | KATNA1 | −1.22168 |
| Hs.243596 | katanin p60 subunit A-like 1 | KATNAL1 | −1.21293 |
| Hs.153521 | potassium voltage-gated channel, Shaw-related subfamily, member 4 | KCNC4 | 1.19395 |
| Hs.463985 | potassium inwardly-rectifying channel, subfamily J, member 16 | KCNJ16 | 3.12427 |
| Hs.420016 | potassium channel, subfamily T, member 2 | KCNT2 | 1.42217 |
| Hs.520210 | KDEL (Lys-Asp-Glu-Leu) endoplasmic reticulum protein retention receptor 2 | KDELR2 | −1.19309 |
| Hs.520210 | KDEL (Lys-Asp-Glu-Leu) endoplasmic reticulum protein retention receptor 2 | KDELR2 | −1.18837 |
| Hs.554798 | KDEL (Lys-Asp-Glu-Leu) endoplasmic reticulum protein retention receptor 3 | KDELR3 | −2.2101 |
| Hs.554798 | KDEL (Lys-Asp-Glu-Leu) endoplasmic reticulum protein retention receptor 3 | KDELR3 | −1.50849 |
| Hs.151761 | KIAA0100 gene product | KIAA0100 | 1.84019 |
| Hs.81892 | KIAA0101 /// KIAA0101 | KIAA0101 | −2.32423 |
| Hs.81892 | KIAA0101 | KIAA0101 | −1.43559 |
| Hs.9997 | KIAA0256 gene product | KIAA0256 | 1.18229 |
| Hs.520710 | KIAA0265 protein | KIAA0265 | −1.95842 |
| Hs.520710 | KIAA0265 protein | KIAA0265 | −1.51772 |
| Hs.520710 | KIAA0265 protein | KIAA0265 | −1.42047 |
| Hs.529959 | KIAA0274 | KIAA0274 | 1.24735 |
| Hs.475334 | KIAA0280 protein | KIAA0280 | 1.31133 |
| Hs.475334 | KIAA0280 protein | KIAA0280 | 1.74146 |
| Hs.533787 | KIAA0286 protein | KIAA0286 | −1.98542 |
| Hs.533787 | KIAA0286 protein | KIAA0286 | −1.74506 |
| Hs.456507 | KIAA0319-like | KIAA0319L | 1.02549 |
| Hs.558466 | KIAA0323 | KIAA0323 | −1.02258 |
| Hs.195667 | KIAA0329 | KIAA0329 | 1.14037 |
| Hs.35490 | KIAA0350 protein | KIAA0350 | 1.08686 |
| Hs.100874 | KIAA0494 | KIAA0494 | −2.58555 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.100874 | KIAA0494 | KIAA0494 | −2.2072 |
| Hs.100874 | KIAA0494 | KIAA0494 | −1.27129 |
| — | KIAA0500 protein | KIAA0500 | 2.05514 |
| Hs.552801 | KIAA0507 | KIAA0507 | −1.97595 |
| Hs.301658 | KIAA0513 | KIAA0513 | 1.31685 |
| Hs.495349 | KIAA0515 | KIAA0515 | 1.31926 |
| Hs.7426 | KIAA0841 | KIAA0841 | −1.49066 |
| Hs.480819 | KIAA0882 protein | KIAA0882 | 1.28729 |
| Hs.91662 | KIAA0888 protein | KIAA0888 | 1.18916 |
| Hs.91662 | KIAA0888 protein | KIAA0888 | 1.31162 |
| Hs.65135 | KIAA0913 | KIAA0913 | 1.2604 |
| Hs.432397 | KIAA0934 | KIAA0934 | 1.32651 |
| Hs.120855 | KIAA0960 protein | KIAA0960 | 1.28359 |
| Hs.120855 | KIAA0960 protein | KIAA0960 | 1.37374 |
| Hs.151220 | palladin | KIAA0992 | −1.22682 |
| Hs.151220 | palladin | KIAA0992 | −1.17649 |
| Hs.151220 | palladin | KIAA0992 | −1.1354 |
| Hs.443673 | KIAA1002 protein | KIAA1002 | 1.44265 |
| Hs.387856 | KIAA1043 protein | KIAA1043 | 1.18433 |
| Hs.21554 | KIAA1107 | KIAA1107 | 1.08839 |
| Hs.408142 | KIAA1109 | KIAA1109 | 1.41971 |
| Hs.368548 | Family with sequence similarity 63, member B | KIAA1164 | −1.2885 |
| Hs.368548 | Family with sequence similarity 63, member B | KIAA1164 | −1.09906 |
| Hs.292925 | KIAA1212 | KIAA1212 | −1.35975 |
| Hs.527524 | KIAA1280 protein | KIAA1280 | 1.76698 |
| Hs.509008 | KIAA1333 | KIAA1333 | −1.36628 |
| Hs.509008 | KIAA1333 | KIAA1333 | −1.315 |
| Hs.509008 | KIAA1333 | KIAA1333 | −1.11062 |
| Hs.509008 | KIAA1333 | KIAA1333 | −1.04474 |
| Hs.211700 | KIAA1411 | KIAA1411 | 1.91421 |
| Hs.472044 | hypothetical protein KIAA1434 | KIAA1434 | 1.36436 |
| Hs.472044 | hypothetical protein KIAA1434 | KIAA1434 | 1.49113 |
| Hs.472044 | hypothetical protein KIAA1434 | KIAA1434 | 2.22034 |
| Hs.479677 | KIAA1458 protein | KIAA1458 | −1.55098 |
| Hs.479677 | KIAA1458 protein | KIAA1458 | −1.37582 |
| Hs.130435 | KIAA1524 | KIAA1524 | −1.40287 |
| Hs.130435 | KIAA1524 | KIAA1524 | −1.23312 |
| Hs.515351 | KIAA1533 | KIAA1533 | 1.74878 |
| Hs.514554 | KIAA1618 | KIAA1618 | 1.51785 |
| Hs.419171 | KIAA1671 protein | KIAA1671 | −1.06096 |
| — | KIAA1702 protein | KIAA1702 | −1.75231 |
| Hs.507922 | KIAA1704 | KIAA1704 | −1.27003 |
| Hs.209561 | KIAA1715 | KIAA1715 | −1.85742 |
| Hs.87128 | KIAA1815 | KIAA1815 | −1.48463 |
| Hs.117136 | KIAA1912 protein | KIAA1912 | 1.4711 |
| Hs.28872 | KIAA1946 | KIAA1946 | 3.24543 |
| Hs.483329 | KIAA1961 gene | KIAA1961 | −1.48319 |
| Hs.8878 | kinesin family member 11 | KIF11 | −1.49293 |
| Hs.3104 | kinesin family member 14 | KIF14 | −2.89786 |
| Hs.3104 | kinesin family member 14 | KIF14 | −2.75907 |
| Hs.307529 | kinesin family member 15 | KIF15 | −2.88846 |
| Hs.301052 | kinesin family member 18A /// kinesin family member 18A | KIF18A | −1.84792 |
| Hs.97858 | Kinesin family member 1B | KIF1B | −1.82461 |
| Hs.97858 | kinesin family member 1B | KIF1B | −1.35829 |
| Hs.73625 | kinesin family member 20A | KIF20A | −2.08686 |
| Hs.119324 | kinesin family member 22 | KIF22 | −1.93115 |
| Hs.119324 | kinesin family member 22 | KIF22 | −1.11284 |
| Hs.270845 | kinesin family member 23 | KIF23 | −2.90771 |
| Hs.69360 | kinesin family member 2C | KIF2C | −2.06125 |
| Hs.69360 | kinesin family member 2C | KIF2C | −1.71731 |
| Hs.369670 | kinesin family member 3B | KIF3B | 1.14989 |
| Hs.369670 | kinesin family member 3B | KIF3B | 1.37049 |
| Hs.21611 | kinesin family member 3C | KIF3C | 1.31582 |
| Hs.279766 | kinesin family member 4A | KIF4A | −2.29215 |
| Hs.435557 | kinesin family member 5C | KIF5C | 1.39683 |
| Hs.376206 | Kruppel-like factor 4 (gut) | KLF4 | −1.78421 |
| Hs.4055 | Kruppel-like factor 6 | KLF6 | −1.66734 |
| Hs.4055 | Kruppel-like factor 6 | KLF6 | −1.54399 |
| Hs.4055 | Kruppel-like factor 6 | KLF6 | −1.46888 |
| Hs.150557 | Kruppel-like factor 9 | KLF9 | 2.20737 |
| Hs.495854 | kelch-like 15 (*Drosophila*) | KLHL15 | −1.79347 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 − NC #2) |
|---|---|---|---|
| Hs.512576 | killer cell lectin-like receptor subfamily C, member | KLRC1 /// KLRC2 | 1.01631 |
| Hs.20107 | kinesin 2 | KNS2 | 1.38069 |
| Hs.300559 | kinetochore associated 1 | KNTC1 | −1.56558 |
| Hs.414407 | kinetochore associated 2 | KNTC2 | −2.76939 |
| Hs.159557 | karyopherin alpha 2 (RAG cohort 1, importin alpha 1) | KPNA2 | −1.44524 |
| Hs.229335 | Kringle containing transmembrane protein 1 | KREMEN1 | 1.35716 |
| — | ubiquitin-conjugating enzyme variant Kua | Kua | −1.46174 |
| Hs.118554 | lactamase, beta 2 | LACTB2 | 1.44974 |
| Hs.118554 | lactamase, beta 2 | LACTB2 | 2.12263 |
| Hs.497039 | laminin, gamma 1 (formerly LAMB2) | LAMC1 | −2.45129 |
| Hs.496684 | lysosomal-associated membrane protein 2 | LAMP2 | −1.48459 |
| Hs.496684 | lysosomal-associated membrane protein 2 | LAMP2 | −1.2167 |
| Hs.496684 | lysosomal-associated membrane protein 2 | LAMP2 | 1.60281 |
| Hs.467807 | lysosomal-associated protein transmembrane 4 alpha | LAPTM4A | −1.10012 |
| Hs.292078 | La ribonucleoprotein domain family, member 1 | LARP1 | −1.35604 |
| Hs.416755 | La ribonucleoprotein domain family, member 6 | LARP6 | 1.19353 |
| Hs.285976 | LAG1 longevity assurance homolog 2 (*S. cerevisiae*) | LASS2 | −2.73956 |
| Hs.270525 | LAG1 longevity assurance homolog 5 (*S. cerevisiae*) | LASS5 | 1.62465 |
| Hs.468044 | likely ortholog of mouse limb-bud and heart gene /// likely ortholog of mouse li | LBH | 2.98095 |
| Hs.435166 | lamin B receptor | LBR | −2.36514 |
| Hs.213289 | low density lipoprotein receptor (familial hypercholesterolemia) | LDLR | −2.03319 |
| Hs.213289 | low density lipoprotein receptor (familial hypercholesterolemia) | LDLR | −1.55439 |
| Hs.23581 | Leptin receptor | LEPR | −2.49346 |
| Hs.23581 | leptin receptor | LEPR | −2.30081 |
| Hs.374191 | leprecan-like 1 | LEPREL1 | 1.18867 |
| — | leptin receptor overlapping transcript | LEPROT | −1.25243 |
| Hs.531776 | lectin, galactoside-binding, soluble, 2 (galectin 2) | LGALS2 | 1.68289 |
| Hs.4082 | lectin, galactoside-binding, soluble, 8 (galectin 8) | LGALS8 | −1.56978 |
| Hs.507798 | lipoma HMGIC fusion partner | LHFP | −1.77146 |
| Hs.445265 | LIM homeobox 2 | LHX2 | −1.72893 |
| Hs.496545 | LIM homeobox 4 | LHX4 | 1.20242 |
| Hs.469593 | LIM and senescent cell antigen-like domains 1 | LIMS1 | −2.74954 |
| Hs.469593 | LIM and senescent cell antigen-like domains 1 | LIMS1 | −1.51863 |
| Hs.23616 | lin-28 homolog B (*C. elegans*) | LIN28B | −2.56884 |
| Hs.91393 | lin-7 homolog C (*C. elegans*) | LIN7C | −2.25246 |
| Hs.91393 | lin-7 homolog C (*C. elegans*) | LIN7C | −2.20511 |
| Hs.91393 | lin-7 homolog C (*C. elegans*) | LIN7C | −1.44311 |
| Hs.120817 | lin-9 homolog (*C. elegans*) | LIN9 | −1.3572 |
| Hs.127445 | lipase A, lysosomal acid, cholesterol esterase (Wolman disease) | LIPA | −1.87712 |
| Hs.459940 | lipopolysaccharide-induced TNF factor | LITAF | −2.92415 |
| Hs.459940 | lipopolysaccharide-induced TNF factor | LITAF | −2.49069 |
| Hs.465295 | lectin, mannose-binding, 1 | LMAN1 | −1.26264 |
| Hs.158852 | lectin, mannose-binding 2-like /// lectin, mannose-binding 2-like | LMAN2L | −1.3844 |
| Hs.491359 | lamin A/C | LMNA | −1.33749 |
| Hs.89497 | lamin B1 | LMNB1 | −3.36368 |
| Hs.518084 | Hypothetical protein LOC116064 | LOC116064 | −2.41821 |
| Hs.518084 | hypothetical protein LOC116064 | LOC116064 | −1.46921 |
| Hs.106510 | hypothetical protein LOC116236 | LOC116236 | 1.35506 |
| Hs.31409 | hypothetical protein LOC120376 | LOC120376 | 1.76479 |
| Hs.74655 | Hypothetical protein LOC124512 | LOC124512 | −1.33014 |
| Hs.171130 | hypothetical protein BC014608 | LOC128153 | 1.1545 |
| Hs.171130 | hypothetical protein BC014608 | LOC128153 | 2.01562 |
| Hs.474210 | hypothetical protein LOC128977 | LOC128977 | 1.37265 |
| Hs.100743 | hypothetical protein BC015395 | LOC130940 | 1.18246 |
| Hs.483259 | hypothetical protein MGC12103 | LOC133619 | −1.40895 |
| Hs.481569 | hypothetical protein LOC134145 | LOC134145 | −1.22968 |

TABLE 1-continued

Genes with increased (positive values) or decreased (negative values) expression
following transfection of human cancer cells with pre-miR hsa-miR-124a.

| UniGene ID | Gene Title | Gene Symbol | Log2 (mir124 − NC #2) |
|---|---|---|---|
| Hs.192586 | similar to mouse 2310016A09Rik gene | LOC134147 | 1.83777 |
| — | hypothetical protein LOC144871 | LOC144871 | −1.47892 |
| Hs.410126 | hypothetical protein LOC145837 | LOC145837 | 1.14848 |
| Hs.135094 | hypothetical protein LOC146909 | LOC146909 | −2.72781 |
| Hs.336588 | hypothetical protein LOC147670 | LOC147670 | 1.07518 |
| Hs.355162 | hypothetical protein LOC147965 | LOC147965 | 1.33707 |
| Hs.531822 | hypothetical protein LOC150759 | LOC150759 | 1.23594 |
| Hs.4988 | hypothetical protein LOC151162 | LOC151162 | 1.00691 |
| Hs.558655 | similar to hepatocellular carcinoma-associated antigen HCA557b | LOC151194 | 1.48618 |
| Hs.259046 | hypothetical protein BC010062 | LOC152078 | 1.92028 |
| Hs.153799 | hypothetical protein LOC158402 | LOC158402 | 1.10633 |
| Hs.192877 | hypothetical protein LOC169834 | LOC169834 | 1.19901 |
| Hs.380920 | hypothetical protein LOC201725 | LOC201725 | −2.62 |
| Hs.380920 | hypothetical protein LOC201725 | LOC201725 | −2.60329 |
| Hs.205952 | Hypothetical protein LOC201895 | LOC201895 | −1.5966 |
| Hs.205952 | Hypothetical protein LOC201895 | LOC201895 | −1.24914 |
| Hs.175563 | hypothetical protein LOC203274 | LOC203274 | 2.18005 |
| Hs.496658 | similar to solute carrier family 25, member 16 | LOC203427 | −1.26066 |
| Hs.7626 | hypothetical protein LOC219854 | LOC219854 | −1.0769 |
| Hs.131417 | Hypothetical protein LOC253039 | LOC253039 | 1.53062 |
| Hs.12326 | hypothetical protein LOC257396 | LOC257396 | 1.51933 |
| Hs.376041 | hypothetical protein LOC283070 | LOC283070 | 1.23583 |
| Hs.558716 | hypothetical protein LOC283130 | LOC283130 | 1.73938 |
| Hs.436276 | hypothetical protein LOC283400 | LOC283400 | 1.51226 |
| Hs.259347 | hypothetical protein LOC283464 | LOC283464 | −2.24683 |
| Hs.259347 | hypothetical protein LOC283464 | LOC283464 | −2.17741 |
| — | hypothetical protein LOC283481 | LOC283481 | 1.49339 |
| Hs.117167 | hypothetical protein LOC283537 | LOC283537 | 1.13913 |
| Hs.561967 | hypothetical protein LOC283788 | LOC283788 | 1.16912 |
| Hs.406976 | hypothetical protein LOC283874 | LOC283874 | 1.18679 |
| — | hypothetical protein LOC285943 | LOC285943 | −1.62171 |
| Hs.558072 | hypothetical protein LOC338620 | LOC338620 | −2.30874 |
| Hs.103939 | hypothetical protein LOC339448 | LOC339448 | −1.58204 |
| Hs.103939 | hypothetical protein LOC339448 | LOC339448 | −1.35804 |
| Hs.533212 | hypothetical protein LOC340109 | LOC340109 | 3.23497 |
| Hs.450057 | hypothetical LOC344595 | LOC344595 | 1.30361 |
| Hs.351582 | similar to hypothetical testis protein from macaque | LOC352909 | 1.3257 |
| Hs.458285 | hypothetical LOC375010 /// hypothetical LOC401131 | LOC375010 /// LOC401131 | 2.00067 |
| Hs.23459 | hypothetical LOC388727 | LOC388727 | 1.85395 |
| Hs.5215 | hypothetical LOC400843 | LOC400843 | 1.27083 |
| Hs.517791 | hypothetical LOC401052 | LOC401052 | 1.60118 |
| Hs.385650 | hypothetical gene supported by BC028186 | LOC401068 | 1.22439 |
| Hs.534807 | hypothetical LOC401394 /// hypothetical LOC402578 | LOC401394 /// LOC402578 | 1.07536 |
| Hs.534807 | hypothetical LOC401394 /// hypothetical LOC402578 | LOC401394 /// LOC402578 | 1.57808 |
| Hs.512257 | hypothetical LOC401449 /// family with sequence similarity 66, member C | LOC401449 /// FAM66C /// FAM66E | 1.15272 |
| — | LOC401629 /// LOC401630 | LOC401629 /// LOC401630 | 1.72622 |
| Hs.474095 | hypothetical gene supported by AK022914; AK095211; BC016035; BC041856; BX248778 | LOC440160 | 1.24066 |
| Hs.192643 | LOC440173 | LOC440173 | 1.20596 |
| Hs.549433 | LOC440667 /// LOC440669 /// LOC440688 | LOC440667 /// LOC440669 /// LOC440688 | 1.34729 |
| Hs.474401 | hypothetical gene supported by AK026843; BX640678 | LOC441130 | −1.13484 |
| Hs.559431 | similar to RIKEN cDNA 2310016C16 | LOC493869 | −1.22366 |
| Hs.556510 | similar to RIKEN cDNA 2510006C20 gene | LOC494143 | −2.71573 |
| Hs.559276 | putative NFkB activating protein | LOC497661 | 1.26885 |
| Hs.469254 | hypothetical protein LOC51315 | LOC51315 | 1.39745 |
| Hs.469254 | hypothetical protein LOC51315 | LOC51315 | 1.52108 |
| Hs.469254 | hypothetical protein LOC51315 | LOC51315 | 1.96249 |
| Hs.549342 | hypothetical protein LOC54103 | LOC54103 | 1.16933 |
| Hs.355559 | hypothetical protein LOC550643 | LOC550643 | 2.54798 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 − NC #2) |
|---|---|---|---|
| Hs.185489 | hypothetical protein A-211C6.1 | LOC57149 | −1.90502 |
| Hs.350700 | hypothetical protein LOC90288 | LOC90288 | 1.01511 |
| Hs.351461 | hypothetical protein BC016861 /// hypothetical protein DKFZp434E2321 | LOC90557 /// DKFZp434E2321 | 2.33225 |
| Hs.444338 | prematurely terminated mRNA decay factor-like | LOC91431 | −1.04871 |
| Hs.280990 | novel 58.3 KDA protein | LOC91614 | 1.8188 |
| Hs.190394 | Hypothetical protein BC001610 | LOC91661 | −1.07787 |
| Hs.369763 | hypothetical protein LOC92558 | LOC92558 | 1.37412 |
| Hs.398111 | hypothetical protein BC015148 | LOC93081 | −1.42127 |
| Hs.152944 | loss of heterozygosity, 11, chromosomal region 2, gene A | LOH11CR2A | 1.3699 |
| Hs.180178 | LON peptidase N-terminal domain and ring finger 1 | LONRF1 | −1.85202 |
| Hs.143792 | leucine rich repeat and fibronectin type III domain containing 3 | LRFN3 | 1.44215 |
| Hs.408355 | low density lipoprotein receptor-related protein 11 | LRP11 | −1.43395 |
| Hs.128071 | leucine rich repeat containing 19 | LRRC19 | 1.61682 |
| Hs.12692 | leucine rich repeat containing 49 | LRRC49 | 1.65546 |
| Hs.471779 | leucine rich repeat (in FLII) interacting protein 1 | LRRFIP1 | 1.55611 |
| Hs.103106 | LSM2 homolog, U6 small nuclear RNA associated (S. cerevisiae) | LSM2 | −1.19716 |
| Hs.515255 | LSM4 homolog, U6 small nuclear RNA associated (S. cerevisiae) | LSM4 | −1.10515 |
| Hs.515255 | LSM4 homolog, U6 small nuclear RNA associated (S. cerevisiae) | LSM4 | −1.0212 |
| Hs.524648 | leukotriene A4 hydrolase | LTA4H | −1.22343 |
| Hs.289019 | latent transforming growth factor beta binding protein 3 | LTBP3 | 1.8186 |
| Hs.155048 | Lutheran blood group (Auberger b antigen included) | LU | 1.24443 |
| Hs.18616 | leucine zipper protein 5 | LUZP5 | −1.84564 |
| Hs.425427 | hypothetical protein FLJ20425 | LYAR | −1.61007 |
| Hs.468048 | lysocardiolipin acyltransferase | LYCAT | −2.35965 |
| Hs.158665 | Ly6/neurotoxin 1 | LYNX1 | 1.29112 |
| Hs.432395 | LY6/PLAUR domain containing 1 | LYPD1 | 1.18646 |
| Hs.125291 | Lysophospholipase-like 1 | LYPLAL1 | 1.89692 |
| Hs.136235 | LysM, putative peptidoglycan-binding, domain containing 3 | LYSMD3 | −1.1191 |
| Hs.523221 | leucine zipper, putative tumor suppressor 2 | LZTS2 | 1.23552 |
| Hs.140452 | mannose-6-phosphate receptor binding protein 1 | M6PRBP1 | −1.94943 |
| Hs.28312 | MAD2 mitotic arrest deficient-like 1 (yeast) | MAD2L1 | −2.51145 |
| Hs.567455 | MAD2 mitotic arrest deficient-like 1 (yeast) | MAD2L1 | −2.48232 |
| Hs.517617 | v-maf musculoaponeurotic fibrosarcoma oncogene homolog F (avian) | MAFF | −1.66059 |
| Hs.269528 | Mak3 homolog (S. cerevisiae) | MAK3 | −2.16189 |
| Hs.269528 | Mak3 homolog (S. cerevisiae) | MAK3 | −1.75418 |
| Hs.185055 | mal, T-cell differentiation protein-like | MALL | −1.19366 |
| Hs.444627 | mastermind-like 3 (Drosophila) | MAML3 | 1.03755 |
| Hs.188464 | mannosidase, alpha, class 2B, member 2 | MAN2B2 | 1.19584 |
| Hs.368281 | Microtubule-associated protein 2 | MAP2 | 3.27489 |
| Hs.433332 | Mitogen-activated protein kinase kinase 1 interacting protein 1 | MAP2K1IP1 | 1.70622 |
| Hs.211601 | mitogen-activated protein kinase kinase kinase 12 | MAP3K12 | 1.21363 |
| Hs.211601 | mitogen-activated protein kinase kinase kinase 12 | MAP3K12 | 1.75107 |
| Hs.145605 | mitogen-activated protein kinase kinase kinase 2 | MAP3K2 | −1.30602 |
| Hs.145605 | Mitogen-activated protein kinase kinase kinase 2 | MAP3K2 | −1.24925 |
| Hs.269775 | mitogen-activated protein kinase kinase kinase 7 interacting protein 2 | MAP3K7IP2 | −1.58644 |
| Hs.269775 | mitogen-activated protein kinase kinase kinase 7 interacting protein 2 | MAP3K7IP2 | −1.36177 |
| Hs.517949 | microtubule-associated protein 4 | MAP4 | 1.34906 |
| Hs.431550 | mitogen-activated protein kinase kinase kinase kinase 4 | MAP4K4 | 1.10562 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.431550 | mitogen-activated protein kinase kinase kinase kinase 4 | MAP4K4 | 1.21588 |
| Hs.485233 | mitogen-activated protein kinase 14 | MAPK14 | −1.17889 |
| Hs.513661 | mitogen activated protein kinase binding protein 1 | MAPKBP1 | 1.11226 |
| Hs.515860 | microtubule-associated protein, RP/EB family, member 3 | MAPRE3 | 1.64105 |
| Hs.515860 | microtubule-associated protein, RP/EB family, member 3 | MAPRE3 | 1.7594 |
| Hs.519909 | myristoylated alanine-rich protein kinase C substrate | MARCKS | −1.59242 |
| Hs.209614 | MARVEL domain containing 1 | MARVELD1 | −1.30457 |
| Hs.513706 | MARVEL domain containing 3 | MARVELD3 | 1.08477 |
| Hs.276905 | microtubule associated serine/threonine kinase-like | MASTL | −2.62644 |
| Hs.189445 | matrilin 2 | MATN2 | −1.2392 |
| Hs.198158 | MAWD binding protein | MAWBP | 2.064 |
| Hs.517586 | myoglobin | MB | 1.82459 |
| Hs.458312 | methyl-CpG binding domain protein 5 | MBD5 | 1.24077 |
| Hs.478000 | muscleblind-like (Drosophila) | MBNL1 | −1.92316 |
| Hs.478000 | muscleblind-like (Drosophila) | MBNL1 | −1.41977 |
| Hs.478000 | muscleblind-like (Drosophila) | MBNL1 | −1.28311 |
| Hs.478000 | Muscleblind-like (Drosophila) | MBNL1 | 1.17164 |
| Hs.511397 | melanoma cell adhesion molecule /// melanoma cell adhesion molecule | MCAM | −2.21725 |
| Hs.483104 | mutated in colorectal cancers | MCC | 1.6236 |
| Hs.167531 | methylcrotonoyl-Coenzyme A carboxylase 2 (beta) | MCCC2 | −1.16197 |
| Hs.170422 | MCF.2 cell line derived transforming sequence-like | MCF2L | 1.07163 |
| Hs.170422 | MCF.2 cell line derived transforming sequence-like | MCF2L | 1.21451 |
| Hs.532826 | myeloid cell leukemia sequence 1 (BCL2-related) | MCL1 | −2.38298 |
| Hs.198363 | MCM10 minichromosome maintenance deficient 10 (S. cerevisiae) | MCM10 | −3.67476 |
| Hs.198363 | MCM10 minichromosome maintenance deficient 10 (S. cerevisiae) | MCM10 | −3.14371 |
| Hs.198363 | MCM10 minichromosome maintenance deficient 10 (S. cerevisiae) | MCM10 | −2.6166 |
| Hs.477481 | MCM2 minichromosome maintenance deficient 2, mitotin (S. cerevisiae) | MCM2 | −1.64223 |
| Hs.179565 | MCM3 minichromosome maintenance deficient 3 (S. cerevisiae) | MCM3 | −1.45867 |
| Hs.460184 | MCM4 minichromosome maintenance deficient 4 (S. cerevisiae) | MCM4 | −2.80012 |
| Hs.460184 | MCM4 minichromosome maintenance deficient 4 (S. cerevisiae) | MCM4 | −2.40207 |
| Hs.460184 | MCM4 minichromosome maintenance deficient 4 (S. cerevisiae) | MCM4 | −2.0644 |
| Hs.460184 | MCM4 minichromosome maintenance deficient 4 (S. cerevisiae) | MCM4 | −1.90396 |
| Hs.517582 | MCM5 minichromosome maintenance deficient 5, cell division cycle 46 (S. cerevisiae) | MCM5 | −2.28141 |
| Hs.517582 | MCM5 minichromosome maintenance deficient 5, cell division cycle 46 (S. cerevisiae) | MCM5 | −1.64733 |
| Hs.444118 | MCM6 minichromosome maintenance deficient 6 (MIS5 homolog, S. pombe) (S. cerevisae) | MCM6 | −1.3262 |
| Hs.438720 | MCM7 minichromosome maintenance deficient 7 (S. cerevisiae) | MCM7 | −2.11744 |
| Hs.438720 | MCM7 minichromosome maintenance deficient 7 (S. cerevisiae) | MCM7 | −1.98814 |
| Hs.437582 | MCM8 minichromosome maintenance deficient 8 (S. cerevisiae) | MCM8 | −1.58228 |
| Hs.535239 | mucolipin 3 | MCOLN3 | 1.33364 |
| Hs.427236 | MyoD family inhibitor domain containing /// MyoD family inhibitor domain contain | MDFIC | −2.25427 |
| Hs.427236 | MyoD family inhibitor domain containing | MDFIC | −1.44874 |
| Hs.427236 | MyoD family inhibitor domain containing | MDFIC | 1.77906 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.369849 | Mdm2, transformed 3T3 cell double minute 2, p53 binding protein (mouse) | MDM2 | 1.14346 |
| Hs.368866 | hypothetical protein MDS025 | MDS025 | 1.15319 |
| Hs.233119 | malic enzyme 2, NAD(+)-dependent, mitochondrial | ME2 | −1.34462 |
| Hs.233119 | malic enzyme 2, NAD(+)-dependent, mitochondrial | ME2 | −1.17652 |
| Hs.33032 | Mediator of RNA polymerase II transcription, subunit 28 homolog (yeast) | MED28 | −1.06214 |
| Hs.268675 | MADS box transcription enhancer factor 2, polypeptide A (myocyte enhancer factor | MEF2A | 1.71546 |
| Hs.184339 | maternal embryonic leucine zipper kinase | MELK | −3.00861 |
| Hs.433213 | methyltransferase like 2 /// hypothetical protein FLJ12760 | METTL2 /// FLJ12760 | −1.08206 |
| Hs.432818 | Microfibrillar-associated protein 3 | MFAP3 | −1.33928 |
| Hs.7678 | major facilitator superfamily domain containing 3 | MFSD3 | 1.40961 |
| Hs.130692 | Hypothetical protein MGC10946 | MGC10946 | −1.08651 |
| Hs.425178 | hypothetical protein MGC11102 | MGC11102 | −1.22482 |
| Hs.546428 | hypothetical protein MGC11266 | MGC11266 | −1.6299 |
| Hs.99196 | hypothetical protein MGC11324 /// hypothetical protein MGC11324 | MGC11324 | −2.27527 |
| Hs.460617 | hypothetical protein MGC13024 | MGC13024 | 1.79446 |
| Hs.347408 | Hypothetical protein MGC13102 | MGC13102 | 1.17064 |
| Hs.256301 | multidrug resistance-related protein /// multidrug resistance-related protein | MGC13170 | −1.23603 |
| Hs.533747 | hypothetical protein MGC13183 /// hypothetical protein MGC13183 | MGC13183 | −1.58484 |
| Hs.368399 | FERM domain containing 5 | MGC14161 | 1.72705 |
| Hs.558588 | similar to RIKEN cDNA 1200014N16 gene | MGC14289 | −1.89713 |
| Hs.30323 | hypothetical protein MGC15634 | MGC15634 | −1.62444 |
| Hs.373941 /// Hs.533723 | Hypothetical gene MGC16733 similar to CG12113 | MGC16733 | 1.49468 |
| Hs.380228 | hypothetical protein MGC17839 | MGC17839 | 1.29437 |
| Hs.257664 | hypothetical protein MGC17943 | MGC17943 | −1.34111 |
| Hs.314261 | Hypothetical protein MGC21644 | MGC21644 | 1.2091 |
| Hs.347524 | hypothetical protein MGC24665 | MGC24665 | −1.9388 |
| Hs.4253 | hypothetical protein MGC2574 | MGC2574 | −1.70946 |
| Hs.48343 | hypothetical protein MGC26963 | MGC26963 | −3.61698 |
| Hs.356467 | Hypothetical protein MGC2747 | MGC2747 | 1.34962 |
| Hs.483796 | hypothetical protein MGC3265 | MGC3265 | 1.8559 |
| Hs.40808 | hypothetical protein MGC33926 | MGC33926 | 1.14901 |
| Hs.413457 /// Hs.559182 | Chromosome 11 open reading frame 35 /// CDNA clone IMAGE: 4837775 | MGC35138 | 1.95509 |
| Hs.351133 | hypothetical protein MGC35558 | MGC35558 | 1.17753 |
| Hs.374414 | hypothetical protein MGC39606 | MGC39606 | 1.2437 |
| Hs.6920 | Hypothetical protein MGC45562 | MGC45562 | 1.56375 |
| Hs.6920 | hypothetical protein MGC45562 | MGC45562 | 2.51953 |
| Hs.441708 | leucine-rich repeat kinase 1 | MGC45866 | −1.20743 |
| Hs.345588 | hypothetical protein MGC45871 | MGC45871 | −1.5647 |
| Hs.345588 | hypothetical protein MGC45871 | MGC45871 | −1.35041 |
| Hs.560915 | hypothetical protein MGC4677 /// hypothetical LOC541471 | MGC4677 /// LOC541471 | −1.56693 |
| — | hypothetical protein MGC5370 | MGC5370 | 1.06303 |
| Hs.13662 | hypothetical protein MGC5508 | MGC5508 | −2.29289 |
| Hs.507584 | hypothetical protein MGC9850 | MGC9850 | 1.28469 |
| Hs.526494 | mahogunin, ring finger 1 | MGRN1 | 1.12992 |
| Hs.501928 | microtubule associated monoxygenase, calponin and LIM domain containing 2 | MICAL2 | 2.27797 |
| Hs.80976 | antigen identified by monoclonal antibody Ki-67 | MKI67 | −2.89189 |
| Hs.80976 | antigen identified by monoclonal antibody Ki-67 | MKI67 | −2.41542 |
| Hs.80976 | antigen identified by monoclonal antibody Ki-67 | MKI67 | −2.12196 |
| Hs.80976 | antigen identified by monoclonal antibody Ki-67 | MKI67 | −1.7532 |
| Hs.481307 | MLF1 interacting protein | MLF1IP | −3.50592 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.493585 | myeloid/lymphoid or mixed-lineage leukemia (trithorax homolog, Drosophila) | MLLT3 | −1.31182 |
| Hs.487188 | Myeloid/lymphoid or mixed-lineage leukemia (trithorax homolog, Drosophila) | MLLT4 | 1.94359 |
| Hs.533499 | Membrane associated DNA binding protein | MNAB | 1.68856 |
| Hs.253552 | MAX binding protein | MNT | 1.32128 |
| Hs.196437 | MOB1, Mps One Binder kinase activator-like 1B (yeast) | MOBK1B | −3.20419 |
| Hs.196437 | MOB1, Mps One Binder kinase activator-like 1B (yeast) | MOBK1B | −2.19267 |
| Hs.196437 | MOB1, Mps One Binder kinase activator-like 1B (yeast) | MOBK1B | −2.06639 |
| Hs.196437 | MOB1, Mps One Binder kinase activator-like 1B (yeast) | MOBK1B | −1.35494 |
| Hs.437153 | MondoA | MONDOA | 1.03873 |
| Hs.521086 | motile sperm domain containing 3 | MOSPD3 | 1.15951 |
| Hs.240 | M-phase phosphoprotein 1 | MPHOSPH1 | −1.04733 |
| Hs.344400 | M-phase phosphoprotein 6 | MPHOSPH6 | −1.6802 |
| Hs.507175 | M-phase phosphoprotein 9 | MPHOSPH9 | −1.33309 |
| Hs.507175 | M-phase phosphoprotein 9 | MPHOSPH9 | −1.27568 |
| Hs.493919 | myelin protein zero-like 1 | MPZL1 | −1.58706 |
| Hs.493919 | myelin protein zero-like 1 | MPZL1 | −1.21636 |
| Hs.493919 | myelin protein zero-like 1 | MPZL1 | −1.20361 |
| Hs.101840 | major histocompatibility complex, class I-related | MR1 | 1.13452 |
| Hs.279652 | mitochondrial ribosomal protein L4 | MRPL4 | −1.2165 |
| Hs.75859 | mitochondrial ribosomal protein L49 | MRPL49 | −1.25511 |
| Hs.411125 | mitochondrial ribosomal protein S12 | MRPS12 | −1.24674 |
| Hs.533291 | MRS2-like, magnesium homeostasis factor (S. cerevisiae) | MRS2L | 1.05364 |
| Hs.156519 | mutS homolog 2, colon cancer, nonpolyposis type 1 (E. coli) | MSH2 | −1.27183 |
| Hs.134470 | Musashi homolog 2 (Drosophila) | MSI2 | 1.34406 |
| Hs.87752 | moesin | MSN | −1.35017 |
| Hs.339024 | methionine sulfoxide reductase B3 | MSRB3 | −1.05195 |
| Hs.89404 | msh homeo box homolog 2 (Drosophila) | MSX2 | 1.11101 |
| Hs.513626 | metallothionein 1F (functional) | MT1F | 1.18931 |
| Hs.513626 | metallothionein 1F (functional) | MT1F | 1.49789 |
| Hs.193268 | methylthioadenosine phosphorylase | MTAP | −1.25422 |
| Hs.502773 | membrane-type 1 matrix metalloproteinase cytoplasmic tail binding protein-1 | MTCBP-1 | −3.68512 |
| Hs.502773 | membrane-type 1 matrix metalloproteinase cytoplasmic tail binding protein-1 | MTCBP-1 | −2.92784 |
| Hs.269944 | mitochondrial carrier homolog 2 (C. elegans) | MTCH2 | 1.12443 |
| Hs.377155 | metadherin | MTDH | −1.96269 |
| Hs.377155 | metadherin | MTDH | −1.93929 |
| Hs.31016 | metal response element binding transcription factor 2 | MTF2 | −1.04464 |
| Hs.435974 | methylenetetrahydrofolate dehydrogenase (NADP+ dependent) 1 | MTHFD1 | −1.69882 |
| Hs.479954 | methylenetetrahydrofolate dehydrogenase (NADP+ dependent) 2-like | MTHFD2L | −1.4306 |
| Hs.507536 | myotubularin related protein 6 | MTMR6 | −1.77082 |
| Hs.498187 | 5-methyltetrahydrofolate-homocysteine methyltransferase | MTR | −1.323 |
| Hs.485527 | methylmalonyl Coenzyme A mutase | MUT | 1.10356 |
| Hs.501023 | MAX interactor 1 | MXI1 | 1.95993 |
| Hs.380906 | myeloid-associated differentiation marker | MYADM | −1.43997 |
| Hs.380906 | myeloid-associated differentiation marker | MYADM | −1.38718 |
| Hs.445898 | v-myb myeloblastosis viral oncogene homolog (avian)-like 1 | MYBL1 | −3.26889 |
| Hs.179718 | v-myb myeloblastosis viral oncogene homolog (avian)-like 2 | MYBL2 | −1.32601 |
| Hs.370040 | c-myc binding protein | MYCBP | −3.2538 |
| Hs.370040 | c-myc binding protein | MYCBP | −1.34931 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.82116 | myeloid differentiation primary response gene (88) | MYD88 | −1.09524 |
| Hs.460109 | Myosin, heavy polypeptide 11, smooth muscle | MYH11 | −1.90836 |
| Hs.504687 | myosin, light polypeptide 9, regulatory | MYL9 | 1.26146 |
| Hs.481720 | myosin X | MYO10 | −1.67665 |
| Hs.481720 | Myosin X | MYO10 | −1.15977 |
| Hs.462777 | myosin ID | MYO1D | 1.68759 |
| Hs.21213 | myosin VA (heavy polypeptide 12, myoxin) | MYO5A | 1.45005 |
| Hs.21213 | myosin VA (heavy polypeptide 12, myoxin) | MYO5A | 1.62243 |
| Hs.503137 | NAD synthetase 1 | NADSYN1 | 1.44189 |
| Hs.503137 | NAD synthetase 1 | NADSYN1 | 1.49212 |
| Hs.50727 | N-acetylglucosaminidase, alpha- (Sanfilippo disease IIIB) | NAGLU | 1.17799 |
| Hs.104305 | NACHT, leucine rich repeat and PYD (pyrin domain) containing 1 | NALP1 | 1.82885 |
| Hs.351851 | nanos homolog 1 (Drosophila) | NANOS1 | 2.72079 |
| Hs.524599 | nucleosome assembly protein 1-like 1 | NAP1L1 | −1.66365 |
| Hs.524599 | nucleosome assembly protein 1-like 1 | NAP1L1 | −1.49322 |
| Hs.524599 | 60S ribosomal protein L6 (RPL6A) | NAP1L1 | −1.12756 |
| Hs.66180 | nucleosome assembly protein 1-like 2 | NAP1L2 | 1.1834 |
| Hs.21365 | nucleosome assembly protein 1-like 3 | NAP1L3 | 1.42937 |
| Hs.516471 | Nck-associated protein 5 | NAP5 | 1.57263 |
| Hs.324271 | N-acyl-phosphatidylethanolamine-hydrolyzing phospholipase D | NAPE-PLD | −1.63822 |
| Hs.324271 | N-acyl-phosphatidylethanolamine-hydrolyzing phospholipase D | NAPE-PLD | −1.59187 |
| Hs.324271 | N-acyl-phosphatidylethanolamine-hydrolyzing phospholipase D | NAPE-PLD | −1.52464 |
| Hs.555985 | NMDA receptor regulated 1 | NARG1 | −1.17163 |
| Hs.200943 | NMDA receptor regulated 2 | NARG2 | −1.66609 |
| Hs.200943 | NMDA receptor regulated 2 | NARG2 | −1.4174 |
| Hs.200943 | NMDA receptor regulated 2 | NARG2 | −1.2328 |
| Hs.319334 | nuclear autoantigenic sperm protein (histone-binding) | NASP | −1.02505 |
| Hs.491172 | neurobeachin | NBEA | 1.65917 |
| Hs.491172 | neurobeachin | NBEA | 1.92913 |
| Hs.412293 | nuclear receptor coactivator 1 | NCOA1 | 1.21726 |
| Hs.322430 | NDRG family member 4 | NDRG4 | 2.21026 |
| Hs.502528 | NADH dehydrogenase (ubiquinone) Fe—S protein 3, 30 kDa (NADH-coenzyme Q reductase | NDUFS3 | −1.31414 |
| Hs.555882 | nebulin | NEB | 4.13713 |
| Hs.437385 | NECAP endocytosis associated 2 | NECAP2 | −1.60539 |
| Hs.1565 | neural precursor cell expressed, developmentally down-regulated 4 | NEDD4 | −2.34889 |
| Hs.521461 | neurofilament, light polypeptide 68 kDa | NEFL | 1.63415 |
| Hs.521461 | Neurofilament, light polypeptide 68 kDa | NEFL | 1.63614 |
| Hs.521461 | neurofilament, light polypeptide 68 kDa | NEFL | 1.73377 |
| Hs.405467 | nei endonuclease VIII-like 3 (E. coli) | NEIL3 | −2.42887 |
| Hs.153704 | NIMA (never in mitosis gene a)-related kinase 2 /// NIMA (never in mitosis gene | NEK2 | −2.69612 |
| Hs.153704 | NIMA (never in mitosis gene a)-related kinase 2 | NEK2 | −2.33339 |
| Hs.129550 | NIMA (never in mitosis gene a)-related kinase 4 | NEK4 | −1.31387 |
| Hs.197071 | NIMA (never in mitosis gene a)-related kinase 6 | NEK6 | −2.53692 |
| Hs.197071 | NIMA (never in mitosis gene a)-related kinase 6 | NEK6 | −1.8551 |
| Hs.24119 | NIMA (never in mitosis gene a)-related kinase 7 | NEK7 | 1.53595 |
| Hs.455336 | nasal embryonic LHRH factor | NELF | 1.48971 |
| Hs.370359 | Nuclear factor I/B | NFIB | −1.06797 |
| Hs.73090 | nuclear factor of kappa light polypeptide gene enhancer in B-cells 2 (p49/p100) | NFKB2 | −1.93871 |
| Hs.448588 | nerve growth factor receptor (TNFRSF16) associated protein 1 | NGFRAP1 | −1.52893 |
| Hs.369924 | NHL repeat containing 2 | NHLRC2 | −1.39749 |
| Hs.494457 | ninjurin 1 | NINJ1 | 1.05039 |
| Hs.370367 | non imprinted in Prader-Willi/Angelman syndrome 2 | NIPA2 | −1.36816 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.567289 | nipsnap homolog 3B (*C. elegans*) | NIPSNAP3B | 1.26388 |
| Hs.567289 | nipsnap homolog 3B (*C. elegans*) | NIPSNAP3B | 2.15883 |
| Hs.54473 | NK2 transcription factor related, locus 5 (*Drosophila*) | NKX2-5 | 1.60664 |
| Hs.208759 | nemo like kinase | NLK | 1.22495 |
| Hs.208759 | nemo like kinase | NLK | 1.23634 |
| Hs.112242 | normal mucosa of esophagus specific 1 | NMES1 | −3.76104 |
| Hs.418367 | neuromedin U | NMU | −1.35758 |
| Hs.503911 | nicotinamide N-methyltransferase | NNMT | −2.5314 |
| Hs.503911 | nicotinamide N-methyltransferase | NNMT | −2.32083 |
| Hs.376064 | nucleolar protein 5A (56 kDa with KKE/D repeat) | NOL5A | −1.26261 |
| Hs.69851 | nucleolar protein family A, member 1 (H/ACA small nucleolar RNPs) | NOLA1 | −1.33268 |
| Hs.523238 | nucleolar and coiled-body phosphoprotein 1 | NOLC1 | −1.13473 |
| Hs.458607 | likely ortholog of mouse neighbor of Punc E11 | NOPE | 1.01313 |
| Hs.189780 | nitric oxide synthase trafficker | NOSTRIN | −1.25711 |
| Hs.132370 | NADPH oxidase 1 | NOX1 | −1.8453 |
| Hs.75514 | nucleoside phosphorylase | NP | −1.87778 |
| Hs.237028 | natriuretic peptide receptor C/guanylate cyclase C | NPR3 | −1.67883 |
| Hs.91622 | neuronal pentraxin receptor | NPTXR | 1.65391 |
| Hs.37125 | neuropeptide Y receptor Y2 | NPY2R | 2.87693 |
| Hs.521926 | nuclear receptor binding protein 2 | NRBP2 | 1.53575 |
| Hs.453951 | neuregulin 1 | NRG1 | 1.77579 |
| Hs.471200 | Neuropilin 2 | NRP2 | −2.51084 |
| Hs.363558 | HCV NS3-transactivated protein 2 | NS3TP2 | 1.62867 |
| Hs.372000 | neutral sphingomyelinase (N-SMase) activation associated factor | NSMAF | −1.01183 |
| Hs.153952 | 5'-nucleotidase, ecto (CD73) | NT5E | −2.25153 |
| Hs.213061 | Nuclear casein kinase and cyclin-dependent kinase substrate 1 | NUCKS | −1.83593 |
| Hs.213061 | Nuclear casein kinase and cyclin-dependent kinase substrate 1 | NUCKS | −1.41169 |
| Hs.213061 | Nuclear casein kinase and cyclin-dependent kinase substrate 1 | NUCKS | −1.25709 |
| Hs.213061 | nuclear casein kinase and cyclin-dependent kinase substrate 1 | NUCKS1 | −1.43043 |
| Hs.203961 | nudix (nucleoside diphosphate linked moiety X)-type motif 19 | NUDT19 | −1.85138 |
| Hs.188882 | Nudix (nucleoside diphosphate linked moiety X)-type motif 3 | NUDT3 | −1.45819 |
| Hs.506325 | nudix (nucleoside diphosphate linked moiety X)-type motif 4 | NUDT4 | −1.22772 |
| Hs.356699 | nudix (nucleoside diphosphate linked moiety X)-type motif 4 | NUDT4 /// NUDT4P1 | −2.53923 |
| Hs.356699 | nudix (nucleoside diphosphate linked moiety X)-type motif 4 | NUDT4 /// NUDT4P1 | −1.60875 |
| Hs.525006 | nuclear fragile X mental retardation protein interacting protein 1 | NUFIP1 | −1.34278 |
| Hs.525006 | nuclear fragile X mental retardation protein interacting protein 1 | NUFIP1 | −1.27415 |
| Hs.524574 | nucleoporin 107 kDa | NUP107 | −1.26355 |
| Hs.372099 | nucleoporin 160 kDa | NUP160 | −1.63572 |
| Hs.444276 | nucleoporin 37 kDa | NUP37 | −1.28191 |
| Hs.475103 | nucleoporin 50 kDa | NUP50 | −1.45184 |
| Hs.475103 | nucleoporin 50 kDa | NUP50 | −1.39414 |
| Hs.430435 | nucleoporin 54 kDa | NUP54 | −1.59421 |
| Hs.511093 | nucleolar and spindle associated protein 1 | NUSAP1 | −2.3605 |
| Hs.511093 | nucleolar and spindle associated protein 1 | NUSAP1 | −2.33333 |
| Hs.25010 | nuclear transport factor 2-like export factor 2 | NXT2 | −2.04794 |
| Hs.25010 | nuclear transport factor 2-like export factor 2 | NXT2 | −1.87275 |
| Hs.404088 | sarcoma antigen NY-SAR-48 | NY-SAR-48 | −1.26639 |
| Hs.467634 | O-acyltransferase (membrane bound) domain containing 2 | OACT2 | −1.4826 |
| Hs.549512 | Opa interacting protein 5 | OIP5 | −3.00223 |
| Hs.357004 | olfactomedin-like 2A | OLFML2A | 1.49582 |
| Hs.478708 | optic atrophy 1 (autosomal dominant) | OPA1 | −1.17613 |
| Hs.478708 | optic atrophy 1 (autosomal dominant) | OPA1 | −1.10312 |
| Hs.409081 | opsin 3 (encephalopsin, panopsin) | OPN3 | −1.32804 |

TABLE 1-continued

Genes with increased (positive values) or decreased (negative values) expression
following transfection of human cancer cells with pre-miR hsa-miR-124a.

| UniGene ID | Gene Title | Gene Symbol | Log2 (mir124 − NC #2) |
|---|---|---|---|
| Hs.522087 | opioid receptor, sigma 1 | OPRS1 | −1.90353 |
| Hs.522087 | opioid receptor, sigma 1 | OPRS1 | −1.62272 |
| Hs.17908 | origin recognition complex, subunit 1-like (yeast) | ORC1L | −1.60903 |
| Hs.49760 | origin recognition complex, subunit 6 homolog-like (yeast) | ORC6L | −2.38188 |
| Hs.502688 | oxysterol binding protein | OSBP | −1.10455 |
| Hs.520259 | oxysterol binding protein-like 3 | OSBPL3 | −1.52275 |
| Hs.520259 | oxysterol binding protein-like 3 | OSBPL3 | −1.14884 |
| Hs.270851 | OTU domain containing 4 | OTUD4 | −1.59582 |
| Hs.30532 | OTU domain containing 6B | OTUD6B | −2.29222 |
| Hs.524331 | ovostatin 2 | OVOS2 | −1.68574 |
| Hs.148778 | oxidation resistance 1 | OXR1 | 1.3573 |
| Hs.148778 | oxidation resistance 1 | OXR1 | 1.41333 |
| Hs.475970 | oxidative-stress responsive 1 | OXSR1 | −1.4717 |
| Hs.321709 | purinergic receptor P2X, ligand-gated ion channel, 4 | P2RX4 | 1.34502 |
| Hs.500047 | procollagen-proline, 2-oxoglutarate 4-dioxygenase (proline 4-hydroxylase), alpha | P4HA1 | −2.25798 |
| Hs.118964 | GATA zinc finger domain containing 2A | p66alpha | −1.18512 |
| Hs.525626 | phosphofurin acidic cluster sorting protein 2 | PACS2 | 1.41153 |
| Hs.525626 | phosphofurin acidic cluster sorting protein 2 | PACS2 | 1.99778 |
| Hs.435714 | p21/Cdc42/Rac1-activated kinase 1 (STE20 homolog, yeast) | PAK1 | 1.78254 |
| Hs.310231 | PAK1 interacting protein 1 | PAK1IP1 | −1.49793 |
| Hs.465933 | pantothenate kinase 1 | PANK1 | 1.5753 |
| Hs.253726 | poly(A) polymerase alpha | PAPOLA | 1.49923 |
| Hs.524491 | 3'-phosphoadenosine 5'-phosphosulfate synthase 2 | PAPSS2 | −4.30952 |
| Hs.524491 | 3'-phosphoadenosine 5'-phosphosulfate synthase 2 | PAPSS2 | −2.91296 |
| Hs.147229 | progestin and adipoQ receptor family member V | PAQR5 | −1.38694 |
| Hs.391828 | par-6 partitioning defective 6 homolog beta (*C. elegans*) | PARD6B | 1.31316 |
| Hs.504538 | poly (ADP-ribose) polymerase family, member 11 | PARP11 | 1.27914 |
| Hs.409412 | poly (ADP-ribose) polymerase family, member 2 | PARP2 | −1.66216 |
| Hs.409412 | poly (ADP-ribose) polymerase family, member 2 | PARP2 | −1.28179 |
| Hs.409412 | poly (ADP-ribose) polymerase family, member 2 | PARP2 | −1.26004 |
| Hs.436319 | parvin, alpha | PARVA | −1.20289 |
| Hs.104741 | PDZ binding kinase | PBK | −3.13144 |
| Hs.493096 | Pre-B-cell leukemia transcription factor 1 | PBX1 | 1.47769 |
| Hs.533055 | p300/CBP-associated factor | PCAF | 2.20792 |
| Hs.199343 | protocadherin alpha 9 /// protocadherin alpha subfamily C, 2 /// protocadherin a | PCDHA9 /// PCDHAC2 /// PCDHAC1 /// PCDHA13 /// PCDHA12 /// PCDHA11 /// PCDHA10 / | 1.39255 |
| Hs.199343 | protocadherin alpha 9 /// protocadherin alpha subfamily C, 2 /// protocadherin a | PCDHA9 /// PCDHAC2 /// PCDHAC1 /// PCDHA13 /// PCDHA12 /// PCDHA11 /// PCDHA10 / | 1.42632 |
| Hs.500512 | polycomb group ring finger 5 | PCGF5 | −1.49539 |
| Hs.500512 | polycomb group ring finger 5 | PCGF5 | −1.46584 |
| Hs.500512 | polycomb group ring finger 5 | PCGF5 | −1.38566 |
| Hs.308480 | protein-L-isoaspartate (D-aspartate) O-methyltransferase domain containing 1 | PCMTD1 | 1.08009 |
| Hs.308480 | protein-L-isoaspartate (D-aspartate) O-methyltransferase domain containing 1 | PCMTD1 | 1.22917 |
| Hs.362817 | pericentrin 1 | PCNT1 | −1.42821 |
| Hs.370605 | pecanex-like 2 (*Drosophila*) | PCNXL2 | 1.45518 |

TABLE 1-continued

Genes with increased (positive values) or decreased (negative values) expression
following transfection of human cancer cells with pre-miR hsa-miR-124a.

| UniGene ID | Gene Title | Gene Symbol | Log2 (mir124 - NC #2) |
|---|---|---|---|
| Hs.370605 | pecanex-like 2 (Drosophila) | PCNXL2 | 1.52687 |
| Hs.370605 | Pecanex-like 2 (Drosophila) | PCNXL2 | 1.68659 |
| Hs.8944 | procollagen C-endopeptidase enhancer 2 | PCOLCE2 | −2.65874 |
| Hs.522640 | proprotein convertase subtilisin/kexin type 1 inhibitor | PCSK1N | 1.85419 |
| Hs.368542 | proprotein convertase subtilisin/kexin type 5 | PCSK5 | 1.01193 |
| Hs.368542 | proprotein convertase subtilisin/kexin type 5 | PCSK5 | 1.05504 |
| Hs.368542 | Proprotein convertase subtilisin/kexin type 5 | PCSK5 | 1.65711 |
| Hs.478150 | programmed cell death 10 | PDCD10 | −2.03829 |
| Hs.352298 | platelet derived growth factor D | PDGFD | 1.29642 |
| Hs.458573 | platelet-derived growth factor receptor-like | PDGFRL | 1.46289 |
| Hs.468801 | PDLIM1 interacting kinase 1 like | PDIK1L | 1.19335 |
| Hs.470633 | pyruvate dehydrogenase kinase, isoenzyme 1 | PDK1 | 1.61172 |
| Hs.8364 | pyruvate dehydrogenase kinase, isoenzyme 4 | PDK4 | 1.19434 |
| Hs.480311 | PDZ and LIM domain 5 | PDLIM5 | −1.48602 |
| Hs.480311 | PDZ and LIM domain 5 /// PDZ and LIM domain 5 | PDLIM5 | −1.43123 |
| Hs.480311 | PDZ and LIM domain 5 | PDLIM5 | −1.23481 |
| Hs.480311 | PDZ and LIM domain 5 | PDLIM5 | −1.09421 |
| Hs.480311 | PDZ and LIM domain 5 | PDLIM5 | −1.00615 |
| Hs.533040 | PDZ and LIM domain 7 (enigma) | PDLIM7 | 1.55311 |
| Hs.533040 | PDZ and LIM domain 7 (enigma) | PDLIM7 | 2.36693 |
| Hs.444751 | PDZ domain containing 1 | PDZK1 | 3.06013 |
| Hs.391481 | PDZ domain containing 6 | PDZK6 | 1.52836 |
| Hs.517216 | phosphoprotein enriched in astrocytes 15 | PEA15 | −1.6779 |
| Hs.517216 | phosphoprotein enriched in astrocytes 15 | PEA15 | −1.17028 |
| Hs.7886 | pellino homolog 1 (Drosophila) | PELI1 | 1.53945 |
| Hs.105103 | pellino homolog 2 (Drosophila) | PELI2 | 1.52135 |
| Hs.523816 | pellino homolog 3 (Drosophila) | PELI3 | 1.23966 |
| Hs.164682 | peroxisome biogenesis factor 1 | PEX1 | 1.24024 |
| Hs.507680 | phosphonoformate immuno-associated protein 5 | PFAAP5 | 1.29441 |
| Hs.282702 | 6-phosphofructo-2-kinase/fructose-2,6-biphosphatase 2 | PFKFB2 | 1.44929 |
| Hs.433180 | DNA replication complex GINS protein PSF2 | Pfs2 | −2.90308 |
| Hs.229988 | GPI deacylase | PGAP1 | 1.44515 |
| Hs.156178 | plasma glutamate carboxypeptidase | PGCP | 1.23044 |
| Hs.23363 | phosphoglucomutase 2 | PGM2 | −2.32892 |
| Hs.23363 | phosphoglucomutase 2 | PGM2 | −1.77539 |
| Hs.23363 | phosphoglucomutase 2 | PGM2 | −1.3856 |
| Hs.26612 | phosphoglucomutase 2-like 1 | PGM2L1 | 1.25726 |
| Hs.553496 | phosphoglucomutase 3 | PGM3 | −1.05073 |
| Hs.126706 | 1-aminocyclopropane-1-carboxylate synthase | PHACS | 1.50676 |
| Hs.514303 | prohibitin | PHB | −1.00059 |
| Hs.23862 | phytoceramidase, alkaline | PHCA | −1.70081 |
| Hs.23862 | phytoceramidase, alkaline | PHCA | −1.47105 |
| Hs.23862 | phytoceramidase, alkaline | PHCA | −1.3924 |
| Hs.435933 | PHD finger protein 10 | PHF10 | −1.55222 |
| Hs.159918 | PHD finger protein 14 | PHF14 | 1.2242 |
| Hs.371977 | PHD finger protein 16 | PHF16 | −1.42662 |
| Hs.460124 | PHD finger protein 19 | PHF19 | −1.56515 |
| Hs.460124 | PHD finger protein 19 | PHF19 | −1.32722 |
| Hs.304362 | PHD finger protein 20-like 1 | PHF20L1 | 1.30542 |
| Hs.502458 | PHD finger protein 21A | PHF21A | 1.25549 |
| Hs.356501 | PHD finger protein 6 | PHF6 | −1.44838 |
| Hs.154036 | pleckstrin homology-like domain, family A, member 2 | PHLDA2 | −2.7486 |
| Hs.477114 | pleckstrin homology-like domain, family B, member 2 | PHLDB2 | −1.38182 |
| Hs.558732 | pleckstrin homology-like domain, family B, member 3 | PHLDB3 | 1.33169 |
| Hs.499704 | phytanoyl-CoA hydroxylase interacting protein-like | PHYHIPL | 1.59009 |
| Hs.443733 | phosphatidylinositol 4-kinase type 2 beta | PI4K2B | −1.62981 |
| Hs.514846 | protein inhibitor of activated STAT, 2 | PIAS2 | 1.67722 |
| Hs.514846 | Protein inhibitor of activated STAT, 2 | PIAS2 | 1.76893 |

TABLE 1-continued

Genes with increased (positive values) or decreased (negative values) expression
following transfection of human cancer cells with pre-miR hsa-miR-124a.

| UniGene ID | Gene Title | Gene Symbol | Log2 (mir124 - NC #2) |
|---|---|---|---|
| Hs.137154 | phosphatidylinositol glycan, class A (paroxysmal nocturnal hemoglobinuria) | PIGA | −1.64119 |
| Hs.175343 | phosphoinositide-3-kinase, class 2, alpha polypeptide | PIK3C2A | −1.77584 |
| Hs.175343 | Phosphoinositide-3-kinase, class 2, alpha polypeptide | PIK3C2A | −1.30933 |
| Hs.175343 | Phosphoinositide-3-kinase, class 2, alpha polypeptide | PIK3C2A | −1.07223 |
| Hs.553498 | phosphoinositide-3-kinase, catalytic, alpha polypeptide | PIK3CA | −1.33909 |
| Hs.132225 | phosphoinositide-3-kinase, regulatory subunit 1 (p85 alpha) | PIK3R1 | 1.13739 |
| Hs.371344 | phosphoinositide-3-kinase, regulatory subunit 2 (p85 beta) | PIK3R2 | 1.06086 |
| Hs.170510 | phosphoinositide-3-kinase, regulatory subunit 3 (p55, gamma) | PIK3R3 | 1.48927 |
| Hs.149032 | phosphoinositide-3-kinase, regulatory subunit 4, p150 | PIK3R4 | −1.13893 |
| Hs.556578 | phosphatidylinositol 4-kinase, catalytic, alpha polypeptide | PIK4CA | 1.21523 |
| Hs.529438 | phosphatidylinositol 4-kinase, catalytic, alpha polypeptide | PIK4CA /// LOC220686 | 1.17674 |
| Hs.260603 | Phosphatidylinositol-4-phosphate 5-kinase, type II, beta | PIP5K2B | 1.14329 |
| Hs.413525 | polycystic kidney disease 1-like 2 | PKD1L2 | 1.15593 |
| Hs.181272 | polycystic kidney disease 2 (autosomal dominant) | PKD2 | 1.35233 |
| Hs.407580 | plakophilin 4 | PKP4 | 3.46089 |
| Hs.437451 | phospholipase A1 member A | PLA1A | 1.13547 |
| Hs.154104 | pleiomorphic adenoma gene-like 2 | PLAGL2 | −1.55709 |
| Hs.431173 | phospholipase C, beta 1 (phosphoinositide-specific) | PLCB1 | 1.7594 |
| Hs.202010 | phospholipase C-like 2 | PLCL2 | 1.94862 |
| Hs.202010 | phospholipase C-like 2 | PLCL2 | 2.32691 |
| Hs.128933 | phospholipase C-like 3 | PLCL3 | 1.01731 |
| Hs.292419 | Phosphatidylinositol-specific phospholipase C, X domain containing 2 | PLCXD2 | 1.61892 |
| Hs.478230 | phospholipase D1, phophatidylcholine-specific | PLD1 | 1.00323 |
| Hs.478230 | phospholipase D1, phophatidylcholine-specific | PLD1 | 1.05373 |
| Hs.498252 | phospholipase D family, member 5 | PLD5 | 1.95598 |
| Hs.7037 | pallidin homolog (mouse) | PLDN | −1.80514 |
| Hs.7037 | pallidin homolog (mouse) | PLDN | −1.18319 |
| Hs.445489 | pleckstrin homology domain containing, family B (evectins) member 1 | PLEKHB1 | 1.01316 |
| Hs.509343 | pleckstrin homology domain containing, family C (with FERM domain) member 1 | PLEKHC1 | −2.61276 |
| Hs.509343 | pleckstrin homology domain containing, family C (with FERM domain) member 1 | PLEKHC1 | −2.25718 |
| Hs.509343 | pleckstrin homology domain containing, family C (with FERM domain) member 1 | PLEKHC1 | −1.88276 |
| Hs.189781 | pleckstrin homology domain containing, family G (with RhoGef domain) member 1 | PLEKHG1 | 1.05708 |
| Hs.164162 | pleckstrin homology domain containing, family H (with MyTH4 domain) member 2 | PLEKHH2 | 2.40781 |
| Hs.514242 | pleckstrin homology domain containing, family M (with RUN domain) member 1 | PLEKHM1 | 1.30239 |
| Hs.329989 | polo-like kinase 1 (Drosophila) | PLK1 | −2.07924 |
| Hs.172052 | polo-like kinase 4 (Drosophila) | PLK4 | −2.32191 |
| Hs.172052 | polo-like kinase 4 (Drosophila) | PLK4 | −2.27272 |
| Hs.172052 | polo-like kinase 4 (Drosophila) /// polo-like kinase 4 (Drosophila) | PLK4 | −1.92856 |
| Hs.477866 | procollagen-lysine, 2-oxoglutarate 5-dioxygenase 2 | PLOD2 | −2.13748 |
| Hs.477866 | procollagen-lysine, 2-oxoglutarate 5-dioxygenase 2 | PLOD2 | −2.11609 |
| Hs.77422 | proteolipid protein 2 (colonic epithelium-enriched) | PLP2 | −1.22623 |
| Hs.477869 | phospholipid scramblase 4 | PLSCR4 | −2.80174 |
| Hs.476209 | plexin B1 | PLXNB1 | 1.62737 |
| Hs.2182 | pro-melanin-concentrating hormone | PMCH | −1.86413 |
| Hs.372031 | peripheral myelin protein 22 | PMP22 | −2.63762 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 − NC #2) |
|---|---|---|---|
| Hs.558367 | postmeiotic segregation increased 2-like 5 | PMS2L5 | 1.26411 |
| Hs.264 | patatin-like phospholipase domain containing 4 | PNPLA4 | 1.06474 |
| Hs.16426 | podocalyxin-like | PODXL | −1.32073 |
| Hs.421608 | polymerase (DNA directed), alpha | POLA | −1.32853 |
| Hs.201897 | polymerase (DNA directed), alpha 2 (70 kD subunit) | POLA2 | −1.80002 |
| Hs.279413 | polymerase (DNA directed), delta 1, catalytic subunit 125 kDa | POLD1 | −1.03211 |
| Hs.162777 | polymerase (DNA directed), epsilon 2 (p59 subunit) | POLE2 | −2.7769 |
| Hs.108112 | polymerase (DNA directed), epsilon 3 (p17 subunit) | POLE3 | −1.60352 |
| Hs.135756 | polymerase (DNA directed) kappa | POLK | −1.0252 |
| Hs.241517 | polymerase (DNA directed), theta | POLQ | −1.61821 |
| Hs.460298 | polymerase (RNA) III (DNA directed) polypeptide E (80 kD) | POLR3E | 1.55522 |
| Hs.282387 | Polymerase (RNA) III (DNA directed) polypeptide G (32 kD) | POLR3G | −2.46957 |
| Hs.530077 | paraoxonase 2 | PON2 | −1.13258 |
| Hs.331420 | phosphoribosyl pyrophosphate amidotransferase | PPAT | −1.93237 |
| Hs.331420 | phosphoribosyl pyrophosphate amidotransferase | PPAT | −1.71664 |
| Hs.530749 | protein tyrosine phosphatase, receptor type, f polypeptide (PTPRF), interacting | PPFIA1 | −1.12563 |
| Hs.517076 | protective protein for beta-galactosidase (galactosialidosis) | PPGB | 1.11581 |
| Hs.381072 | peptidylprolyl isomerase F (cyclophilin F) | PPIF | −2.05479 |
| Hs.381072 | peptidylprolyl isomerase F (cyclophilin F) | PPIF | −1.80713 |
| Hs.256639 | peptidyl prolyl isomerase H (cyclophilin H) | PPIH | −1.00601 |
| Hs.451090 | peptidylprolyl isomerase (cyclophilin)-like 5 | PPIL5 | −1.93631 |
| Hs.192233 | periplakin | PPL | 1.74529 |
| Hs.286073 | protein phosphatase 1D magnesium-dependent, delta isoform | PPM1D | 1.31417 |
| Hs.444403 | protein phosphatase 1, regulatory (inhibitor) subunit 12B | PPP1R12B | 1.36524 |
| Hs.521937 | protein phosphatase 1, regulatory (inhibitor) subunit 16A | PPP1R16A | 1.49094 |
| Hs.518155 | protein phosphatase 2 (formerly 2A), regulatory subunit B", alpha | PPP2R3A | 1.04353 |
| Hs.334868 | protein phosphatase 2, regulatory subunit B (B56), epsilon isoform | PPP2R5E | −1.31338 |
| Hs.495128 | Protein phosphatase 6, catalytic subunit | PPP6C | −1.37405 |
| Hs.366401 | protein regulator of cytokinesis 1 | PRC1 | −1.61069 |
| Hs.523302 | peroxiredoxin 3 | PRDX3 | −1.58887 |
| Hs.148105 | prickle-like 2 (Drosophila) | PRICKLE2 | 1.18704 |
| Hs.534339 | primase, polypeptide 1, 49 kDa | PRIM1 | −1.46383 |
| Hs.485640 | primase, polypeptide 2A, 58 kDa | PRIM2A | −1.50349 |
| Hs.485640 | primase, polypeptide 2A, 58 kDa | PRIM2A | −1.38518 |
| Hs.485640 | primase, polypeptide 2A, 58 kDa | PRIM2A | −1.33074 |
| Hs.433068 | protein kinase, cAMP-dependent, regulatory, type II, beta | PRKAR2B | 1.35769 |
| Hs.531704 | protein kinase C, alpha | PRKCA | 1.2181 |
| Hs.221497 | PRO0149 protein | PRO0149 | −1.03492 |
| Hs.304792 | proline synthetase co-transcribed homolog (bacterial) | PROSC | −2.37988 |
| Hs.304792 | proline synthetase co-transcribed homolog (bacterial) | PROSC | −1.92295 |
| Hs.304792 | proline synthetase co-transcribed homolog (bacterial) | PROSC | −1.65093 |
| Hs.374973 | PRP4 pre-mRNA processing factor 4 homolog (yeast) | PRPF4 | −1.69717 |
| Hs.374973 | PRP4 pre-mRNA processing factor 4 homolog (yeast) | PRPF4 | −1.60194 |
| Hs.77498 | phosphoribosyl pyrophosphate synthetase-associated protein 1 | PRPSAP1 | −1.18715 |
| Hs.534492 | proline rich 7 (synaptic) | PRR7 | 1.16679 |
| Hs.435699 | protease, serine, 3 (mesotrypsin) | PRSS3 | 1.19249 |

TABLE 1-continued

Genes with increased (positive values) or decreased (negative values) expression
following transfection of human cancer cells with pre-miR hsa-miR-124a.

| UniGene ID | Gene Title | Gene Symbol | Log2 (mir124 − NC #2) |
|---|---|---|---|
| Hs.191215 | pleckstrin homology, Sec7 and coiled-coil domains 1(cytohesin 1) | PSCD1 | 1.169 |
| Hs.360033 | DNA replication complex GINS protein PSF1 | PSF1 | −2.78898 |
| Hs.193725 | proteasome (prosome, macropain) 26S subunit, non-ATPase, 5 | PSMD5 | −1.61581 |
| Hs.413801 | proteasome (prosome, macropain) activator subunit 4 | PSME4 | −2.00632 |
| Hs.413801 | proteasome (prosome, macropain) activator subunit 4 | PSME4 | 1.61373 |
| Hs.471917 | proteasome (prosome, macropain) inhibitor subunit 1 (PI31) | PSMF1 | −1.21949 |
| Hs.172550 | polypyrimidine tract binding protein 1 | PTBP1 | −2.78375 |
| Hs.172550 | polypyrimidine tract binding protein 1 | PTBP1 | −2.65173 |
| Hs.172550 | polypyrimidine tract binding protein 1 | PTBP1 | −2.63976 |
| Hs.172550 | polypyrimidine tract binding protein 1 | PTBP1 | −2.63633 |
| Hs.172550 | polypyrimidine tract binding protein 1 | PTBP1 | −2.61287 |
| Hs.172550 | polypyrimidine tract binding protein 1 | PTBP1 | −2.48951 |
| Hs.269895 | polypyrimidine tract binding protein 2 | PTBP2 | 1.81453 |
| Hs.269895 | polypyrimidine tract binding protein 2 | PTBP2 | 2.00615 |
| Hs.494538 | patched homolog (Drosophila) | PTCH | 1.9786 |
| Hs.491322 | PTK2B protein tyrosine kinase 2 beta | PTK2B | 1.23034 |
| Hs.227777 | protein tyrosine phosphatase type IVA, member 1 | PTP4A1 | −1.88222 |
| Hs.227777 | protein tyrosine phosphatase type IVA, member 1 | PTP4A1 | −1.72964 |
| Hs.227777 | protein tyrosine phosphatase type IVA, member 1 | PTP4A1 | −1.59097 |
| Hs.227777 | protein tyrosine phosphatase type IVA, member 1 | PTP4A1 | −1.35933 |
| Hs.227777 | Protein tyrosine phosphatase type IVA, member 1 | PTP4A1 | 1.98833 |
| Hs.470477 | protein tyrosine phosphatase type IVA, member 2 | PTP4A2 | −1.26364 |
| Hs.470477 | protein tyrosine phosphatase type IVA, member 2 | PTP4A2 | −1.25613 |
| Hs.61812 | protein tyrosine phosphatase, non-receptor type 12 | PTPN12 | −2.50939 |
| Hs.63489 | protein tyrosine phosphatase, non-receptor type 6 | PTPN6 | 1.87317 |
| Hs.558433 | pituitary tumor-transforming 1 | PTTG1 | −2.20164 |
| Hs.474010 | pituitary tumor-transforming 1 interacting protein | PTTG1IP | −1.55298 |
| Hs.521097 | pituitary tumor-transforming 3 | PTTG3 | −1.58106 |
| Hs.506652 | PWP1 homolog (S. cerevisiae) | PWP1 | −1.09208 |
| Hs.332197 | peroxidasin homolog (Drosophila) | PXDN | 1.14244 |
| Hs.332197 | peroxidasin homolog (Drosophila) | PXDN | 1.29412 |
| Hs.75438 | quinoid dihydropteridine reductase | QDPR | −1.4076 |
| Hs.510324 | quaking homolog, KH domain RNA binding (mouse) | QKI | −1.11137 |
| Hs.513484 | quinolinate phosphoribosyltransferase | QPRT | 1.1253 |
| Hs.191179 | RAB11 family interacting protein 1 (class I) | RAB11FIP1 | −1.32558 |
| Hs.406788 | RAB11 family interacting protein 4 (class II) | RAB11FIP4 | 1.39055 |
| Hs.512492 | RAB15, member RAS oncogene family | RAB15 | 1.56277 |
| Hs.512492 | RAB15, member RAS oncogene family | RAB15 | 1.62729 |
| Hs.369017 | RAB2, member RAS oncogene family | RAB2 | −1.03651 |
| Hs.369017 | RAB2, member RAS oncogene family | RAB2 | −1.01457 |
| Hs.524590 | RAB21, member RAS oncogene family | RAB21 | −1.58636 |
| Hs.524590 | RAB21, member RAS oncogene family | RAB21 | −1.44147 |
| Hs.524590 | RAB21, member RAS oncogene family | RAB21 | −1.13511 |
| Hs.3797 | RAB26, member RAS oncogene family | RAB26 | 1.9821 |
| Hs.3797 | RAB26, member RAS oncogene family | RAB26 | 2.55672 |
| Hs.298651 | RAB27A, member RAS oncogene family | RAB27A | −1.60256 |
| Hs.301853 | RAB34, member RAS oncogene family | RAB34 | −2.03641 |
| Hs.301853 | RAB34, member RAS oncogene family | RAB34 | −1.96036 |
| Hs.24970 | RAB39B, member RAS oncogene family | RAB39B | 2.42681 |
| Hs.24970 | RAB39B, member RAS oncogene family | RAB39B | 2.93719 |
| Hs.25367 | RAB4B, member RAS oncogene family | RAB4B | 1.41231 |
| Hs.25367 | RAB4B, member RAS oncogene family | RAB4B | 1.55256 |

TABLE 1-continued

Genes with increased (positive values) or decreased (negative values) expression
following transfection of human cancer cells with pre-miR hsa-miR-124a.

| UniGene ID | Gene Title | Gene Symbol | Log2 (mir124 − NC #2) |
|---|---|---|---|
| Hs.25367 | RAB4B, member RAS oncogene family | RAB4B | 1.57251 |
| Hs.503222 | RAB6A, member RAS oncogene family | RAB6A | −1.91365 |
| Hs.503222 | RAB6A, member RAS oncogene family | RAB6A | −1.42256 |
| Hs.554921 | RAB6A, member RAS oncogene family /// RAB6C, member RAS oncogene family | RAB6A /// RAB6C | −1.9879 |
| Hs.5947 | RAB8A, member RAS oncogene family | RAB8A | −1.41121 |
| Hs.389733 | RAB8B, member RAS oncogene family | RAB8B | −1.4505 |
| Hs.551518 | rabaptin, RAB GTPase binding effector protein 1 | RABEP1 | 1.11893 |
| Hs.555978 | rabaptin, RAB GTPase binding effector protein 2 | RABEP2 | 1.09546 |
| Hs.446425 | RAB, member of RAS oncogene family-like 2B /// RAB, member of RAS oncogene family-like 2A | RABL2B /// RABL2A | 1.16822 |
| Hs.446425 | RAB, member of RAS oncogene family-like 2B /// RAB, member of RAS oncogene family-like 2A | RABL2B /// RABL2A | 1.72341 |
| Hs.444360 | RAB, member of RAS oncogene family-like 3 | RABL3 | −1.81614 |
| Hs.558376 | ras-related C3 botulinum toxin substrate 1 (rho family, small GTP binding protei | RAC1 | −1.28282 |
| Hs.558376 | ras-related C3 botulinum toxin substrate 1 | RAC1 | −1.1215 |
| Hs.505469 | Rac GTPase activating protein 1 | RACGAP1 | −2.95039 |
| Hs.375684 | RAD18 homolog (S. cerevisiae) | RAD18 | −1.67716 |
| Hs.81848 | RAD21 homolog (S. pombe) | RAD21 | −1.22098 |
| Hs.446554 | RAD51 homolog (RecA homolog, E. coli) (S. cerevisiae) | RAD51 | −2.27717 |
| Hs.504550 | RAD51 associated protein 1 | RAD51AP1 | −3.55496 |
| Hs.30561 | RAD54 homolog B (S. cerevisiae) | RAD54B | −1.08081 |
| Hs.292154 | recombination activating gene 1 activating protein 1 | RAG1AP1 | −1.13271 |
| Hs.431400 | retinoic acid induced 14 | RAI14 | −2.11871 |
| Hs.6906 | v-ral simian leukemia viral oncogene homolog A (ras related) | RALA | −1.57377 |
| Hs.106185 | ral guanine nucleotide dissociation stimulator | RALGDS | 1.33841 |
| Hs.106185 | ral guanine nucleotide dissociation stimulator | RALGDS | 1.86441 |
| Hs.432842 | Ral GEF with PH domain and SH3 binding motif 1 | RALGPS1 | 1.16611 |
| Hs.24763 | RAN binding protein 1 | RANBP1 | −1.53333 |
| Hs.183800 | Ran GTPase activating protein 1 | RANGAP1 | −1.70082 |
| Hs.183800 | Ran GTPase activating protein 1 | RANGAP1 | −1.58115 |
| Hs.369920 | RAP1B, member of RAS oncogene family | RAP1B | −2.23787 |
| Hs.148178 | RAP1, GTPase activating protein 1 | RAP1GA1 | 1.27096 |
| Hs.508480 | RAP2A, member of RAS oncogene family | RAP2A | −1.91799 |
| Hs.119889 | RAP2C, member of RAS oncogene family | RAP2C | −1.58749 |
| Hs.119889 | RAP2C, member of RAS oncogene family | RAP2C | −1.47988 |
| Hs.119889 | RAP2C, member of RAS oncogene family | RAP2C | −1.41492 |
| Hs.113912 | Rap guanine nucleotide exchange factor (GEF) 2 | RAPGEF2 | −1.46202 |
| Hs.558443 | RAS p21 protein activator 4 /// hypothetical protein FLJ21767 | RASA4 /// FLJ21767 | 1.5824 |
| Hs.558443 | RAS p21 protein activator 4 /// hypothetical protein FLJ21767 | RASA4 /// FLJ21767 | 3.61211 |
| Hs.129136 | RAS and EF-hand domain containing | RASEF | −2.3736 |
| Hs.125293 | RasGEF domain family, member 1A | RASGEF1A | 2.00713 |
| Hs.379970 | Ras association (RalGDS/AF-6) domain family 2 | RASSF2 | 1.94318 |
| Hs.346527 | Ras association (RalGDS/AF-6) domain family 3 | RASSF3 | −1.16186 |
| Hs.529677 | Ras association (RalGDS/AF-6) domain family 6 | RASSF6 | 1.62967 |
| Hs.269941 | Ras association (RalGDS/AF-6) domain family 8 | RASSF8 | −1.32982 |
| Hs.408528 | retinoblastoma 1 (including osteosarcoma) | RB1 | −1.20143 |
| Hs.188553 | retinoblastoma binding protein 6 | RBBP6 | 1.11464 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.434993 | Ras-associated protein Rap1 | RBJ | 1.18327 |
| Hs.207745 | retinoblastoma-like 1 (p107) | RBL1 | −2.00961 |
| Hs.11170 | RNA binding motif protein 14 | RBM14 | −1.53215 |
| Hs.116630 | RNA binding motif protein 20 | RBM20 | 1.14796 |
| Hs.470412 | RNA binding motif, single stranded interacting protein 1 | RBMS1 | −1.99679 |
| Hs.470412 | RNA binding motif, single stranded interacting protein 1 | RBMS1 | −1.59702 |
| Hs.470412 | RNA binding motif, single stranded interacting protein 1 | RBMS1 | −1.51043 |
| Hs.470412 | RNA binding motif, single stranded interacting protein 1 | RBMS1 | −1.47133 |
| Hs.263671 | radixin | RDX | 1.39089 |
| Hs.263671 | radixin | RDX | 1.80454 |
| Hs.235069 | RecQ protein-like (DNA helicase Q1-like) | RECQL | −2.28531 |
| Hs.235069 | RecQ protein-like (DNA helicase Q1-like) | RECQL | −2.07482 |
| Hs.235069 | RecQ protein-like (DNA helicase Q1-like) | RECQL | −2.03886 |
| Hs.235069 | RecQ protein-like (DNA helicase Q1-like) | RECQL | −1.87239 |
| Hs.463041 | arginine-glutamic acid dipeptide (RE) repeats | RERE | 1.30624 |
| Hs.440401 | all-trans-13,14-dihydroretinol saturase | RetSat | 1.02155 |
| Hs.440401 | all-trans-13,14-dihydroretinol saturase | RetSat | 1.25994 |
| Hs.232021 | REV3-like, catalytic subunit of DNA polymerase zeta (yeast) | REV3L | 1.37671 |
| Hs.139226 | replication factor C (activator 1) 2, 40 kDa | RFC2 | −1.48632 |
| Hs.139226 | replication factor C (activator 1) 2, 40 kDa | RFC2 | −1.4243 |
| Hs.115474 | replication factor C (activator 1) 3, 38 kDa | RFC3 | −2.31176 |
| Hs.115474 | replication factor C (activator 1) 3, 38 kDa | RFC3 | −2.01625 |
| Hs.518475 | replication factor C (activator 1) 4, 37 kDa | RFC4 | −1.99843 |
| Hs.506989 | replication factor C (activator 1) 5, 36.5 kDa | RFC5 | −2.93661 |
| Hs.506989 | replication factor C (activator 1) 5, 36.5 kDa | RFC5 | −2.69851 |
| Hs.13680 | ring finger and FYVE-like domain containing 1 | RFFL | −1.73088 |
| Hs.444899 | RFT1 homolog (S. cerevisiae) | RFT1 | −1.35848 |
| Hs.77510 | ring finger and WD repeat domain 3 | RFWD3 | −1.7061 |
| Hs.509622 | ral guanine nucleotide dissociation stimulator-like 2 | RGL2 | 1.30131 |
| Hs.501728 | ras homolog gene family, member G (rho G) | RHOG | −1.27666 |
| Hs.552455 | RAP1 interacting factor homolog (yeast) | RIF1 | −1.0823 |
| Hs.552455 | RAP1 interacting factor homolog (yeast) | RIF1 | −1.00523 |
| — | regulated in glioma | RIG | 1.09335 |
| Hs.434924 | regulating synaptic membrane exocytosis 3 | RIMS3 | 2.15065 |
| Hs.491234 | Ras-like without CAAX 1 | RIT1 | 1.46481 |
| Hs.491234 | Ras-like without CAAX 1 | RIT1 | 1.53593 |
| Hs.491234 | Ras-like without CAAX 1 | RIT1 | 1.57192 |
| Hs.491234 | Ras-like without CAAX 1 | RIT1 | 1.70037 |
| Hs.491234 | Ras-like without CAAX 1 | RIT1 | 2.22167 |
| Hs.127032 | relaxin 2 | RLN2 | 1.58052 |
| Hs.532851 | ribonuclease H2, large subunit | RNASEH2A | −1.70633 |
| Hs.518545 | ribonuclease L (2',5'-oligoisoadenylate synthetase-dependent) | RNASEL | 1.12248 |
| Hs.469199 | ring finger protein 103 | RNF103 | 1.35088 |
| Hs.44685 | ring finger protein 141 | RNF141 | −1.35539 |
| Hs.17820 | Rho-associated, coiled-coil containing protein kinase 1 | ROCK1 | −1.22899 |
| Hs.306307 | Rho-associated, coiled-coil containing protein kinase 1 | ROCK1 | −1.0587 |
| Hs.269988 | ROD1 regulator of differentiation 1 (S. pombe) | ROD1 | −1.18649 |
| Hs.469264 | ribose 5-phosphate isomerase A (ribose 5-phosphate epimerase) | RPIA | −1.78744 |

TABLE 1-continued

Genes with increased (positive values) or decreased (negative values) expression
following transfection of human cancer cells with pre-miR hsa-miR-124a.

| UniGene ID | Gene Title | Gene Symbol | Log2 (mir124 - NC #2) |
|---|---|---|---|
| Hs.558384 | ribosomal protein L19 /// ribosomal protein L19 | RPL19 | −1.30271 |
| Hs.380933 | ribosomal protein L22-like 1 | RPL22L1 | −2.32985 |
| Hs.356371 | ribosomal protein L28 | RPL28 | −1.05916 |
| Hs.478582 | ribosomal protein L39-like | RPL39L | −1.07522 |
| Hs.518244 | ribophorin I | RPN1 | −2.13441 |
| Hs.408073 | Ribosomal protein S6 | RPS6 | −1.78218 |
| Hs.148767 | RCD1 required for cell differentiation1 homolog (S. pombe) | RQCD1 | −1.50748 |
| Hs.532461 | Ras-related GTP binding C | RRAGC | 1.22188 |
| Hs.515536 | related RAS viral (r-ras) oncogene homolog | RRAS | −1.08608 |
| Hs.502004 | related RAS viral (r-ras) oncogene homolog 2 | RRAS2 | −3.41426 |
| Hs.502004 | related RAS viral (r-ras) oncogene homolog 2 | RRAS2 | −2.95738 |
| Hs.472213 | Ribosome binding protein 1 homolog 180 kDa (dog) | RRBP1 | −1.64308 |
| Hs.472213 | ribosome binding protein 1 homolog 180 kDa (dog) | RRBP1 | −1.57318 |
| Hs.472213 | ribosome binding protein 1 homolog 180 kDa (dog) | RRBP1 | −1.49967 |
| Hs.558393 | ribonucleotide reductase M1 polypeptide | RRM1 | −1.73693 |
| Hs.558393 | ribonucleotide reductase M1 polypeptide | RRM1 | −1.57029 |
| Hs.226390 | ribonucleotide reductase M2 polypeptide | RRM2 | −3.67646 |
| Hs.226390 | ribonucleotide reductase M2 polypeptide | RRM2 | −3.3362 |
| Hs.524809 | restin (Reed-Steinberg cell-expressed intermediate filament-associated protein) | RSN | −1.23138 |
| Hs.524809 | restin (Reed-Steinberg cell-expressed intermediate filament-associated protein) | RSN | −1.07857 |
| Hs.526920 | rhabdoid tumor deletion region gene 1 | RTDR1 | 1.66682 |
| Hs.511096 | Rtf1, Paf1/RNA polymerase II complex component, homolog (S. cerevisiae) | RTF1 | 1.40165 |
| Hs.47517 | reticulon 2 | RTN2 | 1.66199 |
| Hs.47517 | reticulon 2 | RTN2 | 1.7177 |
| Hs.133337 | RWD domain containing 4A | RWDD4A | −2.37591 |
| Hs.54649 | putative nucleic acid binding protein RY-1 | RY1 | 1.79623 |
| Hs.54649 | putative nucleic acid binding protein RY-1 | RY1 | 2.02502 |
| Hs.65641 | sterile alpha motif domain containing 9 | SAMD9 | 1.2507 |
| Hs.413835 | sin3-associated polypeptide, 30 kDa | SAP30 | −1.53811 |
| Hs.499960 | SAR1 gene homolog A (S. cerevisiae) | SAR1A | −1.19671 |
| Hs.486292 | squamous cell carcinoma antigen recognized by T cells 2 | SART2 | 1.55722 |
| Hs.506663 | squamous cell carcinoma antigen recognised by T cells 3 | SART3 | −1.73216 |
| Hs.145497 | spindle assembly 6 homolog (C. elegans) | SASS6 | −1.14581 |
| Hs.28491 | spermidine/spermine N1-acetyltransferase | SAT | 1.16964 |
| Hs.10846 | spermidine/spermine N1-acetyltransferase 2 | SAT2 | 1.62909 |
| Hs.110445 | Shwachman-Bodian-Diamond syndrome | SBDS | −1.08895 |
| Hs.110445 | Shwachman-Bodian-Diamond syndrome /// Shwachman-Bodian-Diamond syndrome pseudoge | SBDS /// SBDSP | −1.20921 |
| Hs.438794 | SET binding factor 2 | SBF2 | 1.09612 |
| Hs.482587 | Secretory carrier membrane protein 1 | SCAMP1 | 1.45542 |
| Hs.482587 | secretory carrier membrane protein 1 | SCAMP1 | 1.78245 |
| Hs.482587 | secretory carrier membrane protein 1 | SCAMP1 | 2.06156 |
| Hs.482587 | secretory carrier membrane protein 1 | SCAMP1 | 2.48393 |
| Hs.482587 | secretory carrier membrane protein 1 | SCAMP1 | 2.54707 |
| Hs.482587 | secretory carrier membrane protein 1 | SCAMP1 | 3.02503 |
| Hs.558396 | stearoyl-CoA desaturase (delta-9-desaturase) | SCD | −1.46391 |
| Hs.558396 | stearoyl-CoA desaturase (delta-9-desaturase) | SCD | −1.37392 |
| Hs.379191 | stearoyl-CoA desaturase 5 | SCD5 | 1.21783 |
| Hs.492938 | sciellin | SCEL | −1.42502 |
| Hs.93485 | Sodium channel, voltage-gated, type II, alpha 2 | SCN2A2 | 1.55241 |
| Hs.435274 | sodium channel, voltage-gated, type III, alpha | SCN3A | 2.49334 |

TABLE 1-continued

Genes with increased (positive values) or decreased (negative values) expression
following transfection of human cancer cells with pre-miR hsa-miR-124a.

| UniGene ID | Gene Title | Gene Symbol | Log2 (mir124 - NC #2) |
|---|---|---|---|
| Hs.130989 | sodium channel, nonvoltage-gated 1 alpha | SCNN1A | 1.22373 |
| Hs.480815 | short coiled-coil protein | SCOC | 1.06333 |
| Hs.476365 | Sterol carrier protein 2 | SCP2 | −2.09018 |
| Hs.270107 | SDA1 domain containing 1 | SDAD1 | −1.55494 |
| Hs.200804 | syndecan binding protein (syntenin) | SDCBP | −3.15907 |
| Hs.356270 | succinate dehydrogenase complex, subunit D, integral membrane protein | SDHD | −1.33721 |
| Hs.435719 | sidekick homolog 2 (chicken) | SDK2 | 1.60915 |
| Hs.120790 | CTCL tumor antigen se57-1 | SE57-1 | −2.09234 |
| Hs.166924 | SEC13-like 1 (S. cerevisiae) | SEC13L1 | −1.34897 |
| Hs.211612 | SEC24 related gene family, member A (S. cerevisiae) | SEC24A | −1.35121 |
| Hs.59804 | SECIS binding protein 2 | SECISBP2 | 1.3938 |
| Hs.301048 | SEH1-like (S. cerevisiae) | SEH1L | −2.38946 |
| Hs.301048 | SEH1-like (S. cerevisiae) | SEH1L | −1.54378 |
| Hs.528721 | sema domain, immunoglobulin domain (Ig), short basic domain, secreted, (semaphor | SEMA3E | 2.03993 |
| Hs.550526 | sema domain, immunoglobulin domain (Ig), transmembrane domain (TM) and short cyt | SEMA4G | 1.66918 |
| Hs.371957 | SUMO1/sentrin specific peptidase 1 | SENP1 | −1.21968 |
| Hs.275775 | selenoprotein P, plasma, 1 | SEPP1 | 3.35585 |
| Hs.518326 | stress-associated endoplasmic reticulum protein 1 | SERP1 | −2.55068 |
| Hs.518326 | stress-associated endoplasmic reticulum protein 1 | SERP1 | −2.29199 |
| Hs.518326 | stress-associated endoplasmic reticulum protein 1 | SERP1 | −1.55424 |
| Hs.525557 | serpin peptidase inhibitor, clade A (alpha-1 antiproteinase, antitrypsin), membe | SERPINA1 | 1.93719 |
| Hs.525557 | serpin peptidase inhibitor, clade A (alpha-1 antiproteinase, antitrypsin), membe | SERPINA1 | 2.69097 |
| Hs.104879 | serpin peptidase inhibitor, clade B (ovalbumin), member 9 | SERPINB9 | −2.06905 |
| Hs.104879 | serpin peptidase inhibitor, clade B (ovalbumin), member 9 | SERPINB9 | −1.83307 |
| Hs.478153 | serpin peptidase inhibitor, clade I (neuroserpin), member 1 | SERPINI1 | 1.54454 |
| Hs.548672 | sestrin 1 | SESN1 | 1.99351 |
| Hs.469543 | sestrin 2 | SESN2 | 1.31211 |
| Hs.120633 | Sestrin 3 | SESN3 | 1.00409 |
| Hs.480792 | SET domain-containing protein 7 | SET7 | −1.09659 |
| Hs.443735 | PR/SET domain containing protein 8 | SET8 | −1.61495 |
| Hs.471011 | splicing factor 3b, subunit 1, 155 kDa | SF3B1 | −1.24028 |
| Hs.471011 | splicing factor 3b, subunit 1, 155 kDa | SF3B1 | −1.1432 |
| Hs.68714 | Splicing factor, arginine/serine-rich 1 (splicing factor 2, alternate splicing f | SFRS1 | −1.17971 |
| Hs.533122 | splicing factor, arginine/serine-rich 10 (transformer 2 homolog, Drosophila) | SFRS10 | −1.38503 |
| Hs.479693 | splicing factor, arginine/serine-rich 11 | SFRS11 | 1.00768 |
| Hs.6891 | splicing factor, arginine/serine-rich 6 | SFRS6 | −1.5006 |
| Hs.44269 | shugoshin-like 2 (S. pombe) | SGOL2 | −2.66873 |
| Hs.44269 | shugoshin-like 2 (S. pombe) | SGOL2 | −2.56864 |
| Hs.499984 | sphingosine-1-phosphate lyase 1 | SGPL1 | −1.67514 |
| Hs.499984 | sphingosine-1-phosphate lyase 1 | SGPL1 | −1.38589 |
| Hs.159368 | SH3 multiple domains 1 | SH3MD1 | 1.72135 |
| Hs.301804 | SH3 multiple domains 2 | SH3MD2 | 1.13498 |
| Hs.556866 | SH3 domain containing, Ysc84-like 1 (S. cerevisiae) | SH3YL1 | 1.48937 |
| Hs.123253 | SHC SH2-domain binding protein 1 | SHCBP1 | −3.50024 |
| Hs.75069 | serine hydroxymethyltransferase 2 (mitochondrial) | SHMT2 | −1.38347 |
| Hs.75069 | serine hydroxymethyltransferase 2 (mitochondrial) | SHMT2 | −1.16072 |
| Hs.410977 | SID1 transmembrane family, member 2 | SIDT2 | 1.38653 |
| Hs.525198 | TAL1 (SCL) interrupting locus | SIL | −2.38936 |
| Hs.146186 | single-minded homolog 2 (Drosophila) | SIM2 | 1.60666 |
| Hs.268774 | signal-induced proliferation-associated 1 like 2 | SIPA1L2 | 1.15833 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.112058 | CD27-binding (Siva) protein | SIVA | −1.2054 |
| Hs.112058 | CD27-binding (Siva) protein | SIVA | −1.06964 |
| Hs.23348 | S-phase kinase-associated protein 2 (p45) | SKP2 | −3.35993 |
| Hs.23348 | S-phase kinase-associated protein 2 (p45) | SKP2 | −3.20865 |
| Hs.23348 | S-phase kinase-associated protein 2 (p45) | SKP2 | −2.68355 |
| Hs.298345 | stem-loop (histone) binding protein | SLBP | −2.63949 |
| Hs.505545 | solute carrier family 11 (proton-coupled divalent metal ion transporters), membe | SLC11A2 | 1.70586 |
| Hs.505545 | solute carrier family 11 (proton-coupled divalent metal ion transporters), membe | SLC11A2 | 1.9944 |
| Hs.75231 | solute carrier family 16 (monocarboxylic acid transporters), member 1 | SLC16A1 | −2.33265 |
| Hs.75231 | solute carrier family 16 (monocarboxylic acid transporters), member 1 | SLC16A1 | −2.31664 |
| Hs.75231 | solute carrier family 16 (monocarboxylic acid transporters), member 1 | SLC16A1 | −2.08744 |
| Hs.75231 | solute carrier family 16 (monocarboxylic acid transporters), member 1 | SLC16A1 | −1.72763 |
| Hs.504317 | solute carrier family 16 (monocarboxylic acid transporters), member 14 | SLC16A14 | 1.97925 |
| Hs.75317 | solute carrier family 16 (monocarboxylic acid transporters), member 2 | SLC16A2 | 1.11369 |
| Hs.485760 | solute carrier family 17 (anion/sugar transporter), member 5 | SLC17A5 | −1.39441 |
| Hs.30246 | solute carrier family 19 (thiamine transporter), member 2 | SLC19A2 | −1.6085 |
| Hs.125482 | solute carrier family 22 (organic cation transporter), member 15 | SLC22A15 | 1.10374 |
| Hs.143436 | solute carrier family 22 (extraneuronal monoamine transporter), member 3 | SLC22A3 | 1.12722 |
| Hs.443572 | solute carrier family 22 (organic cation transporter), member 5 | SLC22A5 | −1.54401 |
| Hs.310449 | solute carrier family 23 (nucleobase transporters), member 1 | SLC23A1 | 1.73231 |
| Hs.111024 | solute carrier family 25 (mitochondrial carrier; citrate transporter), member 1 | SLC25A1 | −1.43875 |
| Hs.4866 | solute carrier family 26, member 11 | SLC26A11 | 1.03764 |
| Hs.302738 | solute carrier family 26 (sulfate transporter), member 2 | SLC26A2 | −2.88899 |
| Hs.302738 | solute carrier family 26 (sulfate transporter), member 2 | SLC26A2 | −1.91058 |
| Hs.302738 | solute carrier family 26 (sulfate transporter), member 2 | SLC26A2 | −1.61653 |
| Hs.419240 | solute carrier family 2 (facilitated glucose transporter), member 3 | SLC2A3 | 1.10459 |
| Hs.419240 | solute carrier family 2 (facilitated glucose transporter), member 3 | SLC2A3 | 1.70527 |
| Hs.419240 | solute carrier family 2 (facilitated glucose transporter), member 3 | SLC2A3 | 1.90675 |
| Hs.419240 | solute carrier family 2 (facilitated glucose transporter), member 3 | SLC2A3 /// SLC2A14 | 1.90763 |
| Hs.542233 | solute carrier family 30 (zinc transporter), member 6 | SLC30A6 | −2.09805 |
| Hs.542233 | solute carrier family 30 (zinc transporter), member 6 | SLC30A6 | −1.31222 |
| Hs.533903 | solute carrier family 30 (zinc transporter), member 7 | SLC30A7 | −1.2746 |
| Hs.533903 | Solute carrier family 30 (zinc transporter), member 7 | SLC30A7 | −1.24817 |
| Hs.532315 | solute carrier family 31 (copper transporters), member 1 | SLC31A1 | −2.29064 |
| Hs.532315 | solute carrier family 31 (copper transporters), member 1 | SLC31A1 | −1.41874 |
| Hs.154073 | solute carrier family 35, member B1 | SLC35B1 | −1.19479 |
| Hs.182885 | solute carrier family 35, member B2 | SLC35B2 | −1.0296 |
| Hs.158748 | solute carrier family 35, member F3 | SLC35F3 | −1.66741 |
| Hs.292509 | solute carrier family 35, member F5 | SLC35F5 | −2.13878 |
| Hs.413434 | solute carrier family 39 (zinc transporter), member 10 | SLC39A10 | −1.46413 |
| Hs.491232 | solute carrier family 39 (zinc transporter), member 14 | SLC39A14 | −1.3285 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 − NC #2) |
|---|---|---|---|
| Hs.432690 | solute carrier family 39 (zinc transporter), member 9 | SLC39A9 | −1.52698 |
| Hs.306448 | solute carrier family 41, member 2 | SLC41A2 | −1.13911 |
| Hs.306448 | solute carrier family 41, member 2 | SLC41A2 | −1.0582 |
| Hs.518220 | solute carrier family 41, member 3 | SLC41A3 | 1.3 |
| Hs.518220 | solute carrier family 41, member 3 | SLC41A3 | 1.4211 |
| Hs.494700 | solute carrier family 44, member 1 | SLC44A1 | −1.91768 |
| Hs.494700 | solute carrier family 44, member 1 | SLC44A1 | −1.63703 |
| Hs.494700 | solute carrier family 44, member 1 | SLC44A1 | −1.30969 |
| Hs.480188 | solute carrier family 44, member 5 | SLC44A5 | 1.38426 |
| Hs.105607 | solute carrier family 4, sodium bicarbonate transporter-like, member 11 | SLC4A11 | 1.54877 |
| Hs.560907 | Solute carrier family 4, sodium bicarbonate cotransporter, member 5 | SLC4A5 | −1.36366 |
| Hs.370636 | solute carrier family 4, sodium bicarbonate cotransporter, member 8 | SLC4A8 | 1.17528 |
| Hs.44424 | solute carrier family 6, member 15 | SLC6A15 | 1.39234 |
| Hs.14846 | solute carrier family 7 (cationic amino acid transporter, y+ system), member 1 | SLC7A1 | −1.52518 |
| Hs.504966 | solute carrier organic anion transporter family, member 1B3 | SLCO1B3 | −1.67878 |
| Hs.521557 | SLD5 homolog /// SLD5 homolog | SLD5 | −1.51953 |
| Hs.500972 | STE20-like kinase (yeast) | SLK | −1.80416 |
| Hs.517070 | secretory leukocyte peptidase inhibitor | SLPI | −1.00064 |
| Hs.167700 | SMAD, mothers against DPP homolog 5 (Drosophila) | SMAD5 | −1.17949 |
| Hs.167700 | SMAD, mothers against DPP homolog 5 (Drosophila) | SMAD5 | −1.11905 |
| Hs.546339 | small acidic protein | SMAP | −1.48376 |
| Hs.546339 | small acidic protein /// small acidic protein | SMAP | −1.18439 |
| Hs.476179 | SWI/SNF related, matrix associated, actin dependent regulator of chromatin, subf | SMARCC1 | −1.55548 |
| Hs.476179 | SWI/SNF related, matrix associated, actin dependent regulator of chromatin, subf | SMARCC1 | −1.54247 |
| Hs.476179 | SWI/SNF related, matrix associated, actin dependent regulator of chromatin, subf | SMARCC1 | −1.26259 |
| Hs.119023 | SMC2 structural maintenance of chromosomes 2-like 1 (yeast) | SMC2L1 | −2.39835 |
| Hs.119023 | SMC2 structural maintenance of chromosomes 2-like 1 (yeast) | SMC2L1 | −2.21741 |
| Hs.58992 | SMC4 structural maintenance of chromosomes 4-like 1 (yeast) | SMC4L1 | −2.23418 |
| Hs.58992 | SMC4 structural maintenance of chromosomes 4-like 1 (yeast) | SMC4L1 | −1.88314 |
| Hs.8118 | structural maintenance of chromosomes flexible hinge domain containing 1 | SMCHD1 | −1.55959 |
| Hs.8118 | structural maintenance of chromosomes flexible hinge domain containing 1 | SMCHD1 | −1.28447 |
| Hs.8118 | structural maintenance of chromosomes flexible hinge domain containing 1 | SMCHD1 | −1.24675 |
| Hs.331268 | SMILE protein | SMILE | −1.49332 |
| Hs.202179 | survival of motor neuron 1, telomeric /// survival of motor neuron 2, centromeric | SMN1 /// SMN2 | −1.14845 |
| Hs.433337 | spermine oxidase | SMOX | −1.28388 |
| Hs.433337 | spermine oxidase | SMOX | −1.03309 |
| Hs.486357 | sphingomyelin phosphodiesterase, acid-like 3A | SMPDL3A | −1.62965 |
| Hs.5212 | single-strand selective monofunctional uracil DNA glycosylase | SMUG1 | 1.1219 |
| Hs.515011 | SMAD specific E3 ubiquitin protein ligase 2 | SMURF2 | 1.60074 |
| Hs.515011 | SMAD specific E3 ubiquitin protein ligase 2 | SMURF2 | 1.71702 |
| Hs.127406 | SET and MYND domain containing 3 | SMYD3 | −1.81401 |
| Hs.432755 | Sorting nexin associated golgi protein 1 | SNAG1 | −1.35123 |
| Hs.167317 | synaptosomal-associated protein, 25 kDa | SNAP25 | 2.2641 |
| Hs.167317 | synaptosomal-associated protein, 25 kDa | SNAP25 | 2.37493 |
| Hs.459952 | stannin | SNN | 2.44046 |
| Hs.280378 | small nuclear ribonucleoprotein polypeptide B" | SNRPB2 | −2.39942 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.464734 | small nuclear ribonucleoprotein D1 polypeptide 16 kDa | SNRPD1 | −1.8753 |
| Hs.192326 | sorting nexin family member 27 | SNX27 | 1.1421 |
| Hs.316890 | sorting nexin 5 | SNX5 | −1.14759 |
| Hs.316890 | sorting nexin 5 | SNX5 | −1.03699 |
| Hs.356647 | sorting nexin 6 | SNX6 | −2.19379 |
| Hs.356647 | sorting nexin 6 | SNX6 | −2.05642 |
| Hs.496383 | Sterol O-acyltransferase (acyl-Coenzyme A: cholesterol acyltransferase) 1 | SOAT1 | 1.19849 |
| Hs.517262 | SON DNA binding protein | SON | −1.22097 |
| Hs.517262 | SON DNA binding protein | SON | −1.09787 |
| Hs.558450 | sorbin and SH3 domain containing 1 | SORBS1 | 1.13729 |
| Hs.878 | sorbitol dehydrogenase | SORD | −1.48759 |
| Hs.485195 | sortilin 1 | SORT1 | 1.01531 |
| Hs.518438 | SRY (sex determining region Y)-box 2 | SOX2 | 1.51679 |
| Hs.357901 | SRY (sex determining region Y)-box 4 | SOX4 | 1.25978 |
| Hs.357901 | SRY (sex determining region Y)-box 4 | SOX4 | 1.47878 |
| Hs.2316 | SRY (sex determining region Y)-box 9 (campomelic dysplasia, autosomal sex-revers | SOX9 | −1.89741 |
| Hs.2316 | SRY (sex determining region Y)-box 9 (campomelic dysplasia, autosomal sex-revers | SOX9 | −1.50674 |
| Hs.524461 | Sp1 transcription factor | SP1 | −1.25481 |
| Hs.524461 | Sp1 transcription factor | SP1 | −1.2495 |
| Hs.524461 | Sp1 transcription factor | SP1 | −1.2019 |
| Hs.514033 | sperm associated antigen 5 | SPAG5 | −2.08749 |
| Hs.527090 | spermatogenesis associated 18 homolog (rat) | SPATA18 | 2.13251 |
| Hs.103147 | spermatogenesis associated 20 | SPATA20 | 1.74075 |
| Hs.408467 | Spermatogenesis associated 6 | SPATA6 | 1.08874 |
| Hs.525518 | spermatogenesis associated 7 | SPATA7 | 1.16118 |
| Hs.525518 | spermatogenesis associated 7 | SPATA7 | 1.60602 |
| Hs.381225 | spindle pole body component 24 homolog (S. cerevisiae) | SPBC24 | −1.29212 |
| Hs.421956 | spindle pole body component 25 homolog (S. cerevisiae) | SPBC25 | −3.85245 |
| Hs.42194 | signal peptidase complex subunit 3 homolog (S. cerevisiae) | SPCS3 | −1.17448 |
| Hs.431045 | spectrin domain with coiled-coils 1 | SPECC1 | 1.41964 |
| Hs.150087 | SPFH domain family, member 1 | SPFH1 | −1.7124 |
| Hs.150087 | SPFH domain family, member 1 | SPFH1 | −1.22728 |
| Hs.440414 | spastic paraplegia 20, spartin (Troyer syndrome) | SPG20 | −2.13037 |
| Hs.241503 | spastic paraplegia 3A (autosomal dominant) | SPG3A | 1.06782 |
| Hs.522672 | spindlin family, member 3 | SPIN3 | 1.74925 |
| Hs.62604 | SPOC domain containing 1 | SPOCD1 | 1.34155 |
| Hs.401537 | signal peptide peptidase-like 2A | SPPL2A | −1.25698 |
| Hs.301540 | sepiapterin reductase (7,8-dihydrobiopterin:NADP+ oxidoreductase) | SPR | −1.82932 |
| Hs.503178 | Spectrin, beta, non-erythrocytic 1 | SPTBN1 | −1.2976 |
| Hs.529892 | sequestosome 1 | SQSTM1 | −1.42587 |
| Hs.195659 | v-src sarcoma (Schmidt-Ruppin A-2) viral oncogene homolog (avian) | SRC | −1.32887 |
| Hs.489040 | sorcin | SRI | −1.34605 |
| Hs.76244 | spermidine synthase | SRM | −1.60483 |
| Hs.237825 | signal recognition particle 72 kDa | SRP72 | −1.17216 |
| Hs.15154 | sushi-repeat-containing protein, X-linked | SRPX | −2.07806 |
| Hs.288178 | TROVE domain family, member 2 | SSA2 | −1.73081 |
| Hs.102735 | single-stranded DNA binding protein 2 | SSBP2 | 1.464 |
| Hs.102735 | single-stranded DNA binding protein 2 | SSBP2 | 2.06512 |
| Hs.196983 | sperm specific antigen 2 | SSFA2 | −1.13277 |
| Hs.207459 | ST6 beta-galactosamide alpha-2,6-sialyltranferase 1 | ST6GAL1 | 1.21227 |
| Hs.98265 | ST6 beta-galactosamide alpha-2,6-sialyltranferase 2 | ST6GAL2 | 1.84133 |
| Hs.308628 | ST8 alpha-N-acetyl-neuraminide alpha-2,8-sialyltransferase 4 | ST8SIA4 | 1.38116 |
| Hs.308628 | ST8 alpha-N-acetyl-neuraminide alpha-2,8-sialyltransferase 4 | ST8SIA4 | 1.6526 |

TABLE 1-continued

Genes with increased (positive values) or decreased (negative values) expression
following transfection of human cancer cells with pre-miR hsa-miR-124a.

| UniGene ID | Gene Title | Gene Symbol | Log2 (mir124 - NC #2) |
|---|---|---|---|
| Hs.188606 | START domain containing 10 | STARD10 | 1.06176 |
| Hs.470943 | signal transducer and activator of transcription 1, 91 kDa | STAT1 | −1.11395 |
| Hs.80642 | signal transducer and activator of transcription 4 | STAT4 | 1.32949 |
| Hs.25590 | Stanniocalcin 1 | STC1 | −1.96514 |
| Hs.25590 | stanniocalcin 1 | STC1 | −1.29341 |
| Hs.352341 | stress 70 protein chaperone, microsome-associated, 60 kDa | STCH | −1.11468 |
| Hs.20805 | STEAP family member 3 | STEAP3 | 1.60471 |
| Hs.337295 | stress-induced-phosphoprotein 1 (Hsp70/Hsp90-organizing protein) | STIP1 | −1.31807 |
| Hs.250822 | serine/threonine kinase 6 | STK6 | −3.40582 |
| Hs.250822 | serine/threonine kinase 6 | STK6 | −2.83369 |
| Hs.250822 | serine/threonine kinase 6 | STK6 | −2.22636 |
| Hs.348326 | stathmin-like 3 | STMN3 | 1.61593 |
| Hs.253903 | stomatin | STOM | −1.52633 |
| Hs.253903 | stomatin | STOM | −1.0987 |
| Hs.21958 | storkhead box 2 | STOX2 | 1.05666 |
| Hs.522578 | steroid sulfatase (microsomal), arylsulfatase C, isozyme S | STS | 1.62674 |
| Hs.43812 | syntaxin 10 | STX10 | −1.05792 |
| Hs.523855 | syntaxin 12 | STX12 | 1.01497 |
| Hs.130643 | Syntaxin 17 | STX17 | −1.77384 |
| Hs.288229 | syntaxin binding protein 1 | STXBP1 | 1.43683 |
| Hs.508958 | syntaxin binding protein 6 (amisyn) | STXBP6 | 2.67956 |
| Hs.24979 | serine/threonine/tyrosine kinase 1 | STYK1 | 1.07694 |
| Hs.448070 | SUB1 homolog (*S. cerevisiae*) /// SUB1 homolog (*S. cerevisiae*) pseudogene 1 | SUB1 /// SUB1P1 | 1.22735 |
| Hs.186512 | succinate-CoA ligase, GDP-forming, beta subunit | SUCLG2 | −3.47892 |
| Hs.186512 | succinate-CoA ligase, GDP-forming, beta subunit | SUCLG2 | −3.2152 |
| Hs.186512 | succinate-CoA ligase, GDP-forming, beta subunit | SUCLG2 | −2.98048 |
| Hs.281902 | SGT1, suppressor of G2 allele of SKP1 (*S. cerevisiae*) | SUGT1 | −1.31 |
| Hs.162016 | sulfatase 2 | SULF2 | 2.66907 |
| Hs.162016 | sulfatase 2 | SULF2 | 2.73783 |
| Hs.436123 | sulfotransferase family, cytosolic, 1C, member 1 | SULT1C1 | 2.01252 |
| Hs.436123 | sulfotransferase family, cytosolic, 1C, member 1 | SULT1C1 | 2.12614 |
| Hs.213724 | suppressor of Ty 16 homolog (*S. cerevisiae*) | SUPT16H | −1.4652 |
| Hs.286145 | SRB7 suppressor of RNA polymerase B homolog (yeast) | SURB7 | −2.06851 |
| Hs.286145 | SRB7 suppressor of RNA polymerase B homolog (yeast) | SURB7 | −1.74676 |
| Hs.512465 | surfeit 4 | SURF4 | −1.57149 |
| Hs.512465 | surfeit 4 | SURF4 | −1.42496 |
| Hs.494827 | sushi domain containing 1 | SUSD1 | 1.21596 |
| Hs.435277 | synaptogyrin 3 | SYNGR3 | 1.93769 |
| Hs.480615 | synaptopodin 2 | SYNPO2 | −1.95139 |
| Hs.480615 | synaptopodin 2 | SYNPO2 | 1.12017 |
| Hs.80919 | synaptophysin-like 1 | SYPL1 | −3.38439 |
| Hs.80919 | synaptophysin-like 1 | SYPL1 | −1.95282 |
| Hs.310545 | synaptotagmin I | SYT1 | 1.60701 |
| Hs.310545 | synaptotagmin I | SYT1 | 1.81623 |
| Hs.32984 | synaptotagmin XI | SYT11 | 1.33604 |
| Hs.188256 | TAK1-binding protein 3 | TAB3 | 1.25396 |
| Hs.279245 | transforming, acidic coiled-coil containing protein 1 | TACC1 | −1.23007 |
| Hs.104019 | transforming, acidic coiled-coil containing protein 3 | TACC3 | −1.58666 |
| Hs.692 | tumor-associated calcium signal transducer 1 | TACSTD1 | 2.30134 |
| Hs.503998 | transgelin | TAGLN | 1.91915 |
| Hs.503998 | transgelin | TAGLN | 2.56072 |
| Hs.61590 | TPR domain, ankyrin-repeat and coiled-coil-containing | TANC | 1.28123 |
| Hs.13854 | T-cell activation protein phosphatase 2C | TA-PP2C | −1.13956 |
| Hs.6918 | threonyl-tRNA synthetase-like 2 | TARSL2 | 1.19846 |
| Hs.12956 | Tax1 (human T-cell leukemia virus type I) binding protein 3 | TAX1BP3 | −1.43209 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 − NC #2) |
|---|---|---|---|
| Hs.12956 | Tax1 (human T-cell leukemia virus type I) binding protein 3 | TAX1BP3 | −1.34309 |
| Hs.558562 | TBC1 domain family, member 10A | TBC1D10A | −1.75425 |
| Hs.369819 | TBC1 domain family, member 16 | TBC1D16 | 1.20748 |
| Hs.105891 | TBC1 domain family, member 3 /// TBC1 domain family, member 3C | TBC1D3 /// TBC1D3C | 1.08387 |
| Hs.475629 | TBC1 domain family, member 5 | TBC1D5 | −1.45511 |
| Hs.475629 | TBC1 domain family, member 5 | TBC1D5 | −1.32512 |
| Hs.484678 | TBC1 domain family, member 7 | TBC1D7 | 1.5709 |
| Hs.442657 | TBC1 domain family, member 8 (with GRAM domain) | TBC1D8 | 1.73295 |
| Hs.495656 | transducin (beta)-like 1X-linked | TBL1X | −1.47039 |
| Hs.251830 | T-box 18 | TBX18 | −1.22633 |
| Hs.505004 | transcription elongation factor A (SII), 2 | TCEA2 | 1.31996 |
| Hs.511504 | Transcription factor 12 (HTF4, helix-loop-helix transcription factors 4) | TCF12 | −1.53336 |
| Hs.555894 | transcription factor 19 (SC1) | TCF19 | −1.5746 |
| Hs.371282 | transcription factor 3 (E2A immunoglobulin enhancer binding factors E12/E47) | TCF3 | −1.2752 |
| Hs.446392 | t-complex-associated-testis-expressed 1-like | TCTE1L | −2.58705 |
| Hs.516087 | testis expressed sequence 261 | TEX261 | −1.21638 |
| Hs.511476 | testis expressed sequence 9 | TEX9 | 2.01224 |
| Hs.473152 | transcription factor AP-2 gamma (activating enhancer binding protein 2 gamma) | TFAP2C | 1.19787 |
| Hs.473152 | transcription factor AP-2 gamma (activating enhancer binding protein 2 gamma) | TFAP2C | 1.25248 |
| Hs.79353 | transcription factor Dp-1 | TFDP1 | −2.62562 |
| Hs.79353 | transcription factor Dp-1 | TFDP1 | −2.29669 |
| Hs.79353 | transcription factor Dp-1 | TFDP1 | −2.19872 |
| Hs.79353 | Transcription factor Dp-1 | TFDP1 | −1.42905 |
| Hs.516578 | tissue factor pathway inhibitor (lipoprotein-associated coagulation inhibitor) | TFPI | −2.02628 |
| Hs.516578 | Tissue factor pathway inhibitor (lipoprotein-associated coagulation inhibitor) | TFPI | −1.98713 |
| Hs.516578 | tissue factor pathway inhibitor (lipoprotein-associated coagulation inhibitor) | TFPI | −1.40011 |
| Hs.529618 | transferrin receptor (p90, CD71) | TFRC | −2.06349 |
| Hs.12393 | TDP-glucose 4,6-dehydratase | TGDS | −1.09049 |
| Hs.513530 | transforming growth factor beta 1 induced transcript 1 | TGFB1I1 | 1.38866 |
| Hs.133379 | Transforming growth factor, beta 2 | TGFB2 | 1.93103 |
| Hs.82028 | transforming growth factor, beta receptor II (70/80 kDa) | TGFBR2 | −1.94501 |
| Hs.482390 | transforming growth factor, beta receptor III (betaglycan, 300 kDa) | TGFBR3 | −2.12203 |
| Hs.482390 | Transforming growth factor, beta receptor III (betaglycan, 300 kDa) | TGFBR3 | −2.10583 |
| Hs.517033 | transglutaminase 2 (C polypeptide, protein-glutamine-gamma-glutamyltransferase) | TGM2 | −3.20595 |
| Hs.517033 | transglutaminase 2 (C polypeptide, protein-glutamine-gamma-glutamyltransferase) | TGM2 | −2.04406 |
| Hs.517033 | transglutaminase 2 (C polypeptide, protein-glutamine-gamma-glutamyltransferase) | TGM2 | −1.78471 |
| Hs.14894 | trans-golgi network protein 2 | TGOLN2 | −1.12887 |
| Hs.479971 | THAP domain containing 6 | THAP6 | 1.40583 |
| Hs.2030 | thrombomodulin | THBD | −2.01692 |
| Hs.2030 | thrombomodulin | THBD | −1.01679 |
| Hs.164226 | thrombospondin 1 | THBS1 | 1.46471 |
| Hs.164226 | thrombospondin 1 | THBS1 | 1.76749 |
| Hs.20000 | three prime histone mRNA exonuclease 1 | THEX1 | −1.69473 |
| Hs.553878 | thrombospondin, type I, domain containing 1 /// thrombospondin, type I, domain c | THSD1 /// THSD1P | 1.0871 |
| Hs.443081 | THUMP domain containing 3 | THUMPD3 | −1.19184 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.278391 | toll-like receptor adaptor molecule 2 | TICAM2 | −1.80389 |
| Hs.118631 | timeless homolog (Drosophila) | TIMELESS | −1.03072 |
| Hs.104839 | TIMP metallopeptidase inhibitor 2 | TIMP2 | 1.09933 |
| Hs.209431 | TIP41, TOR signalling pathway regulator-like (S. cerevisiae) | TIPRL | −1.93302 |
| Hs.209431 | TIP41, TOR signalling pathway regulator-like (S. cerevisiae) | TIPRL | −1.4105 |
| Hs.515122 | thymidine kinase 1, soluble | TK1 | −2.489 |
| Hs.515122 | thymidine kinase 1, soluble | TK1 | −2.3099 |
| Hs.512619 | thymidine kinase 2, mitochondrial | TK2 | 2.00304 |
| Hs.375001 | talin 1 | TLN1 | 1.27688 |
| Hs.529591 | translocation protein 1 | TLOC1 | −1.45673 |
| Hs.529591 | translocation protein 1 | TLOC1 | −1.32688 |
| Hs.351316 | transmembrane 4 L six family member 1 | TM4SF1 | −1.24857 |
| Hs.31130 | transmembrane 7 superfamily member 2 | TM7SF2 | 1.45683 |
| Hs.555971 | transmembrane BAX inhibitor motif containing 1 | TMBIM1 | −1.25666 |
| Hs.510745 | transmembrane emp24 protein transport domain containing 4 | TMED4 | 1.71641 |
| Hs.482873 | transmembrane emp24 protein transport domain containing 5 | TMED5 | −1.33367 |
| Hs.144513 | transmembrane protein with EGF-like and two follistatin-like domains 2 | TMEFF2 | 1.41511 |
| Hs.437409 | Transmembrane protein 20 | TMEM20 | −1.87807 |
| Hs.129614 | transmembrane protein 27 | TMEM27 | 1.13364 |
| Hs.8769 | transmembrane protein 47 | TMEM47 | 1.42559 |
| Hs.476525 | transmembrane protein 48 | TMEM48 | −1.34569 |
| Hs.433668 | transmembrane protein 50B | TMEM50B | 1.98389 |
| Hs.202517 | transmembrane protein 55A | TMEM55A | 1.14151 |
| Hs.523262 | transmembrane protein 59 | TMEM59 | −1.06308 |
| Hs.116240 | transmembrane protein 67 | TMEM67 | 1.06596 |
| Hs.420076 | transmembrane protein 68 | TMEM68 | 1.67253 |
| Hs.485606 | transmembrane protein 77 | TMEM77 | −1.5814 |
| Hs.513734 | Tropomodulin 2 (neuronal) | TMOD2 | 2.41916 |
| Hs.11355 | thymopoietin | TMPO | −2.65071 |
| Hs.11355 | thymopoietin | TMPO | −2.6112 |
| Hs.11355 | Thymopoietin | TMPO | −1.85058 |
| Hs.11355 | thymopoietin | TMPO | −1.70745 |
| Hs.556258 | trophoblast-derived noncoding RNA | TncRNA | −1.56784 |
| Hs.523789 | Trophoblast-derived noncoding RNA | TncRNA | 1.83062 |
| Hs.443577 | tumor necrosis factor receptor superfamily, member 21 | TNFRSF21 | −1.99853 |
| Hs.443577 | tumor necrosis factor receptor superfamily, member 21 | TNFRSF21 | −1.83323 |
| Hs.482497 | Transportin 1 | TNPO1 | −2.38902 |
| Hs.193613 | transportin 3 | TNPO3 | −1.26913 |
| Hs.193613 | transportin 3 | TNPO3 | −1.21284 |
| Hs.407740 | trinucleotide repeat containing 6A | TNRC6A | 1.53347 |
| Hs.80618 | trinucleotide repeat containing 6C | TNRC6C | 1.41076 |
| Hs.471381 | tensin 1 /// tensin 1 | TNS1 | 2.23004 |
| Hs.528574 | topoisomerase (DNA) I, mitochondrial | TOP1MT | 1.61288 |
| Hs.156346 | topoisomerase (DNA) II alpha 170 kDa | TOP2A | −3.45121 |
| Hs.156346 | topoisomerase (DNA) II alpha 170 kDa | TOP2A | −2.71292 |
| Hs.53454 | topoisomerase (DNA) II binding protein 1 | TOPBP1 | −1.48618 |
| Hs.496459 | torsin A interacting protein 1 | TOR1AIP1 | −1.34467 |
| Hs.496459 | torsin A interacting protein 1 | TOR1AIP1 | −1.14929 |
| Hs.496459 | torsin A interacting protein 1 | TOR1AIP1 | −1.14894 |
| Hs.252682 | torsin family 1, member B (torsin B) | TOR1B | −1.50129 |
| Hs.554791 | tumor protein p53 inducible protein 11 | TP53I11 | 1.18773 |
| Hs.50649 | tumor protein p53 inducible protein 3 | TP53I3 | 1.8759 |
| Hs.492261 | tumor protein p53 inducible nuclear protein 1 | TP53INP1 | 2.56175 |
| Hs.516994 | tumor protein p53 inducible nuclear protein 2 | TP53INP2 | 1.22242 |
| Hs.473296 | tumor protein D52-like 2 | TPD52L2 | −1.90007 |
| Hs.133892 | tropomyosin 1 (alpha) | TPM1 | 3.2798 |
| Hs.300772 | Tropomyosin 2 (beta) | TPM2 | 1.24243 |
| Hs.300772 | tropomyosin 2 (beta) | TPM2 | 2.25258 |
| Hs.466088 | Tropomyosin 4 | TPM4 | 1.19271 |
| Hs.432424 | tripeptidyl peptidase II | TPP2 | −1.06767 |
| Hs.279640 | translocated promoter region (to activated MET oncogene) | TPR | −1.18552 |
| Hs.558468 | trans-prenyltransferase | TPRT | −1.32401 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.244580 | TPX2, microtubule-associated, homolog (*Xenopus laevis*) | TPX2 | −2.48558 |
| Hs.524078 | trafficking protein particle complex 4 | TRAPPC4 | −1.63407 |
| Hs.524078 | trafficking protein particle complex 4 | TRAPPC4 | −1.6043 |
| Hs.466929 | trafficking protein particle complex 6A | TRAPPC6A | 1.6066 |
| Hs.278434 | Trf (TATA binding protein-related factor)-proximal homolog (*Drosophila*) | TRFP | −1.26727 |
| Hs.516826 | tribbles homolog 3 (*Drosophila*) | TRIB3 | −1.01059 |
| Hs.555909 | tripartite motif-containing 14 | TRIM14 | −2.18727 |
| Hs.490287 | tripartite motif-containing 24 | TRIM24 | 1.38135 |
| Hs.490287 | tripartite motif-containing 24 | TRIM24 | 1.38717 |
| Hs.159408 | tripartite motif-containing 3 | TRIM3 | 1.20424 |
| Hs.159408 | tripartite motif-containing 3 | TRIM3 | 1.89824 |
| Hs.212957 | tripartite motif-containing 59 | TRIM59 | −1.54122 |
| Hs.368928 | tripartite motif-containing 9 | TRIM9 | 1.89995 |
| Hs.368985 | Thyroid hormone receptor interactor 12 | TRIP12 | −2.16301 |
| Hs.436187 | thyroid hormone receptor interactor 13 | TRIP13 | −1.08916 |
| Hs.524399 | trophinin associated protein (tastin) | TROAP | −1.31723 |
| Hs.288178 | TROVE domain family, member 2 | TROVE2 | −1.47133 |
| Hs.288178 | TROVE domain family, member 2 | TROVE2 | −1.34204 |
| Hs.250687 | transient receptor potential cation channel, subfamily C, member 1 | TRPC1 | 1.51598 |
| Hs.250687 | transient receptor potential cation channel, subfamily C, member 1 | TRPC1 | 1.6526 |
| Hs.250687 | transient receptor potential cation channel, subfamily C, member 1 | TRPC1 | 1.73898 |
| Hs.21187 | TruB pseudouridine (psi) synthase homolog 1 (*E. coli*) | TRUB1 | −2.42347 |
| Hs.21187 | TruB pseudouridine (psi) synthase homolog 1 (*E. coli*) | TRUB1 | −2.25384 |
| Hs.21187 | TruB pseudouridine (psi) synthase homolog 1 (*E. coli*) | TRUB1 | −1.03454 |
| Hs.145925 | testis specific A2 homolog (mouse) | TSGA2 | 1.33296 |
| Hs.75066 | translin | TSN | −2.38669 |
| Hs.75066 | translin | TSN | −2.17376 |
| Hs.75066 | translin | TSN | −1.94214 |
| Hs.16529 | tetraspanin 12 | TSPAN12 | −1.5222 |
| Hs.310453 | tetraspanin 14 /// tetraspanin 14 | TSPAN14 | −1.36207 |
| Hs.310458 | tetraspanin 2 | TSPAN2 | 1.13685 |
| Hs.441664 | tetraspanin 7 | TSPAN7 | 1.74728 |
| Hs.284141 | TSPY-like 4 | TSPYL4 | 1.16724 |
| Hs.513195 | tetratricopeptide repeat domain 23 | TTC23 | 2.04805 |
| Hs.510213 | tetratricopeptide repeat domain 7B | TTC7B | 1.52316 |
| Hs.79170 | tetratricopeptide repeat domain 9 | TTC9 | 1.26096 |
| Hs.169840 | TTK protein kinase | TTK | −2.80142 |
| Hs.358997 | tubulin tyrosine ligase | TTL | −1.38282 |
| Hs.358997 | tubulin tyrosine ligase | TTL | −1.21128 |
| Hs.440899 | tweety homolog 3 (*Drosophila*) | TTYH3 | 1.55269 |
| Hs.75318 | tubulin, alpha 1 (testis specific) | TUBA1 | −1.08001 |
| Hs.436035 | tubulin alpha 6 /// tubulin alpha 6 | TUBA6 | −1.19356 |
| Hs.436035 | tubulin alpha 6 | TUBA6 | −1.14334 |
| Hs.533059 | tubulin, beta polypeptide | TUBB | −1.47079 |
| Hs.533059 | tubulin, beta polypeptide | TUBB | −1.15728 |
| Hs.533059 | tubulin, beta polypeptide /// tubulin, beta polypeptide | TUBB | −1.14511 |
| Hs.433615 | tubulin, beta, 2 | TUBB2 | −1.61272 |
| Hs.433615 | tubulin, beta, 2 | TUBB2 | −1.52911 |
| Hs.512712 | tubulin, beta 2 /// tubulin, beta polypeptide paralog | TUBB2 /// TUBB-PARALOG | −1.06679 |
| Hs.511743 | tubulin, beta 3 | TUBB3 | −1.24198 |
| Hs.511743 | tubulin, beta 3 | TUBB3 | −1.10955 |
| Hs.193491 | tubulin, beta 6 | TUBB6 | −1.91894 |
| Hs.279669 | tubulin, gamma 1 | TUBG1 | −2.30037 |
| Hs.426324 | tumor suppressor candidate 3 | TUSC3 | 1.22834 |
| Hs.353035 | TWIST neighbor | TWISTNB | −2.4257 |
| Hs.353035 | TWIST neighbor | TWISTNB | −1.67295 |
| Hs.514685 | twisted gastrulation homolog 1 (*Drosophila*) | TWSG1 | −1.05709 |
| Hs.17987 | taxilin alpha | TXLNA | −1.48329 |
| Hs.125221 | thioredoxin domain containing | TXNDC | −2.39992 |
| Hs.125221 | thioredoxin domain containing | TXNDC | −2.29287 |
| Hs.385986 | ubiquitin-conjugating enzyme E2B (RAD6 homolog) | UBE2B | −1.21338 |

TABLE 1-continued

Genes with increased (positive values) or decreased (negative values) expression
following transfection of human cancer cells with pre-miR hsa-miR-124a.

| UniGene ID | Gene Title | Gene Symbol | Log2 (mir124 − NC #2) |
|---|---|---|---|
| Hs.93002 | ubiquitin-conjugating enzyme E2C | UBE2C | −2.75961 |
| Hs.344165 | Ubiquitin-conjugating enzyme E2H (UBC8 homolog, yeast) | UBE2H | 1.1387 |
| Hs.163776 | ubiquitin-conjugating enzyme E2, J1 (UBC6 homolog, yeast) | UBE2J1 | −1.21165 |
| Hs.406068 | ubiquitin-conjugating enzyme E2M (UBC12 homolog, yeast) | UBE2M | −1.13928 |
| Hs.462306 | ubiquitin-conjugating enzyme E2S | UBE2S | −1.70792 |
| Hs.5199 | ubiquitin-conjugating enzyme E2T (putative) | UBE2T | −1.45046 |
| Hs.491695 | Ubiquitin-conjugating enzyme E2 variant 2 | UBE2V2 | −1.45046 |
| Hs.491695 | Ubiquitin-conjugating enzyme E2 variant 2 | UBE2V2 | −1.28108 |
| Hs.118351 | ubiquitin protein ligase E3C | UBE3C | −1.91103 |
| Hs.153678 | UBX domain containing 6 | UBXD6 | −1.03407 |
| Hs.145469 | ubiquitin carboxyl-terminal hydrolase L5 | UCHL5 | −1.36253 |
| Hs.145469 | ubiquitin carboxyl-terminal hydrolase L5 | UCHL5 | −1.26492 |
| Hs.144197 | UDP glycosyltransferase 8 (UDP-galactose ceramide galactosyltransferase) | UGT8 | −1.20054 |
| Hs.127310 | U2AF homology motif (UHM) kinase 1 | UHMK1 | −1.46655 |
| Hs.108106 | ubiquitin-like, containing PHD and RING finger domains, 1 | UHRF1 | −2.73893 |
| Hs.2057 | uridine monophosphate synthetase (orotate phosphoribosyl transferase and orotidi | UMPS | −1.26768 |
| Hs.2057 | uridine monophosphate synthetase (orotate phosphoribosyl transferase and orotidi | UMPS | −1.21064 |
| Hs.158357 | Unc-5 homolog C (*C. elegans*)-like | UNC5CL | 1.93767 |
| Hs.438072 | unc-84 homolog A (*C. elegans*) | UNC84A | 1.25936 |
| Hs.438072 | unc-84 homolog A (*C. elegans*) | UNC84A | 1.37302 |
| Hs.191334 | uracil-DNA glycosylase | UNG | −1.12501 |
| Hs.159309 | uroplakin 1A | UPK1A | 1.25889 |
| Hs.136778 | ubiquitin specific peptidase 10 | USP10 | −1.06342 |
| Hs.464416 | ubiquitin specific peptidase 14 (tRNA-guanine transglycosylase) | USP14 | −1.40594 |
| Hs.166068 | ubiquitin specific peptidase 37 | USP37 | −1.17024 |
| Hs.96513 | Ubiquitin specific peptidase 40 | USP40 | −1.12769 |
| Hs.467524 | Ubiquitin specific peptidase 48 | USP48 | −1.06636 |
| Hs.406703 | UTP15, U3 small nucleolar ribonucleoprotein, homolog (yeast) | UTP15 | −1.13351 |
| Hs.20021 | vesicle-associated membrane protein 1 (synaptobrevin 1) | VAMP1 | 1.83895 |
| Hs.25348 | vesicle-associated membrane protein 2 (synaptobrevin 2) | VAMP2 | 1.0336 |
| Hs.25348 | vesicle-associated membrane protein 2 (synaptobrevin 2) | VAMP2 | 1.25148 |
| Hs.66708 | vesicle-associated membrane protein 3 (cellubrevin) | VAMP3 | −3.43922 |
| Hs.66708 | vesicle-associated membrane protein 3 (cellubrevin) | VAMP3 | −3.00517 |
| Hs.66708 | vesicle-associated membrane protein 3 (cellubrevin) | VAMP3 | −2.95829 |
| Hs.515130 | vang-like 1 (van gogh, *Drosophila*) | VANGL1 | −2.38658 |
| Hs.515130 | Vang-like 1 (van gogh, *Drosophila*) | VANGL1 | −1.63434 |
| Hs.515130 | vang-like 1 (van gogh, *Drosophila*) | VANGL1 | −1.58932 |
| Hs.99477 | vang-like 2 (van gogh, *Drosophila*) | VANGL2 | 1.90408 |
| Hs.165195 | VAMP (vesicle-associated membrane protein)-associated protein A, 33 kDa | VAPA | −1.27708 |
| Hs.514199 | vesicle amine transport protein 1 homolog (*T californica*) | VAT1 | 1.10246 |
| Hs.267659 | vav 3 oncogene | VAV3 | 1.18062 |
| Hs.249170 | ventral anterior homeobox 2 | VAX2 | 1.05896 |
| Hs.355927 | voltage-dependent anion channel 2 | VDAC2 | −1.37345 |
| Hs.491597 | voltage-dependent anion channel 3 | VDAC3 | −1.29732 |
| Hs.491597 | voltage-dependent anion channel 3 | VDAC3 | −1.04455 |
| Hs.24135 | transmembrane protein vezatin | VEZATIN | 1.62615 |
| Hs.534364 | villin 1 | VIL1 | 3.89723 |
| Hs.487027 | villin 2 (ezrin) | VIL2 | −2.02301 |
| Hs.511668 | vacuolar protein sorting 13C (yeast) | VPS13C | 1.0261 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.511668 | Vacuolar protein sorting 13C (yeast) | VPS13C | 1.65247 |
| Hs.255015 | vacuolar protein sorting 24 (yeast) | VPS24 | 1.14503 |
| Hs.255015 | vacuolar protein sorting 24 (yeast) | VPS24 | 1.2101 |
| Hs.255015 | vacuolar protein sorting 24 (yeast) | VPS24 | 1.32152 |
| Hs.447547 | vacuolar protein sorting 35 (yeast) | VPS35 | −1.05515 |
| Hs.148721 | vacuolar protein sorting 41 (yeast) | VPS41 | 1.34209 |
| Hs.148721 | vacuolar protein sorting 41 (yeast) | VPS41 | 1.5398 |
| Hs.422662 | vaccinia related kinase 1 | VRK1 | −1.36691 |
| Hs.443330 | vaccinia related kinase 3 | VRK3 | 1.624 |
| Hs.516114 | WW domain binding protein 1 | WBP1 | 1.31978 |
| Hs.385998 | WD repeat and HMG-box DNA binding protein 1 | WDHD1 | −2.67897 |
| Hs.385998 | WD repeat and HMG-box DNA binding protein 1 | WDHD1 | −1.92371 |
| Hs.385998 | WD repeat and HMG-box DNA binding protein 1 | WDHD1 | −1.85968 |
| Hs.128548 | WD repeat domain 1 | WDR1 | 1.02563 |
| Hs.128548 | WD repeat domain 1 | WDR1 | 1.07342 |
| Hs.532056 | WD repeat domain 17 | WDR17 | 1.98877 |
| Hs.133331 | WD repeat domain 31 | WDR31 | 1.39708 |
| Hs.493750 | WD repeat domain 40A | WDR40A | −1.37629 |
| Hs.463465 | WD repeat domain 50 | WDR50 | −1.78047 |
| Hs.478095 | WD repeat domain 56 | WDR56 | 1.44822 |
| Hs.478095 | WD repeat domain 56 | WDR56 | 1.46879 |
| Hs.97933 | WD repeat domain 63 | WDR63 | 2.30932 |
| Hs.250154 | WD repeat domain 76 | WDR76 | −1.28428 |
| Hs.389438 | WD and tetratricopeptide repeats 2 | WDTC2 | 1.35418 |
| Hs.113876 | Wolf-Hirschhorn syndrome candidate 1 | WHSC1 | −1.10369 |
| Hs.113876 | Wolf-Hirschhorn syndrome candidate 1 | WHSC1 | 1.21057 |
| Hs.32099 | Wolf-Hirschhorn syndrome candidate 1-like 1 | WHSC1L1 | −1.01105 |
| Hs.386299 | p53 target zinc finger protein | WIG1 | 1.21836 |
| Hs.506985 | WD repeat and SOCS box-containing 2 | WSB2 | −2.6357 |
| Hs.506985 | WD repeat and SOCS box-containing 2 | WSB2 | −2.55938 |
| Hs.477921 | WW domain containing transcription regulator 1 | WWTR1 | −1.51793 |
| Hs.475538 | xeroderma pigmentosum, complementation group C | XPC | 1.44 |
| Hs.370770 | Exportin 1 (CRM1 homolog, yeast) | XPO1 | 1.25975 |
| Hs.85951 | exportin, tRNA (nuclear export receptor for tRNAs) | XPOT | −1.11526 |
| Hs.227656 | Xenotropic and polytropic retrovirus receptor | XPR1 | 2.88274 |
| Hs.503692 | Yes-associated protein 1, 65 kDa | YAP1 | −1.70202 |
| Hs.503692 | Yes-associated protein 1, 65 kDa | YAP1 | −1.66827 |
| Hs.82719 | Yip1 domain family, member 6 | YIPF6 | −2.06789 |
| Hs.82719 | Yip1 domain family, member 6 | YIPF6 | −1.39079 |
| Hs.82719 | Yip1 domain family, member 6 | YIPF6 | −1.31724 |
| Hs.391944 | YOD1 OTU deubiquinating enzyme 1 homolog (yeast) | YOD1 | −2.26119 |
| Hs.391944 | YOD1 OTU deubiquinating enzyme 1 homolog (yeast) | YOD1 | −2.10226 |
| Hs.517436 | yippee-like 1 (*Drosophila*) | YPEL1 | 1.19587 |
| Hs.463613 | yippee-like 2 (*Drosophila*) | YPEL2 | 1.94554 |
| Hs.513491 | yippee-like 3 (*Drosophila*) | YPEL3 | 2.75211 |
| Hs.10056 | Ysg2 homolog (mouse) /// Ysg2 homolog (mouse) | YSG2 | 1.12171 |
| Hs.11747 | YTH domain family, member 1 | YTHDF1 | −1.17086 |
| Hs.98365 | zinc binding alcohol dehydrogenase, domain containing 1 | ZADH1 | 1.55913 |
| Hs.444451 | sterile alpha motif and leucine zipper containing kinase AZK | ZAK | −1.37311 |
| Hs.444451 | sterile alpha motif and leucine zipper containing kinase AZK | ZAK | −1.10919 |
| Hs.444451 | sterile alpha motif and leucine zipper containing kinase AZK | ZAK | 1.2113 |
| Hs.444451 | sterile alpha motif and leucine zipper containing kinase AZK | ZAK | 1.34285 |
| Hs.518301 | zinc finger and BTB domain containing 38 | ZBTB38 | −1.21687 |
| Hs.190477 | Zinc finger CCCH-type containing 6 | ZC3HDC6 | 1.09859 |
| Hs.370424 | zinc finger protein, X-linked | ZFX | 1.14659 |
| Hs.482660 | zinc finger, FYVE domain containing 16 | ZFYVE16 | 1.09813 |
| Hs.533986 | zinc finger, MYM-type 6 | ZMYM6 | −1.61165 |

TABLE 1-continued

Genes with increased (positive values) or decreased (negative values) expression following transfection of human cancer cells with pre-miR hsa-miR-124a.

| UniGene ID | Gene Title | Gene Symbol | Log2 (mir124 - NC #2) |
|---|---|---|---|
| Hs.499453 | zinc finger protein 11B | ZNF11B | 1.50934 |
| Hs.181552 | zinc finger protein 140 (clone pHZ-39) | ZNF140 | −1.04575 |
| Hs.145956 | zinc finger protein 226 | ZNF226 | 1.75717 |
| Hs.499429 | zinc finger protein 25 (KOX 19) | ZNF25 | 1.27101 |
| Hs.314246 | zinc finger protein 271 | ZNF271 | −1.41129 |
| Hs.489722 | zinc finger protein 277 | ZNF277 | 1.11347 |
| Hs.458986 | zinc finger protein 291 | ZNF291 | 1.33906 |
| Hs.458986 | zinc finger protein 291 | ZNF291 | 1.39406 |
| Hs.288773 | zinc finger protein 294 | ZNF294 | −1.61094 |
| Hs.436350 | zinc finger protein 302 | ZNF302 | 1.55881 |
| Hs.435774 | zinc finger protein 33A | ZNF33A | 1.69754 |
| Hs.494557 | zinc finger protein 367 | ZNF367 | −3.04638 |
| Hs.530930 | zinc finger protein 423 | ZNF423 | 1.90391 |
| Hs.529178 | zinc finger protein 512 | ZNF512 | 1.33088 |
| Hs.529178 | zinc finger protein 512 | ZNF512 | 1.35578 |
| Hs.349444 | zinc finger protein 558 | ZNF558 | 1.48459 |
| Hs.511848 | zinc finger protein 569 | ZNF569 | −1.11338 |
| Hs.522147 | zinc finger protein 658 | ZNF658 | 1.21013 |
| Hs.427284 | zinc and ring finger 1 | ZNRF1 | 1.25766 |
| Hs.21331 | Zwilch, kinetochore associated, homolog (*Drosophila*) | ZWILCH | −2.23041 |
| Hs.42650 | ZW10 interactor | ZWINT | −2.92582 |

Manipulation of the expression levels of the genes listed in Table 1 represents a potentially useful therapy for cancer and other diseases in which increased or reduced expression of hsa-miR-124a has a role in the disease.

Example 2

Cellular Pathways Affected by Hsa-miR-124a

The mis-regulation of gene expression by hsa-miR-124a (Table 1) affects many cellular pathways that represent potential therapeutic targets for the control of cancer and other diseases and disorders. The inventors determined the identity and nature of the cellular genetic pathways affected by the regulatory cascade induced by hsa-miR-124a expression. Cellular pathway analyses were performed using Ingenuity Pathways Analysis (Version 4.0, Ingenuity® Systems; Redwood City, Calif., USA). Alteration of a given pathway was determined by Fisher's Exact test (Fisher, 1922). The most significantly affected pathways following over-expression of hsa-miR-124a in A549 cells are shown in Table 2.

TABLE 2

Significantly affected functional cellular pathways following hsa-miR-124a overexpression in human cancer cells.

| Number of Genes | Pathway Functions |
|---|---|
| 33 | Cell Cycle, Gene Expression, Cancer |
| 33 | Cell Cycle, Cell Death, Gene Expression |
| 32 | Cellular Function and Maintenance, Cell Signaling, Molecular Transport |
| 32 | Cancer, Reproductive System Disease, DNA Replication, Recombination, and Repair |
| 32 | Nucleic Acid Metabolism, Cellular Assembly and Organization, DNA Replication, Recombination, and Repair |
| 32 | RNA Post-Transcriptional Modification, Gene Expression, Connective Tissue Development and Function |
| 30 | Cell Death, Embryonic Development, Dermatological Diseases and Conditions |
| 29 | Cell Signaling, Cancer, Cell Morphology |
| 29 | Cell Cycle, Cell Morphology, Connective Tissue Development and Function |
| 29 | Cellular Development, Hematological System Development and Function, Immune and Lymphatic System Development and Function |
| 29 | DNA Replication, Recombination, and Repair, Cellular Assembly and Organization, Cell Cycle |
| 29 | Lipid Metabolism, Molecular Transport, Small Molecule Biochemistry |
| 29 | Cell Cycle, Cellular Assembly and Organization, DNA Replication, Recombination, and Repair |
| 28 | Cell Cycle, Cellular Movement, Cardiovascular System Development and Function |
| 28 | Tissue Development, Genetic Disorder, Immunological Disease |
| 27 | Cell Cycle, Cell Signaling, Embryonic Development |
| 25 | Cell Signaling, Cell Cycle, Hair and Skin Development and Function |
| 24 | Cellular Movement, Connective Tissue Development and Function, Cellular Assembly and Organization |

TABLE 2-continued

Significantly affected functional cellular pathways following hsa-miR-124a overexpression in human cancer cells.

| Number of Genes | Pathway Functions |
|---|---|
| 24 | Cell Signaling, Neurological Disease, Nervous System Development and Function |
| 23 | Cell Morphology, Connective Tissue Development and Function, Cell Signaling |
| 22 | Cellular Assembly and Organization, Tissue Morphology, Cellular Function and Maintenance |
| 22 | DNA Replication, Recombination, and Repair, Cancer, Cell Cycle |
| 22 | Hematological Disease, Drug Metabolism, Lipid Metabolism |
| 21 | Cellular Assembly and Organization, Cell-To-Cell Signaling and Interaction, Cellular Function and Maintenance |
| 16 | Gene Expression, Cancer, Cell-To-Cell Signaling and Interaction |
| 20 | Cell Cycle, Connective Tissue Development and Function, Reproductive System Development and Function |
| 20 | Cancer, Reproductive System Disease, Protein Synthesis |
| 20 | DNA Replication, Recombination, and Repair, Cell Death, Cancer |
| 20 | Cancer, Cardiovascular System Development and Function, Cell Cycle |
| 17 | Gene Expression, Cell Cycle, Reproductive System Development and Function |
| 19 | Cell Cycle, Gene Expression, Connective Tissue Development and Function |
| 19 | Cell Cycle, DNA Replication, Recombination, and Repair, Cancer |
| 19 | Organismal Functions, Digestive System Development and Function, Cell Morphology |
| 19 | Cell Signaling, Hair and Skin Development and Function, Cell Morphology |
| 19 | Drug Metabolism, Nucleic Acid Metabolism, Small Molecule Biochemistry |
| 19 | Cell Signaling, Cellular Assembly and Organization, Cellular Function and Maintenance |
| 19 | Post-Translational Modification, Gene Expression, Skeletal and Muscular System Development and Function |
| 18 | Cell-To-Cell Signaling and Interaction, Tissue Development, Dermatological Diseases and Conditions |
| 18 | Endocrine System Disorders, Metabolic Disease, Cell Cycle |
| 18 | Cancer, Cellular Response to Therapeutics, Reproductive System Disease |
| 17 | Cancer, Cell Cycle, Reproductive System Disease |
| 17 | Cell Cycle, Cell Death, Cancer |
| 17 | Cell-To-Cell Signalin and Interaction, Cellular Compromise, Amino Acid Metabolism |
| 17 | Cell Morphology, Cell-To-Cell Signaling and Interaction, Hematological System Development and Function |
| 17 | Cell-To-Cell Signaling and Interaction, Cellular Growth and Proliferation, Hematological System Development and Function |
| 17 | Cardiovascular System Development and Function, Cardiovascular Disease, Organismal Injury and Abnormalities |
| 15 | Gene Expression, Organ Development, Organ Morphology |
| 16 | Gastrointestinal Disease, Hepatic System Disease, Cell Death |
| 16 | Cell Cycel, Post-Translational Modification, Neurological Disease |
| 16 | Cell Death, Hematological Disease, Immunological Disease |
| 16 | Cancer, Immune Response, Hematological Disease |
| 16 | Amino Acid Metabolism, Post-Translational Modification, Small Molecule Biochemistry |
| 15 | Cell Cycle, Cellular Movement, Connective Tissue Development and Function |
| 15 | Embryonic Development, Tissue Development, Cellular Development |
| 15 | Cell Death, Hematological Disease, Immunological Disease |
| 15 | Amino Acid Metabolism, Hematological Disease, Cellular Assembly and Organization |
| 15 | RNA Post-Transcriptional Modification, Cellular Assembly and Organization, Cell Cycle |
| 14 | Cell Cycle, DNA Replication, Recombination, and Repair, Cellular Assembly and Organization |
| 14 | Cell Signaling, Gene Expression, Cancer |
| 13 | Cancer, Dermatological Diseases and Conditions, Carbohydrate Metabolism |
| 13 | Protein Synthesis, Nucleic Acid Metabolism, Protein Degradation |
| 9 | Lipid Metabolism, Molecular Transport, Small Molecule Biochemistry |

These data demonstrate that hsa-miR-124a directly or indirectly affects the expression of numerous cancer-, cellular proliferation-, cellular development-, cell signaling-, and cell cycle-related genes and thus primarily affects functional pathways related to cancer, cellular growth, development, and proliferation. Those cellular processes all have integral roles in the development and progression of various cancers. Manipulation of the expression levels of genes in the cellular pathways shown in Table 2 represents a potentially useful therapy for cancer and other diseases in which increased or reduced expression of hsa-miR-124a has a role in the disease.

Example 3

Predicted Gene Targets of Hsa-miR-124a

Gene targets for binding of and regulation by hsa-miR-124a were predicted using the proprietary algorithm miRNA-Target™ (Asuragen), which is an implementation of the method proposed by Krek et al. (Krek et al., 2005). Predicted target genes are shown in Table 3.

TABLE 3

Predicted target genes of hsa-miR-124a.

| Gene Symbol | RefSeq Transcript ID (Pruitt et al., 2005) | Description |
| --- | --- | --- |
| ABCA2 | NM_001606 | ATP-binding cassette, sub-family A, member 2 |
| ABCA2 | NM_212533 | ATP-binding cassette, sub-family A, member 2 |
| ABCC4 | NM_005845 | ATP-binding cassette, sub-family C, member 4 |
| ABHD3 | NM_138340 | alpha/beta hydrolase domain containing protein |
| ABHD7 | NM_173567 | abhydrolase domain containing 7 |
| ABR | NM_001092 | active breakpoint cluster region-related |
| ABR | NM_021962 | active breakpoint cluster region-related |
| ACACA | NM_198834 | acetyl-Coenzyme A carboxylase alpha isoform 1 |
| ACACA | NM_198836 | acetyl-Coenzyme A carboxylase alpha isoform 2 |
| ACACA | NM_198837 | acetyl-Coenzyme A carboxylase alpha isoform 3 |
| ACACA | NM_198838 | acetyl-Coenzyme A carboxylase alpha isoform 4 |
| ACACA | NM_198839 | acetyl-Coenzyme A carboxylase alpha isoform 2 |
| ACCN2 | NM_001095 | amiloride-sensitive cation channel 2, neuronal |
| ACCN2 | NM_020039 | amiloride-sensitive cation channel 2, neuronal |
| ACSL1 | NM_001995 | acyl-CoA synthetase long-chain family member 1 |
| ACVR2A | NM_001616 | activin A receptor, type IIA precursor |
| ADCY1 | NM_021116 | brain adenylate cyclase 1 |
| ADIPOR2 | NM_024551 | adiponectin receptor 2 |
| AFF3 | NM_001025108 | AF4/FMR2 family, member 3 isoform 2 |
| AFF3 | NM_002285 | AF4/FMR2 family, member 3 isoform 1 |
| AFF4 | NM_014423 | ALL1 fused gene from 5q31 |
| AHCYL1 | NM_006621 | S-adenosylhomocysteine hydrolase-like 1 |
| AHR | NM_001621 | aryl hydrocarbon receptor |
| AKAP1 | NM_139275 | A-kinase anchor protein 1 isoform 2 precursor |
| AKT3 | NM_005465 | v-akt murine thymoma viral oncogene homolog 3 |
| ALCAM | NM_001627 | activated leukocyte cell adhesion molecule |
| ALG2 | NM_033087 | alpha-1,3-mannosyltransferase ALG2 isoform 1 |
| ALG2 | NM_197973 | alpha-1,3-mannosyltransferase ALG2 isoform 2 |
| ANGEL1 | NM_015305 | angel homolog 1 |
| ANK1 | NM_000037 | ankyrin 1 isoform 3 |
| ANK1 | NM_020475 | ankyrin 1 isoform 4 |
| ANK1 | NM_020476 | ankyrin 1 isoform 1 |
| ANK1 | NM_020477 | ankyrin 1 isoform 2 |
| ANK1 | NM_020478 | ankyrin 1 isoform 5 |
| ANK1 | NM_020479 | ankyrin 1 isoform 6 |
| ANK1 | NM_020480 | ankyrin 1 isoform 7 |
| ANK1 | NM_020481 | ankyrin 1 isoform 8 |
| ANKFY1 | NM_016376 | ankyrin repeat and FYVE domain containing 1 |
| ANKRD13 | NM_033121 | ankyrin repeat domain 13 |
| ANKRD15 | NM_015158 | ankyrin repeat domain protein 15 isoform a |
| ANKRD15 | NM_153186 | ankyrin repeat domain protein 15 isoform b |
| ANTXR2 | NM_058172 | anthrax toxin receptor 2 |
| ANXA11 | NM_001157 | annexin A11 |
| ANXA11 | NM_145868 | annexin A11 |
| ANXA11 | NM_145869 | annexin A11 |
| ANXA5 | NM_001154 | annexin 5 |
| ANXA7 | NM_001156 | annexin VII isoform 1 |
| ANXA7 | NM_004034 | annexin VII isoform 2 |
| AOF1 | NM_153042 | amine oxidase (flavin containing) domain 1 |
| AP1G1 | NM_001030007 | adaptor-related protein complex 1, gamma 1 |
| AP1G1 | NM_001128 | adaptor-related protein complex 1, gamma 1 |
| AP3M1 | NM_012095 | adaptor-related protein complex 3, mu 1 subunit |
| AP3M1 | NM_207012 | adaptor-related protein complex 3, mu 1 subunit |
| ARFIP1 | NM_001025593 | ADP-ribosylation factor interacting protein 1 |
| ARFIP1 | NM_001025595 | ADP-ribosylation factor interacting protein 1 |
| ARFIP1 | NM_014447 | ADP-ribosylation factor interacting protein 1 |
| ARG2 | NM_001172 | arginase, type II precursor |
| ARHGDIA | NM_004309 | Rho GDP dissociation inhibitor (GDI) alpha |
| ARHGEF4 | NM_032995 | Rho guanine nucleotide exchange factor 4 isoform |
| ARHGEF4 | NM_015320 | Rho guanine nucleotide exchange factor 4 isoform |
| ARHGEF7 | NM_003899 | Rho guanine nucleotide exchange factor 7 isoform |
| ARL8B | NM_018184 | ADP-ribosylation factor-like 10C |
| ARPC5 | NM_005717 | actin related protein 2/3 complex subunit 5 |
| ARPP-19 | NM_006628 | cyclic AMP phosphoprotein, 19 kD |
| ASB1 | NM_016114 | ankyrin repeat and SOCS box-containing protein |
| ASCC2 | NM_032204 | activating signal cointegrator 1 complex subunit |
| ASCIZ | NM_015251 | ATM/ATR-Substrate Chk2-Interacting Zn2+-finger |
| ATF7IP | NM_018179 | activating transcription factor 7 interacting |
| ATP11A | NM_032189 | ATPase, Class VI, type 11A isoform b |
| ATP11A | NM_015205 | ATPase, Class VI, type 11A isoform a |
| ATP6V0A2 | NM_012463 | ATPase, H+ transporting, lysosomal V0 subunit a |
| ATP6V0E | NM_003945 | ATPase, H+ transporting, lysosomal, V0 subunit |
| ATP7A | NM_000052 | ATPase, Cu++ transporting, alpha polypeptide |
| ATRX | NM_000489 | transcriptional regulator ATRX isoform 1 |

TABLE 3-continued

Predicted target genes of hsa-miR-124a.

| Gene Symbol | RefSeq Transcript ID (Pruitt et al., 2005) | Description |
|---|---|---|
| ATRX | NM_138270 | transcriptional regulator ATRX isoform 2 |
| ATRX | NM_138271 | transcriptional regulator ATRX isoform 3 |
| B4GALT1 | NM_001497 | UDP-Gal:betaGlcNAc beta 1,4- |
| BACE1 | NM_012104 | beta-site APP-cleaving enzyme 1 isoform A |
| BACE1 | NM_138971 | beta-site APP-cleaving enzyme 1 isoform C |
| BACE1 | NM_138972 | beta-site APP-cleaving enzyme 1 isoform B |
| BACE1 | NM_138973 | beta-site APP-cleaving enzyme 1 isoform D |
| BACH2 | NM_021813 | BTB and CNC homology 1, basic leucine zipper |
| BAHD1 | NM_014952 | bromo adjacent homology domain containing 1 |
| BAZ2B | NM_013450 | bromodomain adjacent to zinc finger domain, 2B |
| BC002942 | NM_033200 | hypothetical protein LOC91289 |
| BCL2L11 | NM_006538 | BCL2-like 11 isoform 6 |
| BCL2L11 | NM_138621 | BCL2-like 11 isoform 1 |
| BCL2L11 | NM_138622 | BCL2-like 11 isoform 2 |
| BCL2L11 | NM_138623 | BCL2-like 11 isoform 3 |
| BCL2L11 | NM_138624 | BCL2-like 11 isoform 4 |
| BCL2L11 | NM_138626 | BCL2-like 11 isoform 7 |
| BCL2L11 | NM_138627 | BCL2-like 11 isoform 8 |
| BCL2L11 | NM_207003 | BCL2-like 11 isoform 10 |
| BRP44L | NM_016098 | brain protein 44-like |
| BRWD1 | NM_033656 | bromodomain and WD repeat domain containing 1 |
| BRWD3 | NM_153252 | bromo domain-containing protein disrupted in |
| BTBD14B | NM_052876 | transcriptional repressor NAC1 |
| C10orf12 | NM_015652 | hypothetical protein LOC26148 |
| C10orf39 | NM_194303 | hypothetical protein LOC282973 |
| C10orf56 | NM_153367 | hypothetical protein LOC219654 |
| C11orf9 | NM_013279 | hypothetical protein LOC745 |
| C13orf23 | NM_025138 | hypothetical protein LOC80209 |
| C13orf23 | NM_170719 | hypothetical protein LOC80209 |
| C14orf162 | NM_020181 | chromosome 14 open reading frame 162 |
| C15orf29 | NM_024713 | hypothetical protein LOC79768 |
| C17orf63 | NM_018182 | hypothetical protein LOC55731 |
| C1orf108 | NM_024595 | hypothetical protein LOC79647 |
| C1orf121 | NM_016076 | hypothetical protein LOC51029 |
| C1orf198 | NM_032800 | hypothetical protein LOC84886 |
| C1orf21 | NM_030806 | chromosome 1 open reading frame 21 |
| C1QL3 | NM_001010908 | complement component 1, q subcomponent-like 3 |
| C20orf133 | NM_001033086 | hypothetical protein LOC140733 isoform 1 |
| C20orf133 | NM_001033087 | hypothetical protein LOC140733 isoform 2 |
| C4orf13 | NM_001029998 | hypothetical protein LOC84068 isoform b |
| C9orf25 | NM_147202 | hypothetical protein LOC203259 |
| CACNA2D2 | NM_001005505 | calcium channel, voltage-dependent, alpha |
| CACNA2D2 | NM_006030 | calcium channel, voltage-dependent, alpha |
| CACNB3 | NM_000725 | calcium channel, voltage-dependent, beta 3 |
| CADPS | NM_003716 | Ca2+-dependent secretion activator isoform 1 |
| CADPS | NM_183393 | Ca2+-dependent secretion activator isoform 3 |
| CADPS | NM_183394 | Ca2+-dependent secretion activator isoform 2 |
| CAPN2 | NM_001748 | calpain 2, large subunit |
| CAPN6 | NM_014289 | calpain 6 |
| CASC3 | NM_007359 | cancer susceptibility candidate 3 |
| CASC4 | NM_138423 | cancer susceptibility candidate 4 isoform a |
| CASC4 | NM_177974 | cancer susceptibility candidate 4 isoform b |
| CAST1 | NM_015576 | cytomatrix protein p110 |
| CBFB | NM_022845 | core-binding factor, beta subunit isoform 1 |
| CBFB | NM_001755 | core-binding factor, beta subunit isoform 2 |
| CBLN2 | NM_182511 | cerebellin 2 precursor |
| CCDC28A | NM_015439 | hypothetical protein LOC25901 |
| CCL2 | NM_002982 | small inducible cytokine A2 precursor |
| CCND2 | NM_001759 | cyclin D2 |
| CCNL2 | NM_030937 | cyclin L2 isoform A |
| CD164 | NM_006016 | CD164 antigen, sialomucin |
| CD276 | NM_001024736 | CD276 antigen isoform a |
| CD276 | NM_025240 | CD276 antigen isoform b |
| CDH11 | NM_001797 | cadherin 11, type 2 preproprotein |
| CDK4 | NM_000075 | cyclin-dependent kinase 4 |
| CDK6 | NM_001259 | cyclin-dependent kinase 6 |
| CEACAM1 | NM_001024912 | carcinoembryonic antigen-related cell adhesion |
| CEACAM1 | NM_001712 | carcinoembryonic antigen-related cell adhesion |
| CEBPG | NM_001806 | CCAAT/enhancer binding protein gamma |
| CELSR3 | NM_001407 | cadherin EGF LAG seven-pass G-type receptor 3 |
| CEP350 | NM_014810 | centrosome-associated protein 350 |
| CFL2 | NM_021914 | cofilin 2 |
| CFL2 | NM_138638 | cofilin 2 |
| CGN | NM_020770 | Cingulin |

TABLE 3-continued

Predicted target genes of hsa-miR-124a.

| Gene Symbol | RefSeq Transcript ID (Pruitt et al., 2005) | Description |
|---|---|---|
| CHMP2B | NM_014043 | chromatin modifying protein 2B |
| CHP | NM_007236 | calcium binding protein P22 |
| CHST1 | NM_003654 | carbohydrate (keratan sulfate Gal-6) |
| CHSY1 | NM_014918 | carbohydrate (chondroitin) synthase 1 |
| CLDN11 | NM_005602 | claudin 11 |
| CNOT7 | NM_013354 | CCR4-NOT transcription complex, subunit 7 |
| CNTN3 | NM_020872 | contactin 3 |
| COL12A1 | NM_004370 | alpha 1 type XII collagen long isoform |
| COL12A1 | NM_080645 | alpha 1 type XII collagen short isoform |
| COL4A1 | NM_001845 | alpha 1 type IV collagen preproprotein |
| CPNE5 | NM_020939 | copine V |
| CPNE8 | NM_153634 | copine VIII |
| CREB1 | NM_004379 | cAMP responsive element binding protein 1 |
| CREB1 | NM_134442 | cAMP responsive element binding protein 1 |
| CRSP7 | NM_004831 | cofactor required for Sp1 transcriptional |
| CSNK1G1 | NM_001011664 | casein kinase 1, gamma 1 isoform L |
| CSNK1G1 | NM_022048 | casein kinase 1, gamma 1 isoform S |
| CSTF3 | NM_001326 | cleavage stimulation factor subunit 3 isoform 1 |
| CTDSP2 | NM_005730 | nuclear LIM interactor-interacting factor 2 |
| CTDSPL | NM_001008392 | small CTD phosphatase 3 isoform 1 |
| CTDSPL | NM_005808 | small CTD phosphatase 3 isoform 2 |
| CTNS | NM_001031681 | cystinosis, nephropathic isoform 1 |
| CTNS | NM_004937 | cystinosis, nephropathic isoform 2 |
| CUL5 | NM_003478 | Vasopressin-activated calcium-mobilizing |
| DCHS1 | NM_003737 | dachsous 1 precursor |
| DDX6 | NM_004397 | DEAD (Asp-Glu-Ala-Asp) box polypeptide 6 |
| DHX40 | NM_024612 | DEAH (Asp-Glu-Ala-His) box polypeptide 40 |
| DIAPH1 | NM_005219 | diaphanous 1 |
| DIXDC1 | NM_033425 | DIX domain containing 1 isoform b |
| DKFZp564K142 | NM_032121 | implantation-associated protein |
| DKFZP686A01247 | NM_014988 | hypothetical protein LOC22998 |
| DKFZp686K16132 | NM_001012987 | hypothetical protein LOC388957 |
| DLGAP2 | NM_004745 | discs large-associated protein 2 |
| DMD | NM_000109 | dystrophin Dp427c isoform |
| DMD | NM_004006 | dystrophin Dp427m isoform |
| DMD | NM_004007 | dystrophin Dp427l isoform |
| DMD | NM_004009 | dystrophin Dp427p1 isoform |
| DMD | NM_004010 | dystrophin Dp427p2 isoform |
| DMD | NM_004011 | dystrophin Dp260-1 isoform |
| DMD | NM_004012 | dystrophin Dp260-2 isoform |
| DMD | NM_004013 | dystrophin Dp140 isoform |
| DMD | NM_004014 | dystrophin Dp116 isoform |
| DMD | NM_004015 | dystrophin Dp71 isoform |
| DMD | NM_004016 | dystrophin Dp71b isoform |
| DMD | NM_004017 | dystrophin Dp71a isoform |
| DMD | NM_004018 | dystrophin Dp71ab isoform |
| DMD | NM_004020 | dystrophin Dp140c isoform |
| DMD | NM_004021 | dystrophin Dp140b isoform |
| DMD | NM_004022 | dystrophin Dp140ab isoform |
| DMD | NM_004023 | dystrophin Dp140bc isoform |
| DMXL1 | NM_005509 | Dmx-like 1 |
| DNAJB12 | NM_001002762 | DnaJ (Hsp40) homolog, subfamily B, member 12 |
| DNAJB12 | NM_017626 | DnaJ (Hsp40) homolog, subfamily B, member 12 |
| DUSP15 | NM_001012644 | dual specificity phosphatase 15 isoform b |
| DUSP15 | NM_080611 | dual specificity phosphatase 15 isoform a |
| DUSP15 | NM_177991 | dual specificity phosphatase 15 isoform b |
| DYNC1LI2 | NM_006141 | dynein, cytoplasmic, light intermediate |
| DYNLT3 | NM_006520 | t-complex-associated-testis-expressed 1-like |
| E2F6 | NM_001952 | E2F transcription factor 6 isoform 1 |
| E2F6 | NM_198256 | E2F transcription factor 6 isoform 2 |
| E2F6 | NM_198257 | E2F transcription factor 6 isoform 3 |
| E2F6 | NM_198258 | E2F transcription factor 6 isoform 3 |
| E2F6 | NM_198325 | E2F transcription factor 6 isoform 3 |
| E2F6 | NM_212540 | E2F transcription factor 6 isoform 4 |
| EBF | NM_024007 | early B-cell factor |
| EBF3 | NM_001005463 | early B-cell factor 3 |
| EDEM1 | NM_014674 | ER degradation enhancer, mannosidase alpha-like |
| EDNRB | NM_000115 | endothelin receptor type B isoform 1 |
| EFNB2 | NM_004093 | ephrin B2 |
| EGR1 | NM_001964 | early growth response 1 |
| EIF2C1 | NM_012199 | eukaryotic translation initiation factor 2C, 1 |
| EIF3S1 | NM_003758 | eukaryotic translation initiation factor 3, |
| ELAVL1 | NM_001419 | ELAV-like 1 |
| ELK3 | NM_005230 | ELK3 protein |

TABLE 3-continued

Predicted target genes of hsa-miR-124a.

| Gene Symbol | RefSeq Transcript ID (Pruitt et al., 2005) | Description |
| --- | --- | --- |
| ELL2 | NM_012081 | elongation factor, RNA polymerase II, 2 |
| ELOVL2 | NM_017770 | elongation of very long chain fatty acids |
| ELOVL5 | NM_021814 | homolog of yeast long chain polyunsaturated |
| EMD | NM_000117 | Emerin |
| EMP2 | NM_001424 | epithelial membrane protein 2 |
| EN2 | NM_001427 | engrailed homolog 2 |
| EPB41L3 | NM_012307 | erythrocyte membrane protein band 4.1-like 3 |
| EPHA3 | NM_005233 | ephrin receptor EphA3 isoform a precursor |
| ERF | NM_006494 | Ets2 repressor factor |
| ETF1 | NM_004730 | eukaryotic translation termination factor 1 |
| ETS1 | NM_005238 | v-ets erythroblastosis virus E26 oncogene |
| ETV1 | NM_004956 | ets variant gene 1 |
| EVI1 | NM_005241 | ecotropic viral integration site 1 |
| EXTL3 | NM_001440 | Reg receptor |
| EYA1 | NM_000503 | eyes absent 1 isoform b |
| EYA1 | NM_172058 | eyes absent 1 isoform b |
| EYA1 | NM_172059 | eyes absent 1 isoform c |
| EYA1 | NM_172060 | eyes absent 1 isoform a |
| EYA2 | NM_005244 | eyes absent 2 isoform a |
| EYA2 | NM_172110 | eyes absent 2 isoform c |
| EYA2 | NM_172111 | eyes absent 2 isoform a |
| EYA2 | NM_172112 | eyes absent 2 isoform a |
| EYA2 | NM_172113 | eyes absent 2 isoform b |
| EYA4 | NM_004100 | eyes absent 4 isoform a |
| EYA4 | NM_172103 | eyes absent 4 isoform b |
| EYA4 | NM_172104 | eyes absent 4 isoform c |
| EYA4 | NM_172105 | eyes absent 4 isoform d |
| F11R | NM_016946 | F11 receptor isoform a precursor |
| F11R | NM_144501 | F11 receptor isoform a precursor |
| F11R | NM_144502 | F11 receptor isoform b |
| F11R | NM_144503 | F11 receptor isoform a precursor |
| F11R | NM_144504 | F11 receptor isoform a precursor |
| FAM107B | NM_031453 | hypothetical protein LOC83641 |
| FAM38B | NM_022068 | hypothetical protein LOC63895 |
| FAM53B | NM_014661 | hypothetical protein LOC9679 |
| FAM78A | NM_033387 | hypothetical protein LOC286336 |
| FARP1 | NM_005766 | FERM, RhoGEF, and pleckstrin domain protein 1 |
| FBXL7 | NM_012304 | F-box and leucine-rich repeat protein 7 |
| FGFR2 | NM_023028 | fibroblast growth factor receptor 2 isoform 10 |
| FGFR2 | NM_000141 | fibroblast growth factor receptor 2 isoform 1 |
| FGFR2 | NM_022969 | fibroblast growth factor receptor 2 isoform 2 |
| FGFR2 | NM_022970 | fibroblast growth factor receptor 2 isoform 3 |
| FGFR2 | NM_022972 | fibroblast growth factor receptor 2 isoform 5 |
| FGFR2 | NM_022975 | fibroblast growth factor receptor 2 isoform 8 |
| FGFR2 | NM_023029 | fibroblast growth factor receptor 2 isoform 11 |
| FGFR2 | NM_023030 | fibroblast growth factor receptor 2 isoform 12 |
| FGFR2 | NM_023031 | fibroblast growth factor receptor 2 isoform 13 |
| FLJ10154 | NM_018011 | hypothetical protein LOC55082 |
| FLJ11021 | NM_023012 | hypothetical protein LOC65117 isoform a |
| FLJ11021 | NM_198261 | hypothetical protein LOC65117 isoform b |
| FLJ11021 | NM_198262 | hypothetical protein LOC65117 isoform c |
| FLJ13576 | NM_022484 | hypothetical protein LOC64418 |
| FLJ20054 | NM_019049 | hypothetical protein LOC54530 |
| FLJ20489 | NM_017842 | hypothetical protein LOC55652 |
| FLJ20701 | NM_017933 | hypothetical protein LOC55022 |
| FLJ22222 | NM_175902 | hypothetical protein LOC79701 isoform 2 |
| FLJ22222 | NM_024648 | hypothetical protein LOC79701 isoform 1 |
| FLJ25476 | NM_152493 | hypothetical protein LOC149076 |
| FLJ25530 | NM_152722 | hepatocyte cell adhesion molecule |
| FLJ33814 | NM_173510 | hypothetical protein LOC150275 |
| FLJ34931 | NM_001029883 | hypothetical protein LOC388939 |
| FLOT2 | NM_004475 | flotillin 2 |
| FNBP1L | NM_001024948 | formin binding protein 1-like isoform 1 |
| FNBP1L | NM_017737 | formin binding protein 1-like isoform 2 |
| FOXQ1 | NM_033260 | forkhead box Q1 |
| GAS2 | NM_005256 | growth arrest-specific 2 |
| GAS2 | NM_177553 | growth arrest-specific 2 |
| GAS2L1 | NM_006478 | growth arrest-specific 2 like 1 isoform a |
| GAS2L1 | NM_152236 | growth arrest-specific 2 like 1 isoform a |
| GAS2L1 | NM_152237 | growth arrest-specific 2 like 1 isoform b |
| GCN1L1 | NM_006836 | GCN1 general control of amino-acid synthesis |
| Gcom1 | NM_001018100 | GRINL1A upstream protein isoform 7 |
| Gcom1 | NM_001018101 | GRINL1A upstream protein isoform 8 |
| GLCE | NM_015554 | D-glucuronyl C5-epimerase |

TABLE 3-continued

Predicted target genes of hsa-miR-124a.

| Gene Symbol | RefSeq Transcript ID (Pruitt et al., 2005) | Description |
|---|---|---|
| GLRB | NM_000824 | glycine receptor, beta |
| GLT8D1 | NM_001010983 | glycosyltransferase 8 domain containing 1 |
| GLT8D1 | NM_018446 | glycosyltransferase 8 domain containing 1 |
| GLT8D1 | NM_152932 | glycosyltransferase 8 domain containing 1 |
| GLTP | NM_016433 | glycolipid transfer protein |
| GNA13 | NM_006572 | guanine nucleotide binding protein (G protein), |
| GNPDA2 | NM_138335 | glucosamine-6-phosphate deaminase 2 |
| GOLT1B | NM_016072 | golgi transport 1 homolog B |
| GPR85 | NM_018970 | G protein-coupled receptor 85 |
| GRIA2 | NM_000826 | glutamate receptor, ionotropic, AMPA 2 |
| GRID1 | NM_017551 | glutamate receptor, ionotropic, delta 1 |
| GRM1 | NM_000838 | glutamate receptor, metabotropic 1 |
| HDAC4 | NM_006037 | histone deacetylase 4 |
| HDAC5 | NM_001015053 | histone deacetylase 5 isoform 3 |
| HDAC5 | NM_005474 | histone deacetylase 5 isoform 1 |
| HIAT1 | NM_033055 | hippocampus abundant transcript 1 |
| HIATL1 | NM_032558 | hypothetical protein LOC84641 |
| HIC1 | NM_006497 | hypermethylated in cancer 1 |
| HIPK1 | NM_181358 | homeodomain-interacting protein kinase 1 isoform |
| HIPK1 | NM_198268 | homeodomain-interacting protein kinase 1 isoform |
| HIPK1 | NM_198269 | homeodomain-interacting protein kinase 1 isoform |
| HMFN0839 | NM_032717 | hypothetical protein LOC84803 |
| HMG2L1 | NM_001003681 | high-mobility group protein 2-like 1 isoform b |
| HMG2L1 | NM_005487 | high-mobility group protein 2-like 1 isoform a |
| HMG2L1 | NM_014250 | high-mobility group protein 2-like 1 isoform a |
| HMGA1 | NM_002131 | high mobility group AT-hook 1 isoform b |
| HMGA1 | NM_145899 | high mobility group AT-hook 1 isoform a |
| HMGA1 | NM_145901 | high mobility group AT-hook 1 isoform a |
| HMGA1 | NM_145902 | high mobility group AT-hook 1 isoform b |
| HMGA1 | NM_145903 | high mobility group AT-hook 1 isoform b |
| HMGA1 | NM_145904 | high mobility group AT-hook 1 isoform a |
| HMGA1 | NM_145905 | high mobility group AT-hook 1 isoform b |
| ICMT | NM_012405 | isoprenylcysteine carboxyl methyltransferase |
| IGSF4 | NM_014333 | immunoglobulin superfamily, member 4 |
| ILKAP | NM_176799 | integrin-linked kinase-associated protein |
| IQGAP1 | NM_003870 | IQ motif containing GTPase activating protein 1 |
| ITGA11 | NM_001004439 | integrin, alpha 11 precursor |
| ITGA11 | NM_012211 | integrin, alpha 11 precursor |
| ITPR3 | NM_002224 | inositol 1,4,5-triphosphate receptor, type 3 |
| JAG1 | NM_000214 | jagged 1 precursor |
| JAKMIP1 | NM_144720 | multiple coiled-coil GABABR1-binding protein |
| JPH1 | NM_020647 | junctophilin 1 |
| KCNK10 | NM_138317 | potassium channel, subfamily K, member 10 |
| KCNK10 | NM_138318 | potassium channel, subfamily K, member 10 |
| KCNK10 | NM_021161 | potassium channel, subfamily K, member 10 |
| KCNK2 | NM_001017424 | potassium channel, subfamily K, member 2 isoform |
| KCNK2 | NM_001017425 | potassium channel, subfamily K, member 2 isoform |
| KCNK2 | NM_014217 | potassium channel, subfamily K, member 2 isoform |
| KCNQ2 | NM_004518 | potassium voltage-gated channel KQT-like protein |
| KCTD12 | NM_138444 | potassium channel tetramerisation domain |
| KIAA0174 | NM_014761 | putative MAPK activating protein PM28 |
| KIAA0376 | NM_015330 | cytospin A |
| KIAA0408 | NM_014702 | hypothetical protein LOC9729 |
| KIAA0494 | NM_014774 | hypothetical protein LOC9813 |
| KIAA0564 | NM_015058 | hypothetical protein LOC23078 isoform a |
| KIAA0676 | NM_015043 | hypothetical protein LOC23061 isoform b |
| KIAA0676 | NM_198868 | hypothetical protein LOC23061 isoform a |
| KIAA1024 | NM_015206 | hypothetical protein LOC23251 |
| KIAA1161 | NM_020702 | hypothetical protein LOC57462 |
| KIAA1244 | NM_020340 | hypothetical protein LOC57221 |
| KIAA1324L | NM_152748 | hypothetical protein LOC222223 |
| KIAA1522 | NM_020888 | hypothetical protein LOC57648 |
| KIAA1576 | NM_020927 | hypothetical protein LOC57687 |
| KIAA1815 | NM_024896 | hypothetical protein LOC79956 |
| KIAA2022 | NM_001008537 | hypothetical protein LOC340533 |
| KIF5A | NM_004984 | kinesin family member 5A |
| KLC2 | NM_022822 | likely ortholog of kinesin light chain 2 |
| KLF12 | NM_007249 | Kruppel-like factor 12 isoform a |
| KLF13 | NM_015995 | Kruppel-like factor 13 |
| KLF4 | NM_004235 | Kruppel-like factor 4 (gut) |
| KLHL24 | NM_017644 | DRE1 protein |
| KRAS | NM_004985 | c-K-ras2 protein isoform b |
| LAMC1 | NM_002293 | laminin, gamma 1 precursor |
| LARP4 | NM_052879 | c-Mpl binding protein isoform a |

TABLE 3-continued

Predicted target genes of hsa-miR-124a.

| Gene Symbol | RefSeq Transcript ID (Pruitt et al., 2005) | Description |
|---|---|---|
| LARP4 | NM_199188 | c-Mpl binding protein isoform b |
| LARP4 | NM_199190 | c-Mpl binding protein isoform c |
| LARP5 | NM_015155 | La ribonucleoprotein domain family, member 5 |
| LASS2 | NM_013384 | LAG1 longevity assurance homolog 2 isoform 2 |
| LASS2 | NM_022075 | LAG1 longevity assurance homolog 2 isoform 1 |
| LASS2 | NM_181746 | LAG1 longevity assurance homolog 2 isoform 1 |
| LHX2 | NM_004789 | LIM homeobox protein 2 |
| LIN28B | NM_001004317 | lin-28 homolog B |
| LITAF | NM_004862 | LPS-induced TNF-alpha factor |
| LMAN2L | NM_030805 | lectin, mannose-binding 2-like |
| LMBRD2 | NM_001007527 | LMBR1 domain containing 2 |
| LMNA | NM_170707 | lamin A/C isoform 1 precursor |
| LMNA | NM_170708 | lamin A/C isoform 3 |
| LMNB1 | NM_005573 | lamin B1 |
| LNK | NM_005475 | lymphocyte adaptor protein |
| LOC144097 | NM_138471 | hypothetical protein LOC144097 |
| LOC153364 | NM_203406 | similar to metallo-beta-lactamase superfamily |
| LOC285382 | NM_001025266 | hypothetical protein LOC285382 |
| LOC339745 | NM_001001664 | hypothetical protein LOC339745 |
| LONRF1 | NM_152271 | hypothetical protein LOC91694 |
| LPIN1 | NM_145693 | lipin 1 |
| LPP | NM_005578 | LIM domain containing preferred translocation |
| LRIG1 | NM_015541 | leucine-rich repeats and immunoglobulin-like |
| LRP6 | NM_002336 | low density lipoprotein receptor-related protein |
| LRRC57 | NM_153260 | hypothetical protein LOC255252 |
| LSM16 | NM_025083 | LSM16 homolog (EDC3, S. cerevisiae) |
| LYCAT | NM_001002257 | lysocardiolipin acyltransferase isoform 2 |
| LYCAT | NM_182551 | lysocardiolipin acyltransferase isoform 1 |
| MACF1 | NM_012090 | microfilament and actin filament cross-linker |
| MACF1 | NM_033044 | microfilament and actin filament cross-linker |
| MAGI2 | NM_012301 | membrane associated guanylate kinase, WW and PDZ |
| MAP1B | NM_005909 | microtubule-associated protein 1B isoform 1 |
| MAP1B | NM_032010 | microtubule-associated protein 1B isoform 2 |
| MAP2K4 | NM_003010 | mitogen-activated protein kinase kinase 4 |
| MAP7 | NM_003980 | microtubule-associated protein 7 |
| MAPK14 | NM_001315 | mitogen-activated protein kinase 14 isoform 1 |
| MAPK14 | NM_139012 | mitogen-activated protein kinase 14 isoform 2 |
| MAPK14 | NM_139014 | mitogen-activated protein kinase 14 isoform 4 |
| MAPK4 | NM_002747 | mitogen-activated protein kinase 4 |
| MDGA1 | NM_153487 | MAM domain containing |
| MECP2 | NM_004992 | methyl CpG binding protein 2 |
| MICALCL | NM_032867 | hypothetical protein LOC84953 |
| MIPOL1 | NM_138731 | mirror-image polydactyly 1 |
| MITF | NM_000248 | microphthalmia-associated transcription factor |
| MITF | NM_006722 | microphthalmia-associated transcription factor |
| MITF | NM_198158 | microphthalmia-associated transcription factor |
| MITF | NM_198159 | microphthalmia-associated transcription factor |
| MITF | NM_198177 | microphthalmia-associated transcription factor |
| MITF | NM_198178 | microphthalmia-associated transcription factor |
| MKLN1 | NM_013255 | muskelin 1, intracellular mediator containing |
| MKRN3 | NM_005664 | makorin, ring finger protein, 3 |
| MLLT3 | NM_004529 | myeloid/lymphoid or mixed-lineage leukemia |
| MN1 | NM_002430 | meningioma 1 |
| MOCS1 | NM_005943 | molybdenum cofactor synthesis-step 1 protein |
| MORC4 | NM_024657 | zinc finger, CW type with coiled-coil domain 2 |
| MPZL1 | NM_003953 | myelin protein zero-like 1 isoform a |
| MPZL1 | NM_024569 | myelin protein zero-like 1 isoform b |
| MTF2 | NM_007358 | metal response element-binding transcription |
| MTMR12 | NM_019061 | myotubularin related protein 12 |
| MTPN | NM_145808 | Myotrophin |
| MYADM | NM_001020818 | myeloid-associated differentiation marker |
| MYADM | NM_001020819 | myeloid-associated differentiation marker |
| MYADM | NM_001020820 | myeloid-associated differentiation marker |
| MYADM | NM_001020821 | myeloid-associated differentiation marker |
| MYADM | NM_138373 | myeloid-associated differentiation marker |
| MYCBP | NM_012333 | c-myc binding protein |
| MYLIP | NM_013262 | myosin regulatory light chain interacting |
| MYNN | NM_018657 | Myoneurin |
| MYO10 | NM_012334 | myosin X |
| MYO1C | NM_033375 | myosin IC |
| MYO9B | NM_004145 | myosin IXB |
| MYRIP | NM_015460 | myosin VIIA and Rab interacting protein |
| NAB1 | NM_005966 | NGFI-A binding protein 1 |
| NARG1 | NM_057175 | NMDA receptor regulated 1 |

TABLE 3-continued

Predicted target genes of hsa-miR-124a.

| Gene Symbol | RefSeq Transcript ID (Pruitt et al., 2005) | Description |
|---|---|---|
| NAV1 | NM_020443 | neuron navigator 1 |
| NAV2 | NM_145117 | neuron navigator 2 isoform 2 |
| NAV2 | NM_182964 | neuron navigator 2 isoform 1 |
| NAV3 | NM_014903 | neuron navigator 3 |
| NCKIPSD | NM_016453 | NCK interacting protein with SH3 domain isoform |
| NCKIPSD | NM_184231 | NCK interacting protein with SH3 domain isoform |
| NCOR2 | NM_006312 | nuclear receptor co-repressor 2 |
| NDFIP1 | NM_030571 | Nedd4 family interacting protein 1 |
| NEGR1 | NM_173808 | neuronal growth regulator 1 |
| NEK4 | NM_003157 | NIMA (never in mitosis gene a)-related kinase 4 |
| NFIB | NM_005596 | nuclear factor I/B |
| NFIX | NM_002501 | nuclear factor I/X (CCAAT-binding transcription |
| NOPE | NM_020962 | DDM36 |
| NPLOC4 | NM_017921 | nuclear protein localization 4 |
| NPTN | NM_012428 | neuroplastin isoform b precursor |
| NPTN | NM_017455 | neuroplastin isoform a precursor |
| NR3C1 | NM_000176 | nuclear receptor subfamily 3, group C, member 1 |
| NR3C1 | NM_001018074 | nuclear receptor subfamily 3, group C, member 1 |
| NR3C1 | NM_001018075 | nuclear receptor subfamily 3, group C, member 1 |
| NR3C1 | NM_001018076 | nuclear receptor subfamily 3, group C, member 1 |
| NR3C1 | NM_001018077 | nuclear receptor subfamily 3, group C, member 1 |
| NR3C1 | NM_001024094 | nuclear receptor subfamily 3, group C, member 1 |
| NR3C2 | NM_000901 | nuclear receptor subfamily 3, group C, member 2 |
| NR5A2 | NM_003822 | nuclear receptor subfamily 5, group A, member 2 |
| NR5A2 | NM_205860 | nuclear receptor subfamily 5, group A, member 2 |
| NRP1 | NM_003873 | neuropilin 1 isoform a |
| NRP2 | NM_018534 | neuropilin 2 isoform 4 precursor |
| NRP2 | NM_201267 | neuropilin 2 isoform 5 precursor |
| NT5M | NM_020201 | 5',3'-nucleotidase, mitochondrial precursor |
| NTRK2 | NM_001018064 | neurotrophic tyrosine kinase, receptor, type 2 |
| NTRK2 | NM_006180 | neurotrophic tyrosine kinase, receptor, type 2 |
| NUP35 | NM_001008544 | nucleoporin 35 kDa isoform b |
| NUPL1 | NM_001008564 | nucleoporin like 1 isoform b |
| NUPL1 | NM_014089 | nucleoporin like 1 isoform a |
| OACT2 | NM_138799 | O-acyltransferase (membrane bound) domain |
| OACT5 | NM_005768 | gene rich cluster, C3f gene |
| OGT | NM_003605 | O-linked GlcNAc transferase isoform 3 |
| OPN3 | NM_001030012 | opsin 3 isoform 3 |
| OPN3 | NM_001030011 | opsin 3 isoform 2 |
| OPRS1 | NM_005866 | opioid receptor, sigma 1 isoform 1 |
| OPRS1 | NM_147157 | opioid receptor, sigma 1 isoform 2 |
| OPRS1 | NM_147158 | opioid receptor, sigma 1 isoform 3 |
| OSBP | NM_002556 | oxysterol binding protein |
| OSBP2 | NM_030758 | oxysterol binding protein 2 isoform a |
| OSBPL11 | NM_022776 | oxysterol-binding protein-like protein 11 |
| OSBPL3 | NM_015550 | oxysterol-binding protein-like protein 3 isoform |
| OSBPL3 | NM_145320 | oxysterol-binding protein-like protein 3 isoform |
| OSBPL3 | NM_145321 | oxysterol-binding protein-like protein 3 isoform |
| OSBPL3 | NM_145322 | oxysterol-binding protein-like protein 3 isoform |
| OSBPL5 | NM_020896 | oxysterol-binding protein-like protein 5 isoform |
| OSBPL5 | NM_145638 | oxysterol-binding protein-like protein 5 isoform |
| OSBPL6 | NM_032523 | oxysterol-binding protein-like protein 6 isoform |
| OSBPL6 | NM_145739 | oxysterol-binding protein-like protein 6 isoform |
| OTUD4 | NM_199324 | OTU domain containing 4 protein isoform 1 |
| OXSR1 | NM_005109 | oxidative-stress responsive 1 |
| PALLD | NM_016081 | Palladin |
| PAPOLG | NM_022894 | poly(A) polymerase gamma |
| PAQR8 | NM_133367 | progestin and adipoQ receptor family member |
| PARP16 | NM_017851 | poly (ADP-ribose) polymerase family, member 16 |
| PBEF1 | NM_005746 | pre-B-cell colony enhancing factor 1 isoform a |
| PBX3 | NM_006195 | pre-B-cell leukemia transcription factor 3 |
| PCDH8 | NM_002590 | protocadherin 8 isoform 1 precursor |
| PCDH8 | NM_032949 | protocadherin 8 isoform 2 precursor |
| PCSK6 | NM_002570 | paired basic amino acid cleaving system 4 |
| PCSK6 | NM_138319 | paired basic amino acid cleaving system 4 |
| PCTK3 | NM_002596 | PCTAIRE protein kinase 3 isoform b |
| PCTK3 | NM_212502 | PCTAIRE protein kinase 3 isoform b |
| PCTK3 | NM_212503 | PCTAIRE protein kinase 3 isoform a |
| PCYOX1 | NM_016297 | prenylcysteine oxidase 1 |
| PDCD10 | NM_007217 | programmed cell death 10 |
| PDCD10 | NM_145859 | programmed cell death 10 |
| PDCD10 | NM_145860 | programmed cell death 10 |
| PDE2A | NM_002599 | phosphodiesterase 2A, cGMP-stimulated |
| PDE4A | NM_006202 | phosphodiesterase 4A, cAMP-specific |

TABLE 3-continued

Predicted target genes of hsa-miR-124a.

| Gene Symbol | RefSeq Transcript ID (Pruitt et al., 2005) | Description |
|---|---|---|
| PDE7B | NM_018945 | phosphodiesterase 7B |
| PDZD2 | NM_178140 | PDZ domain containing 2 |
| PEA15 | NM_003768 | phosphoprotein enriched in astrocytes 15 |
| PEG3 | NM_006210 | paternally expressed 3 |
| PELI1 | NM_020651 | pellino protein |
| PHC2 | NM_004427 | polyhomeotic 2-like isoform b |
| PHC2 | NM_198040 | polyhomeotic 2-like isoform a |
| PHF20L1 | NM_024878 | PHD finger protein 20-like 1 isoform 3 |
| PHF20L1 | NM_198513 | PHD finger protein 20-like 1 isoform 2 |
| PHF6 | NM_001015877 | PHD finger protein 6 isoform 1 |
| PHF6 | NM_032458 | PHD finger protein 6 isoform 1 |
| PHLDB1 | NM_015157 | pleckstrin homology-like domain, family B, |
| PHTF2 | NM_020432 | putative homeodomain transcription factor 2 |
| PICALM | NM_001008660 | phosphatidylinositol-binding clathrin assembly |
| PICALM | NM_007166 | phosphatidylinositol-binding clathrin assembly |
| PIK3CA | NM_006218 | phosphoinositide-3-kinase, catalytic, alpha |
| PLAGL2 | NM_002657 | pleiomorphic adenoma gene-like 2 |
| PLCXD3 | NM_001005473 | phosphatidylinositol-specific phospholipase C, X |
| PLDN | NM_012388 | Pallidin |
| PLEKHA6 | NM_014935 | phosphoinositol 3-phosphate-binding protein-3 |
| PLEKHC1 | NM_006832 | pleckstrin homology domain containing, family C |
| PLEKHH1 | NM_020715 | pleckstrin homology domain containing, family H |
| PLSCR3 | NM_020360 | phospholipid scramblase 3 |
| PLXNA3 | NM_017514 | plexin A3 |
| PNN | NM_002687 | pinin, desmosome associated protein |
| PODXL | NM_001018111 | podocalyxin-like precursor isoform 1 |
| PODXL | NM_005397 | podocalyxin-like precursor isoform 2 |
| PPARA | NM_001001928 | peroxisome proliferative activated receptor, |
| PPARA | NM_001001929 | peroxisome proliferative activated receptor, |
| PPARA | NM_001001930 | peroxisome proliferative activated receptor, |
| PPARA | NM_005036 | peroxisome proliferative activated receptor, |
| PPFIBP2 | NM_003621 | PTPRF interacting protein, binding protein 2 |
| PPM1F | NM_014634 | protein phosphatase 1F |
| PPP1R13L | NM_006663 | protein phosphatase 1, regulatory (inhibitor) |
| PPP2R5E | NM_006246 | epsilon isoform of regulatory subunit B56, |
| PPP4R1 | NM_005134 | protein phosphatase 4, regulatory subunit 1 |
| PRKD1 | NM_002742 | protein kinase D1 |
| PRPF39 | NM_017922 | PRP39 pre-mRNA processing factor 39 homolog |
| PRRX1 | NM_006902 | paired mesoderm homeobox 1 isoform pmx-1a |
| PRRX1 | NM_022716 | paired mesoderm homeobox 1 isoform pmx-1b |
| PTBP1 | NM_002819 | polypyrimidine tract-binding protein 1 isoform |
| PTBP1 | NM_031990 | polypyrimidine tract-binding protein 1 isoform |
| PTBP1 | NM_031991 | polypyrimidine tract-binding protein 1 isoform |
| PTBP1 | NM_175847 | polypyrimidine tract-binding protein 1 isoform |
| PTBP2 | NM_021190 | polypyrimidine tract binding protein 2 |
| PTPN1 | NM_002827 | protein tyrosine phosphatase, non-receptor type |
| PTPN12 | NM_002835 | protein tyrosine phosphatase, non-receptor type |
| PTPN9 | NM_002833 | protein tyrosine phosphatase, non-receptor type |
| PTTG1IP | NM_004339 | pituitary tumor-transforming gene 1 |
| PURB | NM_033224 | purine-rich element binding protein B |
| QKI | NM_206853 | quaking homolog, KH domain RNA binding isoform |
| QKI | NM_206854 | quaking homolog, KH domain RNA binding isoform |
| QKI | NM_206855 | quaking homolog, KH domain RNA binding isoform |
| QKI | NM_006775 | quaking homolog, KH domain RNA binding isoform |
| QRICH1 | NM_017730 | hypothetical protein LOC54870 |
| QRICH1 | NM_198880 | hypothetical protein LOC54870 |
| RAB10 | NM_016131 | ras-related GTP-binding protein RAB10 |
| RAB11A | NM_004663 | Ras-related protein Rab-11A |
| RAB1B | NM_030981 | RAB1B, member RAS oncogene family |
| RAB27A | NM_004580 | Ras-related protein Rab-27A |
| RAB27A | NM_183234 | Ras-related protein Rab-27A |
| RAB27A | NM_183235 | Ras-related protein Rab-27A |
| RAB27A | NM_183236 | Ras-related protein Rab-27A |
| RAB34 | NM_031934 | RAB39 |
| RAB43 | NM_198490 | RAB43 protein |
| RAB6A | NM_002869 | RAB6A, member RAS oncogene family isoform a |
| RAB6A | NM_198896 | RAB6A, member RAS oncogene family isoform b |
| RAD17 | NM_002873 | RAD17 homolog isoform 1 |
| RAD17 | NM_133338 | RAD17 homolog isoform 1 |
| RAD17 | NM_133339 | RAD17 homolog isoform 2 |
| RAD17 | NM_133340 | RAD17 homolog isoform 3 |
| RAD17 | NM_133341 | RAD17 homolog isoform 4 |
| RAD17 | NM_133342 | RAD17 homolog isoform 1 |
| RAD17 | NM_133343 | RAD17 homolog isoform 1 |

TABLE 3-continued

Predicted target genes of hsa-miR-124a.

| Gene Symbol | RefSeq Transcript ID (Pruitt et al., 2005) | Description |
|---|---|---|
| RAD17 | NM_133344 | RAD17 homolog isoform 1 |
| RAI14 | NM_015577 | retinoic acid induced 14 |
| RALA | NM_005402 | ras related v-ral simian leukemia viral oncogene |
| RALGPS1 | NM_014636 | Ral GEF with PH domain and SH3 binding motif 1 |
| RANBP10 | NM_020850 | RAN binding protein 10 |
| RAP1B | NM_001010942 | RAP1B, member of RAS oncogene family |
| RAP1B | NM_015646 | RAP1B, member of RAS oncogene family |
| RAP2A | NM_021033 | RAP2A, member of RAS oncogene family |
| RAP2C | NM_021183 | RAP2C, member of RAS oncogene family |
| RASGEF1A | NM_145313 | RasGEF domain family, member 1A |
| RASL10B | NM_033315 | RAS-like, family 10, member B |
| RAVER1 | NM_133452 | RAVER1 |
| RAVER2 | NM_018211 | ribonucleoprotein, PTB-binding 2 |
| RBM24 | NM_153020 | hypothetical protein LOC221662 |
| RBM33 | NM_001008408 | hypothetical protein LOC155435 |
| RBMS1 | NM_002897 | RNA binding motif, single stranded interacting |
| RBMS1 | NM_016836 | RNA binding motif, single stranded interacting |
| RBMS1 | NM_016839 | RNA binding motif, single stranded interacting |
| REEP1 | NM_022912 | receptor expression enhancing protein 1 |
| RERE | NM_012102 | atrophin-1 like protein |
| RFFL | NM_001017368 | Rififylin |
| RFFL | NM_057178 | Rififylin |
| RFX1 | NM_002918 | regulatory factor X1 |
| RGS9 | NM_003835 | regulator of G-protein signalling 9 |
| RHBDL3 | NM_138328 | rhomboid, veinlet-like 3 |
| RHOG | NM_001665 | ras homolog gene family, member G |
| RICTOR | NM_152756 | rapamycin-insensitive companion of mTOR |
| RNF11 | NM_014372 | ring finger protein 11 |
| RNF144 | NM_014746 | ring finger protein 144 |
| RNF165 | NM_152470 | ring finger protein 165 |
| ROD1 | NM_005156 | ROD1 regulator of differentiation 1 |
| RPIA | NM_144563 | ribose 5-phosphate isomerase A (ribose |
| RPS6KB1 | NM_003161 | ribosomal protein S6 kinase, 70 kDa, polypeptide |
| RREB1 | NM_001003698 | ras responsive element binding protein 1 isoform |
| RREB1 | NM_001003699 | ras responsive element binding protein 1 isoform |
| RREB1 | NM_002955 | ras responsive element binding protein 1 isoform |
| RTN3 | NM_006054 | reticulon 3 isoform a |
| RTN3 | NM_201428 | reticulon 3 isoform b |
| RTN3 | NM_201429 | reticulon 3 isoform c |
| RTN3 | NM_201430 | reticulon 3 isoform d |
| RWDD4A | NM_152682 | hypothetical protein LOC201965 |
| RXRA | NM_002957 | retinoid X receptor, alpha |
| RYR2 | NM_001035 | ryanodine receptor 2 |
| RYR3 | NM_001036 | ryanodine receptor 3 |
| SAPS2 | NM_014678 | hypothetical protein LOC9701 |
| SASH1 | NM_015278 | SAM and SH3 domain containing 1 |
| SCAMP2 | NM_005697 | secretory carrier membrane protein 2 |
| SCD | NM_005063 | stearoyl-CoA desaturase |
| SCN4B | NM_174934 | sodium channel, voltage-gated, type IV, beta |
| SDAD1 | NM_018115 | SDA1 domain containing 1 |
| SDC2 | NM_002998 | syndecan 2 precursor |
| SDCBP | NM_001007067 | syntenin isoform 1 |
| SDCBP | NM_001007068 | syntenin isoform 2 |
| SDCBP | NM_001007069 | syntenin isoform 3 |
| SDCBP | NM_001007070 | syntenin isoform 3 |
| SDCBP | NM_005625 | syntenin isoform 1 |
| SEC13L1 | NM_030673 | SEC13-like 1 isoform a |
| SEC13L1 | NM_183352 | SEC13-like 1 isoform b |
| SEC61A2 | NM_018144 | Sec61 alpha form 2 |
| SELI | NM_033505 | selenoprotein I |
| SELS | NM_018445 | selenoprotein S |
| SEMA4F | NM_004263 | semaphorin W |
| SEMA6A | NM_020796 | sema domain, transmembrane domain (TM), and |
| SEMA6C | NM_030913 | semaphorin Y |
| SEMA6D | NM_020858 | semaphorin 6D isoform 1 precursor |
| SEMA6D | NM_153616 | semaphorin 6D isoform 2 precursor |
| SEMA6D | NM_153617 | semaphorin 6D isoform 3 precursor |
| SEMA6D | NM_153618 | semaphorin 6D isoform 4 precursor |
| SEMA6D | NM_153619 | semaphorin 6D isoform 5 precursor |
| SEPT11 | NM_018243 | septin 11 |
| SERINC2 | NM_178865 | tumor differentially expressed 2-like |
| SERP1 | NM_014445 | stress-associated endoplasmic reticulum protein |
| SERTAD3 | NM_013368 | RPA-binding trans-activator |
| SERTAD3 | NM_203344 | RPA-binding trans-activator |

TABLE 3-continued

Predicted target genes of hsa-miR-124a.

| Gene Symbol | RefSeq Transcript ID (Pruitt et al., 2005) | Description |
|---|---|---|
| SESTD1 | NM_178123 | SEC14 and spectrin domains 1 |
| SFRS12 | NM_139168 | splicing factor, arginine/serine-rich 12 |
| SH3BP5L | NM_030645 | SH3-binding domain protein 5-like |
| SHRM | NM_020859 | Shroom |
| SIRT1 | NM_012238 | sirtuin 1 |
| SIX4 | NM_017420 | sine oculis homeobox homolog 4 |
| SLBP | NM_006527 | histone stem-loop binding protein |
| SLC16A1 | NM_003051 | solute carrier family 16, member 1 |
| SLC16A14 | NM_152527 | solute carrier family 16 (monocarboxylic acid |
| SLC1A4 | NM_003038 | solute carrier family 1, member 4 |
| SLC25A20 | NM_000387 | carnitine/acylcarnitine translocase |
| SLC25A25 | NM_001006641 | solute carrier family 25, member 25 isoform b |
| SLC25A25 | NM_001006642 | solute carrier family 25, member 25 isoform c |
| SLC25A25 | NM_001006643 | solute carrier family 25, member 25 isoform d |
| SLC25A25 | NM_052901 | solute carrier family 25, member 25 isoform a |
| SLC31A2 | NM_001860 | solute carrier family 31 (copper transporters), |
| SLC35A1 | NM_006416 | solute carrier family 35 (CMP-sialic acid |
| SLC35F5 | NM_025181 | solute carrier family 35, member F5 |
| SLC41A2 | NM_032148 | solute carrier family 41, member 2 |
| SLC7A8 | NM_012244 | solute carrier family 7 (cationic amino acid |
| SLC7A8 | NM_182728 | solute carrier family 7 (cationic amino acid |
| SLITRK6 | NM_032229 | slit and trk like 6 |
| SLK | NM_014720 | serine/threonine kinase 2 |
| SLMAP | NM_007159 | sarcolemma associated protein |
| SMARCAD1 | NM_020159 | SWI/SNF-related, matrix-associated |
| SNIP1 | NM_024700 | Smad nuclear interacting protein |
| SNX4 | NM_003794 | sorting nexin 4 |
| SNX6 | NM_021249 | sorting nexin 6 isoform a |
| SNX6 | NM_152233 | sorting nexin 6 isoform b |
| SORCS2 | NM_020777 | VPS10 domain receptor protein SORCS 2 |
| SOX9 | NM_000346 | transcription factor SOX9 |
| SP2 | NM_003110 | Sp2 transcription factor |
| SP3 | NM_001017371 | Sp3 transcription factor isoform 2 |
| SP3 | NM_003111 | Sp3 transcription factor isoform 1 |
| SPRED2 | NM_181784 | sprouty-related protein with EVH-1 domain 2 |
| SPRY1 | NM_005841 | sprouty homolog 1, antagonist of FGF signaling |
| SPRY1 | NM_199327 | sprouty homolog 1, antagonist of FGF signaling |
| SPRY2 | NM_005842 | sprouty 2 |
| SRGAP3 | NM_001033116 | SLIT-ROBO Rho GTPase activating protein 3 |
| SRGAP3 | NM_001033117 | SLIT-ROBO Rho GTPase activating protein 3 |
| SRGAP3 | NM_014850 | SLIT-ROBO Rho GTPase activating protein 3 |
| STAG2 | NM_006603 | stromal antigen 2 |
| STC1 | NM_003155 | stanniocalcin 1 precursor |
| STK4 | NM_006282 | serine/threonine kinase 4 |
| SUGT1 | NM_006704 | suppressor of G2 allele of SKP1 |
| SURF4 | NM_033161 | surfeit 4 |
| SYNC1 | NM_030786 | syncoilin, intermediate filament 1 |
| SYT11 | NM_152280 | synaptotagmin 12 |
| TACC1 | NM_006283 | transforming, acidic coiled-coil containing |
| TACC2 | NM_006997 | transforming, acidic coiled-coil containing |
| TACC2 | NM_206860 | transforming, acidic coiled-coil containing |
| TACC2 | NM_206861 | transforming, acidic coiled-coil containing |
| TACC2 | NM_206862 | transforming, acidic coiled-coil containing |
| TBC1D14 | NM_020773 | TBC1 domain family, member 14 |
| TCBA1 | NM_153355 | T-cell lymphoma breakpoint-associated target 1 |
| TEAD1 | NM_021961 | TEA domain family member 1 |
| TEX261 | NM_144582 | testis expressed sequence 261 |
| TFDP2 | NM_006286 | transcription factor Dp-2 (E2F dimerization |
| THAP2 | NM_031435 | THAP domain containing, apoptosis associated |
| TIPRL | NM_152902 | TIP41, TOR signalling pathway regulator-like |
| TLL1 | NM_012464 | tolloid-like 1 |
| TLL2 | NM_012465 | tolloid-like 2 |
| TLOC1 | NM_003262 | translocation protein 1 |
| TMCC3 | NM_020698 | transmembrane and coiled-coil domains 3 |
| TMED1 | NM_006858 | interleukin 1 receptor-like 1 ligand precursor |
| TMEM109 | NM_024092 | hypothetical protein LOC79073 |
| TMEM129 | NM_138385 | hypothetical protein LOC92305 |
| TMEM134 | NM_025124 | hypothetical protein LOC80194 |
| TMEPAI | NM_020182 | transmembrane prostate androgen-induced protein |
| TMEPAI | NM_199169 | transmembrane prostate androgen-induced protein |
| TMEPAI | NM_199170 | transmembrane prostate androgen-induced protein |
| TMEPAI | NM_199171 | transmembrane prostate androgen-induced protein |
| TNRC6B | NM_001024843 | trinucleotide repeat containing 6B isoform 2 |
| TNRC6B | NM_015088 | trinucleotide repeat containing 6B isoform 1 |

TABLE 3-continued

Predicted target genes of hsa-miR-124a.

| Gene Symbol | RefSeq Transcript ID (Pruitt et al., 2005) | Description |
|---|---|---|
| TOB2 | NM_016272 | transducer of ERBB2, 2 |
| TOR3A | NM_022371 | torsin family 3, member A |
| TOX | NM_014729 | thymus high mobility group box protein TOX |
| TPD52L2 | NM_003288 | tumor protein D52-like 2 isoform e |
| TPD52L2 | NM_199359 | tumor protein D52-like 2 isoform f |
| TPD52L2 | NM_199360 | tumor protein D52-like 2 isoform a |
| TPD52L2 | NM_199361 | tumor protein D52-like 2 isoform b |
| TPD52L2 | NM_199362 | tumor protein D52-like 2 isoform c |
| TPD52L2 | NM_199363 | tumor protein D52-like 2 isoform d |
| TRAM2 | NM_012288 | translocation-associated membrane protein 2 |
| TRIM2 | NM_015271 | tripartite motif-containing 2 |
| TRIM9 | NM_015163 | tripartite motif protein 9 isoform 1 |
| TUBB6 | NM_032525 | tubulin, beta 6 |
| UBE1L2 | NM_018227 | hypothetical protein LOC55236 |
| UBE2B | NM_003337 | ubiquitin-conjugating enzyme E2B |
| UBL3 | NM_007106 | ubiquitin-like 3 |
| UBOX5 | NM_014948 | U-box domain containing 5 isoform a |
| UBOX5 | NM_199415 | U-box domain containing 5 isoform b |
| UGT8 | NM_003360 | UDP glycosyltransferase 8 (UDP-galactose |
| ULK2 | NM_014683 | unc-51-like kinase 2 |
| USP14 | NM_005151 | ubiquitin specific protease 14 isoform a |
| USP37 | NM_020935 | ubiquitin specific protease 37 |
| USP48 | NM_032236 | ubiquitin specific protease 48 isoform a |
| VAMP3 | NM_004781 | vesicle-associated membrane protein 3 |
| VAT1 | NM_006373 | vesicle amine transport protein 1 |
| VDAC2 | NM_003375 | voltage-dependent anion channel 2 |
| VDAC3 | NM_005662 | voltage-dependent anion channel 3 |
| VPS13A | NM_001018037 | vacuolar protein sorting 13A isoform C |
| VPS13A | NM_033305 | vacuolar protein sorting 13A isoform A |
| VPS37B | NM_024667 | vacuolar protein sorting 37B |
| VSNL1 | NM_003385 | visinin-like 1 |
| WAPAL | NM_015045 | KIAA0261 |
| WASPIP | NM_003387 | WASP-interacting protein |
| WDFY1 | NM_020830 | WD repeat and FYVE domain containing 1 |
| WDFY3 | NM_014991 | WD repeat and FYVE domain containing 3 isoform |
| WDFY3 | NM_178585 | WD repeat and FYVE domain containing 3 isoform |
| WDR40B | NM_178470 | WD repeat domain 40B |
| WIRE | NM_133264 | WIRE protein |
| WTAP | NM_152857 | Wilms' tumour 1-associating protein isoform 2 |
| WTAP | NM_152858 | Wilms' tumour 1-associating protein isoform 2 |
| XKR6 | NM_173683 | XK-related protein 6 isoform b |
| XKR6 | NM_001012239 | XK-related protein 6 isoform a |
| XPO4 | NM_022459 | exportin 4 |
| YEATS2 | NM_018023 | YEATS domain containing 2 |
| YIPF6 | NM_173834 | Yip1 domain family, member 6 |
| YOD1 | NM_018566 | hypothetical protein LOC55432 |
| YTHDF1 | NM_017798 | YTH domain family, member 1 |
| ZBED4 | NM_014838 | zinc finger, BED domain containing 4 |
| ZBTB39 | NM_014830 | zinc finger and BTB domain containing 39 |
| ZBTB5 | NM_014872 | zinc finger and BTB domain containing 5 |
| ZCCHC14 | NM_015144 | zinc finger, CCHC domain containing 14 |
| ZDHHC16 | NM_032327 | Abl-philin 2 isoform 1 |
| ZDHHC16 | NM_198043 | Abl-philin 2 isoform 2 |
| ZDHHC16 | NM_198044 | Abl-philin 2 isoform 3 |
| ZDHHC16 | NM_198045 | Abl-philin 2 isoform 4 |
| ZDHHC16 | NM_198046 | Abl-philin 2 isoform 1 |
| ZDHHC20 | NM_153251 | DHHC-containing protein 20 |
| ZDHHC3 | NM_016598 | DHHC1 protein |
| ZFAND3 | NM_021943 | testis expressed sequence 27 |
| ZFPM2 | NM_012082 | zinc finger protein, multitype 2 |
| ZNF148 | NM_021964 | zinc finger protein 148 (pHZ-52) |
| ZNF219 | NM_016423 | zinc finger protein 219 |
| ZNF336 | NM_022482 | zinc finger protein 336 |
| ZNF447 | NM_023926 | zinc finger protein 447 |
| ZNF608 | NM_020747 | zinc finger protein 608 |
| ZNF654 | NM_018293 | zinc finger protein 654 |
| ZNF706 | NM_016096 | HSPC038 protein |

The predicted gene targets that exhibited altered mRNA expression levels in human cancer cells, following transfection with Pre-miR hsa-miR-124a, are shown in Table 4.

TABLE 4

Predicted hsa-miR-124a targets that exhibited altered mRNA expression levels in human cancer cells after transfection with Pre-miR hsa-miR-124a.

| Gene Symbol | RefSeq Transcript ID | Description |
|---|---|---|
| SEPT11 | NM_018243 | septin 11 |
| ACVR2A | NM_001616 | activin A receptor, type IIA precursor |
| ADCY1 | NM_021116 | brain adenylate cyclase 1 |
| ALCAM | NM_001627 | activated leukocyte cell adhesion molecule |
| ALG2 | NM_033087 | alpha-1,3-mannosyltransferase ALG2 isoform 1 |
| ALG2 | NM_197973 | alpha-1,3-mannosyltransferase ALG2 isoform 2 |
| ANKFY1 | NM_016376 | ankyrin repeat and FYVE domain containing 1 |
| ANXA5 | NM_001154 | annexin 5 |
| ANXA7 | NM_001156 | annexin VII isoform 1 |
| ANXA7 | NM_004034 | annexin VII isoform 2 |
| AP3M1 | NM_012095 | adaptor-related protein complex 3, mu 1 subunit |
| AP3M1 | NM_207012 | adaptor-related protein complex 3, mu 1 subunit |
| ARFIP1 | NM_001025593 | ADP-ribosylation factor interacting protein 1 |
| ARFIP1 | NM_001025595 | ADP-ribosylation factor interacting protein 1 |
| ARFIP1 | NM_014447 | ADP-ribosylation factor interacting protein 1 |
| ARHGDIA | NM_004309 | Rho GDP dissociation inhibitor (GDI) alpha |
| ARPP-19 | NM_006628 | cyclic AMP phosphoprotein, 19 kD |
| ASCIZ | NM_015251 | ATM/ATR-Substrate Chk2-Interacting Zn2+-finger |
| ATP6V0E | NM_003945 | ATPase, H+ transporting, lysosomal, V0 subunit |
| ATRX | NM_000489 | transcriptional regulator ATRX isoform 1 |
| ATRX | NM_138270 | transcriptional regulator ATRX isoform 2 |
| ATRX | NM_138271 | transcriptional regulator ATRX isoform 3 |
| B4GALT1 | NM_001497 | UDP-Gal:betaGlcNAc beta 1,4- |
| BCL2L11 | NM_006538 | BCL2-like 11 isoform 6 |
| BCL2L11 | NM_138621 | BCL2-like 11 isoform 1 |
| BCL2L11 | NM_138622 | BCL2-like 11 isoform 2 |
| BCL2L11 | NM_138623 | BCL2-like 11 isoform 3 |
| BCL2L11 | NM_138624 | BCL2-like 11 isoform 4 |
| BCL2L11 | NM_138626 | BCL2-like 11 isoform 7 |
| BCL2L11 | NM_138627 | BCL2-like 11 isoform 8 |
| BCL2L11 | NM_207003 | BCL2-like 11 isoform 10 |
| C11orf9 | NM_013279 | hypothetical protein LOC745 |
| C15orf29 | NM_024713 | hypothetical protein LOC79768 |
| C1orf108 | NM_024595 | hypothetical protein LOC79647 |
| C1orf121 | NM_016076 | hypothetical protein LOC51029 |
| CAPN2 | NM_001748 | calpain 2, large subunit |
| CASC4 | NM_138423 | cancer susceptibility candidate 4 isoform a |
| CASC4 | NM_177974 | cancer susceptibility candidate 4 isoform b |
| CBFB | NM_022845 | core-binding factor, beta subunit isoform 1 |
| CBFB | NM_001755 | core-binding factor, beta subunit isoform 2 |
| CCDC28A | NM_015439 | hypothetical protein LOC25901 |
| CCL2 | NM_002982 | small inducible cytokine A2 precursor |
| CD164 | NM_006016 | CD164 antigen, sialomucin |
| CDK4 | NM_000075 | cyclin-dependent kinase 4 |
| CDK6 | NM_001259 | cyclin-dependent kinase 6 |
| CEACAM1 | NM_001024912 | carcinoembryonic antigen-related cell adhesion |
| CEACAM1 | NM_001712 | carcinoembryonic antigen-related cell adhesion |
| CFL2 | NM_021914 | cofilin 2 |
| CFL2 | NM_138638 | cofilin 2 |
| CHMP2B | NM_014043 | chromatin modifying protein 2B |
| CHSY1 | NM_014918 | carbohydrate (chondroitin) synthase 1 |
| COL12A1 | NM_004370 | alpha 1 type XII collagen long isoform |
| COL12A1 | NM_080645 | alpha 1 type XII collagen short isoform |
| COL4A1 | NM_001845 | alpha 1 type IV collagen preproprotein |
| DHX40 | NM_024612 | DEAH (Asp-Glu-Ala-His) box polypeptide 40 |
| DKFZp564K142 | NM_032121 | implantation-associated protein |
| EIF3S1 | NM_003758 | eukaryotic translation initiation factor 3, |
| ELK3 | NM_005230 | ELK3 protein |
| ELL2 | NM_012081 | elongation factor, RNA polymerase II, 2 |
| ELOVL5 | NM_021814 | homolog of yeast long chain polyunsaturated |
| ETS1 | NM_005238 | v-ets erythroblastosis virus E26 oncogene |
| ETV1 | NM_004956 | ets variant gene 1 |
| EYA4 | NM_004100 | eyes absent 4 isoform a |
| EYA4 | NM_172103 | eyes absent 4 isoform b |
| EYA4 | NM_172104 | eyes absent 4 isoform c |
| EYA4 | NM_172105 | eyes absent 4 isoform d |
| F11R | NM_016946 | F11 receptor isoform a precursor |
| F11R | NM_144501 | F11 receptor isoform a precursor |
| F11R | NM_144502 | F11 receptor isoform b |
| F11R | NM_144503 | F11 receptor isoform a precursor |
| F11R | NM_144504 | F11 receptor isoform a precursor |
| FLJ20054 | NM_019049 | hypothetical protein LOC54530 |
| FLJ22222 | NM_175902 | hypothetical protein LOC79701 isoform 2 |
| FLJ22222 | NM_024648 | hypothetical protein LOC79701 isoform 1 |

TABLE 4-continued

Predicted hsa-miR-124a targets that exhibited altered mRNA expression levels in human cancer cells after transfection with Pre-miR hsa-miR-124a.

| Gene Symbol | RefSeq Transcript ID | Description |
| --- | --- | --- |
| FLJ33814 | NM_173510 | hypothetical protein LOC150275 |
| FOXQ1 | NM_033260 | forkhead box Q1 |
| GAS2L1 | NM_006478 | growth arrest-specific 2 like 1 isoform a |
| GAS2L1 | NM_152236 | growth arrest-specific 2 like 1 isoform a |
| GAS2L1 | NM_152237 | growth arrest-specific 2 like 1 isoform b |
| GLTP | NM_016433 | glycolipid transfer protein |
| GNA13 | NM_006572 | guanine nucleotide binding protein (G protein), |
| GOLT1B | NM_016072 | golgi transport 1 homolog B |
| HDAC4 | NM_006037 | histone deacetylase 4 |
| HDAC5 | NM_001015053 | histone deacetylase 5 isoform 3 |
| HDAC5 | NM_005474 | histone deacetylase 5 isoform 1 |
| HIAT1 | NM_033055 | hippocampus abundant transcript 1 |
| HIATL1 | NM_032558 | hypothetical protein LOC84641 |
| HMG2L1 | NM_001003681 | high-mobility group protein 2-like 1 isoform b |
| HMG2L1 | NM_005487 | high-mobility group protein 2-like 1 isoform a |
| HMG2L1 | NM_014250 | high-mobility group protein 2-like 1 isoform a |
| IQGAP1 | NM_003870 | IQ motif containing GTPase activating protein 1 |
| KIAA0494 | NM_014774 | hypothetical protein LOC9813 |
| KIAA1815 | NM_024896 | hypothetical protein LOC79956 |
| KLF4 | NM_004235 | Kruppel-like factor 4 (gut) |
| LAMC1 | NM_002293 | laminin, gamma 1 precursor |
| LASS2 | NM_013384 | LAG1 longevity assurance homolog 2 isoform 2 |
| LASS2 | NM_022075 | LAG1 longevity assurance homolog 2 isoform 1 |
| LASS2 | NM_181746 | LAG1 longevity assurance homolog 2 isoform 1 |
| LHX2 | NM_004789 | LIM homeobox protein 2 |
| LIN28B | NM_001004317 | lin-28 homolog B |
| LITAF | NM_004862 | LPS-induced TNF-alpha factor |
| LMAN2L | NM_030805 | lectin, mannose-binding 2-like |
| LMNA | NM_170707 | lamin A/C isoform 1 precursor |
| LMNA | NM_170708 | lamin A/C isoform 3 |
| LMNB1 | NM_005573 | lamin B1 |
| LONRF1 | NM_152271 | hypothetical protein LOC91694 |
| LYCAT | NM_001002257 | lysocardiolipin acyltransferase isoform 2 |
| LYCAT | NM_182551 | lysocardiolipin acyltransferase isoform 1 |
| MAPK14 | NM_001315 | mitogen-activated protein kinase 14 isoform 1 |
| MAPK14 | NM_139012 | mitogen-activated protein kinase 14 isoform 2 |
| MAPK14 | NM_139014 | mitogen-activated protein kinase 14 isoform 4 |
| MLLT3 | NM_004529 | myeloid/lymphoid or mixed-lineage leukemia |
| MPZL1 | NM_003953 | myelin protein zero-like 1 isoform a |
| MPZL1 | NM_024569 | myelin protein zero-like 1 isoform b |
| MTF2 | NM_007358 | metal response element-binding transcription |
| MYADM | NM_001020818 | myeloid-associated differentiation marker |
| MYADM | NM_001020819 | myeloid-associated differentiation marker |
| MYADM | NM_001020820 | myeloid-associated differentiation marker |
| MYADM | NM_001020821 | myeloid-associated differentiation marker |
| MYADM | NM_138373 | myeloid-associated differentiation marker |
| MYCBP | NM_012333 | c-myc binding protein |
| MYO10 | NM_012334 | myosin X |
| NARG1 | NM_057175 | NMDA receptor regulated 1 |
| NEK4 | NM_003157 | NIMA (never in mitosis gene a)-related kinase 4 |
| NFIB | NM_005596 | nuclear factor I/B |
| NOPE | NM_020962 | DDM36 |
| NRP2 | NM_018534 | neuropilin 2 isoform 4 precursor |
| NRP2 | NM_201267 | neuropilin 2 isoform 5 precursor |
| OACT2 | NM_138799 | O-acyltransferase (membrane bound) domain |
| OPN3 | NM_001030012 | opsin 3 isoform 3 |
| OPN3 | NM_001030011 | opsin 3 isoform 2 |
| OPRS1 | NM_005866 | opioid receptor, sigma 1 isoform 1 |
| OPRS1 | NM_147157 | opioid receptor, sigma 1 isoform 2 |
| OPRS1 | NM_147158 | opioid receptor, sigma 1 isoform 3 |
| OSBP | NM_002556 | oxysterol binding protein |
| OSBPL3 | NM_015550 | oxysterol-binding protein-like protein 3 isoform |
| OSBPL3 | NM_145320 | oxysterol-binding protein-like protein 3 isoform |
| OSBPL3 | NM_145321 | oxysterol-binding protein-like protein 3 isoform |
| OSBPL3 | NM_145322 | oxysterol-binding protein-like protein 3 isoform |
| OTUD4 | NM_199324 | OTU domain containing 4 protein isoform 1 |
| OXSR1 | NM_005109 | oxidative-stress responsive 1 |
| PDCD10 | NM_007217 | programmed cell death 10 |
| PDCD10 | NM_145859 | programmed cell death 10 |
| PDCD10 | NM_145860 | programmed cell death 10 |
| PEA15 | NM_003768 | phosphoprotein enriched in astrocytes 15 |
| PELI1 | NM_020651 | pellino protein |
| PHF20L1 | NM_024878 | PHD finger protein 20-like 1 isoform 3 |
| PHF20L1 | NM_198513 | PHD finger protein 20-like 1 isoform 2 |

TABLE 4-continued

Predicted hsa-miR-124a targets that exhibited altered mRNA expression levels in human cancer cells after transfection with Pre-miR hsa-miR-124a.

| Gene Symbol | RefSeq Transcript ID | Description |
| --- | --- | --- |
| PHF6 | NM_001015877 | PHD finger protein 6 isoform 1 |
| PHF6 | NM_032458 | PHD finger protein 6 isoform 1 |
| PIK3CA | NM_006218 | phosphoinositide-3-kinase, catalytic, alpha |
| PLAGL2 | NM_002657 | pleiomorphic adenoma gene-like 2 |
| PLDN | NM_012388 | Pallidin |
| PLEKHC1 | NM_006832 | pleckstrin homology domain containing, family C |
| PODXL | NM_001018111 | podocalyxin-like precursor isoform 1 |
| PODXL | NM_005397 | podocalyxin-like precursor isoform 2 |
| PPP2R5E | NM_006246 | epsilon isoform of regulatory subunit B56, |
| PTBP1 | NM_002819 | polypyrimidine tract-binding protein 1 isoform |
| PTBP1 | NM_031990 | polypyrimidine tract-binding protein 1 isoform |
| PTBP1 | NM_031991 | polypyrimidine tract-binding protein 1 isoform |
| PTBP1 | NM_175847 | polypyrimidine tract-binding protein 1 isoform |
| PTBP2 | NM_021190 | polypyrimidine tract binding protein 2 |
| PTPN12 | NM_002835 | protein tyrosine phosphatase, non-receptor type |
| PTTG1IP | NM_004339 | pituitary tumor-transforming gene 1 |
| QKI | NM_206853 | quaking homolog, KH domain RNA binding isoform |
| QKI | NM_206854 | quaking homolog, KH domain RNA binding isoform |
| QKI | NM_206855 | quaking homolog, KH domain RNA binding isoform |
| QKI | NM_006775 | quaking homolog, KH domain RNA binding isoform |
| RAB27A | NM_004580 | Ras-related protein Rab-27A |
| RAB27A | NM_183234 | Ras-related protein Rab-27A |
| RAB27A | NM_183235 | Ras-related protein Rab-27A |
| RAB27A | NM_183236 | Ras-related protein Rab-27A |
| RAB34 | NM_031934 | RAB39 |
| RAB6A | NM_002869 | RAB6A, member RAS oncogene family isoform a |
| RAB6A | NM_198896 | RAB6A, member RAS oncogene family isoform b |
| RAI14 | NM_015577 | retinoic acid induced 14 |
| RALA | NM_005402 | ras related v-ral simian leukemia viral oncogene |
| RALGPS1 | NM_014636 | Ral GEF with PH domain and SH3 binding motif 1 |
| RAP1B | NM_001010942 | RAP1B, member of RAS oncogene family |
| RAP1B | NM_015646 | RAP1B, member of RAS oncogene family |
| RAP2A | NM_021033 | RAP2A, member of RAS oncogene family |
| RAP2C | NM_021183 | RAP2C, member of RAS oncogene family |
| RASGEF1A | NM_145313 | RasGEF domain family, member 1A |
| RBMS1 | NM_002897 | RNA binding motif, single stranded interacting |
| RBMS1 | NM_016836 | RNA binding motif, single stranded interacting |
| RBMS1 | NM_016839 | RNA binding motif, single stranded interacting |
| RERE | NM_012102 | atrophin-1 like protein |
| RFFL | NM_001017368 | Rififylin |
| RFFL | NM_057178 | Rififylin |
| RHOG | NM_001665 | ras homolog gene family, member G |
| ROD1 | NM_005156 | ROD1 regulator of differentiation 1 |
| RPIA | NM_144563 | ribose 5-phosphate isomerase A (ribose |
| RWDD4A | NM_152682 | hypothetical protein LOC201965 |
| SCD | NM_005063 | stearoyl-CoA desaturase |
| SDAD1 | NM_018115 | SDA1 domain containing 1 |
| SDCBP | NM_001007067 | syntenin isoform 1 |
| SDCBP | NM_001007068 | syntenin isoform 2 |
| SDCBP | NM_001007069 | syntenin isoform 3 |
| SDCBP | NM_001007070 | syntenin isoform 3 |
| SDCBP | NM_005625 | syntenin isoform 1 |
| SEC13L1 | NM_030673 | SEC13-like 1 isoform a |
| SEC13L1 | NM_183352 | SEC13-like 1 isoform b |
| SERP1 | NM_014445 | stress-associated endoplasmic reticulum protein |
| SLBP | NM_006527 | histone stem-loop binding protein |
| SLC16A1 | NM_003051 | solute carrier family 16, member 1 |
| SLC16A14 | NM_152527 | solute carrier family 16 (monocarboxylic acid |
| SLC35F5 | NM_025181 | solute carrier family 35, member F5 |
| SLC41A2 | NM_032148 | solute carrier family 41, member 2 |
| SLK | NM_014720 | serine/threonine kinase 2 |
| SNX6 | NM_021249 | sorting nexin 6 isoform a |
| SNX6 | NM_152233 | sorting nexin 6 isoform b |
| SOX9 | NM_000346 | transcription factor SOX9 |
| STC1 | NM_003155 | stanniocalcin 1 precursor |
| SUGT1 | NM_006704 | suppressor of G2 allele of SKP1 |
| SURF4 | NM_033161 | surfeit 4 |
| SYT11 | NM_152280 | synaptotagmin 12 |
| TACC1 | NM_006283 | transforming, acidic coiled-coil containing |
| TEX261 | NM_144582 | testis expressed sequence 261 |
| TIPRL | NM_152902 | TIP41, TOR signalling pathway regulator-like |
| TLOC1 | NM_003262 | translocation protein 1 |
| TPD52L2 | NM_003288 | tumor protein D52-like 2 isoform e |
| TPD52L2 | NM_199359 | tumor protein D52-like 2 isoform f |

TABLE 4-continued

Predicted hsa-miR-124a targets that exhibited altered mRNA expression levels in human cancer cells after transfection with Pre-miR hsa-miR-124a.

| Gene Symbol | RefSeq Transcript ID | Description |
|---|---|---|
| TPD52L2 | NM_199360 | tumor protein D52-like 2 isoform a |
| TPD52L2 | NM_199361 | tumor protein D52-like 2 isoform b |
| TPD52L2 | NM_199362 | tumor protein D52-like 2 isoform c |
| TPD52L2 | NM_199363 | tumor protein D52-like 2 isoform d |
| TRIM9 | NM_015163 | tripartite motif protein 9 isoform 1 |
| TUBB6 | NM_032525 | tubulin, beta 6 |
| UBE2B | NM_003337 | ubiquitin-conjugating enzyme E2B |
| UGT8 | NM_003360 | UDP glycosyltransferase 8 (UDP-galactose |
| USP14 | NM_005151 | ubiquitin specific protease 14 isoform a |
| USP37 | NM_020935 | ubiquitin specific protease 37 |
| USP48 | NM_032236 | ubiquitin specific protease 48 isoform a |
| VAMP3 | NM_004781 | vesicle-associated membrane protein 3 |
| VAT1 | NM_006373 | vesicle amine transport protein 1 |
| VDAC2 | NM_003375 | voltage-dependent anion channel 2 |
| VDAC3 | NM_005662 | voltage-dependent anion channel 3 |
| YIPF6 | NM_173834 | Yip1 domain family, member 6 |
| YOD1 | NM_018566 | hypothetical protein LOC55432 |
| YTHDF1 | NM_017798 | YTH domain family, member 1 |

The predicted gene targets of hsa-miR-124a whose mRNA expression levels are affected by hsa-miR-124a represent particularly useful candidates for cancer therapy and therapy of other diseases through manipulation of their expression levels.

Example 4

Cancer Related Gene Expression Altered by Hsa-miR-124a

Cell proliferation and survival pathways are commonly altered in tumors (Hanahan and Weinberg, 2000). The inventors have shown that hsa-miR-124a directly or indirectly regulates the transcripts of proteins that are critical in the regulation of these pathways. Many of these targets have inherent oncogenic or tumor suppressor activity. Hsa-miR-124a targets that are associated with various cancer types are shown in Table 5.

TABLE 5

Tumor associated mRNAs altered by hsa-miR-124a having prognostic or therapeutic value for the treatment of various malignancies.

| Gene Symbol | Gene Title | Cellular Process | Cancer Type | Reference |
|---|---|---|---|---|
| AKAP12 | Akap-12/SSeCKS/Gravin | Signal transduction | CRC, PC, LC, GC, AML, CML | (Xia et al., 2001; Wikman et al., 2002; Boultwood et al., 2004; Choi et al., 2004; Keen and Taylor, 2004; Mori et al., 2006; Reiter et al., 2006; Ulisse et al., 2006) |
| AURKA/STK6 | aurora kinase A | chromosomal stability | BC, CRC, PaC, OC, GC, SCCHN, TC | (Keen and Taylor, 2004; Reiter et al., 2006; Ulisse et al., 2006) |
| AURKB/STK12 | aurora kinase B | chromosomal stability | PC, NSCLC, BC, CRC | (Keen and Taylor, 2004; Smith et al., 2005; Chieffi et al., 2006) |
| BCL10 | BCL-10 | signal transduction | MALT BCL | (Thome, 2004) |
| BCL2L11 | Bim | apoptosis | M, MCL, NSCLC, G, | (Gomez-Bougie et al., 2004; Austin and Cook, 2005; Li et al., 2005; Tagawa et al., 2005) |
| BRAF | B-Raf | signal transduction | M, TC, CRC, OepC, AML, SCCHN, NSCLC, GC, OC, NHL, CC | (Tuveson et al., 2003; Beeram et al., 2005) |

TABLE 5-continued

Tumor associated mRNAs altered by hsa-miR-124a having prognostic or therapeutic value for the treatment of various malignancies.

| Gene Symbol | Gene Title | Cellular Process | Cancer Type | Reference |
|---|---|---|---|---|
| BRCA1 | BRCA-1 | chromosomal stability | BC, OC | (Wooster and Weber, 2003) |
| BRCA2 | BRCA-2 | chromosomal stability | BC, OC | (Wooster and Weber, 2003) |
| BUB1 | BUB1 | chromosomal stability | AML, SGT, ALL, HL, L, CRC, GC | (Cahill et al., 1998; Qian et al., 2002; Ru et al., 2002; Grabsch et al., 2003; Shigeishi et al., 2006) |
| BUB1B | BUBR1 | chromosomal stability | LC, GC | (Seike et al., 2002; Grabsch et al., 2003) |
| CCNA2 | cyclin A2 | cell cycle | AML | (Qian et al., 2002) |
| CCNB1 | cyclin B1 | cell cycle | HCC, BC, CHN, PC, CRC, LC | (Egloff et al., 2006) |
| CCNE2 | cyclin E2 | cell cycle | BC, LC, OC, EC | (Payton and Coats, 2002; Payton et al., 2002) |
| CDC2 | CDK1 | cell cycle | NHL, CRC, SCCHN, OepC | (Wolowiec et al., 1999; Egilmez et al., 2001; Chang et al., 2005; Hansel et al., 2005) |
| CDC20 | cell division cycle 20 | cell cycle | GC | (Kim et al., 2005) |
| CDC23 | cell division cycle 23 | cell cycle | CRC | (Wang et al., 2003) |
| CDC25A | cell division cycle 25A | cell cycle | HCC, OepC, BC, CRC, CHN, NSCLC, OC, TC, NHL | (Kristjansdottir and Rudolph, 2004) |
| CDC6 | cell division cycle 6 | cell cycle | PC, CeC, NSCLC | (Robles et al., 2002; Karakaidos et al., 2004; Semple and Duncker, 2004; Murphy et al., 2005) |
| CDK2 | CDK-2 | cell cycle | OC, CRC, PC | (Cipriano and Chen, 1998; Marone et al., 1998; Yamamoto et al., 1998) |
| CDK4 | CDK-4 | cell cycle | G, GB, BC, LC, GC, EC, L, OS, OC, TT, HCC, CHN | (Malumbres and Barbacid, 2001) |
| CDK6 | CDK-6 | cell cycle | G, GB, GBM, MB, B-cell CLL | (Costello et al., 1997; Lam et al., 2000; Hayette et al., 2003; Mendrzyk et al., 2005) |
| CDKN2C | CDK inhibitor 2C | cell cycle | HB, MB, HCC, HL, MM | (Iolascon et al., 1998; Kulkarni et al., 2002; Morishita et al., 2004; Sanchez-Aguilera et al., 2004) |
| CDT1 | Cdt1 | chromosomal stability | NSCLC | (Karakaidos et al., 2004) |
| CHUK | IKK alpha | signal transduction | LSCC, BC | (Cao et al., 2001; Nakayama et al., 2001; Romieu-Mourez et al., 2001) |
| CKS1B | Cks1 | cell cycle | NSCLC, BC, CRC | (Inui et al., 2003; Shapira et al., 2005; Slotky et al., 2005) |
| ETS1 | Ets-1 | transcription | L, BCL, NHL, GC, PaC, TC, AC, SCCHN, HCC, MG, OC, BC, LC, CeC, EC, CRC, M, PC, ALL | (Sacchi et al., 1988; Dreyfus et al., 1989; Kerckaert et al., 1990; Crossen and Morrison, 1993; Crossen et al., 1995; Nakayama et al., 1996; Ito et al., 1998; Kitange et al., 1999; Nakayama et al., 1999; Ito et al., 2000; Kitange et al., 2000; Ozaki et al., 2000; Saeki et al., 2000; Behrens et al., 2001; Davidson et al., 2001; Sasaki et al., 2001; Fujimoto et al., 2002a; Fujimoto et al., 2002b; Span et al., 2002; Dittmer, 2003; Tokuhara et al., 2003; Buggy et al., 2004; Rothhammer et al., 2004; Alipov et al., 2005) |
| FAS | Fas | apoptosis | NSCLC, G, L, CRC, OepC | (Moller et al., 1994; Gratas et al., 1998; Martinez-Lorenzo et al., 1998; Shinoura et al., 2000; Viard-Leveugle et al., 2003), |
| FGF2 | FGF-2 | signal transduction | BC, RCC, OC, M, NSCLC | (Chandler et al., 1999) |
| FGFR3 | FGF receptor-3 | signal transduction | BldC, CRC, CeC, MM | (L'Hote and Knowles, 2005) |
| FOXM1 | forkhead box M1 | transcription | GB, LC, PC | (Kalin et al., 2006; Kim et al., 2006; Liu et al., 2006) |
| FOXO1A | FOXO1, FKHR | transcription | RMS, EC | (Barr, 2001; Goto et al., 2007) |

TABLE 5-continued

Tumor associated mRNAs altered by hsa-miR-124a having prognostic or therapeutic value for the treatment of various malignancies.

| Gene Symbol | Gene Title | Cellular Process | Cancer Type | Reference |
| --- | --- | --- | --- | --- |
| FZD7 | Frizzled-7 | signal transduction | OepC, GC, HCC | (Tanaka et al., 1998; Kirikoshi et al., 2001; Merle et al., 2004) |
| GMNN | geminin | DNA replication | CRC, BC, CeC | (Wohlschlegel et al., 2002; Bravou et al., 2005; Shetty et al., 2005) |
| IGFBP1 | IGFBP-1 | signal transduction | BC, CRC | (Firth and Baxter, 2002) |
| IGFBP3 | IGFBP-3 | signal transduction | BC, PC, LC, CRC | (Firth and Baxter, 2002) |
| IL8 | IL-8 | signal transduction | BC, CRC, PaC, NSCLC, PC, HCC | (Akiba et al., 2001; Sparmann and Bar-Sagi, 2004) |
| LHFP | lipoma HMGIC fusion partner | transcription | Li | (Petit et al., 1999) |
| MCAM | MCAM | cell adhesion | M, AS, KS, LMS | (McGary et al., 2002) |
| MCL1 | Mcl-1 | apoptosis | HCC, MM, TT, CLL, ALCL, BCL, PC | (Krajewska et al., 1996; Kitada et al., 1998; Cho-Vega et al., 2004; Rust et al., 2005; Sano et al., 2005; Wuilleme-Toumi et al., 2005; Fleischer et al., 2006; Sieghart et al., 2006) |
| MDM2 | Mdm2 | proteasomal degradation | AC, GB, BC, CeC, OepC, L, HB, NSCLC, NPC, NB, OS, OC, EWS, Li, LS, Schw, TT, UC, WT, RMS | (Momand et al., 1998) |
| MXI1 | Max-interacting protein 1 | transcription | M, PC, GB | (Wechsler et al., 1997; Prochownik et al., 1998; Ariyanayagam-Baksh et al., 2003) |
| MYBL1 | A-Myb | transcription | BL | (Golay et al., 1996) |
| MYBL2 | Myb L2 | transcription | BC, NSCLC, PC, OC | (Tanner et al., 2000; Bar-Shira et al., 2002; Borczuk et al., 2003; Ginestier et al., 2006) |
| NRG1 | neuregulin 1 | signal transduction | BC, PaC, G | (Adelaide et al., 2003; Ritch et al., 2003; Prentice et al., 2005) |
| PBX1 | PBX-1 | transcription | ALL | (Aspland et al., 2001) |
| PDGFD | PDGF-D | signal transduction | GB, MB, EWS | (Li et al., 2003) |
| PDGFRL | PDGFR-like, PRLTS | signal transduction | CRC, NSCLC, HCC, PC | (Fujiwara et al., 1995; Komiya et al., 1997) |
| PIK3CA | PI 3-kinase, p110 alpha | signal transduction | BC, CRC, LC, OC, G, GB, HCC, GC, CeC | (Bader and Vogt, 2004; Bader et al., 2005) |
| PLCB1 | PLC-beta1 | signal transduction | AML | (Lo Vasco et al., 2004) |
| PLK1 | polo-like kinase 1 | chromosomal stability | NSCLC, OrpC, OepC, GC, M, BC, OC, BC, CRC, GB, PapC, PaC, PC, HB, NHL | (Strebhardt and Ullrich, 2006) |
| PRKCA | PKC alpha | signal transduction | BldC, PC, EC, BC, CRC, HCC, M, GC, OC | (Koivunen et al., 2006; Weichert et al., 2003; Jiang et al., 2004; Lahn and Sundell, 2004) |
| RASSF2 | RASSF2 | signal transduction | GC, CRC, OC | (Akino et al., 2005; Endoh et al., 2005; Lambros et al., 2005) |
| RB1 | Rb | cell cycle | RB, SCLC, NSCLC | (Sherr and McCormick, 2002; Dyer and Bremner, 2005) |
| RBL1 | p107 | cell cycle | BCL, PC, CRC, TC | (Takimoto et al., 1998; Claudio et al., 2002; Wu et al., 2002; Ito et al., 2003) |
| RRAS | R-RAS | signal transduction | CeC, BC | (Yu and Feig, 2002; Rincon-Arano et al., 2003) |
| SKP2 | SKP-2 | proteasomal degradation | PaC, OC, BC, MFS, GB, EC, NSCLC, PC | (Kamata et al., 2005; Saigusa et al., 2005; Shibahara et al., 2005; Takanami, 2005; Einama et al., 2006; Huang et al., 2006; Sui et al., 2006; Traub et al., 2006), |

TABLE 5-continued

Tumor associated mRNAs altered by hsa-miR-124a having prognostic or therapeutic value for the treatment of various malignancies.

| Gene Symbol | Gene Title | Cellular Process | Cancer Type | Reference |
| --- | --- | --- | --- | --- |
| SRC | c-Src | signal transduction | CRC, HCC, PaC, GC, OepC, BC, OC, LC | (Yeatman, 2004) |
| SRI | Sorcin | multi drug resistance | OC, BC, AML | (Parekh et al., 2002; Tan et al., 2003) |
| TACC1 | TACC1 | cell cycle | BC, OC | (Cully et al., 2005; Lauffart et al., 2005) |
| TACC3 | TACC3 | cell cycle | OC, NSCLC, | (Lauffart et al., 2005; Jung et al., 2006) |
| TACSTD1 | tumor-associated calcium signal transducer 1 | cell adhesion, vesicle trafficking | NSCLC, CRC | (Xi et al., 2006a; Xi et al., 2006b) |
| TGFB2 | TGF beta-2 | signal transduction | PaC, CRC, BC, M | (Krasagakis et al., 1998; Jonson et al., 2001; Nakagawa et al., 2004; Beisner et al., 2006) |
| TGFBR2 | TGF beta receptor type II | signal transduction | BC, CRC | (Markowitz, 2000; Lucke et al., 2001; Biswas et al., 2004) |
| TGFBR3 | TGF beta receptor III | signal transduction | CeC, high grade NHL, CRC, BC | (Venkatasubbarao et al., 2000; Bandyopadhyay et al., 2002; Woszczyk et al., 2004; Soufla et al., 2005) |
| VAV3 | Vav3 | signal transduction | PC | (Dong et al., 2006) |

Abbreviations:
AC, astrocytoma;
ALCL, anaplastic large cell lymphoma;
ALL, acute lymphoblastic leukemia;
AML, acute myeloid leukemia;
AS, angiosarcoma;
BC, breast carcinoma;
BCL, B-cell lymphoma;
BL, Burkitt's lymphoma;
BldC, bladder carcinoma;
CC, cholangiocarcinoma;
CeC, cervical carcinoma;
CHN, carcinoma of the head and neck;
CLL, chronic lymphoblastic leukemia;
CML, chronic myeloid leukemia;
CRC, colorectal carcinoma;
EC, endometrial carcinoma;
EWS, Ewing's sarcoma;
G, glioma;
GB, glioblastoma;
GBM, glioblastoma multiforme;
GC, gastric carcinoma;
HB, hepatoblastoma;
HCC, hepatocellular carcinoma;
HL, Hodgkin lymphoma;
KS, Kaposi's sarcoma;
L, leukemia;
LC, lung carcinoma;
Li, lipoma;
LMS, leiomyosarcoma;
LS, liposarcoma;
LSCC, laryngeal squamous cell carcinoma;
M, melanoma;
MALT BCL, mucosa-associated lymphoid tissue B-cell lymphoma;
MB, medulloblastoma;
MCL, mantle cell lymphoma;
MFS, myxofibrosarcoma;
MG, meningioma;
MM, multiple myeloma;
NB, neuroblastoma,
NHL, non-Hodgkin lymphoma;
NPC, nasopharyngeal carcinoma;
NSCLC, non-small cell lung carcinoma;
OC, ovarian carcinoma;
OepC, oesophageal carcinoma;
OrpC, oropharyngeal carcinoma;
OS, osteosarcoma;
PaC, pancreatic carcinoma;
PapC, papillary carcinoma;
PC, prostate carcinoma;
RB, retinoblastoma;
RCC, renal cell carcinoma;

TABLE 5-continued

Tumor associated mRNAs altered by hsa-miR-124a having prognostic or therapeutic value for the treatment of various malignancies.

| Gene Symbol | Gene Title | Cellular Process | Cancer Type | Reference |
| --- | --- | --- | --- | --- |

RMS, rhabdomyosarcoma;
SCCHN, squamous cell carcinoma of the head and neck;
Schw, schwannoma;
SCLC, small cell lung cancer;
SGT, salivary gland tumor;
TC, thyroid carcinoma;
TT, testicular tumor;
UC, urothelial carcinoma;
WT, Wilm's tumor Hsa-miR-124a targets of particular interest are genes and their products that function in the regulation of intracellular signal transduction in response to mitotic or apoptotic stimuli. When deregulated, many of these proteins contribute to the malignant phenotype in vitro and in vivo. Hsa-miR-124a affects intracellular signaling at various layers and controls the expression of secretory proteins, transmembrane growth factor receptors as well as cytoplasmic signaling molecules. Among secretory proteins are fibroblast growth factor 2 (FGF2), insulin growth factor binding protein 1 and 3 (IGFBP1, IGFBP3), transforming growth factor β-2 (TGFB2) and the inflammatory chemokine interleukin 8. FGF-2 is a secretory protein with potent mitogenic and angiogenic activity that transmits the signal into cells via transmembrane receptors (FGFRs) composed of 2-3 extracellular immunoglobulin-like domains and an intracellular tyrosine kinase domain (Chandler et al., 1999). FGF-2 mRNAs levels are increased in renal, oral and non-small lung cancer cells (Chandler et al., 1999). Similarly, IL-8 is frequently upregulated in various cancers and correlates with tumor vascularization, metastasis and poor prognosis (Rosenkilde and Schwartz, 2004; Sparmann and Bar-Sagi, 2004). TGFB2 is the corresponding ligand to TGF-β receptors (TGFBR), a class of receptors that may function as tumor suppressors (Massague et al., 2000).

Membrane-associated proteins regulated by hsa-miR-124a are platelet-derived growth factor receptor-like (PDGFRL; also referred to as PDGF receptor beta-like tumor suppressor, PRLTS) and the Ras association domain family protein 2 (RASSF2). RASSF2 is a tumor suppressor candidate that is frequently downregulated in lung tumor cell lines (Vos et al., 2003). RASSF2 interacts with K-Ras and promotes cell cycle arrest and apoptosis. PDGFRL also functions as a tumor suppressor that shows loss of function in a broad variety of cancers either by loss of heterozygosity (LOH) or missense and frame-shift mutation (Fujiwara et al., 1995; Komiya et al., 1997). Since treatment of cancer cells with hsa-miR-124a leads to reduced expression levels of FGF2, IL8 and IGFBPs, and to increased expression levels of TGFB2, RASSF2 and PDGFRL, hsa-miR-124a is likely to induce a therapeutic response in cancer patients that show aberrant expression or function of these growth-stimulatory or inhibitory proteins.

Intracellular signaling molecules regulated by hsa-miR-124a include IkappaB kinase alpha (IKKalpha, CHUK), c-Src (SRC), the catalytic subunit of class IA phosphoinositide 3-kinases p110α (PIK3CA) and phospholipase C beta-1 (PLCB1). PLC beta-1 catalyzes the generation of inositol-1,4,5-trisphosphate (IP3) and diacylglycerol (DAG) from phosphatidylinositol-bis-phosphate (PIP2), regulating proliferative signals and checkpoints of the cell cycle (Lo Vasco et al., 2004). IKKalpha is a positive regulator of the intracellular signaling cascade and functions to activate the transcription factor nuclear factor kappa B (NFkappaB) (Karin et al., 2002). NFkappaB is constitutively activated in several cancer types and promotes anti-apoptotic and survival pathways. The proto-oncoprotein c-Src is the human homolog of avian v-Src that has been isolated as the tumorigenic component of Rous Sarcoma virus (RSV) (Rous, 1911; Stehelin et al., 1976; Yeatman, 2004). c-Src is a membrane-associated tyrosine kinase that is activated in response to intracellular signaling or indirectly to extracellular stimuli by binding to activated receptor tyrosine kinases, including EGFR, ERBB2, PDGFR and FGFR. Src is a crucial molecule in a complex network of interacting proteins, regulating cell adhesion, motility, invasion and proliferation. c-Src is frequently overexpressed or hyperactivated in numerous cancer types (Yeatman, 2004). The gene product of PIK3CA activates the Akt signaling pathway in response to most upstream receptor tyrosine kinases (Vanhaesebroeck et al., 1997). PIK3CA frequently acquires a gain of function in the vast majority of human cancers, either by amplification or overexpression, such as in ovarian and cervical cancers, or by activating somatic mutations (Bader and Vogt, 2004; Bader et al., 2005). PIK3CA has become a novel drug target in the pharmaceutical industry and is also a predicted target of hsa-miR-124a (Table 3). Based on our data, hsa-miR-124a negatively regulates these proteins and therefore is likely to function as a tumor-suppressor miRNA.

Another class of genes and their corresponding proteins that are regulated by hsa-miR-124a, functions in the progression of the cell cycle. Some of these proteins are critical in the transition through G1 and S phases, such as cyclins A2 and E2 (CCNA2, CCNE2), cyclin dependent kinases 2, 4 and 6 (CDK2, CDK4, CDK6) and cell division cycle 6 (CDC6). Others are required for progressing through the G2/M spindle checkpoint and proper segregation of sister chromatids during mitosis to maintain chromosomal stability. These include aurora kinases A and B (AURKA, a.k.a. STK6; AURKB, a.k.a. STK12), breast cancer 1 and 2 (BRCA1; BRCA2), budding uninhibited by benzimidazoles 1 (BUB1), budding uninhibited by benzimidazoles 1 beta (BUB1B), polo-like kinase 1 (PLK1), cyclin dependent kinase 1 (CDK1, a.k.a. CDC2), cyclins B1 and B2 (CCNB1, CCNB2), and cell division cycle 20 and 23 (CDC20, CDC23, a.k.a. anaphase promoting complex subunit 8). Most of these transcripts are regulated in a manner that suggests that hsa-miR-124a blocks cell cycle progression. All of these targets also have an evident role in carcinogenesis.

For instance, the tumor suppressor proteins BRCA1 and BRCA2, as well as the growth-promoting aurora kinases A and B show deregulated expression in a various solid tumors, e.g. carcinomas of the breast, ovary, thyroid gland, lung, prostate and colorectum (Wooster and Weber, 2003; Keen and Taylor, 2004; Turner et al., 2004; Smith et al., 2005; Chieffi et al., 2006; Ulisse et al., 2006). Aurora kinases are preferred drug targets in the pharmaceutical industry. PLK1 (also referred to as serine-threonine protein kinase 13; STPK13) is a protein kinase that regulates mitotic spindle function to maintain chromosomal stability (Strebhardt and Ullrich, 2006). PLK1 expression is tightly regulated during the cell cycle and peaks in M phase. PLK1 is inherently oncogenic and directly inhibits the tumor suppressor function of p53 (Ando et al., 2004). Overexpression of PLK1 induces a polynucleated phenotype and cellular transformation of NIH3T3 cells (Mundt et al., 1997; Smith et al., 1997). Likewise, PLK1 shows increased expression levels in most solid tumors, including carcinomas of the breast, colon, lung, stomach and prostate (Table 5). PLK1 overexpression is associated with disease progression and, when depleted, induces apoptosis in cancer cells (Liu and Erikson, 2003; Strebhardt and Ullrich, 2006). Currently, PLK1 is being tested as a target of various small molecule inhibitors for future therapeutic intervention (Strebhardt and Ullrich, 2006).

CDC6 is regulated in response to mitogenic signals through transcriptional control mechanisms involving E2F proteins and is required for initiation of DNA replication in mammalian cells. CDC6 is overexpressed in various human cancers and has inherent oncogenic potential (Karakaidos et al., 2004; Semple and Duncker, 2004; Murphy et al., 2005; Gonzalez et al., 2006). Cyclins are co-factors of cyclin-dependent kinases (CDKs) (Malumbres and Barbacid, 2001). The expression of cyclins is tightly controlled during the cell cycle to govern the activity of individual CDKs. Cyclin A2 and cyclin E2 associate with CDK2 during S phase; cyclin D1 is the predominant co-factor of CDK4/6 in G1 phase. Most cyclins are promoters of cell growth, and several, such as cyclin A2, B1, or E2, are frequently expressed at high levels in various tumor types (Payton and Coats, 2002; Payton et al., 2002; Qian et al., 2002; Egloff et al., 2006). CDK4 and CDK6 form active complexes with D-type cyclins, including D1, D2 and D3. The primary function of CDK2, CDK4 and CDK6 is to inactivate members of the retinoblastoma protein family. CDK2, CDK4 and CDK6 are overexpressed in numerous cancers and are currently being explored as a potential cancer drug targets (Costello et al., 1997; Cipriano and Chen, 1998; Marone et al., 1998; Yamamoto et al., 1998; Lam et al., 2000; Malumbres and Barbacid, 2001; Hayette et al., 2003; Mendrzyk et al., 2005).

CDK1 (CDC2) is a catalytic subunit of a protein kinase complex, called the M-phase promoting factor that induces entry into mitosis and is universal among eukaryotes. Activation of CDK1 requires binding to B cyclins and dephosphorylation by CDC25. Similar to other CDKs, CDK1 is expressed at increased levels in various cancers (Table 5). The CDC25 protein phosphatase family plays a critical role in activating cyclin-dependent kinases (CDKs) via dephosphorylation of conserved threonine 15 and tyrosine 15 inhibitory phosphorylation sites. While CDC25C is primarily responsible for activating CDK1 to overcome G2/M checkpoint and allow mitotic entry, the primary substrate of CDC25A is CDK2 and CDK6 which, when active, allows progression through the G1/S and intra-S checkpoints (Kristjansdottir and Rudolph, 2004). CDC25A is frequently amplified and overexpressed in human cancers, including cancers of the breast, lung, rectum and brain (Kristjansdottir and Rudolph, 2004).

Other molecules regulated by hsa-miR-124a that indirectly control cell cycle progression are SKP2, MDM2 and AKAP12. AKAP12, also referred to as gravin or SSeCKS (Src suppressed C kinase substrate), functions as a kinase scaffold protein that tethers the enzyme-substrate interaction (Nauert et al., 1997). Expression of AKAP12 interferes with oncogenic cell transformation induced by the Src or Jun oncoproteins in vitro and is lost or reduced in numerous cancers, such as leukemia and carcinomas of the rectum, lung and stomach (Lin and Gelman, 1997; Cohen et al., 2001; Xia et al., 2001; Wikman et al., 2002; Boultwood et al., 2004; Choi et al., 2004; Mori et al., 2006). An apparent anti-oncogenic activity of AKAP12 in prostate and gastric cancers marks this protein as a putative tumor suppressor (Xia et al., 2001; Choi et al., 2004). Skp2 is a component of the multisubunit E3 ubiquitin ligase complex that ear-marks proteins for proteasomal degradation. A well characterized target is the CDK inhibitor p27 which offers an explanation for the cell cycle promoting activity of Skp2 (Carrano et al., 1999). Skp2 is inherently oncogenic and shows elevated levels in various cancer types (Gstaiger et al., 2001; Kamata et al., 2005; Saigusa et al., 2005; Einama et al., 2006).

Hsa-miR-124a also governs the expression of FAS, Bim (BCL2L11) and MCL1, all of which are functionally linked to the apoptotic pathway. Bim and MCL 1 are members of the BCL-2 (B cell lymphoma 2) gene family. MCL1 gives rise to two alternatively spliced gene products with opposing functions (Bae et al., 2000). The predominant species is MCL1-L that has anti-apoptotic activity. High levels of MCL1 are correlated with poor prognosis of patients with ovarian carcinoma and is indicative for leukemic relapse (Kaufmann et al., 1998; Shigemasa et al., 2002). RNA interference against MCL1 induces a therapeutic response in gastric and hepatocellular carcinoma cells (Schulze-Bergkamen et al., 2006; Zangemeister-Wittke and Huwiler, 2006).

In contrast to MCL1, Bim induces apoptosis by binding to and antagonizing anti-apoptotic members of the Bcl-2 family. Interactions have been observed with Bcl-2, Bcl-xL, Mcl-1, Bcl-w, Bfl-1 and BHRF-1 (Hsu et al., 1998; O'Connor et al., 1998). Loss of Bim promotes oncogenesis, suggesting a tumor suppressor role for Bim (Egle et al., 2004). In agreement with this observation is the fact that Bim is frequently lost or expressed at reduced levels in many cancers (Gomez-Bougie et al., 2004; Austin and Cook, 2005; Li et al., 2005; Tagawa et al., 2005). FAS, also known as CD95 or APO-1, is a transmembrane cell surface receptor that functions in the transduction of apoptotic signals in response to its ligand FasL (Houston and O'Connell, 2004). Reduced FAS expression is a common mechanism of cells to decrease the sensitivity to FasL-mediated cell death. Similarly, many different cancer types show lost or decreased Fas expression levels (Table 5). In colorectal carcinoma, FAS expression is progressively reduced in the transformation of normal epithelium to benign neoplasm, adenocarcinomas and metastases (Moller et al., 1994). Thus, despite expression of FasL, tumor cells may escape the FasL induced apoptotic signal. Transient transfection of hsa-miR-124a increases expression of FAS and Bim and decreases MCL1 transcripts and therefore may antagonize the anti-apoptotic phenotype of cancer cells.

Transcription factors regulated by hsa-miR-124a include the mammalian homolog of the v-Ets oncoprotein (ETS1), the forkhead box/winged-helix transcription factors FOXO1 (FOXO1A) and FOXM1, as well as the v-myb myeloblastosis viral oncogene homolog-like proteins A-MYB (MYBL1) and MYB-L2 (MYBL2). The transcription factor Ets-1 (ETS1) is the mammalian homolog of the v-Ets oncoprotein originally isolated from the transforming erythroblastosis virus E26 (Leprince et al., 1983). Similar to viral Ets, the endogenous proto-oncoprotein Ets-1 has oncogenic potential and transforms murine NIH3T3 fibroblasts in culture (Dittmer, 2003). Ets-1 stimulates angiogenesis by regulating VEGF expression levels. Ets-1 plays a role in making tumors more invasive and is indicative for poor prognosis (Dittmer, 2003). Ets-1 is upregulated in a vast variety of solid tumors and malignancies of the hematopoietic system (Dittmer, 2003). The ETS1 gene is also frequently subject to chromosomal translocation in acute myeloid leukemia (AML) and acute lymphoblastic leukemia (ALL) and may be critical in the development of the disease (Sacchi et al., 1986; Goyns et al., 1987).

FoxM1 controls the expression of cell cycle genes, such as cyclins B and D (Wang et al., 2001). FoxM1 is expressed at high levels in human glioblastomas and shows tumorigenic activity in various model systems (Kalin et al., 2006; Kim et al., 2006; Liu et al., 2006). Mice deficient in FoxM1 fail to develop chemically induced hepatocellular carcinomas (Kalinichenko et al., 2004). In contrast to Ets-1 and FoxM1, FOXO1, also known as FKHR, belongs to a class of lineage-restricted tumor suppressor proteins with redundant functions, including FOXO3a and FOXO4 (Vogt et al., 2005; Paik et al., 2007). FOXO proteins are pro-apoptotic by transcribing the FasL gene and induce cell cycle arrest by upregulating the CDK inhibitor p27kip1 (Carter and Brunet, 2007). FOXO1 also induces the expression of the CDK inhibitor p21cip1 and the pro-apoptotic protein Bim, and reduces expression of the cyclins D1 and D2 (Bader et al., 2005). In alveolar rhabdomyosarcoma, the FOXO1 gene frequently undergoes chromosomal rearrangements which fuses C-terminal sequences of FOXO1 to N-terminal sequences of PAX3 or PAX7, resulting in a hybrid protein with altered DNA-binding specificity (Vogt et al., 2005). A recombinant FOXO1 protein carries a transcriptional repressor domain, instead of the FOXO1-specific activator domain, is oncogenic in cell culture (Aoki et al., 2004). Since transfection of hsa-miR-124a leads to elevated mRNA levels of FOXO1 and reduced levels of FOXM1 and ETS1, hsa-miR-124a may induce a therapeutic response in cancer cells by regulating these targets.

Based on the function of most targets and how they are regulated by hsa-miR-124a, hsa-miR-124a appears to function as a tumor suppressor miRNA. However, hsa-miR-124a also regulates cancer-associated genes in a fashion indicating that this miRNA might promote tumorigenesis and that inhibition of hsa-miR-124a might be able to intercept with tumor development when appropriate. Among these targets are the retinoblastoma tumor suppressor proteins Rb (RB1) and p107 (RBL1), MDM2, B Raf (BRAF), platelet-derived growth factor D (PDGFD), protein kinase C-alpha (PRKCA) and transforming growth factor-beta receptors 2 and 3 (TGFBR2, TGFBR3). TGFBR-2 and TGFBR-3 are putative tumor suppressors. TGFBR-2 forms a functional complex with TGFBR-1 and is the primary receptor for TGF-β (Massague et al., 2000). A central role of TGF-β is inhibition of cellular growth of numerous cell types, such as epithelial, endothelial, hematopoietic neural and mesenchymal cells. Many mammary and colorectal carcinomas with microsatellite instability harbor inactivating mutations of TGFBR-2, and therefore escape the growth-inhibitory function of TGF-β (Markowitz et al., 1995; Lucke et al., 2001). TGFBR-3, also referred to as beta-glycan, binds all three TGF-β isoforms with high affinity. TGFBR-3 associates with TGFBR-2 to signal to downstream effector molecules (Blobe et al., 2001). Similar to TGFBR-2, TGFBR-3 is frequently downregulated in multiple cancer types (Table 5) (Hishikawa et al., 1999; Lin et al., 2005).

PRKCA belongs to a family of serine-threonine kinases that are activated in response to signaling induced by receptor tyrosine kinases. Functional studies have suggested that PKCs play a role in carcinogenesis and maintenance of the malignant phenotype (Koivunen et al., 2006). PRKCA is overexpressed in endometrial, prostate and high grade urinary bladder carcinomas (Koivunen et al., 2006). PRKCA activity is linked to increased motility and invasion of cancer cells, a phenotype that can be reversed by PRKCA inhibition (Koivunen et al., 2004). PDGFs are structurally related to the v-sis oncogene of simian sarcoma virus, and compelling evidence has demonstrated the transforming activity of PDGF-D in NIH3T3 cells (Li et al., 2003). PDGF-D is expressed in many tumors and tumor cell lines, including glioblastoma, medulloblastoma, Ewing family tumor cell lines and several other tumor cell lines (Li et al., 2003). PDGFD-induced tumors displayed signs of increased vascularization with elevated levels of VEGF (vascular endothelial growth factor), suggesting that PDGFD is angiogenic. Therefore, PDGFD is currently investigated as a potential drug target in the intervention of cancer signaling (Pietras et al., 2003).

Human MDM2 functions as an E3 ubiquitin ligase and inhibitor of the p53 tumor suppressor (Momand et al., 1998; Bartel et al., 2002). MDM2 directly binds to p53, facilitates nuclear export and marks p53 for proteasomal degradation. MDM2 is amplified or overexpressed in approximately one third of human malignancies, including sarcomas of soft tissue and bone. To date, MDM2 amplification has been observed in at least 19 tumor types with varying frequencies (Momand et al., 1998; Bartel et al., 2002). In accord, overexpression of MDM2 leads to oncogenic transformation of NIH3T3 and Rat2 cells (Fakharzadeh et al., 1991). The pocket proteins RB1 and RBL1, also known as p107, interact with the E2F family of transcription factors and block cell cycle progression and DNA replication (Sherr and McCormick, 2002). Accordingly, a large subset of cancers show deregulated expression of RB1 or RBL1 (Takimoto et al., 1998; Claudio et al., 2002; Sherr and McCormick, 2002; Wu et al., 2002; Ito et al., 2003; Dyer and Bremner, 2005).

B-Raf (BRAF) belongs to a family of Raf serine-threonine kinases that are homologous to the viral oncoproteins isolated from transforming murine or avian viruses (Coll et al., 1983; Jansen et al., 1983; Rapp et al., 1983). Raf proteins are activated by the RAS GTPase and activate the mitogen-activated protein kinase pathway (MAPK). B-Raf is frequently hyperactivated by somatic mutation in a broad variety of cancers (Tuveson et al., 2003; Beeram et al., 2005). Raf kinases and B-Raf in particular have long been preferred drug targets; sorafenib (Nexavar; Bayer) represents an example of an FDA-approved inhibitory small molecule that specifically targets this inherently oncogenic protein (Beeram et al., 2005).

In summary, hsa-miR-124a governs the activity of proteins that are critical regulators of cell proliferation and tumor development. These targets are frequently deregulated in human cancers. Based on this review of the genes and related pathways that are regulated by miR-124a, introduction of hsa-miR-124a or inhibitory anti-hsa-miR-124a into a variety of cancer cell types would likely result in a therapeutic response.

Example 5

Hsa-miR-124a is a Regulator of Cell Cycle Progression

Figure 1:
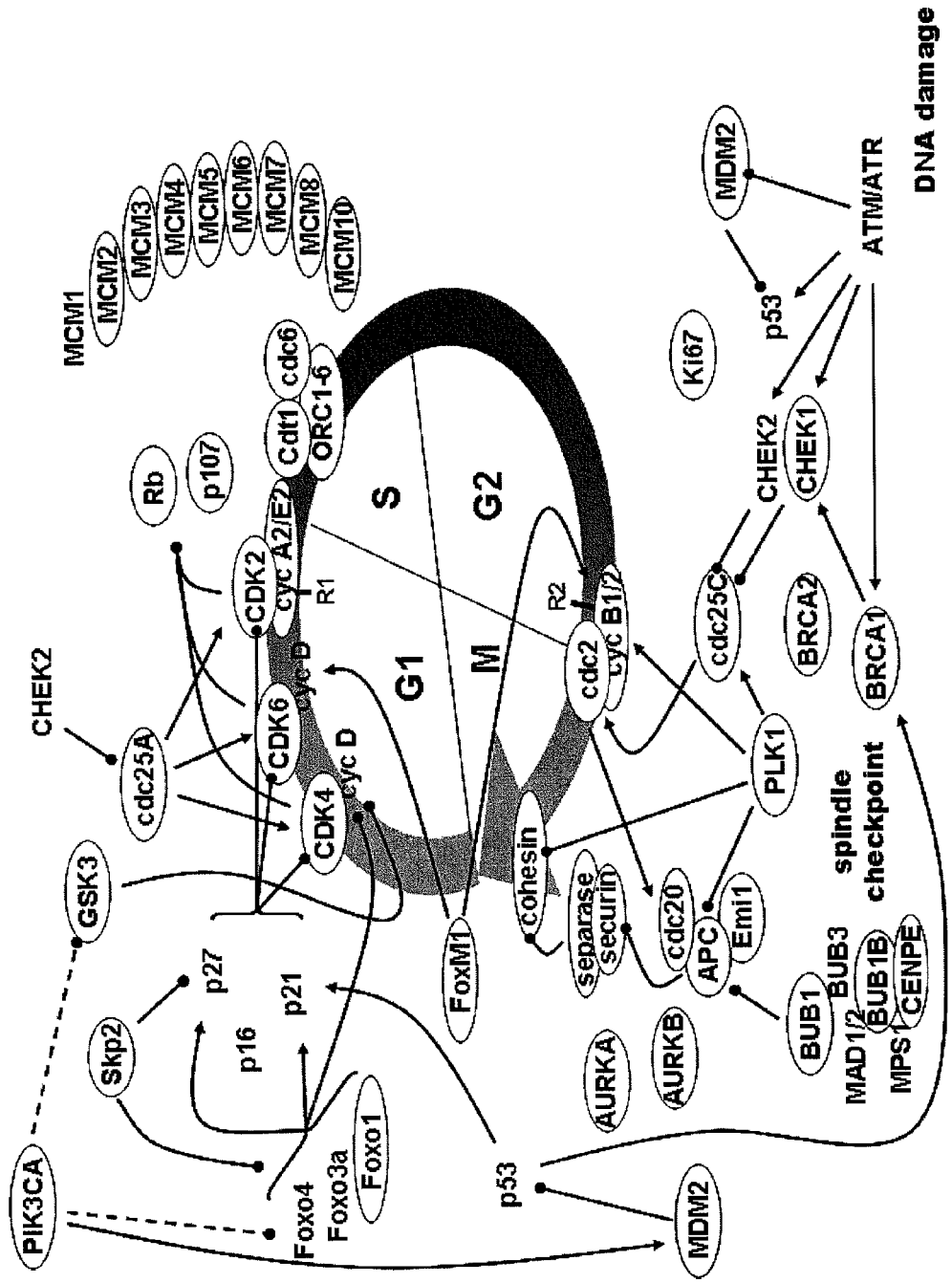
FIG. 1. Genes affected by hsa-miR-124a that function in the regulation of the cell cycle. A description of the graph and the function of each molecule are presented in Table 9. Molecules in circles are differentially expressed upon transfection with hsa-miR-124a (see also Table 1). Solid lines represent direct interactions between molecules (e.g., phosphorylation); dotted lines indicate indirect interactions. Lines that end in arrows indicate an activating action; lines that end into circles denote an inhibitory action. G1, gap 1 phase; S, synthesis phase; G2, gap 2 phase; M, mitosis phase; R1, restriction point 1; R2, restriction point 2.

A review of genes that are differentially expressed in response to introduction of hsa-miR-124a (Table 1) revealed that hsa-miR-124a controls many genes that function in the regulation of the cell cycle. Although some of these genes have not yet been directly linked to human disease, they are essential in the proper progression of the cell cycle in normal cells. A summary of these gene products and their role during the cell cycle is provided in FIG. 1 and Table 6. Comprehensive information about the cell cycle and these molecules has been reviewed in Kops et al., 2005; Bell and Dutta, 2002; Malumbres and Barbacid, 2001; Kastan and Lim, 2000; Sherr and Roberts, 1999 and references therein and can also be found in the OMIM Entrez and Gene Entrez sections of the NCBI website at the world wide web address ncbi.nlm.nih.gov/sites/entrez. Considering the function of these proteins and how they are regulated by hsa-miR-124a, hsa-miR-124a appears to block cell cycle progression during all major phases: G1, S, G2 and M phase (FIG. 1, Table 1, Table 6). Therefore, hsa-miR-124a-based therapies are contemplated as being particularly useful in the treatment of neoplastic and other hyperproliferative disorders. In addition, it is contemplated that hsa-miR-124a inhibitors can be for clinical applications that are directed toward tissue regeneration, such as skin regeneration or the generation of tissue grafts. Since hsa-miR-124a is highly expressed in neuronal cells and plays an important role in the development of the central nervous system, hsa-miR-124a or hsa-miR-124a inhibitors it is contemplated that it can be useful in the regeneration of neuron cells to treat brain disorders that include but are not limited to brain tumors, neuronal degeneration, mental retardation, multiple sclerosis, Parkinson's disease or Alzheimer's disease (Kapsimali et al., 2007; Makeyev et al., 2007; Visvanathan et al., 2007; Cao et al., 2007; Lukiw, 2007; Mishima et al., 2007; Smirnova et al., 2005).

TABLE 6

Summary of information about miR-124a-controlled genes shown in FIG. 1. n/a not applicable because not directly involved in the cell cycle.

| Icon | Gene Title | Name | Cycle of Action | Protein Function |
|---|---|---|---|---|
| APC | n/a | anaphase-promoting complex | M phase, spindle checkpoint | multiprotein complex including CDC16, CDC23, CDC27; E3 ubiquitin ligase; induces degradation of securin |
| ATM | ATM | ataxia-telangiectasia mutated | R2 restriction point | kinase; induces cell cycle arrest upon DNA damage; substrates include CHEK2, p53 and MDM2 |
| AURKA | AURKA, STK15 | aurora kinase A | M phase, spindle checkpoint | proper formation of the spindle apparatus |
| AURKB | AURKB, STK12 | aurora kinase B | M phase, spindle checkpoint | serine/threonine kinase; regulates amphitelic attachment of spindle microtubuli to the kinetochore; vs. monotelic, merotelic, syntelic attachments |
| BRCA1 | BRCA1 | breast cancer 1 | R2 restriction point | required for DNA repair induced by DNA damage; ATM/ATR signaling; peeks in G1/M phase; more universal role in transcription, chromatin remodelling |
| BRCA2 | BRCA2 | breast cancer 2 | R2 restriction point | required for DNA repair induced by DNA damage (doublestranded DNA breaks); activated by ATM/ATR signaling; peeks in G2/M phase; required in homologous recombination during meiosis |
| BUB1 | BUB1 | budding uninhibited by benzimidazoles 1 | M phase, spindle checkpoint | kinase; phosphorylates and inhibits cdc20 |
| BUB1B | BUB1B, BUBR1 | budding uninhibited by benzimidazoles 1B | M phase, spindle checkpoint | kinase; directly binds to cdc20 and inhibits APC activity |
| BUB3 | BUB3 | budding uninhibited by benzimidazoles 3 | M phase, spindle checkpoint | localizes BUB1 and BUB1B to kinetochores |
| cdc2 | CDC2 | cell division cycle 2, cyclin-dependen kinase 1 (CDK1) | G2/M phase transition | kinase; phosphorylates cytoskeleton proteins and is necessary for inducing mitosis, phosphorylates and activates APC |
| cdc20 | CDC20 | cell division cycle 20 | M phase, spindle checkpoint | cofactor of APC necessary for APC activity |
| cdc25A | CDC25A | cell division cycle 25A | G1/S phase transition | phosphatase; removes inhibitory phosphate groups from CDK2, CDK4 and CDK6 |
| cdc25C | CDC25C | cell division cycle 25C | G2/M phase transition | phosphatase; removes inhibitory phosphate groups from cdc2 |
| cdc6 | CDC6 | cell division cycle 6 | replication | component of the pre-replication complex (pre-RC); required for recruitment of MCM proteins to the pre-RC |
| CDK2 | CDK2 | cyclin-dependent kinase 2 | G1/S phase transition | serine/threonine kinase; phosphorylates and inactivates members of the retinoblastoma protein family |
| CDK4 | CDK4 | cyclin-dependent kinase 4 | G1/S phase transition | serine/threonine kinase; phosphorylates and inactivates members of the retinoblastoma protein family |
| CDK6 | CDK6 | cyclin-dependent kinase 6 | G1/S phase transition | serine/threonine kinase; phosphorylates and inactivates members of the retinoblastoma protein family |

TABLE 6-continued

Summary of information about miR-124a-controlled genes shown in FIG. 1. n/a not applicable because not directly involved in the cell cycle.

| Icon | Gene Title | Name | Cycle of Action | Protein Function |
|---|---|---|---|---|
| Cdt1 | CDT1 | chromatin licensing and DNA replication factor 1 | replication | component of the pre-replication complex (pre-RC); cooperatively with cdc6 recruits MCM proteins to the pre-RC |
| CENPE | CENPE | centromeric protein E | M phase, spindle checkpoint | cofactor of BUB1B: activates BUB1B when bound to free kinetochores; inactivates BUB1B when bound to kinetochore microtubuli |
| CHEK1 | CHEK1 | checkpoint kinase 1 | G2/M phase transition | serine/threonine kinase; phosphorylates and inhibits CDC25B and CDC25C |
| CHEK2 | CHEK2 | checkpoint kinase 2 | G1/S and G2/M transitions | serine/threonine kinase; phosphorylates and inhibits CDC25A, CDC25B and CDC25C |
| cohesin | n/a | cohesin protein complex | M phase | multiprotein complex that holds sister chromatids together; components include RAD21, SMC genes |
| cyc A2 | CCNA2 | cyclin A2 | G1/S phase transition | cofactor of CDK2; necessary for CDK activity |
| cyc B1 | CCNB1 | cyclin B1 | G2/M phase transition | cofactor of cdc2 (CDK1); necessary for cdc2 activity |
| cyc B2 | CCNB2 | cyclin B2 | G2/M phase transition | cofactor of cdc2 (CDK1); necessary for cdc2 activity |
| cyc D | CCND1, CCND2, CCND3 | cyclin D | G1/S phase transition | cofactor of CDK4 and CDK6; necessary for CDK activity |
| cyc E2 | CCNE2 | cyclin E2 | G1/S phase transition | cofactor of CDK2; necessary for CDK activity |
| Emi1 | FXBO5 | early mitotic inhibitor 1 | M phase | binds to APC and inhibits it |
| FoxM1 | FOXM1 | forkhead box M1 | all but G0 | transcription factor; regulates expression of many G2/M-specific genes; induces expression of D and B type cyclins |
| Foxo1 | FOXO1A | forkhead/winged helix transcription factor O1 | G1 phase | suppresses transcription of cyclin D and activates transcription of p21 and p27 |
| Foxo3a | FOXO3A | forkhead/winged helix transcription factor O3a | G1 phase | suppresses transcription of cyclin D and activates transcription of p21 and p27 |
| Foxo4 | FOXO4, MLLT1 | forkhead/winged helix transcription factor O4 | G1 phase | suppresses transcription of cyclin D and activates transcription of p21 and p27 |
| GSK3 | GSK3B | glycogen synthase 3 | n/a | serine/threonine kinase; phosphorylates cyclin D1 and induces cytoplasmic translocation and proteasomal degradation of cyclin D1 |
| Ki67 | MKI67 | antigen identified by monoclonal antibody Ki-67 | all but G0 | Unknown; cellular marker for cell proliferation |
| MAD1 | MAD1L1 | mitotic arrest deficient homolog 1 | M phase, spindle checkpoint | coiled coil protein; binds to and recruits MAD2 to unattached kinetochores |
| MAD2 | MAD2L1 | mitotic arrest deficient homolog 2 | M phase, spindle checkpoint | part of APC inhibitory complex; binds to cdc20 and inhibits APC activity |
| MCM1-10 | MCM1, MCM2, ...etc. | minichromosome maintenance complex component | replication | required for initiation and elongation of DNA replication; function as replication fork |
| MDM2 | MDM2 | murine double-minute 2 homolog | n/a | E3 ubiquitin ligase; induces proteasomal degradation of p53 |
| MPS1 | MPS1 | monopolar spindle 1 | M phase, spindle checkpoint | kinase; required for spindle pole body duplication and spindle checkpoint function |
| ORC1-6 | ORC1L, ORC2L, ...etc. | origin of recognition complex subunit | replication | binds to DNA at origins of replication; initiates replication; recruites proteins of the pre-replication complex (pre-RC) |
| p107 | RBL1 | retinoblastoma protein p107 | G1/S phase transition | binds to and inactivates E2F transcription factors that are necessary for the G1/S transition |
| p16 | CDKN2A | p16 INK4a | G1/S phase transition | CDK inhibitor, binds to and inactivates CDK4 and CDK6 |
| p21 | CDKN1A | p21 CIP1/WAF1 | G1/S phase transition | CDK inhibitor, binds to and inactivates CDK2 |
| p27 | CDKN1B | p27 KIP1 | G1/S phase transition | CDK inhibitor, binds to and inactivates CDK2 and other CDKs |

TABLE 6-continued

Summary of information about miR-124a-controlled genes shown in FIG. 1. n/a not applicable because not directly involved in the cell cycle.

| Icon | Gene Title | Name | Cycle of Action | Protein Function |
|---|---|---|---|---|
| p53 | TP53 | tumor suppressor protein 53 | R1 and R2 restriction points | transcription factor; induces transcription of p21 |
| PIK3CA | PIK3CA | phosphatidylinositol 3-kinase, p110alpha catalytic subunit | n/a | lipid kinase; induces nuclear translocation of MDM2; indirectly inactivates the FOXO1, FOXO3a and FOXO4 tumor suppressors, as well as GSK3 |
| PLK1 | PLK1 | polo-like kinase 1 | M phase, spindle checkpoint | serine/threonine kinase; peaks in M phase; phosphorylates cohesin and induces dissociation from sister chromatids; phosphorylates cdc25C and activates it; phosphorylates cdc2 and activates it; phosphorylates Emi1 and induces proteasomal degradation |
| Rb | RB1 | retinoblastoma protein | G1/S phase transition | binds to and inactivates E2F transcription factors that are necessary for the G1/S transition |
| securin | PTTG1 | pituitary tumor-transforming 1 | M phase | binds and inhibits separase |
| separase | ESPL1 | extra spindle pole bodies homolog 1, separin | M phase | peptidase; cleaves cohesin and induces dissociation of sister chromatids |
| Skp2 | SKP2 | S-phase kinase-associated protein 2 | n/a | E3 ubiquitin ligase; induces proteasomal degradation of p27 and Foxo proteins |

Example 6

Delivery of Synthetic Hsa-miR-124a Inhibits Proliferation of Lung Cancer Cells

The inventors have previously demonstrated that hsa-miR-124a is involved in the regulation of numerous cell activities that represent intervention points for cancer therapy and for therapy of other diseases and disorders (U.S. patent application Ser. No. 11/141,707 filed May 31, 2005 and Ser. No. 11/273,640 filed Nov. 14, 2005). For example, overexpression of hsa-miR-124a decreases the proliferation and/or viability of certain normal or cancerous cell lines.

The development of effective therapeutic regimes requires evidence that demonstrates efficacy and utility of the therapeutic in various cancer models and multiple cancer cell lines that represent the same disease. The inventors assessed the therapeutic effect of hsa-miR-124a for lung cancer by using 12 individual lung cancer cell lines. To measure cellular proliferation of lung cancer cells, the following non-small cell lung cancer (NSCLC) cells were used: cells derived from lung adenocarcinoma (A549, H1299, H522, H838, Calu-3, HCC827, HCC2935), cells derived from lung squamous cell carcinoma (H520, H226), cells derived from lung adenosquamous cell carcinoma (H596), cells derived from lung bronchioalveolar carcinoma (H1650), and cells derived from lung large cell carcinoma (H460). Synthetic hsa-miR-124a (Pre-miR™-hsa-miR-124a, Ambion cat. no. AM17100) or negative control (NC) miRNA (Pre-miR™ microRNA Precursor Molecule-Negative Control #2; Ambion cat. no. AM17111) was delivered via lipid-based transfection into A549, H1299, H522, H838, Calu-3, HCC827, HCC2935, H520, H596, H1650, and H460 cells and via electroporation into H226 cells.

Lipid-based reverse transfections were carried out in triplicate according to a published protocol and the following parameters: 5,000-12,000 cells per 96 well, 0.1-0.2 μl Lipofectamine™ 2000 (cat. no. 11668-019, Invitrogen Corp., Carlsbad, Calif., USA) in 20 μl OptiMEM (Invitrogen), 30 nM final concentration of miRNA in 100 μl (Ovcharenko et al., 2005). Electroporation of H226 cells was carried out using the BioRad Gene Pulser Xcell™ instrument (BioRad Laboratories Inc., Hercules, Calif., USA) with the following settings: $5 \times 10^6$ cells with 5 μg miRNA in 200 μl OptiMEM (1.6 μM miRNA), square wave pulse at 250 V for 5 ms. Electroporated H226 cells were seeded at 7,000 cells per 96-well in a total volume of 100 μl. All cells except for Calu-3 cells were harvested 72 hours post transfection or electroporation for assessment of cellular proliferation. Calu-3 cells were harvested 10 days post transfection.

Proliferation assays were performed using Alamar Blue (Invitrogen) following the manufacturer's instructions. As a control for inhibition of cellular proliferation, siRNA against the motor protein kinesin 11, also known as Eg5, was used. Eg5 is essential for cellular survival of most eukaryotic cells and a lack thereof leads to reduced cell proliferation and cell death (Weil et al., 2002). siEg5 was used in lipid-based transfection following the same experimental parameters that apply to miRNA. The inventors also used a DNA topoisomerase II inhibitor, etoposide, at final concentrations of 10 μM and 50 μM as an internal standard for the potency of miRNAs. Etoposide is an FDA-approved DNA topoisomerase II inhibitor in the treatment of lung cancer. IC50 values for various lung cancer cells have been reported to range between <1-25 μM for SCLC and NSCLC cells (Ohsaki et al., 1992; Tsai et al., 1993). Percent (%) proliferation values from the Alamar Blue assay were normalized to values from cells treated with negative control miRNA. Percent proliferation of hsa-miR-124a treated cells relative to cells treated with negative control miRNA (100%) are shown below in Table 7 and in FIG. 2.

TABLE 7

Percent (%) proliferation of lung cancer cell lines treated with hsa-miR-124a, Eg5-specific siRNA (siEg5), etoposide, or negative control miRNA (NC).

| Cells | hsa-miR-124a (39 nM) | | siEg5 (30 nM) | | etoposide (10 µM) | | etoposide (50 µM) | | NC (30 nM) | |
|---|---|---|---|---|---|---|---|---|---|---|
| | % Proliferation | % SD | % Proliferation | % SD | % Proliferation | % SD | % Proliferation | % SD | % Proliferation | % SD |
| A549 | 70.74 | 20.55 | 37.84 | 1.06 | 49.13 | 2.55 | 42.18 | 3.57 | 100.00 | 19.53 |
| H1299 | 64.70 | 2.17 | 54.32 | 2.83 | 79.65 | 5.02 | 54.38 | 2.73 | 100.00 | 8.89 |
| H460 | 17.03 | 1.45 | 27.97 | 0.33 | 32.13 | 1.14 | 27.82 | 0.58 | 100.00 | 2.52 |
| H520 | 71.10 | 1.46 | 70.40 | 3.49 | 66.80 | 3.93 | 48.53 | 2.54 | 100.00 | 4.15 |
| H522 | 77.69 | 1.15 | 53.45 | 2.35 | 82.13 | 3.14 | 61.08 | 2.65 | 100.00 | 7.48 |
| H838 | 53.79 | 7.09 | 69.14 | 4.15 | 89.71 | 6.17 | 36.97 | 0.62 | 100.00 | 7.74 |
| H596 | 87.37 | 4.98 | 83.48 | 2.82 | 88.75 | 1.11 | 73.39 | 2.67 | 100.00 | 1.89 |
| H1650 | 69.57 | 2.30 | 87.96 | 1.73 | 90.98 | 8.44 | 60.31 | 4.59 | 100.00 | 7.21 |
| HCC827 | 78.08 | 4.94 | 91.68 | 8.89 | 98.95 | 3.00 | 82.53 | 7.75 | 100.00 | 4.32 |
| Calu-3 | 23.45 | 2.51 | 34.59 | 1.33 | 20.81 | 0.19 | 13.53 | 0.64 | 100.00 | 5.54 |
| H226 | 77.16 | 1.42 | n.d. | n.d. | 28.17 | 2.32 | 9.33 | 2.70 | 100.00 | 2.43 |
| HCC2935 | 74.26 | 6.18 | 63.61 | 6.12 | n.d. | n.d. | n.d. | n.d. | 100.00 | 13.92 |

Values are normalized to values obtained from cells transfected with negative control miRNA (100% proliferation).
NC, negative control miRNA;
siEg5, Eg5-specific siRNA;
SD, standard deviation;
n.d., not determined.

Figure 2:
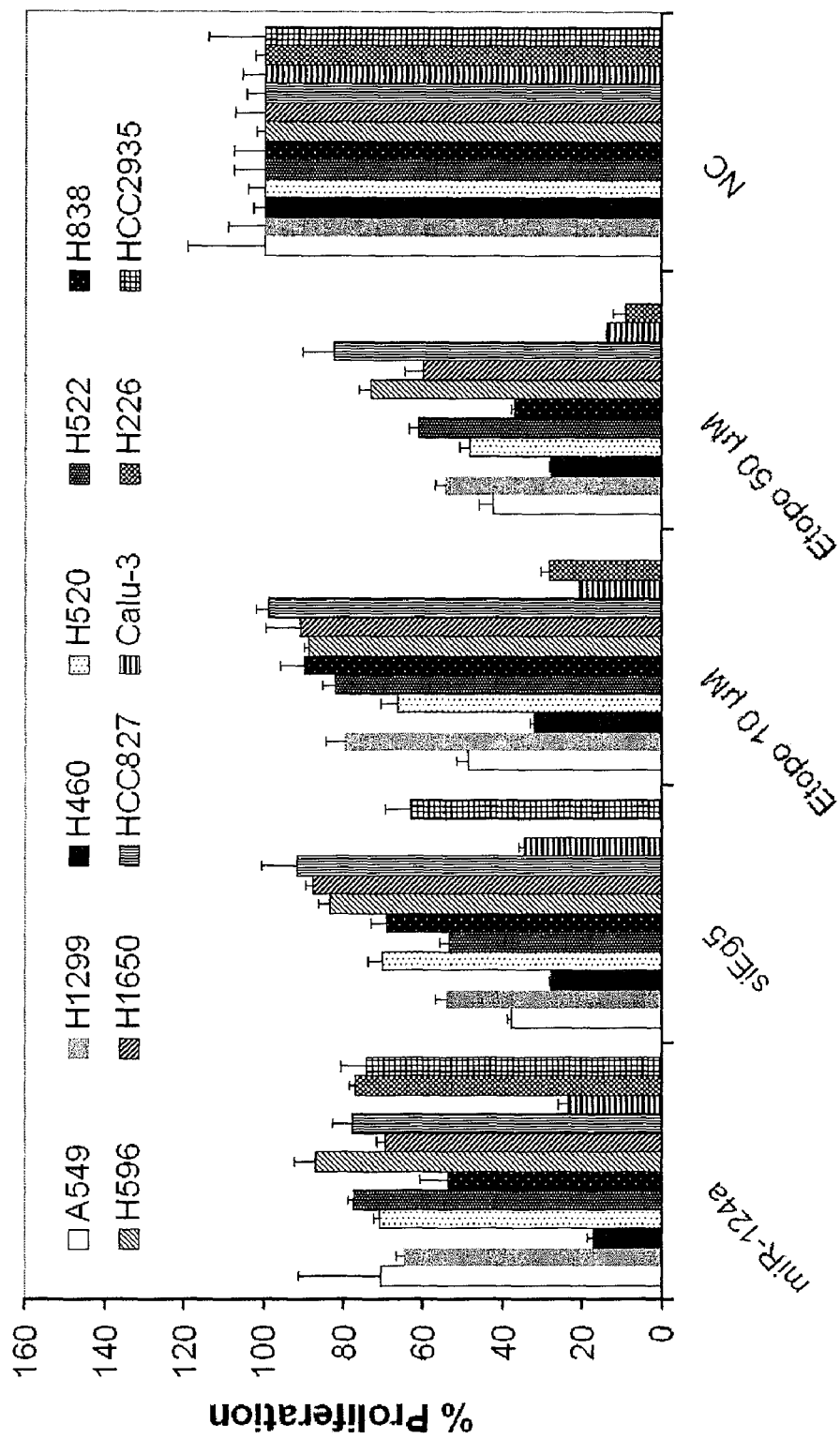
FIG. 2. Percent (%) proliferation of hsa-miR-124a-treated lung cancer cells relative to cells treated with negative control miRNA (100%). Abbreviations: miR-124a, hsa-miR-124a; siEg5, siRNA against the motor protein kinesin 11 (Eg5); Etopo, etoposide; NC, negative control miRNA. Standard deviations are indicated in the graph.

Delivery of hsa-miR-124a inhibits cellular proliferation of lung cancer cells A549, H1299, H522, H838, Calu-3, HCC827, HCC2935, H520, H596, H1650, H460 and H226 (Table 7 and FIG. 2). On average, hsa-miR-124a inhibits cellular proliferation by 36.25% (Table 7, FIG. 2). Hsa-miR-124a has maximal inhibitory activity in H460 cells, reducing proliferation by 83%. The growth-inhibitory activity of hsa-miR-124a is comparable to that of etoposide at concentrations ≧10 µM. Since hsa-miR-124a induces a therapeutic response in all lung cancer cells tested, hsa-miR-124a may provide therapeutic benefit to a broad range of patients with lung cancer and other malignancies.

Figure 3:
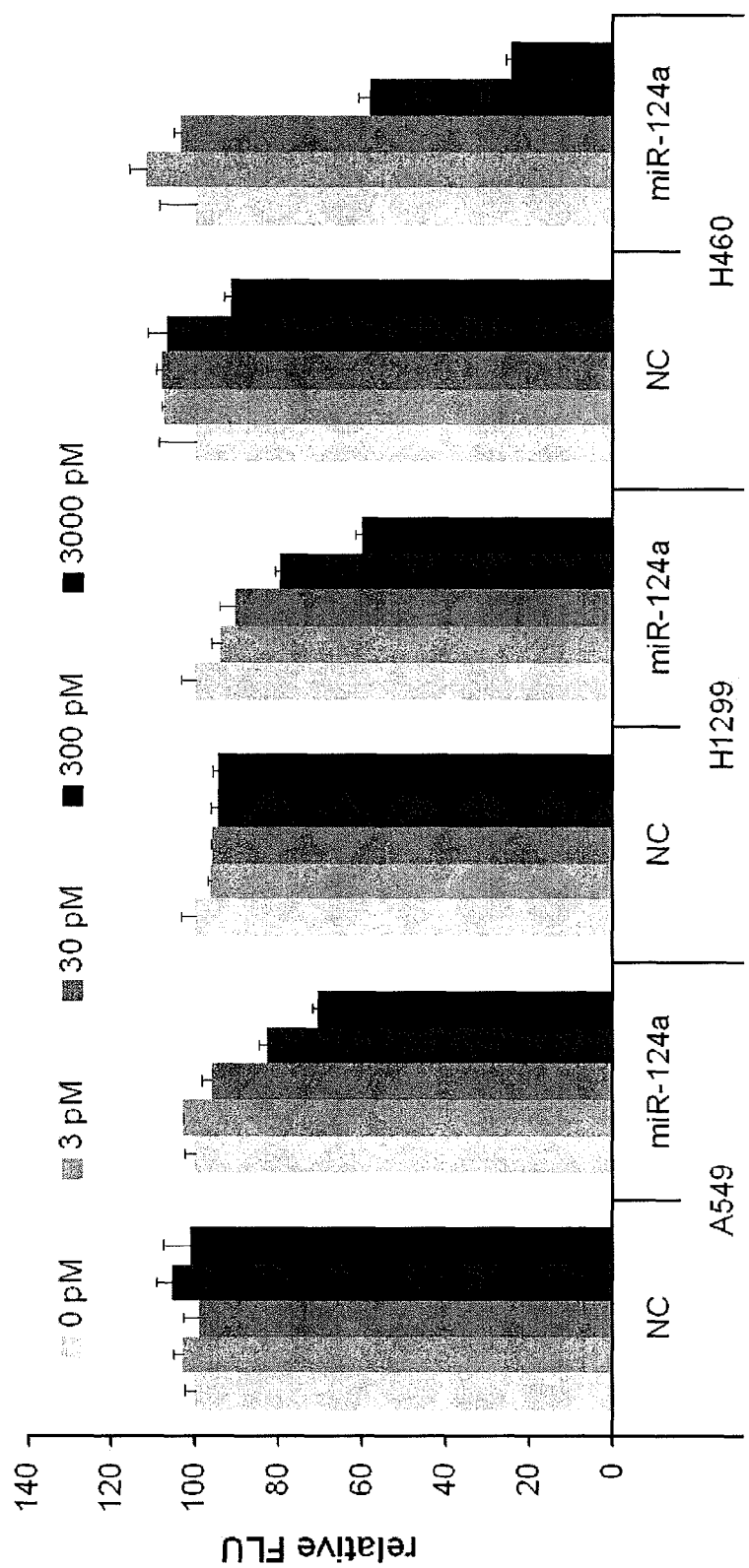
FIG. 3. Dose dependent inhibition of various lung cancer cell lines by hsa-miR-124a using Alamar Blue proliferation assays. Cell proliferation is reported as % proliferation relative to % proliferation of mock-transfected cells (0 pM=100% proliferation). Standard deviations are indicated in the graphs. Abbreviations: NC, negative control miRNA.

The inventors determined sensitivity and specificity of hsa-miR-124a by administering hsa-miR-124a or negative control miRNA at increasing concentrations, ranging from 0 pM to 3,000 pM (FIG. 3). Delivery of miRNA and assessment of cellular proliferation of A549, H1299 and H460 cells were done as described above. Proliferation values from the Alamar Blue assay were normalized to values obtained from mock-transfected cells (0 pM=100% proliferation). Increasing amounts of negative control miRNA (NC) had no effect on cellular proliferation of A549, H1299 or H460 cells (Table 8; FIG. 3). In contrast, the growth-inhibitory phenotype of hsa-miR-124a is dose-dependent and correlates with increasing amounts of hsa-miR-124a (Table 8; FIG. 3). Hsa-miR-124a induces a specific therapeutic response at concentrations as low as 300 pM.

TABLE 8

Dose-dependent inhibition of cellular proliferation of lung cancer cell lines by hsa-miR-124a.

| Concentration (pM) | A549 | | | | H1299 | | | | H460 | | | |
|---|---|---|---|---|---|---|---|---|---|---|---|---|
| | hsa-miR-124a | | NC | | hsa-miR-124a | | NC | | hsa-miR-124a | | NC | |
| | % Proliferation | % SD | % Proliferation | % SD | % Proliferation | % SD | % Proliferation | % SD | % Proliferation | % SD | % Proliferation | % SD |
| 0 | 100.00 | 2.61 | 100.00 | 2.61 | 100.00 | 3.28 | 100.00 | 3.28 | 100.00 | 8.84 | 100.00 | 8.84 |
| 3 | 102.71 | 0.07 | 102.82 | 2.23 | 93.92 | 2.51 | 96.51 | 0.51 | 111.99 | 4.17 | 107.60 | 0.79 |
| 30 | 96.22 | 2.16 | 99.36 | 3.51 | 90.66 | 3.54 | 95.89 | 0.61 | 103.59 | 2.03 | 108.04 | 1.46 |
| 300 | 82.92 | 1.81 | 105.53 | 3.72 | 79.78 | 1.39 | 94.45 | 1.99 | 58.11 | 2.81 | 106.99 | 4.74 |
| 3000 | 70.83 | 0.98 | 101.30 | 6.35 | 60.04 | 1.74 | 94.56 | 1.24 | 24.51 | 1.24 | 91.41 | 2.14 |

Values are normalized to values obtained from mock-transfected cells (0 pM miRNA).
NC, negative control miRNA;
SD, standard deviation.

Figure 4:
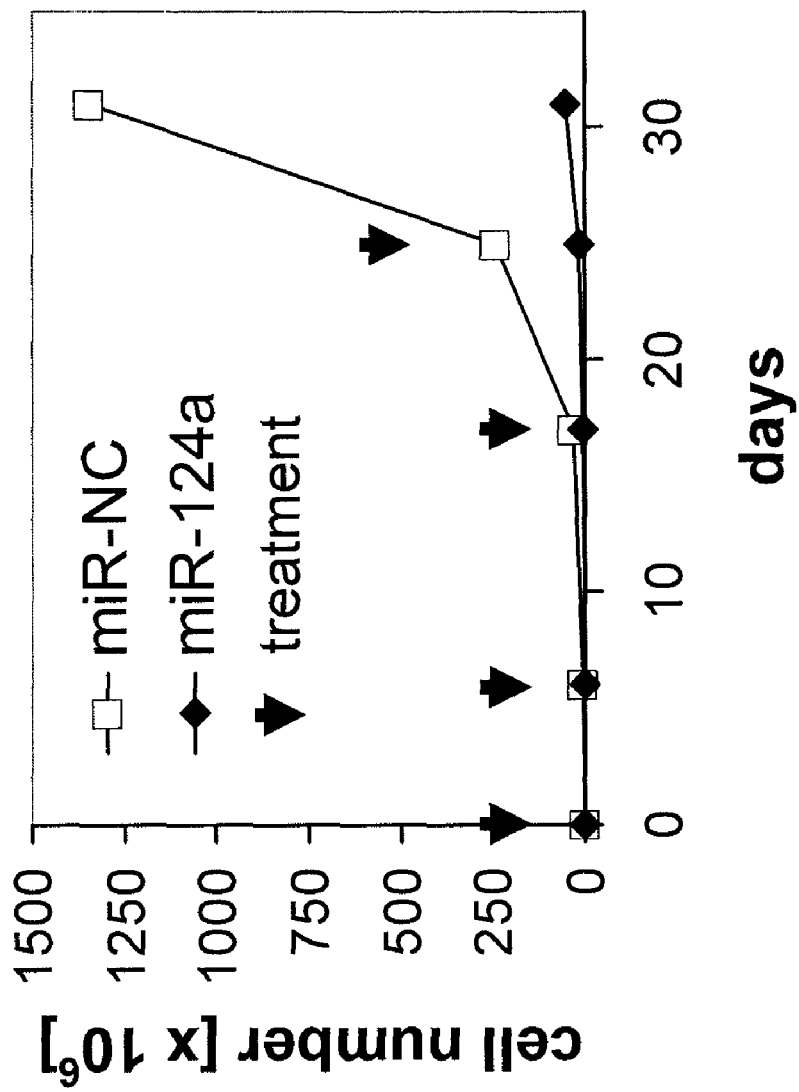
FIG. 4. Long-term effects of hsa-miR-124a on cultured human H226 lung cancer cells. Equal numbers of H226 cells were electroporated with 1.6 µM hsa-miR-124a or negative control miRNA (NC), seeded and propagated in regular growth medium. When the control cells reached confluence (days 6, and 17 and 25), cells were harvested, counted and electroporated again with the respective miRNAs. The population doubling and cumulative cell counts was calculated and plotted on a linear scale. Arrows represent electroporation days. Abbreviation: miR-124a, hsa-miR-124a; NC, negative control miRNA.

To evaluate the therapeutic activity of hsa-miR-124a over an extended period of time, the inventors conducted growth curve experiments in the presence of miRNA for up to 31 days in H226 lung cancer cells. Since in vitro transfections of naked interfering RNAs, such as synthetic miRNA, are transient by nature and compromised by the dilution of the oligo during ongoing cell divisions, miRNA was administered at multiple time points (Bartlett et al., 2006; Bartlett et al., 2007). To accommodate miRNA delivery into a large quantity of cells, hsa-miR-124a or negative control miRNA were delivered by the electroporation method. Briefly, 1×10$^6$ H226 cells were electroporated in triplicate with 1.6 µM hsa-miR-124a or negative control using the BioRad Gene Pulser Xcell™ instrument (BioRad Laboratories Inc., Hercules, Calif., USA), seeded, and propagated in regular growth medium. When the control cells reached confluence (days 6, 17 and 25), cells were harvested, counted, and electroporated again with the respective miRNAs. To ensure similar treatment of both conditions as well as to accommodate exponential growth, the cell numbers used for the second and third electroporation were titrated down to the lowest count. The population doubling was calculated from these electroporation events using the formula PD=ln(Nf/N0)/ln 2 and adjusting for the fact that approximately 72% of newly seeded cells adhere to the plate. Cell counts were extrapolated and plotted on a linear scale (FIG. 4). Arrows represent electroporation days. Standard deviations are included in the graphs.

Repeated administration of hsa-miR-124a robustly inhibited proliferation of human lung cancer cells (FIG. 4). In contrast, cells treated with negative control miRNA showed normal exponential growth. hsa-miR-124a treatment resulted in 96.3% inhibition of H226 cell growth on day 31 (3.7% remaining cells) relative to the proliferation of control cells (100%).

The data suggest that hsa-miR-124a provides a useful therapeutic tool in the treatment of human lung cancer cells.

Example 7

Hsa-miR-124a in Combination with Specific Human Micro-RNAs Synergistically Inhibits Proliferation of Lung Cancer Cell Lines miRNAs function in multiple pathways controlling multiple cellular processes. Cancer cells frequently show aberrations in several different pathways, which determine their oncogenic properties. Therefore, administration of multiple miRNAs to cancer patients may result in a superior therapeutic benefit over administration of a single miRNA. The inventors assessed the efficacy of pair-wise miRNA combinations, administering hsa-miR-124a concurrently with either hsa-miR-34a, hsa-miR-126, hsa-miR-147, hsa-let-7b, hsa-let-7c or hsa-let-7g (Pre-miR™ miRNA, Ambion cat. no. AM17100). H460 lung cancer cells were transiently reverse-transfected in triplicates with each miRNA at a final concentration of 300 pM, resulting in 600 pM of oligonucleotide. For negative controls, 600 pM of Pre-miR™ microRNA Precursor Molecule-Negative Control #2 (Ambion cat. no. AM17111) were used. To correlate the effect of various combinations with the effect of the sole miRNA, each miRNA at 300 pM was also combined with 300 pM negative control miRNA. Reverse transfection was performed using the following parameters: 7,000 cells per well of a 96 well plate, 0.15 µl Lipofectamine™ 2000 (Invitrogen) in 20 µl Opti-MEM (Invitrogen), 100 µl total transfection volume. As an internal control for the potency of miRNA, etoposide was added at 10 µM and 50 µM to mock-transfected cells 24 hours after transfection for the following 48 hours. Cells were harvested 72 hours after transfection and subjected to Alamar Blue assays (Invitrogen). Percent proliferation values from the Alamar Blue assay were normalized to those obtained from cells treated with 600 µM negative control miRNA. Data are expressed as % proliferation relative to negative control miRNA-treated cells.

Figure 5:
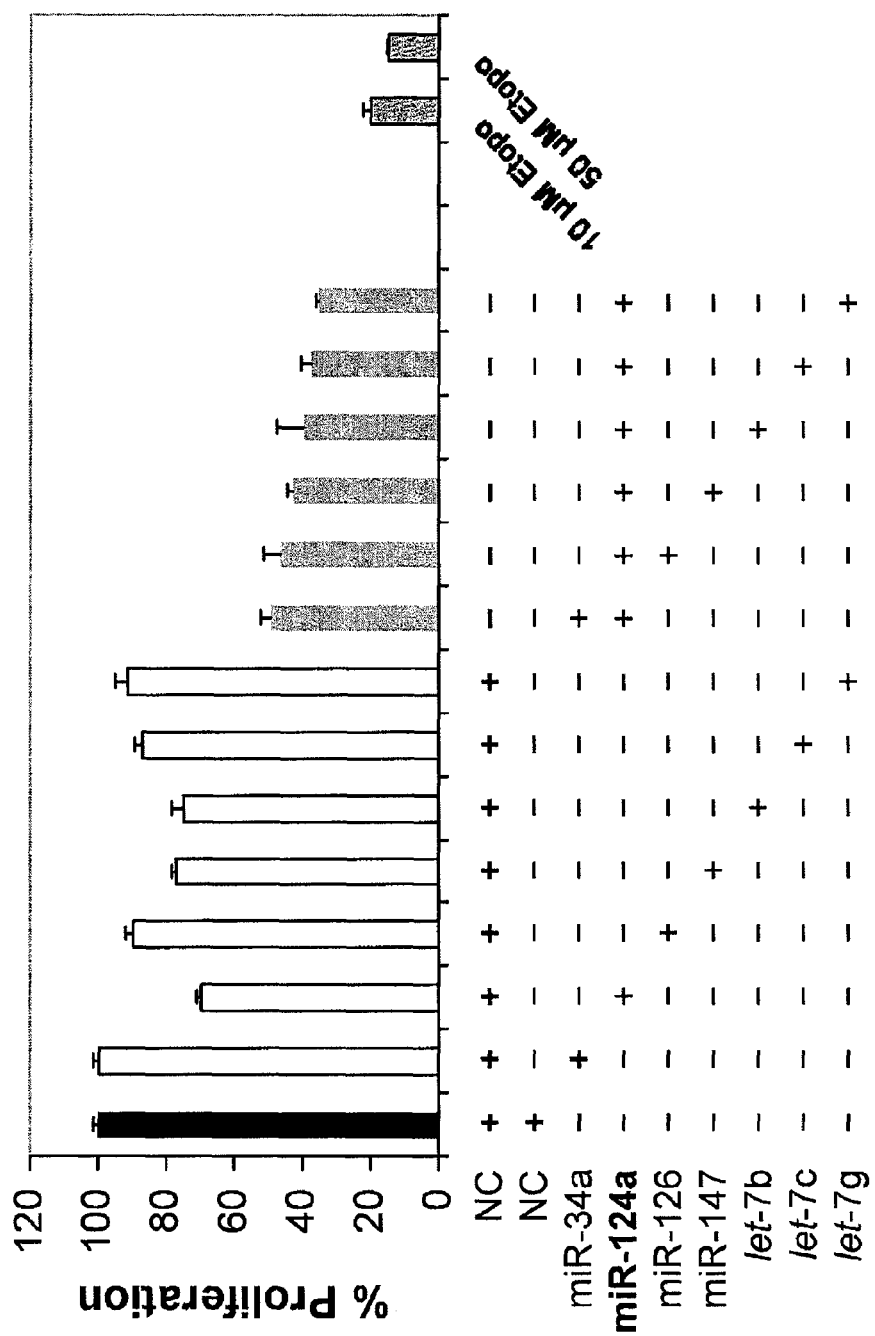
FIG. 5. Percent (%) proliferation of H460 lung cancer cells following administration of various combinations of microRNAs. A positive sign under each bar in the graph indicates that the miRNA was present in the administered combination. Standard deviations are shown in the graph. Abbreviations: Etopo, etoposide; NC, negative control miRNA.

Transfection of 300 pM hsa-miR-124a reduces proliferation of H460 cells by 30.57% (Table 9; FIG. 5). Additive activity of pair-wise combinations (e.g. hsa-miR-124a plus hsa-let-7g) is defined as an activity that is greater than the sole activity of each miRNA (e.g., the activity of hsa-miR-124a plus hsa-let-7g is greater than that observed for hsa-miR-124a plus NC and the activity of hsa-miR-124a plus hsa-let-7g is greater than that observed for hsa-let-7g plus NC). Synergistic activity of pair-wise combinations is defined as an activity that is greater than the sum of the sole activity of each miRNA (e.g., the activity of hsa-miR-124a plus hsa-let-7g is greater than that observed for the sum of the activity of hsa-miR-124a plus NC and the activity of hsa-let-7g plus NC). The data indicate that hsa-miR-124a combined with hsa-miR-34a, hsa-miR-126, hsa-miR-147, hsa-let-7b, hsa-let-7c, or hsa-let-7g results in synergistic activity (Table 9, FIG. 5). Therefore, it is contemplated that administering combinations of hsa-miR-124a with other miRNAs to cancer patients can induce a superior therapeutic response in the treatment of lung cancer. The combinatorial use of miRNAs represents a potentially useful therapy for cancer and other diseases.

TABLE 9

Cellular proliferation of H460 lung cancer cells in the presence of pair-wise miR-124a miRNA combinations.

|  | % Proliferation | % SD |
|---|---|---|
| miRNA [300 pM] + miRNA [300 pM] |  |  |
| NC + NC | 100.00 | 1.45 |
| NC + miR-34a | 99.58 | 1.66 |
| NC + miR-124a | 69.43 | 1.38 |
| NC + miR-126 | 89.46 | 2.27 |
| NC + miR-147 | 76.97 | 1.46 |
| NC + let-7b | 74.92 | 3.38 |
| NC + let-7c | 86.74 | 2.28 |
| NC + let-7g | 91.41 | 3.26 |
| miR-124a + miR-34a | 49.12 | 3.13 |
| miR-124a + miR-126 | 46.49 | 4.89 |
| miR-124a + 147 | 42.81 | 1.73 |
| miR-124a + let-7b | 39.77 | 7.61 |
| miR-124a + let-7c | 37.35 | 3.08 |
| miR-124a + let-7g | 35.15 | 0.84 |
| Etoposide |  |  |
| 10 µM | 20.19 | 1.89 |
| 50 µM | 14.94 | 0.31 |

Values are normalized to values obtained from cells transfected with 600 pM negative control (NC) miRNA.
SD, standard deviation.

Example 8

Delivery of Synthetic Hsa-miR-124a Inhibits Tumor Growth of Lung Cancer Cells in Mice The inventors assessed the growth-inhibitory activity of hsa-miR-124a in human lung cancer xenografts grown in immunodeficient mice. Hsa-miR-124a was delivered into A549 and H460 lung cancer cells via electroporation using the Gene Pulser Xcell™ (BioRad) with the following settings: $15 \times 10^6$ cells with 5 µg miRNA in 200 µl OptiMEM, square wave pulse at 150 V for 10 ms. Electroporated cells ($5 \times 10^6$) were mixed with BD Matrigel™, (BD Biosciences; San Jose, Calif., USA; cat. no. 356237) in a 1:1 ratio and injected subcutaneously into the flank of NOD/SCID mice (Jackson Laboratories; Bar Harbor, Me., USA). As a negative control, A549 and H460 cells were electroporated with negative control (NC) miRNA (Pre-miR™ microRNA Precursor Molecule-Negative Control #2; Ambion cat. no. AM17111) as described above. To assess the anti-oncogenic activity of hsa-miR-124a, a group of 4 animals was injected with A459 cells and a group of 6 animals was injected with H460 cells. NC miRNA-treated cells were injected into the opposite flank of the same animal to control for animal-to-animal variability. Once tumors reached a measurable size (A549: 9 days post injection; H460: 5 days post injection), the length and width of tumors were determined every day for up to 8 days. Tumor volumes were calculated using the formula, Volume=length×width×width/2, in which the length is greater than the width.

Figure 6:
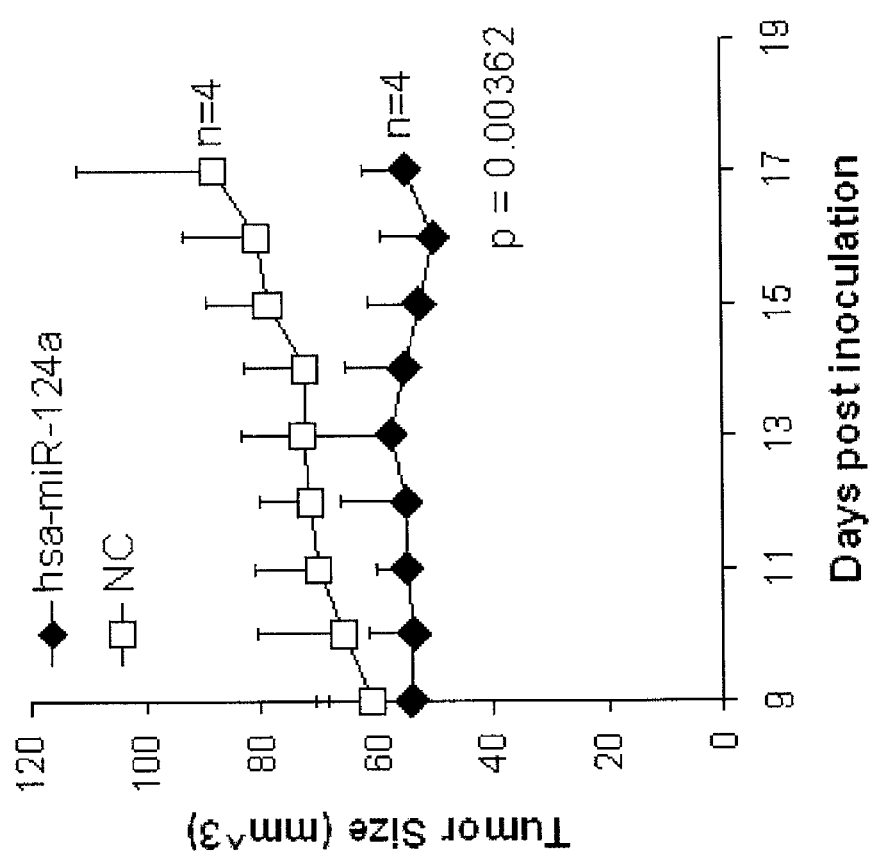
FIG. 6. Average tumor volumes in mice harboring xenografts of A549 lung cancer cells treated with hsa-miR-124a or with a negative control miRNA (NC). Standard deviations are shown in the graph. The p value, indicating statistical significance, is shown for values obtained on day 16 (p=0.0036).

For animals carrying A549 xenografts, tumor volumes derived from NC-treated cells and hsa-miR-124a-treated cells were averaged and plotted over time (FIG. 6). The p value, indicating statistical significance, is shown for values obtained on day 16 (p=0.0036). For animals carrying H460 xenografts, tumor volumes of individual mice are shown (FIG. 7).

Figure 7:
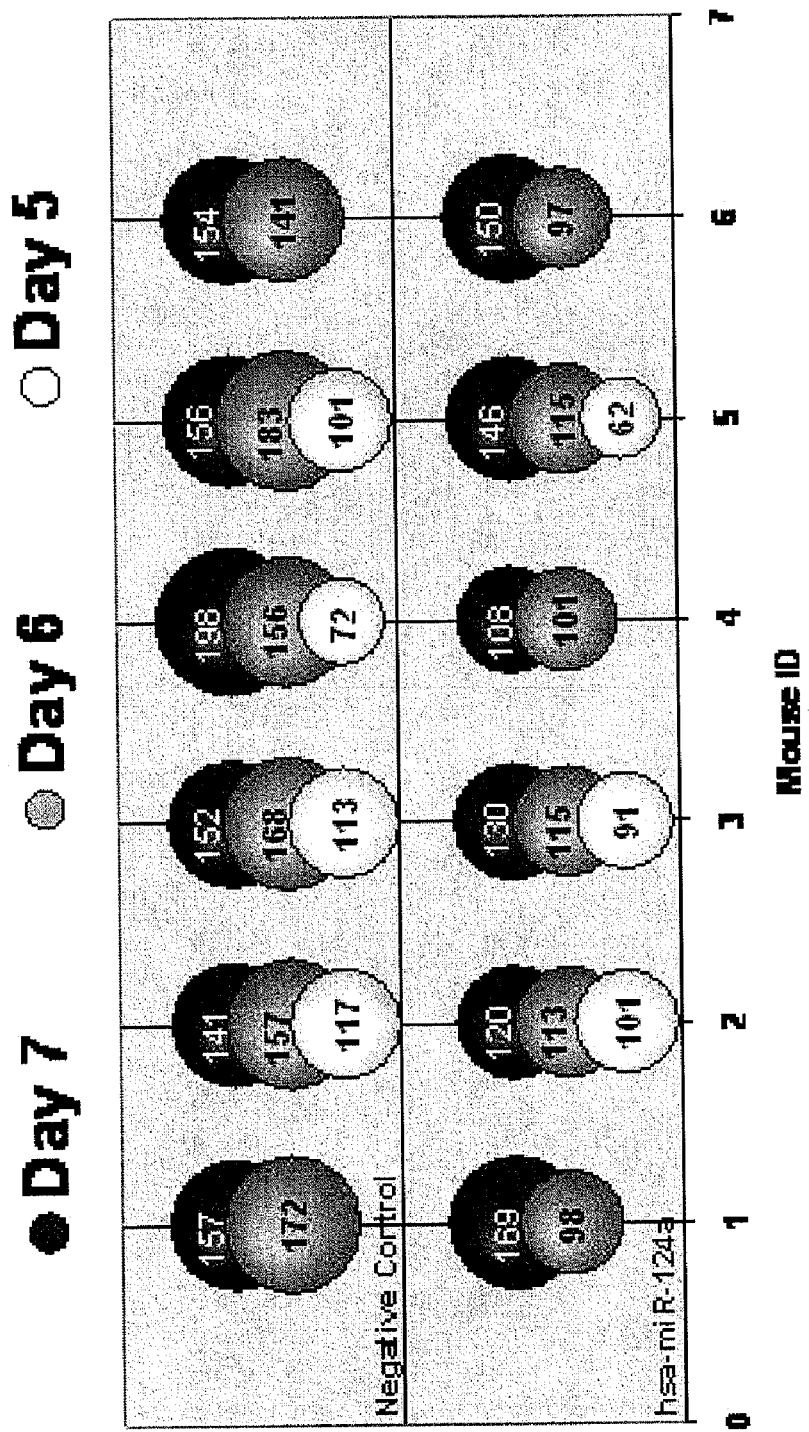
FIG. 7. Tumor volumes in mice harboring xenografts of H460 lung cancer cells treated with hsa-miR-124a or with a negative control miRNA (NC). Circles represent the presence of a tumor in a mouse on the indicated day. Numbers inside circles represent the tumor volume in mm$^3$.

Administration of hsa-miR-124a into the A549 and H460 lung cancer xenografts inhibited tumor growth in vivo (FIG. 6 and FIG. 7). Cancer cells that received negative control miRNA developed tumors more rapidly than cells treated with hsa-miR-124a. Administration of hsa-miR-124a into A549 delayed and suppressed the onset of tumor growth.

Delivery of hsa-miR-124a into human lung cancer cells prior to implantation into the animal inhibited the formation of lung tumor xenografts. These results demonstrate the anti-oncogenic activity of hsa-miR-124a and suggest that hsa-miR-124a provides a powerful therapeutic tool to treat established lung tumors. To explore this possibility, $3 \times 10^6$ human H460 non-small lung cancer cells were mixed with BD Matrigel™, (BD Biosciences; San Jose, Calif., USA; cat. no. 356237) in a 1:1 ratio and subcutaneously injected into the lower back of each of 23 NOD/SCID mice (Jackson Laboratories; Bar Harbor, Me., USA). Once animals developed palpable tumors (day 11 post xenograft implantation), each animal in a group of six animals received intratumoral injections of 6.25 µg hsa-miR-124a (Dharmacon, Lafayette, Colo.) formulated with the lipid-based siPORT™ amine delivery agent (Ambion, Austin, Tex.; cat. no. AM4502) on days 11, 14 and 17. Each animal in a control group of six animals received intratumoral injections of 6.25 µg negative control miRNA (NC; Dharmacon, Lafayette, Colo.), following the same injection schedule that was used for hsa-miR-124a. Given an average mouse weight of 20 g, this dose equals 0.3125 mg/kg. In addition, a group of six H460 tumor-bearing mice received intratumoral injections of the siPORT™ amine delivery formulation lacking any oligonucleotide, and a group of five animals received intratumoral injections of phosphate-buffered saline (PBS). Caliper measurements were taken every 1-2 days, and tumor volumes were calculated using the formula, Volume=length×width×width/2, in which the length is greater than the width.

Figure 8:
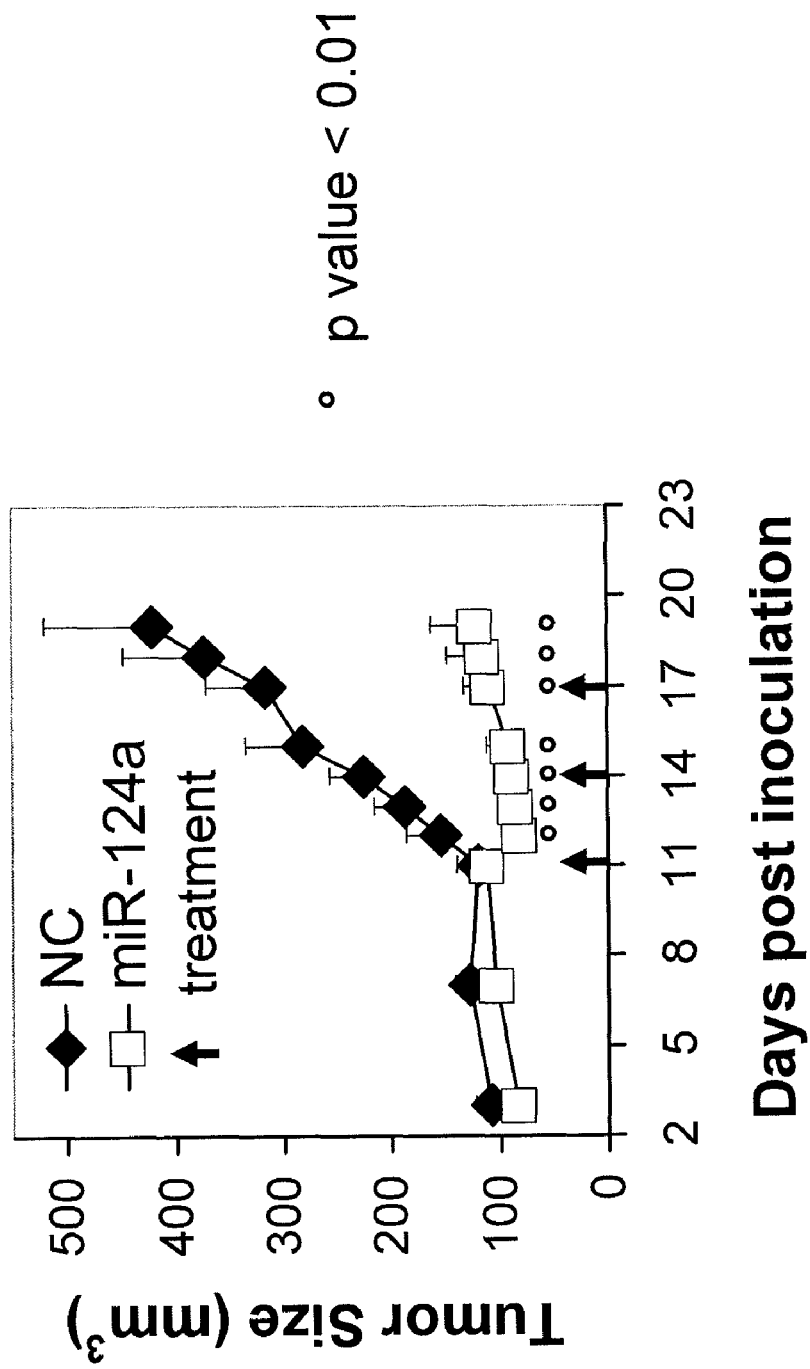
FIG. 8. Average tumor volumes in groups of six (n=6) mice carrying human H460 lung cancer xenografts. Palpable tumors were treated with hsa-miR-124a (white squares) or with a negative control miRNA (NC, black diamonds) on days 11, 14, and 17 (arrows). Standard deviations are shown in the graph. Data points with p values <0.05 and <0.01 are indicated by an asterisk or circles, respectively. Abbreviation: miR-124a, hsa-miR-124a; NC, negative control miRNA.

As shown in FIG. 8, three doses of hsa-miR-124a robustly inhibited growth of established H460 lung tumors (white squares). On day 19, the average volume of tumors treated with hsa-miR-124a was 122 mm$^3$. In contrast, tumors treated with negative control miRNA (black diamonds) grew at a steady pace and yielded tumors with an average size of 421 mm$^3$ on day 19. Negative control tumors developed as quickly as tumors treated with either PBS or the siPORT amine only control, indicating that the therapeutic activity of hsa-miR-124a is specific.

The data indicate that hsa-miR-124a represents a particularly useful candidate in the treatment of patients with lung cancer. The therapeutic activity of hsa-miR-124a is highlighted by the fact that hsa-miR-124a inhibits tumor growth of tumors that had developed prior to treatment.

In addition, the data demonstrate the therapeutic utility of hsa-miR-124a in a lipid-based formulation.

Example 9

Delivery of Synthetic Hsa-miR-124a Inhibits Proliferation of Human Prostate Cancer Cells The inventors assessed the therapeutic effect of hsa-miR-124a for prostate cancer by using four individual human prostate cancer cell lines. To measure cellular proliferation of prostate cancer cells, the following prostate cancer cell lines were used: PPC-1, derived from a bone metastasis; Du145, derived from a brain metastasis; RWPE2, derived from prostate cells immortalized by human papillomavirus 18 and transformed by the K-RAS oncogene; and LNCaP, derived from a lymph node metastasis (Bello et al., 1997; Pretlow et al., 1993; Stone et al., 1978; Brothman et al., 1991; Horoszewicz et al., 1980). PPC-1 and Du145 cells lack expression of the prostate-specific antigen (PSA) and are independent of androgen receptor (AR) signaling. In contrast, RWPE2 and LNCaP cells test positive for PSA and AR. Cells were transfected with synthetic hsa-miR-124a (Pre-miR™-hsa-miR-124a, Ambion cat. no. AM17100) or negative control miRNA (NC; Pre-miR™ microRNA Precursor Molecule-Negative Control #2; Ambion cat. no. AM17111) in a 96-well plate format using a lipid-based transfection reagent. Lipid-based reverse transfections were carried out in triplicate according to a published protocol (Ovcharenko et al. 2005) and the following parameters: Cells (6,000-7,000 per 96 well), 0.1-0.2 µl Lipofectamine™ 2000 (cat. no. 11668-019, Invitrogen Corp., Carlsbad, Calif., USA) in 20 µl OptiMEM (Invitrogen), 30 nM final concentration of miRNA in 100 µl. Proliferation was assessed 4-7 days post-transfection using Alamar Blue™ (Invitrogen) following the manufacturer's instructions. As a control for inhibition of cellular proliferation, siRNA against the motor protein kinesin 11, also known as Eg5, was used. Eg5 is essential for cellular survival of most eukaryotic cells and a lack thereof leads to reduced cell proliferation and cell death (Weil et al. 2002). siEg5 was used in lipid-based transfection following the same experimental parameters that apply to miRNA. Fluorescent light units (FLU) were measured after 3 hours, normalized to the control, and plotted as percent change in proliferation. Percent proliferation of hsa-miR-124a-treated cells relative to cells treated with negative control miRNA (100%) is shown in Table 10 and in FIG. 9.

TABLE 10

Percent (%) proliferation of human prostate cancer cell lines treated with hsa-miR-124a, Eg5-specific siRNA (siEg5), or negative control miRNA (NC).

| Cells | hsa-miR-124a (30 nM) | | siEg5 (30 nM) | | NC (30 nM) | |
|---|---|---|---|---|---|---|
| | % proliferation | % SD | % proliferation | % SD | % proliferation | % SD |
| PPC-1 | 45.91 | 4.34 | 52.90 | 6.97 | 100.00 | 5.82 |
| LNCaP | 72.42 | 7.43 | 66.01 | 6.26 | 100.00 | 10.73 |
| Du145 | 68.38 | 3.02 | 44.47 | 4.23 | 100.00 | 4.12 |
| RWPE2 | 70.61 | 9.74 | 61.87 | 6.56 | 100.00 | 12.28 |

Values are normalized to values obtained from cells transfected with negative control miRNA (100% proliferation).
NC, negative control miRNA;
siEg5, Eg5-specific siRNA;
SD, standard deviation.

Figure 9:
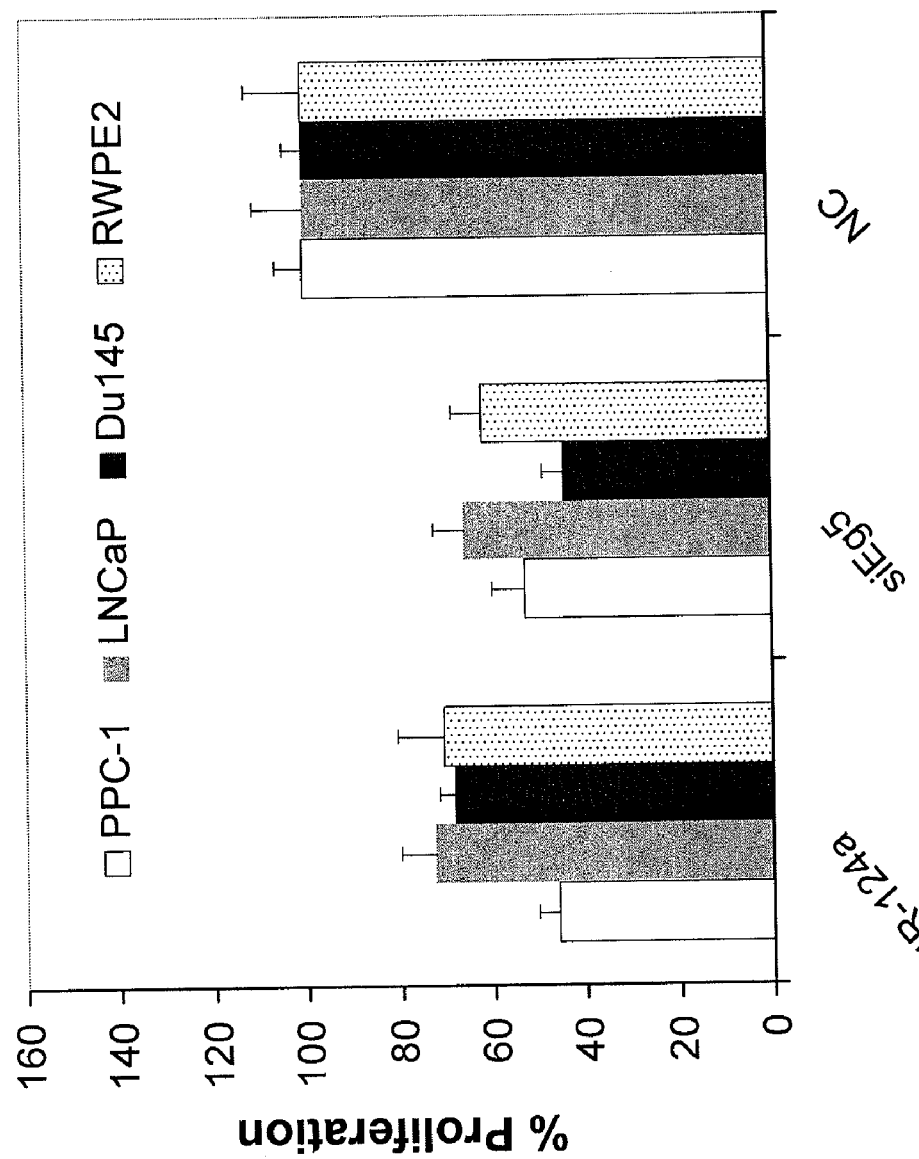
FIG. 9. Percent (%) proliferation of hsa-miR-124a treated human prostate cancer cells relative to cells treated with negative control miRNA (100%). Abbreviations: miR-124a, hsa-miR-124a; siEg5, siRNA against the motor protein kinesin 11 (Eg5); NC, negative control miRNA. Standard deviations are indicated in the graph.

Delivery of hsa-miR-124a inhibits cellular proliferation of human prostate cancer cells PPC-1, Du145, LNCaP and RWPE2 (Table 10 and FIG. 9). On average, hsa-miR-124a inhibits cellular proliferation by 35.67%. The growth-inhibitory activity of hsa-miR-124a is comparable to that of Eg5-directed siRNA. Since hsa-miR-124a induces a therapeutic response in all prostate cancer cells tested, it is contemplated that hsa-miR-124a can provide therapeutic benefit to a broad range of patients with prostate cancer and other malignancies.

Figure 10:
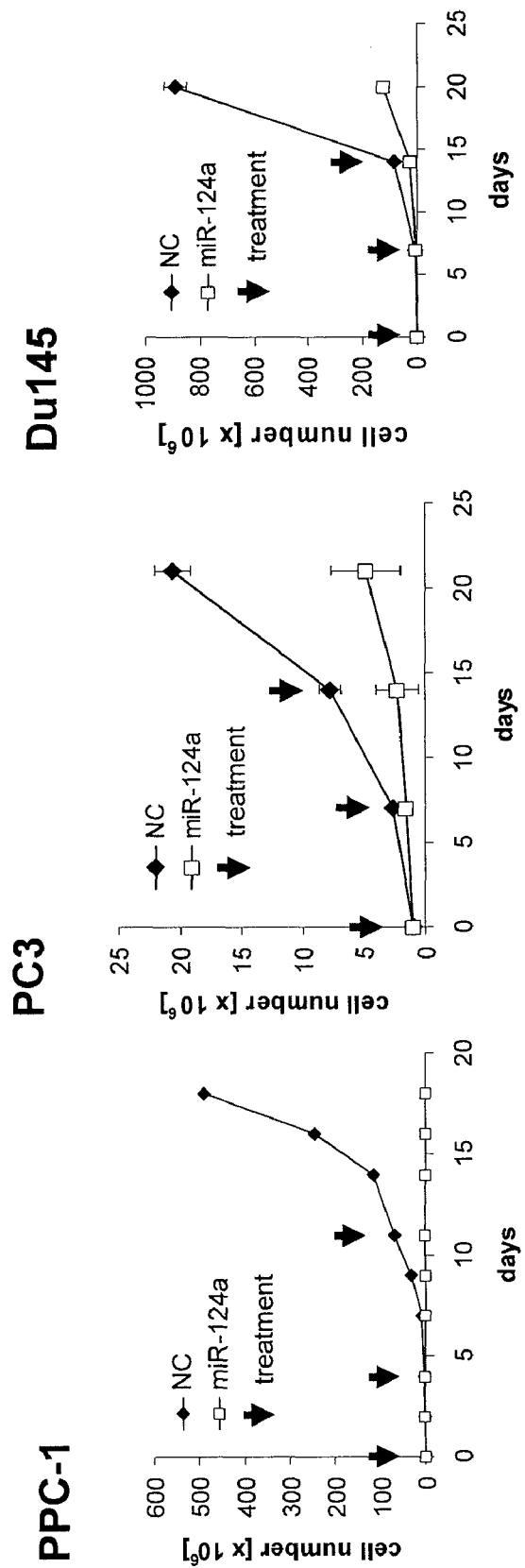
FIG. 10. Long-term effects of hsa-miR-124a on cultured human PPC-1, PC3 and Du145 prostate cancer cells. Equal numbers of prostate cancer cells were electroporated with 1.6 µM hsa-miR-124a or negative control miRNA (NC), seeded and propagated in regular growth medium. When the control cells reached confluence (days 4 and 11 for PPC-1; days 7 and 14 for PC3 and Du145), cells were harvested, counted and electroporated again with the respective miRNAs. The population doubling and cumulative cell counts were calculated and plotted on a linear scale. Arrows represent electroporation days. Abbreviation: miR-124a, hsa-miR-124a; NC, negative control miRNA.

To evaluate the therapeutic activity of hsa-miR124a over an extended period of time, we conducted growth curve experiments in the presence of miRNA for up to 21 days. Since in vitro transfections of naked interfering RNAs, such as synthetic miRNA, are transient by nature and compromised by the dilution of the oligo during ongoing cell divisions, we administered miRNA at multiple time points (Bartlett et al., 2006; Bartlett et al., 2007). To accommodate miRNA delivery into a large quantity of cells, we employed the electroporation method to deliver hsa-miR-124a or negative control miRNA into PPC-1, PC3, and Du145 human prostate cancer cells. Briefly, $1\times10^6$ PPC-1 or PC3 cells, and $0.5\times10^6$ Du145 cells were electroporated with 1.6 µM hsa-miR-124a or negative control using the BioRad Gene Pulser Xcell™ instrument (BioRad Laboratories Inc., Hercules, Calif., USA), seeded, and propagated in regular growth medium. Experiments with PC3 and Du145 cells were carried out in triplicates. When the control cells reached confluence (days 4 and 11 for PPC-1; days 7 and 14 for PC3 and Du145), cells were harvested, counted, and electroporated again with the respective miRNAs. To ensure similar treatment of both conditions as well as to accommodate exponential growth, the cell numbers used for the second and third electroporation were titrated down to the lowest count. The population doubling was calculated from these electroporation events using the formula PD=ln(Nf/N0)/ln 2, and cell counts were extrapolated and plotted on a linear scale (FIG. 10). Arrows represent electroporation days. Standard deviations are shown in the graphs.

Repeated administration of hsa-miR-124a robustly inhibited proliferation of human prostate cancer cells (FIG. 10). In contrast, cells treated with negative control miRNA showed normal exponential growth. hsa-miR-124a treatment resulted in complete inhibition (99.9%) of PPC-1 cell growth by day 18; hsa-miR-124a treatment also resulted in 76.4% inhibition of PC3 cell growth on day 21 (23.6% remaining cells), and 86.2% inhibition of Du145 cell growth on day 20 (13.8% remaining cells) relative to the proliferation of control cells (100%).

The data suggest that hsa-miR-124a provides a useful therapeutic tool in the treatment of human prostate cancer cells.

Example 10

Figure 11:
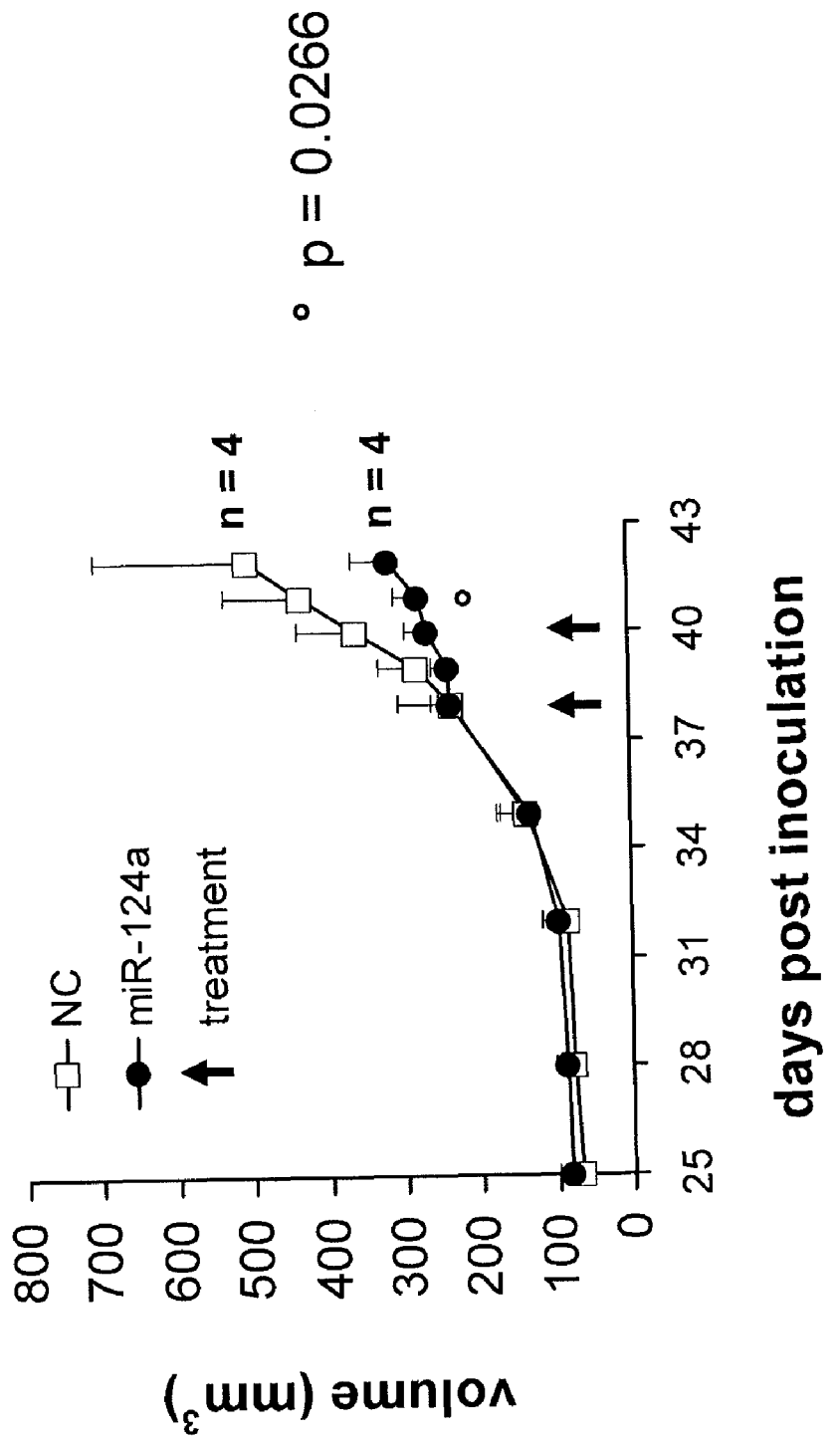
FIG. 11. Average tumor volumes in groups of four (n=4) mice carrying human PC3 prostate cancer xenografts. Palpable tumors were treated with hsa-miR-124a (black circles)

Delivery of Synthetic Hsa-miR-124a Inhibits Tumor Growth of Human Prostate Cancer Xenografts in Mice The in vitro studies demonstrate the therapeutic activity of hsa-miR-124a in cultured human prostate cancer cells. Therefore, hsa-miR-124a is likely to interfere with prostate tumor growth in the animal. To explore this possibility, the therapeutic potential of synthetic hsa-miR-124a miRNA was evaluated in the animal using the PC3 human prostate cancer xenograft. As described in Example 8, $5\times10^6$ PC3 cells per animal were mixed with BD Matrigel™, (BD Biosciences; San Jose, Calif., USA; cat. no. 356237) in a 1:1 ratio and implanted subcutaneously into the lower back of NOD/SCID mice (Jackson Laboratories; Bar Harbor, Me., USA). Once animals developed palpable tumors (day 38 post xenograft implantation), each animal in a group of 4 animals received intratumoral injections of 6.25 µl hsa-miR-124a (Dharmacon, Lafayette, Colo.) formulated with the lipid-based siPORT™ amine delivery agent (Ambion, Austin, Tex.; cat. no. AM4502) on days 38 and 40. Each animal in a control group of 4 animals received intratumoral injections of 6.25 µg negative control miRNA (NC; Dharmacon, Lafayette, Colo.), following the same injection schedule that was used for hsa-miR-124a. Given an average mouse weight of 20 g, this dose equals 0.3125 mg/kg. Caliper measurements were taken daily, and tumor volumes were calculated using the formula, Volume=length×width×width/2, in which the length is greater than the width. Repeated dosing with hsa-miR-124a blocked tumor growth of the human PC3 prostate cancer xenograft (FIG. 11). On day 42, the average size of tumors treated with hsa-miR-124a was 37.1% less than that of tumors treated with negative control miRNA.

The data suggest that hsa-miR-124a provides a useful therapeutic tool in the treatment of patients with prostate cancer. The therapeutic activity of hsa-miR-124a is highlighted by the fact that hsa-miR-124a inhibits tumor growth of tumors that had developed prior to treatment.

In addition, the data demonstrate the therapeutic utility of hsa-miR-124a in a lipid-based formulation.

Example 11

Delivery of Synthetic Hsa-miR-124a Inhibits Proliferation of Human Liver Cancer Cells The inventors assessed the therapeutic effect of hsa-miR-124a for liver cancer by using five individual human liver cancer cell lines. To measure cellular proliferation of liver cancer cells, the following liver cancer cell lines were used: HepG2, hepatocellular carcinoma derived from the liver; C3A, hepatocellular carcinoma derived from the liver; SK-Hep-1, adenocarcinoma derived from ascites; SNU-398, hepatocellular carcinoma derived from the liver; and PLC/PRF/5, Alexander cells derived from a hepatoma. Cells were transfected with synthetic hsa-miR-124a (Pre-miR™-hsa-miR-124a, Ambion cat. no. AM17100) or negative control miRNA (NC; Pre-miR™ microRNA Precursor Molecule-Negative Control #2; Ambion cat. no. AM17111) in a 96-well plate format using a lipid-based transfection reagent. Lipid-based reverse transfections were carried out in triplicate according to a published protocol (Ovcharenko et al. 2005) and the following parameters: Cells (6,000-7,000 per well), 0.1-0.15 µl Lipofectamine™ 2000 (cat. no. 11668-019, Invitrogen Corp., Carlsbad, Calif., USA) in 20 µl OptiMEM (Invitrogen), 30 nM final concentration of miRNA in 100 µl. Proliferation was assessed 4-7 days post-transfection using Alamar Blue™ (Invitrogen) following the manufacturer's instructions. As a control for inhibition of cellular proliferation, siRNA against the motor protein kinesin 11, also known as Eg5, was used. Eg5 is essential for cellular survival of most eukaryotic cells and a lack thereof leads to reduced cell proliferation and cell death (Weil et al. 2002). siEg5 was used in lipid-based transfection following the same experimental parameters that apply to miRNA. Fluorescent light units (FLU) were measured after 2-4 hours, normalized to the negative control, and plotted as percent change in proliferation. Percent proliferation of hsa-miR-124a-treated cells relative to cells treated with negative control miRNA (100%) is shown in Table 11 and in FIG. 12.

TABLE 11

Percent (%) proliferation of human liver cancer cell lines treated with hsa-miR-124a, Eg5-specific siRNA (siEg5), or negative control miRNA (NC).

| Cells | hsa-miR-124a (30 nM) | | siEg5 (30 nM) | | NC (30 nM) | |
|---|---|---|---|---|---|---|
| | % proliferation | % SD | % proliferation | % SD | % proliferation | % SD |
| SNU-398 | 38.67 | 6.75 | 25.26 | 3.23 | 100.00 | 8.01 |
| SK-Hep-1 | 75.7 | 2.94 | 34.68 | 5.13 | 100.00 | 3.21 |
| C3A | 41.09 | 3.59 | 40.63 | 23.48 | 100.00 | 7.49 |
| HepG2 | 77.67 | 6.61 | 46.51 | 0.66 | 100.00 | 1.06 |
| PLC/PRF/5 | 65.12 | 7.84 | 62.8 | 12.84 | 100.00 | 9.85 |

Values are normalized to values obtained from cells transfected with negative control miRNA (100% proliferation).
NC, negative control miRNA;
siEg5, Eg5-specific siRNA;
SD, standard deviation.

Delivery of hsa-miR-124a inhibits cellular proliferation of liver cancer cells SNU-398, SK-Hep-1, C3A, HepG2 and PLC/PRF/5 (Table 11 and FIG. 12). On average, hsa-miR-124a inhibits cellular proliferation by 40.35% (Table 11, FIG. 12). Hsa-miR-124a has maximal inhibitory activity in SNU-398 cells, reducing proliferation by 61%. Since hsa-miR-124a induces a therapeutic response in all liver cancer cells tested, it is contemplated that hsa-miR-124a can provide therapeutic benefit to a broad range of patients with liver cancer and other malignancies.

REFERENCES

The following references, to the extent that they provide exemplary procedural or other details supplementary to those set forth herein, are specifically incorporated herein by reference.

U.S. Pat. No. 4,337,063
U.S. Pat. No. 4,404,289
U.S. Pat. No. 4,405,711
U.S. Pat. No. 4,659,774
U.S. Pat. No. 4,682,195
U.S. Pat. No. 4,683,202
U.S. Pat. No. 4,704,362
U.S. Pat. No. 4,816,571
U.S. Pat. No. 4,870,287
U.S. Pat. No. 4,959,463
U.S. Pat. No. 5,141,813
U.S. Pat. No. 5,143,854
U.S. Pat. No. 5,202,231
U.S. Pat. No. 5,214,136
U.S. Pat. No. 5,221,619
U.S. Pat. No. 5,223,618
U.S. Pat. No. 5,242,974
U.S. Pat. No. 5,264,566
U.S. Pat. No. 5,268,486
U.S. Pat. No. 5,288,644
U.S. Pat. No. 5,324,633
U.S. Pat. No. 5,378,825
U.S. Pat. No. 5,384,261
U.S. Pat. No. 5,399,363
U.S. Pat. No. 5,405,783
U.S. Pat. No. 5,412,087
U.S. Pat. No. 5,424,186
U.S. Pat. No. 5,428,148
U.S. Pat. No. 5,429,807
U.S. Pat. No. 5,432,049
U.S. Pat. No. 5,436,327
U.S. Pat. No. 5,445,934
U.S. Pat. No. 5,446,137
U.S. Pat. No. 5,466,468
U.S. Pat. No. 5,466,786
U.S. Pat. No. 5,468,613
U.S. Pat. No. 5,470,710
U.S. Pat. No. 5,470,967
U.S. Pat. No. 5,472,672
U.S. Pat. No. 5,480,980
U.S. Pat. No. 5,492,806
U.S. Pat. No. 5,503,980
U.S. Pat. No. 5,510,270
U.S. Pat. No. 5,525,464
U.S. Pat. No. 5,527,681
U.S. Pat. No. 5,529,756
U.S. Pat. No. 5,532,128
U.S. Pat. No. 5,543,158
U.S. Pat. No. 5,545,531
U.S. Pat. No. 5,547,839
U.S. Pat. No. 5,554,501
U.S. Pat. No. 5,554,744
U.S. Pat. No. 5,556,752
U.S. Pat. No. 5,561,071
U.S. Pat. No. 5,571,639
U.S. Pat. No. 5,574,146
U.S. Pat. No. 5,580,726
U.S. Pat. No. 5,580,732
U.S. Pat. No. 5,583,013
U.S. Pat. No. 5,593,839
U.S. Pat. No. 5,599,672
U.S. Pat. No. 5,599,695
U.S. Pat. No. 5,602,240
U.S. Pat. No. 5,602,244
U.S. Pat. No. 5,610,287
U.S. Pat. No. 5,610,289
U.S. Pat. No. 5,614,617
U.S. Pat. No. 5,623,070
U.S. Pat. No. 5,624,711
U.S. Pat. No. 5,631,134
U.S. Pat. No. 5,637,683
U.S. Pat. No. 5,639,603
U.S. Pat. No. 5,641,515
U.S. Pat. No. 5,645,897
U.S. Pat. No. 5,652,099
U.S. Pat. No. 5,654,413
U.S. Pat. No. 5,658,734
U.S. Pat. No. 5,661,028
U.S. Pat. No. 5,665,547

U.S. Pat. No. 5,667,972
U.S. Pat. No. 5,670,663
U.S. Pat. No. 5,672,697
U.S. Pat. No. 5,677,195
U.S. Pat. No. 5,681,947
U.S. Pat. No. 5,695,940
U.S. Pat. No. 5,700,637
U.S. Pat. No. 5,700,922
U.S. Pat. No. 5,705,629
U.S. Pat. No. 5,708,153
U.S. Pat. No. 5,708,154
U.S. Pat. No. 5,714,606
U.S. Pat. No. 5,728,525
U.S. Pat. No. 5,739,169
U.S. Pat. No. 5,744,305
U.S. Pat. No. 5,760,395
U.S. Pat. No. 5,763,167
U.S. Pat. No. 5,770,358
U.S. Pat. No. 5,777,092
U.S. Pat. No. 5,789,162
U.S. Pat. No. 5,792,847
U.S. Pat. No. 5,800,992
U.S. Pat. No. 5,801,005
U.S. Pat. No. 5,807,522
U.S. Pat. No. 5,824,311
U.S. Pat. No. 5,830,645
U.S. Pat. No. 5,830,880
U.S. Pat. No. 5,837,196
U.S. Pat. No. 5,846,225
U.S. Pat. No. 5,846,945
U.S. Pat. No. 5,847,219
U.S. Pat. No. 5,856,174
U.S. Pat. No. 5,858,988
U.S. Pat. No. 5,859,221
U.S. Pat. No. 5,871,928
U.S. Pat. No. 5,872,232
U.S. Pat. No. 5,876,932
U.S. Pat. No. 5,886,165
U.S. Pat. No. 5,919,626
U.S. Pat. No. 5,922,591
U.S. Pat. No. 6,004,755
U.S. Pat. No. 6,040,193
U.S. Pat. No. 6,087,102
U.S. Pat. No. 6,251,666
U.S. Pat. No. 6,368,799
U.S. Pat. No. 6,383,749
U.S. Pat. No. 6,617,112
U.S. Pat. No. 6,638,717
U.S. Pat. No. 6,720,138
U.S. Pat. No. 6,723,509
U.S. application Ser. No. 09/545,207
U.S. application Ser. No. 10/667,126
U.S. application Ser. No. 11/141,707
U.S. application Ser. No. 11/273,640
U.S. application Ser. No. 11/349,727
U.S. Prov. Appln. 60/575,743
U.S. Prov. Appln. 60/649,584
U.S. Prov. Appln. 60/650,807
Adelaide et al., Genes Chromosomes Cancer, 37(4):333-345, 2003.
Akiba et al., Int J Oncol, 18(2):257-264, 2001.
Akino et al., Gastroenterology, 129(1):156-169, 2005.
Alipov et al., Histopathology, 46(2):202-208, 2005.
Ando et al., J Biol Chem, 279(24):25549-25561, 2004.
Aoki et al., Proc Natl Acad Sci USA, 101(37):13613-13617, 2004.
Arap et al., Cancer Res., 55(6):1351-1354, 1995.
Ariyanayagam-Baksh et al., Mod Pathol, 16(10):992-995, 2003.
Aspland et al., Oncogene, 20(40):5708-5717, 2001.
Austin and Cook, J Biol Chem, 280(39):33280-33288, 2005.
Austin-Ward and Villaseca, Revista Medica de Chile, 126(7): 838-845, 1998.
Bader and Vogt, Oncogene, 23(18):3145-3150, 2004.
Bader et al., Nat Rev Cancer, 5(12):921-929, 2005.
Bae et al., J Biol Chem, 275(33):25255-25261, 2000.
Bagga et al., Cell, 122(4):553-563, 2005.
Bandyopadhyay et al., Oncogene, 21(22):3541-3551, 2002.
Barr, Oncogene, 20(40):5736-5746, 2001.
Bar-Shira et al., Cancer Res. 62(23):6803-6807, 2002.
Bartel et al., Cancer Cell, 2(1):9-15, 2002.
Bartlett et al., *Nucleic Acids Res.* 34(1):322-33, 2006
Bartlett et al., *Biotechnol Bioeng.* 97(4):909-2, 2007.
Beeram et al., J Clin Oncol, 23(27):6771-6790, 2005.
Behrens et al., J Pathol, 194(1):43-50, 2001.
Beisner et al., Cancer Res, 66(15):7554-7561, 2006.
Bell and Dutta, Annu Rev Biochem, 71:333-374, 2002.
Bello et al., Carcinogenesis, 18(6):1215-1223, 1997.
Biswas et al., Cancer Res, 64(14):4687-4692, 2004.
Blobe et al., J Biol Chem, 276(27):24627-24637, 2001.
Borczuk et al., Am J Pathol, 163(5):1949-1960, 2003.
Boultwood et al., Br J Haematol, 126(4):508-511, 2004.
Bravou et al., Int J Oncol, 27(6):1511-1518, 2005.
Brothman et al., J Urol., 145(5):1088-1091, 1991.
Buggy et al., Br J Cancer, 91(7):1308-1315, 2004.
Bukowski et al., Clinical Cancer Res., 4(10):2337-2347, 1998.
Cahill et al., Nature, 392(6673):300-303, 1998.
Caldas et al., Cancer Res., 54:3568-3573, 1994.
Calin and Croce, Nat Rev Cancer, 6(11):857-866, 2006.
Cao et al., Cell, 107(6):763-775, 2001.
Cao et al., Genes Dev, 21(5):531-536, 2007.
Carrano et al., Nat Cell Biol, 1(4):193-199, 1999.
Carrington and Ambros, Science, 301(5631):336-338, 2003.
Carter and Brunet, Curr Biol, 17(4):R113-114, 2007.
Chandler et al., Int J Cancer, 81(3):451-458, 1999.
Chang et al., Int J Cancer, 114(6):942-949, 2005.
Chendrimada et al., Nature, 447(7146):823-828, 2007.
Cheng et al., Cancer Res., 54(21):5547-5551, 1994.
Chieffi et al., Prostate, 66(3):326-333, 2006.
Choi et al., Oncogene, 23(42):7095-7103, 2004.
Cho-Vega et al., Hum Pathol, 35(9):1095-1100, 2004.
Christodoulides et al., Microbiology, 144(Pt 11):3027-3037, 1998.
Cipriano and Chen, Oncogene, 17(12):1549-1556, 1998.
Claudio et al., Clin Cancer Res, 8(6):1808-1815, 2002.
Cohen et al., Oncogene, 20(2):141-146, 2001.
Coll et al., Embo J, 2(12):2189-2194, 1983.
Costello et al., Cancer Res, 57(7):1250-1254, 1997.
Crossen and Morrison, Hum Genet, 91(4):380-382, 1993.
Crossen et al., Cancer Genet Cytogenet, 79(1):70-73, 1995.
Cully et al., Cancer Res, 65(22):10363-10370, 2005.
Cummins et al., In: IRT: Nucleosides and nucleosides, La Jolla Calif., 72, 1996.
Davidson et al., Clin Cancer Res, 7(3):551-557, 2001.
Davidson et al., J. Immunother., 21(5):389-398, 1998.
Denli et al., Trends Biochem. Sci., 28:196, 2003.
Didenko, Biotechniques, 31(5):1106-1116, 1118, 1120-1121, 2001.
Dillman, Cancer Biother. Radiopharm., 14(1):5-10, 1999.
Dittmer, Mol Cancer, 2:29, 2003.
Dong et al., Mol Endocrinol, 20(10):2315-2325, 2006.
Dreyfus et al., Nouv Rev Fr Hematol, 31(3):217-221, 1989.
Dyer and Bremner, Nat Rev Cancer, 5(2):91-101, 2005.

Egilmez et al., J Exp Clin Cancer Res, 20(4):549-552, 2001.
Egle et al., Proc Natl Acad Sci USA, 101(16):6164-6169, 2004.
Egloff et al., Cancer Res, 66(1):6-9, 2006.
Einama et al., Pancreas, 32(4):376-381, 2006.
Emptage et al., Neuron, 29(1):197-208, 2001.
Endoh et al., Br J Cancer, 93(12):1395-1399, 2005.
EP 266,032
EP 373 203
EP 785 280
EP 799 897
Esquela-Kerscher and Slack, Nat Rev Cancer, 6(4):259-269, 2006.
Fakharzadeh et al., Embo J, 10(6):1565-1569, 1991.
Firth and Baxter, Endocr Rev, 23(6):824-854, 2002.
Fisher, J Royal Statistical Soc, 85(1):87-94, 1922.
Fleischer et al., Int J Oncol, 28(1):25-32, 2006.
Fodor et al., Biochemistry, 30(33):8102-8108, 1991.
Froehler et al., Nucleic Acids Res., 14(13):5399-5407, 1986.
Fujimoto et al., Ann Oncol, 13(10):1598-1604, 2002a.
Fujimoto et al., Ann Oncol, 13(10):1605-1611, 2002b.
Fujiwara et al., Oncogene, 10(5):891-895, 1995.
Ginestier et al., Clin Cancer Res, 12(15):4533-4544, 2006.
Golay et al., Blood, 87(5):1900-1911, 1996.
Gomez-Bougie et al., Eur J Immunol, 34(11):3156-3164, 2004.
Gonzalez et al., Nature, 440(7084):702-706, 2006.
Goto et al., Oncogene, 2007.
Goyns et al., Br J Cancer, 56(5):611-613, 1987.
Grabsch et al., J Pathol, 200(1):16-22, 2003.
Gratas et al., Cancer Res, 58(10):2057-2062, 1998.
Griffey et al., J. Mass Spectrom, 32(3):305-13, 1997.
Gstaiger et al., Proc Natl Acad Sci USA, 98(9):5043-5048, 2001.
Hanahan and Weinberg, Cell, 100(1):57-70, 2000.
Hanibuchi et al., Int. J. Cancer, 78(4):480-485, 1998.
Hansel et al., Am J Surg Pathol, 29(3):390-399, 2005.
Hayette et al., Blood, 102(4):1549-1550, 2003.
Hellstrand et al., Acta Oncologica, 37(4):347-353, 1998.
Hishikawa et al., J Biol Chem, 274(52):37461-37466, 1999.
Horoszewicz et al., Prog Clin Biol Res., 37:115-32, 1980.
Houston and O'Connell, Curr Opin Pharmacol, 4(4):321-326, 2004.
Hsu et al., Mol Endocrinol, 12(9):1432-1440, 1998.
Huang et al., Clin Cancer Res, 12(2):487-498, 2006.
Hui and Hashimoto, Infection Immun., 66(11):5329-5336, 1998.
Hussussian et al., Nat. Genet., 8(1):15-21, 1994.
Inui et al., Biochem Biophys Res Commun, 303(3):978-984, 2003.
Iolascon et al., Hepatology, 27(4):989-995, 1998.
Itakura and Riggs, Science, 209:1401-1405, 1980.
Ito et al., Am J Clin Pathol, 114(5):719-725, 2000.
Ito et al., Anticancer Res, 23(5A):3819-3824, 2003.
Ito et al., Mod Pathol, 11(2):209-215, 1998.
Jansen et al., Embo J, 2(11): 1969-1975, 1983.
Jiang et al., Cancer Res, 64(16):5787-5794, 2004.
Jonson et al., Int J Oncol, 19(1):71-81, 2001.
Ju et al., Gene Ther., 7(19):1672-1679, 2000.
Jung et al., Pathol Int, 56(9):503-509, 2006.
Kalin et al., Cancer Res, 66(3):1712-1720, 2006.
Kalinichenko et al., Genes Dev, 18(7):830-850, 2004.
Kamata et al., J Cancer Res Clin Oncol, 131(9):591-596, 2005.
Kamb et al., Nat. Genet., 8(1):23-26, 1994.
Kamb et al., Science, 2674:436-440, 1994.
Kapsimali et al., Genome Biol, 8(8):R173 [Epub ahead of print] 2007.
Karakaidos et al., Am J Pathol, 165(4):1351-1365, 2004.
Karin et al., Nat Rev Cancer, 2(4):301-310, 2002.
Kastan and Lim, Nat Rev Mol Cell Biol, 1(3):179-186, 2000.
Kaufmann et al., Blood, 91(3):991-1000, 1998.
Keen and Taylor, Nat Rev Cancer, 4(12):927-936, 2004.
Kerckaert et al., Leukemia, 4(1):16-19, 1990.
Kim et al., Cancer Res, 66(4):2153-2161, 2006.
Kim et al., Clin Cancer Res, 11(2 Pt 1):473-482, 2005.
Kiriakidou et al., Cell, 129(6): 1141-1151, 2007.
Kirikoshi et al., Int J Oncol, 19(1):111-115, 2001.
Kitada et al., Blood, 91(9):3379-3389, 1998.
Kitange et al., Cancer, 89(11):2292-2300, 2000.
Kitange et al., Mod Pathol, 12(6):618-626, 1999.
Klostermeier and Millar, Biopolymers, 61(3):159-79, 2001-2002.
Koivunen et al., Cancer Lett, 235(1):1-10, 2006.
Koivunen et al., Cancer Res, 64(16):5693-5701, 2004.
Komiya et al., Jpn J Cancer Res, 88(4):389-393, 1997.
Kops et al., Nat Rev Cancer, 5(10):773-785, 2005.
Kornberg and Baker, In: DNA Replication, 2d Ed., Freeman, San Francisco, 1992.
Krajewska et al., Am J Pathol, 148(5):1567-1576, 1996.
Krasagakis et al., Br J Cancer, 77(9):1492-1494, 1998.
Krek et al., Nat Genet, 37(5):495-500, 2005.
Kristjansdottir and Rudolph, Chem Biol, 11(8):1043-1051, 2004.
Kulkarni et al., Leukemia, 16(1):127-134, 2002.
Lagos-Quintana et al., Rna, 9(2):175-179, 2003.
Lahn and Sundell, Melanoma Res, 14(2):85-89, 2004.
Lam et al., Br J Neurosurg, 14(1):28-32, 2000.
Lambros et al., J Pathol, 205(1):29-40, 2005.
Lau et al., Science, 294(5543):858-862, 2001.
Lauffart et al., BMC Womens Health, 5:8, 2005.
Lee and Ambros, Science, 294(5543):862-864, 2001.
Leprince et al., Nature, 306(5941):395-397, 1983.
L'Hote and Knowles, Exp Cell Res, 304(2):417-431, 2005.
Li et al., Cell Death Differ, 12(3):292-303, 2005.
Li et al., Oncogene, 22(10):1501-1510, 2003.
Lim et al., Nature, 433(7027):769-773, 2005.
Lin and Gelman, Cancer Res, 57(11):2304-2312, 1997.
Lin et al., Gastroenterology, 128(1):9-23, 2005.
Liu and Erikson, Proc Natl Acad Sci USA, 100(10):5789-5794, 2003.
Liu et al., Cancer Res, 66(7):3593-3602, 2006.
Lo Vasco et al., Leukemia, 18(6):1122-1126, 2004.
Lucke et al., Cancer Res, 61(2):482-485, 2001.
Lujambio et al., Cancer Res, 67(4):1424-1429, 2007.
Lukiw, Neuroreport, 18(3):297-300, 2007.
Makeyev et al., Mol Cell, 27(3):435-448, 2007.
Malumbres and Barbacid, Nat Rev Cancer, 1(3):222-231, 2001.
Markowitz et al., Science, 268(5215):1336-1338, 1995.
Markowitz, Biochim Biophys Acta, 1470(1):M13-20, 2000.
Marone et al., Int J Cancer, 75(1):34-39, 1998.
Marsters et al., Recent Prog. Horm. Res., 54:225-234, 1999.
Martinez-Lorenzo et al., Int J Cancer, 75(3):473-481, 1998.
Massague et al., Cell, 103(2):295-309, 2000.
McGary et al., Cancer Biol Ther, 1(5):459-465, 2002.
Mendrzyk et al., J Clin Oncol, 23(34):8853-8862, 2005.
Merle et al., Gastroenterology, 127(4):1110-1122, 2004.
Mishima et al., Brain Res, 1131(1):37-43, Epub Dec. 19, 2006. 2007.
Moller et al., Int J Cancer, 57(3):371-377, 1994.
Momand et al., Nucleic Acids Res, 26(15):3453-3459, 1998.
Mori et al., Cancer Res., 54(13):3396-3397, 1994.

Mori et al., Gastroenterology, 131(3):797-808, 2006.
Morishita et al., Hepatology, 40(3):677-686, 2004.
Mundt et al., Biochem Biophys Res Commun, 239(2):377-385, 1997.
Murphy et al., J Clin Pathol, 58(5):525-534, 2005.
Nakagawa et al., Oncogene, 23(44):7366-7377, 2004.
Nakayama et al., Am J Pathol, 149(6):1931-1939, 1996.
Nakayama et al., Cancer, 92(12):3037-3044, 2001.
Nakayama et al., Mod Pathol, 12(1):61-68, 1999.
Nauert et al., Curr Biol, 7(1):52-62, 1997.
Nobori et al., Nature (London), 368:753-756, 1995.
O'Connor et al., Embo J, 17(2):384-395, 1998.
Ohsaki et al., Cancer Res, 52(13):3534-3538, 1992.
Okamoto et al., Proc. Natl. Acad. Sci. USA, 91(23):11045-11049, 1994.
Olsen et al., Dev. Biol., 216:671, 1999.
Orlow et al., Cancer Res, 54(11):2848-2851, 1994.
Orlow et al., Int. J. Oncol., 15(1):17-24, 1994.
Ovcharenko et al., Rna, 11(6):985-993, 2005.
Ozaki et al., Cancer Res, 60(22):6519-6525, 2000.
Paik et al., Cell, 128(2):309-323, 2007.
Parekh et al., Biochem Pharmacol, 63(6):1149-1158, 2002.
Payton and Coats, Int J Biochem Cell Biol, 34(4):315-320, 2002.
Payton et al., Oncogene, 21(55):8529-8534, 2002.
PCT Appln. WO 0138580
PCT Appln. WO 0168255
PCT Appln. WO 03020898
PCT Appln. WO 03022421
PCT Appln. WO 03023058
PCT Appln. WO 03029485
PCT Appln. WO 03040410
PCT Appln. WO 03053586
PCT Appln. WO 03066906
PCT Appln. WO 03067217
PCT Appln. WO 03076928
PCT Appln. WO 03087297
PCT Appln. WO 03091426
PCT Appln. WO 03093810
PCT Appln. WO 03100012
PCT Appln. WO 03100448A1
PCT Appln. WO 04020085
PCT Appln. WO 04027093
PCT Appln. WO 09923256
PCT Appln. WO 09936760
PCT Appln. WO 93/17126
PCT Appln. WO 95/11995
PCT Appln. WO 95/21265
PCT Appln. WO 95/21944
PCT Appln. WO 95/21944
PCT Appln. WO 95/35505
PCT Appln. WO 96/31622
PCT Appln. WO 97/10365
PCT Appln. WO 97/27317
PCT Appln. WO 9743450
PCT Appln. WO 99/35505
Petit et al., Genomics, 57(3):438-441, 1999.
Pietras et al., Cancer Cell, 3(5):439-443, 2003.
Pietras et al., Oncogene, 17(17):2235-2249, 1998.
Prentice et al., Oncogene, 24(49):7281-7289, 2005.
Pretlow et al., Natl Cancer Inst., 85(24):2004-2007, 1993.
Prochownik et al., Genes Chromosomes Cancer, 22(4):295-304, 1998.
Pruitt et al., Nucleic Acids Res, 33(Database issue):D501-504, 2005.
Qian et al., Proc Natl Acad Sci USA, 99(23):14925-14930, 2002.
Qin et al., Proc. Natl. Acad. Sci. USA, 95(24):14411-14416, 1998.
Rapp et al., Proc Natl Acad Sci USA, 80(14):4218-4222, 1983.
Reiter et al., Clin Cancer Res, 12(17):5136-5141, 2006.
Remington's Pharmaceutical Sciences" 15$^{th}$ Ed., 1035-1038 and 1570-1580, 1990.
Remington's Pharmaceutical Sciences" 15$^{th}$ Ed., 1035-1038 and 1570-1580, 1990.
Rincon-Arano et al., Cancer, 97(3):575-585, 2003.
Ritch et al., J Biol Chem, 278(23):20971-20978, 2003.
Robles et al., J Biol Chem., 277(28):25431-25438, 2002.
Romieu-Mourez et al., Cancer Res, 61(9):3810-3818, 2001.
Rosenkilde and Schwartz, Apmis, 112(7-8):481-495, 2004.
Rothhammer et al., Cell Mol Life Sci, 61(1):118-128, 2004.
Rous, J Exp Med, 13:397-411, 1911.
Ru et al., Oncogene, 21(30):4673-4679, 2002.
Rust et al., J Clin Pathol, 58(5):520-524, 2005.
Sacchi et al., Leukemia, 2(1):12-18, 1988.
Sacchi et al., Science, 231(4736):379-382, 1986.
Saeki et al., Cancer, 89(8):1670-1676, 2000.
Saigusa et al., Cancer Sci, 96(10):676-683, 2005.
Sanchez-Aguilera et al., Blood, 103(6):2351-2357, 2004.
Sano et al., Histopathology, 46(5):532-539, 2005.
Sasaki et al., J Surg Res, 101(2):242-247, 2001.
Schulze-Bergkamen et al., BMC Cancer, 6:232, 2006.
Seggerson et al., Dev. Biol., 243:215, 2002.
Seike et al., Lung Cancer, 38(3):229-234, 2002.
Semple and Duncker, Biotechnol Adv, 22(8):621-631, 2004.
Serrano et al., Nature, 366:704-707, 1993.
Serrano et al., Science, 267(5195):249-252, 1995.
Shapira et al., Cancer, 103(7):1336-1346, 2005.
Sherr and McCormick, Cancer Cell, 2(2):103-112, 2002.
Sherr and Roberts, Genes Dev, 13(12):1501-1512, 1999.
Shetty et al., Br J Cancer, 93(11):1295-1300, 2005.
Shibahara et al., Anticancer Res, 25(3B):1881-1888, 2005.
Shigeishi et al., Oncol Rep, 15(4):933-938, 2006.
Shigemasa et al., Jpn J Cancer Res, 93(5):542-550, 2002.
Shinoura et al., Cancer Gene Ther, 7(2):224-232, 2000.
Sieghart et al., J Hepatol, 44(1):151-157, 2006.
Slotky et al., Breast Cancer Res, 7(5):R737-744, 2005.
Smirnova et al., Eur J Neurosci, 21(6):1469-1477, 2005.
Smith et al., Biochem Biophys Res Commun, 234(2):397-405, 1997.
Smith et al., Br J Cancer, 93(6):719-729, 2005.
Soufla et al., Cancer Lett, 221(1):105-118, 2005.
Span et al., Oncogene, 21(55):8506-8509, 2002.
Sparmann and Bar-Sagi, Cancer Cell, 6(5):447-458, 2004.
Stehelin et al., Nature, 260(5547):170-173, 1976.
Stone et al., Int J Cancer., 21(3):274-81, 1978.
Strebhardt and Ullrich, Nat Rev Cancer, 6(4):321-330, 2006.
Sui et al., Oncol Rep, 15(4):765-771, 2006.
Tagawa et al., Oncogene, 24(8):1348-1358, 2005.
Takanami, Oncol Rep, 13(4):727-731, 2005.
Takimoto et al., Biochem Biophys Res Commun, 251(1):264-268, 1998.
Tan et al., Leuk Res, 27(2):125-131, 2003.
Tanaka et al., Proc Natl Acad Sci USA, 95(17):10164-10169, 1998.
Tanner et al., Clin Cancer Res, 6(5):1833-1839, 2000.
Thome, Nat Rev Immunol, 4(5):348-359, 2004.
Tokuhara et al., Int Surg, 88(1):25-33, 2003.
Traub et al., Breast Cancer Res Treat, 99(2):185-191, 2006.
Tsai et al., J Natl Cancer Inst, 85(11):897-901, 1993.
Turner et al., Nat Rev Cancer, 4(10):814-819, 2004.
Tuveson et al., Cancer Cell, 4(2):95-98, 2003.
U.K. Patent 1,529,202

U.K. Patent 8 803 000
Ulisse et al., Int J Cancer, 119(2):275-282, 2006.
Vanhaesebroeck et al., Trends Biochem Sci, 22(7):267-272, 1997.
Venkatasubbarao et al., Anticancer Res, 20(1A):43-51, 2000.
Viard-Leveugle et al., J Pathol, 201(2):268-277, 2003.
Visvanathan et al., Genes Dev, 21(7):744-749, 2007.
Vogt et al., Cell Cycle, 4(7):908-913, 2005.
Vos et al., J Biol Chem, 278(30):28045-28051, 2003.
Wang et al., Oncogene, 22(10):1486-1490, 2003.
Wang et al., Proc Natl Acad Sci USA, 98(20):11468-11473, 2001.
Wechsler et al., Cancer Res, 57(21):4905-4912, 1997.
Weichert et al., Int J Oncol, 23(3):633-639, 2003.
Weil et al., Biotechniques, 33(6):1244-1248, 2002.
Wiemer, Eur J Cancer, 43(10):1529-1544, 2007.
Wikman et al., Oncogene, 21(37):5804-5813, 2002.
Wohlschlegel et al., Am J Pathol, 161(1):267-273, 2002.
Wolowiec et al., Leuk Lymphoma, 35(1-2):147-157, 1999.
Wooster and Weber, N Engl J Med, 348(23):2339-2347, 2003.
Woszczyk et al., Med Sci Monit, 10(1):CR33-37, 2004.
Wu et al., Eur J Cancer, 38(14):1838-1848, 2002.
Wuilleme-Toumi et al., Leukemia, 19(7):1248-1252, 2005.
Xi et al., Clin Cancer Res, 12(8):2484-2491, 2006a.
Xi et al., Clin Chem, 52(3):520-523, 2006b.
Xia et al., Cancer Res, 61(14):5644-5651, 2001.
Yamamoto et al., Int J Oncol, 13(2):233-239, 1998.
Yeatman, Nat Rev Cancer, 4(6):470-480, 2004.
Yu and Feig, Oncogene, 21(49):7557-7568, 2002.
Zangemeister-Wittke and Huwiler, Cancer Biol Ther, 5(10):1355-1356, 2006.

What is claimed is:

1. A method of inhibiting proliferation of a prostate or liver cancer cell comprising administering to a subject having a prostate cancer or liver cancer cell an isolated nucleic acid comprising a miR-124 nucleic acid sequence in combination with an isolated nucleic acid comprising a miR-34a, let-7b, let-7c, or let-7g nucleic acid sequence in an amount sufficient to inhibit proliferation of the prostate or liver cancer cell.

2. The method of claim 1, wherein the prostate carcinoma is associated with detectable prostate-specific antigen (PSA).

3. The method of claim 1, wherein the prostate carcinoma is androgen independent.

4. The method of claim 1, wherein the liver carcinoma is hepatoma, hepatocarcinoma or an hepatic adenocarcinoma.

5. The method of claim 1, wherein the liver carcinoma is hepatoblastoma, or a cholangiocarcinoma.

6. The method of claim 1, wherein the isolated miR-124, miR-34a, let-7b, let-7c, or let-7g nucleic acid is a recombinant nucleic acid.

7. The method of claim 1, wherein the miR-124, miR-34a, let-7b, let-7c, or let-7g nucleic acid is a synthetic nucleic acid.

8. The method of claim 1, wherein the nucleic acid is administered enterally or parenterally.

9. The method of claim 1, wherein the nucleic acid is comprised in a pharmaceutical formulation.

10. The method of claim 9, wherein the pharmaceutical formulation is a lipid composition or a nanoparticle composition.

11. The method of claim 9, wherein the pharmaceutical formulation consists of biocompatible and biodegradable molecules.

* * * * *